(12) United States Patent
Yasukouchi et al.

(10) Patent No.: US 7,399,775 B2
(45) Date of Patent: Jul. 15, 2008

(54) β-AMYLOID PROTEIN PRODUCTION/SECRETION INHIBITOR

(75) Inventors: Takanori Yasukouchi, Tokyo (JP); Masayuki Ito, Tokyo (JP); Hideki Kubota, Tokyo (JP); Satoru Miyauchi, Tokyo (JP); Masanori Saito, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 293 days.

(21) Appl. No.: 10/500,156

(22) PCT Filed: Dec. 27, 2002

(86) PCT No.: PCT/JP02/13792

§ 371 (c)(1), (2), (4) Date: Jun. 25, 2004

(87) PCT Pub. No.: WO03/055850

PCT Pub. Date: Jul. 10, 2003

(65) Prior Publication Data

US 2005/0234109 A1    Oct. 20, 2005

(30) Foreign Application Priority Data

Dec. 27, 2001 (JP) ............................. 2001-395701

(51) Int. Cl.
 A61K 31/44 (2006.01)
 C07D 211/70 (2006.01)
(52) U.S. Cl. .................... 514/352; 546/339; 546/268.1; 546/304; 514/336
(58) Field of Classification Search ................ 546/339, 546/268.1, 304; 514/352, 336
See application file for complete search history.

(56) References Cited

U.S. PATENT DOCUMENTS

| | | | |
|---|---|---|---|
| 4,055,652 A | 10/1977 | Walker | |
| 4,116,665 A | 9/1978 | Krumkalns | |
| 4,157,399 A | 6/1979 | Sauter | |
| 4,257,954 A | 3/1981 | Schmidt et al. | |
| 4,675,316 A | 6/1987 | Chan | |
| 6,689,909 B1 * | 2/2004 | Butlin et al. | 564/202 |
| 2005/0234109 A1 | 10/2005 | Yasukouchi et al. | |

FOREIGN PATENT DOCUMENTS

| | | |
|---|---|---|
| DE | 4215437 | 11/1993 |
| EP | 112 | 12/1978 |
| EP | 752 | 2/1979 |
| EP | 46658 | 3/1982 |
| EP | 117485 | 9/1984 |
| EP | 153657 | 9/1985 |
| FR | 2509725 | 1/1983 |
| GB | 1554299 | 10/1979 |
| JP | 55-33473 | 3/1980 |
| JP | 62-39563 | 2/1987 |
| JP | 6-25168 | 2/1994 |
| JP | 6-56780 | 3/1994 |
| JP | 9-95444 | 4/1997 |
| WO | WO 93/25536 | 12/1993 |
| WO | WO 96/41799 | 12/1996 |
| WO | 98/38156 | 9/1998 |
| WO | 00 50391 | 8/2000 |
| WO | 01 70677 | 9/2001 |
| WO | 02/081433 | 10/2002 |
| WO | 02/081435 | 10/2002 |
| WO | 03 013527 | 2/2003 |
| WO | 03 014075 | 2/2003 |
| WO | 03/018543 | 3/2003 |
| WO | 03 053912 | 7/2003 |
| WO | WO 03/055850 A1 | 7/2003 |
| WO | WO 03/059335 A1 | 7/2003 |
| WO | 03 066592 | 8/2003 |
| WO | 03 093251 | 11/2003 |
| WO | 03 093252 | 11/2003 |
| WO | 03 093253 | 11/2003 |
| WO | 03 093264 | 11/2003 |
| WO | 03 103660 | 12/2003 |
| WO | WO 2004/017977 A2 | 3/2004 |
| WO | WO 2004/031137 A1 | 4/2004 |
| WO | WO 2004/031138 A1 | 4/2004 |
| WO | WO 2004/031139 A1 | 4/2004 |
| WO | 2004 039370 | 5/2004 |
| WO | 2004 039800 | 5/2004 |

OTHER PUBLICATIONS

Kurahashi et al., 1994, CAS: 121:3287.*
Anders et al., 1989, CAS:110:74541.*
Traynelis et al., 1974, CAS: 80:14814.*
Cai, Xiao-Dan et al. "Release of Excess Amyloid β Protein from a Mutant Amyloid β Protein Precursor", Science, vol. 259, pp. 514-516 Jan. 22, 1993.

(Continued)

*Primary Examiner*—Rei-tsang Shiao
(74) *Attorney, Agent, or Firm*—Oblon, Spivak, McClelland, Maier & Neustadt, P.C.

(57) ABSTRACT

Provided are novel compounds having an inhibitory activity against production or secretion of β-amyloid protein. They embrace compounds represented by the following formula (1):

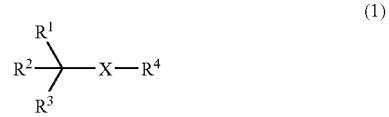

and capable of being replaced with a variety of substituents; and salts thereof, and solvates of any one of them.

18 Claims, No Drawings

OTHER PUBLICATIONS

Gravina, Stephen A. et al. "Amyloid β Protein (Aβ) in Alzheimer's Disease Brain", The Journal of Biological Chemistry, vol. 270, No. 13, pp. 7013-7016 Mar. 31, 1995.

Vassar, Robert et al. "β-Secretase Cleavage of Alzheimer's Amyloid Precursor Protein by the Transmembrane Aspartic Protease BACE", Science, vol. 286, pp. 735-741 Oct. 22, 1999.

Hussain, I. et al. "ASP1 (BACE2) Cleaves the Amyloid Precursor Protein at the β-Secretase Site", Molecular and Cellular Neuroscience, vol. 16, pp. 609-619 2000.

Wolfe, Michael et al. "Two transmembrane aspartates in presenilin-1 required for presenilin endoproteolysis and γ-secretase activity", Nature, vol. 398, pp. 513-517 Apr. 8, 1999.

Wolfe, Michael "Secretase Targets for Alzheimer's Disease: Identification and Therapeutic Potential", Journal of Medicinal Chemistry, vol. 44, No. 13, pp. 2039-2060 Jun. 21, 2001.

Anders, Ernst et al. "'Ferngesteuerte' nucleophile Eigenschaften der Anionen einiger 4-Alkylpyridine: AM 1- und MNDO-Berechnungen sowie experimentelle Untersuchungen", Chem. Ber., vol. 122, pp. 105-111 1989.

Skarzewski, J., Simple preparation of enantiometric Michael adducts of thiophenol to chalcones, Tetrahedron: Asymmetry, Jul. 30, 2001, vol. 12, No. 13, pp. 1923 to 1928.

Ishibashi, Hiroyuki, Lewis acid-promoted alkylations of arenes and 1-trimethylsilylalkynes with beta-chloro-beta-thiopropanoic esters, Chemical & Pharmaceutical Bulletin, 1991, vol. 39, No. 5, pp. 1148 to 1151.

Karavan, V.S., Isoselectivity relation in the halophilic reaction of alpha-chlorodesyl aryl sulfones with sodium thiophenolate, Zhurnal Organicheskoi Khimii, 1989, vol. 25, No. 5, pp. 905 to 910.

Muehlstaedt, M., Cyclization reaction of beta, gamma-unsaturated derivatives of carbonic acid, Journla fuer Praktische Chemie, 1986, vol. 328, No. 3, pp. 309 to 313.

Fournier, Jean Paul, Hypolipernic activity of 2-hydroxyalkyl and 3-hydroxyalkyl phenyl sulfones., European Journal of Medicinal Chemistry, 1982, vol. 17, No. 1, pp. 53 to 58.

Walker, Keith A.M., A convenient preparation of thioethers from alcohols, Tetrahedron Letters, 1977, No. 51, pp. 4475 to 4478.

Lapkin, I.I., Reactions of halo metal alcoholates, Khimiya Geterotsiklicheskikh Soedinenii, 1968, No. 1, pp. 53 to 57.

Panteleimonov, A.V., Addition of nucleophilic agents to 1-aryl-2-trifluoro-methylsulfonylethylenes, Zhurnal Obshchei Khimii, 1966, vol. 36, No. 11, pp. 1976 to 1980.

Wragg, A.H., Rearrangement of sulfinic esters, J. Chem. Soc., 1958, pp. 3603 to 3605.

Cranham, J.E., Toxicity of organic sulfides to the eggs and larvae of the two-spotted spider mite, J. Sci. Food Agr., 1958, vol. 9, pp. 147 to 150.

Krzysztof Wojciechowski, "Synthesis of Nitrobenzophenones from Nitro-α-Sulfonyldiphenylmethane Derivatives", Synthetic Communications, 27(1), 1997, pp. 135-144.

Eric K. Yau, et al., "Synthesis of Complex 6'-Alkynyl-6'-dethia Nucleoside Analogues of S-Adenosylhomocysteine as Potential Inhibitors of Methyltransferases", Journal of Organic Chemistry, vol. 55, No. 10, American Chemical Society 1990, pp. 3147-3158.

I. I. Lapkin, et al., "Reactions of halogen metal alcoholates, XXI, New method of synthesizing sulfides of thiophenic series", Khimiya Geterotsiklicheskih Geterotsiklicheskih Soedinenii, No. 1, 1968, pp. 52-57 (with partial English translation).

U.S. Appl. No. 10/561,838, filed Dec. 22, 2005, Kubota et al.

Ibro Tabakovic, et al., "The Alkylation of Coumarin at C-3 of 4-Hydroxycoumarin", Organic Preparations and Procedures International, vol. 29, No. 2, Apr. 1997, pp. 223-226.

* cited by examiner

β-AMYLOID PROTEIN PRODUCTION/SECRETION INHIBITOR

TECHNICAL FIELD

The present invention relates to novel compounds having an inhibitory activity against production or secretion of β-amyloid protein; and a medicament to treat for various diseases caused by abnormal production or secretion of β-amyloid protein such as Alzheimer disease, Down syndrome and the other diseases associated with amyloid deposition.

BACKGROUND ART

Alzheimer disease is a neurodegenerative disease having pathological features such as degeneration or loss of nerve cells, formation of senile plaques and neurofibrillary tangles. Alzheimer disease causes symptoms of dementia such as gradual loss of memory, recognition, thinking, judgment or the like, and it eventually leads to death. No effective method for treating or preventing this disease has hitherto been known.

The main protein constituting a senile plaque deposited in the brain is β-amyloid protein which is composed of from 39 to 43 amino acids. β-Amyloid protein exhibits cytotoxicity, which is presumed to induce Alzheimer disease (Science, 259, 514 (1993)). β-Amyloid protein secreted from cells is a polypeptide composed mainly of 40 or 42 amino acids and particularly, that composed of 42 amino acids is known to deposit in the brain quickly because of strong aggregation property and in addition, have strong cytotoxicity (Journal of Biological Chemistry, 270, 7013 (1995)). β-Amyloid protein is produced ubiquitously in vivo, but its function remains unknown.

β-Amyloid protein is produced by processing of a β-amyloid precursor protein (APP) which is a membrane protein. Mutation of an APP gene is observed from patients suffering from familial Alzheimer disease. An increase in the production or secretion amount of β-amyloid protein is known to occur in the cells having this mutated gene introduced therein. This suggests that a medicament inhibiting the production or secretion of β-amyloid protein is effective for the prevention or treatment of Alzheimer disease.

In the processing of APP, BACE (β-site APP Cleaving Enzyme) (Science, 286, 735 (1999)) or Asp1 (Molecular and Cellular Neuroscience, 16, 609 (2000)), each an aspartic protease, is reported as a β secretase for cleaving the N terminal of β-amyloid protein. It is suggested strongly that presenilin participates in C-terminal cleavage events by γ-secretase (Nature, 398, 513 (1999)). Inhibitors of the secretase have been reported (Journal of Medicinal Chemistry, 44, 2039 (2001)), but most of the inhibitors are peptide compounds.

In WO00/50391, SMITH, et al., disclose compounds having a sulfonamide skeleton and capable of controlling production of β-amyloid protein. In WO01/70677 (GB 026827) BELANGER, et al., disclose compounds having a bicycloalkylsulfonamide skeleton and inhibiting γ-secretase.

An object of the present invention is to provide compounds having a structure different from that of the above-described known compounds, having excellent inhibitory action against production or secretion of β-amyloid protein and having desirable properties as pharmaceuticals.

DISCLOSURE OF THE INVENTION

The present inventors have carried out various investigations. As a result, it has been found that thiomethane, sulfinylmethane or sulfonylmethane compounds represented by the below-described formula (1) have excellent inhibitory action against production or secretion of β-amyloid protein and are therefore useful as a medicament for treatment of various diseases resulting from the abnormal production or secretion of β-amyloid protein, leading to the completion of the present invention.

In the present invention, there is thus provided a compound represented by the following formula (1):

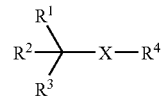

(1)

{wherein:
X represents —S—, —SO— or —SO$_2$—;
R$^1$ represents:
—C(R$^5$)(R$^6$)(R$^7$)
  [in which, R$^5$, R$^6$ and R$^7$ each independently represents a halogen atom, cyano group, nitro group or -Q$^{51}$-Q$^{52}$-Q$^{53}$-Q$^{54}$ [in which, Q$^{51}$ represents a single bond, —CO—, —CS—, —SO—, —SO$_2$—, —CO—CO—, —CO—CS—, —CS—CO— or —CS—CS—,
  Q$^{52}$ represents a single bond, —O—, —O—N(A$^{51}$)-, —O—N(COA$^{51}$)-, —N(A$^{51}$)-, —N(COA$^{51}$)-, —N(COOA$^{51}$)-, —N(CON(A$^{51}$)(A$^{52}$)-, —N(OA$^{51}$)-, —N(NA$^{51}$A$^{52}$)-, —N(A$^{51}$)-N(A$^{52}$)-, —N(COA$^{51}$)-N(A$^{52}$)-, —N(A$^{51}$)-O—, —N(COA$^{51}$)—O—, —S—, —N═N, —C(A$^{51}$)═N—, —C(A$^{51}$)═N—O—, —C(A$^{51}$)═N—N(A$^{52}$)-, —N═C(A$^{51}$)-, —O—N═C(A$^{51}$)-, —(NA$^{51}$)-N═C(A$^{52}$)- or —C(═NA$^{51}$)-N(A$^{52}$)-,
  (in which, A$^{51}$ and A$^{52}$ each independently represents a hydrogen atom, a hydrocarbon group which may have a substituent or a heterocyclic group which may have a substituent),
  Q$^{53}$ represents a single bond, —CO—, —CS—, —SO—, —SO$_2$—, —CO—CO—, —CO—CS—, —CS—CO— or —CS—CS—,
  Q$^{54}$ represents -A$^{53}$, —OA$^{53}$, —N(A$^{53}$)(A$^{54}$), —SA$^{53}$, —NA$^{54}$—OA$^{53}$ —NA$^{55}$-N(A$^{53}$)(A$^{54}$) or —O—N(A$^{53}$)(A$^{54}$)
  (in which, A$^{53}$, A$^{54}$ and A$^{55}$ each independently represents a hydrogen atom, a hydrocarbon group which may have a substituent or a heterocyclic group which may have a substituent)], or
R$^5$ and R$^6$ may be coupled together to form a cyclic hydrocarbon group which may have a substituent or a heterocyclic group which may have a substituent (when the cyclic hydrocarbon group or heterocyclic group formed by coupling of R$^5$ and R$^6$ is unsaturated, R$^7$ may represent the corresponding unsaturated bond)],
—N(R$^8$) (R$^9$)
[in which, R$^8$ and R$^9$ each independently represents -Q$^{81}$-Q$^{82}$-Q$^{83}$-Q$^{84}$
[in which, Q$^{81}$ represents a single bond, —CO—, —CS—, —SO—, —SO$_2$—, —CO—CO—, —CO—CS—, —CS—CO— or —CS—CS—, $Q^{82}$ represents a single bond, —O—, —O—N($A^{81}$)-, —O—N(CO$A^{81}$)-, —N($A^{81}$)-, —N(CO$A^{81}$)-, —N(COO$A^{81}$)-, —N(CON($A^{81}$)($A^{82}$))-, —N(O$A^{81}$)-, —N(N$A^{81}A^{82}$)-, —N($A^{81}$)-N($A^{82}$)-, —N(CO$A^{81}$)-N($A^{82}$)-, —N($A^{81}$)-O—, —N(CO$A^{81}$)-O—, —S—, —N=N—, —C($A^{81}$)=N—, —C($A^{81}$)=N—O—, —C($A^{81}$)=N—N($A^{82}$)-, —N=C($A^{81}$)-, —O—N=C($A^{81}$)-, —(N$A^{81}$)—N=C($A^{82}$)- or —C(=N$A^{81}$)—N($A^{82}$)-, (in which, $A^{81}$ and $A^{82}$ each independently represents a hydrogen atom, a hydrocarbon group which may have a substituent or a heterocyclic group which may have a substituent), $Q^{83}$ represents a single bond, —CO—, —CS—, —SO—, —SO$_2$—, —CO—CO—, —CO—CS—, —CS—CO— or —CS—CS—, $Q^{84}$ represents -$A^{83}$, —O$A^{83}$, —N($A^{83}$)($A^{84}$), —S$A^{83}$, —N$A^{84}$-O$A^{83}$, —N$A^{85}$-N($A^{83}$)($A^{84}$) or —O—N($A^{83}$)($A^{84}$)

(in which, $A^{83}$, $A^{84}$ and $A^{85}$ each independently represents a hydrogen atom, a hydrocarbon group which may have a substituent or a heterocyclic group which may have a substituent)]],

—$X^1R^{10}$

[in which, $X^1$ represents —O— or —S— and $R^{10}$ represents -$Q^{101}$-$Q^{102}$-$Q^{103}$-$Q^{104}$,

[in which, $Q^{101}$ represents a single bond, —CO—, —CS—, —SO—, —SO$_2$—, —CO—CO—, —CO—CS—, —CS—CO— or —CS—CS—, $Q^{102}$ represents a single bond, —O—, —O—N($A^{101}$)-, —O—N(CO$A^{101}$)-, —N($A^{101}$)-, —N(CO$A^{101}$)-, —N(COO$A^{101}$)-, —N(CON($A^{101}$)($A^{102}$))-, —N(O$A^{101}$)-, —N(N$A^{101}A^{102}$)-, —N($A^{101}$)-N($A^{102}$)-, —N(CO$A^{101}$)—N($A^{102}$)-, —N($A^{101}$)-O—, —N(CO$A^{101}$)-O—, —S—, —N=N—, —C($A^{101}$)=N—, —C($A^{101}$)=N—O—, —C($A^{101}$)=N—N($A^{102}$)-, —N=C($A^{101}$)-, —O—N=C($A^{101}$)-, —(N$A^{101}$)-N=C($A^{102}$)- or —C(=N$A^{101}$)-N($A^{102}$)-, (in which, $A^{101}$ and $A^{102}$ each independently represents a hydrogen atom, a hydrocarbon group which may have a substituent or a heterocyclic group which may have a substituent), $Q^{103}$ represents a single bond, —CO—, —CS—, —SO—, —SO$_2$—, —CO—CO—, —CO—CS—, —CS—CO— or —CS—CS—, $Q^{104}$ represents -$A^{103}$, —O$A^{103}$, —N($A^{103}$)($A^{104}$), —S$A^{103}$, —N$A^{104}$-O$A^{103}$, —N$A^{105}$-N($A^{103}$)($A^{104}$) or —O—N($A^{103}$)($A^{104}$)

(in which, $A^{103}$, $A^{104}$ and $A^{105}$ each independently represents a hydrogen atom, a hydrocarbon group which may have a substituent or a heterocyclic group which may have a substituent)]], or

—$X^2R^{11}$

[in which, $X^2$ represents —SO— or —SO$_2$— and $R^{11}$ represents -$Q^{111}$-$Q^{112}$-$Q^{113}$-$Q^{114}$,

[in which, $Q^{111}$ represents a single bond, —CO—, —CS—, —SO—, —SO$_2$—, —CO—CO—, —CO—CS—, —CS—CO— or —CS—CS—, $Q^{112}$ represents a single bond, —O—, —O—N($A^{111}$)-, —O—N(CO$A^{111}$)-, —N($A^{111}$)-, —N(CO$A^{111}$)-, —N(COO$A^{111}$)-, —N(CON($A^{111}$)($A^{112}$))-, —N(O$A^{111}$)-, —N(N$A^{111}A^{112}$)-, —N($A^{111}$)-N($A^{112}$)-, —N(CO$A^{111}$)-N($A^{112}$)-, —N($A^{111}$)-O—, —N(CO$A^{111}$)-O—, —S—, —N=N—, —C($A^{111}$)=N—, —C($A^{111}$)=N—O—, —C($A^{111}$)=N—N($A^{112}$)-, —N=C($A^{111}$)-, —O—N=C($A^{111}$)-, —(N$A^{111}$)-N=C($A^{112}$)- or —C(=N$A^{111}$)-N($A^{112}$)-, (in which, $A^{111}$ and $A^{112}$ each independently represents a hydrogen atom, a hydrocarbon group which may have a substituent or a heterocyclic group which may have a substituent), $Q^{113}$ represents a single bond, —CO—, —CS—, —SO—, —SO$_2$—, —CO—CO—, —CO—CS—, —CS—CO— or —CS—CS—, $Q^{114}$ represents -$A^{113}$, —O$A^{113}$, —N($A^{113}$)($A^{114}$), —S$A^{113}$, —N$A^{114}$-O$A^{113}$, —N$A^{115}$-N($A^{113}$)($A^{114}$) or —O—N($A^{113}$)($A^{114}$)

(in which, $A^{113}$, $A^{114}$ and $A^{115}$ each independently represents a hydrogen atom, a hydrocarbon group which may have a substituent or a heterocyclic group which may have a substituent)]];

$R^2$ represents -$Q^{21}$-$Q^{22}$-$Q^{23}$-$Q^{24}$

[in which, $Q^{21}$ represents a single bond, —CO—, —CS—, —SO—, —SO$_2$—, —CO—CO—, —CO—CS—, —CS—CO— or —CS—CS—, $Q^{22}$ represents a single bond, —O—, —O—N($A^{21}$)-, —O—N(CO$A^{21}$)-, —N($A^{21}$)-, —N(CO$A^{21}$)-, —N(COO$A^{21}$)-, —N(CON($A^{21}$)($A^{22}$))-, —N(O$A^{21}$)-, —N(N$A^{21}A^{22}$)-, —N($A^{21}$)-N($A^{22}$)-, —N(CO$A^{21}$)—N($A^{22}$)-, —N($A^{21}$)-O—, —N(CO$A^{21}$)-O—, —S—, —N=N—, —C($A^{21}$)=N—, —C($A^{21}$)=N—O—, —C($A^{21}$)=N—N($A^{22}$)-, —N=C($A^{21}$)-, —O—N=C($A^{21}$)-, —(N$A^{21}$)-N=C($A^{22}$)- or —C(=N$A^{21}$)—N($A^{22}$)-, (in which, $A^{21}$ and $A^{22}$ each independently represents a hydrogen atom, a hydrocarbon group which may have a substituent or a heterocyclic group which may have a substituent), $Q^{23}$ represents a single bond, —CO—, —CS—, —SO—, —SO$_2$—, —CO—CO—, —CO—CS—, —CS—CO— or —CS—CS—, $Q^{24}$ represents -$A^{23}$, —O$A^{23}$, —N($A^{23}$)($A^{24}$), —S$A^{23}$, —N$A^{24}$-O$A^{23}$, —N$A^{25}$-N($A^{23}$)($A^{24}$) or —N$A^{25}$-N($A^{23}$)($A^{24}$)

(in which, $A^{23}$, $A^{24}$ and $A^{25}$ each independently represents a hydrogen atom, a hydrocarbon group which may have a substituent or a heterocyclic group which may have a substituent)]; or $R^1$ and $R^2$ may be coupled together to form a cyclic hydrocarbon group which may have a substituent or a heterocyclic group which may have a substituent, or may be coupled together to form =C$R^{12}R^{13}$

[in which, $R^{12}$ and $R^{13}$ each independently represents a halogen atom, cyano group, nitro group or -$Q^{121}$-$Q^{122}$-$Q^{123}$-$Q^{124}$,

[in which, $Q^{121}$ represents a single bond, —CO—, —CS—, —SO—, —SO$_2$—, —CO—CO—, —CO—CS—, —CS—CO— or —CS—CS—, $Q^{122}$ represents a single bond, —O—, —O—N($A^{121}$)-, —O—N(CO$A^{121}$)-, —N($A^{121}$), —N(CO$A^{121}$)-, —N(COO$A^{121}$)-, —N(CON($A^{121}$)($A^{122}$))-, —N(O$A^{121}$)-, —N(N$A^{121}A^{122}$)-, —N($A^{121}$)-N($A^{122}$)-, —N(CO$A^{121}$)-N($A^{122}$)-, —N($A^{121}$)-O—, —N(CO$A^{121}$)-O—, —S—, —N=N—, —C($A^{121}$)=N—, —C($A^{121}$)=N—O—, —C($A^{121}$)=N—N($A^{122}$)-, —N=C($A^{121}$)-, —O—N=C($A^{121}$)-, —(N$A^{121}$)-N=C($A^{122}$)- or —C(=N$A^{121}$)-N($A^{122}$)-, (in which, $A^{121}$ and $A^{122}$ each independently represents a hydrogen atom, a hydrocarbon group which may have a substituent or a heterocyclic group which may have a substituent), $Q^{123}$ represents a single bond, —CO—, —CS—, —SO—, —SO$_2$—, —CO—CO—, —CO—CS—, —CS—CO— or —CS—CS—, $Q^{124}$ represents -$A^{123}$, —$OA^{123}$, —$N(A^{123})(A^{124})$, —$SA^{123}$, —$NA^{124}$-$OA^{123}$, —$NA^{125}$—$N(A^{123})(A^{124})$ or —O—$N(A^{123})(A^{124})$ (in which, $A^{123}$, $A^{124}$ and $A^{125}$ each independently represents a hydrogen atom, a hydrocarbon group which may have a substituent or a heterocyclic group which may have a substituent)]];

$R^3$ represents -$Q^{31}$-$Q^{32}$-$Q^{33}$-$Q^{34}$,

[in which, $Q^{31}$ represents a single bond, —CO—, —CS—, —SO—, —$SO_2$—, —CO—CO—, —CO—CS—, —CS—CO— or —CS—CS—, $Q^{32}$ represents a single bond, —O—, —O—$N(A^{31})$-, —O—$N(COA^{31})$-, —$N(A^{31})$-, —$N(COA^{31})$-, —$N(COOA^3)$-, —$N(CON(A^{31})(A^{32}))$-, —$N(OA^{31})$-, —$N(NA^{31}A^{32})$-, —$N(A^{31})$—$N(A^{32})$-, —$N(COA^{31})$—$N(A^{32})$-, —$N(A^{31})$-O—, —$N(COA^{31})$-O—, —S—, —N=N—, —$C(A^{31})$=N—, —$C(A^{31})$=N—O—, —$C(A^{31})$=N—$N(A^{32})$-, —N=$C(A^{31})$-, —O—N=$C(A^{31})$-, —$(NA^{31})$—N=$C(A^{32})$- or —C(=$NA^{31}$)—$N(A^{32})$-, (in which, $A^{31}$ and $A^{32}$ each independently represents a hydrogen atom, a hydrocarbon group which may have a substituent or a heterocyclic group which may have a substituent), $Q^{33}$ represents a single bond, —CO—, —CS—, —SO—, —$SO_2$—, —CO—CO—, —CO—CS—, —CS—CO— or —CS—CS—, $Q^{34}$ represents -$A^{33}$, —$OA^{33}$, —$N(A^{33})(A^{34})$, —$SA^{33}$, —$NA^{34}$-$OA^{33}$, —$NA^{35}$—$N(A^{33})(A^{34})$ or —O—$N(A^{33})(A^{34})$ (in which, $A^{33}$, $A^{34}$ and $A^{35}$ each independently represents a hydrogen atom, a hydrocarbon group which may have a substituent or a heterocyclic group which may have a substituent)];

$R^4$ represents -$Q^{41}$-$Q^{42}$-$Q^{43}$-$Q^{44}$,

[in which, $Q^{41}$ represents a single bond, —CO—, —CS—, —SO—, —$SO_2$—, —CO—CO—, —CO—CS—, —CS—CO— or —CS—CS—, $Q^{42}$ represents a single bond, —O—, —O—$N(A^{41})$-, —O—$N(COA^{41})$-, —$N(A^{41})$-, —$N(COA^{41})$-, —$N(COOA^{41})$-, —$N(CON(A^{41})(A^{42}))$-, —$N(OA^{41})$-, —$N(NA^{41}A^{42})$-, —$N(A^{41})$—$N(A^{42})$-, —$N(COA^{41})$—$N(A^{42})$-, —$N(A^{41})$-O—, —$N(COA^{41})$-O—, —S—, —N=N—, —$C(A^{41})$=N—, —$C(A^{41})$=N—O—, —$C(A^{41})$=N—$N(A^{42})$-, —N=$C(A^{41})$, —O—N=$C(A^{41})$-, —$(NA^{41})$—N=$C(A^{42})$- or —C(=$NA^{41}$)—$N(A^{42})$-, (in which, $A^{41}$ and $A^{42}$ each independently represents a hydrogen atom, a hydrocarbon group which may have a substituent or a heterocyclic group which may have a substituent), $Q^{43}$ represents a single bond, —CO—, —CS—, —SO—, —$SO_2$—, —CO—CO—, —CO—CS—, —CS—CO— or —CS—CS—, $Q^{44}$ represents -$A^{43}$, —$OA^{43}$, —$N(A^{43})(A^{44})$, —$SA^{43}$, —$NA^{44}$-$OA^{43}$, —$NA^{45}$—$N(A^{43})(A^{44})$ or —O—$N(A^{43})(A^{44})$ (in which, $A^{43}$, $A^{44}$ and $A^{45}$ each independently represents a hydrogen atom, a hydrocarbon group which may have a substituent or a heterocyclic group which may have a substituent)]; or $R^3$ and $R^4$ may be coupled together to form a cyclic hydrocarbon group which may have a substituent or a heterocyclic group which may have a substituent}, N-oxide or S-oxide of the compound, salt thereof, or solvate of the above-described compound.

In the present invention, there is also provided a medicament containing, as an effective ingredient, the compound represented by the formula (1), N-oxide or S-oxide thereof, or salt thereof, or solvate of thereof.

In the present invention, there is also provided a pharmaceutical composition containing the compound represented by the formula (1), N-oxide or S-oxide thereof, or salt thereof, or solvate of thereof; and a pharmaceutically acceptable carrier.

In the present invention, there is also provided use of the compound represented by the formula (1), N-oxide or S-oxide thereof, or salt thereof, or solvate of thereof for the preparation of a medicament.

In the present invention, there is also provided a method of treating a disease resulting from abnormal production or secretion of β-amyloid protein, which comprises administering an effective amount of the compound represented by the formula (1), N-oxide or S-oxide thereof, or salt thereof, or solvate of thereof.

BEST MODE FOR CARRYING OUT THE INVENTION

A description will next be made of the compound represented by the formula (1).

The term "hydrocarbon group" as used herein means a group composed only of carbon and hydrogen atoms. The group may be any one of linear, branched and cyclic, or a combination of any two or three of them and it may be either one of saturated and unsaturated groups.

Typical examples of the linear or branched hydrocarbon group include alkyl, alkenyl and alkynyl groups, and combinations thereof. These linear or branched hydrocarbon groups embrace those having a plurality of double bonds or triple bonds, or those having both a double bond and triple bond.

As the alkyl group, linear or branched alkyl groups having from 1 to 18 carbon atoms, especially linear or branched alkyl groups having from 1 to 12 carbon atoms are preferred. Specific examples of such an alkyl group include methyl, ethyl, n-propyl, isopropyl, n-butyl, isobutyl, sec-butyl, tert-butyl, n-pentyl, 2-methylpentyl, 2-ethylpentyl, n-hexyl, n-heptyl, n-octyl, n-nonyl, n-decyl, n-undecyl and n-decyl groups.

As the alkenyl group, linear or branched alkenyl groups having from 2 to 18 carbon atoms, especially linear or branched alkenyl groups having from 2 to 12 carbon atoms are preferred. Specific examples of such an alkenyl group include vinyl, allyl, propenyl, butenyl and pentenyl groups.

As the alkynyl group, linear or branched alkynyl groups having from 2 to 18 carbon atoms, especially linear or branched alkynyl groups having from 2 to 12 carbon atoms are preferred. Specific examples of such an alkynyl group include ethynyl, 2-butynyl and 3-pentynyl groups.

Typical cyclic hydrocarbon groups include cycloalkyl, cycloalkenyl, cycloalkynyl, aryl, spiro-hydrocarbon, crosslinked cyclic hydrocarbon, and condensed polycyclic hydrocarbon groups. A combination thereof is also usable. The cyclic hydrocarbons groups embrace those having a plurality of double bonds or triple bonds and those having both a double bond and a triple bond.

Examples of the cycloalkyl group include cycloalkyl groups having from 3 to 7 carbon atoms such as cyclopropyl, cyclobutyl, cyclopentyl, cyclohexyl and cycloheptyl.

Examples of the cycloalkenyl group include cycloalkenyl groups having from 4 to 7 carbon atoms such as cyclopentenyl and cyclohexenyl. Examples of the cycloalkynyl group include cycloalkynyl groups having from 4 to 7 carbon atoms.

Examples of the aryl group include monocyclic or polycyclic aromatic hydrocarbon groups having from 6 to 14 carbon atoms. Specific examples include phenyl, indenyl, naphthyl, anthracenyl and biphenyl.

Examples of the spiro-hydrocarbon group include spiro-hydrocarbon groups having from 7 to 11 carbon atoms such as spiro[3.4]octanyl and spiro[4.5]deca-1,6-dienyl groups.

Examples of the crosslinked cyclic hydrocarbon group include crosslinked cyclic hydrocarbon groups having from 7 to 10 carbon atoms such as bicyclo[2.2.1]heptanyl, adamantyl, bicyclo[3.2.1]octanyl, bicyclo[2.2.1]hept-2-enyl, tricyclo[2.2.1.0$^{2.6}$]heptanyl and bicyclo[4.3.1]decanyl groups.

Examples of the condensed polycyclic hydrocarbon group include condensed polycyclic hydrocarbon groups having from 8 to 14 carbon atoms such as indanyl, tetrahydronaphthalenyl, hexahydroindanyl and octahydronaphthalenyl groups.

The term "heterocyclic group" as used herein means a cyclic group having one or more hetero atoms (N, O, S, etc.) as a component of its cyclic structure and it may be any one of a saturated ring, an unsaturated ring or aromatic ring, or may be either one of a monocylic or polycyclic group. It also embraces a group introduced from a heterocyclic spiro compound or a heterocyclic compound having a crosslinked cyclic structure.

Examples of the saturated monocyclic heterocyclic group include from 3- to 7-membered groups each having from 1 to 4 atoms selected from nitrogen, oxygen and sulfur atoms. Specific examples include pyrrolidinyl, tetrahydrofuranyl, oxetanyl, tetrahydrothienyl, piperidinyl, piperazinyl, morpholinyl, thiomorpholinyl, oxiranyl, thioranyl, dioxanyl, aziridinyl, imidazolidinyl, pyrazolidinyl, tetrahydropyranyl, tetrahydrothiopyranyl, tetrahydroxazolyl, tetrahydrothiazolyl, tetrahydroisoxazolyl, tetrahydroisothiazolyl, dioxolanyl and oxathioranyl groups.

Examples of the unsaturated monocyclic heterocyclic group include from 4- to 7-membered groups having 1 to 4 atoms selected from nitrogen, oxygen and sulfur atoms. Specific examples include pyrrolyl, furyl, thienyl, pyrazolyl, imidazolyl, triazolyl, oxazolyl, thiazolyl, isoxazolyl, isothiazolyl, dihydrooxazolyl, dihydrothiazolyl, dihydroisoxazolyl, dihydroisothiazolyl, pyridyl, pyrimidinyl, triazinyl, tetrazolyl, pyrrolinyl, imidazolinyl, pyrazolinyl, thiadiazolyl, oxadiazolyl, dihydroxazolyl, dihydrothiazolyl, dihydroisoxazolyl, dihydroisothiazolyl, pyrazinyl, pyridazinyl, pyranyl, dihydropyridinyl, dihydropyrrolyl, dihydroquinolyl, dihydroimidazolyl, dihydropyrazolyl, dihydropyrazinyl and dihydropyridazinyl groups.

Examples of the polycyclic heterocyclic group include from 7- to 14-membered groups having 1 to 4 atoms selected from nitrogen, oxygen and sulfur atoms. Specific examples include benzofuranyl, benzothiazolyl, indolyl, quinolyl, isoquinolyl, benzopyranyl, benzoxazolyl, benzothiazolyl, benzimidazolyl, benzodioxanyl, benzothiophenyl, benzisothiazolyl, benzisoxazolyl, chromenyl, chromanyl, isochromenyl, isochromanyl, indolinyl, indazolyl, indolizinyl, isoindolyl, isoindolinyl, quinolizinyl, quinoxalinyl, quinazolyl, cinnolinyl, phthalazinyl, naphthyridinyl, purinyl, carbazolyl, xanthenyl, acridinyl, phenazinyl, phenoxazinyl, phenothiazinyl and quinuclidinyl groups.

Examples of the combination of cycloalkyl and alkyl groups include cycloalkyl-alkyl groups, with ($C_{3-7}$ cycloalkyl)-($C_{1-12}$ alkyl) groups being especially preferred.

As the combination of aryl and alkyl groups, ($C_{6-10}$ aryl)-($C_{1-12}$ alkyl) groups are preferred.

Examples of the substituent for these hydrocarbon groups and heterocyclic groups include -$Q^{201}$-$Q^{202}$-$Q^{203}$-$Q^{204}$-$Q^{205}$-$Q^{206}$-$Q^{207}$, in which $Q^{201}$ represents a single bond, an alkyl group having from 1 to 6 carbon atoms, an alkenyl group having from 2 to 6 carbon atoms or heterocyclic group; $Q^{202}$ represents a single bond, —O—, —NH—, —CH=N—, —C(alkyl)=N—, —N(alkyl)- or —S—; $Q^{203}$ represents a single bond, —CO—, —CS—, —SO—, —SO$_2$— or —CONH—; $Q^{204}$ represents a single bond, an alkyl group from 1 to 6 carbon atoms, an alkenyl group having from 2 to 6 carbon atoms, a cycloalkyl group, a cycloalkenyl group, an aromatic hydrocarbon group or a heterocyclic group; $Q^{205}$ represents a single bond, —O—, —NH— or —N(alkyl)-; $Q^{206}$ represents a single bond, —CO—, —CS—, —SO$_2$—, —SO— or —S—; and $Q^{207}$ represents a hydrogen atom, a halogen atom, a hydroxy group, an oxo group, a $C_{1-6}$ alkyl group, a $C_{2-6}$ alkenyl group, a $C_{3-8}$ cycloalkyl group, a $C_{1-6}$ alkoxy group, a $C_{2-6}$ alkenyloxy group, an azide group, a cyano group, an amino group, a $C_{1-6}$ alkylamino group, a di($C_{1-6}$ alkyl)amino group, a $C_{2-6}$ alkanoylamino group, di($C_{2-6}$ alkanoyl)amino group, a carboxyamino group, a $C_{1-6}$ alkoxycarbonylamino group, a di($C_{1-6}$ alkoxy)carbonylamino group, a heterocyclic group, an aromatic hydrocarbon group, a cycloalkenyl group, a heterocyclic oxy group, or an aromatic hydrocarbon-oxy group. The alkyl group having from 1 to 6 carbon atoms, alkenyl group having from 2 to 6 carbon atoms, cycloalkyl group, cycloalkenyl group, heterocyclic group, heterocyclic-oxy group, aromatic hydrocarbon group or aromatic hydrocarbon-oxy group may be substituted with 1 to 3 substituents selected from halogen atoms, $C_{1-6}$ alkyl groups, $C_{1-6}$ alkoxy groups, $C_{2-6}$ alkenyl groups, carboxyamino($C_{1-6}$ alkyl) groups, ($C_{1-6}$ alkoxy)carbonylamino ($C_{1-6}$ alkyl) groups, formyl group, $C_{2-6}$ alkanoyl groups, oxo group, nitro group, cyano group, azide group, amidino group, $C_{2-6}$ alkenyloxy groups, hydroxy group, carboxyl group, $C_{7-16}$ aralkyl groups, thioxo group, $C_{2-7}$ alkanoyl groups, $C_{2-7}$ thioalkanoyl groups, thioformyl group, amino group, $C_{1-6}$ alkylamino groups, di($C_{1-6}$ alkyl)amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, $C_{1-6}$ alkoxycarbamoylamino groups, $C_{1-6}$ alkoxycarbamoyl($C_{1-6}$ alkyl)amino groups, $C_{2-7}$ alkanoylamino groups, ($C_{2-7}$ alkanoyl)($C_{1-6}$ alkyl)amino groups, thio ($C_{2-7}$ alkanoyl)amino groups, thio($C_{2-7}$ alkanoyl)($C_{1-6}$ alkyl) amino groups, formylamino group, formyl($C_{1-6}$ alkyl)amino groups, thioformylamino group, thioformyl($C_{1-6}$ alkyl) amino groups, $C_{2-7}$ alkanoyloxy groups, formyloxy group, $C_{1-6}$ alkoxycarbonyloxy groups, carbamoyloxy group, $C_{1-6}$ alkylcarbamoyloxy groups, di($C_{1-6}$ alkyl)carbamoyloxy groups, aminocarbonylamino group, ($C_{1-6}$ alkyl)aminocarbonylamino groups, di($C_{1-6}$ alkyl)aminocarbonylamino groups, aminocarbonyl($C_{1-6}$ alkyl)amino groups, ($C_{1-6}$ alkyl) aminocarbonyl($C_{1-6}$ alkyl)amino groups, di($C_{1-6}$ alkyl)aminocarbonyl($C_{1-6}$ alkyl)amino groups, mercapto group, $C_{1-6}$ alkylthio groups, $C_{1-6}$ alkylsulfinyl groups, $C_{1-6}$ alkylsulfonyl groups, aminosulfonyl group, $C_{1-6}$ alkylaminosulfonyl groups, di($C_{1-6}$ alkyl)aminosulfonyl groups, $C_{1-6}$ alkylsulfonylamino groups, ($C_{1-6}$ alkylsulfonyl($C_{1-6}$ alkyl)amino groups, aminosulfonylamino group, $C_{1-6}$ alkylaminosulfonylamino groups, di($C_{1-6}$ alkyl)aminosulfonylamino groups, aminosulfonyl($C_{1-6}$ alkyl)amino groups, $C_{1-6}$ alkylaminosulfonyl($C_{1-6}$ alkyl)amino groups, and di($C_{1-6}$ alkyl)aminosulfonyl($C_{1-6}$ alkyl)amino groups.

Examples of the aromatic hydrocarbon groups include $C_{6-14}$ aromatic hydrocarbon groups, for example, phenyl, naphthyl, indenyl, anthracenyl and biphenyl groups. Of these, phenyl and naphthyl groups are especially preferred. The heterocyclic groups include the above-described saturated or unsaturated, monocyclic or polycyclic heterocyclic groups, for example, pyrrolidinyl, tetrahydrofuranyl, oxetanyl, tetrahydrothienyl, piperidinyl, piperazinyl, morpholinyl, thiomorpholinyl, oxiranyl, thiolanyl, dioxanyl, pyrrolyl, aziridinyl, imidazolidinyl, pyrazolidinyl, tetrahydropyranyl, tetrahydrothiopyranyl, tetrahydrooxazolyl, tetrahydrothiazolyl, tetrahydroisoxazolyl, tetrahydroisothiazolyl, dioxolanyl, oxathiolanyl, furyl, thienyl, pyrazolyl, imidazolyl, triazolyl, oxazolyl, thiazolyl, isoxazolyl, isothiazolyl, dihydroxazolyl, dihydrothiazolyl, dihydroisoxazolyl, dihydroisothiazolyl, pyridyl, pyrimidinyl, triazinyl, tetrazolyl, pyrrolinyl, imidazolinyl, pyrazolinyl, thiadiazolyl, oxadiazolyl, dihydrooxazolyl, dihydrothiazolyl, dihydroisoxazolyl, dihydroisothiazolyl, pyrazinyl, pyridazinyl, pyranyl, dihydropyridinyl, dihydropyrrolyl, dihydroquinolyl, dihydroimidazolyl, dihydropyrazolyl, dihydropyrazinyl, dihydropyridazinyl, benzofuranyl, benzothiazolyl, indolyl, quinolyl, isoquinolyl, benzopyranyl, benzoxazolyl, benzothiazolyl, benzimidazolyl, benzodioxanyl, benzothiophenyl, benzisothiazolyl, benzisoxazolyl, chromenyl, chromanyl, isochromenyl, isochromanyl, indolinyl, indazolyl, indolizinyl, isoindolyl, isoindolinyl, quinolizinyl, quinoxalinyl, quinazolinyl, cinnolinyl, phthalazinyl, naphthyridinyl, purinyl, carbazolyl, xanthenyl, acridinyl, phenazinyl, phenoxazinyl, phenothiazinyl and quinuclidinyl groups. Of these pyrrolidinyl, tetrahydrofuranyl, oxetanyl, tetrahydrothienyl, piperidinyl, dihydrooxazolyl, dihydrothiazolyl, dihydroisoxazolyl, dihydroisothiazolyl, piperazinyl, morpholinyl, thiomorpholinyl, oxiranyl, dioxanyl, pyrrolyl, furyl, thienyl, pyrazolyl, imidazolyl, triazolyl, oxazolyl, thiazolyl, isoxazolyl, isothiazolyl, pyridyl, pyrimidinyl, triazinyl, tetrazolyl, benzofuranyl, benzothiophenyl, indolyl, quinolyl, isoquinolyl, benzopyranyl, benzoxazolyl, benzothiazolyl, benzimidazolyl, benzodioxanyl, dioxolanyl, tetrahydropyranyl, tetrahydrothiopyranyl, oxadiazolyl, thiadiazolyl, pyrazinyl, pyridazinyl, dihydropyridinyl, dihydropyrrolyl, dihydroquinolyl, dihydroimidazolyl, dihydropyrazolyl, dihydropyrazinyl, dihydropyridazinyl, tetrahydrooxazolyl, chromenyl, chromanyl, isochromenyl, and isochromanyl groups are preferred, with pyrrolidinyl, piperidinyl, piperazinyl, morpholinyl, thiomorpholinyl, dioxolanyl, pyridyl, furyl and thienyl groups being especially preferred.

In the formula (1), X represents any one of —S—, —SO— and —SO$_2$—. Of these, —SO— are —SO$_2$— are preferred, with —SO$_2$— being especially preferred.

In the formula (1), $R^1$ represents any one of —C($R^5$)($R^6$)($R^7$), —N($R^8$)($R^9$), -$X^1R^{10}$, and —$X^2R^{11}$. Of these, $R^1$ representing —C($R^5$)($R^6$)($R^7$) is preferred. Especially, $R^1$ representing —C($R^5$)($R^6$)($R^7$) in which $R^5$, and $R^6$ may be coupled together to form a cyclic hydrocarbon group which may have a substituent or a heterocyclic group which may have a substituent is preferred.

In the formula (1), $R^2$ represents -$Q^{21}$-$Q^{22}$-$Q^{23}$-$Q^{24}$, with $R^2$ representing -$Q^{21}$-$Q^{22}$-$Q^{23}$-$Q^{24}$ in which $Q^{21}$, $Q^{22}$, and $Q^{23}$ each represents a single bond and $Q^{24}$ represents $A^{23}$ in which $A^{23}$ represents a hydrogen atom or an alkyl group being preferred.

Or, $R^1$ and $R^2$ may be coupled together to form a cyclic hydrocarbon group which may have a substituent, a heterocyclic group which may have a substituent, or =C($R^{12}$)($R^{13}$).

In the formula (1), $R^3$ represents -$Q^{31}$-$Q^{32}$-$Q^{33}$-$Q^{34}$, with $R^3$ representing -$A^{33}$, —CO-$A^{33}$ or —COO$A^{33}$ in which $A^{33}$ represents a hydrogen atom, a hydrocarbon group which may have a substituent or a heterocyclic group which may have a substituent being preferred.

$R^4$ represents $Q^{41}$-$Q^{42}$-$Q^{43}$-$Q^{44}$-, with $R^4$ representing -$A^{43}$ in which $A^{43}$ represents a cyclic hydrocarbon group which may have a substituent or a heterocyclic group which may have a substituent being preferred.

In the present invention, compounds of the formula (1) in which $R^1$ represents a heterocyclic group which may have a substituent, $R^2$ represents a hydrogen atom or a $C_{1-6}$ alkyl group, $R^3$ represents a cyclic hydrocarbon group which may have a substituent or a heterocyclic group which may have a substituent, and $R^4$ represents a cyclic hydrocarbon group which may have a substituent or a heterocyclic group which may have a substituent are especially preferred. These compounds are represented by the following formula (3):

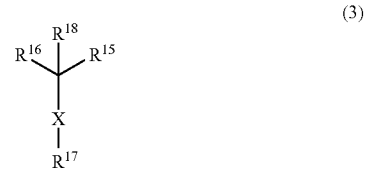

(3)

(wherein, $R^{15}$ represents a heterocyclic group which may have a substituent, $R^{16}$ represents a cyclic hydrocarbon group which may have a substituent or a heterocyclic group which may have a substituent, $R^{17}$ represents a cyclic hydrocarbon group which may have a substituent or a heterocyclic group which may have a substituent, $R^{18}$ represents a hydrogen atom or a $C_{1-6}$ alkyl group and X represents —S—, —SO— or —SO$_2$—).

As the heterocyclic group represented by $R^{15}$, $R^{16}$ or $R^{17}$, the above-described heterocyclic groups can be given as examples. As the cyclic hydrocarbon group represented by $R^{16}$ or $R^{17}$, the above-described cyclic hydrocarbon groups can be given as examples. As the substituents on these groups, the above-described ones can be given as examples. As X, —SO— or —SO$_2$— is preferred, with —SO$_2$— being especially preferred.

As the heterocyclic group represented by $R^{15}$, $R^{16}$ or $R^{17}$, from 3- to 7-membered saturated or from 4- to 7-membered unsaturated monocylic heterocyclic groups having from 1 to 4 atoms selected from nitrogen atom, oxygen atom and sulfur atom, and from 7- to 14-membered polycyclic heterocyclic groups having from 1 to 4 atoms selected from nitrogen atom, oxygen atom and sulfur atom are preferred.

As the cyclic hydrocarbon group represented by $R^{16}$ or $R^{17}$, cycloalkyl groups having from 3 to 7 carbon atoms, cycloalkenyl groups having from 4 to 7 carbon atoms, monocylic or polycyclic aromatic hydrocarbon groups having from 6 to 14 carbon atoms, spirohydrocarbon groups having from 7 to 11 carbon atoms, crosslinked cyclic hydrocarbon groups having from 7 to 10 carbon atoms and condensed polycyclic hydrocarbon groups having from 8 to 14 carbon atoms are preferred.

As the substituent for the cyclic hydrocarbon group or heterocyclic group of $R^{15}$, $R^{16}$ or $R^{17}$, groups represented by the above-described -$Q^{201}$-$Q^{202}$-$Q^{203}$-$Q^{204}$-$Q^{205}$-$Q^{206}$-$Q^{207}$ can be given as examples.

As the cyclic hydrocarbon group represented by $R^{16}$ or $R^{17}$, monocylic or polycyclic aromatic hydrocarbon groups having from 6 to 14 carbon atoms are preferred, with phenyl, naphthyl, indenyl and anthracenyl groups being more preferred, and a phenyl group being especially preferred. These hydrocarbon groups may have 1 to 3 substituents selected from halogen atoms, $C_{1-6}$ alkyl groups, $C_{1-6}$ alkoxy groups, $C_{2-6}$ alkenyl groups, formyl group, $C_{2-6}$ alkanoyl groups, carboxyl group, carboxyamino $C_{1-6}$ alkyl groups, $C_{1-6}$ alkoxycarbonylamino $C_{1-6}$ alkyl groups, oxo group, nitro group, cyano group, amidino group, $C_{2-7}$ alkenyloxy groups, hydroxy group, thioxo group, amino group, $C_{1-6}$ alkylamino groups, di($C_{1-6}$ alkyl)amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, mercapto group, $C_{1-6}$ alkylthio groups, $C_{1-6}$ alkylsulfinyl groups and $C_{1-6}$ alkylsulfonyl groups.

Examples of the heterocyclic group represented by $R^{16}$ or $R^{17}$ include pyrrolidinyl, tetrahydrofuranyl, oxetanyl, tetrahydrothienyl, piperidinyl, piperazinyl, morpholinyl, thiomorpholinyl, oxiranyl, thiolanyl, dioxanyl, pyrrolyl, aziridinyl, imidazolidinyl, pyrazolidinyl, tetrahydropyranyl, tetrahydrothiopyranyl, tetrahydrooxazolyl, tetrahydrothiazolyl, tetrahydroisoxazolyl, tetrahydroisothiazolyl, dioxolanyl, oxathiolanyl, furyl, thienyl, pyrazolyl, imidazolyl, triazolyl, oxazolyl, thiazolyl, isoxazolyl, isothiazolyl, dihydroxazolyl, dihydrothiazolyl, dihydroisoxazolyl, dihydroisothiazolyl, pyridyl, pyrimidinyl, triazinyl, tetrazolyl, pyrrolinyl, imidazolinyl, pyrazolinyl, thiadiazolyl, oxadiazolyl, dihydrooxazolyl, dihydrothiazolyl, dihydroisoxazolyl, dihydroisothiazolyl, pyrazinyl, pyridazinyl, pyranyl, dihydropyridinyl, dihydropyrrolyl, dihydroquinolyl, dihydroimidazolyl, dihydropyrazolyl, dihydropyrazinyl, dihydropyridazinyl, benzofuranyl, benzothiazolyl, indolyl, quinolyl, isoquinolyl, benzopyranyl, benzoxazolyl, benzothiazolyl, benzimidazolyl, benzodioxanyl, benzothiophenyl, benzisothiazolyl, benzisoxazolyl, chromenyl, chromanyl, isochromenyl, isochromanyl, indolinyl, indazolyl, indolizinyl, isoindolyl, isoindolinyl, quinolizinyl, quinoxalinyl, quinazolinyl, cinnolinyl, phthalazinyl, naphthyridinyl, purinyl, carbazolyl, xanthenyl, acridinyl, phenazinyl, phenoxazinyl, phenothiazinyl and quinuclidinyl groups. Of these pyrrolidinyl, tetrahydrofuranyl, oxetanyl, tetrahydrothienyl, piperidinyl, dihydrooxazolyl, dihydrothiazolyl, dihydroisoxazolyl, dihydroisothiazolyl, piperazinyl, morpholinyl, thiomorpholinyl, oxiranyl, dioxanyl, pyrrolyl, furyl, thienyl, pyrazolyl, imidazolyl, triazolyl, oxazolyl, thiazolyl, isoxazolyl, isothiazolyl, pyridyl, pyrimidinyl, triazinyl, tetrazolyl, benzofuranyl, benzothiophenyl, indolyl, quinolyl, isoquinolyl, benzopyranyl, benzoxazolyl, benzothiazolyl, benzimidazolyl, benzodioxanyl, dioxolanyl, tetrahydropyranyl, tetrahydrothiopyranyl, oxadiazolyl, thiadiazolyl, pyrazinyl, pyridazinyl, dihydropyridinyl, dihydropyrrolyl, dihydroquinolyl, dihydroimidazolyl, dihydropyrazolyl, dihydropyrazinyl, dihydropyridazinyl, tetrahydrooxazolyl, chromenyl, chromanyl, isochromenyl, and isochromanyl groups are preferred, with tetrahydropyranyl, piperidinyl, pyridyl and pyrimidinyl groups being especially preferred. These heterocyclic groups may have 1 to 3 substituents selected from halogen atoms, $C_{1-6}$ alkyl groups, $C_{1-6}$ alkoxy groups, $C_{2-6}$ alkenyl groups, formyl group, $C_{2-6}$ alkanoyl groups, carboxyl group, carboxyamino $C_{1-6}$ alkyl groups, $C_{1-6}$ alkoxycarbonylamino $C_{1-6}$ alkyl groups, oxo group, nitro group, cyano group, amidino group, $C_{2-7}$ alkenyloxy groups, hydroxy group, thioxo group, amino group, $C_{1-6}$ alkylamino groups, di($C_{1-6}$ alkyl)amino groups, $C_{1-6}$ alkoxycarbonyl groups, carbamoyl groups, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, mercapto group, $C_{1-6}$ alkylthio groups, $C_{1-6}$ alkylsulfinyl groups and $C_{1-6}$ alkylsulfonyl groups.

Examples of the heterocyclic group represented by $R^{15}$ include pyrrolidinyl, tetrahydrofuranyl, oxetanyl, tetrahydrothienyl, piperidinyl, piperazinyl, morpholinyl, thiomorpholinyl, oxiranyl, thiolanyl, dioxanyl, pyrrolyl, aziridinyl, imidazolidinyl, pyrazolidinyl, tetrahydropyranyl, tetrahydrothiopyranyl, tetrahydrooxazolyl, tetrahydrothiazolyl, tetrahydroisoxazolyl, tetrahydroisothiazolyl, dioxolanyl, oxathiolanyl, furyl, thienyl, pyrazolyl, imidazolyl, triazolyl, oxazolyl, thiazolyl, isoxazolyl, isothiazolyl, dihydroxazolyl, dihydrothiazolyl, dihydroisoxazolyl, dihydroisothiazolyl, pyridyl, pyrimidinyl, triazinyl, tetrazolyl, pyrrolinyl, imidazolinyl, pyrazolinyl, thiadiazolyl, oxadiazolyl, dihydrooxazolyl, dihydrothiazolyl, dihydroisoxazolyl, dihydroisothiazolyl, pyrazinyl, pyridazinyl, pyranyl, dihydropyridinyl, dihydropyrrolyl, dihydroquinolyl, dihydroimidazolyl, dihydropyrazolyl, dihydropyrazinyl, dihydropyridazinyl, benzofuranyl, benzothiazolyl, indolyl, quinolyl, isoquinolyl, benzopyranyl, benzoxazolyl, benzothiazolyl, benzimidazolyl, benzodioxanyl, benzothiophenyl, benzisothiazolyl, benzisoxazolyl, chromenyl, chromanyl, isochromenyl, isochromanyl, indolinyl, indazolyl, indolizinyl, isoindolyl, isoindolinyl, quinolizinyl, quinoxalinyl, quinazolinyl, cinnolinyl, phthalazinyl, naphthyridinyl, purinyl, carbazolyl, xanthenyl, acridinyl, phenazinyl, phenoxazinyl, phenothiazinyl and quinuclidinyl groups which may be substituted with the above-described -$Q^{201}$-$Q^{202}$-$Q^{203}$-$Q^{204}$-$Q^{205}$-$Q^{206}$-$Q^{207}$. Of these groups, pyrrolidinyl, tetrahydrofuranyl, oxetanyl, tetrahydrothienyl, piperidinyl, dihydrooxazolyl, dihydrothiazolyl, dihydroisoxazolyl, dihydroisothiazolyl, piperazinyl, morpholinyl, thiomorpholinyl, oxiranyl, dioxanyl, pyrrolyl, furyl, thienyl, pyrazolyl, imidazolyl, triazolyl, oxazolyl, thiazolyl, isoxazolyl, isothiazolyl, pyridyl, pyrimidinyl, triazinyl, tetrazolyl, benzofuranyl, benzothiophenyl, indolyl, quinolyl, isoquinolyl, benzopyranyl, benzoxazolyl, benzothiazolyl, benzimidazolyl, benzodioxanyl, dioxolanyl, tetrahydropyranyl, tetrahydrothiopyranyl, oxadiazolyl, thiadiazolyl, pyperizinyl, pyridazinyl, dihydropyridinyl, dihydropyrrolyl, dihydroquinolyl, dihydroimidazolyl, dihydropyrazolyl, dihydropyrazinyl, dihydropyridazinyl, tetrahydrooxazolyl, chromenyl, chromanyl, isochromenyl, and isochromanyl groups are preferred, with tetrahydropyranyl, tetrahydrothiopyranyl, piperidinyl, pyridyl, pyrimidinyl, imidazolyl, thiazolyl, benzimidazolyl and chromenyl groups being especially preferred. The heterocyclic group may be substituted with a halogen atom, $C_{1-6}$ alkyl group, $C_{1-6}$ alkoxy group, $C_{2-6}$ alkenyl group, $C_{2-6}$ alkenyloxy group, hydroxy group, carboxyl group, carboxy $C_{1-6}$ alkyl group, $C_{1-6}$ alkoxycarbonyl $C_{1-6}$ alkyl group, $C_{1-6}$ alkoxycarbonyl-$C_{2-6}$ alkenyl group, hydroxyl $C_{1-6}$ alkyl group, ($C_{6-14}$ aromatic hydrocarbon)sulfonyl $C_{1-6}$ alkyl group, heterocyclic-$C_{1-6}$ alkylamino group, heterocyclic group, heterocyclic-$C_{1-6}$ alkyl group, $C_{6-14}$ aromatic hydrocarbon group, ($C_{6-14}$ aromatic hydrocarbon) ($C_{1-6}$ alkyl) group, ($C_{6-14}$ aromatic hydrocarbon)thio $C_{1-6}$ alkyl group, azido-$C_{1-6}$ alkyl group, amino $C_{1-6}$ alkyl group, $C_{1-6}$ alkylamino $C_{1-6}$ alkyl group, di $C_{1-6}$ alkylamino $C_{1-6}$ alkyl group, hydroxy($C_{1-6}$ alkylamino) ($C_{1-8}$ alkyl) group, $C_{1-6}$ alkoxy($C_{1-6}$ alkyl)amino $C_{1-6}$ alkyl group, (hydroxy $C_{1-6}$ alkyl) ($C_{1-6}$ alkoxy $C_{1-6}$ alkyl)amino $C_{1-6}$ alkyl group, $C_{2-6}$ alkanoylamino $C_{1-6}$ alkyl group, ($C_{6-14}$ aromatic hydrocarbon)sulfonylamino $C_{1-6}$ alkyl group, ($C_{1-6}$ alkoxy)carbonylamino $C_{1-6}$ alkyl group, carbamoylamino $C_{1-6}$ alkyl group, N-alkylcarbamoylamino $C_{1-6}$ alkyl group, N,N-dialkylcarbamoylamino $C_{1-6}$ alkyl group, aminosulfonylamino $C_{1-6}$ alkyl group, N-alkylsulfonylamino $C_{1-6}$ alkyl group, N,N-dialkylsulfonylamino $C_{1-6}$ alkyl group, ($C_{6-14}$ aromatic hydrocarbon)($C_{1-6}$ alkyl)amino group, heterocyclic $C_{1-6}$ alkylamino group, carbamoyloxy $C_{1-6}$ alkyl group, N-alkylcarbamoyloxy $C_{1-6}$ alkyl group, N,N-dialkylcarbamoyloxy $C_{1-6}$ alkyl group, ($C_{6-14}$ aromatic hydrocarbon)-($C_{1-6}$ alkyl)carbamoyloxy $C_{1-6}$ alkyl group, $C_{1-6}$ alkoxycarbonyloxy-$C_{1-6}$ alkyl group, ($C_{6-14}$ aromatic hydrocarbon)oxycarbonyloxy $C_{1-6}$ alkyl group, ($C_{6-14}$ aromatic hydrocarbon)sulfonylamino-($C_{1-6}$ alkanoyl)amino $C_{1-6}$ alkyl group, $C_{1-6}$ alkoxycarbonylamino $C_{1-6}$ alkylamino group, amino $C_{1-6}$ alkylamino group, $C_{1-6}$ alkylamino $C_{1-6}$ alkylamino group, di($C_{1-6}$ alkyl)amino $C_{1-6}$ alkylamino group, carboxyamino ($C_{1-6}$ alkyl) group, $C_{1-6}$ alkoxycarbonylamino $C_{1-6}$ alkyl group, $C_{1-6}$ alkylsulfonylamino $C_{1-6}$ alkyl group, amino $C_{1-6}$ alkylcarbonylamino $C_{1-6}$ alkyl group, N-($C_{1-6}$ alkyl)amino $C_{1-6}$ alkylcarbonylamino $C_{1-6}$ alkyl group, N,N-di($C_{1-6}$ alkyl) amino $C_{1-6}$ alkylcarbonylamino $C_{1-6}$ alkyl group, heterocyclic carbonyl group, heterocyclic carbonylamino group, ($C_{6-14}$ aromatic hydrocarbon)carbonyl group, $C_{6-14}$ aromatic carbonylamino group, heterocyclic $C_{1-6}$ alkylcarbonylamino $C_{1-6}$ alkyl group, heterocyclic $C_{2-6}$ alkenylcarbonylamino $C_{1-6}$ alkyl group, $C_{6-14}$ aromatic hydrocarbon alkenylcarbonylamino $C_{1-6}$ alkyl group, $C_{6-14}$ aromatic hydrocarbon carbonylamino $C_{1-6}$ alkyl group, heterocyclic carbonylamino $C_{1-6}$ alkyl group, $C_{1-6}$ alkoxyoxalylamino $C_{1-6}$ alkyl group, carbamoyl group, N-($C_{1-6}$ alkyl)carbamoyl group, N,N-di($C_{1-6}$ alkyl)carbamoyl group, $C_{1-6}$ alkyl-$C_{3-8}$ cycloalkylcarbamoyl group, $C_{3-8}$ cycloalkyl-$C_{1-6}$ alkylcarbamoyl group, heterocyclic carbamoyl group, $C_{1-6}$ aromatic carbamoyl group, heterocyclic carbonylhydrazonomethyl group, $C_{6-14}$ aromatic hydrocarbon carbonylhydrazonomethyl group, $C_{1-6}$ alkylthio $C_{1-6}$ alkylcarbamoyl group, $C_{1-6}$ alkylsulfinyl $C_{1-6}$ alkylcarbamoyl group, $C_{1-6}$ alkylsulfonyl $C_{1-6}$ alkylcarbamoyl group, hydroxyaminocarbonyl group, hydrazinocarbonyl group or N—$C_{1-6}$ alkylhydrazinocarbonyl group, thioformylamino-($C_{6-14}$ aromatic hydrocarbon)-thiocarbonylamino $C_{1-6}$ alkyl group, thioformyl-$C_{1-6}$ alkylamino-$C_{6-14}$ aromatic hydrocarbon-thiocarbonylamino $C_{1-6}$ alkyl group, formylamino-($C_{6-14}$ aromatic hydrocarbon)-carbonylamino($C_{1-6}$ alkyl) group, formyl-$C_{1-6}$ alkylamino-($C_{6-14}$ aromatic hydrocarbon)-carbonylamino $C_{1-6}$ alkyl group, $C_{1-6}$ alkanoyl-heterocycle-carbonylamino $C_{1-6}$ alkyl group, di($C_{2-6}$ alkanoyl)amino $C_{1-6}$ alkyl group, di($C_{1-6}$ alkoxycarbonyl)amino $C_{1-6}$ alkyl group, $C_{1-6}$ alkyl-heterocycle-carbonyl group, $C_{3-7}$ cycloalkyl $C_{1-6}$ alkylaminocarbonyl group, $C_{1-6}$ alkoxyaminocarbonyl group, (hydroxy) ($C_{1-6}$ alkyl)aminocarbonyl group, ($C_{1-6}$ alkoxy)($C_{1-6}$ alkyl)aminocarbonyl group, N'—$C_{1-6}$ alkylhydrazinocarbonyl group, N',N'-di($C_{1-6}$ alkyl)hydrazinocarbonyl group, N,N'-di($C_{1-6}$ alkyl)hydrazinocarbonyl group, N,N',N'-tri($C_{1-6}$ alkyl)hydrazinocarbonyl group, N'-(heterocycle-carbonyl)-hydrazinocarbonyl group, formyl group, hydroxyimino group, $C_{1-6}$ alkoxyimino group, bis($C_{1-6}$ alkoxy $C_{1-6}$ alky)amino $C_{1-6}$ alkyl group, hydroxy-$C_{1-6}$ alkyl-heterocyclic group, $C_{1-6}$ alkoxy-$C_{1-6}$ alkyl-heterocyclic group, $C_{1-6}$ alkoxycarbonylamino $C_{1-6}$ alkyl-heterocyclic group, amino ($C_{1-6}$ alkyl)-heterocyclic group, N—$C_{1-6}$ alkylamino $C_{1-6}$ alkyl-heterocyclic group, N,N-di($C_{1-6}$ alkyl)amino $C_{1-6}$ alkyl-heterocyclic group, hydroxy-heterocyclic group, $C_{1-6}$ alkoxy-heterocyclic group, carboxy-$C_{2-5}$ alkenyl group, or oxo group (wherein, the above-described $C_{6-14}$ aromatic hydrocarbon group or heterocyclic group may be substituted with a halogen atom, $C_{1-6}$ alkyl group, $C_{1-6}$ alkoxy group, $C_{2-6}$ alkenyl group, formyl group, $C_{2-6}$ alkanoyl group, carboxyl group, carboxyamino($C_{1-6}$ alkyl) group, $C_{1-6}$ alkoxycarbonylamino($C_{1-6}$ alkyl) group, oxo group, nitro group, cyano group, amidino group, $C_{2-6}$ alkenyloxy group, hydroxy group, thioxo group, amino group, $C_{1-6}$ alkylamino group, di($C_{1-6}$ alkyl)amino group, amino($C_{1-6}$ alkyl) group, $C_{1-6}$ alkoxycarbonyl group, carbamoyl group, $C_{1-6}$ alkylcarbamoyl group, di($C_{1-6}$ alkyl)carbamoyl group, thiocarbamoyl group, $C_{1-6}$ alkylthiocarbamoyl group, di($C_{1-6}$ alkyl)thiocarbamoyl group, $C_{2-7}$ alkanoylamino group, $C_{2-7}$ alkanoyl($C_{1-6}$ alkyl)amino group, thio $C_{2-7}$ alkanoylamino group, thio $C_{2-7}$ alkanoyl($C_{1-6}$ alkyl)amino group, formylamino group, formyl($C_{1-6}$ alkyl)amino group, thioformylamino group, thioformyl($C_{1-6}$ alkyl)amino group, $C_{2-7}$ alkanoyloxy group, formyloxy group, mercapto group, $C_{1-6}$ alkylthio group, $C_{1-6}$ alkylsulfinyl group, $C_{1-6}$ alkylsulfonyl group, aminosulfonyl group, $C_{1-6}$ alkylaminosulfonyl group, di $C_{1-6}$ alkylaminosulfonyl group, $C_{1-6}$ alkylsulfonylamino group or $C_{1-6}$ alkylsulfonyl($C_{1-6}$ alkyl)amino group.

The compounds of the present invention represented by the formula (1) may have a stereoisomer or an enantiomer derived from an asymmetric hydrocarbon. Any one of the stereoisomer and enantiomer, and mixture thereof are all embraced in the present invention. The S-oxide of the invention compound exists when the heterocyclic group contains a sulfur atom. Either one of a monoxide or dioxide is embraced in the S-oxide.

No particular limitation is imposed on the salt of the compound of the present invention represented by the formula (1) insofar as it is a pharmaceutically acceptable salt. Specific examples of the salt include mineral acid salts such as hydrochloride, hydrobromide, hydroiodide, phosphate, nitrate and sulfate, benzoates, organic sulfonates such as methanesulfonate, 2-hydroxyethanesulfonate and p-toluenesulfonate, and organic carboxylates such as acetate, propanoate, oxalate, malonate, succinate, glutarate, adipate, tartrate, maleate, malate and mandelate.

When the compound represented by the formula (1) has an acid group, the salt may be a salt of an alkali metal ion or alkaline earth metal ion. No particular limitation is imposed on the solvate insofar as it is pharmaceutically acceptable. Specific examples of it include hydrates and ethanol solvates.

Preparation processes of the compounds of the present invention represented by the formula (1) will next be described.

The compounds of the present invention represented by the formula (1) or salts thereof, or solvates thereof can be prepared using generally known chemical preparation processes in combination. Typical synthesis processes will next be described.

Upon synthesis of each invention compound, a substituent such as nitrogen atom, hydroxyl group or carboxyl group which needs protection may be protected by a generally known protecting group which can be removed as needed. The protecting group can be eliminated by the general organic chemical method if necessary.

The sulfide compound (1) having S as X can be prepared by the substitution of a thiol compound with carbon or addition of carbon to the thiol compound (below-descried formulas 2, 4 and 5).

The sulfinyl compound (1) having SO as X can be prepared by oxidizing a sulfide compound (below-described formula 2).

The sulfonyl compound (1) having $SO_2$ as X may be prepared by condensing a sulfonyl compound ($R^1$ and/or $R^2$ and/or $R^3$=H) with a substituent ($R^1$ and/or $R^2$ and/or $R^3$), or by oxidizing the sulfide compound (X represents S) or sulfinyl compound (X represents SO) (the below-described formulas 1 and 2). It can also be prepared by substituting a sulfinic acid compound with carbon or adding carbon to the sulfinic acid compound (the below-described formulas 3, 4 and 5). Use of these processes in combination may also be employed for the preparation.

The substituent portion of the compound (1) thus prepared can be converted and have another structure. Described specifically, $R^1$ and/or $R^2$ and/or $R^3$ and/or $R^4$ can be substituted with another substituent in a known manner.

For example, the compound (1) having, as $R^1$ and/or $R^2$ and/or $R^3$ and/or $R^4$, an alkyl group having a hydroxyl group protected with a vinyl or silyl group can be converted into the corresponding hydroxyalkyl group by deprotection in a conventional manner. Moreover, the hydroxyl group portion can be introduced into a functional group such as ester, carbonate, carbamate, halogen or sulfonate in a known manner. Or, some of them can be introduced into a substituent such as hydrocarbon, alkoxy, amine, amide or sulfide or into a functional group in a conventional manner. Alternatively, a cyclic portion can be formed with the other $R^1$, $R^2$, $R^3$ or $R^4$.

Various functional groups besides a hydroxyl group can be obtained by such conversion and the conversion method can be performed based on the known technique. The reagent, solvent and reaction conditions known per se in the art may be employed for these conversion steps.

Preparation Process of the Sulfonyl Compound (1:X=$SO_2$):

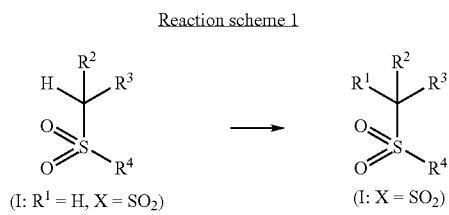

Reaction scheme 1

For example, various compounds (1) different in $R^1$ can be prepared by reacting a compound (1) having a hydrogen atom as $R^1$ and $SO_2$ as X, which compound is known or can be prepared in a known manner, with an electrophilic reagent in the presence of a base in an inert solvent. In this reaction, $R^1$ can be introduced as an independent substituent by utilizing an intramolecular reaction with the electrophilic reagent, but alternatively, a cyclic structure can be formed together with $R^2$ by an intermolecular reaction with $R^2$ having an electrophilic functional group on its side chain.

Described specifically, the reaction is effected by adding the compound (1: $R^1$=H, X=$SO_2$) and at least an equivalent amount of a base with at least an equivalent amount of an electrophilic reagent in an inert solvent.

The reaction temperature is usually from −78° C. to 200° C.

The reaction time is usually from 0.5 hour to 1 day.

Examples of the inert solvent which can be used in the above-described reaction include ether solvents, halogen solvents, aromatic solvents, nitrile solvents and amide solvents. They may be used either singly or in combination of two or more. Of these, tetrahydrofuran, dimethoxyethane, diethyl ether, dimethylformamide and toluene and so on are preferred.

Examples of the electrophilic reagent usable in the above reaction include $R^1$—Y [in which, Y represents an eliminating group], carbonyl compounds (such as aldehyde, ketone, ester and amide), and epoxy compounds. Alternatively, $R^2$ containing Y, carbonyl group or epoxy group may be used as the electrophilic functional group.

Examples of the eliminating group represented by Y include halogen atoms (such as chlorine, bromine and iodine), alkylsulfonyloxy groups having from 1 to 6 carbon atoms, which groups may be halogenated (such as methanesulfonyloxy, ethanesulfonyloxy and trifluoromethanesulfonyloxy), and arylsulfonyloxy groups which have from 6 to 10 carbon atoms and may have a substituent. Substituents for the arylsulfonyloxy group include 1 to 3 halogen atoms, alkyl groups which have from 1 to 6 carbon atoms and may be halogenated, and alkoxy groups having from 1 to 6 carbon atoms.

Specific examples of the eliminating group include benzenesulfonyloxy, p-toluenesulfonyloxy, 1-naphthalenesulfonyloxy and 2-naphthalensulfonyloxy groups.

Examples of the base which can be used for the above reaction include alkyl lithiums (such as n-butyl lithium, sec-butyl lithium and t-butyl lithium), hydrides of an alkali metal or alkaline earth metal (such as lithium hydride, sodium hydride, potassium hydride and calcium hydride), amides of an alkali metal or alkaline earth metal (such as lithium amide, sodium amide, lithium diisopropylamide, lithium dicyclohexylamide, lithium hexamethyldisilazide, sodium hexamethyldisilazide, and potassium hexamethyldisilazide), lower alkoxides of an alkali metal or alkaline earth metal (such as sodium methoxide, sodium ethoxide, and potassium t-butoxide), hydroxides of an alkali metal, alkaline earth metal or silver (such as silver hydroxide, sodium hydroxide, potassium hydroxide, lithium hydroxide and barium hydroxide), carbonates of an alkali metal, alkaline earth metal or silver (sodium carbonate, potassium carbonate, cesium carbonate and silver carbonate), bicarbonates of an alkali metal (such as sodium bicarbonate and potassium bicarbonate), and silver oxide.

The sulfonyl compound (1:X=$SO_2$) can also be prepared by reacting the compound (1) which has a hydrogen atom as $R^1$ and $SO_2$ as X and is known or can be prepared in a known manner with 1 to 3 equivalents of $R^1$—OH in the presence of a condensing agent in an inert solvent.

The reaction temperature is usually from −20° C. to 200° C., preferably from 0° C. to 150° C.

The reaction time is usually from 0.5 hour to 3 days.

Examples of the inert solvent which can be used in the above-described reaction include ether solvents, halogen solvents and aromatic solvents. They may be used either singly or in combination of two or more. Of these, tetrahydrofuran and toluene are preferred.

Examples of the condensing agent which can be used in the above reaction include any one of cyanomethylene trialkylphosphoranes (such as cyanomethylene trimethylphosphorane and cyanomethylene tri-n-butylphosphorane), triarylphosphines (such as triphenylphosphine) and trialkylphosphines (such as tributylphosphine), and azodicarboxylic acid compounds (such as diethyl azodicarboxylate, diisopropyl azodicarboxylate, dipiperizineamide azodicarboxylate and bisdimethylamide azodicarboxylate).

Preparation Process of a Sulfonyl Compound (1:X=$SO_2$) Having $SR^{10}$ as $R^1$ The sulfonyl compound (1:X=$SO_2$) having $SR^{10}$ as $R^1$ is available by reacting a compound (1), which has a hydrogen atom as $R^1$ and $SO_2$ as X and is known or can be prepared in a known manner, with from 1 to 3 equivalents or $R^{10}S$—Y (Y has the same meaning as described above) in the presence of from 1 to 3 equivalents of a base (such as sodium hydride) in an inert solvent.

The reaction temperature is usually from −20° C. to 150° C.

The reaction time is usually from 0.5 hour to 1 day.

Examples of the inert solvent which can be used in the above-described reaction include ether solvents, halogen solvents, aromatic solvents, and amide solvents. They may be used either singly or in combination of two or more. Of these, dimethylformamide is preferred.

Preparation Process of a Sulfonyl Compound (1:X=SO$_2$) in Which R$^1$ and R$^2$ Have Been Coupled Together to Form =CR$^{12}$R$^{13}$ The sulfonyl compound (1:X=SO$_2$) in which R$^1$ and R$^2$ have been coupled together to form =CR$^{12}$R$^{13}$ can be prepared by acting a base on a compound (1) having a hydrogen atom as R$^1$, SO$_2$ as X and —CYR$^{12}$R$^{13}$ [Y has the same meaning as described above] as R$^2$.

More specifically, the compound which has a hydrogen atom as R$^1$, SO$_2$ as X and —CYR$^{12}$R$^{13}$ as R$^2$ [Y has the same meaning as described above] and is known or available in a conventional manner is treated with at least an equivalent amount of a base in an inert solvent.

The reaction temperature is usually from −78° C. to 150° C., preferably from −78° C. to 50° C. The reaction time is usually from 0.5 hour to 1 day.

Examples of the inert solvent which can be used in the above-described reaction include alcohol solvents, ether solvents, halogen solvents, aromatic solvents, nitrile solvents, amide solvents, ketone solvents, sulfoxide solvents and water. They may be used either singly or in combination of two or more. Of these, methylene chloride, tetrahydrofuran and diethyl ether and so on are preferred.

Examples of the base which can be used for the above reaction include hydrides of an alkali metal or alkaline earth metal (such as lithium hydride, sodium hydride, potassium hydride and calcium hydride); amides of an alkali metal or alkaline earth metal (such as lithium amide, sodium amide, lithium diisopropylamide, lithium dicyclohexylamide, lithium hexamethyldisilazide, sodium hexamethyldisilazide, and potassium hexamethyldisilazide); lower alkoxides of an alkali metal or alkaline earth metal (such as sodium methoxide, sodium ethoxide, and potassium t-butoxide); hydroxides of an alkali metal, alkaline earth metal or silver (such as silver hydroxide, sodium hydroxide, potassium hydroxide, lithium hydroxide and barium hydroxide); carbonates of an alkali metal, alkaline earth metal or silver (sodium carbonate, potassium carbonate, cesium carbonate and silver carbonate); bicarbonates of an alkali metal (such as sodium bicarbonate and potassium bicarbonate); alkyl lithiums (such as n-butyl lithium) or alkyl Grignards (such as methyl magnesium bromide); inorganic bases such as silver oxide or amines (such as triethylamine, diisopropylethylamine and N-methylmorpholine); and organic bases, for example, basic heterocyclic compounds (such as dimethylaminopyridine, pyridine, imidazole, 2,6-lutidine, collidine, 1,8-diazabicyclo[5.4.0]undec-7-en, 1,5-diazabicyclo[4.3.0]non-5-en, and 1,4-diazabicyclo[2.2.2]octane).

Preparation Process of a Sulfide Compound (1:X=S), a Sulfinyl Compound (1:X=SO), a Sulfonyl Compound (1:X=SO$_2$)

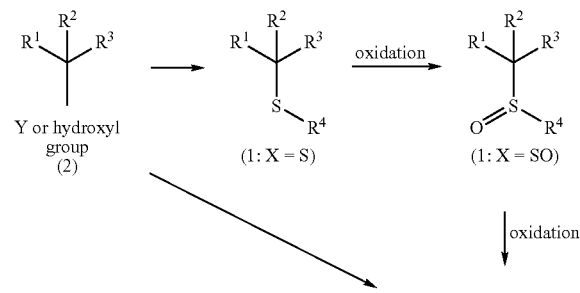

Reaction scheme 2

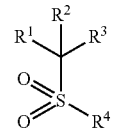

(1: X = SO$_2$)

1) Preparation Process of the Sulfide Compound (1:X=S)

The compound (1) having S as X is available by reacting the compound (2) with a thiol compound in the presence of a base in an inert solvent.

The compound (2) having a hydroxyl group can be prepared in a known manner. Various processes are known and one example will next be described. The compound (2) having a hydroxyl group is available by adding an organometal reagent (as a metal, lithium or magnesium representative of a Grignard reagent is usually employed) in an amount of from equivalent to excess to an aldehyde or ketone represented by R$^1$(C=O)R$^2$ in an inert solvent such as tetrahydrofuran or diethyl ether to react them. The organometal reagent represented by R$^3$-M can be prepared, for example when R$^3$ represents an aromatic ring or aromatic heterocycle, by adding an alkyl lithium reagent or alkyl Grignard reagent to an aryl halide to cause metal exchange, as reported in the paper of H. Gilman, et. al., J. Org. Chem. 1951, 16, 1788-1791, or in the paper of F. Trecourt, et al., Tetrahedron 2000, 56, 1349-1460. The compound (2) having an eliminating group Y can be prepared by converting the hydroxyl group of the hydroxyl-containing compound (2) to an eliminating group in a known manner.

The compound (1) having S as X is also obtainable by reacting the compound (2) with an alkali metal or alkaline earth metal salt (such as lithium, sodium or potassium) of a thiol compound in an inert solvent.

The reaction temperature is usually from −20° C. to 200° C., preferably from room temperature to 100° C. When the R substituent of the compound is a bulky one, reaction at a temperature higher than the above one or reaction in a sealed tube is sometimes preferred.

The reaction time usually ranges from 0.5 hour to 1 hour.

Examples of the base which can be used in the above-described reaction include hydrides of an alkali metal or alkaline earth metal (such as lithium hydride, sodium hydride, potassium hydride and calcium hydride), amides of an alkali metal or alkaline earth metal (such as lithium amide, sodium amide, lithium diisopropylamide, lithium dicyclohexylamide, lithium hexamethyldisilazide, sodium hexamethyldisilazide, and potassium hexamethyldisilazide), lower alkoxides of an alkali metal or alkaline earth metal (such as sodium methoxide, sodium ethoxide, and potassium t-butoxide), hydroxides of an alkali metal, alkaline earth metal or silver (such as silver hydroxide, sodium hydroxide, potassium hydroxide, lithium hydroxide and barium hydroxide), carbonates of an alkali metal, alkaline earth metal or silver (sodium carbonate, potassium carbonate, cesium carbonate and silver carbonate), bicarbonates of an alkali metal (such as sodium bicarbonate and potassium bicarbonate), alkyl lithiums (such as n-butyl lithium) or alkyl Grignard reagents (such as methyl magnesium bromide), inorganic bases such as silver oxide, or amines (such as triethylamine, diisopropylethylamine and N-methylmorpholine), and organic bases, for example, basic heterocyclic compounds (such as dimethylaminopyridine, pyridine, imidazole, 2,6-lutidine, collidine, 1,8-diazabicyclo[5.4.0]undece-7-en, 1,5-diazabicyclo[4.3.0] non-5-en, and 1,4-diazabicyclo[2.2.2]octane).

Examples of the inert solvent which can be used in the above-described reaction include alcohol solvents, ether solvents, halogen solvents, aromatic solvents, nitrile solvents, amide solvents, ketone solvents, sulfoxide solvents and water. They may be used either singly or in combination of two or more. Of these, methylene chloride, tetrahydrofuran and diethyl ether are preferred.

The compound (2) has a hydroxyl group instead of the eliminating group Y, a condensate can be prepared by the Mitsunobu reaction.

The compound (1) can be prepared by reacting the hydroxyl-containing compound (2) which is known or can be prepared in a known manner with 1 to 3 equivalents of a thiophenol compound in the presence of both 1 to 3 equivalents of a triarylphosphine (such as triphenylphosphine) or trialkylphosphine (such as tributylphosphine) and 1 to 2 equivalents of an azodicarboxylic acid compound (such as diethyl azodicarboxylate, diisopropyl azodicarboxylate, dipiperidineamide dicarboxylate or bisdimethylamide azodicarboxylate) in an inert solvent.

The reaction temperature is usually from −20° C. to 150° C., preferably from room temperature to 80° C. When the R substituent of the compound is a bulky one, reaction at a high temperature or reaction in a sealed tube is sometimes preferred.

The reaction time usually ranges from 0.5 hour to 1 day.

Examples of the inert solvent which can be used in the above-described reaction include ether solvents, halogen solvents, and aromatic solvents. Two or more of these solvents may be used as a mixture. Of these, tetrahydrofuran is preferred.

2) Preparation Process of the Sulfinyl Compound (1:X=SO)

The sulfinyl compound (1:X=SO) can be synthesized by oxidizing the sulfide compound (1:X=S), more specifically, reacting the sulfide compound (1) in the presence of an oxidizing agent in an inert solvent.

The reaction temperature usually ranges from −20° C. to 200° C., preferably from 0° C. to 100° C.

Examples of the inert solvent which can be used in the above reaction include alcohol solvents, ether solvents, halogen solvents, aromatic solvents, nitrile solvents, amide solvents, ketone solvents, sulfoxide compounds and water. Two or more of these solvents may be used in combination. Of these, methylene chloride, chloroform, methanol and ethanol are preferred.

Examples of the oxidizing agent which can be used in the above reaction include hydrogen peroxide, organic peracid compounds (such as peracetic acid and meta-chloroperbenzoic acid), metaperiodates (such as sodium metaperiodate), acyl nitrate, dinitrogen tetroxide, halogen, N-halogen compounds (such as N-chlorosuccinimide and N-bromosuccinimide), hydroperoxides (such as t-butylhydroperoxide), iodobenzene diacetate, iodobenzene dichloride, t-butyl hypochlorite, sulfuryl chloride, singlet oxygen, ozone, selenium oxide, and seleninic acid. An optically active sulfoxide (1:X=SO) can be prepared by using titanium tetraisopropoxide/diethyl tartrate/t-butylhydroperoxide, titanium tetraisopropoxide/diethyl tartrate/peracetic acid or the like.

Described specifically, the sulfide compound (1:X=S) and from 1 to 2 equivalents of an oxidizing agent such as meta-chloroperbenzoic acid, sodium periodate or hydrogen peroxide may be stirred in an inert solvent such as methylene chloride, tetrahydrofuran-water, methanol or the like at 0 to 100° C. for from about 1 hour to 2 days.

3) Preparation Process of the Sulfonyl Compound (1:X=SO₂)

The sulfonyl compound (1:X=SO₂) can be synthesized by oxidizing the sulfide compound (1:X=S) or sulfinyl compound (1:X=SO₂), more specifically, by reacting the sulfide compound (1:X=S) or sulfinyl compound (1:X=SO) with an oxidizing agent in an inert solvent.

The reaction temperature usually ranges from −20° C. to 150° C., preferably from 0° C. to 80° C.

Examples of the inert solvent which can be used in the above-described reaction include alcohol solvents, ether solvents, halogen solvents, aromatic solvents, carboxylic acid solvents, nitrile solvents, amide solvents, ketone solvents, sulfoxide solvents and water. Two or more of these solvents may be used as a mixture. Of these, methylene chloride, chloroform, methanol, ethanol and acetic acid are preferred.

Examples of the oxidizing agent which can be used in the above reaction include hydrogen peroxide, hydrogen peroxide-transition metal catalyst (such as ammonium molybdate or iron (III) chloride), organic peracid compounds (such as peracetic acid and meta-chloroperbenzoic acid), metaperiodates (such as sodium metaperiodate), potassium peroxysulfate, permanganates (such as potassium permanganate), sodium perborate, halogen, N-halogen compounds (such as N-chlorosuccinimide and N-bromosuccinimide), hydroperoxides (such as t-butylhydroperoxide), iodobenzene diacetate, iodobenzene dichloride, hypochlorites (such as sodium hypochlorite, or t-butyl hypochlorite), singlet oxygen, ozone, selenium oxide, and seleninic acid. The preferred example of the reaction conditions include reaction of the sulfide compound (1:X=S) with from 2 to 5 equivalents of an oxidizing agent (such as meta-chloroperbenzoic acid, sodium periodate, hydrogen peroxide or hydrogen peroxide-ammonium molybdate) in methylene chloride, tetrahydrofuran-water or methanol at from 0 to 100° C. for from about 1 hour to 2 days.

Preparation Process of the Sulfonyl Compound (1:X=SO₂):

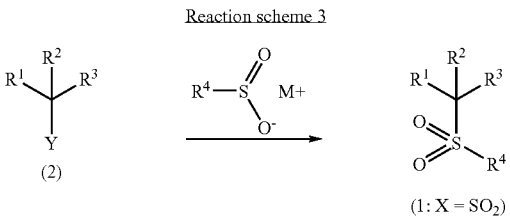

Reaction scheme 3

The sulfonyl compound (1:X=SO₂) can be synthesized by introducing a sulfonyl group into the compound (2), more specifically, by reacting the compound (2) with an alkali metal, alkaline earth metal or tetrabutylammonium salt of sulfinic acid.

Described specifically, the compound (2) is reacted with from an equivalent to excess amount of sulfinic acid or salt thereof in an inert solvent.

The reaction temperature usually ranges from −20° C. to 200° C., preferably from room temperature to 100° C. When the R substituent of the compound is a bulky one, reaction at higher reaction temperature than that described above or reaction in a sealed tube is sometimes preferred.

The reaction time usually ranges from 0.5 hour to 1 day.

Examples of the inert solvent which can be used in the above reaction include alcohol solvents, ether solvents, halogen solvents, aromatic solvents, nitrile solvents, amide solvents, ketone solvents, sulfoxide solvents and water. Two or more of these solvents may be used as a mixture. Of these, butanol and dimethoxyethane are preferred.

Preparation Process of the Sulfide Compound (1:X=S):

Reaction scheme 4

$$\underset{(4)}{\overset{R^2}{\underset{Y^1}{>}}\!\!\!=\!\!\!\overset{R^3}{\underset{Y^2}{<}}} \longrightarrow \underset{(1)}{\overset{R^2}{\underset{X-R^4}{\overset{|}{R^1-\!\!\!\!\!\!-}}\overset{R^3}{|}}} \quad R^1 = CHY^1Y^2$$

Preparation Process of the Sulfide Compound (1:X=S)

(1) When $Y^1$ or $Y^2$ is an Electron Attractive Group

The compound (1) can be prepared by subjecting the compound (4) which is known or is available in a known manner to the Michael reaction, more specifically, by reacting the compound (4) with a thiol ($R^4SH$) in the presence of a base.

Described specifically, the compound (4) is reacted with from an equivalent to excess amount of a thiol in an inert solvent in the presence of from a catalytic amount to equivalent amount of a base.

The reaction temperature usually ranges from −20° C. to 100° C., preferably at room temperature.

The reaction time usually ranges from 0.5 hour to 1 day.

Examples of the electron attractive group include carbonyl groups (such as acyl, ester, carboxylic acid, and amide), cyano group, nitro group, sulfinyl group and sulfonyl group. Examples of the inert solvent which can be used in the above-described reaction include alcohol solvents, ether solvents, halogen solvents, aromatic solvents, nitrile solvents, amide solvents, ketone solvents, sulfoxide solvents and water. Two or more of these solvents may be used as a mixture. Of these, methanol, methylene chloride, and tetrahydrofuran and so on are preferred.

(2) When $R^2$ Represents an Alkoxy Group or a Sulfide Group:

The compound (1) can be prepared by treating the compound (4), which is known or can be prepared in a known manner, in the presence of an acid catalyst, more specifically, by reacting the compound (4) with a thiol in the presence of an acid.

Described specifically, the compound (4) is reacted with from an equivalent to excess amount of a thiol in an inert solvent in the presence of from a catalytic amount to equivalent amount of an acid catalyst.

The reaction temperature usually ranges from −20° C. to 100° C., preferably at room temperature.

The reaction time usually ranges from 0.5 hour to 1 day.

Examples of the acid which can be used in the above reaction include water-free acid such as para-toluenesulfonic acid, camphor-sulfonic acid, hydrogen chloride and acid ion exchange resin; and Lewis acid catalysts such as trimethylsilyl trifluoromethanesulfonate and boron trifluoride.

Examples of the inert solvent which can be used in the above reaction include ether solvents, halogen solvents, aromatic solvents, nitrile solvents, and amide solvents. Two or more of thee solvents may be used as a mixture. Of these, methylene chloride is preferred.

Preparation Process of the Sulfide Compound (1:X=S) and the Sulfonyl Compound (1:X=SO$_2$): Reaction Scheme 5

Reaction scheme 5

$$\underset{(5)}{\overset{R^2}{\underset{Y^1}{>}}\!\!\!=\!\!\!\overset{R^3}{\underset{N}{<}}} \longrightarrow \underset{(1)}{\overset{R^2}{\underset{X-R^4}{\overset{|}{R^1-\!\!\!\!\!\!-}}\overset{R^3}{|}}} \quad R^1 = NHY^1$$

1) Preparation Process of the Sulfide Compound (1:X=S)

The compound (1) can be prepared by subjecting an imine to the nucleophilic substitution reaction, more specifically, reacting an imine or iminium salt, which is the compound (5), with from an equivalent to an excess amount of a thiol in the presence of from a catalytic amount to excess amount of a base or an acid. The compound (5) can be prepared by mixing a carbonyl compound ($R^2COR^3$) with a primary or secondary amine or amide in a proper solvent.

The reaction temperature usually ranges from 0 to 100° C., preferably at room temperature.

The reaction time usually ranges from 0.5 hour to 1 day.

Examples of the base which can be used in the above reaction include hydrides of an alkali metal or alkaline earth metal (such as lithium hydride, sodium hydride, potassium hydride and calcium hydride); amides of an alkali metal or alkaline earth metal (such as lithium amide, sodium amide, lithium diisopropylamide, lithium dicyclohexylamide, lithium hexamethyldisilazide, sodium hexamethyldisilazide, and potassium hexamethyldisilazide); lower alkoxides of an alkali metal or alkaline earth metal (such as sodium methoxide, sodium ethoxide, and potassium t-butoxide); hydroxides of an alkali metal, alkaline earth metal or silver (such as silver hydroxide, sodium hydroxide, potassium hydroxide, lithium hydroxide and barium hydroxide); carbonates of an alkali metal, alkaline earth metal or silver (sodium carbonate, potassium carbonate, cesium carbonate and silver carbonate); bicarbonates of an alkali metal (such as sodium bicarbonate and potassium bicarbonate); alkyl lithiums (such as n-butyl lithium) or alkyl Grignard reagents (such as methyl magnesium bromide); inorganic bases such as silver oxide, or amines (such as triethylamine, diisopropylethylamine and N-methylmorpholine); and organic bases, for example, basic heterocyclic compounds (such as dimethylaminopyridine, pyridine, imidazole, 2,6-lutidine, collidine, 1,8-diazabicyclo [5.4.0]undece-7-en, 1,5-diazabicyclo[4.3.0]non-5-en, and 1,4-diazabicyclo[2.2.2]octane).

Examples of the acid which can be used in the above reaction include formic acid, acetic acid, benzoic acid, para-toluenesulfonic acid and hydrochloric acid.

Examples of the inert solvent which can be used in the above reaction include alcohol solvents, ether solvents, nitrile solvents, amide solvents, ketone solvents, sulfoxide solvents and water. Two or more of thee solvents may be used as a mixture. Of these, a mixed solvent of water and tetrahydrofuran is preferred.

2) Preparation Process of the Sulfonyl Compound (1:X=SO$_2$)

The compound (1) can be prepared by subjecting an imine to the nucleophilic substitution reaction, more specifically, by reacting the imine or iminium salt, which is the compound (5), with from an equivalent amount to an excess amount of a sulfinic acid in the presence of from a catalytic amount to excess amount of an acid.

The reaction temperature usually ranges from 0 to 100° C., preferably at room temperature.

The reaction time usually ranges from 0.5 hour to 1 day.

Examples of the acid which can be used in the above reaction include formic acid, acetic acid, benzoic acid, para-toluenesulfonic acid and hydrochloric acid.

The compound (5) can be prepared by mixing a carbonyl compound ($R^2COR^3$) with a primary or secondary amine or amide in a proper solvent.

The compound (1) is also available without isolation of the compound (5). For example, it is available only by reacting an aldehyde with an equivalent amount of amide or sulfinic acid in the presence of an excess amount of an acid in an inert solvent.

The reaction time usually ranges from 0 to 100° C., preferably at room temperature.

The reaction time ranges from 1 hour to 1 day.

Examples of the inert solvent which can be used in the above reaction include alcohol solvents, ether solvents, nitrile solvents, amide solvents, ketone solvents, sulfoxide solvents and water. Two or more of these solvents may be used as a mixture. Of these, a mixed solvent of water and tetrahydrofuran is preferred.

The compounds (1) of the present invention, particularly the compounds of the formula (3) strongly inhibit production or secretion of β-amyloid protein so that they are useful as a medicament for prevention or treatment for diseases resulting from abnormal production or secretion of β-amyloid protein, such as Alzheimer disease and Down syndrome or diseases associated with amyloid deposition.

When the compound of the present invention is used as a pharmaceutical for human, the dose ranges from 1 mg to 1 g daily for adult, preferably from 10 mg to 300 mg. When it is administered to animals, the dose varies, depending on the purpose of administration (treatment or prevention), kind or size of the animal to be treated, the kind or degree of bacteria with which the animal has been infected, but daily dose usually ranges from 0.1 mg to 200 mg, preferably from 0.5 mg to 100 mg per kg of the weight of the animal. The daily dose is administered once a day or from two to four portions a day. The daily dose may exceed the above-described amount, if necessary.

The pharmaceutical composition containing the compound of the present invention can be formulated into a desired form selected in accordance with the administration route by using various ordinarily employed preparation processes. Examples of the form of the pharmaceutical composition having the invention compound as a main ingredient include oral administrable preparations such as tablets, powders, granules, capsules, liquids, syrups, elixirs, oily or aqueous suspensions.

Injections may contain therein a stabilizer, antiseptic, solubilizing agent or the like. It is also possible to reconstitute a solid preparation, which has been obtained by filling a vessel with a solution which may contain such an agent and then lyophilizing it, upon use. An amount to be administered once may be filled in one vessel or an amount to be administered plural times may be filled in one container.

Examples of the preparation for external use include liquids, suspensions, emulsions, ointments, gels, creams, lotions, sprays and plasters.

The solid preparation contains, together with the invention compound, pharmaceutically acceptable additives. It can be prepared by mixing the invention compound with additives selected from fillers, extenders, binders, disintegrants, solubilizing promoters, humetants and lubricants as needed.

Examples of the liquid preparations include solutions, suspensions and emulsions. They may contain a suspending agent or emulsifier as an additive.

EXAMPLES

The present invention will be described hereinafter in detail with reference to embodiments of the present invention, but should not be construed as limited to the embodiments set forth herein. Also, all the compounds exemplified hereinafter should be construed as belonging either to E type or Z type unless specifically indicated.

Referential Example 1

1-(2,5-Difluorophenyl)-1-pentanol

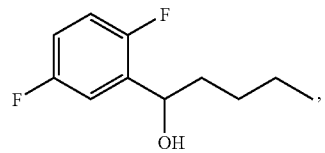

At −78° C. under an argon atmosphere, n-butyl lithium (a 1.52M hexane solution, 14.5 ml, 22.0 mmol) was added dropwise to a solution of 1,4-difluorobenzaldehyde (2.84 g, 20.0 mmol) in tetrahydrofuran (40 ml). While stirring, the temperature of the reaction mixture was raised to −20° C. over 2 hours. To the reaction mixture was added a saturated aqueous ammonium chloride solution, followed by extraction with ethyl acetate. The extracts were combined, washed successively with water and brine, dried over $MgSO_4$, and then concentrated. The residue thus obtained was purified by chromatography on a silica gel column (9% ethyl acetate-hexane), whereby the title compound (2.62 g, 66%) was obtained as a pale yellow oil.

$^1$H-NMR (400 MHz, $CDCl_3$) δ: 0.90(3H,t,J=7.3 Hz), 1.28-1.50(4H,m), 1.70-1.82(2H,m), 1.91-1.95(1H,br m), 4.98(1H, dd,J=11.7, 5.9 Hz), 6.88-7.00(2H,m), 7.18(1H,ddd,J=8.8, 5.6,3.2 Hz).

Example 1

2-[1-[(4-Chlorophenyl)thio]pentyl]-1,4-difluorobenzene

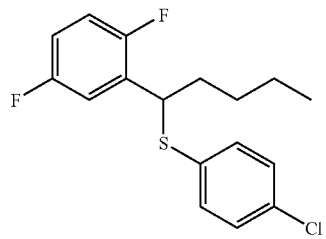

At 0° C., 4-chlorobenzenethiol (435 mg, 3.00 mmol), triphenylphosphine (798 mg, 3.00 mmol), and diisopropyl azodicarboxylate (588 µl, 3.00 mmol) were successively added to a solution of 1-(2,5-difluorophenyl)-1-pentanol (300 mg, 1.50 mmol) in methylene chloride (6 ml). The reaction mixture was stirred at room temperature for 15 hours, diluted with methylene chloride, and then washed successively with a 1N aqueous solution of sodium hydroxide and brine. After drying over $MgSO_4$, the mixture was concentrated. The residue thus obtained was purified twice by medium-pressure chromatography on a silica gel column (first time with 1% ethyl acetate-hexane, and second time with hexane), whereby the title compound (266 mg, 54%) was obtained as a colorless oil.

IR (ATR) ν: 2958, 2931, 1624, 1595, 1574, 1493, 1475, 1425, 1389, 1234, 1215, 1171, 1095, 1012, 874, 814 cm$^{-1}$.

$^1$H-NMR (400 MHz, CDCl$_3$) δ: 0.86(3H,t,J=7.3 Hz), 1.22-1.41(4H,m), 1.78-1.88(1H,m), 1.89-1.99(1H,m), 4.48(1H, ddd,J=8.6,6.6,1.7 Hz), 6.81-6.86(1H,m), 6.90(1H,td,J=9.0, 4.6 Hz), 7.06(1H,ddd,J=9.0,5.8,3.2 Hz), 7.17(4H,s).

MS (m/z): 326 (M$^+$).

HRMS (EI): as C$_{17}$H$_{17}$ClF$_2$S (M$^+$)
Calculated: 326.0708
Found: 326.0696

Example 2

2-[1-[(4-Chlorophenyl)sulfinyl]pentyl]-1,4-difluorobenzene (Isomer 2-A and Isomer 2-B)

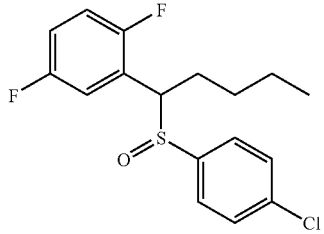

After addition of 3-chloroperbenzoic acid (301 mg, 1.74 mmol) to a solution of 2-[1-[(4-chlorophenyl)thio]pentyl]-1,4-difluorobenzene (515 mg, 1.58 mmol) in methylene chloride (10 ml) at 0° C., the mixture was stirred for 18 hours at room temperature. After further addition of 3-chloroperbenzoic acid (100 mg, 0.578 mmol), the mixture was stirred for 3 hours at room temperature. The reaction mixture was diluted with methylene chloride, washed successively with a 1N aqueous solution of sodium hydroxide, water, and brine, dried over MgSO$_4$, and concentrated. The residue thus obtained was purified by medium-pressure chromatography on a silica gel column (10% ethyl acetate-hexane), whereby the title Isomer 2-A (low-polarity) and the title Isomer 2-B (high-polarity) (230 mg, 43%) were obtained each as a colorless oil. The resulting title Isomer 2-A was then recrystallized from hexane and obtained as colorless needle crystals (79.8 mg, 15%).

Isomer 2-A

Melting point: 108.5-109.0° C.

IR (ATR) ν: 2929, 2854, 1493, 1275, 1132, 1174, 1086, 1043, 1011, 962, 862, 823, 735, 503 cm$^{-1}$.

$^1$H-NMR (400 MHz,CDCl$_3$) δ: 0.90(3H,t,J=7.1 Hz), 1.30-1.50(4H,m), 1.96-2.06(1H,m), 2.27-2.36(1H,m), 4.03(1H, ddd,J=9.6,6.1,1.2 Hz), 6.71(1H,td,J=9.1, 4.4 Hz), 6.85-6.92 (1H,m), 7.07-7.12(1H,m), 7.10(2H,d,J=8.6 Hz), 7.28 (2H,d, J=8.6 Hz).

MS (m/z) 343 (M$^+$+H).

Elemental Analysis for C$_{17}$H$_{17}$ClF$_2$OS
Calculated: C 59.56%; H 5.00%; Cl 10.34%; F 11.08%; S 9.35%.
Found: C 59.27%; H 4.91%; Cl 10.42%; F 11.05%; S 9.45%.

Isomer 2-B

IR (ATR) ν: 3078, 2958, 2931, 2862, 1574, 1495, 1425, 1390, 1213, 1090, 1051, 1012, 818, 741 cm$^{-1}$.

$^1$H-NMR (400 MHz,CDCl$_3$) δ: 0.83(3H,t,J=7.1 Hz), 1.17-1.40(4H,m), 1.94-2.05(1H,m), 2.24-2.34(1H,m), 4.03(1H, dd,J=12.0, 3.2 Hz), 6.87-6.99(3H,m), 7.26(2H,d,J=8.3 Hz), 7.35(2H,d,J=8.3 Hz).

MS (m/z): 343(M$^+$+H).

HRMS (FAB) for C$_{17}$H$_{18}$OClF$_2$S (M$^+$+H)
Calculated: 343.0735
Found: 343.0750

Example 3

2-[1-[(4-Chlorophenyl)sulfonyl]pentyl]-1,4-difluorobenzene

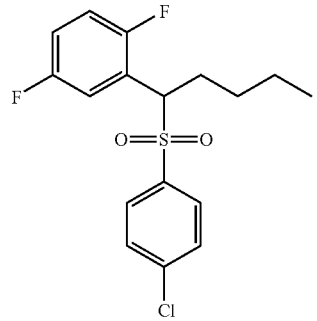

After addition of 3-chloroperbenzoic acid (98.8 mg, 0.571 mmol) to a solution of 2-[1-[(4-chlorophenyl)sulfinyl]pentyl]-1,4-difluorobenzene (Isomer 2-B) (150 mg, 0.439 mmol) in methylene chloride (5 ml), the resulting mixture was stirred at room temperature for 18 hours. The reaction mixture was diluted with methylene chloride, washed successively with a 1N aqueous solution of sodium hydroxide, water and brine, dried over MgSO$_4$, and concentrated. The residue thus obtained was purified by medium-pressure chromatography on a silica gel column (10% ethyl acetate-hexane), whereby the title compound (122 mg, 77%) was obtained as a colorless oil.

IR (ATR) ν: 3089, 2958, 2933, 2873, 1583, 1496, 1475, 1427, 1394, 1321, 1279, 1219, 1176, 1149, 1086, 1014, 829, 754 cm$^{-1}$.

$^1$H-NMR (400 MHz, CDCl$_3$) δ: 0.85(3H,t,J=7.3 Hz), 1.15-1.40(4H,m), 2.03-2.14(1H,m), 2.38-2.47(1H,m), 4.51(1H, dd,J=10.5, 3.7 Hz), 6.83(1H,td,J=9.0, 4.6 Hz), 6.94-7.01(1H, m), 7.25(1H,ddd,J=8.8,5.4,3.2 Hz), 7.38(2H,d,J=8.5 Hz), 7.53(2H,d,J=8.5 Hz).

MS (m/z): 359 (M$^+$+H)
HRMS (FAB) for C$_{17}$H$_{18}$ClF$_2$O$_2$S (M$^+$+H)
Calculated: 359.0684
Found: 359.0688

Example 4

2-[(4-Chlorophenyl)thiomethyl]-1,4-difluorobenzene

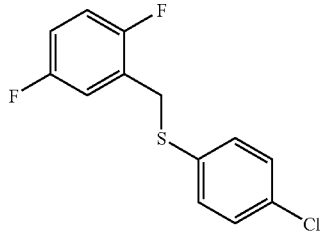

Process 1: At 0° C., 4-chlorobenzenethiol (5.45 g, 38.2 mmol), triphenylphosphine (11.1 g, 41.6 mmol), and diisopropyl azodicarboxylate (8.16 ml, 41.6 mmol) were added successively to a solution of 2,5-difluorobenzyl alcohol (5.00 g, 34.7 mmol) in tetrahydrofuran (150 ml). The reaction mixture was stirred at room temperature for 4 days, followed by concentration. The residue thus obtained was purified by chromatography on a silica gel column (1% ethyl acetate-hexane), whereby the title compound (2.68 g, 29%) was obtained as a colorless oil.

Process 2: After addition of potassium carbonate (4.00 g, 29.0 mmol) and 2-bromomethyl-1,4-difluorobenzene (5.00 g, 24.2 mmol) to a solution of 4-chlorobenzenethiol (3.86 g, 26.6 mmol) in N,N-dimethylformamide (120 ml), the mixture was stirred for 3 hours at room temperature. To the reaction mixture were added saturated ammonium chloride (50 ml) and water (20 ml), followed by extraction with diethyl ether. The extracts were combined, washed with water and brine, dried over $MgSO_4$, and concentrated. The residue thus obtained was purified by chromatography on a silica gel column (1% ethyl acetate-hexane), whereby the title compound (6.41 g, 98%) was obtained as a colorless oil.

$^1$H-NMR (400 MHz, CDCl$_3$) δ: 4.04(2H,s), 6.85-7.00(3H, m), 7.23(4H,s).

Example 5

2-[(4-Chlorophenyl)sulfonylmethyl]-1,4-difluorobenzene

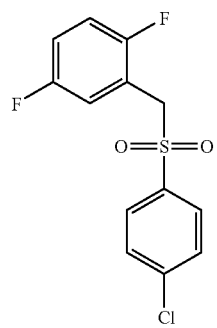

Process 1: At 0° C., 3-chloroperbenzoic acid (225 mg, 1.30 mmol) was added to a solution of 2-[(4-chlorophenyl)thiomethyl]-1,4-difluorobenzene (271 mg, 1.00 mmol) in methylene chloride (5 ml). The mixture was then stirred at room temperature for 15 hours. The reaction mixture was diluted with methylene chloride, washed with a saturated aqueous solution of potassium bicarbonate and brine, dried over $MgSO_4$, and concentrated. The residue thus obtained was dissolved in methylene chloride (5 ml). After cooling to 0° C., 3-chloroperbenzoic acid (450 mg, 2.60 mmol) was added to the solution and then the mixture was stirred at room temperature for 15 hours. The reaction mixture was diluted with methylene chloride, washed with a saturated aqueous solution of potassium bicarbonate and brine, dried over $MgSO_4$, then concentrated. The residue thus obtained was purified by chromatography on a silica gel column (9% ethyl acetate-hexane), whereby the title compound (210 mg, 69%) was obtained as a colorless solid.

Process 2: After addition of $H_2O$ (16.4 ml), 30% $H_2O_2$ (16.4 ml, 145 mmol) and hexaammonium heptamolybdate tetrahydrate (425 mg, 0.344 mmol) to a solution of 2-[(4-chlorophenyl)thiomethyl]-1,4-difluorobenzene (6.54 g, 24.1 mmol) in methanol (100 ml) at 0° C., the mixture was stirred for 1 hour and then stirred further for 15 hours at room temperature. The solid thus precipitated was collected by filtration and the filtrate was concentrated to about half of its amount. The resulting aqueous solution was extracted with methylene chloride. The solid was then dissolved in the extract. The resulting solution was washed successively with water and brine, dried over $MgSO_4$, and concentrated. The residue thus obtained was recrystallized from hexane, whereby the title compound (6.34 g, 87%) was obtained as colorless needle crystals.

Process 3: After addition of 2-bromomethyl-1,4-difluorobenzene (12.3 ml, 95.5 mmol) to a suspension of sodium 4-chlorobenzenesulfinate (19.0 g, 95.5 mmol) in butanol (200 ml), the mixture was heated under reflux for 5 hours. The solid thus precipitated was collected by filtration and dissolved in methylene chloride. The resulting solution was washed with brine, dried over $MgSO_4$, and concentrated. The solid thus obtained was recrystallized from hexane, whereby the title compound (12.3 g, 43%) was obtained as colorless needle crystals.

IR (ATR) v: 3089, 2991, 2943, 1581, 1496, 1315, 1279, 1213, 1149, 1090, 1080, 1012,958, 816, 779, 756, 729, 708, 646, 517, 469 cm$^{-1}$.

$^1$H-NMR (400 MHz, CDCl$_3$) δ:4.36(2H,s), 6.91(1H, td, J=9.0, 4.4 Hz), 6.99-7.06(1H,m),
7.11(1H, ddd, J=8.3, 5.6, 3.2 Hz), 7.45(2H, d, J=8.8 Hz), 7.62(2H, d, J=8.8 Hz).
MS (m/z): 303(M$^+$+H).

Example 6

E-2-[1-[(4-Chlorophenyl)sulfonyl]-2-phenylethenyl]-1,4-difluorobenzene

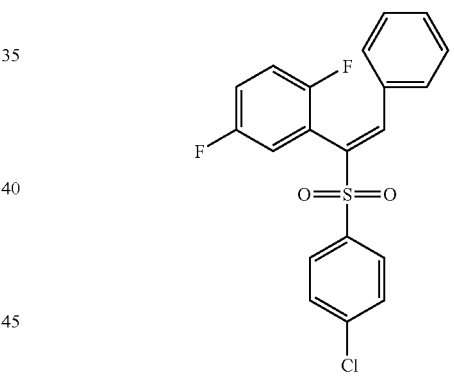

Under a nitrogen atmosphere and at 0° C., potassium hexamethyldisilazide (a 0.5M toluene solution, 2.20 ml, 1.10 mmol) was added to a tetrahydrofuran (5 ml) solution of the 2-[(4-chlorophenyl)sulfonylmethyl]-1,4-difluorobenzene (303 mg, 1.00 mmol) obtained in Example 5 was added. The resulting mixture was stirred at 0° C. for 1 hour. After addition of benzaldehyde (127 mg, 1.20 mmol), the mixture was stirred at room temperature for 15 hours. The reaction mixture was added with a saturated aqueous solution of ammonium chloride, followed by extraction with ethyl acetate. The extracts were combined, washed successively with water and brine, dried over $MgSO_4$, and concentrated. The residue thus obtained was purified by medium-pressure chromatography on a silica gel column (10% ethyl acetate-hexane), whereby the title compound (220 mg, 56%) was obtained as a colorless solid. The solid was recrystallized from methanol to yield a colorless solid (111 mg, 28%). Based on the observation test of NOE (Nuclear Overhauser Effect), the olefin of the title compound was determined as an E-form.

Melting point: 144.5-145.0° C.

IR (KBr) ν: 3068, 1637, 1581, 1489, 1450, 1419, 1315, 1246, 1155, 1086, 887, 814, 752, 725, 690, 648, 627, 613, 534, 467 cm$^{-1}$.

$^1$H-NMR (400 MHz, CDCl$_3$) δ: 6.88(1H,td,J=9.1, 4.4 Hz), 7.06-7.18(4H,m), 7.22-7.28(2H,m), 7.30-7.36(1H,m), 7.39 (2H,d,J=8.8 Hz), 7.60(2H,d,J=8.8 Hz), 8.09(1H,s).

MS (m/z): 391 (M$^+$+H).

Elemental Analysis for C$_{20}$H$_{13}$ClF$_2$O$_2$S

Calculated: C 61.46%; H 3.35%; Cl 9.07%; F 9.72%; S 8.20%.

Found: C 61.39%; H 3.28%; Cl 8.95%; F 9.82%; S 8.30%.

Example 7

1-[(4-Chlorophenyl)sulfonyl]-1-(2,5-difluorophenyl)-2-pentanone

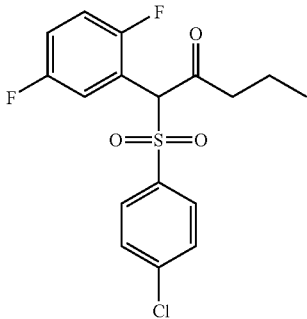

In an argon gas stream and at −78° C., n-butyl lithium (a 1.57M hexane solution, 1.27 ml, 2.00 mmol) was added to a tetrahydrofuran (10 ml) solution of the 2-[(4-chlorophenyl) sulfonylmethyl]-1,4-difluorobenzene (606 mg, 2.00 mmol) obtained in Example 5. The temperature of the resulting mixture was then raised to room temperature. After cooling to −78° C., butyryl chloride (0.218 ml, 2.10 mmol) was added dropwise to the reaction mixture. The reaction mixture was stirred at −78° C. for 1.5 hours, and added with 1N hydrochloric acid (2.0 ml). The temperature of the mixture was then raised to room temperature. The reaction mixture was extracted with diethyl ether. The extracts were combined, washed successively with water and brine, dried over MgSO$_4$, and concentrated. The residue thus obtained was purified by medium-pressure chromatography on a silica gel column (10% ethyl acetate-hexane). The solid thus obtained was recrystallized from hexane, whereby the title compound (330 mg, 44%) was obtained as colorless needle crystals.

Melting point: 85.5-86.0° C.

IR (ATR) ν: 2968, 1724, 1581, 1491, 1394, 1335, 1323, 1155, 1088, 1034, 1011, 906, 829, 816, 758, 725, 615, 546, 469 cm$^{-1}$.

$^1$H-NMR (400 MHz, CDCl$_3$) δ: 0.90(3H,t,J=7.6 Hz), 1.52-1.68(2H,m), 2.62(1H,ddd,J=18.1,7.6,6.8 Hz), 2.84(1H,ddd, J=18.1,7.6,6.8 Hz), 5.66(1H,s), 6.95(1H,td,J=9.0, 4.4 Hz), 7.02-7.08(1H,m), 7.39-7.43(1H,m), 7.43(2H,d,J=8.5 Hz), 7.56(2H,d,J=8.5 Hz).

MS (m/z) 372 (M$^+$).

Elemental Analysis for C$_{17}$H$_{15}$ClF$_2$O$_3$S

Calculated: C 54.77%; H 4.06%; Cl 9.51%; F 10.19%; S 8.60%.

Found: C 54.47%; H 3.92%; Cl 9.68%; F 10.26%; S 8.76%.

Example 8

2-[(4-Chlorophenyl)sulfonyl]-2-(2,5-difluorophenyl)-1-phenyl-1-ethanone

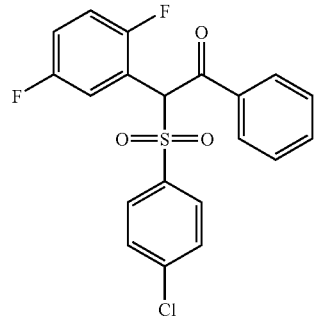

In an argon gas stream and at −78° C., n-butyl lithium (a 1.57M hexane solution, 0.701 ml, 1.10 mmol) was added to a tetrahydrofuran (5 ml) solution of the 2-[(4-chlorophenyl) sulfonylmethyl]-1,4-difluorobenzene (303 mg, 1.00 mmol) obtained in Example 5. The temperature of the resulting mixture was raised to room temperature and then stirred for 10 minutes. After cooling the reaction mixture to −78° C., benzoyl chloride (0.140 ml, 1.20 mmol) was added thereto dropwise. The reaction mixture was stirred at −78° C. for 30 minutes. The temperature of the mixture was then raised to OC over 3 hours. After addition of 1N hydrochloric acid (2.0 ml), the mixture was extracted with ethyl acetate. The extracts were combined, washed successively with water, a saturated aqueous solution of sodium bicarbonate, and brine, dried over MgSO$_4$, and then concentrated. The residue was purified by medium-pressure chromatography on a silica gel column (10% ethyl acetate-hexane). The solid thus obtained was washed with hexane, whereby the title compound (200 mg, 49%) was obtained as a colorless solid.

Melting point: 179.5-180.0° C.

IR (ATR) ν: 1682, 1595, 1579, 1495, 1475, 1315, 1284, 1240, 1209, 1153, 1082, 991, 874, 766, 708, 687, 607, 547, 509, 453 cm$^{-1}$.

$^1$H-NMR (400 MHz, CDCl$_3$) δ: 6.54(1H,s), 7.01-7.10(2H, m), 7.34-7.38(1H,m), 7.44-7.50(4H,m), 7.58-7.65(1H,m), 7.67(2H,d,J=8.8 Hz), 7.88-7.93(2H,m).

MS (m/z): 406 (M$^+$)

HRMS (EI): as C$_{20}$H$_{13}$ClF$_2$O$_3$S (M$^+$)

Calculated: 406.0242

Found: 406.0230

Example 9

2-[(4-Chlorophenyl)sulfonyl]-2-(2,5-difluorophenyl)-1-phenylethenyl benzoate

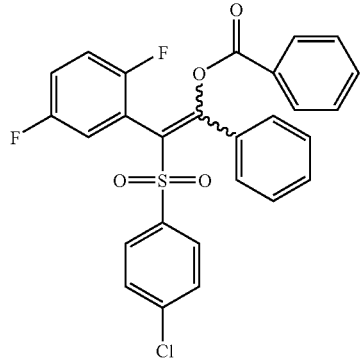

In an argon gas stream and at −78° C., n-butyl lithium (a 1.57M hexane solution, 0.701 ml, 1.10 mmol) was added to a dimethoxyethane (5 ml) solution of the 2-[(4-chlorophenyl)sulfonylmethyl]-1,4-difluorobenzene (303 mg, 1.00 mmol) obtained in Example 5. The temperature of the mixture was then raised to room temperature, followed by stirring for 10 minutes. After cooling to −78° C., benzoyl chloride (0.140 ml, 1.20 mmol) was added dropwise to the reaction mixture. The reaction mixture was stirred at −78° C. for 30 minutes. The temperature of the mixture was then raised to 0° C. over 3 hours. A saturated aqueous ammonium chloride solution was added to the reaction mixture, followed by extraction with diethyl ether. The extracts were combined, washed successively with water and brine, dried over $MgSO_4$, and then concentrated. The residue was purified by medium-pressure chromatography on a silica gel column (10% ethyl acetate-hexane). The solid thus obtained was recrystallized from ethyl acetate, whereby the title compound (80.0 mg, 26%) was obtained as a colorless solid.

Melting point: 224.5-227.0° C.

IR (ATR) ν: 1756, 1610, 1491, 1450, 1325, 1228, 1155, 1092, 1072, 1011, 808, 756, 694, 606, 553, 462 $cm^{-1}$.

$^1$H-NMR (400 MHz, $CDCl_3$) δ: 6.97(1H,ddd,J=8.8, 4.4 Hz), 7.02-7.09(1H,m), 7.15-7.21(3H,m), 7.23-7.30(3H,m), 7.34(2H,d,J=8.5 Hz), 7.51-7.57(2H,m), 7.77(2H,d,J=8.5 Hz), 8.02-8.06(2H,m).

MS (m/z): 528 ($M^+$+$NH_4$).

Elemental Analysis for $C_{27}H_{17}ClF_2O_4S$

Calculated: C 63.47%; H 3.35%; Cl 6.94%; F 7.44%; S 6.28%.

Analyzed: C 63.04%; H 3.24%; Cl 6.92%; F 7.39%; S 6.44%.

Example 10

1-[(4-Chlorophenyl)sulfonyl]-1-(2,5-difluorophenyl)-2-pentanol

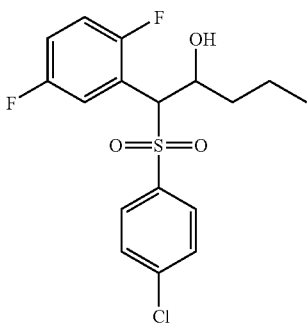

Under a nitrogen atmosphere and at −78° C., n-butyl lithium (a 1.60M hexane solution, 0.688 ml, 1.10 mmol) was added to a tetrahydrofuran (5 ml) solution of the 2-[(4-chlorophenyl)sulfonylmethyl]-1,4-difluorobenzene (303 mg, 1.00 mmol) obtained in Example 5. The mixture was stirred at −78° C. for 1 hour. After addition of butanal (0.108 ml, 1.20 mmol), the mixture was stirred at −78° C. for 2 hours. A saturated aqueous ammonium chloride solution was added to the reaction mixture, followed by extraction with ethyl acetate. The extracts were combined, washed successively with water and brine, dried over $MgSO_4$, and then concentrated. The residue was purified by medium-pressure chromatography on a silica gel column (10% ethyl acetate-hexane) as a low-polarity isomer to yield by a colorless solid. The solid thus obtained was washed with hexane, whereby the title compound (30.5 mg, 8%) was obtained as a colorless solid.

Melting point: 134.5-135.0° C.

IR (ATR) ν: 3502, 2966, 2931, 2873, 1585, 1491, 1309, 1277, 1227, 1173, 1147, 1084, 1083, 1014, 810, 756, 721, 613, 542, 445 $cm^{-1}$.

$^1$H-NMR (400 MHz, $CDCl_3$) δ: 0.87(3H,t,J=7.1 Hz), 1.20-1.65(4H,m), 3.06(1H,d,J=2.2 Hz), 4.48(1H,s), 4.85-4.90(1H,m), 6.84(1H,td,J=9.1, 4.7 Hz), 6.96-7.02(1H,m), 7.40(2H,d,J=8.6 Hz), 7.58(2H,d,J=8.6 Hz), 7.85(1H,ddd,J=9.1,5.4,3.4 Hz).

MS (m/z): 374 ($M^+$).

HRMS (EI) m/z as $C_{17}H_{17}O_3ClF_2S$ ($M^+$):

Calculated: 374.0555

Found: 374.0540

Example 11

1-[(4-Chlorophenyl)sulfonyl]-1-(2,5-difluorophenyl)-2-pentanol

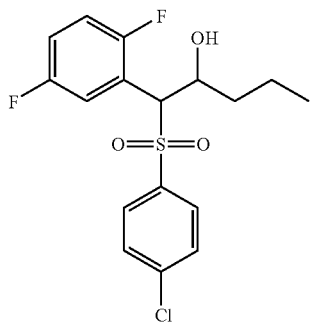

In an argon gas stream and at −78° C., n-butyl lithium (a 1.57M hexane solution, 7.01 ml, 11.0 mmol) was added to a tetrahydrofuran (50 ml) solution of the 2-[(4-chlorophenyl)sulfonylmethyl]-1,4-difluorobenzene (3.03 g, 10.0 mmol) obtained in Example 5 and the mixture was stirred at −78° C. for 1 hour. Butanal (1.08 ml, 12.0 mmol) was added dropwise to the reaction mixture. The mixture was stirred for 15 hours while elevating its temperature to room temperature. After cooling to 0° C. and addition of a saturated aqueous ammonium chloride solution, the mixture was extracted with diethyl ether. The extracts were combined, washed successively with water and brine, dried over $MgSO_4$, and then concentrated. The solid thus precipitated was collected by filtration and washed with hexane. The filtrate and washing with hexane were combined, followed by concentration. The residue was purified by medium-pressure chromatography on a silica gel column (10% ethyl acetate-hexane) as a high-polarity isomer to yield a colorless solid. The resulting colorless solid was recrystallized from hexane, whereby the title compound (396 mg, 11%) was obtained as colorless needle crystals.

Melting point: 76.5-78.0° C.

IR (ATR) ν: 3533, 2960, 1581, 1498, 1394, 1329, 1306, 1242, 1178, 1146, 1082, 987, 887, 754, 712, 644, 594, 515 $cm^{-1}$.

$^1$H-NMR (400 MHz, $CDCl_3$) δ: 0.82(3H,t,J=7.3 Hz), 1.22-1.53(4H,m), 3.78(1H,br s), 4.55-4.80(2H,br m), 6.84(1H,td,

J=9.0, 4.4 Hz), 6.96-7.04(1H,m), 7.15-7.26(1H,br s), 7.39 (2H,d,J=8.3 Hz), 7.52(2H,d,J=8.3 Hz).

MS (m/z): 374 (M+).

Elemental Analysis for $C_{17}H_{17}ClF_2O_3S$

Calculated: C 54.47%; H 4.57%; Cl 9.46%; F 10.14%; S 8.55%.

Found: C 54.27%; H 4.51%; Cl 9.44%; F 10.20%; S 8.70%.

Example 12

2-[1-[(4-Chlorophenyl)sulfonyl]-1-penten-1-yl]-1,4-difluorobenzene

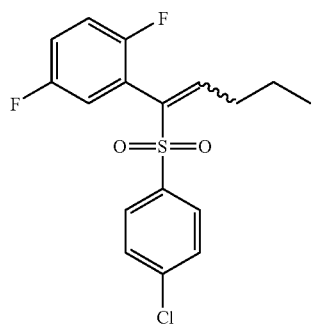

At 0° C., triethylamine (0.131 ml, 0.942 mmol) and methanesulfonyl chloride (0.0665 ml, 0.856 mmol) were added to a solution of 1-[(4-chlorophenyl)sulfonyl]-1-(2,5-difluorophenyl)-2-pentanol (204 mg, 0.544 mmol) in methylene chloride (10 ml). After stirring at 0° C. for 1 hour, the reaction mixture was diluted with methylene chloride, washed successively with a saturated aqueous ammonium chloride solution, water and brine, dried over MgSO₄, and then concentrated. The residue was dissolved in tetrahydrofuran (5 ml). After cooling the solution to 0° C., potassium hexamethyldisilazide (a 0.5M toluene solution, 1.30 ml, 0.650 mmol) was added thereto. The resulting mixture was stirred at 0° C. for 3 hours, and saturated ammonium chloride was added thereto. The resulting mixture was extracted with ethyl acetate, washed successively with water and brine, dried over MgSO₄, and then concentrated. The residue thus obtained was purified by medium-pressure chromatography on a silica gel column (15% ethyl acetate-hexane). The resulting solid was recrystallized from hexane, whereby the title compound (33.0 mg, 17%) was obtained as colorless needle crystals.

Melting point: 95.5-97.0° C.

IR (ATR) ν: 2960, 1645, 1579, 1489, 1421, 1311, 1252, 1198, 1165, 1140, 1086, 1012, 818, 769, 752, 640, 606, 552, 467 cm⁻¹.

¹H-NMR (400 MHz, CDCl₃) δ: 0.89 (3H,t,J=7.3 Hz), 1.45-1.56(2H,m), 2.00(2H,br s), 6.89(1H,td,J=8.3, 4.4 Hz), 7.01-7.08(2H,m), 7.31(1H,t,J=8.3 Hz), 7.38(2H,d,J=8.5 Hz), 7.55(2H,d,J=8.5 Hz).

MS (m/z): 356 (M+).

HRMS (EI): as $C_{17}H_{15}ClF_2O_2S$ (M+)

Calculated: 356.0449

Found: 356.0450

Elemental Analysis for $C_{17}H_{15}ClF_2O_2S$

Calculated: C 57.22%; H 4.24%; Cl 9.94%; F 10.65%; S 8.99%.

Found: C 56.80%; H 4.21%; Cl 10.04%; F 10.65%; S 9.11%.

Example 13

1-[(4-Chlorophenyl)sulfonyl]-1-(2,5-difluorophenyl)-2-pentyl Methanesulfonate

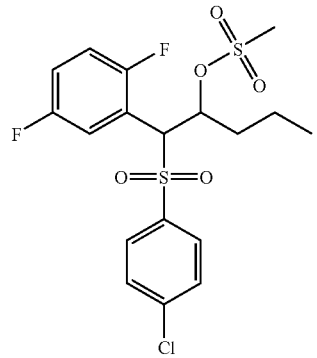

At 0° C., triethylamine (0.300 ml, 2.16 mmol) and methanesulfonyl chloride (0.150 ml, 1.93 mmol) were added to a methylene chloride (10 ml) solution of the 1-[(4-chlorophenyl)sulfonyl]-1-(2,5-difluorophenyl)-2-pentanol (449 mg, 1.20 mmol) obtained in Example 11. The resulting mixture was then stirred at 0° C. for 2 hours. The reaction mixture was diluted with methylene chloride, washed successively with a saturated aqueous solution of ammonium chloride, water and brine, dried over MgSO₄, then concentrated. The residue thus obtained was purified by medium-pressure chromatography on a silica gel column (15% ethyl acetate-hexane), whereby the title compound (503 mg, 93%) was obtained as a colorless solid.

IR (ATR) ν: 2966, 1498, 1350, 1176, 1149, 1086, 928, 879, 789, 752, 636, 592, 550, 525, 455 cm⁻¹.

¹H-NMR (400 MHz, CDCl₃) δ: 0.86(3H,t,J=7.1 Hz), 1.33-1.61(3H,m), 1.88-1.96(1H,m), 3.21(3H,d,J=0.7 Hz), 5.03 (1H,d,J=7.7 Hz), 5.58-5.66(1H,m), 6.83(1H,td,J=9.0, 4.4 Hz), 6.97-7.05(1H,m), 7.33-7.40(1H,m,including 2H,d, J=8.3 Hz at 7.35 ppm), 7.54 (2H,d,J=8.3 Hz).

Example 14

2-[1-[(4-Chlorophenyl)sulfonyl]-2-penten-1-yl]-1,4-difluorobenzene

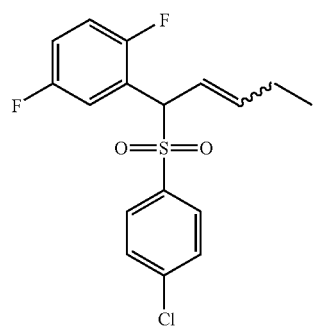

To a solution of 1-[(4-chlorophenyl)sulfonyl]-1-(2,5-difluorophenyl)-2-pentyl=methanesulfonato (200 mg, 0.442 mmol) in methylene chloride (4 ml) was added 1,8-diazabicyclo[5,4,0]undec-7-ene (69.1 μl, 0.464 mmol) at room temperature. The mixture was stirred for 15 hours. The reaction mixture was concentrated. The residue was purified by medium-pressure chromatography on a silica gel column (8% ethyl acetate-hexane), whereby the title compound (72.0 mg, 46%) was obtained as a colorless solid. The resulting solid was recrystallized from hexane to yield a colorless solid (60.0 mg).

Melting point: 99.0-100.0° C.

IR (ATR) ν: 1581, 1496, 1392, 1309, 1279, 1232, 1173, 1149, 1084, 978, 837, 816, 806, 758, 731, 710, 644, 598, 561, 521 cm$^{-1}$.

$^1$H-NMR (400 MHz, CDCl$_3$) δ: 0.99(3H,t,J=7.3 Hz), 2.12 (2H,m), 5.06(2H,d,J=7.3 Hz), 5.74-5.85(2H,m), 6.92(1H,td, J=9.0, 4.4 Hz), 6.97-7.04(1H,m), 7.32(1H,ddd,J=8.5,5.4,3.2 Hz), 7.43(2H,d,J=8.5 Hz), 7.64 (2H,d,J=8.5 Hz).

MS (m/z): 374 (M$^+$+NH$_4$).

Elemental Analysis for C$_{17}$H$_{15}$ClF$_2$O$_2$S

Calculated: C 57.22%; H 4.24%; Cl 9.94%; F 10.65%; S 8.99%.

Analyzed: C 57.15%; H 4.18%; Cl 9.90%; F 10.74%; S 9.09%.

Example 15

2-[5-(t-Butyldimethylsilyloxy)-1-[(4-chlorophenyl)sulfonyl]pentyl]-1,4-difluorobenzene

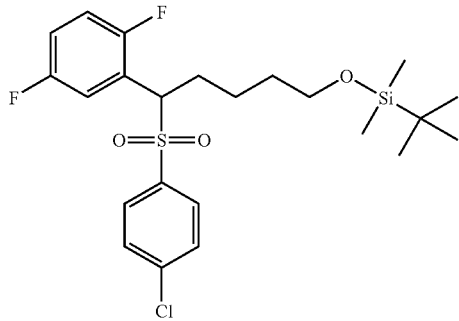

In an argon gas stream and at −78° C., n-butyl lithium (a 1.57M hexane solution, 0.701 ml, 1.10 mmol) was added to a dimethoxyethane (5 ml) solution of the 2-[(4-chlorophenyl)sulfonylmethyl]-1,4-difluorobenzene (303 mg, 1.00 mmol) obtained in Example 5. The mixture was stirred at −78° C. for 1 hour and then, at room temperature for 30 minutes. The reaction mixture was cooled to −78° C., followed by the dropwise addition of 4-(t-butyldimethylsilyloxy)-1-iodobutane (0.260 ml, 1.00 mmol). While elevating the temperature of the reaction mixture to room temperature, stirring was conducted for 15 hours. Water was added to the reaction mixture, followed by extraction with diethyl ether. The extracts were combined, washed successively with water and brine, dried over MgSO$_4$, and concentrated. The residue thus obtained was purified by medium-pressure chromatography on a silica gel column (8% ethyl acetate-hexane), whereby the title compound (401 mg, 82%) was obtained as a colorless solid. The resulting solid was recrystallized from hexane to yield colorless needle crystals.

IR (ATR) ν: 2945, 2927, 2854, 1583, 1496, 1427, 1392, 1321, 1248, 1144, 1082, 1038, 1012, 941, 822, 775, 748, 708, 623, 542, 467 cm$^{-1}$.

$^1$H-NMR (400 MHz, CDCl$_3$) δ: −0.02(3H,s), −0.02(3H,s), 0.82(9H,s), 1.23-1.33(2H,m), 1.42-1.58(2H,m), 2.06-2.18 (1H,m), 2.39-2.48(1H,m), 3.53(2H,t,J=6.3 Hz), 4.52(1H,dd, J=11.6, 2.6 Hz), 6.83(1H,td,J=9.0, 4.4 Hz), 6.94-7.00(1H,m), 7.22-7.26(1H,m), 7.38(2H,d,J=8.5 Hz), 7.53(2H,d,J=8.5 Hz).

MS (m/z): 489 (M$^+$+H).

Elemental Analysis for C$_{23}$H$_{31}$ClF$_2$O$_3$SSi

Calculated: C 56.48%; H 6.39%; Cl 7.25%; F 7.77%; S 6.56%.

Analyzed: C 56.29%; H 6.28%; Cl 7.29%; F 7.75%; S 6.70%.

Example 16

2-[5-(t-Butyldimethylsilyloxy)-1-[(4-chlorophenyl)sulfonyl]-1-methylpentyl]-1,4-difluorobenzene

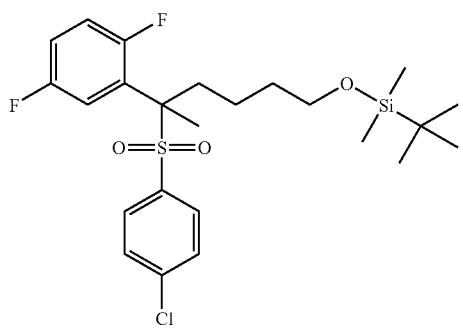

In an argon gas stream and at −78° C., n-butyl lithium (a 1.57M hexane solution, 0.294 ml, 0.461 mmol) was added to a solution of 2-[5-(t-butyldimethylsilyloxy)-1-[(4-chlorophenyl)sulfonyl]pentyl]-1,4-difluorobenzene (205 mg, 0.419 mmol) in tetrahydrofuran (4 ml). The mixture was stirred at room temperature for 1 hour. After cooling to −78° C., iodomethane (0.339 ml, 0.545 mmol) was added dropwise to the reaction mixture and the mixture was stirred at room temperature for 4 hours. Water was added to the reaction mixture, followed by extraction with diethyl ether. The extracts were combined, washed successively with water and brine, dried over MgSO$_4$, and then concentrated. The residue thus obtained was purified by medium-pressure chromatography on a silica gel column (6% ethyl acetate-hexane), whereby the title compound (168 mg, 80%) was obtained as a colorless oil.

IR (ATR) ν: 2952, 2929, 2856, 1583, 1496, 1473, 1392, 1311, 1255, 1192, 1149, 1090, 1014, 833, 760, 710, 629, 552 cm$^{-1}$.

$^1$H-NMR (400 MHz, CDCl$_3$) δ: −0.01(3H,s), 0.00(3H,s), 0.84(9H,s), 1.05-1.18(1H,m), 1.29-1.41(1H,m), 1.52-1.60 (2H,m), 1.81(3H,d,J=2.9 Hz), 1.95-2.05(1H,m), 2.61-2.71 (1H,m), 3.57(2H,t,J=6.1 Hz), 6.82-6.88(1H,m), 6.98-7.07 (2H,m), 7.38(2H,d,J=9.1 Hz), 7.40(2H,d,J=9.1 Hz).

MS (m/z): 503 (M$^+$).

HRMS (FAB) for C$_{24}$H$_{34}$ClF$_2$O$_3$SSi (M$^+$+H)

Calculated: 503.1655

Analyzed: 503.1704

Example 17

5-(4-Chlorophenylsulfonyl)-5-(2,5-difluorophenyl)-1-hexanol

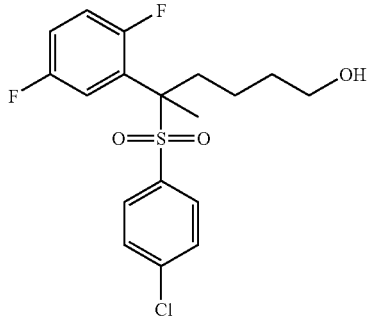

After addition of tetrabutylammonium fluoride (a 1M tetrahydrofuran solution, 0.978 ml, 0.978 mmol) to a solution of 2-[5-(t-butyldimethylsilyloxy)-1-[(4-chlorophenyl)sulfonyl]-1-methylpentyl]-1,4-difluorobenzene (164 mg, 0.326 mmol) in tetrahydrofuran (4 ml), the mixture was stirred at room temperature for 3 hours. The reaction mixture was diluted with diethyl ether, washed successively with saturated ammonium chloride, water and brine, dried over MgSO$_4$, and then concentrated. The residue thus obtained was purified by medium-pressure chromatography on a silica gel column (50% ethyl acetate-hexane), whereby the title compound (122 mg, 96%) was obtained as a colorless oil.

IR (ATR) ν: 3516, 3089, 2939, 2870, 1583, 1495, 1475, 1412, 1394, 1306, 1279, 1188, 1146, 1088, 1070, 1012, 823, 758, 710, 679, 649, 602, 546, 474 cm$^{-1}$.

$^1$H-NMR (400 MHz, CDCl$_3$) δ: 2.09-2.20(1H,m), 1.23 (1H,br s), 1.34-1.46(1H,m), 1.63(1H,quint,J=7.1 Hz), 1.82 (3H,d,J=2.7 Hz), 1.98-2.07(1H,m), 2.71(1H,td,J=13.0, 3.4 Hz), 3.63(2H,t,J=6.4 Hz), 6.83-6.90(1H,m), 6.99-7.06(2H, m), 7.38(4H,s).

MS (m/z): 389 (M$^+$+H).

HRMS (FAB) for C$_{18}$H$_{20}$ClF$_2$O$_3$S (M$^+$+H)
Calculated: 389.0790
Analyzed: 389.0795

Example 18

2-[5-(t-Butyldimethylsilyloxy)-1-[4-(t-butyldimethylsilyloxy)butyl]-1-(4-chlorophenylsulfonyl)pentyl]-1,4-difluorobenzene

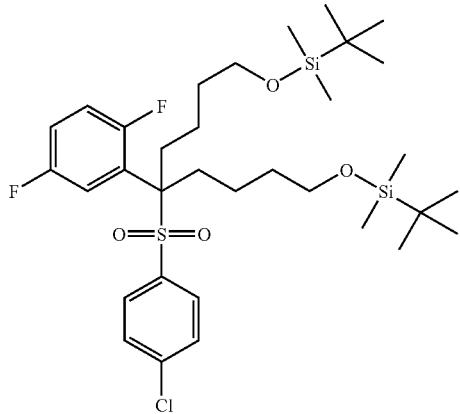

In an argon gas stream and at −78° C., n-butyl lithium (a 1.57M hexane solution, 0.358 ml, 0.562 mmol) was added to a tetrahydrofuran (4 ml) solution of the 2-[5-(t-butyldimethylsilyloxy)-1-[(4-chlorophenyl)sulfonyl]pentyl]-1,4-difluorobenzene (250 mg, 0.511 mmol) obtained in Example 15. The temperature of the resulting mixture was raised to room temperature. After cooling to −78° C., 4-(t-butyldimethylsilyloxy)-1-iodobutane (0.146 ml, 0.562 mmol) was added dropwise to the reaction mixture. The reaction mixture was stirred at room temperature for 3 days. Water was added to the reaction mixture, followed by extraction with diethyl ether. The extracts were combined, washed successively with water and brine, dried over MgSO$_4$, and then concentrated. The residue thus obtained was purified by medium-pressure chromatography on a silica gel column (6% ethyl acetate-hexane), whereby the title compound (167 mg, 48%) was obtained as a colorless solid.

IR (ATR) ν: 3082, 2927, 2856, 1583, 1495, 1462, 1308, 1250, 1146, 1080, 1012, 833, 758, 675, 646, 607, 579, 544, 455 cm$^{-1}$.

$^1$H-NMR (400 MHz, CDCl$_3$) δ: 0.03(12H,s), 0.87(18H,s), 1.25-1.70(8H,m), 2.23-2.34(2H,m), 2.40-2.48(2H,m), 3.58-3.68(4H,m), 6.74-6.82(1H,m), 6.97-7.06(2H,m), 7.30(2H,d, J=8.8 Hz), 7.34(2H,d,J=8.8 Hz).

MS (m/z): 675 (M$^+$+H).

HRMS (FAB) for C$_{33}$H$_{54}$ClF$_2$O$_4$SSi$_2$ (M$^+$+H)
Calculated: 675.2938
Analyzed: 675.2900

Elemental Analysis for C$_{33}$H$_{53}$ClF$_2$O$_4$SSi$_2$
Calculated: C 58.68%; H 7.91%; Cl 5.25%; F 5.63%.
Analyzed: C 58.63%; H 7.91%; Cl 5.32%; F 5.69%.

Example 19

5-[(4-Chlorophenyl)sulfonyl]-5-(2,5-difluorophenyl)-1,9-nonanediol

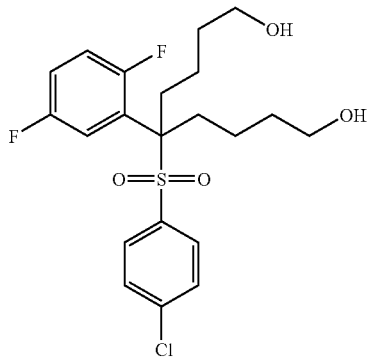

To a solution of 2-[5-(t-butyldimethylsilyloxy)-1-[4-(t-butyldimethylsilyloxy)butyl]-1-(4-chlorophenylsulfonyl)pentyl]-1,4-difluorobenzene (158 mg, 0.234 mmol) in tetrahydrofuran (4 ml) was added tetrabutylammonium fluoride (a 1M tetrahydrofuran solution, 0.702 ml, 0.702 mmol). The resulting mixture was stirred at room temperature for 24 hours. After concentration of the reaction mixture, the residue was dissolved in diethyl ether, followed by successive washing with water and brine, drying over MgSO$_4$, and concentration. The residue thus obtained was purified by medium-pressure chromatography on a silica gel column (5% methanol-methylene chloride) to yield a colorless solid. The resulting solid was recrystallized from ethyl acetate-hexane, whereby the title compound (97.0 mg, 93%) was obtained as a colorless solid.

Melting point: 107.0-108.5° C.

IR (ATR) ν: 3275, 2939, 1572, 1495, 1414, 1306, 1261, 1140, 1078, 1066, 847, 812, 754, 710, 679, 644, 606, 544, 474, 449 cm$^{-1}$.

$^1$H-NMR (400 MHz, CDCl$_3$) δ: 1.36-1.82(10H,m), 2.24-2.35(2H,m), 2.47-2.57(2H,m), 3.70(4H,t,J=5.9 Hz), 6.79 (1H,ddd,J=12.4,8.3,4.6 Hz), 6.97-7.08(2H,m), 7.29(2H,d, J=8.8 Hz), 7.34(2H,d,J=8.8 Hz).

MS (m/z): 447 (M$^+$+H).

HRMS (FAB) for C$_{21}$H$_{26}$ClF$_2$O$_4$S (M$^+$+H)

Calculated: 447.1208

Found: 447.1227

Elemental Analysis for C$_{21}$H$_{25}$ClF$_2$O$_4$S.0.25H$_2$O

Calculated: C 55.87%; H 5.69%; Cl 7.85%; F 8.42%; S 7.10%.

Analyzed: C 55.62%; H 5.40%; Cl 7.89%; F 8.58%; S 7.26%.

Example 20

2-[5-(t-Butyldimethylsilyloxy)-1-[(4-chlorophenyl) sulfonyl]-1-butylpentyl]-1,4-difluorobenzene

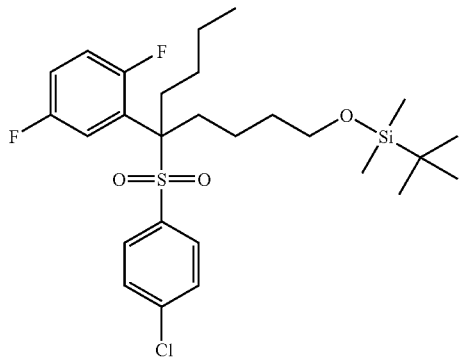

In an argon gas stream and at −78° C., n-butyl lithium (a 1.57M hexane solution, 0.287 ml, 0.450 mmol) was added to a tetrahydrofuran (4 ml) solution of the 2-[5-(t-butyldimethylsilyloxy)-1-[(4-chlorophenyl)sulfonyl]pentyl]-1,4-difluorobenzene (200 mg, 0.409 mmol) obtained in Example 15. The temperature of the resulting mixture was raised to room temperature. After cooling to −78° C., hexamethylphosphoric triamide (0.214 ml, 1.23 mmol) and iodobutane (51.1 μl, 0.450 mmol) were added dropwise to the reaction mixture. The resulting mixture was stirred at room temperature for 20 hours. Isopropanol (0.5 ml) was added to the reaction mixture, followed by concentration. The residue thus obtained was purified by medium-pressure chromatography on a silica gel column (5% ethyl acetate-hexane), whereby the title compound (163 mg, 73%) was obtained as a colorless oil.

IR (ATR) ν: 2954, 2929, 2858, 1583, 1495, 1473, 1412, 1394, 1311, 1255, 1192, 1147, 1090, 1014, 833, 756, 710, 677, 606 cm$^{-1}$.

$^1$H-NMR (400 MHz, CDCl$_3$) δ: 0.03(6H,s), 0.87(9H,s), 0.95(3H,t,J=7.4 Hz), 1.20-1.45(5H,m), 1.52-1.70(3H,m), 2.21-2.32(2H,m), 2.40-2.49(2H,m), 3.64(2H,t,J=6.1 Hz), 6.74-6.82(1H,m), 6.97-7.07(2H,m), 7.29(2H,d,J=8.8 Hz), 7.34 (2H,d,J=8.8 Hz).

MS (m/z): 545 (M$^+$).

HRMS (FAB) for C$_{27}$H$_{40}$ClF$_2$O$_3$SSi (M$^+$+H)

Calculated: 545.2124

Analyzed: 545.2087

Example 21

5-[(4-Chlorophenyl)sulfonyl]-5-(2,5-difluorophenyl)-1-nonanol

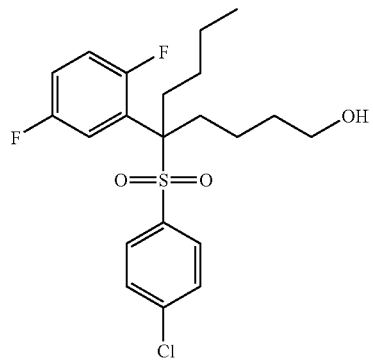

After addition of tetrabutylammonium fluoride (a 1M tetrahydrofuran solution, 0.532 ml, 0.532 mmol) to a solution of 2-[5-(t-butyldimethylsilyloxy)-1-[(4-chlorophenyl)sulfonyl]-1-butylpentyl]-1,4-difluorobenzene (154 mg, 0.283 mmol) in tetrahydrofuran (4 ml), the mixture was stirred at room temperature for 18 hours. The reaction mixture was then concentrated. The residue thus obtained was dissolved in diethyl ether, followed by successive washing with water and brine, drying over MgSO$_4$, and concentration. The residue thus obtained was purified by medium-pressure chromatography on a silica gel column (50% ethyl acetate-hexane), whereby the title compound (122 mg, 0.283 mmol) was obtained as a colorless oil.

IR (ATR) ν: 3539, 2958, 2873, 1583, 1495, 1412, 1308, 1277, 1192, 1146, 1090, 1014, 829, 758, 710, 675, 606, 548, 463 cm$^{-1}$.

$^1$H-NMR (400 MHz, CDCl$_3$) δ: 0.95(3H,t,J=7.3 Hz), 1.19-1.77(9H,m), 2.21-2.34(2H,m), 2.38-2.53(2H,m), 3.70(2H,br s), 6.75-6.83(1H,m), 6.98-7.08(2H,m), 7.29(2H,d,J=8.8 Hz), 7.34 (2H, d, J=8.8 Hz).

MS (m/z): 431 (M$^+$+H).

HRMS (EI): as C$_{21}$H$_{26}$ClF$_2$O$_3$S (M$^+$+H)

Calculated: 431.1259

Found: 431.1237

Example 22

1-[(4-Chlorophenyl)sulfonyl]-1-(2,5-difluorophenyl)-3-octanol (Isomer 22-A and Isomer 22-B)

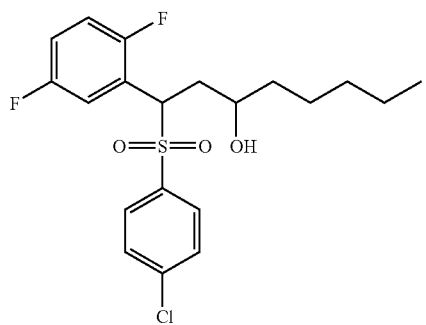

In an argon gas stream and at −78° C., n-butyl lithium (a 1.57M hexane solution, 0.701 ml, 1.10 mmol) was added to a tetrahydrofuran (5 ml) solution of the 2-[(4-chlorophenyl)

sulfonylmethyl]-1,4-difluorobenzene (303 mg, 1.00 mmol) obtained in Example 5. The temperature of the resulting mixture was raised to room temperature. After cooling to −78° C., a trifluoroborane-ether complex (0.133 ml, 1.05 mmol) and 1,2-epoxyheptane (0.163 ml, 1.20 mmol) were added dropwise to the reaction mixture. The mixture was stirred at room temperature for 2 days. Water was added to the reaction mixture, followed by extraction with diethyl ether. The extracts were combined, washed successively with a saturated aqueous solution of sodium bicarbonate, water and brine, dried over MgSO$_4$, and then concentrated. The residue thus obtained was purified by medium-pressure chromatography on a silica gel column (20% ethyl acetate-hexane), whereby a low-polarity isomer, an isomer mixture and a high-polarity isomer were obtained as a first fraction, a second fraction and a third fraction, respectively, each as a colorless solid. The low-polarity isomer and high-polarity isomer were recrystallized from hexane to yield the title Isomer 22-A (low-polarity) (98.0 mg, 24%), and the title Isomer 22-B (high-polarity) (199 mg, 48%), each as colorless needle crystals.

Isomer 22-A

Melting point: 84.0-84.5° C.

IR (ATR) ν: 3533, 2933, 2860, 1574, 1495, 1429, 1278, 1240, 1182, 1142, 1092, 1080, 1014, 962, 885, 829, 766, 737, 710, 681, 619, 526, 476 cm$^{-1}$.

$^1$H-NMR (400 MHz, CDCl$_3$) δ: 0.88(3H,t,J=6.8 Hz), 1.20-1.50(8H,m), 1.57(1H,d,J=5.1 Hz), 2.07(1H,ddd,J=14.7,8.1, 6.8 Hz), 2.70(1H,ddd,J=14.7,6.8,4.6 Hz), 3.93-4.01(1H,m), 4.85(1H,t,J=6.8 Hz), 6.77(1H,td,J=9.0, 4.4 Hz), 6.91-6.98 (1H,m), 7.24-7.30(1H,m), 7.36(2H,d,J=8.5 Hz), 7.51 (2H, d, J=8.5 Hz).

MS (m/z): 417 (M$^+$+H).
HRMS (FAB) for C$_{20}$H$_{24}$ClF$_2$O$_3$S (M$^+$+H)
Calculated: 417.1103
Analyzed: 417.1102

Elemental Analysis for C$_{20}$H$_{23}$ClF$_2$O$_3$S.0.25H$_2$O
Calculated: C 57.00%; H 5.62%; Cl 8.41%; F 9.02%; S 7.61%.
Analyzed: C 57.18%; H 5.38%; Cl 8.57%; F 9.22%; S 7.79%.

Isomer 22-B

Melting point: 123.0-123.5° C. IR (ATR) ν: 3502, 2925, 2858, 1583, 1496, 1410, 1304, 1275, 1213, 1184, 1149, 1086, 1045, 1014, 958, 910, 829, 796, 752, 725, 710, 627, 552, 503, 467 cm$^{-1}$.

$^1$H-NMR (400 MHz, CDCl$_3$) δ: 0.87 (3H,t,J=7.1 Hz), 1.20-1.60(9H,m), 2.21-2.30(1H,m), 2.41(1H,ddd, J=13.9, 10.5,3.4 Hz), 3.23-3.32(1H,m), 4.94(1H,dd,J=11.7, 2.9 Hz), 6.85(1H,td,J=9.0, 4.4 Hz), 6.96-7.03(1H,m), 7.23-7.29(1H, m), 7.39(2H,d,J=8.5 Hz), 7.55(2H,d,J=8.5 Hz).

MS (m/z) 417 (M$^+$+H).
HRMS (FAB) for C$_{20}$H$_{24}$ClF$_2$O$_3$S (M$^+$+H)
Calculated: 417.1103
Analyzed: 417.1122

Elemental Analysis for C$_{20}$H$_{23}$ClF$_2$O$_3$S.0.25H$_2$O
Calculated: C 57.00%; H 5.62%; Cl 8.41%; F 9.02%; S 7.61%.

Analyzed: C 57.16%; H 5.34%; Cl 8.55%; F 9.18%; S 7.82%.

Example 23

2-[5-Chloro-1-[(4-chlorophenyl)sulfonyl]pentyl]-1,4-difluorobenzene

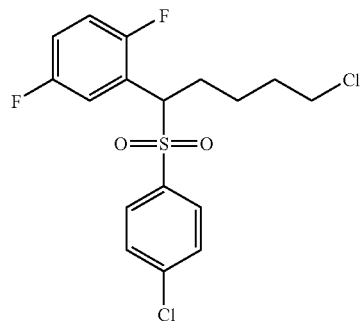

Under an argon atmosphere and at −78° C., n-butyl lithium (a 1.57M hexane solution, 3.52 ml) was added to a dimethoxyethane solution (30 ml) of the 2-[(4-chlorophenyl) sulfonylmethyl]-1,4-difluorobenzene (1.52 g, 5.02 mmol) obtained in Example 5. The temperature of the reaction mixture was elevated to room temperature, at which stirring was conducted for 15 minutes. After cooling the reaction mixture to −78° C., 4-chloro-1-iodobutane (672 μl, 5.52 mmol) was added thereto and the mixture was stirred at room temperature for 24 hours. A saturated ammonium chloride solution was added to the reaction mixture, followed by extraction with diethyl ether. The extracts were combined, washed successively with water, a saturated aqueous solution of sodium thiosulfate and brine, dried over MgSO$_4$, and then distilled under reduced pressure to remove the solvent. The residue thus obtained was recrystallized from hexane, whereby the title compound (1.64 g, 83%) was obtained as colorless needle crystals.

IR (ATR) ν: 2945, 1583, 1495, 1475, 1311, 1277, 1230, 1149, 1142, 1082, 1014, 872, 822, 793, 752, 708, 629, 557, 532, 465 cm$^{-1}$.

$^1$H-NMR (400 MHz, CDCl$_3$) δ: 1.33-1.48(2H,m), 1.72-1.87(2H,m), 2.08-2.18(1H,m), 2.43-2.52(1H,m), 3.44-3.53 (2H,m), 4.52(1H,ddd,J=11.5,3.9,1.2 Hz), 6.84(1H,td,J=9.0, 4.4 Hz), 6.96-7.02(1H,m), 7.23-7.28(1H,m), 7.39(2H,d, J=8.8 Hz), 7.53(2H,d,J=8.8 Hz).

MS (m/z): 393 (M$^+$+H).

Elemental Analysis for C$_{17}$H$_{16}$Cl$_2$F$_2$O$_2$S
Calculated: C 51.92%; H 4.10%; Cl 18.03%; F 9.66%; S 8.15%.
Found: C 51.33%; H 4.07%; Cl 17.64%; F 9.72%; S 8.25%.

Example 24

1-[5-[(4-Chlorophenyl)sulfonyl]-5-(2,5-difluorophenyl)pentyl]pyrrolidine Hydrochloride

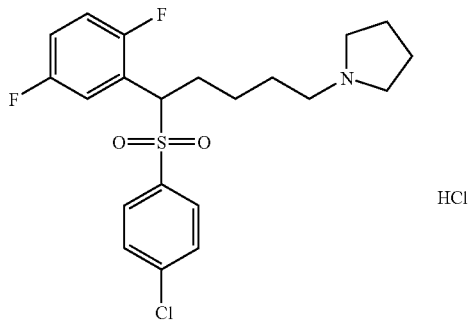

To a solution of 2-[5-chloro-1-[(4-chlorophenyl)sulfonyl]pentyl]-1,4-difluorobenzene (200 mg, 0.509 mmol) in acetonitrile (6 ml) were added pyrrolidine (213 μl, 2.55 mmol), potassium carbonate (73.7 mg, 0.534 mmol) and potassium iodide (15 mg). The resulting mixture was heated at 70° C. for 18 hours. The temperature of the reaction mixture was cooled back to room temperature. The residue thus obtained was partitioned between water and methylene chloride. After separation of the organic layer, the water layer was extracted with methylene chloride. The organic layer and the extract were combined, washed with water and brine, dried over $MgSO_4$, and then concentrated. The crude product thus obtained was subjected to a short column ($SiO_2$, methylene chloride-methanol, 10:1). The resulting oil was dissolved in ethanol. After addition of 1N hydrochloric acid-ethanol (2 ml) to the resulting solution, the mixture was concentrated. The solid substance thus obtained was recrystallized from ethyl acetate, whereby the title compound (128 mg, 54%) was obtained as a pale yellow solid.

Melting point: 167.0-170.5° C.

IR (ATR) ν: 2960, 2565, 2453, 1583, 1495, 1321, 1277, 1211, 1173, 1145, 1084, 1011, 879, 820, 787, 754, 721, 708, 627, 557, 540, 467 $cm^{-1}$.

$^1$H-NMR (400 MHz, $CDCl_3$) δ: 1.31-1.47(2H,m), 1.93-2.30(6H,m), 2.42-2.51(1H,m), 2.66-2.78(2H,m), 2.87-3.03 (2H,m), 3.76(2H,br s), 4.51(1H,dd,J=10.7, 4.4 Hz), 6.85(1H, td,J=8.8, 4.4 Hz), 6.96-7.03(1H,m), 7.22(1H,ddd,J=8.8,5.4, 3.2 Hz), 7.40(2H,d,J=8.3 Hz), 7.54(2H,d,J=8.3 Hz), 12.54 (1H,br s).

MS (m/z): 428 ($M^+$+H).

Elemental Analysis for $C_{21}H_{24}ClF_2NO_2S \cdot HCl$

Calculated: C 54.31%; H 5.43%; Cl 15.27%; F 8.18%; N 3.02%; S 6.90%.

Analyzed: C 54.19%; H 5.37%; Cl 15.07%; F 8.10%;N 3.21%; S 6.98%.

Example 25

Ethyl 3-[(4-chlorophenyl)sulfonyl]-3-(2,5-difluorophenyl)propionate

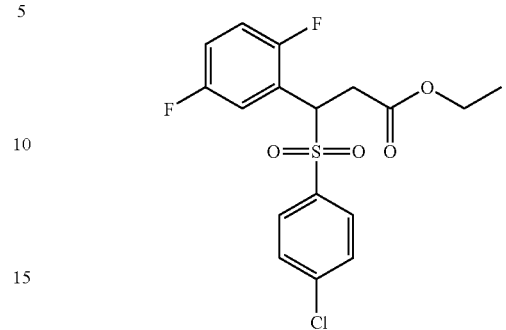

Under an argon atmosphere and at −78° C., n-butyl lithium (a 1.57M hexane solution, 7.01 ml) was added to a dimethoxyethane solution (50 ml) of the 2-[(4-chlorophenyl)sulfonylmethyl]-1,4-difluorobenzene (3.03 g, 10.0 mmol) obtained in Example 5. The temperature of the reaction mixture was raised to room temperature, at which stirring was conducted for 15 minutes. After cooling to −78° C., bromoethyl acetate (1.33 ml, 12.0 mmol) was added to the reaction mixture. The mixture was stirred at room temperature for 3 hours. To the reaction mixture was added a saturated ammonium chloride solution, followed by extraction with diethyl ether. The extracts were combined, washed successively with water, a saturated aqueous solution of sodium thiosulfate, and brine, dried over $MgSO_{41}$ and then distilled under reduced pressure to remove the solvent. The residue thus obtained was recrystallized from hexane, whereby the title compound (1.95 g, 50%) was obtained as colorless needle crystals.

Melting point: 99.5-100.5° C.

IR (ATR) ν: 3078, 2952, 1734, 1587, 1493, 1419, 1377, 1327, 1279, 1213, 1149, 1047, 1014, 829, 779, 754, 727, 611, 542, 453 $cm^{-1}$.

$^1$H-NMR ($CDCl_3$) δ: 1.15(3H,t,J=7.1 Hz), 3.08(1H,dd, J=16.6, 10.3 Hz), 3.46(1H,dd,J=16.6, 4.6 Hz), 3.99-4.12(2H, m), 5.06(1H,dd,J=10.3, 4.6 Hz), 6.85(1H,td,J=9.0, 4.4 Hz), 6.96-7.02(1H,m), 7.19(1H,ddd,J=8.6,5.4,3.2 Hz), 7.42(2H, d,J=8.8 Hz), 7.56(2H,d,J=8.8 Hz).

MS (m/z): 389 ($M^+$+H).

Elemental Analysis for $C_{17}H_{15}ClF_2O_4S$

Calculated: C 52.51%; H 3.89%; Cl 9.12%; F 9.77%; S 8.25%.

Found: C 52.33%; H 3.86%; Cl 9.10%; F 9.88%; S 8.37%.

Example 26

2-[1-[(4-Chlorophenyl)sulfonyl]-5-(methylthio)pentyl]-1,4-difluorobenzene

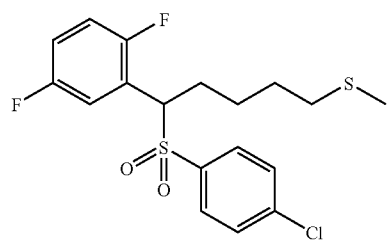

The 2-[(4-chlorophenyl)sulfonylmethyl]-1,4-difluorobenzene (0.94 g, 3.1 mmol) obtained in Example 5 was dissolved in toluene (15 ml). After addition of 4-(methylthio)-1-butanol (0.25 ml, 2.1 mmol) and cyanomethylenetri-n-butylphosphorane (1.0 g, 4.1 mmol), the resulting mixture was heated under reflux for 14 hours under an argon atmosphere. The reaction mixture was allowed to cool down. Then, 4-(methylthio)-1-butanol (0.25 ml, 2.1 mmol) was added, followed by heating under reflux for 6 hours under an argon atmosphere. The reaction mixture was allowed to cool down and then, concentrated under reduced pressure. The residue thus obtained was purified by silica gel chromatography (hexane:ethyl acetate=10:1) to yield a colorless oil. The resulting colorless oil was solidified with hexane, whereby the title compound (0.55 g, 44%) was obtained as a white powder.

Melting point: 103-106° C.

IR (ATR) ν: 3066, 2960, 2935, 1583, 1493, 1147, 1082, 1012, 893, 829, 752, 625, 542, 465 cm$^{-1}$.

$^1$H-NMR (400 MHz, CDCl$_3$) δ: 1.23-1.45(2H,m), 1.50-1.75(2H,m), 2.04(3H,s), 2.04-2.20(1H,m), 2.35-2.60(3H,m), 4.52(1H,dd,J=11.5, 2.4 Hz), 6.78-6.88(1H,m), 6.95-7.01(1H,m), 7.20-7.30(1H,m), 7.38(2H,dm,J=8.4 Hz), 7.53(2H,dm, J=8.4 Hz). MS (m/z): 405, 407 (M$^+$+H).

HRMS (FAB) for C$_{18}$H$_{20}$ClF$_2$O$_2$S$_2$ (M$^+$+H)
Calculated: 405.0561
Found: 405.0581

Example 27

2-[1-[(4-Chlorophenyl)sulfonyl]-5-(methylsulfonyl)pentyl]-1,4-difluorobenzene (Compound A) and 2-[1-[(4-chlorophenyl)sulfonyl]-5-(methylsulfinyl)pentyl]-1,4-difluorobenzene (Compound B)

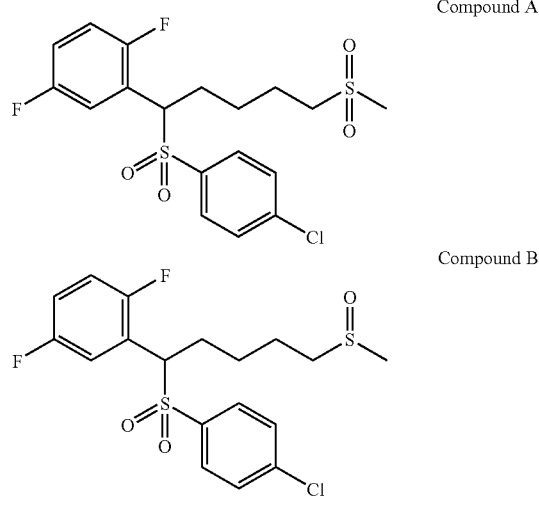

Compound A

Compound B

In methylene chloride (30 ml) was dissolved 2-[1-[(4-chlorophenyl)sulfonyl]-5-(methylthio)pentyl]-1,4-difluorobenzene (500 mg, 1.23 mmol). Under ice cooling, 3-chloroperbenzoic acid (340 mg, 1.97 mmol) was added to the resulting solution. The mixture was stirred at room temperature for 14 hours. After concentration of the reaction mixture under reduced pressure, the residue was subjected to silica gel chromatography. From the fraction eluted with hexane:ethyl acetate=10:1, a white solid was obtained. The solid was then washed with diethyl ether/methylene chloride to yield the title compound A (211 mg, 39%) as a white powder. Further, from the fraction eluted with the methylene chloride:methanol=40:1, a white solid was obtained. The solid was washed with diethyl ether/methylene chloride, whereby the title compound B (144 mg, 39%) was obtained as a white powder.

Compound A

Melting point: 145-148° C.

IR (ATR) ν: 1496, 1317, 1292, 1273, 1149, 1124, 1086, 829, 756, 631, 544, 523, 499, 478, 465 cm$^{-1}$.

$^1$H-NMR (400 MHz, CDCl$_3$) δ: 1.38-1.70(2H,m), 1.80-2.00(2H,m), 2.05-2.22(1H,m), 2.45-2.60(1H,m), 2.88(3H,s), 2.96(2H,tm,J=7.0 Hz), 4.51(1H,dm,J=7.6 Hz), 6.80-6.90(1H,m), 6.95-7.05(1H,m), 7.20-7.35(1H,m), 7.39(2H,d, J=8.7 Hz), 7.53(2H,d,J=8.7 Hz).

MS (m/z): 437, 439(M$^+$+H).

Elemental Analysis for C$_{18}$H$_{19}$ClF$_2$O$_4$S$_2$
Calculated: C 49.48%; H 4.38%; Cl 8.11%;F 8.70%; S 14.68%.
Found: C 49.50%; H 4.28%; Cl 8.05%; F 8.77%; S 14.70%.

Compound B

Melting point: 126-129° C.

IR (ATR) ν: 1495, 1475, 1277, 1147, 1086, 1012, 833, 752, 625, 540, 465 cm$^{-1}$.

$^1$H-NMR (400 MHz, CDCl$_3$) δ: 1.32-1.70(2H,m), 1.75-1.93(2H,m), 2.08-2.22(1H,m), 2.46-2.75(3H,m), 2.54(3H,S), 4.52(1H,dd,J=11.4, 2.4 Hz), 6.80-6.90(1H,m), 6.94-7.04(1H,m), 7.20-7.30(1H,m), 7.39(2H,dd,J=8.5, 1.8 Hz), 7.53(2H,dd,J=8.5, 2.7 Hz).

MS (m/z): 421, 423 (M$^+$+H).

Elemental Analysis for C$_{18}$H$_{19}$ClF$_2$O$_3$S$_2$
Calculated: C 51.36%; H 4.55%; Cl 8.42%; F 9.03%; S 15.24%.
Found: C 51.36%; H 4.49%; Cl 8.35%; F 9.00%; S 15.24%.

Example 28

2-[1-[(4-Chlorophenyl)sulfonyl]-5-vinyloxypentyl]-1,4-difluorobenzene

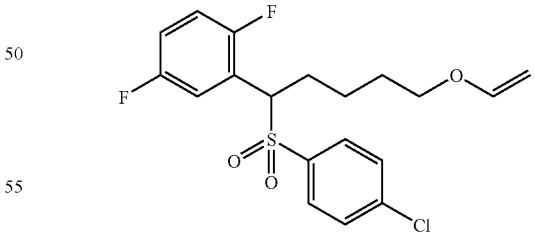

The 2-[(4-chlorophenyl)sulfonylmethyl]-1,4-difluorobenzene (0.94 g, 3.1 mmol) obtained in Example 5 was dissolved in toluene (30 ml). After addition of 4-vinyloxy-1-butanol (0.51 ml, 4.2 mmol) and cyanomethylenetri-n-butylphosphorane (1.0 g, 4.1 mmol), the resulting mixture was heated under reflux for 3 days under an argon atmosphere. The reaction mixture was allowed to cool down and then concentrated under reduced pressure. The residue thus obtained was purified by silica gel chromatography (hexane:ethyl acetate=10:

1) to yield a white solid. The resulting white solid was washed with hexane, whereby the title compound (0.97 g, 78%) was obtained as a white powder.

Melting point: 54-56° C.

IR (ATR) ν: 2943, 1618, 1495, 1475, 1308, 1198, 1147, 1080, 1012, 962, 899, 829, 750, 623, 559, 544, 467 cm$^{-1}$.

$^1$H-NMR (400 MHz, CDCl$_3$) δ: 1.25-1.45(2H,m), 1.55-1.80(2H,m), 2.05-2.22(1H,m), 2.40-2.55(1H,m), 3.62(2H,t, J=6.2 Hz), 3.96(1H,dd,J=6.8, 2.1 Hz), 4.12(1H,dd,J=14.4, 2.1 Hz), 4.53(1H,dd,J=11.5, 2.7 Hz), 6.39(1H,dd,J=14.4, 6.8 Hz), 6.80-6.90(1H,m), 6.95-7.04(1H,m), 7.20-7.30(1H,m), 7.39(2H,d,J=8.6 Hz), 7.54(2H,d,J=8.6 Hz).

MS (m/z): 418, 420 (M$^+$+NH$_4$).

Elemental Analysis for C$_{19}$H$_{19}$ClF$_2$O$_3$S

Calculated: C 56.93%; H 4.78%; Cl 8.84%; F 9.48%; S 8.00%.

Found: C 56.98%; H 4.83%; Cl 8.78%; F 9.51%; S 8.13%.

Example 29

5-[(4-Chlorophenyl)sulfonyl]-5-(2,5-difluorophenyl)-1-pentanol

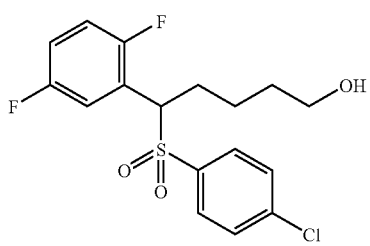

In methanol (30 ml) was dissolved 2-[1-[(4-chlorophenyl)sulfonyl]-5-vinyloxypentyl]-1,4-difluorobenzene (0.90 g, 2.3 mmol). After addition of p-toluenesulfonic acid monohydrate (20 mg, 0.11 mmol), the resulting mixture was stirred at room temperature for 14 hours. The reaction mixture was concentrated under reduced pressure. The residue was purified by silica gel chromatography (hexane:ethyl acetate=3:2) to yield a white solid. The resulting white solid was washed with diisopropyl ether, whereby the title compound (0.73 g, 85%) was obtained as a white powder.

Melting point: 84-86° C.

IR (ATR) ν: 3325, 2941, 2866, 1583, 1496, 1313, 1151, 1084, 825, 752, 629, 534 cm$^{-1}$.

$^1$H-NMR (400 MHz, CDCl$_3$) δ: 1.18-1.29(1H,m), 1.29-1.40(2H,m), 1.40-1.70(2H,m), 2.08-2.22(1H,m), 2.42-2.55 (1H,m), 3.55-3.67(2H,m), 4.53(1H,dd,J=11.4, 3.8 Hz), 6.78-6.88(1H,m), 6.93-7.03(1H,m), 7.20-7.30(1H,m), 7.39(2H,d, J=8.5 Hz), 7.53(2H,d,J=8.5 Hz).

MS (m/z): 375, 377 (M$^+$+H).

Elemental Analysis for C$_{17}$H$_{17}$ClF$_2$O$_3$S.0.25H$_2$O

Calculated: C 53.83%; H 4.65%; Cl 9.35%; F 10.02%; S 8.45%.

Found: C 53.73%; H 4.63%; Cl 9.35%; F 10.03%; S 8.55%.

Example 30

2-[1-[(4-Chlorophenyl)sulfonyl]cyclopentyl]-1,4-difluorobenzene

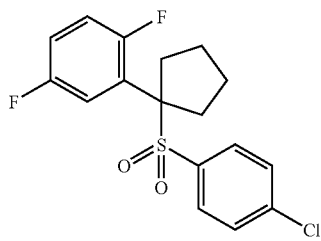

In toluene (10 ml) was dissolved 5-[(4-chlorophenyl)sulfonyl]-5-(2,5-difluorophenyl)-1-pentanol (100 mg, 0.267 mmol). After addition of cyanomethylenetri-n-butylphosphorane (130 mg, 0.539 mmol), the mixture was heated under reflux for 2 days under an argon atmosphere. The reaction mixture was allowed to cool down and then, added with cyanomethylenetri-n-butylphosphorane (130 mg, 0.539 mmol). The mixture was heated under reflux for 3 days under an argon atmosphere. The reaction mixture was allowed to cool down and then concentrated under reduced pressure. The residue thus obtained was purified by silica gel chromatography (hexane:ethyl acetate=15:1) to yield a white solid. The resulting white solid was washed with hexane, whereby the title compound (35 mg, 37%) was obtained as a white powder.

Melting point: 153-155° C.

IR (ATR) ν: 2968, 1581, 1489, 1304, 1277, 1138, 1082, 827, 752, 606, 569, 519, 467 cm$^{-1}$.

$^1$H-NMR (400 MHz, CDCl$_3$) δ: 1.70-1.85 (2H,m), 2.05-2.20 (2H,m), 2.22-2.35(2H,m), 2.88-3.00(2H,m), 6.75-6.83 (1H,m), 6.95-7.05(2H,m), 7.35(4H,s).

MS (m/z): 374, 376(M$^+$+NH$_4$).

Elemental Analysis for C$_{17}$H$_{15}$ClF$_2$O$_2$S

Calculated: C 57.22%; H 4.24%; Cl 9.94%; F 10.65%; S 8.99%.

Found: C 56.87%; H 4.14%; Cl 10.28%; F 10.44%; S 9.05%.

Example 31

2-[6-(t-Butyldimethylsilyloxy)-1-[(4-chlorophenyl)sulfonyl]hexyl]-1,4-difluorobenzene

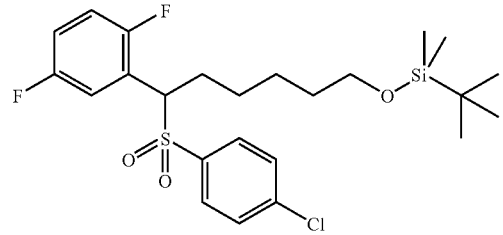

In toluene (30 ml) was dissolved the 2-[(4-chlorophenyl)sulfonylmethyl]-1,4-difluorobenzene (0.94 g, 3.1 mmol) obtained in Example 5, followed by the addition of 5-(t-butyldimethylsilyloxy)-1-pentanol (1.1 ml, 4.6 mmol) and cyanomethylenetri-n-butylphosphorane (1.0 g, 4.1 mmol).

The resulting mixture was heated under reflux for 14 hours under an argon atmosphere. The reaction mixture was allowed to cool down and then concentrated under reduced pressure. The residue thus obtained was purified by silica gel chromatography (hexane:ethyl acetate=15:1), whereby the title compound (1.4 g, 87%) was obtained as a colorless oil.

IR (ATR) ν: 2929, 2856, 1583, 1496, 1325, 1151, 1088, 835, 775, 754, 629 cm$^{-1}$.

$^1$H-NMR (400 MHz, CDCl$_3$) δ: 0.01(6H,s), 0.86(9H,s), 1.18-1.60(6H,m), 2.04-2.17(1H,m), 2.38-2.50(1H,m), 3.54 (2H,t,J=6.1 Hz), 4.53(1H,dd,J=11.5, 2.7 Hz), 6.78-6.88(1H, m), 6.93-7.03(1H,m), 7.20-7.30(1H,m), 7.38(2H,d,J=8.5 Hz), 7.53(2H,d,J=8.5 Hz).

MS (m/z): 503, 505 (M$^+$+H).

Example 32

6-[(4-Chlorophenyl)sulfonyl]-6-(2,5-difluorophenyl)-1-hexanol

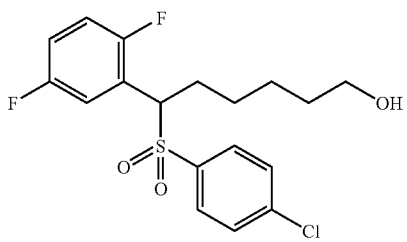

In tetrahydrofuran (30 ml) was dissolved 2-[6-(t-butyldimethylsilyloxy)-1-[(4-chlorophenyl)sulfonyl]hexyl]-1,4-difluorobenzene (0.70 g, 1.4 mmol). Under ice cooling, a tetrahydrofuran solution (1.0M, 4.2 ml, 4.2 mmol) of tetrabutylammonium fluoride was added and the mixture was stirred at room temperature for 1 hour. After addition of water (1.0 ml) to the reaction mixture, the mixture was concentrated under reduced pressure. The residue thus obtained was purified by silica gel chromatography (hexane:ethyl acetate=3:2) to yield a white solid. The resulting white solid was washed with hexane, whereby the title compound (0.47 g, 86%) was obtained as a white powder.

Melting point: 98-99° C.

IR (ATR) ν: 3575, 2929, 1495, 1279, 1146, 1082, 1014, 833, 752, 627, 541, 467 cm$^{-1}$.

$^1$H-NMR (400 MHz, CDCl$_3$) δ: 1.18-1.62(7H,m), 2.04-2.18(1H,m), 2.40-2.53(1H,m), 3.59(2H,dd,J=11.5, 6.4 Hz), 4.52(1H,dd,J=11.5, 2.7 Hz), 6.78-6.88(1H,m), 6.94-7.04(1H, m), 7.20-7.30(1H,m), 7.38(2H,d,J=8.4 Hz), 7.53(2H,d,J=8.4 Hz).

MS (m/z): 389, 391 (M$^+$+H).

Elemental Analysis for C$_{18}$H$_{19}$ClF$_2$O$_3$S

Calculated: C 55.60%; H 4.92%; Cl 9.12%; F 9.77%; S 8.25%.

Found: C 55.38%; H 4.75%; Cl 9.09%; F 9.81%; S 8.34%.

Example 33

2-[1-[(4-Chlorophenyl)sulfonyl]cyclohexyl]-1,4-difluorobenzene

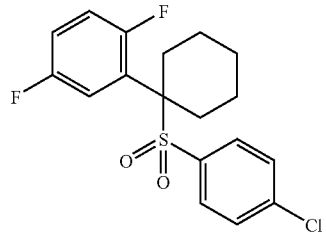

In toluene (20 ml) was dissolved 6-[(4-chlorophenyl)sulfonyl]-6-(2,5-difluorophenyl)-1-hexanol (200 mg, 0.514 mmol). After addition of cyanomethylenetri-n-butylphosphorane (500 mg, 2.07 mmol), the resulting mixture was heated under reflux for 4 days under an argon atmosphere. The reaction mixture was allowed to cool down and then concentrated under reduced pressure. The residue thus obtained was purified by silica gel chromatography (hexane:ethyl acetate=20:1) to yield a white solid. The resulting solid was washed with hexane/methylene chloride, whereby the title compound (97 mg, 51%) was obtained as a white powder.

Melting point: 137-139° C.

IR (ATR) ν: cm$^{-1}$. 2933, 2862, 1495, 1309, 1144, 1082, 885, 814, 750, 619, 559, 464 cm$^{-1}$.

$^1$H-NMR (400 MHz, CDCl$_3$) δ: 1.10-1.45(3H,m), 1.61 (1H,dm,J=12.0 Hz), 1.81(2H,br d,J=13.4 Hz), 2.09(2H,br t,J=13.0 Hz), 2.55-2.95(2H,m), 6.84(1H,ddd,J=12.2,9.0,4.9 Hz), 7.00-7.11(2H,m), 7.36(2H,s), 7.36(2H,s).

MS (m/z): 388, 390 (M$^+$+NH$_4$).

Elemental Analysis for C$_{18}$H$_{17}$ClF$_2$O$_3$S

Calculated: C 58.30%; H 4.62%; Cl 9.56%; F 10.25%; S 8.65%.

Found: C 58.01%; H 4.49%; Cl 9.58%; F 10.35%; S 8.82%.

Example 34

2-[1-[(4-Chlorophenyl)sulfonyl]-3-(2-vinyloxyethoxy)propyl]-1,4-difluorobenzene

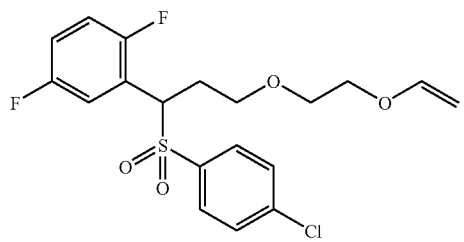

In toluene (30 ml) was dissolved the 2-[(4-chlorophenyl) sulfonylmethyl]-1,4-difluorobenzene (520 mg, 1.72 mmol) obtained in Example 5. After addition of 2,2-(2-vinyloxyethoxy)ethanol (0.270 ml, 2.10 mmol) and cyanomethylenetri-n-butylphosphorane (500 mg, 2.07 mmol), the mixture was heated under reflux for 24 hours under an argon atmosphere. The reaction mixture was then allowed to cool down.

After addition of 2-(2-vinyloxyethoxy)-ethanol (0.170 ml, 1.25 mmol) and cyanomethylenetri-n-butylphosphorane (300 mg, 1.24 mmol), the mixture was heated under reflux for 12 hours under an argon atmosphere. The reaction mixture was allowed to cool down and then concentrated under reduced pressure. The residue thus obtained was purified by silica gel chromatography (hexane:ethyl acetate=7:1) to yield a white solid. The resulting white solid was washed with hexane, whereby the title compound (140 mg, 20%) was obtained as a white powder.

Melting point: 55-56° C.

IR (ATR) ν: 2927, 2877, 1621, 1496, 1323, 1198, 1144, 1084, 1012, 829, 752, 633, 542, 469 cm$^{-1}$.

$^1$H-NMR (400 MHz, CDCl$_3$) δ: 2.20-2.35(1H,m), 2.70-2.85 (1H,m), 3.28(1H,td,J=9.5, 4.6 Hz), 3.40-3.50(1H,m), 3.54-3.68(2H,m), 3.71(2H,t,J=4.6 Hz), 3.99(1H,dd,J=6.7, 2.1 Hz), 4.14(1H,dd,J=14.3, 2.1 Hz), 4.81(1H,dd,J=10.9, 4.0 Hz), 6.41(1H,dd,J=14.3, 6.7 Hz), 6.84(1H,td,J=9.0, 4.4 Hz), 6.94-7.04(1H,m), 7.18-7.30(1H,m), 7.39(2H,dm,J=8.3 Hz), 7.56(2H,dm,J=8.3 Hz).

MS (m/z): 417, 419 (M$^+$+H).

Elemental Analysis for C$_{19}$H$_{19}$ClF$_2$O$_4$S

Calculated: C 54.74%; H 4.59%; Cl 8.50%; F 9.11%; S 7.69%.

Found: C 54.54%; H 4.46%; Cl 8.46%; F 9.02%; S 7.81%.

Example 35

2-[3-[(4-Chlorophenyl)sulfonyl]-3-(2,5-difluorophenyl)propoxy]ethanol

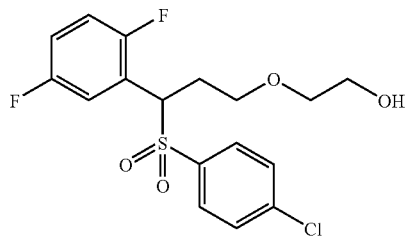

In methanol (10 ml) was dissolved 2-[1-[(4-chlorophenyl)sulfonyl]-3-(2-vinyloxyethoxy)propyl]-1,4-difluorobenzene (123 mg, 0.295 mmol). P-toluenesulfonic acid monohydrate (2.0 mg, 0.011 mmol) was added and the mixture was stirred at room temperature for 4 hours. After concentration under reduced pressure, the residue was purified by silica gel chromatography (methylene chloride:methanol=50:1) to yield a white solid. The resulting white solid was washed with hexane, whereby the title compound (80 mg, 70%) was obtained as a white powder.

Melting point: 41-46° C.

IR (ATR) ν: 3467, 2943, 1495, 1315, 1149, 1086, 1061, 829, 762, 521 cm$^{-1}$.

$^1$H-NMR (400 MHz, CDCl$_3$) δ: 1.78-1.80(1H,m), 2.22-2.36(1H,m), 2.75-2.88(1H,m), 3.20-3.40(2H,m), 3.42-3.52 (1H,m), 3.57-3.73(3H,m), 4.81(1H,dd,J=10.9, 3.8 Hz), 6.84 (1H,td,J=9.0, 4.4 Hz), 6.94-7.04(1H,m), 7.22-7.30(1H,m), 7.39(2H,dm,J=8.4 Hz), 7.55(2H,dm,J=8.4 Hz).

MS (m/z): 391, 393 (M$^+$+H).

Elemental Analysis for C$_{17}$H$_{17}$ClF$_2$O$_4$S

Calculated: C 52.24%; H 4.38%; Cl 9.07%; F 9.72%; S 8.20%.

Found: C 52.12%; H 4.36%; Cl 9.11%; F 9.86%; S 8.32%.

Example 36

2-[[(4-Chlorophenyl)sulfonyl](cylcohexyl)methyl]-1,4-difluorobenzene

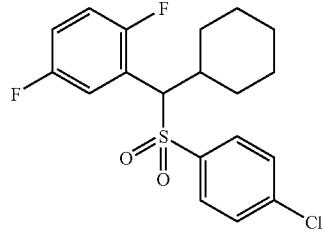

The 2-[(4-chlorophenyl)sulfonylmethyl]-1,4-difluorobenzene (240 mg, 0.793 mmol) obtained in Example 5 was dissolved in toluene (20 ml). To the resulting solution were added cyclohexanol (0.11 ml, 1.0 mmol) and cyanomethylenetri-n-butylphosphorane (250 mg, 1.0 mmol). The resulting mixture was heated under reflux for 14 hours under an argon atmosphere. The reaction mixture was allowed to cool down and then, added with cyclohexanol (0.22 ml, 2.1 mmol) and cyanomethylenetri-n-butylphosphorane (500 mg, 2.08 mmol). The mixture was heated under reflux for 14 hours under an argon atmosphere. After the reaction mixture was allowed to cool down and concentrated under reduced pressure, the residue thus obtained was purified by silica gel chromatography (hexane:ethyl acetate=30:1) to yield a white solid. The resulting white solid was washed with hexane, whereby the title compound (188 mg, 62%) was obtained as a white powder.

Melting point: 107-109° C.

IR (ATR) ν: 2927, 2858, 1495, 1240, 1138, 1080, 874, 831, 796, 750, 708, 615, 548, 507, 469, 444 cm$^{-1}$.

$^1$H-NMR (400 MHz, CDCl$_3$) δ: 0.92-1.08(1H,m), 1.08-1.22(1H,m), 1.22-1.50(3H,m), 1.60-1.75(3H,m), 1.75-1.88 (1H,m), 2.37(1H,br d,J=12.5 Hz), 2.48-2.62(1H,m), 4.44 (1H,d,J=7.6 Hz), 6.68-6.80(1H,m), 6.86-6.95(1H,m), 7.30 (2H,dm,J=8.6 Hz), 7.38-7.52(1H,m), 7.49(2H,dm,J=8.6 Hz).

MS (m/z): 402, 404 (M$^+$+NH$_4$).

Elemental Analysis for C$_{19}$H$_{19}$ClF$_2$O$_2$S

Calculated: C 59.29%; H 4.98%; Cl 9.21%; F 9.87%; S 8.33%.

Found: C 59.11%; H 4.93%; Cl 9.18%; F 9.82%; S 8.49%.

Example 37

2-[6-Bromo-1-[(4-chlorophenyl)sulfonyl]hexyl]-1,4-difluorobenzene

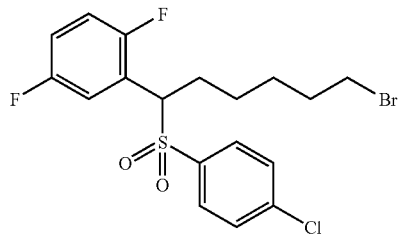

Sodium hydride (60% dispersion in oil, 15 mg, 0.38 mmol) was added to tetrahydrofuran (10 ml). Under ice cooling, the 2-[(4-chlorophenyl)sulfonylmethyl]-1,4-difluorobenzene (100 mg, 0.330 mmol) obtained in Example 5 was added.

After stirring the reaction mixture at room temperature for 30 minutes, 1,5-dibromopentane (0.10 ml, 0.74 mmol) was added. The reaction mixture was stirred at room temperature for 3 days, followed by the addition of sodium hydride (60% dispersion in oil, 15 mg, 0.38 mmol) under ice cooling. The resulting mixture was stirred at room temperature for 15 minutes and then added with 1,5-dibromopentane (0.10 ml, 0.74 mmol). The mixture was stirred at room temperature for 14 hours and then concentrated under reduced pressure. The residue thus obtained was purified by silica gel chromatography (hexane:ethyl acetate=10:1) to yield a white solid. The resulting white solid was washed with hexane, whereby the title compound (51 mg, 30%) was obtained as a white powder.

Melting point: 77-79° C.

IR (ATR) ν: 2937, 1495, 1147, 1084, 1014, 893, 833, 795, 752, 708, 627, 559, 536, 465 $cm^{-1}$.

$^{1}$H-NMR (400 MHz, $CDCl_3$) δ: 1.20-1.35(2H,m), 1.37-1.55(2H,m), 1.74-1.88(2H,m), 2.05-2.20(1H,m), 2.40-2.53(1H,m), 3.34(2H,td,J=6.6, 1.3 Hz), 4.51(1H,dd,J=11.5, 2.7 Hz), 6.83(1H,td,J=9.0, 4.6 Hz), 6.94-7.04(1H,m), 7.20-7.30(1H,m), 7.38(2H,d,J=8.7 Hz), 7.53(2H,d,J=8.7 Hz).

MS (m/z): 468, 470 ($M^{+}+NH_4$).

Elemental Analysis for $C_{18}H_{18}BrClF_2O_2S$

Calculated: C 47.86%; H 4.02%; Br 17.69%; Cl 7.85%; F 8.41%; S 7.10%.

Found: C 47.80%; H 3.83%; Br 17.67%; Cl 7.86%; F 8.65%; S 7.25%.

Referential Example 2

4-(t-Butyldiphenylsilyloxy)-1-methyl-1-butanol

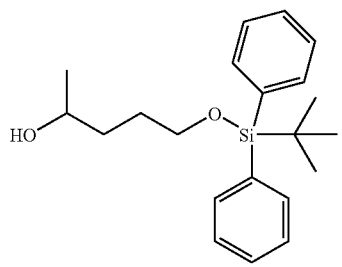

In N,N-dimethylformamide (200 ml) were dissolved 1,4-pentanediol (10.0 g, 96.0 mmol) and imidazole (6.6 g, 96.9 mmol). Under ice cooling, t-butyl chlorodiphenylsilane (25.2 ml, 96.4 mmol) was added dropwise. After completion of the dropwise addition, the reaction mixture was stirred at room temperature for 2 days. To the reaction mixture was added diethyl ether, followed by washing with water. The organic layer was dried over anhydrous magnesium sulfate. After filtration, the residue obtained by concentrating the filtrate under reduced pressure was purified by silica gel chromatography (hexane:ethyl acetate=5:1), whereby the title compound (32.0 g, 97%) was obtained as a colorless oil.

IR (ATR) ν: 3350, 2929, 2856, 1427, 1105, 822, 739, 698, 609, 501 $cm^{-1}$.

$^{1}$H-NMR (400 MHz, $CDCl_3$) δ: 1.05(9H,S), 1.19(3H,d, J=6.3 Hz), 1.46-1.72(4H,m), 2.02-2.08(1H,m), 3.69(2H,t, J=6.0 Hz), 3.78-3.90(1H,m), 7.30-7.50(6H,m), 7.62-7.88(4H,m). MS (m/z): 343 ($M^{+}+H$).

Example 38

2-[5-(t-Butyldiphenylsilyloxy)-1-[(4-chlorophenyl)sulfonyl]-2-methylpentyl]-1,4-difluorobenzene (Isomer 38-A and Isomer 38-B)

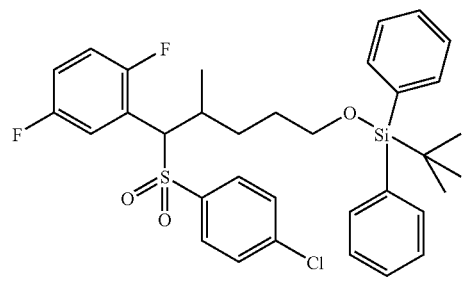

The 2-[(4-chlorophenyl)sulfonylmethyl]-1,4-difluorobenzene (0.94 g, 3.1 mmol) obtained in Example 5 was dissolved in toluene (30 ml), followed by the addition of 4-(t-butyldiphenylsilyloxy)-1-methyl-1-butanol (1.40 g, 4.1 mmol) and cyanomethylenetri-n-butylphosphorane (1.0 g, 4.1 mmol). The resulting mixture was heated under reflux for 2 days under an argon atmosphere. The reaction mixture was allowed to cool down and then, cyanomethylenetri-n-butylphosphorane (1.0 g, 4.1 mmol) was added thereto. Under an argon atmosphere, the resulting mixture was heated under reflux for 3 days. After the reaction mixture was allowed to cool down, the residue obtained by concentrating the mixture under reduced pressure was purified by silica gel chromatography (hexane:ethyl acetate=60:1), whereby the title Isomer 38-A (low-polarity) (0.71 g, 37%) and the title isomer 38-B (high-polarity) (0.45 g, 23%) were obtained, each as a colorless oil.

Isomer 38-A

IR (ATR) ν: 2931, 2858, 1495, 1322, 1149, 1109, 1088, 1012, 822, 752, 700, 613, 503, 488, 469 $cm^{-1}$.

$^{1}$H-NMR (400 MHz, $CDCl_3$) δ: 1.02(9H,s), 1.09(3H,d, J=6.8 Hz), 1.26-1.42(1H,m), 1.50-1.80(3H,m), 2.74-2.86(1H,m), 3.64(2H,t,J=5.7 Hz), 4.51(1H,d,J=5.6 Hz), 6.78(1H, td,J=9.1, 4.6 Hz), 6.90-7.00(1H,m), 7.30-7.48(8H,m), 7.50-7.58(3H,m), 7.60-7.70(4H,m).

MS (m/z): 627 ($M^{+}+H$)

Isomer 38-B

IR (ATR) ν: 2931, 2858, 1495, 1147, 1107, 1088, 822, 752, 729, 700, 613, 559, 503, 471 $cm^{-1.}$ $^{1}$H-NMR (400 MHz, $CDCl_3$) δ: 0.94(9H,s), 1.00-1.20(1H, m), 1.37(3H,d,J=6.8 Hz), 1.40-1.64(3H,m), 2.60-2.74(1H, m), 3.48-3.60(2H,m), 4.43(1H,br d,J=9.3 Hz), 6.69(1H,td, J=9.0, 4.4 Hz), 6.84-6.93(1H,m), 7.24-7.45(9H,m), 7.48(2H, d,J=8.6 Hz), 7.52-7.62(4H,m).

MS (m/z): 627 ($M^{+}+H$).

Example 39

5-[(4-Chlorophenyl)sulfonyl]-5-(2,5-difluorophenyl)-4-methyl-1-pentanol

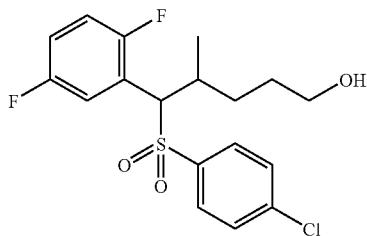

The 2-[5-(t-butyldiphenylsilyloxy)-1-[(4-chlorophenyl)sulfonyl]-2-methylpentyl]-1,4-difluorobenzene (Isomer 38-A) (710 mg, 1.13 mmol) obtained in Example 38 was dissolved in methylene chloride (20 ml). Under ice cooling, hydrogen fluoride-pyridine (0.64 ml) was added dropwise. After completion of the dropwise addition, the reaction mixture was stirred at room temperature for 14 hours. To the reaction mixture was added a saturated aqueous solution (20 ml) of sodium bicarbonate, followed by extraction with diethyl ether. The organic layer was washed successively with 1N hydrochloric acid, a saturated aqueous solution of sodium bicarbonate and brine, and dried over anhydrous magnesium sulfate. After filtration, the filtrate was concentrated under reduced pressure. The residue thus obtained was purified by silica gel chromatography (hexane:ethyl acetate=2:1) to yield a colorless oil. The resulting colorless oil was solidified with hexane, whereby the title compound (283 mg, 64%) was obtained as a white powder.

Melting point: 84-86° C.

IR (ATR) ν: 3367, 2937, 1496, 1138, 1084, 1051, 1012, 829, 754, 729, 708, 621, 561, 532, 471 cm$^{-1}$.

$^1$H-NMR (400 MHz, CDCl$_3$) δ: 1.07(3H,d,J=6.8 Hz), 1.40-1.85(5H,m), 2.75-2.90(1H,m), 3.64-3.75(2H,m), 4.54 (1H,d,J=6.6 Hz), 6.77(1H,td,J=9.0, 4.4 Hz), 6.90-7.00(1H, m), 7.33(2H,d,J=8.4 Hz), 7.43-7.60(1H,m), 7.51(2H,d,J=8.4 Hz).

MS (m/z): 389, 391 (M$^+$+H).

Elemental Analysis for C$_{18}$H$_{19}$ClF$_2$O$_3$S

Calculated: C 55.60%; H 4.92%; Cl 9.12%; F 9.77%; S 8.25%.

Found: C 55.42%; H 4.83%; Cl 9.10%; F 9.85%; S 8.30%.

Example 40

5-[(4-Chlorophenyl)sulfonyl]-5-(2,5-difluorophenyl)-4-methyl-1-pentanol

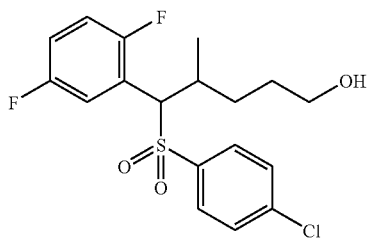

The 2-[5-(t-butyldiphenylsilyloxy)-1-[(4-chlorophenyl)sulfonyl]-2-methylpentyl]-1,4-difluorobenzene (Isomer 38-B) (450 mg, 0.717 mmol) obtained in Example 38 was dissolved in methylene chloride (10 ml). Under ice cooling, hydrogen fluoride-pyridine (0.41 ml) was added dropwise. After completion of the dropwise addition, the reaction mixture was stirred at room temperature for 14 hours. To the reaction mixture was added a saturated aqueous solution (20 ml) of sodium bicarbonate, followed by extraction with diethyl ether. The organic layer was washed successively with 1N hydrochloric acid, a saturated aqueous solution of sodium bicarbonate and brine and dried over anhydrous magnesium sulfate. After filtration, the residue obtained by concentrating the filtrate under reduced pressure was purified by silica gel chromatography (hexane:ethyl acetate=2:1) to yield a colorless oil. The resulting colorless oil was solidified with hexane, whereby the title compound (194 mg, 70%) was obtained as a white powder.

Melting point: 67-69° C.

IR (ATR) ν: 3537, 2933, 2868, 1481, 1308, 1279, 1240, 1144, 1078, 822, 802, 754, 712, 665, 613, 544, 469 cm$^{-1}$.

$^1$H-NMR (400 MHz, CDCl$_3$) δ: 1.08-1.22(1H,m), 1.23 (1H,t,J=5.2 Hz), 1.36(3H,d,J=6.8 Hz), 1.45-1.70(3H,m), 2.67-2.80(1H,m), 3.50-3.65(2H,m), 4.45(1H,d,J=8.3 Hz), 6.73(1H,td,J=9.0, 4.6 Hz), 6.88-6.97(1H,m), 7.31(2H,d, J=8.8 Hz), 7.34-7.48(1H,m), 7.49(2H,d,J=8.8 Hz).

MS (m/z): 389, 391 (M$^+$+H).

Elemental Analysis for C$_{18}$H$_{19}$ClF$_2$O$_3$S

Calculated: C 55.60%; H 4.92%; Cl 9.12%; F 9.77%; S 8.25%.

Found: C 55.48%; H 4.84%; Cl 9.01%; F 9.76%; S 8.32%.

Example 41

2-[5-Bromo-1-[(4-chlorophenyl)sulfonyl]-2-methylpentyl]-1,4-difluorobenzene

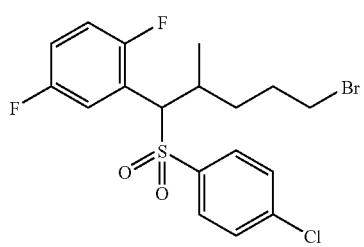

The 5-[(4-chlorophenyl)sulfonyl]-5-(2,5-difluorophenyl)-4-methyl-1-pentanol (290 mg, 0.746 mmol) obtained in Example 39 and carbon tetrabromide (290 mg, 0.874 mmol) were dissolved in methylene chloride (8 ml). While stirring under ice cooling, a solution obtained by dissolving triphenylphosphine (230 mg, 0.877 mmol) in methylene chloride (2 ml) was added dropwise to the resulting solution. After completion of the dropwise addition, the reaction mixture was stirred at room temperature for 3 days. To the reaction mixture were added carbon tetrabromide (290 mg, 0.874 mmol) and triphenylphosphine (230 mg, 0.877 mmol) under ice cooling, followed by stirring at room temperature for 6 hours. The residue obtained by concentrating the reaction mixture under reduced pressure was purified by silica gel chromatography (hexane:ethyl acetate=15:1), whereby the title compound (331 mg, 98%) was obtained as a colorless oil.

IR (ATR) ν: 2966, 1495, 1321, 1238, 1147, 1088, 1012, 789, 752, 729, 712, 613, 559, 536, 471 cm$^{-1}$.

$^1$H-NMR (400 MHz, CDCl$_3$) δ: 1.07(3H,d,J=6.8 Hz), 1.46-1.60(1H,m), 1.77-2.11(3H,m), 2.74-2.90(1H,m), 3.41 (2H,t,J=6.7 Hz), 4.49(1H,d,J=6.6 Hz), 6.78(1H,td,J=9.1, 4.6 Hz), 6.90-7.00(1H,m), 7.33(2H,d,J=8.7 Hz), 7.45-7.60(1H, m), 7.52(2H,d,J=8.7 Hz).

MS(m/z): 451, 453 (M$^+$+H).

Example 42

2-[5-Bromo-1-[(4-chlorophenyl)sulfonyl]-2-methylpentyl]-1,4-difluorobenzene

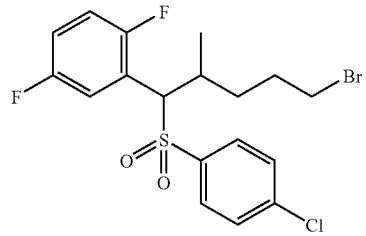

The 5-[(4-chlorophenyl)sulfonyl]-5-(2,5-difluorophenyl)-4-methyl-1-pentanol (170 mg, 0.437 mmol) obtained in Example 40 and carbon tetrabromide (170 mg, 0.648 mmol) were dissolved in methylene chloride (8 ml). While stirring under ice cooling, triphenylphosphine (135 mg, 0.515 mmol) was added to the resulting solution, followed by stirring at room temperature for 14 hours. To the reaction mixture were added carbon tetrabromide (170 mg, 0.437 mmol) and triphenylphosphine (135 mg, 0.515 mmol) under ice cooling. The reaction mixture was stirred at room temperature for 6 hours. The residue obtained by concentrating the reaction mixture under reduced pressure was purified by silica gel chromatography (hexane:ethyl acetate=10:1), whereby the title compound (192 mg, 97%) was obtained as a colorless oil.

IR (ATR) ν: 3091, 2966, 1496, 1296, 1246, 1142, 1080, 889, 839, 754, 710, 627, 553, 513, 471 cm$^{-1}$.

$^1$H-NMR (400 MHz, CDCl$_3$) δ: 1.18-1.31(1H,m), 1.37 (3H,d,J=6.8 Hz), 1.50-1.70(1H,m), 1.78-1.92(2H,m), 2.62-2.80(1H,m), 3.20-3.40(2H,m), 4.44(1H,d,J=8.5 Hz), 6.73 (1H,td,J=9.0, 4.5 Hz), 6.88-6.98(1H,m), 7.30(2H,d,J=8.6 Hz), 7.30-7.50(1H,m), 7.49(2H,d,J=8.6 Hz).

MS (m/z): 451, 453 (M$^+$+H).

Example 43

2-[1-[(4-Chlorophenyl)sulfonyl]-2-methyl-5-(methylthio)pentyl]-1,4-difluorobenzene (Isomer 43-A and Isomer 43-B)

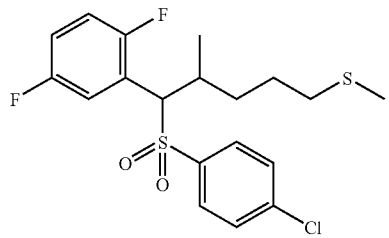

The 2-[5-bromo-1-[(4-chlorophenyl)sulfonyl]-2-methylpentyl]-1,4-difluorobenzene (325 mg, 0.719 mmol) obtained in Example 41 and the 2-[5-bromo-1-[(4-chlorophenyl)sulfonyl]-2-methylpentyl]-1,4-difluorobenzene (185 mg, 0.410 mmol) obtained in Example 42 were dissolved in tetrahydrofuran (25 ml). To the resulting solution was added sodium thiomethoxide (160 mg, 2.28 mmol) under ice cooling. After stirring at room temperature for 14 hours, sodium thiomethoxide (190 mg, 2.71 mmol) was added to the resulting mixture under ice cooling. The residue obtained by concentrating the reaction mixture under reduced pressure was purified by silica gel chromatography (hexane:ethyl acetate=30:1), whereby the title Isomer 43-A (low-polarity) (185 mg, 39%) and the title Isomer 43-B (high-polarity) (186 mg, 39%) were obtained, each as a colorless oil.

Isomer 43-A

IR (ATR) ν: 2916, 1493, 1321, 1238, 1146, 1088, 1012, 789, 752, 712, 613, 559, 536, 469 cm$^{-1}$.

$^1$H-NMR (400 MHz, CDCl$_3$) δ: 1.08(3H,d,J=6.9 Hz), 1.40-1.54(1H,m), 1.55-1.85(3H,m), 2.10(3H,s), 2.50(2H,t, J=7.2 Hz), 2.75-2.90(1H,m), 4.51(1H,d,J=6.1 Hz), 6.78(1H, td,J=9.1, 4.4 Hz), 6.90-7.00(1H,m), 7.33(2H,d,J=8.6 Hz), 7.45-7.60(1H,m), 7.52(2H,d,J=8.6 Hz).

MS (m/z): 419, 421(M$^+$+H).

HRMS (FAB) for C$_{19}$H$_{22}$ClF$_2$O$_2$S$_2$ (M$^+$+H)

Calculated: 419.0718

Found: 419.0733

Isomer 43-B

IR (ATR) ν: 2952, 2920, 1493, 1308, 1232, 1176, 1149, 1090, 827, 750, 629, 590, 557, 532, 472 cm$^{-1}$.

$^1$H-NMR (400 MHz, CDCl$_3$) δ: 1.10-1.30(1H,m), 1.37 (3H,d,J=6.6 Hz), 1.50-1.65(3H,m), 2.03(3H,s), 2.30-2.50 (2H,m), 2.64-2.78(1H,m), 4.44(1H,d,J=8.6 Hz), 6.73(1H,td, J=9.0, 4.5 Hz), 6.86-6.98(1H,m), 7.30(2H,d,J=8.6 Hz), 7.34-7.46(1H,m), 7.48(2H,d,J=8.6 Hz).

MS (m/z): 419, 421(M$^+$+H).

HRMS (FAB) for C$_{19}$H$_{22}$ClF$_2$O$_2$S$_2$ (M$^+$+H)

Calculated: 419.0718

Found: 419.0715

Example 44

2-[1-[(4-Chlorophenyl)sulfonyl]-2-methyl-5-(methylsulfinyl)pentyl]-1,4-difluorobenzene

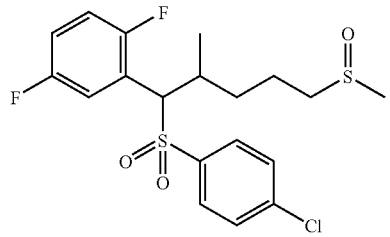

The 2-[1-[(4-chlorophenyl)sulfonyl]-2-methyl-5-(methylthio)pentyl]-1,4-difluorobenzene (Isomer 43-A) (180 mg, 0.430 mmol) obtained in Example 43 was dissolved in methylene chloride (10 ml). Under ice cooling, 3-chloroperbenzoic acid (89 mg, 0.52 mmol) was added, followed by stirring at room temperature for 14 hours. The residue obtained by concentrating the reaction mixture under reduced pressure was purified by silica gel chromatography (methylene chloride:methanol=40:1), whereby the title compound (172 mg, 92%) was obtained a colorless oil.

IR (ATR) ν: 2920, 1495, 1317, 1279, 1238, 1146, 1086, 1036, 829, 789, 752, 712, 615, 559, 471 cm$^{-1}$.

$^1$H-NMR (400 MHz, CDCl$_3$) δ: 1.00-1.10(3H,m), 1.50-1.75(1H,m), 1.78-2.10(3H,m), 2.60(1.5H,s), 2.60(1.5H,s), 2.65-2.90(3H,m), 4.50(1H,d,J=7.6 Hz), 6.77(1H,td,J=9.2, 4.4 Hz), 6.90-7.00(1H,m), 7.32(2H,d,J=8.5 Hz), 7.40-7.60 (1H,m), 7.5(2H,d,J=8.5 Hz).

MS (m/z): 435, 437 (M$^+$+H).

HRMS (FAB) for $C_{19}H_{22}ClF_2O_3S_2$ (M$^+$+H)

Calculated: 435.0667

Found: 435.0655

Example 45

2-[1-[(4-Chlorophenyl)sulfonyl]-2-methyl-5-(methylsulfinyl)pentyl]-1,4-difluorobenzene

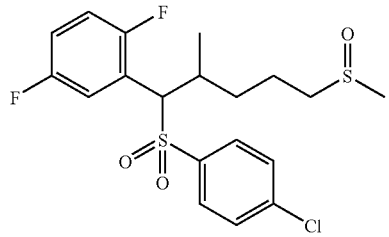

The 2-[1-[(4-chlorophenyl)sulfonyl]-2-methyl-5-(methylthio)pentyl]-1,4-difluorobenzene (Isomer 43-B) (175 mg, 0.418 mmol) obtained in Example 43 was dissolved in methylene chloride (10 ml). Under ice cooling, 3-chloroperbenzoic acid (87 mg, 0.50 mmol) was added. The resulting mixture was stirred at room temperature for 14 hours. The residue obtained by concentrating the reaction mixture under reduced pressure was purified silica gel chromatography (methylene chloride:methanol=40:1) to yield a white solid. The resulting solid was washed with diethyl ether, whereby the title compound (118 mg, 65%) was obtained as a white powder.

Melting point: 107-112° C.

IR (ATR) ν: 3087, 2943, 1496, 1315, 1242, 1178, 1149, 1088, 1028, 829, 731, 623, 584, 538, 457 cm$^{-1}$.

$^1$H-NMR (400 MHz, CDCl$_3$) δ: 1.15-1.40(4H,m), 1.45-2.00(3H,m), 2.50-2.85(3H,m), 2.54(3H,s), 4.46(1H,d,J=8.1 Hz), 6.78(1H,td,J=9.0, 4.7 Hz), 6.90-7.00(1H,m), 7.32(2H,d, J=8.4 Hz), 7.35-7.50(1H,m), 7.49(2H,d,J=8.4 Hz).

MS (m/z): 435, 437 (M$^+$+H).

Elemental Analysis for $C_{19}H_{21}ClF_2O_3S_2$

Calculated: C 52.47%; H 4.87%; Cl 8.15%; F 8.74%; S 14.74%.

Found: C 52.44%; H 4.85%; Cl 8.17%; F 8.79%; S 14.63%.

Example 46

2-[1-[(4-Chlorophenyl)sulfonyl]-2-methyl-5-(methylsulfonyl)pentyl]-1,4-difluorobenzene

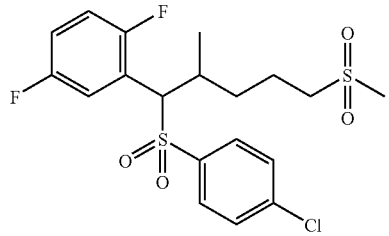

The 2-[1-[(4-chlorophenyl)sulfonyl]-2-methyl-5-(methylsulfinyl)pentyl]-1,4-difluorobenzene (76 mg, 0.18 mmol) obtained in Example 44 was dissolved in methylene chloride (5 ml). Under ice cooling, 3-chloroperbenzoic acid (36 mg, 0.21 mmol) was added. The resulting mixture was stirred at room temperature for 2 hours. The residue obtained by concentrating the reaction mixture was purified by silica gel chromatography (methylene chloride:methanol=100:1) to yield a pale yellowish brown oil. The resulting pale yellowish brown oil was solidified with diethyl ether/methylene chloride, whereby the title compound (61 mg, 77%) was obtained as a white powder.

Melting point: 115-117° C.

IR (ATR) ν: 3078, 2937, 1493, 1311, 1286, 1230, 1151, 1136, 1086, 831, 754, 729, 712, 623, 542, 519, 471, 459 cm$^{-1}$.

$^1$H-NMR (400 MHz, CDCl$_3$) δ: 1.03(3H,d,J=7.1 Hz), 1.60-1.80(1H,m), 1.85-2.20(3H,m), 2.70-2.90(1H,m), 2.94 (3H,s), 3.07(2H,t,J=7.8 Hz), 4.49(1H,d,J=7.8 Hz), 6.76(1H, td,J=9.1, 4.5 Hz), 6.90-7.00(1H,m), 7.32(2H,d,J=8.5 Hz), 7.35-7.60(1H,m), 7.49(2H,d,J=8.5 Hz).

MS (m/z): 451, 453 (M$^+$+H).

Elemental Analysis for $C_{19}H_{21}ClF_2O_4S_2$

Calculated: C 50.61%; H 4.96%; Cl 7.86%; F 8.43%; S 14.22%.

Found: C 50.57%; H 4.74%; Cl 7.85%; F 8.58%; S 14.25%.

Example 47

2-[1-[(4-Chlorophenyl)sulfonyl]-2-methyl-5-(methylsulfonyl)pentyl]-1,4-difluorobenzene

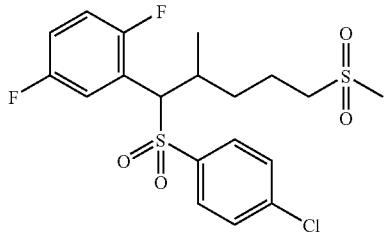

The 2-[1-[(4-chlorophenyl)sulfonyl]-2-methyl-5-(methylsulfinyl)pentyl]-1,4-difluorobenzene (66 mg, 0.15 mmol) obtained in Example 45 was dissolved in methylene chloride (5 ml). Under ice cooling, 3-chloroperbenzoic acid (32 mg, 0.19 mmol) was added. The resulting mixture was stirred at room temperature for 3 hours. The residue obtained by concentrating the reaction mixture under reduced pressure was purified by silica gel chromatography (methylene chloride: methanol=100:1) to yield a white solid. The resulting white solid was washed with diethyl ether/methylene chloride, whereby the title compound (52 mg, 76%) was obtained as a white powder.

Melting point: 142-144° C.

IR (ATR) ν: 3082, 2937, 1495, 1317, 1290, 1234, 1151, 1130, 1092, 831, 769, 754, 731, 712, 625, 544, 525, 503, 472, 449, 417 cm$^{-1}$.

$^1$H-NMR (400 MHz, CDCl$_3$) δ: 1.15-1.40(1H,m), 1.32 (3H,d,J=6.6 Hz), 1.40-2.05(3H,m), 2.65-3.10(3H,m), 2.88 (3H,s), 4.46(1H,d,J=7.1 Hz), 6.77(1H,td,J=9.1, 4.6 Hz), 6.90-7.00(1H,m), 7.32(2H,d,J=8.4 Hz), 7.35-7.50(1H,m), 7.49(2H,d,J=8.4 Hz).

MS (m/z): 451, 453 (M$^+$+H).

Elemental Analysis for $C_{19}H_{21}ClF_2O_4S_2$

Calculated: C 50.61%; H 4.69%; Cl 7.86%; F 8.43%; S 14.22%.

Found: C 50.48%; H 4.59%; Cl 7.93%; F 8.57%; S 14.09%.

Example 48

4-[(4-Chlorophenyl)sulfonyl]-4-(2,5-difluorophenyl)tetrahydropyrane

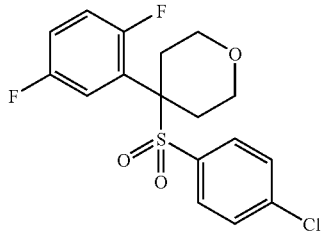

The 2-[(4-chlorophenyl)sulfonylmethyl]-1,4-difluorobenzene (1.0 g, 3.30 mmol) obtained in Example 5 was dissolved in tetrahydrofuran (70 ml). At −78° C., a hexane solution (1.57M, 5.3 ml, 8.3 mmol) of n-butyl lithium was added dropwise. After completion of the dropwise addition, the reaction mixture was stirred at −78° C. for 10 minutes and then stirred for another 30 minutes under ice cooling. At −78° C., 2-bromoethyl ether (0.55 ml, 3.9 mmol) was added dropwise to the reaction mixture. After completion of the dropwise addition, the temperature of the reaction mixture was elevated to room temperature over 14 hours. Water (2.0 ml) was added to the reaction mixture. The residue obtained by concentrating the resulting mixture under reduced pressure was purified by silica gel chromatography (hexane:ethyl acetate=5:1) to yield a white solid. The resulting white solid was washed with diisopropyl ether/methylene chloride, whereby the title compound (317 mg, 26%) was obtained as a white powder.

Melting point: 157-160° C.

IR (ATR) ν: 2966, 2862, 1496, 1309, 1188, 1149, 1086, 1012, 899, 841, 808.750, 710, 629, 592, 569, 536, 515, 471 cm$^{-1}$.

$^1$H-NMR (400 MHz, CDCl$_3$) δ: 2.40-2.80(4H,m), 3.32 (2H,t,J=12.5 Hz), 4.02(2H,dt,J=11.8, 3.3 Hz), 6.82-6.95(1H, m), 7.05-7.17(2H,m), 7.38(2H,s), 7.39(2H,s).

MS (m/z): 373, 375 (M$^+$+H).

Elemental Analysis for C$_{17}$H$_{15}$ClF$_2$O$_3$S

Calculated: C 54.77%; H 4.06%; Cl 9.51%; F 10.19%; S 8.60%.

Found: C 54.55%; H 4.00%; Cl 9.69%; F 10.33%; S 8.64%.

Example 49

5-[(4-Chlorophenyl)sulfonyl]-5-(2,5-difluorophenyl)pentyl=1-pyrrolidinecarboxylato

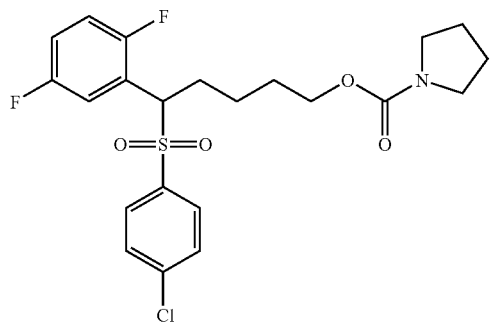

To a methylene chloride (6 ml) solution of the 5-[(4-chlorophenyl)sulfonyl]-5-(2,5-difluorophenyl)-1-pentanol (390 mg, 1.04 mmol) obtained in Example 29 were added triethylamine (152 μl, 1.09 mmol) and 4-nitrophenyl chloroformate (220 mg, 1.09 mmol). The resulting mixture was stirred at room temperature for 24 hours. The reaction mixture was concentrated, whereby crude 5-[(4-chlorophenyl)sulfonyl]-5-(2,5-difluorophenyl)pentyl=4-nitrophenyl=carbonato (759 mg) was obtained. The resulting crude 5-[(4-chlorophenyl)sulfonyl]-5-(2,5-difluorophenyl)pentyl=4-nitrophenyl=carbonato (268 mg) was dissolved in methylene chloride (4 ml), followed by the addition of triethylamine (76.7 μl, 0.551 mmol) and pyrrolidine (46.0 μl, 0.551 mmol). The mixture was stirred at room temperature for 15 hours. The reaction mixture was concentrated and the residue was dissolved in diethyl ether. The resulting solution was washed successively with a saturated aqueous solution of potassium bicarbonate, a saturated aqueous solution of ammonium chloride, water and brine, dried over MgSO$_4$, and then concentrated. The residue thus obtained was purified by medium-pressure chromatography on a silica gel column (40% ethyl acetate-hexane), whereby the title compound (128 mg, 74%) was obtained as a pale brown oil.

IR (ATR) ν: 3086, 2954, 2875, 1689, 1583, 1496, 1423, 1321, 1176, 1147, 1084, 1012, 874, 752, 536, 467 cm$^{-1}$.

$^1$H-NMR (400 MHz, CDCl$_3$) δ: 1.26-1.38(2H,m), 1.54-1.73(2H,m), 1.78-1.90(4H,m), 2.09-2.20(1H,m), 2.42-2.52 (1H,m), 3.19-3.40(4H,m), 3.96-4.05(2H,m), 4.52(1H,dd, J=11.5, 2.7 Hz), 6.83(1H,td,J=9.1, 4.4 Hz), 6.94-7.01(1H,m), 7.21-7.28(1H,m), 7.38(2H,d,J=8.6 Hz), 7.52(2H,d,J=8.6 Hz).

MS (m/z) 472 (M$^+$+H).

HRMS (FAB) for C$_{22}$H$_{24}$ClF$_2$NO$_4$S (M$^+$+H)

Calculated: 472.1161

Analyzed: 472.1124

Referential Example 3

4-(Methylsulfonyl)-1-butanol

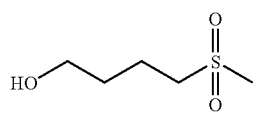

While stirring under ice cooling, 3-chloroperbenzoic acid (3.04 g, 17.6 mmol) was added to a methylene chloride (100 ml) solution of 4-(methylthio)-1-butanol (1.01 g, 8.40 mmol). At room temperature, the mixture was stirred for 20 hours. After completion of the reaction was confirmed, the solvent was concentrated under reduced pressure. To the residue were added diethyl ether and water to separate the water layer. The resulting water layer was concentrated under reduced pressure. Methylene chloride was added to the residue. The mixture was dried over anhydrous sodium sulfate, and then the solvent was concentrated under reduced pressure. The residue was subjected to chromatography on a silica gel column. From the fraction eluted with methanol:methylene chloride (=1:20), the title compound (1.21 g, 95%) was obtained as a pale yellow oil.

IR (ATR) ν: 3494, 2931, 2877, 1457, 1413, 1282, 1122, 1054, 1029, 966, 827, 765, 518, 462 cm$^{-1}$.

$^1$H-NMR (400 MHz, CDCl$_3$) δ: 1.55-1.91(3H,m), 1.91-2.11(2H,m), 2.92(3H,s), 3.09(2H,t,J=7.9 Hz), 3.72(2H,t, J=6.1 Hz).

MS (m/z): 153 (M$^+$+H).

Referential Example 4

4-(Methylsulfinyl)-1-butanol

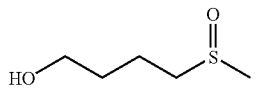

While stirring under ice cooling, sodium periodate (1.24 g, 5.80 mmol) was added to a mixed solution of 4-(methylthio)-1-butanol (465 mg, 3.87 mmol) in tetrahydrofuran (15 ml) and water (3 ml). At room temperature, the resulting mixture was stirred for 21.5 hours. After completion of the reaction was confirmed, the reaction mixture was diluted with methylene chloride and then subjected to Celite filtration. The filtrate was concentrated under reduced pressure. To the residue was added methylene chloride. The resulting mixture was dried over anhydrous sodium sulfate and then, the solvent was concentrated under reduced pressure. The residue thus obtained was subjected to chromatography on a silica gel column, whereby from the fraction eluted with methanol:methylene chloride (=1:10), the title compound (160 mg, 30%) was obtained as a pale yellow oil.

IR (ATR) ν: 3369, 2937, 2867, 1658, 1452, 1411, 1054, 1006, 941, 694 cm$^{-1}$.

$^1$H-NMR (400 MHz, CDCl$_3$) δ: 1.40-1.55(1H,br), 1.68-1.83(2H,m), 1.93-2.08(2H,m), 2.92(3H,s), 3.09(2H,t,J=7.9 Hz), 3.72(2H,t,J=5.5 Hz).

MS (m/z): 137 (M$^+$+H).

Example 50

1-Chloro-4-(benzylsulfonyl)benzene

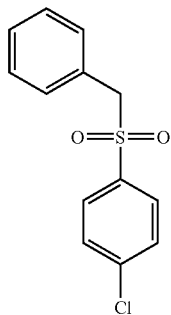

Sodium 4-chlorobenzenesulfinate (306 mg, 1.54 mmol) and benzyl bromide (0.18 ml, 1.54 mmol) were added to n-butanol (15 ml). The resulting mixture was stirred at 70° C. for 5 hours. After cooling to room temperature, the solvent was concentrated under reduced pressure. To the residue were added ethyl acetate. The resulting mixture was washed successively with water and brine, dried over anhydrous sodium sulfate, and concentrated under reduced pressure. The residue was subjected to chromatography on a silica gel column, whereby from the fraction eluted with hexane:ethyl acetate (=8:1), the title compound (299 mg, 73%) was obtained as a white solid.

Melting point: 147.5-148.5° C.

IR (ATR) ν: 3060, 3029, 2994, 2942, 1583, 1571, 1492, 1475, 1454, 1396, 1311, 1294, 1274, 1147, 1087, 1014, 977, 917, 831, 773, 757, 696, 642, 532, 462 cm$^{-1}$.

$^1$H-NMR (400 MHz, CDCl$_3$) δ: 4.31(2H,s), 7.23-7.38(4H,m), 7.38-7.46(2H,m), 7.49-7.58(2H,m).

MS (m/z) 267 (M$^+$+H).

Example 51

1-Chloro-4-(5-methylsulfonyl-1-phenylpentyl)sulfonylbenzene

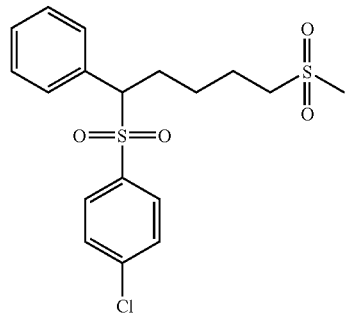

Under an argon atmosphere, a toluene (20 ml) solution of 1-chloro-4-(benzylsulfonyl)benzene (90 mg, 0.337 mmol), the 4-(methylsulfonyl)-1-butanol (69 mg, 0.453 mmol) obtained in Referential Example 3 and cyanomethylenetri-n-butylphosphorane (233 mg, 0.965 mmol) was heated under reflux for 21 hours. After cooling to room temperature, the reaction mixture was concentrated under reduced pressure. The residue was subjected to medium-pressure chromatography on a silica gel column. From the fraction eluted with hexane:ethyl acetate (=2:1), the title compound (44 mg, 33%) was obtained as a white solid.

Melting point: 151-152° C.

IR (ATR) ν: 2937, 2867, 1577, 1467, 1396, 1319, 1270, 1203, 1147, 1087, 1058, 1014, 962, 842, 802, 755, 696, 632, 565, 530, 474, 420 cm$^{-1}$.

$^1$H-NMR (400 MHz, CDCl$_3$) δ: 1.34-1.52(2H,m), 1.79-1.97(2H,m), 2.13-2.28(2H,m), 2.45-2.58(1H,m), 2.86(3H,s), 2.89-3.00(2H,m), 4.01(1H,dd,J=11.2, 3.9 Hz), 7.08(1H,d, J=8.1 Hz), 7.22-7.47(8H,m).

MS (m/z): 401 (M$^+$+H).

Elemental Analysis for C$_{18}$H$_{21}$ClO$_4$S$_2$
  Calculated: C 53.92%; H 5.28%; Cl 8.84%; S 16.00%.
  Found: C 53.92%; H 5.21%; Cl 9.05%; S 15.88%.

Example 52

1-Chloro-4-(5-methylsulfinyl-1-phenylpentyl)sulfonylbenzene

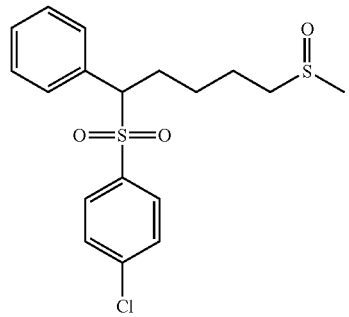

A toluene (15 ml) solution of the 4-chloro-1-(benzylsulfonyl)benzene (122 mg, 0.457 mmol) obtained in Example 50, the 4-(methylsulfinyl)-1-butanol (81 mg, 0.595 mmol) obtained in Referential Example 4 and cyanomethylenetri-n-butylphosphorane (221 mg, 0.916 mmol) was heated under reflux for 2 days under an argon atmosphere. After cooling to room temperature, the reaction mixture was concentrated under reduced pressure. The residue was subjected to medium-pressure chromatography on a silica gel column, whereby from the fraction eluted with methylene chloride:methanol (=100:1), a white solid was obtained. The resulting white solid was recrystallized from diethyl ether to give the title compound (20 mg, 11%) as white needle crystals.

Melting point: 98.5-99.5° C.

IR (ATR) ν: 2935, 2856, 1575, 1473, 1455, 1392, 1309, 1276, 1143, 1081, 1016, 946, 829, 794, 755, 694, 624, 563, 520, 464 cm$^{-1}$.

$^1$H-NMR (400 MHz, CDCl$_3$) δ: 32-1.50(2H,m), 1.70-1.90 (2H,m), 2.15-2.28(1H,m), 2.45-2.70(2H,m), 2.52(3H,s), 4.02(1H,dd,J=11.4, 3.8 Hz), 7.05-7.12(1H,m), 7.20-7.47(8H, m).

MS (m/z): 385 (M$^+$+H).

Elemental Analysis for C$_{18}$H$_{21}$ClO$_3$S$_2$
 Calculated: C 56.16%; H 5.50%; Cl 9.21%; S 16.66%.
 Found: C 56.03%; H 5.37%; Cl 9.29%; S 16.69%.

Example 53

1-[1-[(4-Chlorophenyl)sulfonyl]-5-(methylsulfonyl) pentyl]-2-fluorobenzene

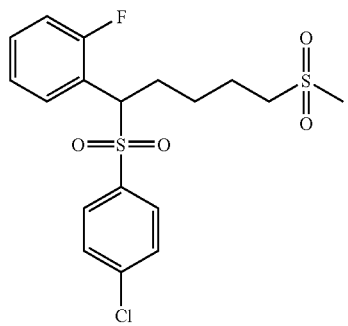

To sodium 4-chlorobenzenesulfinate (203 mg, 1.02 mmol) and 2-fluorobenzyl bromide (124 μL, 1.02 mmol) were added n-butanol (5 ml). The resulting mixture was stirred at 70° C. for 5 hours. After cooling to room temperature, the solvent was concentrated under reduced pressure. To the residue was added methylene chloride and from the resulting mixture, the insoluble matter was filtered off. The filtrate was concentrated under reduced pressure. The residue was washed with diisopropyl ether to yield white powder (111 mg).

A toluene (10 ml) solution of the resulting white powder (35 mg), the 4-(methylsulfonyl)-1-butanol (38 mg, 0.250 mmol) obtained in Referential Example 3 and cyanomethylenetri-n-butylphosphorane (60 mg, 0.246 mmol) was heated under reflux for 17.5 hours under an argon atmosphere. After cooling to room temperature, the reaction mixture was concentrated under reduced pressure. The residue was subjected to medium-pressure chromatography on a silica gel column. From the fraction eluted with hexane:ethyl acetate (=1:1), the title compound was obtained as a white solid (46 mg).

Melting point: 167-168° C.

IR (ATR) ν: 2948, 2867, 1614, 1579, 1488, 1455, 1396, 1319, 1290, 1268, 1230, 1199, 1149, 1126, 1085, 1014, 962, 829, 792, 767, 752, 713, 628, 572, 532, 495, 458, 430 cm$^{-1}$.

$^1$H-NMR (400 MHz, CDCl$_3$) δ: 1.38-1.52(2H,m), 1.80-1.98(2H,m), 2.16-2.29(1H,m), 2.48-2.60(1H,m), 2.87(3H,s), 2.96(2H,t,J=7.9 Hz), 4.55(1H,dd,J=11.0, 4.2 Hz), 6.85(1H, td,J=9.1, 1.1 Hz), 7.17-7.39(4H,m), 7.43-7.58(3H,m).

MS (m/z): 419 (M$^+$+H).

Elemental. Analysis for C$_{18}$H$_{20}$ClFO$_4$S$_2$
 Calculated: C 51.61%; H 4.81%; Cl 8.46%; F 4.53%; S 15.31%.
 Found: C 51.65%; H 4.74%; Cl 8.33%; F 4.50%; S 15.20%.

Example 54

1-[1-[(4-Chlorophenyl)sulfonyl]-5-(methylsulfonyl) pentyl]-3-fluorobenzene

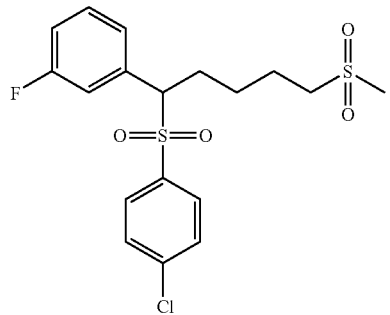

Sodium 4-chlorobenzenesulfinate (216 mg, 1.09 mmol) and 3-fluorobenzyl bromide (136 μL, 1.09 mmol) were added to n-butanol (5 ml). The resulting mixture was stirred at 70° C. for 5 hours. After cooling to room temperature, the solvent was concentrated under reduced pressure. To the residue was added methylene chloride and from the resulting mixture, the insoluble matter was filtered off. The filtrate was concentrated under reduced pressure. The residue thus obtained was washed with diisopropyl ether to yield a white powder (208 mg).

Then, a toluene (10 ml) solution of the resulting white powder (59 mg), the 4-(methylsulfonyl)-1-butanol (65 mg, 0.427 mmol) obtained in Referential Example 3 and cyanomethylenetri-n-butylphosphorane (100 mg, 0.414 mmol) was heated under reflux for 29.5 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=2:3), the title compound was obtained as a white solid (71 mg).

Melting point: 116-117° C.

IR (ATR) ν: 2942, 2875, 1590, 1469, 1394, 1317, 1295, 1270, 1241, 1201, 1145, 1083, 1012, 964, 875, 840, 798, 769, 752, 705, 686, 634, 592, 541, 530, 512, 491, 464 cm$^{-1}$.

$^1$H-NMR (400 MHz, CDCl$_3$) δ: 1.34-1.52(2H,m), 1.78-1.99(2H,m), 2.09-2.22(1H,m), 2.41-2.56(1H,m), 2.81-3.03 (2H,m), 2.88(3H,s), 4.01(1H,dd,J=11.2, 3.9 Hz), 6.83(1H,d, J=7.6 Hz), 6.90(1H,d,J=9.3 Hz), 7.03(1H,td,J=8.1, 2.2 Hz), 7.23(1H,td,J=7.9, 6.0 Hz), 7.32-7.50(4H,m).

MS (m/z): 419 (M$^+$+H).

Elemental Analysis for $C_{18}H_{20}ClFO_4S_2$

Calculated: C 51.61%; H 4.81%; Cl 8.31%; F 4.53%; S 15.31%.

Found: C 51.68%; H 4.72%; Cl 8.31%; F 4.52%; S 15.30%.

Example 55

1-[1-[(4-Chlorophenyl)sulfonyl]-5-(methylsulfonyl)pentyl]-4-fluorobenzene

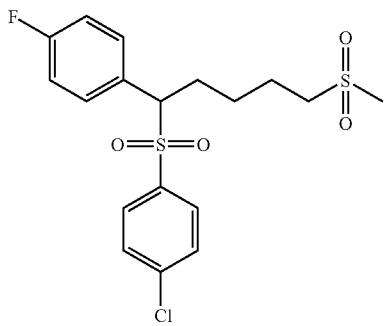

Sodium 4-chlorobenzenesulfinate (183 mg, 0.921 mmol) and 4-fluorobenzyl bromide (112 μL, 0.921 mmol) were added to n-butanol (5 ml). The resulting mixture was stirred at 70° C. for 6 hours. After cooling to room temperature, the solvent was concentrated under reduced pressure. To the residue was added ethyl acetate, and from the resulting mixture, the insoluble matter was filtered off. The filtrate was concentrated under reduced pressure. The residue was washed with diisopropyl ether to yield a white powder (150 mg).

Then, a toluene (10 ml) solution of the resulting white powder (57 mg), the 4-(methylsulfonyl)-1-butanol (62 mg, 0.407 mmol) obtained in Referential Example 3 and cyanomethylenetri-n-butylphosphorane (97 mg, 0.400 mmol) was heated under reflux for 17 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=2:3), the title compound was obtained as a white solid (58 mg).

Melting point: 141-142.5° C.

IR (ATR) ν: 2937, 2865, 1606, 1577, 1508, 1467, 1394, 1317, 1292, 1270, 1236, 1147, 1126, 1085, 1014, 962, 838, 825, 755, 721, 626, 574, 553, 514, 482, 455 cm$^{-1}$.

$^1$H-NMR (400 MHz, CDCl$_3$) δ: 1.35-1.50(2H,m), 1.80-1.97(2H,m), 2.09-2.21(1H,m), 2.43-2.56(1H,m), 2.88(3H,s), 2.90-3.00(2H,m), 4.01(1H,dd,J=11.2, 3.9 Hz), 6.97(2H,t, J=8.5 Hz), 7.03-7.11(2H,m), 7.36-7.48(4H,m).

MS (m/z): 419 (M$^+$+H).

Elemental Analysis for $C_{18}H_{20}ClFO_4S_2$

Calculated: C 51.61%; H 4.74%; Cl 8.46%; F 4.53%; S 15.31%.

Found: C 51.74%; H 4.74%; Cl 8.28%; F 4.53%; S 15.36%.

Example 56

2-[1-[(4-Chlorophenyl)sulfonyl]-1-methylthio]methyl-1,4-difluorobenzene

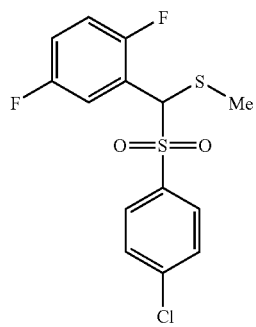

Under a nitrogen atmosphere, the 2-[(4-chlorophenyl)sulfonylmethyl]-1,4-difluorobenzene (82.8 mg, 0.27 mmol) obtained in Example 5 was added to a N,N-dimethylformamide suspension (2.0 ml) of sodium hydride (12 mg, 0.30 mmol) at room temperature. The resulting mixture was stirred for 10 minutes. To the reaction mixture was added methyl methanethiosulfonate (28.1 mg, 0.27 mmol) and the mixture was stirred for another 30 minutes. The reaction mixture was added with a saturated aqueous sodium bicarbonate solution (10 ml), followed by extraction with diethyl ether. The organic layer was washed with water and brine, and dried over anhydrous magnesium sulfate. After filtration, the residue obtained by concentrating the filtrate under reduced pressure was purified by silica gel chromatography (hexane:diethyl ether=4:1), whereby the title compound (36 mg, 38%) was obtained as a white solid.

Melting point: 128-129° C.

IR (ATR) ν: 1489, 1315, 1234, 1147, 1078, 829 cm$^{-1}$.

$^1$H-NMR (400 MHz,CDCl$_3$) δ: 2.47(3H,s), 5.22(1H,s), 6.88(1H,m), 6.97(1H,m), 7.13(1H,m), 7.41(2H,m), 7.60(2H, m).

MS (m/z): 173 (M$^+$-SO$_2$Ar).

Elemental Analysis for $C_{14}H_{11}ClF_2O_2S_2$

Calculated: C 48.21%; H 3.18%; S 18.39%; Cl 10.16%; F 10.89%.

Found: C 48.41%; H 3.28%; S 17.88%; Cl 10.41%; F 10.57%.

Example 57

2-[1-[(4-Chlorophenyl)sulfonyl]-1-phenylthio]methyl-1,4-difluorobenzene

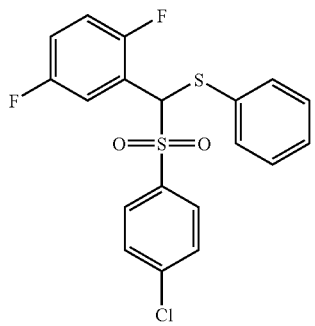

In a similar manner to that employed in Example 56 except for the use of phenyl phenylthiosulfonate, the title compound was synthesized.

Melting point: 84-85° C.

IR (ATR) ν: 1492, 1319, 1149, 1086, 825 cm$^{-1}$.

$^1$H-NMR (400 MHz, CDCl$_3$) δ: 5.53(1H,s), 6.91(1H,m), 7.01(1H,m), 7.23-7.31(4H,m), 7.35-7.40(4H,m), 7.65(2H,m), 7.65(2H,m), 7.40-7.35(4H,m), 7.31-7.23(4H,m), 7.01(1H,m), 6.91(1H,m), 5.53(1H,s).

MS (m/z): 235 (M$^+$-SO$_2$Ar).

Elemental Analysis for $C_{19}H_{13}ClF_2O_2S_2$

Calculated: C 55.54%; H 3.19%; S 15.61%; Cl 8.63%; F 9.25%.

Found: C 55.50%; H 3.18%; S 15.51%; Cl 8.40%; F 9.03%.

Example 58

Benzyl [(4-chlorophenyl)sulfonyl-(2,5-difluorophenyl)methyl]carbamate

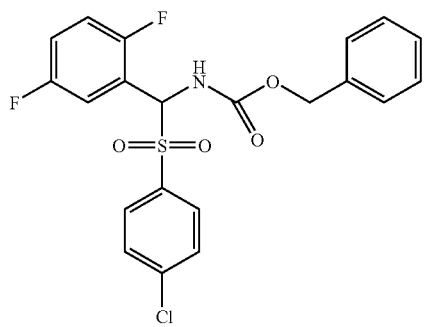

To a tetrahydrofuran solution (0.4 ml) of benzyl carbamate (151 mg, 1.0 mmol) were added water (1.0 ml), sodium chlorobenzenesulfinate (199 mg, 1.0 mmol), 2,5-difluorobenzaldehyde (142 mg, 1.0 mmol) and formic acid (0.24 ml). The resulting mixture was stirred for 19 hours at room temperature. To the reaction mixture having a white precipitate formed therein were added diethyl ether and water. The precipitate was collected by filtration and washed sufficiently with diethyl ether, whereby the title compound (251 mg, 51%) was obtained.

Melting point: 183-184° C.

IR (ATR) ν: 1726, 1518, 1495, 1319, 1230, 1147, 831 cm$^{-1}$.

$^1$H-NMR (400 MHz,DMSO-d$_6$) δ: 4.91(1H,d,J=12.4 Hz), 4.97(1H,d,J=12.4 Hz), 6.25(1H,d,J=10.4 Hz), 7.2-7.45(7H,m), 7.70(2H,d,J=8.4 Hz), 7.71(1H,m), 7.78(2H,d,J=8.4 Hz), 9.33(1H,d,J=10.4 Hz).

MS (m/z): 275 (M$^+$-SO$_2$Ar).

Referential Example 5

Benzyl 2,5-difluorophenylacrylate

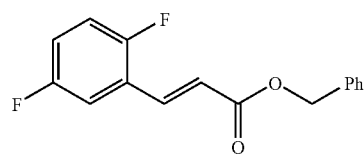

Under a nitrogen atmosphere, dicyclohexyl carbodiimide (206 mg, 1.0 mmol) was added to a methylene chloride solution (10 ml) of 2,5-difluorophenylacrylic acid (184 mg, 1 mmol), benzyl alcohol (104 ml, 1 mmol), and N,N-dimethylaminopyridine (36 mg, 0.3 mmol) at room temperature and the resulting mixture was stirred for 17 hours. After concentration of the reaction mixture under reduced pressure, 10 ml of hexane-diethyl ether (4:1) was added to the residue. The precipitate thus formed was filtered. The filtrate was concentrated under reduced pressure. The residue was purified by silica gel chromatography (hexane:ethyl acetate=5:1), whereby the title compound (242 mg, 88%) was obtained.

Melting point: 45-46° C.

IR (ATR) ν: 1712, 1641, 1305, 1167, 692 cm$^{-1}$.

$^1$H-NMR (400 MHz, CDCl$_3$) δ: 5.24(S,2H), 6.54(d,1H, J=16.4 Hz), 7.03(m,2H), 7.18(m,1H), 7.37(m,5H), 7.77(d, 1H,J=16.4 Hz).

Example 59

Benzyl 3-(4-chlorophenylsulfonyl)-3-(2,5-difluorophenyl)propionate

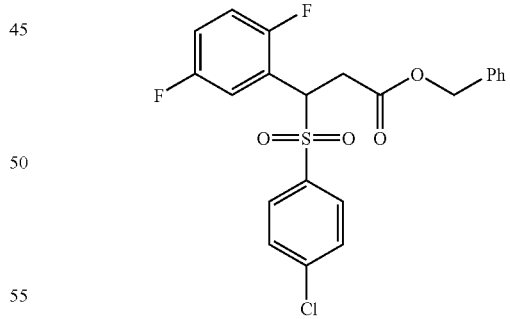

Under a nitrogen atmosphere, a hexane solution (1.57M, 0.05 ml) of n-butyl lithium was added to a tetrahydrofuran (10 ml) solution of benzyl 2,5-difluorophenylacrylate (108 mg, 0.39 mmol) and 4-chlorobenzenethiol (57 mg, 0.39 mmol) at room temperature. The resulting mixture was stirred for 1 hour. After concentrating the reaction mixture under reduced pressure, the residue was subjected to silica gel chromatography. The fraction eluted with hexane:diethyl ether (=10:1) was concentrated under reduced pressure.

Then, the residue was dissolved in methanol (10 ml). To the resulting solution were added water (1.0 ml), hexaammonium heptamolybdate tetrahydrate (5.0 mg), and 30% aqueous hydrogen peroxide (2 ml) at room temperature, followed by stirring for 48 hours. The reaction mixture was diluted with ethyl acetate (50 ml) and then, washed sufficiently with water and brine. The organic layer was dried over anhydrous magnesium sulfate and distilled under reduced pressure to remove the solvent. The residue thus obtained was purified by silica gel chromatography (hexane:ethyl acetate=8:1), whereby the title compound (33 mg, 19%) was obtained.

Melting point: 127-128° C.

IR (ATR) ν: 1734, 1498, 1317, 1211, 1170, 1149, 748 cm$^{-1}$.

$^1$H-NMR (400 MHz, CDCl$_3$) δ: 3.12(dd,1H,J=10.4, 16.8 Hz), 3.48(dd,1H,J=4.4, 16.8 Hz), 4.98(d,1H,J=12.0 Hz), 5.02 (m,1H), 5.03(d,1H,J=12.0 Hz), 6.79(m,1H), 6.81(m,1H), 7.1-7.2(m,3H), 7.23(m,3H), 7.38(d,2H,J=8.4 Hz), 7.52(d, 2H,J=8.4 Hz).

Elemental Analysis for $C_{22}H_{17}ClF_2O_4S \cdot 0.5H_2O$
Calculated: C 57.46%; H 3.91%; S 6.97%; Cl 7.70%; F 8.26%.
Found C 57.60%; H 3.89%; S 7.02%; Cl 7.83%; F 8.31%.
MS (m/z): 450 (M$^+$).
HRMS (EI): as $C_{22}H_{17}ClF_2O_4S$ (M$^+$)
Calculated: 450.0504
Found: 450.0496

Example 60

2-[1-[(4-Chlorophenyl)sulfonyl]-2-pentylcyclopropyl]-1,4-difluorobenzene

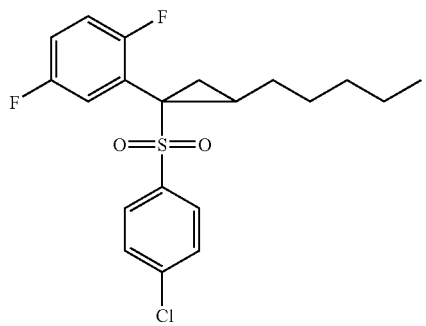

Under a nitrogen atmosphere, triethylamine (36.4 μl, 0.262 mmol) and methanesulfonyl chloride (18.6 μl, 0.240 mmol) were added to a methylene chloride (4 ml) solution of the isomer mixture (91.0 mg, 0.218 mmol) of the 1-[(4-chlorophenyl)sulfonyl]-1-(2,5-difluorophenyl)-3-octanol obtained in Example 22 at 0° C. The resulting mixture was stirred at 0° C. for 2 hours. The reaction mixture was diluted with methylene chloride, washed with water and brine, dried over MgSO$_4$, and then concentrated. The residue thus obtained was subjected to chromatography on a short silica gel column. The fraction eluted with hexane:ethyl acetate (=3:1) was concentrated under reduced pressure to yield a colorless oil.

The resulting colorless oil was dissolved in tetrahydrofuran (4 ml). In an argon gas stream and at −78° C., n-butyl lithium (a 1.57M hexane solution, 0.127 ml, 0.200 mmol) was added to the resulting solution, followed by stirring at −78° C. for 3 hours. The reaction mixture was added with a saturated aqueous ammonium chloride solution, followed by extraction with diethyl ether. The extracts were combined, washed successively with water and brine, dried over MgSO$_4$, and then concentrated. The residue thus obtained was purified by medium-pressure chromatography on a silica gel column (8% ethyl acetate-hexane), whereby the title compound (48.1 mg, 66%) was obtained as a colorless oil.

IR (ATR) ν: 2929, 2925, 2858, 1585, 1496, 1317, 1250, 1176, 1146, 1090, 1014, 889, 827, 796, 760, 715, 602, 565, 478 cm$^{-1}$.

$^1$H-NMR (400 MHz, CDCl$_3$) δ: 0.43-0.62(1H,m), 0.83-0.95(3H,m), 1.13-1.70(7.66H,m), 1.82-1.93(0.33H,m), 1.99 (0.33H,dd,J=9.8, 5.4 Hz), 2.07(0.66H,dd,J=9.8,5.9 Hz), 2.26-2.40(1H,m), 6.74-6.84(1H,m), 6.91(0.33H,td,J=9.0, 4.4 Hz), 6.98-7.05(1H,m), 7.13(0.66H,ddd,J=8.6,5.6,3.2 Hz), 7.35-7.50(4H,m).

MS (m/z) 399 (M$^+$+H).
HRMS (FAB) for $C_{20}H_{22}ClF_2O_2S$ (M$^+$+H)
Calculated: 399.0997
Found: 399.1006

Example 61 t-Butyl 3-[(4-chlorophenyl)sulfonyl]-3-(2,5-difluorophenyl)propionate

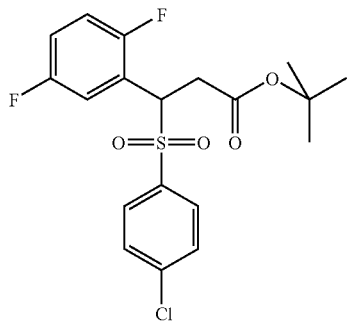

Under an argon atmosphere and at −78° C., n-butyl lithium (a 1.57M hexane solution, 7.01 ml) was added dropwise to a dimethoxyethane solution (50 ml) of the 2-[(4-chlorophenyl) sulfonylmethyl]-1,4-difluorobenzene (3.03 g, 10.0 mmol) obtained in Example 5. The temperature of the reaction mixture was raised to room temperature. Then, the reaction mixture was cooled to −78° C. After the addition of t-butyl bromoacetate (1.48 ml, 10.0 mmol), the resulting mixture was stirred at room temperature for 3 hours. The reaction mixture was added with a saturated aqueous ammonium chloride solution, followed by extraction with diethyl ether. The extracts were combined, washed successively with water and brine, dried over MgSO$_4$, and then distilled to remove the solvent. The residue thus obtained was subjected to chromatography on a short silica gel column (hexane-ethyl acetate 3:1). The solid thus obtained was recrystallized from hexane, whereby the title compound (3.30 g, 79%) was obtained as a colorless solid.

Melting point: 140.5-142.0° C.

IR (ATR) ν: 3074, 2983, 1722, 1585, 1496, 1427, 1396, 1369, 1275, 1257, 1215, 1142, 1086, 955, 835, 781, 750, 712, 665, 606, 559, 467 cm$^{-1}$.

$^1$H-NMR (400 MHz, CDCl$_3$) δ: 1.28(9H,s), 3.00(1H,dd, J=16.4, 10.7 Hz), 3.37(1H,dd,J=16.4, 4.4 Hz), 5.00(1H,dd,

J=10.7, 4.4 Hz), 6.85(1H,td,J=9.0, 4.6 Hz), 6.96-7.03(1H,m), 7.19(1H,ddd,J=8.8,5.6,3.2 Hz), 7.41(2H,d,J=8.3 Hz), 7.50 (2H,d,J=8.3 Hz).

MS (m/z): 417 (M$^+$+H).
HRMS (FAB) for C$_{19}$H$_{19}$ClF$_2$O$_4$S (M$^+$+H).
Calculated: 416.0661
Found: 416.0690

Elemental Analysis for C$_{19}$H$_{19}$ClF$_2$O$_4$S
Calculated: C 54.74%; H 4.59%; Cl 8.50%; F 9.11%; S 7.69%.
Found: C 54.67%; H 4.55%; Cl 8.54%; F 9.17%; S 7.80%.

Example 62

3-[(4-Chlorophenyl)sulfonyl]-3-(2,5-difluorophenyl) propionic Acid

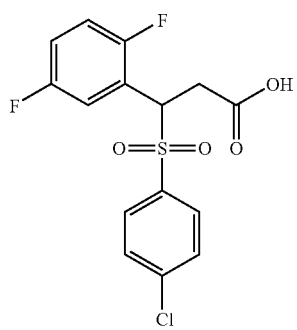

At 0° C., trifluoroacetic acid (10 ml) was added to a methylene chloride (30 ml) solution of t-butyl 3-[(4-chlorophenyl) sulfonyl]-3-(2,5-difluorophenyl)propionate (3.10 g, 7.43 mmol). The resulting mixture was stirred at room temperature for 2 hours. To the residue obtained by concentrating the reaction mixture was added toluene and the resulting mixture was concentrated. The residue thus obtained was recrystallized from ethyl acetate-hexane, whereby the title compound (2.29 g, 85%) was obtained as colorless needle crystals.

Melting point: 152.0-153.0° C.

IR (ATR) ν: 2956, 1707, 1576, 1496, 1427, 1396, 1321, 1255, 1217, 1115, 1086, 1012, 914, 893, 829, 795, 756, 708, 619, 536, 459 cm$^{-1}$.

$^1$H-NMR (400 MHz, CDCl$_3$) δ: 3.13(1H,dd,J=17.1, 10.4 Hz), 3.53(1H,dd,J=17.1, 4.6 Hz), 5.02(1H,dd,J=10.4, 4.6 Hz), 6.85(1H,td,J=9.0, 4.6 Hz), 6.96-7.03(1H,m), 7.18(1H, ddd,J=8.5,5.4,3.2 Hz), 7.41(2H,d,J=8.8 Hz), 7.55(2H,d, J=8.8 Hz).

MS (m/z): 360 (M$^+$).
HRMS (EI): as C$_{15}$H$_{11}$ClF$_2$O$_4$S (M$^+$)
Calculated: 360.0035
Found: 360.0026

Elemental Analysis for C$_{15}$H$_{11}$ClF$_2$O$_4$S
Calculated: C 49.94%; H 3.07%; Cl 9.83%; F 10.53%; S 8.89%.

Found: C 49.74%; H 2.99%; Cl 9.88%; F 10.63%; S 8.98%.

Example 63

1-Chloro-2-[1-[(4-chlorophenyl)sulfonyl]-5-(methyl-sulfonyl)pentyl]benzene

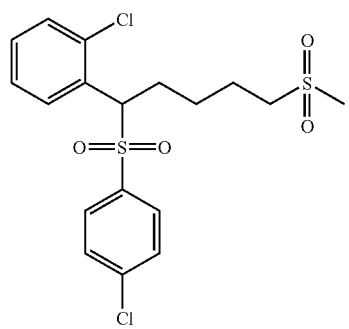

Sodium 4-chlorobenzenesulfinate (205 mg, 1.03 mmol) and 2-chlorobenzyl bromide (134 μl, 1.03 mmol) were added to dimethoxyethane (5 ml). The resulting mixture was stirred at 70° C. for 6 hours. After cooling to room temperature, the solvent was concentrated under reduced pressure. To the residue was added ethyl acetate and from the resulting mixture, the insoluble matter was filtered off. The filtrate was concentrated under reduced pressure. The residue was washed with hexane to yield a white powder (231 mg).

A toluene (10 ml) solution of the resulting white powder (92 mg), the 4-(methylsulfonyl)-1-butanol (96 mg, 0.631 mmol) obtained in Referential Example 3 and cyanomethylenetri-n-butylphosphorane (148 mg, 0.614 mmol) was heated under reflux for 20 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=1:1), the title compound (74 mg) was obtained as a colorless oil.

IR (ATR) ν: 2931, 2873, 1573, 1475, 1442, 1394, 1313, 1276, 1133, 1083, 1033, 1012, 962, 908, 829, 794, 748, 713, 684, 626, 568, 518, 464 cm$^{-1}$.

$^1$H-NMR (400 MHz, CDCl$_3$) δ: 1.33-1.52(2H,m), 1.79-1.98(2H,m), 2.15-2.30(1H,m), 2.50-2.60(1H,m), 2.86(3H,s), 2.94(2H,t,J=7.9 Hz), 4.86(1H,dd,J=11.0, 3.9 Hz), 7.17-7.29 (3H,m), 7.29-7.38(2H,m), 7.41-7.50(2H,m), 7.67 (1H, d,J=7.8 Hz).

MS (m/z): 435 (M$^+$+H).
HRMS (FAB) for C$_{18}$H$_{21}$O$_4$Cl$_2$S$_2$ (M$^+$+H)
Calculated: 435.0258
Found: 435.0264

Example 64

1-Chloro-3-[1-[(4-chlorophenyl)sulfonyl]-5-(methylsulfonyl)pentyl]benzene

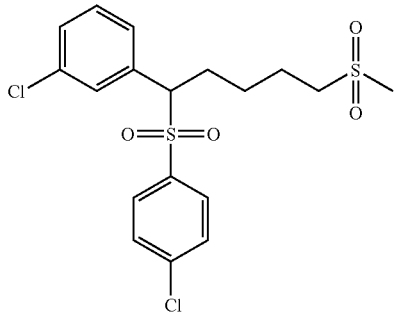

Sodium 4-chlorobenzenesulfinate (219 mg, 1.10 mmol) and 3-chlorobenzyl bromide (142 µl, 1.03 mmol) were added to dimethoxyethane (5 ml). The resulting mixture was stirred at 70° C. for 6 hours. After cooling to room temperature, the solvent was concentrated under reduced pressure. The residue was added with ethyl acetate and from the resulting mixture, the insoluble matter was filtered off. The residue obtained by concentrating the filtrate under reduced pressure was washed with hexane to yield a white powder (304 mg).

A toluene (10 ml) solution of the resulting white powder (92 mg), the 4-(methylsulfonyl)-1-butanol (96 mg, 0.631 mmol) obtained in Referential Example 3 and cyanomethylenetri-n-butylphosphorane (148 mg, 0.614 mmol) was heated under reflux for 20 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=2:3), the title compound (51 mg) was obtained as a colorless oil.

IR (ATR) ν: 3089, 3023, 1573, 1475, 1394, 1278, 1195, 1139, 1081, 1012, 962, 885, 829, 804, 750, 694, 626, 578, 530, 462 cm$^{-1}$.

$^1$H-NMR (400 MHz, CDCl$_3$) δ: 1.32-1.50(2H,m), 1.79-1.97(2H,m), 2.09-2.22(1H,m), 2.40-2.52(1H,m), 2.88(3H,s), 2.90-3.00(2H,m), 3.98(1H,dd,J=11.2, 3.9 Hz), 6.96(1H,d, J=7.6 Hz), 7.10(1H,s), 7.20(1H,t,J=7.6 Hz), 7.28-7.32(1H, m), 7.35-7.47(4H,m).

MS (m/z): 435 (M$^+$+H).

HRMS (FAB): as C$_{18}$H$_{21}$O$_4$Cl$_2$S$_2$ (M$^+$+H)
Calculated: 435.0258
Found: 435.0240

Example 65

1-Chloro-4-[1-[(4-chlorophenyl)sulfonyl]-5-(methylsulfonyl)pentyl]benzene

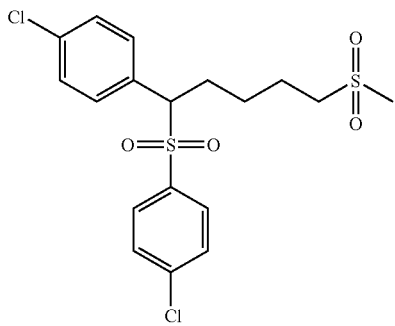

Sodium 4-chlorobenzenesulfinate (211 mg, 1.06 mmol) and 4-chlorobenzyl bromide (218 mg, 1.06 mmol) were added to dimethoxyethane (5 ml), followed by stirring at 70° C. for 6 hours. After cooling to room temperature, the solvent was concentrated under reduced pressure. The residue was added with ethyl acetate and from the resulting mixture, the insoluble matter was filtered off. The residue obtained by concentrating the filtrate under reduced pressure was washed with hexane to yield a white powder (274 mg).

Then, a toluene (10 ml) solution of the resulting white powder (61 mg), the 4-(methylsulfonyl)-1-butanol (63 mg, 0.414 mmol) obtained in Referential Example 3 and cyanomethylenetri-n-butylphosphorane (97 mg, 0.403 mmol) was heated under reflux for 20 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=2:3), the title compound (37 mg) was obtained as a colorless oil.

IR (ATR) ν: 2931, 2871, 1581, 1492, 1475, 1411, 1394, 1276, 1139, 1085, 1012, 962, 908, 827, 752, 713, 661, 620, 566, 518, 470 cm$^{-1}$.

$^1$H-NMR (400 MHz, CDCl$_3$) δ: 1.35-1.51(2H,m), 1.75-1.98(2H,m), 2.05-2.25(1H,m), 2.42-2.55(1H,m), 2.84-3.10 (2H,m), 2.87(3H,s), 3.99(1H,dd,J=11.0, 3.9 Hz), 6.99-7.10 (2H,m), 7.20-7.35(2H,m), 7.35-7.55(4H,m).

MS (m/z): 435(M$^+$+H).

HRMS (FAB) for C$_{18}$H$_{21}$O$_4$Cl$_2$S$_2$ (M$^+$+H)
Calculated: 435.0258
Found: 435.0240

Example 66

1-[1-[(4-Chlorophenyl)sulfonyl]-5-(methylsulfonyl)pentyl]naphthalene

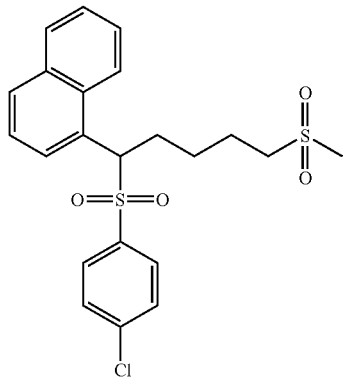

Sodium 4-chlorobenzenesulfinate (183 mg, 0.921 mmol) and 1-bromomethylnaphthalene (204 mg, 0.921 mmol) were added to dimethoxyethane (10 ml). The resulting mixture was stirred at 70° C. for 6 hours. After cooling to room temperature, the solvent was concentrated under reduced pressure. The residue was added with ethyl acetate and from the resulting solution, the insoluble matter was filtered off. The residue obtained by concentrating the filtrate under reduced pressure was washed with hexane to yield a white powder (175 mg).

Then, a toluene (10 ml) solution of the resulting white powder (93 mg), the 4-(methylsulfonyl)-1-butanol (92 mg, 0.604 mmol) obtained in Referential Example 3 and cyanomethylenetri-n-butylphosphorane (142 mg, 0.589 mmol) was heated under reflux for 18 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=1:1), the title compound was obtained as a white solid (80 mg).

IR (ATR) ν: 2929, 2869, 1577, 1511, 1475, 1394, 1301, 1276, 1137, 1083, 1012, 962, 906, 863, 808, 763, 709, 640, 622, 574, 532, 457 cm$^{-1}$.

$^1$H-NMR (400 MHz, CDCl$_3$) δ: 1.35-1.55(2H,m), 1.77-1.95(2H,m), 2.29-2.46(1H,m), 2.62-2.77(1H,m), 2.80(3H,s), 2.83-3.00(2H,m), 5.07(1H,dd,J=10.9, 4.0 Hz), 7.10(2H,d, J=8.3 Hz), 7.22-7.48(4H,m), 7.51(1H,t,J=7.7 Hz), 7.59(1H, d,J=8.6 Hz), 7.67(1H,d,J=7.3 Hz), 7.78(1H,d,J=8.1 Hz), 7.83 (1H,d,J=8.3 Hz).

MS (m/z): 451 (M$^+$+H).

HRMS (FAB) for C$_{22}$H$_{24}$O$_4$ClS$_2$ (M$^+$+H)
Calculated: 451.0805
Found: 451.0816

Example 67

2-[1-[(4-Chlorophenyl)sulfonyl]-5-(methylsulfonyl)pentyl]naphthalene

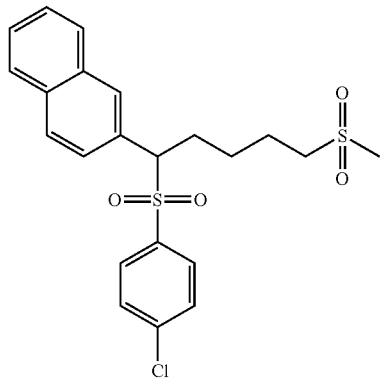

Sodium 4-chlorobenzenesulfinate (211 mg, 1.06 mmol) and 2-bromomethylnaphthalene (235 mg, 1.06 mmol) were added to dimethoxyethane (5 ml). The resulting mixture was stirred at 70° C. for 5 hours. After cooling to room temperature, the solvent was concentrated under reduced pressure. The residue was added with ethyl acetate and from the resulting mixture, the insoluble matter was filtered off. The residue obtained by concentrating the filtrate under reduced pressure was washed with hexane to yield a white powder (90 mg).

Then, a toluene (10 ml) solution of the resulting white powder (60 mg), the 4-(methylsulfonyl)-1-butanol (59 mg, 0.388 mmol) obtained in Referential Example 3 and cyanomethylenetri-n-butylphosphorane (91 mg, 0.379 mmol) was heated under reflux for 21 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=2:3), the title compound was obtained as a white solid (62 mg).

Melting point: 146.0-147.0° C.

IR (ATR) ν: 2931, 2861, 1581, 1508, 1473, 1457, 1392, 1359, 1309, 1274, 1191, 1147, 1126, 1081, 1010, 968, 902, 869, 819, 752, 734, 703, 646, 624, 566, 522, 472, 453 cm$^{-1}$.

$^1$H-NMR (400 MHz, CDCl$_3$) δ: 1.34-1.51(2H,m), 1.78-1.99(2H,m), 2.25-2.40(1H,m), 2.50-2.62(1H,m), 2.84(3H,s), 2.89-3.03(2H,m), 4.19(1H,dd,J=11.2, 3.9 Hz), 7.18-7.36(4H, m), 7.39-7.61(4H,m), 7.69-7.90(3H,m).

MS (m/z): 451 (M$^+$+H).

Elemental Analysis for C$_{22}$H$_{23}$ClO$_4$S$_2$
Calculated: C 58.59%; H 5.14%; Cl 7.86%; S 14.22%.
Found: C 58.46%; H 5.03%; Cl 7.94%; S 14.33%.

Example 68

2-Chloro-1-[1-[(4-chlorophenyl)sulfonyl]-5-(methylsulfonyl)pentyl]-4-fluorobenzene

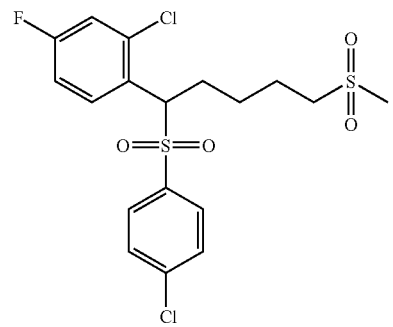

Sodium 4-chlorobenzenesulfinate (197 mg, 0.992 mmol) and 2-chloro-4-fluorobenzyl bromide (222 mg, 0.992 mmol) were added to dimethoxyethane (5 ml). The resulting mixture was stirred at 70° C. for 6 hours. After cooling to room temperature, the solvent was concentrated under reduced pressure. The residue was added with ethyl acetate and from the resulting mixture, the insoluble matter was filtered off. The residue obtained by concentrating the filtrate under reduced pressure was washed with hexane to yield a white powder (225 mg).

Then, a toluene (10 ml) solution of the resulting white powder (61 mg), 4-(methylsulfonyl)-1-butanol (59 mg, 0.394 mmol) obtained in Referential Example 3 and cyanomethylenetri-n-butylphosphorane (93 mg, 0.384 mmol) was heated under reflux for 15 hours under an argon atmosphere. After cooling to room temperature, the reaction mixture was concentrated under reduced pressure. The residue was subjected to medium-pressure chromatography on a silica gel column, whereby from the fraction eluted with hexane:ethyl acetate (=1:1), the title compound was obtained as a white solid (38 mg).

Melting point: 124.0-125.0° C.

IR (ATR) ν: 2969, 2933, 1604, 1575, 1492, 1475, 1461, 1396, 1315, 1276, 1230, 1130, 1085, 1049, 1014, 973, 902, 850, 823, 782, 748, 659, 630, 588, 549, 501, 457 cm$^{-1}$.

$^1$H-NMR (400 MHz, CDCl$_3$) δ: 1.30-1.50(2H,m), 1.79-1.98(2H,m), 2.10-2.25(1H,m), 2.48-2.60(1H,m), 2.87(3H,s), 2.95(2H,t,J=7.7 Hz), 4.79(1H,dd,J=11.1, 4.0 Hz), 6.98(1H, dd,J=8.3, 2.7 Hz), 7.05-7.15(1H,m), 7.38(2H,d,J=8.3 Hz), 7.48(2H,d,J=8.5 Hz), 7.60-7.70(1H,m).

MS (m/z): 453 (M$^+$+H).

Elemental Analysis for $C_{18}H_{19}Cl_2OF_4S_2$

Calculated: C 47.69%; H 4.22%; Cl 15.64%; F 4.19%; S 14.55%.

Found: C 47.44%; H 4.20%; Cl 15.37%; F 4.07%; S 14.33%.

Example 69

1,2-Dichloro-4-[1-[(4-chlorophenyl)sulfonyl]-5-(methylsulfonyl)pentyl]benzene

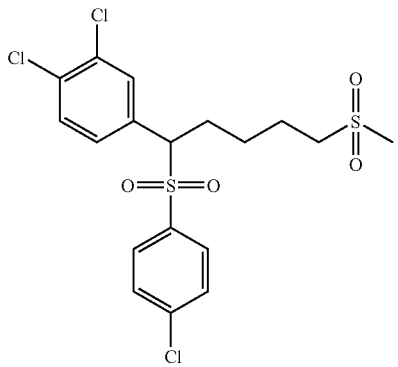

Sodium 4-chlorobenzenesulfinate (208 mg, 1.05 mmol) and 3,4-dichlorobenzyl bromide (251 mg, 1.05 mmol) were added to dimethoxyethane (5 ml). The resulting mixture was stirred at 70° C. for 6 hours. After cooling to room temperature, the solvent was concentrated under reduced pressure. The residue was added with ethyl acetate and from the resulting mixture, the insoluble matter was filtered off. The residue obtained by concentrating the filtrate under reduced pressure was washed with hexane to yield a white powder (270 mg).

Then, a toluene (10 ml) solution of the resulting white powder (66 mg), the 4-(methylsulfonyl)-1-butanol (62 mg, 0.407 mmol) obtained in Referential Example 3 and cyanomethylenetri-n-butylphosphorane (96 mg, 0.397 mmol) was heated under reflux for 15 hours under an argon atmosphere. After cooling to room temperature, the reaction mixture was concentrated under reduced pressure. The residue was subjected to medium-pressure chromatography on a silica gel column. From the fraction eluted with hexane:ethyl acetate (=2:3), the title compound was obtained as a white solid (70 mg).

Melting point: 143.0-144.0° C.

IR (ATR) ν: 2929, 2865, 1573, 1459, 1392, 1365, 1317, 1299, 1276, 1186, 1145, 1079, 1031, 1010, 975, 900, 823, 748, 709, 655, 626, 588, 563, 518, 474, 439 cm$^{-1}$.

$^1$H-NMR (400 MHz, CDCl$_3$) δ: 1.32-1.49(2H,m), 1.79-1.96(2H,m), 2.05-2.19(1H,m), 2.39-2.50(1H,m), 2.88(3H,s), 2.90-3.00(2H,m), 3.97(1H,dd,J=11.2, 3.9 Hz), 6.94(1H,dd, J=8.3, 2.2 Hz), 7.21(1H,d,J=2.0 Hz), 7.36(1H,d,J=8.3 Hz), 7.43(2H,d,J=8.3 Hz), 7.49(2H,d,J=8.6 Hz).

MS (m/z): 469 (M$^+$+H).

Elemental Analysis for $C_{18}H_{19}Cl_3O_4S_2$

Calculated: C 46.02%; H 4.08%; Cl 22.64%; S 13.65%.

Found: C 45.92%; H 4.06%; Cl 22.35%; S 13.59%.

Example 70

2-[1-[(4-Chlorophenyl)sulfonyl]-5-(methylsulfonyl)pentyl]pyridine

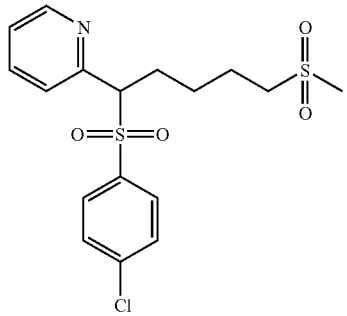

Sodium 4-chlorobenzenesulfinate (200 mg, 1.01 mmol), 2-chloromethylpyridine hydrochloride (166 mg, 1.01 mmol) and potassium acetate (198 mg, 2.02 mmol) were added to n-butanol (5 ml). The resulting mixture was stirred at 70° C. for 5 hours. After cooling to room temperature, the solvent was concentrated under reduced pressure. The residue was added with ethyl acetate and from the resulting mixture, the insoluble matter was filtered off. The filtrate was concentrated under reduced pressure. The residue was subjected to chromatography on a silica gel column. From the fraction eluted with hexane:ethyl acetate (=3:1), a white solid (123 mg) was obtained.

Then, a toluene (10 ml) solution of the resulting solid (49 mg), the 4-(methylsulfonyl)-1-butanol (57 mg, 0.374 mmol) obtained in Referential Example 3 and cyanomethylenetri-n-butylphosphorane (88 mg, 0.366 mmol) was heated under reflux for 2 days under an argon atmosphere. After cooling to room temperature, the reaction mixture was concentrated under reduced pressure. The residue was subjected to medium-pressure chromatography on a silica gel column. From the fraction eluted with methanol:methylene chloride (=1:50), the title compound was obtained as a white solid (40 mg).

Melting point: 140.0-141.0° C.

IR (ATR) ν: 3012, 2948, 1587, 1471, 1436, 1392, 1321, 1290, 1263, 1197, 1149, 1089, 1006, 960, 825, 750, 703, 624, 565, 528, 499, 474, 410 cm$^{-1}$.

$^1$H-NMR (400 MHz, CDCl$_3$) δ: 1.30-1.52(2H,m), 1.79-1.99(2H,m), 2.29-2.49(2H,m), 2.86(3H,s), 2.93(2H,t,J=6.8 Hz), 4.33(1H,dd,J=11.0, 4.2 Hz), 7.20-7.30(1H,m), 7.32-7.52(5H,m), 7.67-7.78(1H,m), 8.40(1H,d,J=4.9 Hz).

MS (m/z): 402 (M$^+$+H).

Elemental Analysis for $C_{17}H_{20}NClO_4S_2$

Calculated: C 50.80%; H 5.02%; N 3.48%; Cl 8.82%; S 15.96%.

Found: C 50.67%; H 4.94%; N 3.53%; Cl 8.72%; S 15.90%.

Example 71

1,4-Dichloro-2-[1-[(4-chlorophenyl)sulfonyl]-5-(methylsulfonyl)pentyl]benzene

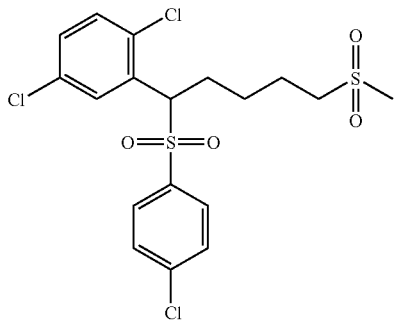

Sodium 4-chlorobenzenesulfinate (38 mg, 0.192 mmol) and 2,5-dichlorobenzyl bromide (46 mg, 0.192 mmol) were added to dimethoxyethane (5 ml). The resulting mixture was stirred at 70° C. for 24 hours. After cooling to room temperature, the reaction mixture was subjected to a short column (silica gel) and the fraction eluted with diethyl ether was concentrated under reduced pressure. The residue thus obtained was dissolved in toluene (5 ml). To the resulting solution were added the 4-(methylsulfonyl)-1-butanol (58 mg, 0.381 mmol) obtained in Referential Example 3 and cyanomethylenetri-n-butylphosphorane (89 mg, 0.370 mmol), followed by heating under reflux for 23 hours under an argon atmosphere. After cooling to room temperature, the reaction mixture was concentrated under reduced pressure. The residue was subjected to medium-pressure chromatography on a silica gel column. From the fraction eluted with hexane:ethyl acetate (=1:1), the title compound (32 mg, 35%) was obtained as a colorless oil.

IR (ATR) ν: 2933, 2869, 1581, 1465, 1394, 1313, 1278, 1191, 1133, 1083, 1039, 1012, 962, 887, 821, 752, 713, 630, 588, 532, 464 cm$^{-1}$.

$^1$H-NMR (400 MHz, CDCl$_3$) δ: 1.33-1.50(2H,m), 1.80-1.96(2H,m), 2.09-2.21(1H,m), 2.48-2.59(1H,m), 2.88(3H,s), 2.90-2.99(2H,t,J=11.0, 4.2 Hz), 4.79(1H,dd,J=11.0, 4.2 Hz), 7.15(1H,d,J=8.6 Hz), 7.20-7.29(1H,m), 7.34-7.40(2H,m), 7.46-7.52(2H,m), 7.63(1H,d,J=2.5 Hz).

MS (m/z): 469, 471 (M$^+$+H).

HRMS (FAB) for C$_{18}$H$_{20}$O$_4$Cl$_3$S$_2$ (M$^+$+H)
Calculated: 468.9869
Found: 468.9907

Example 72

1-[1-[(4-Chlorophenyl)sulfonyl]-5-(methylsulfonyl)pentyl]-3,5-difluorobenzene

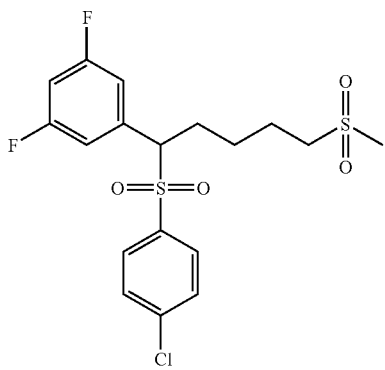

Sodium 4-chlorobenzenesulfinate (49 mg, 0.247 mmol) and 3,5-difluorobenzyl bromide (32 μl, 0.247 mmol) were added to dimethoxyethane (5 ml). The resulting mixture was stirred at 70° C. for 24 hours. After cooling to room temperature, the reaction mixture was subjected to a short column (silica gel) and the fraction eluted with diethyl ether was concentrated under reduced pressure. The residue thus obtained was dissolved in toluene (5 ml). To the resulting solution were added the 4-(methylsulfonyl)-1-butanol (58 mg, 0.381 mmol) obtained in Referential Example 3 and cyanomethylenetri-n-butylphosphorane (89 mg, 0.370 mmol). The mixture was heated under reflux for 23 hours under an argon atmosphere. After cooling to room temperature, the reaction mixture was concentrated under reduced pressure. The residue was subjected to medium-pressure chromatography on a silica gel column. From the fraction eluted with hexane:ethyl acetate (=1:1), the title compound was obtained as a white solid (39 mg, 36%).

Melting point: 126.0-127.0° C.

IR (ATR) ν: 2940, 1623, 1596, 1463, 1392, 1344, 1319, 1270, 1243, 1203, 1145, 1118, 1081, 1010, 987, 952, 863, 823, 752, 707, 680, 624, 539, 501, 478, 449 cm$^{-1}$.

$^1$H-NMR (400 MHz, CDCl$_3$) δ: 1.35-1.62(2H,m), 1.78-1.99(2H,m), 2.05-2.19(1H,m), 2.39-2.51(1H,m), 2.88(3H,s), 2.90-3.05(2H,m), 3.98(1H,dd,J=10.9, 4.0 Hz), 6.62-6.75(2H, m), 6.75-6.85(1H,m), 7.38-7.58(4H,m).

MS (m/z): 436 (M$^+$+H).

Elemental Analysis for C$_{18}$H$_{19}$F$_2$O$_4$S$_2$
Calculated: C 49.48%; H 4.38%; Cl 8.11%; F 8.70%; S 14.68%.
Found: C 49.45%; H 4.33%; Cl 8.10%; F 8.88%; S 14.69%.

Example 73

3-[1-[(4-Chlorophenyl)sulfonyl]-5-(methylsulfonyl)pentyl]pyridine

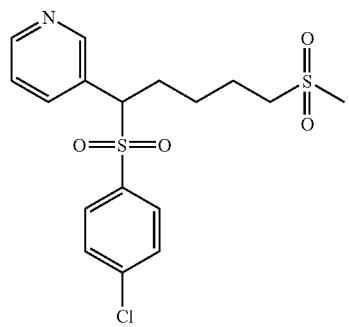

Sodium 4-chlorobenzenesulfinate (207 mg, 1.04 mmol), 3-chloromethylpyridine hydrochloride (171 mg, 1.04 mmol) and potassium acetate (204 mg, 2.08 mmol) were added to n-butanol (5 ml). The resulting mixture was stirred at 70° C. for 5 hours. After cooling to room temperature, the solvent was concentrated under reduced pressure. The residue was added with ethyl acetate and from the resulting mixture, the insoluble matter was filtered off. The filtrate was concentrated under reduced pressure. The residue was subjected to chromatography on a silica gel column and from the fraction eluted with hexane:ethyl acetate (=2:3), a white solid (98 mg) was obtained.

Then, a toluene (10 ml) solution of the resulting solid (29 mg), the 4-(methylsulfonyl)-1-butanol (102 mg, 0.670 mmol)

obtained in Referential Example 3 and cyanomethylenetri-n-butylphosphorane (156 mg, 0.650 mmol) was heated under reflux for 2 days under an argon atmosphere. After cooling to room temperature, the reaction mixture was concentrated under reduced pressure. To the residue was added 1N hydrochloric acid/ethanol and the mixture was concentrated under reduced pressure. The residue was washed with diethyl ether. The residue was added with a saturated aqueous solution of sodium bicarbonate, followed by extraction with ethyl acetate. After the organic layer was dried over anhydrous sodium sulfate, the solvent was concentrated under reduced pressure. The residue was subjected to medium-pressure chromatography on a silica gel column. From the fraction eluted with methanol:methylene chloride (=1:50), the title compound (38 mg) was obtained as a pale yellow oil.

IR (ATR) ν: 2929, 2873, 1575, 1477, 1425, 1394, 1276, 1178, 1132, 1083, 1012, 964, 908, 823, 757, 711, 651, 622, 563, 518, 458 cm$^{-1}$.

$^1$H-NMR (400 MHz, CDCl$_3$) δ: 1.35-1.52(2H,m), 1.80-1.99(2H,m), 2.13-2.26(1H,m), 2.49-2.59(1H,m), 2.88(3H,s), 2.90-2.99(2H,m), 4.05(1H,dd,J=11.1, 4.0 Hz), 7.30(1H,dd, J=7.8, 4.9 Hz), 7.38-7.48(4H,m), 7.64(1H,dt,J=8.1, 2.0 Hz), 8.16(1H,d,J=2.0 Hz), 8.57(1H,dd,J=4.8, 1.6 Hz).

MS (m/z): 402 (M$^+$+H).

HRMS (FAB) for C$_{17}$H$_{21}$O$_4$NClS$_2$ (M$^+$+H)
Calculated: 402.0601
Found: 402.0596

Example 74

4-[1-[(4-Chlorophenyl)sulfonyl]-5-(methylsulfonyl)pentyl]pyridine

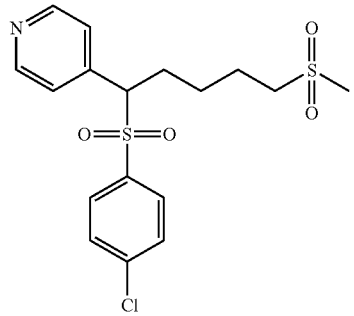

Sodium 4-chlorobenzenesulfinate (207 mg, 1.04 mmol), 3-chloromethylpyridine hydrochloride (171 mg, 1.04 mmol) and potassium acetate (204 mg, 2.08 mmol) were added to n-butanol (5 ml). The resulting mixture was stirred at 70° C. for 5 hours. After cooling to room temperature, the solvent was concentrated under reduced pressure. To the residue was added ethyl acetate and from the resulting mixture, the insoluble matter was filtered off. The filtrate was concentrated under reduced pressure. The residue was subjected to chromatography on a silica gel column and the from the fraction eluted with hexane:ethyl acetate (=2:3), a white solid (117 mg) was obtained.

Then, a toluene (10 ml) solution of the resulting solid (52 mg), the 4-(methylsulfonyl)-1-butanol (90 mg, 0.592 mmol) obtained in Referential Example 3 and cyanomethylenetri-n-butylphosphorane (140 mg, 0.582 mmol) was heated under reflux for 2 days under an argon atmosphere. After cooling to room temperature, the reaction mixture was concentrated under reduced pressure. To the residue was added 1N hydrochloric acid/ethanol. After concentration under reduced pressure, the residue was washed with diethyl ether. To the residue was added a saturated aqueous solution of sodium bicarbonate, followed by extraction with ethyl acetate. The organic layer was dried over anhydrous sodium sulfate, and the solvent was concentrated under reduced pressure. The residue was subjected to medium-pressure chromatography on a silica gel column and from the fraction eluted with methanol: methylene chloride (=1:50), the title compound was obtained as a white solid (62 mg).

Melting point: 181.0-182.0° C.

IR (ATR) ν: 2942, 2863, 1590, 1467, 1415, 1311, 1272, 1241, 1201, 1147, 1085, 1002, 960, 908, 831, 755, 703, 632, 568, 530, 476, 453 cm$^{-1}$.

$^1$H-NMR (400 MHz, CDCl$_3$) δ: 1.30-1.53(2H,m), 1.76-1.99(2H,m), 2.10-2.25(1H,m), 2.40-2.57(1H,m), 2.88(3H,s), 2.90-3.02(2H,m), 4.00(1H,dd,J=11.1, 4.0 Hz), 6.95-7.09(2H, m), 7.32-7.55(4H,m), 8.43-8.60(2H,m).

MS (m/z): 402 (M$^+$+H).

Elemental Analysis for C$_{17}$H$_{20}$NClO$_4$S$_2$
Calculated: C 50.80%; H 5.02%; N 3.48%; Cl 8.82%; S 15.96%.
Found: C 50.70%; H 4.93%; N 3.55%; Cl 8.10%; S 15.83%.

Example 75

2-[1-[(4-Chlorophenyl)sulfonyl]-5-(methylsulfonyl)pentyl]quinoline

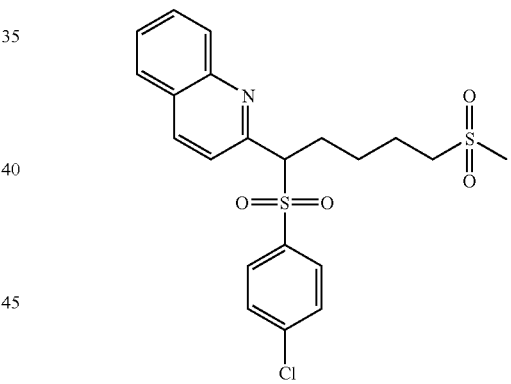

Sodium 4-chlorobenzenesulfinate (196 mg, 0.987 mmol), 2-chloromethylquinoline hydrochloride (211 mg, 0.987 mmol) and potassium acetate (194 mg, 1.97 mmol) were added to n-butanol (5 ml). The resulting mixture was stirred at 70° C. for 5 hours. After cooling to room temperature, the solvent was concentrated under reduced pressure. To the residue was added ethyl acetate and from the resulting mixture, the insoluble matter was filtered off. The residue obtained by concentrating the filtrate under reduced pressure was subjected to chromatography on a silica gel column, whereby from the fraction eluted with hexane:ethyl acetate (=1:1), a white solid (97 mg) was obtained.

Then, a toluene (10 ml) solution of the resulting solid (42 mg), the 4-(methylsulfonyl)-1-butanol (104 mg, 0.684 mmol) obtained in Referential Example 3 and cyanomethylenetri-n-butylphosphorane (160 mg, 0.666 mmol) was heated under reflux for 2 days under an argon atmosphere. After cooling to room temperature, the reaction mixture was concentrated under reduced pressure. The residue was subjected to medium-pressure chromatography on a silica gel column and from the fraction eluted with hexane:ethyl acetate (=1:3), the title compound (49 mg) was obtained as a colorless oil.

IR (ATR) ν: 2931, 2869, 1596, 1581, 1504, 1463, 1428, 1394, 1297, 1278, 1133, 1083, 1012, 960, 875, 829, 755, 705, 663, 624, 568, 516, 457 cm$^{-1}$.

$^1$H-NMR (400 MHz, CDCl$_3$) δ: 1.30-1.60(2H,m), 1.79-1.95(2H,m), 2.40-2.50(2H,m), 2.83(3H,s), 2.91(2H,t,J=7.2 Hz), 4.52(1H,dd,J=9.9, 5.3 Hz), 7.28-7.32(2H,m), 7.39-7.46 (2H,m), 7.55-7.61(2H,m), 7.67-7.73(1H,m), 7.77-7.87(2H, m), 8.19(1H,d,J=8.6 Hz).

MS (m/z): 452 (M$^+$+H).

HRMS (FAB) for C$_{21}$H$_{23}$O$_4$NClS$_2$ (M$^+$+H)

Calculated: 452.0757

Found: 452.0744

Example 76

4-[1-(4-Chlorophenylsulfonyl)-5-(methylsulfonyl)pentyl]-1,2-difluorobenzene

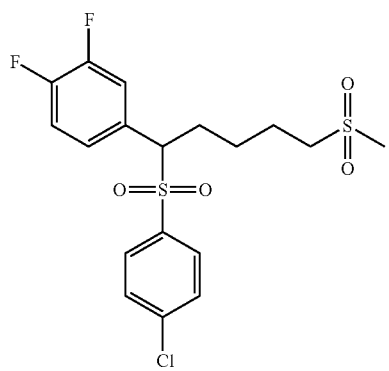

Sodium 4-chlorobenzenesulfinate (45 mg, 0.227 mmol) and 3,4-difluorobenzyl bromide (29 μl, 0.227 mmol) were added to dimethoxyethane (5 ml). The resulting mixture was stirred at 70° C. for 24 hours. After cooling the reaction mixture to room temperature, the solvent was concentrated under reduced pressure. Ethyl acetate was added to the residue and from the mixture, the insoluble matter was filtered off. The filtrate was concentrated under reduced pressure. The residue thus obtained was subjected to chromatography on a silica gel column and the fraction obtained from the ether eluate was concentrated under reduced pressure. A toluene (5 ml) solution of the residue, the 4-(methylsulfonyl)-1-butanol (71 mg, 0.454 mmol) obtained in Referential Example 3 and cyanomethylenetri-n-butylphosphorane (110 mg, 0.454 mmol) was heated under reflux for 16 hours under an argon atmosphere. After cooling to room temperature, the 4-(methylsulfonyl)-1-butanol (71 mg, 0.454 mmol) obtained in Referential Example 3 and cyanomethylenetri-n-butylphosphorane (110 mg, 0.454 mmol) were added, followed by heating under reflux for 22 hours under an argon atmosphere. After cooling to room temperature, the reaction mixture was concentrated under reduced pressure. The residue was subjected to flash chromatography on a silica gel column and the fraction obtained from the hexane:ethyl acetate (=2:3) eluate was concentrated under reduced pressure, whereby the title compound (12 mg, 12%) was obtained as a white solid. The solid was washed with hexane-ether and collected by filtration, whereby the title compound was obtained as a white powder.

Melting point: 122-124° C.

IR (ATR) ν: 2940, 2873, 1610, 1575, 1519, 1467, 1434, 1394, 1317, 1280, 1268, 1205, 1145, 1126, 1083, 1012, 962, 877, 819, 7.65, 754, 707, 632, 592, 549, 526, 514, 507, 484, 451, 404 cm$^{-1}$.

$^1$H-NMR (400 MHz, CDCl$_3$) δ: 1.32-1.50(2H,m), 1.79-1.97(2H,m), 2.03-2.18(1H,m), 2.40-2.50(1H,m), 2.88(3H,s), 2.90-3.00(2H,m), 3.98(1H,dd,J=11.0,3.9 Hz), 6.77-6.81(1H, m), 6.99-7.10(2H,m), 7.38-7.53(4H,m).

MS (m/z): 437 (M$^+$+H).

HRMS (FAB) for C$_{18}$H$_{20}$O$_4$ClF$_2$S$_2$ (M$^+$+H)

Calculated: 437.0460

Found: 437.0494

Example 77

1-[1-(4-Chlorophenylsulfonyl)-5-(methylsulfonyl)pentyl]-2,3-difluorobenzene

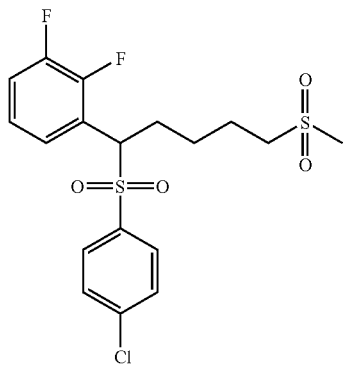

To dimethoxyethane (5 ml) were added sodium 4-chlorobenzenesulfinate (45 mg, 0.227 mmol) and 2,3-difluorobenzyl bromide (29 μl, 0.227 mmol). The resulting mixture was stirred at 70° C. for 24 hours. After cooling at room temperature, the solvent was concentrated under reduced pressure. Ethyl acetate was added to the residue and from the mixture, the insoluble matter was filtered off. The filtrate was concentrated under reduced pressure. The residue was subjected to chromatography on a silica gel column. The fraction obtained from the ether eluate was concentrated under reduced pressure. A toluene (10 ml) solution of the residue, the 4-(methylsulfonyl)-1-butanol (71 mg, 0.454 mmol) obtained in Referential Example 3 and cyanomethylenetri-n-butylphosphorane (110 mg, 0.454 mmol) was heated under reflux for 15 hours under an argon atmosphere. After cooling to room temperature, the reaction mixture was concentrated under reduced pressure. The residue was subjected to flash chromatography on a silica gel column. The fraction obtained from the 55% ethyl acetate/hexane eluate was concentrated under reduced pressure to give the title compound (37 mg, 37%) as a white solid. The solid was washed with hexane-ether and filtered, whereby the title compound was obtained as a white powder.

Melting point: 141-143° C.

IR (ATR) ν: 2948, 2867, 1625, 1575, 1484, 1396, 1317, 1272, 1230, 1199, 1149, 1124, 1085, 1012, 966, 935, 894, 808, 761, 717, 659, 628, 584, 547, 518, 472, 443 cm$^{-1}$.

$^1$H-NMR (400 MHz, CDCl$_3$) δ: 1.37-1.60(2H,m), 1.81-1.96(2H,m), 2.11-2.25(1H,m), 2.45-2.57(1H,m), 2.88(3H,s), 2.96(2H,t,J=7.9 Hz), 4.53(1H,dd,J=11.1, 4.0 Hz), 7.10-7.19 (2H,m), 7.22-7.33(1H,m), 7.39-7.44(2H,m), 7.49-7.54(2H, m).

MS (m/z): 437(M$^+$+H).

Element Analysis for $C_{18}H_{19}ClF_2O_4S_2$

Calculated: C 49.48%; H 4.38%; Cl 8.11%; F 8.70%; S 14.68%.

Found: C 49.38%; H 4.34%; Cl 8.13%; F 8.60%; S 14.56%.

Example 78

1-Chloro-3-[1-(4-chlorophenylsulfonyl)-5-(methylsulfonyl)pentyl]-2-fluorobenzene

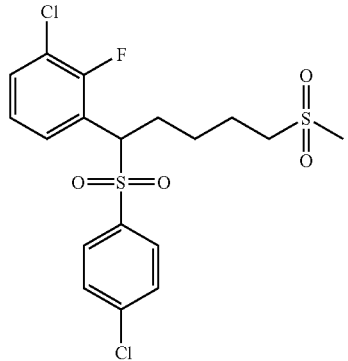

To dimethoxyethane (5 ml) were added sodium 4-chlorobenzenesulfinate (45 mg, 0.227 mmol) and 3-chloro-2-fluorobenzyl bromide (51 mg, 0.227 mmol). The resulting mixture was stirred at 70° C. for 24 hours. After cooling the reaction mixture to room temperature, the solvent was concentrated under reduced pressure. Ethyl acetate was added to the residue and from the resulting mixture, the insoluble matter was filtered off. The filtrate was concentrated under reduced pressure. The residue was subjected to chromatography on a silica gel column and the fraction obtained from the ether eluate was concentrated under reduced pressure. A toluene (5 ml) solution of the resulting residue, the 4-(methylsulfonyl)-1-butanol (71 mg, 0.454 mmol) obtained in Referential Example 3 and cyanomethylenetri-n-butylphosphorane (110 mg, 0.454 mmol) was heated under reflux for 5 days under an argon atmosphere. After cooling to room temperature, the reaction mixture was added with the 4-(methylsulfonyl)-1-butanol (71 mg, 0.454 mmol) obtained in Referential Example 3 and cyanomethylenetri-n-butylphosphorane (110 mg, 0.454 mmol), followed by heating under reflux for 12.5 hours under an argon atmosphere. The reaction mixture was cooled to room temperature and then, concentrated under reduced pressure. The residue was subjected to flash chromatography on a silica gel column, and the fraction obtained from the hexane:ethyl acetate (=1:1) eluate was concentrated under reduced pressure to give the title compound (42 mg, 41%) as a white solid. The resulting solid was washed with hexane-ether and collected by filtration, whereby the title compound was obtained as a white powder.

Melting point: 131-132° C.

IR (ATR) ν: 3038, 2938, 1579, 1459, 1392, 1313, 1286, 1234, 1151, 1120, 1085, 1010, 966, 914, 811, 750, 719, 671, 620, 584, 522, 458 cm$^{-1}$.

$^1$H-NMR (400 MHz, CDCl$_3$) δ: 1.33-1.60(2H,m), 1.80-1.98(2H,m), 2.11-2.25(1H,m), 2.42-2.56(1H,m), 2.88(3H,s), 2.96(2H,t,J=7.9 Hz), 4.53(1H,dd,J=11.1, 4.3 Hz), 7.11-7.20 (1H,m), 7.33-7.46(4H,m), 7.46-7.56(2H,m).

MS (m/z): 453 (M$^+$+H).

Elemental Analysis for $C_{18}H_{19}Cl_2OF_4S_2$

Calculated: C 47.69%; H 4.22%; Cl 15.64%; F 4.19%; S 14.15%.

Found: C 47.40%; H 4.18%; Cl 15.42%; F 4.16%; S 14.08%.

Example 79

4-Chloro-2-[1-(4-chlorophenylsulfonyl)-5-(methylsulfonyl)pentyl]-1-fluorobenzene

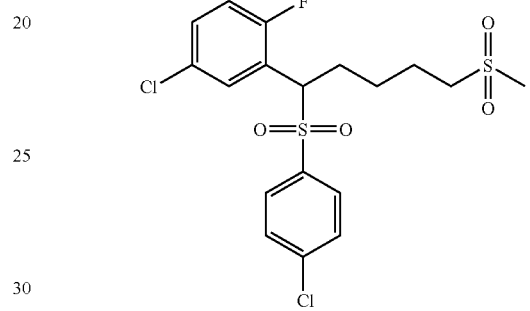

To dimethoxyethane (5 ml) were added sodium 4-chlorobenzenesulfinate (45 mg, 0.227 mmol) and 2-bromomethyl-4-chloro-1-fluorobenzene (51 mg, 0.227 mmol). The resulting mixture was stirred at 70° C. for 24 hours. After cooling the reaction mixture to room temperature, the solvent was concentrated under reduced pressure. Ethyl acetate was added to the residue and from the resulting mixture, the insoluble matter was filtered off. The filtrate was concentrated under reduced pressure. The residue was subjected to chromatography on a silica gel column, and the fraction obtained from the ether eluate was concentrated under reduced pressure. A toluene (5 ml) solution of the residue thus obtained, the 4-(methylsulfonyl)-1-butanol (71 mg, 0.454 mmol) obtained in Referential Example 3 and cyanomethylenetri-n-butylphosphorane (110 mg, 0.454 mmol) was heated under reflux for 16 hours under an argon atmosphere. After cooling to room temperature, the reaction mixture was added with 4-(methylsulfonyl)-1-butanol (71 mg, 0.454 mmol) and cyanomethylenetri-n-butylphosphorane (110 mg, 0.454 mmol), followed by heating under reflux for 22 hours under an argon atmosphere. After cooling to room temperature, the reaction mixture was concentrated under reduced pressure. The residue was subjected to flash chromatography on a silica gel column and the fraction obtained from the hexane:ethyl acetate eluate (=1:1) was concentrated under reduced pressure to give the title compound (53 mg, 51%) as a white solid. The resulting solid was washed with hexane-ether and then collected by filtration, whereby the title compound was obtained as a white powder.

Melting point: 116-117° C.

IR (ATR) ν: 3097, 2946, 1577, 1490, 1407, 1317, 1278, 1240, 1174, 1147, 1083, 1047, 1012, 956, 916, 881, 823, 754, 711, 649, 626, 566, 538, 474, 433 cm$^{-1}$.

$^1$H-NMR (400 MHz, CDCl$_3$) δ: 1.38-1.52(2H,m), 1.81-1.99(2H,m), 2.09-2.21(1H,m), 2.45-2.57(1H,m), 2.89(3H,s), 2.91-3.02(2H,m), 4.48-4.53(1H,m), 6.8.3(1H,t,J=8.9 Hz), 7.23-7.30(1H,m), 7.38-7.45(2H,m), 7.46-7.59(3H,m).

MS (m/z): 453(M$^+$+H).

Elemental Analysis for $C_{18}H_{19}Cl_2OF_4S_2$

Calculated: C 47.69%; H 4.22%; Cl 15.64%; F 4.19%; S 14.15%.

Found: C 47.52%; H 4.19%; Cl 15.47%; F 4.24%; S 14.08%.

Referential Example 7

1-Iodo-4-(methylsulfonyl)butane

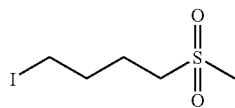

Iodine (1.87 g, 7.35 mmol) was added to a methylene chloride (30 ml) solution of the 4-(methylsulfonyl)-1-butanol (746 mg, 4.90 mmol) obtained in Referential Example 3, imidazole (500 mg, 7.35 mmol) and triphenylphosphine (1.93 g, 7.35 mmol) and the resulting mixture was stirred for 3 hours at room temperature. The reaction mixture was added with a saturated aqueous solution of sodium thiosulfate. The resulting mixture was extracted with methylene chloride. The extract was dried over anhydrous sodium sulfate. After filtration, the filtrate was concentrated under reduced pressure. The residue was subjected to chromatography on a silica gel column. The fraction obtained from the methanol:methylene chloride (=1:100) eluate was concentrated under reduced pressure, whereby the title compound (1.18 g, 92%) was obtained as a pale yellow solid.

$^1$H-NMR (400 MHz, CDCl$_3$) δ: 1.92-2.08(4H,m), 2.93 (3H,s), 3.00-3.10(2H,m), 3.18-3.28(2H,m).

MS (m/z): 263 (M$^+$+H).

Example 80

2-(4-Chlorophenylsulfonylmethyl)-1,3-difluorobenzene

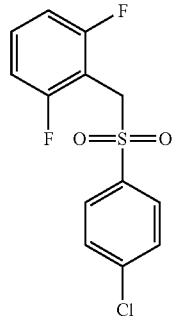

To dimethoxyethane (10 ml) were added sodium 4-chlorobenzenesulfinate (205 mg, 1.03 mmol) and 2,6-difluorobenzyl bromide (214 mg, 1.03 mmol). The resulting mixture was stirred at 70° C. for 18 hours. After cooling the reaction mixture to room temperature, the solvent was concentrated under reduced pressure. Ethyl acetate was added to the residue and from the resulting mixture, the insoluble matter was filtered off. The filtrate was concentrated under reduced pressure. The residue was subjected to chromatography on a silica gel column and the fraction obtained from the ether eluate was concentrated under reduced pressure. The residue was subjected to chromatography on a silica gel column. The fraction obtained from the hexane:ethyl acetate (=10:1) eluate was concentrated under reduced pressure, whereby the title compound (289 mg, 93%) was obtained as a white solid.

IR (ATR) ν: 3097, 2989, 1625, 1575, 1509, 1473, 1407, 1392, 1319, 1272, 1245, 1197, 1182, 1132, 1083, 998, 889, 854, 831, 802, 777, 742, 719, 686, 626, 566, 512, 478, 449, 418 cm$^{-1}$.

$^1$H-NMR (400 MHz, CDCl$_3$) δ: 4.48(2H,s), 6.88(2H,t, J=7.9 Hz), 7.29-7.39(1H,m), 7.47(2H,d,J=8.6 Hz), 7.68(2H, d,J=8.6 Hz).

MS (m/z): 303 (M$^+$+H).

Example 81

2-[1-(4-Chlorophenylsulfonyl)-5-(methylsulfonyl) pentyl]-1,3-difluorobenzene

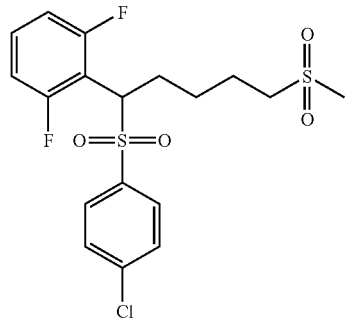

At −78° C., butyl lithium (a 1.57M hexane solution; 0.55 ml, 0.864 mmol) was added dropwise to a dimethoxyethane (10 ml) solution of 2-(4-chlorophenylsulfonylmethyl)-1,3-difluorobenzene (218 mg, 0.720 mmol). After stirring at −0.78° C. for 30 minutes, a dimethoxyethane (5 ml) solution of the 1-iodo-4-(methylsulfonyl)butane (226 mg, 0.864 mmol) obtained in Referential Example 7 was added dropwise. The temperature of the reaction mixture was elevated gradually to room temperature and at room temperature, the mixture was stirred for 15 hours. Water was added to the reaction mixture and the mixture was extracted with ethyl acetate. The organic layer was washed with brine, dried over anhydrous sodium sulfate. After filtration, the filtrate was concentrated under reduced pressure. The residue thus obtained was subjected to flash chromatography on a silica gel column and the fraction obtained from the 55% ethyl acetate/hexane eluate was concentrated under reduced pressure to give the title compound (53 mg, 17%) as a white solid. The resulting solid was washed with hexane and collected by filtration, whereby the title compound was obtained as a white powder.

Melting point: 118-119° C.

IR (ATR) ν: 2946, 1621, 1585, 1471, 1459, 1396, 1355, 1322, 1301, 1274, 1226, 1151, 1132, 1087, 1012, 989, 958, 925, 829, 773, 761, 752, 717, 624, 572, 522, 485, 458, 406 cm$^{-1}$.

$^1$H-NMR (400 MHz, CDCl$_3$) δ: 1.35-1.55(2H,m), 1.81-1.95(2H,m), 2.48-2.58(2H,m), 2.88(3H,s), 2.91-3.10(2H,m), 2.97(1H,dd,J=15.8, 6.7 Hz), 6.75-7.00(2H,m), 7.25-7.35(1H, m), 7.42(2H,d,J=8.6 Hz), 8.30(2H,d,J=8.3 Hz).

MS (m/z): 437 (M$^+$+H).

Elemental Analysis for $C_{18}H_{19}ClF_2O_4S_2$

Calculated: C 49.48%; H 4.38%; Cl 8.11%; F 8.70%; S 14.68%.

Found: C 49.25%; H 4.32%; Cl 8.02%; F 8.50%; S 14.70%.

Example 82

1-(4-Chlorophenylsulfonylmethyl)-3-methoxybenzene

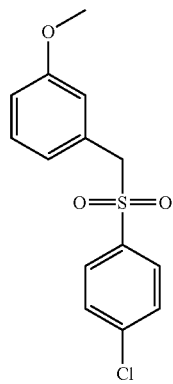

A dimethoxyethane (10 ml) suspension of sodium 4-chlorobenzenesulfinate (210 mg, 1.06 mmol) and 3-methoxybenzyl chloride (154 μl, 1.06 mmol) was stirred at 70° C. for 16 hours. After cooling to room temperature, butanol (2 ml) and tetrabutylammonium bromide (45 mg) were added and the resulting mixture was stirred further at 70° C. for 16 hours. After cooling the reaction mixture to room temperature, the solvent was concentrated under reduced pressure. Ethyl acetate was added to the residue. The mixture was washed successively with water and brine, and dried over anhydrous sodium sulfate. After filtration, the filtrate was concentrated under reduced pressure. The residue was subjected to flash chromatography on a silica gel column, and the fraction obtained from the hexane:ethyl acetate (=5:1) eluate was concentrated under reduced pressure, whereby the title compound (216 mg, 69%) was obtained as a white solid.

IR (ATR) ν: 3064, 2979, 2842, 1598, 1488, 1469, 1434, 1392, 1313, 1268, 1176, 1130, 1085, 1033, 1012, 941, 879, 823, 792, 765, 742, 692, 620, 574, 528, 455 cm$^{-1}$.

$^1$H-NMR (400 MHz, CDCl$_3$) δ: 3.74(3H,s), 4.27(2H,s), 6.59-6.68(2H,m), 6.82-6.90(1H,m), 7.17(1H,t,J=7.8 Hz), 7.42(2H,d,J=8.6 Hz), 7.56(2H,d,J=8.6 Hz).

MS (m/z): 297 (M$^+$+H).

Example 83

1-[1-(4-Chlorophenylsulfonyl)-5-(methylsulfonyl)pentyl]-3-methoxybenzene

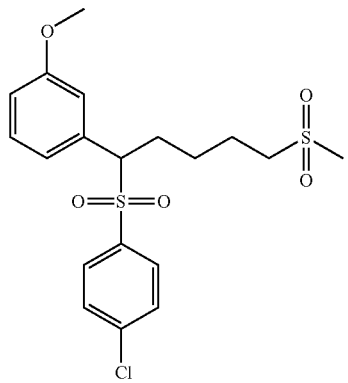

A toluene (10 ml) solution of 1-(4-chlorophenylsulfonylmethyl)-3-methoxybenzene (80 mg, 0.269 mmol), the 4-(methylsulfonyl)-1-butanol (62 mg, 0.404 mmol) obtained in Referential Example 3, and cyanomethylenetri-n-butylphosphorane (98 mg, 0.404 mmol) was heated under reflux for 3 days under an argon atmosphere. After cooling to room temperature, the reaction mixture was concentrated under reduced pressure. The residue thus obtained was subjected to flash chromatography on a silica gel column, and the fraction obtained from the hexane:ethyl acetate (=1:1) eluate was concentrated under reduced pressure to give the title compound (61 mg, 52%) as a white solid. The white solid was washed with hexane, and collected by filtration, whereby the title compound was obtained as a white powder.

Melting point: 91-93° C.

IR (ATR) ν: 2967, 2929, 1594, 1494, 1469, 1455, 1394, 1315, 1272, 1255, 1222, 1189, 1145, 1132, 1085, 1037, 1012, 970, 879, 850, 804, 759, 705, 688, 632, 603, 532, 493, 464 cm$^{-1}$.

$^1$H-NMR (400 MHz, CDCl$_3$) δ: 1.37-1.50(2H,m), 1.79-1.93(2H,m), 2.10-2.23(1H,m), 2.40-2.52(1H,m), 2.86(3H,s), 2.89-2.98(2H,m), 3.73(3H,s), 3.97(1H,dd,J=11.1, 3.8 Hz), 6.59-6.67(2H,m), 6.80-6.89(1H,m), 7.15(1H,d,J=8.0 Hz), 7.35(2H,d,J=8.6 Hz), 7.44(2H,d,J=8.6 Hz).

MS (m/z): 431 (M$^+$+H).

Elemental Analysis for C$_{19}$H$_{23}$ClO$_5$S$_2$

Calculated: C 52.95%; H 5.38%; Cl 8.23%; S 14.88%.

Found: C 52.89%; H 5.25%; Cl 8.33%; S 14.87%.

Example 84

1-(4-Chlorophenylsulfonylmethyl)-4-methoxybenzene

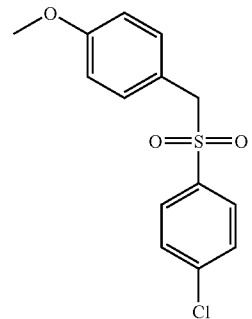

A butanol (5 ml) suspension of sodium 4-chlorobenzenesulfinate (264 mg, 1.33 mmol), 4-methoxybenzyl chloride (181 μl, 1.33 mmol) and tetrabutylammonium bromide (24 mg) was stirred at 70° C. for 3 days. After cooling the reaction mixture to room temperature, the solvent was concentrated under reduced pressure. Ethyl acetate was added to the residue and the mixture was washed successively with water and brine, and then dried over anhydrous sodium sulfate. After filtration, the filtrate was concentrated under reduced pressure. The residue was subjected to flash chromatography on a silica gel column, and the fraction obtained from the hexane:ethyl acetate (=5:1) eluate was concentrated under reduced pressure, whereby the title compound (90 mg, 23%) was obtained as a white solid.

IR (ATR) ν: 3072, 2996, 2942, 2836, 1608, 1583, 1509, 1467, 1396, 1309, 1292, 1240, 1176, 1147, 1089, 1031, 1016, 977, 956, 887, 829, 767, 715, 630, 532, 474, 431 cm$^{-1}$.

$^1$H-NMR (400 MHz, CDCl$_3$) δ: 3.80(3H,s), 4.25(2H,s), 6.80(2H,d,J=8.8 Hz), 7.00(2H,d,J=8.6 Hz), 7.42(2H,d,J=8.3 Hz), 7.54 (2H, d, J=8.6 Hz).

Example 85

1-[1-(4-Chlorophenylsulfonyl)-5-(methylsulfonyl)pentyl]-4-methoxybenzene

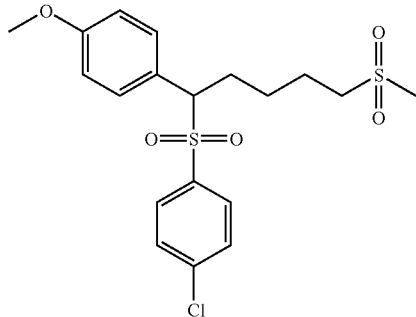

A toluene (10 ml) solution of 1-(4-chlorophenylsulfonyl-methyl)-4-methoxybenzene (72 mg, 0.243 mmol), the 4-(methylsulfonyl)-1-butanol (70 mg, 0.460 mmol) obtained in Referential Example 3 and cyanomethylenetri-n-butylphosphorane (111 mg, 0.460 mmol) was heated under reflux for 15 hours under an argon atmosphere. After cooling to room temperature, the reaction mixture was added with the 4-(methylsulfonyl)-1-butanol (70 mg, 0.460 mmol) obtained in Referential Example 3 and cyanomethylenetri-n-butylphosphorane (111 mg, 0.460 mmol) and the mixture was heated under reflux for 22 hours under an argon atmosphere. After cooling to room temperature, the reaction mixture was concentrated under reduced pressure. The residue thus obtained was subjected to flash chromatography on a silica gel column, and the fraction obtained from the hexane:ethyl acetate (=1:1) eluate was concentrated under reduced pressure to give the title compound (33 mg, 32%) as a white solid. The resulting white solid was washed with hexane and then collected by filtration, whereby the title compound was obtained as a white powder.

Melting point: 136-138° C.
IR (ATR) ν: 3012, 2937, 1608, 1583, 1511, 1471, 1392, 1319, 1292, 1268, 1253, 1178, 1145, 1130, 1085, 1029, 1012, 964, 833, 823, 771, 754, 723, 628, 574, 551, 530, 497, 472, 439 cm$^{-1}$.
$^{1}$H-NMR (400 MHz, CDCl$_3$) δ: 1.37-1.50(2H,m), 1.79-1.93(2H,m), 2.10-2.23(1H,m), 2.40-2.52(1H,m), 2.86(3H,s), 2.89-2.98(2H,m), 3.73(3H,s), 3.97(1H,dd,J=11.1, 3.8 Hz), 6.59-6.67(2H,m), 6.80-6.89(1H,m), 7.15(1H,d,J=8.0 Hz), 7.35(2H,d,J=8.6 Hz), 7.44(2H,d,J=8.6 Hz).
MS (m/z): 431 (M$^{+}$+H).

Elemental Analysis for C$_{19}$H$_{23}$ClO$_5$S$_2$
Calculated: C 52.95%; H 5.38%; Cl 8.23%; S 14.88%.
Found: C 52.99%; H 5.29%; Cl 8.29%; S 14.82%.

Referential Example 8

Methyl 3-(N,N-dimethylcarbamoyl)benzoate

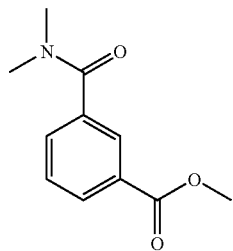

To a methylene chloride (20 ml) solution of monomethyl isophthalate (317 mg, 1.76 mmol) were added dimethylamine hydrochloride (172 mg, 2.11 mmol), 1-hydroxybenzotriazole (287 mg, 1.76 mmol), 1-ethyl-3-(3-dimethylaminopropyl) carbodiimide hydrochloride (404 mg, 2.11 mmol) and N-methylmorpholine (0.23 ml, 2.11 mmol) and the resulting mixture was stirred at room temperature for 21 hours. The reaction mixture was concentrated under reduced pressure. Ethyl acetate was added to the residue. The resulting mixture was washed successively with 1N hydrochloric acid, a saturated aqueous solution of sodium bicarbonate, and brine, and dried over anhydrous sodium sulfate. After filtration, the filtrate was concentrated under reduced pressure. The residue was subjected to chromatography on a silica gel column and the fraction obtained from the methanol:methylene chloride (=1:50) eluate was concentrated under reduced pressure, whereby the title compound (290 mg, 80%) was obtained as a colorless oil.

IR (ATR) ν: 1720, 1633, 1583, 1500, 1436, 1392, 1286, 1255, 1205, 1112, 1076, 979, 933, 823, 773, 730, 696, 669, 638, 580, 489, 439 cm$^{-1}$.
$^{1}$H-NMR (400 MHz, CDCl$_3$) δ: 2.99(3H,s), 3.13(3H,s), 3.93(3H,s), 7.49(1H,t,J=8.2 Hz), 7.63(1H,t,J=7.6 Hz), 8.05-8.15(2H,m).
MS (m/z): 208 (M$^{+}$+H).

Referential Example 9

3-Hydroxymethyl-N,N-dimethylbenzamide

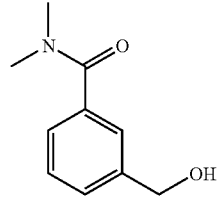

Under ice cooling, sodium borohydride (264 mg, 6.97 mmol) was added to an ethanol (15 ml) solution of methyl 3-(N,N-dimethylcarbamoyl)benzoate (289 mg, 1.39 mmol). The temperature of the resulting mixture was allowed to rise back to room temperature and then, stirring was conducted at 50° C. for 14 hours. After the reaction mixture was cooled back to room temperature, it was ice cooled. Sodium borohydride (264 mg, 6.97 mmol) was added and the mixture was stirred at 50° C. for 6 hours. The reaction mixture was ice cooled, and then added with water, followed by concentration under reduced pressure. The residue thus obtained was added with water, followed by extraction with methylene chloride. The extract was dried over anhydrous sodium sulfate. After filtration, the filtrate was concentrated under reduced pressure. The residue was subjected to chromatography on a silica gel column, and the fraction obtained from the methanol:methylene chloride (=1:30) eluate was concentrated under reduced pressure, whereby the title compound (196 mg, 79%) was obtained as a colorless oil.

IR (ATR) ν: 3367, 2929, 2869, 1600, 1583, 1508, 1479, 1452, 1394, 1267, 1236, 1170, 1097, 1079, 1049, 898, 800, 746, 719, 694, 642, 431 cm$^{-1}$.
$^{1}$H-NMR (400 MHz, CDCl$_3$) δ: 2.46(1H,br s), 2.97(3H,s), 3.11(3H,s), 4.67(2H,br d,J=2.9 Hz), 7.23-7.48(4H,m).
MS (m/z): 180 (M$^{+}$+H).

Example 86

3-(4-Chlorophenylsulfonylmethyl)-N,N-dimethylbenzamide

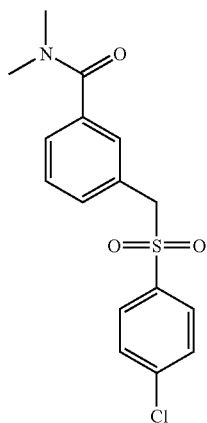

To a methylene chloride (15 ml) solution of 3-hydroxymethyl-N,N-dimethylbenzamide (184 mg, 1.03 mmol) were added carbon tetrabromide (511 mg, 1.59 mmol) and triphenylphosphine (404 mg, 1.54 mmol). The resulting mixture was stirred at room temperature for 4.5 hours. The reaction mixture was concentrated under reduced pressure. The residue thus obtained was subjected to flash column chromatography and the fraction obtained from the hexane:ethyl acetate (=1:1) eluate was concentrated under reduced pressure to give a colorless oil (239 mg).

A dimethoxyethane (15 ml) suspension of the resulting colorless oil (239 mg, 0.987 mmol) and sodium 4-chlorobenzenesulfinate (234 mg, 1.18 mmol) was stirred at 70° C. for 3 days. After cooling the reaction mixture to room temperature, the solvent was concentrated under reduced pressure. Ethyl acetate was added to the residue, followed by successive washing with water and brine and drying over anhydrous sodium sulfate. After filtration, the filtrate was concentrated under reduced pressure. The residue was subjected to flash chromatography on a silica gel column and the fraction obtained from the 70% ethyl acetate/hexane eluate was concentrated under reduced pressure, whereby the title compound (125 mg, 37%) was obtained as a colorless oil.

$^1$H-NMR (400 MHz, CDCl$_3$) δ: 2.89(3H,s), 3.09(3H,s), 4.32(2H,s), 7.10-7.50(6H,m), 7.59(2H,d,J=8.6 Hz).

MS (m/z): 338 (M$^+$+H).

Example 87

3-[1-(4-Chlorophenylsulfonyl)-5-(methylsulfonyl)pentyl]-N,N-dimethylbenzamide

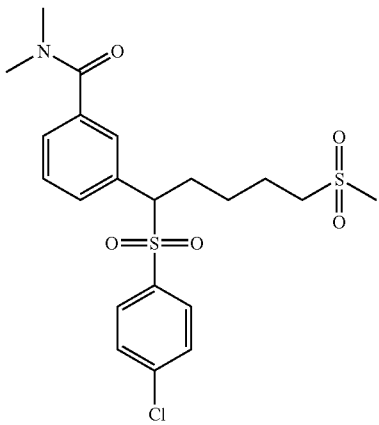

A toluene (10 ml) solution of 3-(4-chlorophenylsulfonylmethyl)-N,N-dimethylbenzamide (69 mg, 0.204 mmol), the 4-(methylsulfonyl)-1-butanol (62 mg, 0.409 mmol) obtained in Referential Example 3 and cyanomethylenetri-n-butylphosphorane (99 mg, 0.409 mol) was heated under reflux for 15 hours under an argon atmosphere. After cooling to room temperature, the 4-(methylsulfonyl)-1-butanol (62 mg, 0.504 mmol) obtained in Referential Example 3 and cyanomethylenetri-n-butylphosphorane (99 mg, 0.504 mmol) were added. The reaction mixture was heated under reflux for 23 hours under an argon atmosphere. After cooling to room temperature, the reaction mixture was concentrated under reduced pressure. The residue was subjected to flash chromatography on a silica gel column, and the fraction obtained from the methanol:methylene chloride (=1:50) eluate was concentrated under reduced pressure, whereby the title compound (37 mg, 38%) was obtained as an amorphous substance.

IR (ATR) ν: 2927, 1625, 1581, 1504, 1475, 1394, 1276, 1172, 1141, 1083, 1012, 964, 908, 819, 754, 705, 626, 551, 516, 468 cm$^{-1}$.

$^1$H-NMR (400 MHz, CDCl$_3$) δ: 1.32-1.49(2H,m), 1.78-1.92(2H,m), 2.12-2.28(1H,m), 2.40-2.50(1H,m), 2.83(3H,br s), 2.87(3H,s), 2.90-2.98(2H,m), 3.08(3H,br s), 4.05(1H,dd, J=11.1, 3.8 Hz), 7.12(1H,br s), 7.19-7.25(1H,m), 7.32-7.40 (4H,m), 7.48 (2H,d,J=8.6 Hz).

MS (m/z): 472 (M$^+$+H).

HRMS (FAB) for C$_{21}$H$_{27}$O$_5$NClS$_2$ (M$^+$+H)

Calculated: 472.1019

Found: 472.1010

Example 88

2-(4-Chlorophenylsulfonylmethyl)-N,N-dimethylbenzamide

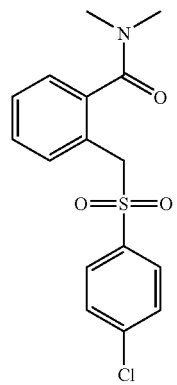

To a methanol (5 ml) solution of phthalide (639 mg, 4.76 mmol) was added a 50% aqueous solution (2 ml) of dimethylamine and the mixture was stirred at 70° C. for 14 hours. After cooling to room temperature, the reaction mixture was concentrated under reduced pressure. To the residue was added methylene chloride. The mixture was dried over anhydrous sodium sulfate. After filtration, the filtrate was concentrated under reduced pressure. The residue was subjected to chromatography on a silica gel column and the fraction obtained from the methanol:methylene chloride (=1:40) eluate was concentrated under reduced pressure to yield a colorless oil (248 mg, 29%). To a methylene chloride (10 ml) solution of the colorless oil (238 mg, 1.33 mmol) were added triphenylphosphine (522 mg, 1.99 mmol) and carbon tetrabromide (660 mg, 1.99 mmol) and the mixture was stirred at room temperature for 2 hours. The reaction mixture was concentrated under reduced pressure. The residue was subjected to chromatography on a silica gel column and the fraction obtained from the hexane:ethyl acetate (=3:2) eluate was concentrated under reduced pressure. The residue was dissolved in butanol (10 ml) followed by the addition thereto sodium 4-chlorobenzenesulfinate (264 mg, 1.33 mmol). The mixture was stirred at 70° C. for 2 days. After cooling to room temperature, the reaction mixture was concentrated under reduced pressure. Ethyl acetate was added to the residue, followed by successive washing with water and brine and drying over anhydrous sodium sulfate. After filtration, the filtrate was concentrated under reduced pressure. The residue was subjected to flash chromatography on a silica gel column, and the fraction obtained from the hexane:ethyl acetate (=3:2) eluate was concentrated under reduced pressure, whereby the title compound (216 mg, 48%) was obtained as an amorphous substance.

$^1$H-NMR (400 MHz, CDCl$_3$) δ: 2.97(3H,s), 3.13(3H,s), 7.50(2H,d,J=8.8 Hz), 7.73(2H,d,J=8.6 Hz).

IR (ATR) ν: 2931, 1621, 1598, 1581, 1504, 1475, 1444, 1392, 1317, 1278, 1191, 1151, 1083, 1068, 1012, 879, 827, 777, 757, 740, 705, 636, 607, 566, 536, 466, 447 cm$^{-1}$.

MS (m/z): 338 (M$^+$+H).

Example 89

2-[1-(4-Chlorophenylsulfonyl)-5-(methylsulfonyl)pentyl]-N,N-dimethylbenzamide

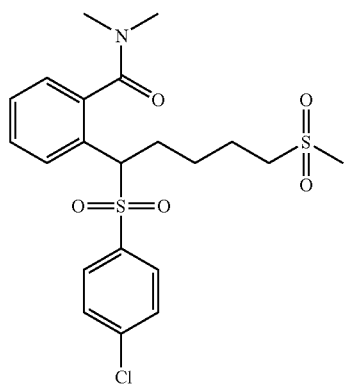

A toluene (5 ml) solution of 2-(4-chlorophenylsulfonylmethyl)-N,N-dimethylbenzamide (161 mg, 0.477 mmol), the 4-(methylsulfonyl)butanol (100 mg, 0.657 mmol) obtained in Referential Example 3 and cyanomethylenetri-n-butylphosphorane (159 mg, 0.657 mmol) was heated under reflux for 17 hours under an argon atmosphere. After cooling to room temperature, the reaction mixture was added with the 4-(methylsulfonyl)butanol (100 mg, 0.657 mmol) obtained in Referential Example 3 and cyanomethylenetri-n-butylphosphorane (159 mg, 0.657 mmol). The mixture was stirred under an argon atmosphere for 24 hours. After cooling to room temperature, the reaction mixture was concentrated under reduced pressure. The residue was subjected to flash chromatography on a silica gel column, and the fraction obtained from the 80% ethyl acetate/hexane eluate was concentrated under reduced pressure, whereby the title compound (79 mg, 35%) was obtained as an amorphous substance.

$^1$H-NMR (400 MHz, CDCl$_3$) δ: 1.25-1.49(2H,m), 1.63-1.80(1H,m), 1.80-1.93(1H,m), 2.00-2.20(2H,m), 2.76-2.95(2H,m), 2.82(3H,s), 2.84(3H,s), 3.11(3H,s), 4.70-4.82(1H,m), 7.22(1H,d,J=7.3 Hz), 7.32-7.46(3H,m), 7.49(2H,d,J=8.6 Hz), 7.63(2H,d,J=8.6 Hz).

IR (ATR) ν: 2931, 2873, 1621, 1581, 1506, 1475, 1448, 1394, 1278, 1222, 1182, 1137, 1083, 1012, 962, 823, 755, 707, 630, 561, 518, 460 cm$^{-1}$.

MS: 472 (M$^+$+H).

HRMS (FAB) for C$_{21}$H$_{27}$O$_5$NClS$_2$ (M$^+$+H)

Calculated: 472.1019

Found: 472.1023

Example 90

3-(4-Chlorophenylsulfonylmethyl)benzonitrile

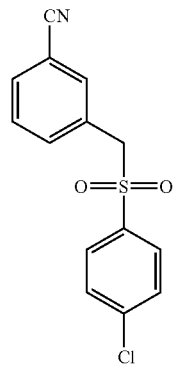

A dimethoxyethane (15 ml) suspension of sodium 4-chlorobenzenesulfinate (270 mg, 1.36 mmol) and 3-bromomethylbenzonitrile (222 mg, 1.13 mmol) was stirred at 70° C. for 3 days. After cooling the reaction mixture to room temperature, the solvent was concentrated under reduced pressure. Ethyl acetate was added to the residue. The mixture was washed successively with water and brine and then, dried over anhydrous sodium sulfate. After filtration, the filtrate was concentrated under reduced pressure. The residue was subjected to flash chromatography on a silica gel column and the fraction obtained from the hexane:ethyl acetate (=3:1) eluate was concentrated under reduced pressure, whereby the title compound (318 mg, 96%) was obtained as a white solid.

IR (ATR) ν: 3087, 2985, 2229, 1581, 1581, 1475, 1432, 1394, 1317, 1282, 1265, 1228, 1145, 1081, 1012, 929, 904, 885, 844, 811, 798, 763, 723, 686, 651, 626, 578, 545, 522, 484, 462 cm$^{-1}$.

$^1$H-NMR (400 MHz, CDCl$_3$) δ: 4.32(2H,s), 7.38-7.52(5H,m), 7.60(2H,d,J=8.8 Hz), 7.66(1H,d,J=7.6 Hz).

MS (m/z): 292 (M$^+$+H).

Example 91

3-[1-[(4-Chlorophenyl)sulfonyl]-5-(methylsulfonyl)pentyl]benzonitrile

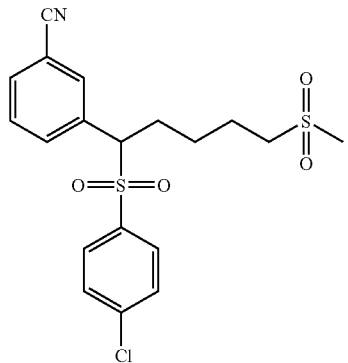

A toluene (10 ml) solution of 3-(4-chlorophenylsulfonylmethyl)benzonitrile (60 mg, 0.204 mmol), the 4-(methylsulfonyl)-1-butanol (62 mg, 0.409 mmol) obtained in Referential Example 3 and cyanomethylenetri-n-butylphosphorane (99 mg, 0.409 mmol) was heated under reflux for 15 hours under an argon atmosphere. After cooling to room temperature, the reaction mixture was added with the 4-(methylsulfonyl)-1-butanol (62 mg, 0.504 mmol) obtained in Referential Example 3 and cyanomethylenetri-n-butylphosphorane (99 mg, 0.504 mmol), followed by heating under reflux for 23 hours under an argon atmosphere. After cooling to room temperature, the reaction mixture was concentrated under reduced pressure. The residue was subjected to flash chromatography on a silica gel column, and the fraction obtained from the hexane:ethyl acetate (=1:2) eluate was concentrated under reduced pressure, whereby the title compound (69 mg, 79%) was obtained as an amorphous substance.

IR (ATR) ν: 2931, 2229, 1579, 1475, 1432, 1394, 1278, 1137, 1083, 1051, 1012, 964, 914, 813, 752, 688, 649, 613, 549, 516, 466 cm$^{-1}$.

$^1$H-NMR (400 MHz, CDCl$_3$) δ: 1.30-1.50(2H,m), 1.79-1.97(2H,m), 2.10-2.22(1H,m), 2.40-2.51(1H,m), 2.89(3H,s), 2.90-3.00(2H,m), 4.06(1H,dd,J=11.1, 4.0 Hz), 7.35-7.50(7H,m), 7.64(1H,d,J=7.3 Hz).

MS (m/z): 426 (M$^+$+H).

Elemental Analysis for C$_{19}$H$_{20}$ClNO$_4$S$_2$.0.25H$_2$O

Calculated: C 53.02%; H 4.80%; Cl 8.24%; N 3.25%; S 14.90%.

Found: C 52.94%; H 4.85%; Cl 8.54%; N 3.25%; S 14.93%.

Example 92

2-(4-Chlorophenylsulfonylmethyl)benzonitrile

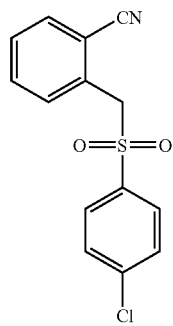

A dimethoxyethane (5 ml) suspension of sodium 4-chlorobenzenesulfinate (218 mg, 1.10 mmol) and 2-bromomethylbenzonitrile (215 mg, 1.10 mmol) was stirred at 70° C. for 17 hours. After cooling the reaction mixture to room temperature, the solvent was concentrated under reduced pressure. The residue thus obtained was subjected to chromatography on a short silica gel column and the fraction obtained from the ether eluate was concentrated under reduced pressure. The residue was subjected to chromatography on a silica gel column and the fraction obtained from the hexane:ethyl acetate (=3:1) eluate was concentrated under reduced pressure to give a white solid. The resulting white solid was washed with ether, and collected by filtration, whereby the title compound (226 mg, 70%) was obtained as a white powder.

IR (ATR) ν: 3079, 2979, 2227, 1573, 1488, 1473, 1450, 1425, 1392, 1321, 1299, 1280, 1253, 1209, 1174, 1143, 1081, 1010, 946, 904, 879, 829, 781, 759, 711, 682, 632, 593, 532, 480, 451 cm$^{-1}$.

$^1$H-NMR (400 MHz, CDCl$_3$) δ: 4.58(2H,s), 7.43-7.51(3H,m), 7.56-7.68(5H,m).

Example 93

2-[1-[(4-chlorophenyl)sulfonyl]-5-(methylsulfonyl)pentyl]benzonitrile

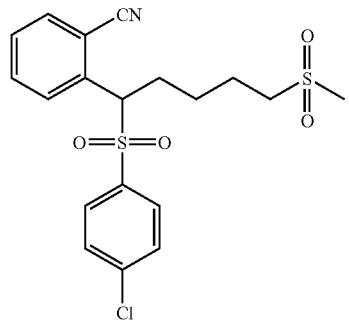

A toluene (5 ml) solution of 2-(4-chlorophenylsulfonylmethyl)benzonitrile (96 mg, 0.329 mmol), the 4-(methylsulfonyl)-1-butanol (100 mg, 0.657 mmol) obtained in Referential Example 3 and cyanomethylenetri-n-butylphosphorane (159 mg, 0.657 mol) was heated under reflux for 22 hours under an argon atmosphere. After cooling to room temperature, the reaction mixture was concentrated under reduced pressure. The residue was subjected to flash chromatography on a silica gel column, and the fraction obtained from the 60% ethyl acetate/hexane eluate was concentrated under reduced pressure, whereby the title compound (139 mg, 99%) was obtained as an amorphous substance.

IR (ATR) ν: 3089, 2931, 2225, 1575, 1475, 1448, 1394, 1315, 1295, 1278, 1214, 1176, 1139, 1124, 1083, 1012, 962, 908, 827, 794, 754, 711, 628, 553, 516, 470 cm$^{-1}$.

$^1$H-NMR (400 MHz, CDCl$_3$) δ: 1.30-1.54(2H,m), 1.81-1.98(2H,m), 2.20-2.31(1H,m), 2.47-2.59(1H,m), 2.88(3H,s), 2.90-3.00(2H,m), 4.63(1H,dd,J=11.0, 4.2 Hz), 7.38-7.60(6H,m), 7.67-7.73(1H,m), 7.79(1H,d,J=8.1 Hz).

MS (m/z): 426 (M$^+$+H).

HRMS (FAB) for C$_{19}$H$_{21}$O$_4$NClS$_2$ (M$^+$+H)

Calculated: 426.0601

Found: 426.0636

Example 94

1-Chloro-4-(cyclohexylmethylsulfonyl)benzene

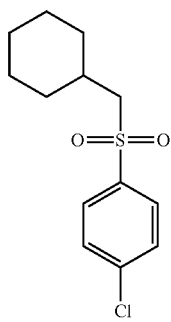

To an acetonitrile (10 ml) solution of 4-chlorobenzenethiol (230 mg, 1.59 mmol and cyclohexylmethyl bromide (222 μl, 1.59 mmol) was added potassium carbonate (329 mg, 2.38 mmol) and the mixture was stirred at room temperature for 3 hours. The reaction mixture was concentrated under reduced pressure. To the residue was added hexane and the insoluble matter was filtered off. The filtrate was concentrated under reduced pressure. The residue thus obtained was dissolved in methylene chloride (20 ml), followed by the addition of 3-chloroperbenzoic acid (576 mg, 3.34 mmol). The mixture was stirred at room temperature for 17.5 hours. The reaction mixture was concentrated under reduced pressure. Ethyl acetate was added and the mixture was washed successively with a saturated aqueous solution of sodium bicarbonate and brine and dried over anhydrous sodium sulfate. After filtration, the filtrate was concentrated under reduced pressure. The residue was dissolved in methylene chloride. To the resulting solution was added a 1N aqueous solution of sodium hydroxide to separate the organic layer. The organic layer was dried over anhydrous sodium sulfate. After filtration, the filtrate was concentrated under reduced pressure. The residue was subjected to chromatography on a silica gel column, and the fraction obtained from the hexane:ethyl acetate (=15:1) eluate was concentrated under reduced pressure, whereby the title compound (301 mg, 69%) was obtained as a white solid.

IR (ATR) ν: 2921, 2850, 1583, 1475, 1446, 1394, 1305, 1274, 1172, 1143, 1083, 1014, 964, 892, 846, 831, 782, 761, 744, 703, 669, 632, 559, 528, 478, 426 cm$^{-1}$.

$^1$H-NMR (400 MHz, CDCl$_3$) δ: 1.00-1.35(5H,m), 1.60-1.76(3H,m), 1.80-2.08(3H,m), 2.97(2H,d,J=6.1 Hz), 7.54 (2H,d,J=8.6 Hz), 7.85(2H,d,J=8.6 Hz).

MS (m/z): 273 (M$^+$+H).

Example 95

1-Chloro-4-[1-cyclohexyl-5-(methylsulfonyl)pentyl-sulfonyl]benzene

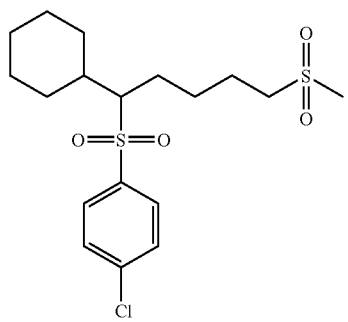

At −78° C., butyl lithium (a 1.57M hexane solution; 0.60 ml, 0.937 mmol) was added dropwise to a dimethoxyethane (3 ml) solution of 1-chloro-4-(cyclohexylmethylsulfonyl)benzene (213 mg, 0.781 mmol). After stirring at −78° C. for 40 minutes, a dimethoxyethane (5 ml) solution of the 1-iodo-4-(methylsulfonyl) butane (246 mg, 0.937 mmol) obtained in Referential Example 7 was added dropwise. The temperature of the reaction mixture was raised gradually to room temperature, at which stirring was conducted for 3 hours. Water was added to the reaction mixture, followed by extraction with ethyl acetate. The organic layer was washed with brine and dried over anhydrous sodium sulfate. After filtration, the filtrate was concentrated under reduced pressure. The residue thus obtained was subjected to flash chromatography on a silica gel column, and the fraction obtained from the hexane:ethyl acetate (=1:1) eluate was concentrated under reduced pressure. The residue was purified by high performance liquid chromatography (using a mixed solvent of water/acetonitrile/formic acid) to give the title compound (54 mg, 17%) as a white solid. The resulting solid was washed with hexane and collected by filtration, whereby the title compound was obtained as a white powder.

Melting point: 104-106° C.

IR (ATR) ν: 2925, 2854, 1583, 1475, 1444, 1423, 1392, 1309, 1288, 1268, 1209, 1176, 1145, 1133, 1128, 1083, 1012, 960; 892, 825, 763, 727, 636, 609, 561, 528, 495, 478, 453, 430 cm$^{-1}$.

$^1$H-NMR (400 MHz, CDCl$_3$) δ: 1.02-1.32(5H,m), 1.44-2.00(12H,m), 2.76-2.83(1H,m), 2.89(3H,s), 2.97(2H,t,J=7.0 Hz), 7.56(2H,d,J=8.3 Hz), 7.82(2H,d,J=8.3 Hz).

MS (m/z): 407 (M$^+$+H).

Elemental Analysis for C$_{18}$H$_{27}$ClO$_4$S$_2$
Calculated: C 53.12%; H 6.69%; Cl 8.71%; S 15.76%.
Found: C 53.11%; H 6.49%; Cl 8.83%; S 15.73%.

Example 96

1-Chloro-4-(2-phenylethylsulfonyl)benzene

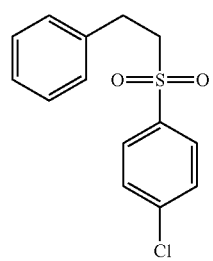

To an acetonitrile (10 ml) solution of 4-chlorobenzenethiol (347 mg, 2.40 mmol) and (2-bromoethyl)benzene (329 μl, 2.40 mmol) was added potassium carbonate (498 mg, 3.60 mmol). The mixture was stirred at room temperature for 1.5 hours. The reaction mixture was concentrated under reduced pressure. To the residue was added hexane and the insoluble matter was filtered off. The filtrate was concentrated under reduced pressure. The residue thus obtained was dissolved in methylene chloride (20 ml). To the resulting solution was added 3-chloroperbenzoic acid (870 mg, 5.04 mmol) and the mixture was stirred at room temperature for 19 hours. The reaction mixture was concentrated under reduced pressure. Ethyl acetate was added. The mixture was washed successively with a saturated aqueous solution of sodium bicarbonate and brine, and dried over anhydrous sodium sulfate. After filtration, the filtrate was concentrated under reduced pressure. The residue was dissolved in methylene chloride, followed by the addition of a 1N aqueous solution of sodium hydroxide to separate an organic layer. The organic layer was dried over anhydrous sodium sulfate. After filtration, the filtrate was concentrated under reduced pressure. The residue was subjected to chromatography on a silica gel column and the fraction obtained from the hexane:ethyl acetate (=10:1) eluate was concentrated under reduced pressure, whereby the title compound (599 mg, 89%) was obtained as a white solid.

IR (ATR) ν: 3023, 2923, 1600, 1581, 1496, 1473, 1454, 1394, 1299, 1276, 1240, 1145, 1083, 1012, 971, 908, 823, 777, 755, 732, 694, 636, 593, 570, 526, 455 cm$^{-1}$.

$^1$H-NMR (400 MHz, CDCl$_3$) δ: 2.98-3.10(2H,m), 3.29-3.42(2H,m), 7.02-7.32(5H,m), 7.55(2H,d,J=8.6 Hz), 7.86 (2H,d,J=8.5 Hz).

MS (m/z): 281 (M$^+$+H).

Example 97

4-[1-Benzyl-5-(methylsulfonyl)pentylsulfonyl]-1-chlorobenzene

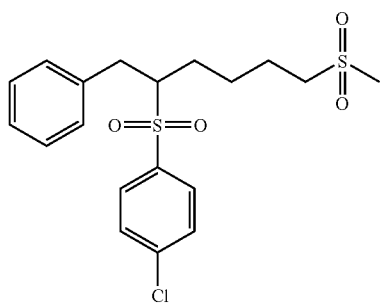

At −78° C., butyl lithium (a 1.57M hexane solution; 0.57 ml, 0.902 mmol) was added dropwise to a dimethoxyethane (3 ml) solution of 1-chloro-4-(2-phenylethylsulfonyl)benzene (211 mg, 0.752 mmol). After stirring at −78° C. for 1 hour, a dimethoxyethane (6 ml) solution of the 1-iodo-4-(methylsulfonyl)butane (236 mg, 0.902 mmol) obtained in Referential Example 7 was added dropwise. The temperature of the reaction mixture was gradually elevated to room temperature, at which stirring was conducted for 3 hours. Water was added to the reaction mixture, followed by extraction with ethyl acetate. The organic layer was washed with brine, and dried over anhydrous sodium sulfate. After filtration, the filtrate was concentrated under reduced pressure. The residue was subjected to flash chromatography on a silica gel column, and the fraction obtained from the hexane:ethyl acetate (=1:1) eluate was concentrated under reduced pressure. The residue was purified by high performance liquid chromatography (using a mixed solvent of water/acetonitrile/formic acid) to give the title compound (72 mg, 23%) as a white solid. The resulting solid was washed with hexane and collected by filtration, whereby the title compound was obtained as a white powder.

Melting point: 68-70° C.

IR (ATR) ν: 3029, 2937, 2867, 1581, 1496, 1421, 1394, 1303, 1280, 1253, 1187, 1133, 1083, 1041, 1012, 964, 848, 825, 759, 690, 649, 588, 553, 522, 493, 455 cm$^{-1}$.

$^1$H-NMR (400 MHz, CDCl$_3$) δ: 1.40-1.77(5H,m), 1.82-1.96(1H,m), 2.60-2.70(1H,m), 2.75-2.91(2H,m), 2.83(3H,s), 3.18-3.29(2H,m), 7.04(2H,d,J=8.3 Hz), 7.19-7.31(3H,m), 7.56(2H,d,J=8.6 Hz), 7.84(2H,d,J=8.6 Hz).

MS (m/z): 415 (M$^+$+H).

Elemental Analysis for $C_{19}H_{23}ClO_4S_2$
Calculated: C 54.99%; H 5.59%; Cl 8.54%; S 15.45%.
Found: C 55.10%; H 5.62%; Cl 8.50%; S 15.56%.

Referential Example 10

(2-Chloropyridin-3-yl)methanol

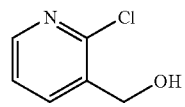

At −78° C., diisobutylaluminum hydride (a 1.0M toluene solution; 4.68 ml) was added dropwise to a methylene chloride (10 ml) solution of ethyl 2-chloronicotinate (347 mg, 1.87 mmol). Thirty minutes later, the reaction mixture was ice cooled, followed by stirring for 15 minutes. After the completion of the reaction was confirmed, brine was added to the reaction mixture and the temperature of the resulting mixture was allowed to rise back to room temperature. The reaction mixture was filtered through Celite. The filtrate was dried over anhydrous sodium sulfate. After filtration, the filtrate was concentrated under reduced pressure. The residue was subjected to chromatography on a silica gel column and the fraction obtained from the hexane:ethyl acetate (=1:1) eluate was concentrated under reduced pressure, whereby the title compound (211 mg, 79%) was obtained as a white solid.

IR (ATR) ν: 3245, 2827, 1587, 1571, 1452, 1407, 1324, 1251, 1193, 1118, 1087, 1041, 796, 732, 713, 655, 593, 511, 466, 414 cm$^{-1}$.

$^1$H-NMR (400 MHz, CDCl$_3$) δ: 2.21(1H,t,J=5.6 Hz), 4.80 (2H,d,J=5.1 Hz), 7.25-7.36(1H,m), 7.85-7.98(1H,m), 8.32 (1H,dd,J=4.6, 1.5 Hz).

MS (m/z): 144 (M$^+$+H).

Example 98

2-Chloro-3-(4-chlorophenylsulfonylmethyl)pyridine

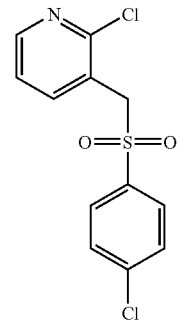

A chloroform (10 ml) solution of (2-chloropyridin-3-yl) methanol (204 mg, 1.42 mmol) and thionyl chloride (0.31 ml, 4.26 mmol) was stirred at 50° C. for 8.5 hours. After cooling to room temperature, the reaction mixture was concentrated under reduced pressure. The residue was dissolved in butanol (15 ml), followed by the addition of sodium 4-chlorobenzenesulfinate (423 mg, 2.13 mmol) and potassium acetate (418 mg, 4.26 mmol). The mixture was stirred at 70 to 80° C. for 15 hours. After cooling to room temperature, the reaction mixture was concentrated under reduced pressure. Ethyl acetate was added to the residue, and the mixture was washed successively with a saturated aqueous solution of sodium bicarbonate and brine, and dried over anhydrous sodium sulfate. After filtration, the filtrate was concentrated under reduced pressure. The residue was subjected to flash chromatography on a silica gel column, and the fraction obtained from the hexane:ethyl acetate (=2:1) eluate was concentrated under reduced pressure, whereby the title compound (252 mg, 59%) was obtained as a white solid.

IR (ATR) ν: 3093, 2992, 2931, 1579, 1562, 1473, 1450, 1407, 1321, 1278, 1249, 1195, 1153, 1133, 1116, 1083, 1060, 1010, 962, 887, 840, 813, 759, 719, 686, 636, 566, 541, 501, 466, 441 cm$^{-1}$.

$^1$H-NMR (400 MHz, CDCl$_3$) δ: 4.54(2H,s), 7.33(1H,dd, J=8.8,4.8 Hz), 7.46(2H,d,J=8.6 Hz), 7.58(2H,d,J=8.3 Hz), 7.92(1H,dd,J=7.7, 1.8 Hz), 8.39(1H,dd,J=4.8, 1.8 Hz).

MS (m/z): 302 (M$^+$+H).

Example 99

2-Chloro-3-[1-(4-chlorophenylsulfonyl)-5-(methylsulfonyl)pentyl]pyridine

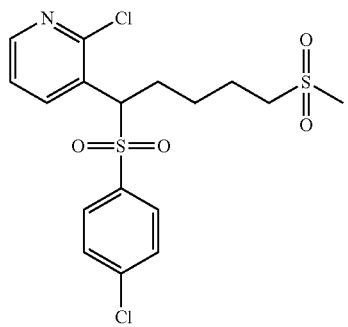

A toluene (10 ml) solution of 2-chloro-3-(4-chlorophenylsulfonylmethyl)pyridine (56 mg, 0.184 mmol), the 4-(methylsulfonyl)-1-butanol (56 mg, 0.368 mmol) obtained in Referential Example 3 and cyanomethylenetri-n-butylphosphorane (89 mg, 0.368 mmol) was heated under reflux for 19 hours under an argon atmosphere. After cooling to room temperature, the reaction mixture was added with 4-(methylsulfonyl)-1-butanol (56 mg, 0.368 mmol) and cyanomethylenetri-n-butylphosphorane (89 mg, 0.368 mmol), followed by heating under reflux for 5 hours under an argon atmosphere. After cooling to room temperature, the reaction mixture was concentrated under reduced pressure. The residue was subjected to flash chromatography on a silica gel column, and the fraction obtained from the hexane:ethyl acetate (=1:2) eluate was concentrated under reduced pressure, whereby the title compound (76 mg, 95%) was obtained as an amorphous substance.

IR (ATR) ν: 3085, 2931, 1579, 1562, 1475, 1407, 1278, 1184, 1139, 1083, 1012, 962, 908, 821, 752, 732, 690, 626, 574, 520, 466 cm$^{-1}$.

$^1$H-NMR (400 MHz, CDCl$_3$) δ: 1.32-1.55(2H,m), 1.80-1.99(2H,m), 2.10-2.25(1H,m), 2.40-2.63(1H,m), 2.88(3H,s), 2.96(2H,t,J=7.8 Hz), 4.79(1H,dd,J=11.0, 4.2 Hz), 7.32-7.42 (3H,m), 7.48(2H,d,J=8.3 Hz), 8.04(1H,dd,J=7.8, 1.7 Hz), 8.36(1H,dd,J=4.8, 1.8 Hz).

MS (m/z): 436 (M$^+$+H).

HRMS (FAB) for C$_{17}$H$_{20}$O$_4$NCl$_2$S$_2$ (M$^+$+H)
Calculated: 436.0211
Found: 436.0195

Referential Example 11

(2-Fluoropyridin-3-yl)methanol

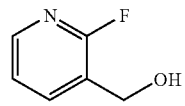

Under ice cooling, trimethylsilyldiazomethane (0.72 ml) was added to a solution of 2-fluoronicotinic acid (210 mg, 1.49 mmol) in tetrahydrofuran (15 ml) and methanol (1 ml), and the mixture was stirred for 30 minutes. The reaction mixture was concentrated under reduced pressure. The residue was subjected to chromatography on a silica gel column, and the fraction obtained from the hexane:ethyl acetate (=4:1) eluate was concentrated under reduced pressure.

At −78° C., diisobutylaluminum hydride (a 1.0M toluene solution; 1.60 ml) was added dropwise to a methylene chloride (10 ml) solution of the residue (95 mg, 0.612 mmol). Fifteen minutes later, the reaction mixture was ice cooled and stirred for 15 minutes. After completion of the reaction was confirmed, brine was added and the temperature of the reaction mixture was allowed to rise back gradually to room temperature. The reaction mixture was filtered through Celite. The filtrate was dried over anhydrous sodium sulfate. After filtration, the filtrate was concentrated under reduced pressure. The residue was subjected to chromatography on a silica gel column, and the fraction obtained from the hexane:ethyl acetate (=2:1) eluate was concentrated under reduced pressure, whereby the title compound (55 mg, 71%) was obtained as a white solid.

IR (ATR) ν: 3338, 2873, 1650, 1608, 1430, 1365, 1241, 1176, 1108, 1045, 1020, 858, 800, 775, 744, 619, 572, 539, 520 cm$^{-1}$.

$^1$H-NMR (400 MHz, CDCl$_3$) δ: 4.78(2H,s), 7.18-7.25(1H, m), 7.85-7.97(1H,m), 8.14(1H,d,J=4.9 Hz).

MS (m/z): 128 (M$^+$+H).

Example 100

3-(4-Chlorophenylsulfonylmethyl)-2-fluoropyridine

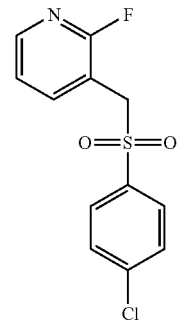

A chloroform (10 ml) solution of (2-fluoropyridin-3-yl) methanol (49 mg, 0.385 mmol) and thionyl chloride (0.14 ml, 1.93 mmol) was stirred at 50° C. for 3.5 hours. After cooling to room temperature, the reaction mixture was concentrated under reduced pressure. The residue thus obtained was dissolved in butanol (5 ml), followed by the addition of sodium 4-chlorobenzenesulfinate (92 mg, 0.462 mmol) and potassium acetate (76 mg, 0.770 mmol). The mixture was stirred at 70 to 80° C. for 12 hours. After cooling to room temperature, the reaction mixture was concentrated under reduced pressure. Ethyl acetate was added to the residue, and the mixture was washed successively with a saturated aqueous solution of sodium bicarbonate and brine, and then, dried over anhydrous sodium sulfate. After filtration, the filtrate was concentrated under reduced pressure. The residue was subjected to flash chromatography on a silica gel column. The fraction obtained from the hexane:ethyl acetate (=2:1) eluate was concentrated under reduced pressure, whereby the title compound (59 mg, 54%) was obtained as a white solid.

IR (ATR) ν: 3097, 2989, 2933, 1643, 1606, 1573, 1469, 1434, 1409, 1392, 1321, 1276, 1240, 1184, 1170, 1149, 1083, 1010, 956, 902, 842, 813, 779, 763, 725, 696, 640, 582, 541, 522, 480, 445 cm$^{-1}$.

$^{1}$H-NMR (400 MHz, CDCl$_3$) δ: 4.38(2H,s), 7.21-7.30(1H, m), 7.47(2H,d,J=8.8 Hz), 7.61(2H,d,J=8.8 Hz), 7.87-7.94 (1H,m), 8.19-8.25(1H,m).

MS (m/z): 286 (M$^{+}$+H).

Example 101

3-[1-(4-Chlorophenylsulfonyl)-5-(methylsulfonyl) pentyl]-2-fluoropyridine

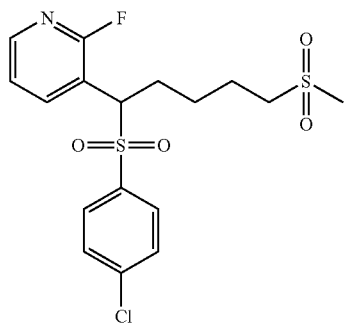

A toluene (10 ml) solution of 3-(4-chlorophenylsulfonylmethyl)-2-fluoropyridine (53 mg, 0.185 mmol), the 4-(methylsulfonyl)-1-butanol (56 mg, 0.370 mmol) obtained in Referential Example 3 and cyanomethylenetri-n-butylphosphorane (89 mg, 0.370 mmol) was heated under reflux for 22 hours under an argon atmosphere. After cooling to room temperature, the reaction mixture was concentrated under reduced pressure. The residue was subjected to flash chromatography on a silica gel column. The fraction obtained from the hexane:ethyl acetate (=1:2) eluate was concentrated under reduced pressure, whereby the title compound (42 mg, 54%) was obtained as an amorphous substance.

IR (ATR) ν: 3089, 2950, 2865, 1604, 1573, 1467, 1434, 1394, 1313, 1290, 1270, 1249, 1199, 1147, 1126, 1083, 1012, 960, 906, 854, 815, 757, 738, 703, 628, 576, 536, 464, 437 cm$^{-1}$.

$^{1}$H-NMR (400 MHz, CDCl$_3$) δ: 1.38-1.55(2H,m), 1.85-1.99(2H,m), 2.14-2.28(1H,m), 2.45-2.60(1H,m), 2.88(3H,s), 2.96(2H,t,J=7.8 Hz), 4.46(1H,dd,J=11.2, 4.2 Hz), 7.25-7.32 (1H,m), 7.41(2H,d,J=8.6 Hz), 7.50(2H,d,J=8.3 Hz), 7.98-8.04(1H,m), 8.20(1H,d,J=4.9 Hz).

MS (m/z): 420 (M$^{+}$+H).
HRMS (FAB) for C$_{17}$H$_{20}$O$_4$NClFS$_2$ (M$^{+}$+H)
Calculated: 420.0506
Found: 420.0509

Example 102

2,5-Dichloro-3-(4-chlorophenylsulfonylmethyl)pyridine

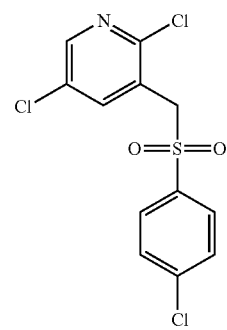

At −78° C., diisobutylaluminum hydride (a 1M hexane solution; 1.92 ml) was added dropwise to a methylene chloride (10 ml) solution of methyl 2,5-dichloronicotinate (188 mg, 0.912 mmol). The resulting mixture was stirred at 0° C. for 30 minutes. The reaction mixture was added with brine, and the mixture was filtered through Celite. The filtrate was dried over anhydrous sodium sulfate. After filtration, the filtrate was concentrated under reduced pressure. The residue was subjected to chromatography on a silica gel column, and the fraction obtained from the hexane:ethyl acetate (=3:1) eluate was concentrated under reduced pressure. To a chloroform (10 ml) solution of the residue (128 mg) was added thionyl chloride (0.26 ml, 3.60 mmol), followed by stirring at 50° C. for 6.5 hours. After cooling to room temperature, the reaction mixture was concentrated under reduced pressure. The residue was dissolved in butanol (10 ml). To the resulting solution were added sodium 4-chlorobenzenesulfinate (171 mg, 0.863 mmol) and potassium acetate (212 mg, 2.16 mmol) and the mixture was stirred at 70° C. for 19 hours. After cooling to room temperature, the reaction mixture was concentrated under reduced pressure. Ethyl acetate was added to the residue, followed by successive washing with water and brine and drying over anhydrous sodium sulfate. After filtration, the filtrate was concentrated under reduced pressure. The resulting solid was washed with hexane-diisopropyl ether, and collected by filtration, whereby the title compound (108 mg, 35%) was obtained as a white powder.

IR (ATR) ν: 3091, 3064, 2998, 2933, 1581, 1550, 1473, 1419, 1392, 1317, 1280, 1255, 1234, 1170, 1135, 1085, 1068, 1010, 910, 833, 821, 767, 727, 709, 646, 582, 539, 507, 464, 430 cm$^{-1}$.

$^{1}$H-NMR (400 MHz, CDCl$_3$) δ: 4.49(2H,s), 7.49(2H,d, J=8.6 Hz), 7.62(2H,d,J=8.8 Hz), 7.90(1H,d,J=2.5 Hz), 8.35 (1H,d,J=2.5 Hz).

MS (m/z): 336 (M$^{+}$+H).

Example 103

2,5-Dichloro-3-[1-(4-chlorophenylsulfonyl)-5-(methylsulfonyl)pentyl]pyridine

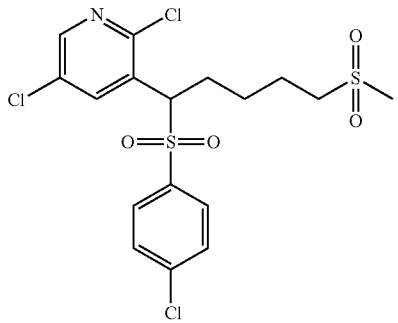

A toluene (10 ml) solution of 2,5-dichloro-3-(4-chlorophenylsulfonylmethyl)pyridine (70 mg, 0.208 mmol), the 4-(methylsulfonyl)-1-butanol (95 mg, 0.624 mmol) obtained in Referential Example 3 and cyanomethylenetri-n-butylphosphorane (151 mg, 0.624 mol) was heated under reflux for 3 hours under an argon atmosphere. After cooling to room temperature, the reaction mixture was concentrated under reduced pressure. The residue was subjected to flash chromatography on a silica gel column, and the fraction obtained from the hexane:ethyl acetate (=1:1) eluate was concentrated under reduced pressure, whereby the title compound (74 mg, 76%) was obtained as an amorphous substance.

IR (ATR) ν: 3091, 3060, 2931, 1581, 1546, 1475, 1413, 1313, 1278, 1209, 1124, 1083, 1049, 1012, 964, 906, 871, 831, 754, 705, 628, 588, 532, 468 cm$^{-1}$.

$^1$H-NMR (400 MHz, CDCl$_3$) δ: 1.38-1.52(2H,m), 1.83-1.98(2H,m), 2.08-2.20(1H,m), 2.49-2.60(1H,m), 2.88(3H,s), 2.97(2H,t,J=7.8 Hz), 4.72(1H,dd,J=10.9, 4.0 Hz), 7.43(2H, d.J=8.6 Hz), 7.53(2H,d,J=8.6 Hz), 8.00(1H,d,J=2.5 Hz), 8.31 (1H,d,J=2.5 Hz).

MS (m/z): 470 (M$^+$+H).

Elemental Analysis for C$_{17}$H$_{18}$Cl$_3$NO$_4$S$_2$.0.25H$_2$O
Calculated: C 42.96%; H 3.92%; Cl 22.38%; N 2.95%; S 13.49%.
Found: C 43.02%; H 3.81%; Cl 22.54%; N 3.01%; S 13.50%.

Example 104

4-Chloro-3-(4-chlorophenylsulfonylmethyl)pyridine

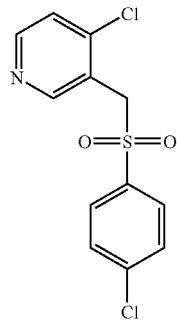

A carbon tetrachloride (15 ml) suspension of 4-chloro-3-methylpyridine hydrochloride (402 mg, 2.45 mmol), N-chlorosuccinic acid imide (327 mg, 2.45 mmol) and 2,2'-azobis(2-methylpropionitrile) (30 mg, 0.183 mmol) was heated under reflux for 13 hours under a nitrogen atmosphere. After cooling to room temperature, the reaction mixture was concentrated under reduced pressure. The residue was dissolved in butanol (10 ml), followed by the addition of sodium 4-chlorophenylsulfinate (487 mg, 2.45 mmol) and potassium acetate (481 mg, 4.90 mmol). The mixture was stirred at 70° C. for 24 hours. The reaction mixture was cooled to room temperature, followed by concentration under reduced pressure. Ethyl acetate was added to the residue. The mixture was washed successively with a saturated aqueous solution of sodium bicarbonate and brine and then, dried over anhydrous sodium sulfate. After filtration, the filtrate was concentrated under reduced pressure. The residue was subjected to chromatography on a silica gel column, and the fraction obtained from the hexane:ethyl acetate (=2:1) eluate was concentrated under reduced pressure, whereby the title compound (130 mg, 18%) was obtained as a white solid.

IR (ATR) ν: 3060, 2917, 1708, 1573, 1556, 1475, 1413, 1403, 1311, 1280, 1232, 1189, 1155, 1120, 1079, 1012, 933, 890, 854, 833, 817, 777, 744, 721, 694, 632, 574, 557, 514, 460 cm$^{-1}$.

$^1$H-NMR (400 MHz, CDCl$_3$) δ: 4.56(2H,s), 7.28(1H,d, J=5.4 Hz), 7.48(2H,d,J=8.3 Hz), 7.63(2H,d,J=8.5 Hz), 8.49 (1H,d,J=5.4 Hz), 8.54(1H,s).

MS (m/z): 302 (M$^+$+H).

Example 105

4-Chloro-3-[1-[(4-chlorophenyl)sulfonyl]-5-(methylsulfonyl)pentyl]pyridine

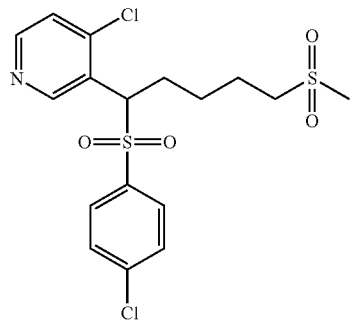

A toluene (10 ml) solution of 4-chloro-3-(4-chlorophenylsulfonylmethyl)pyridine (80 mg, 0.265 mmol), the 4-(methylsulfonyl)-1-butanol (81 mg, 0.529 mmol) obtained in Referential Example 3 and cyanomethylenetri-n-butylphosphorane (128 mg, 0.529 mol) was heated under reflux under an argon atmosphere for 3 days. After cooling to room temperature, the reaction mixture was concentrated under reduced pressure. The residue was subjected to flash chromatography on a silica gel column, and the fraction obtained from the hexane:ethyl acetate (=1:5) eluate was concentrated under reduced pressure to give the title compound (74 mg, 64%) as a white solid. The resulting solid was washed with ether and then, collected by filtration, whereby the title compound was obtained as a white powder.

Melting point: 156-157° C.

IR (ATR) ν: 3087, 3064, 3018, 2933, 1571, 1473, 1409, 1311, 1270, 1207, 1149, 1076, 1014, 968, 906, 831, 794, 752, 700, 617, 576, 536, 497, 466 cm$^{-1}$.

$^1$H-NMR (400 MHz, CDCl$_3$) δ: 1.35-1.60(2H,m), 1.80-1.99(2H,m), 2.20-2.33(1H,m), 2.51-2.65(1H,m), 2.88(3H,s), 2.90-3.00(2H,m), 4.80(1H,dd,J=10.9, 3.8 Hz), 7.20(1H,d, J=5.4 Hz), 7.40(2H,d,J=8.5 Hz), 7.52(2H,d,J=8.6 Hz), 8.46 (1H,d,J=5.4 Hz), 8.80(1H,s).

MS (m/z): 436 (M$^+$+H).

Elemental Analysis for $C_{17}H_{19}Cl_2NO_4S_2$

Calculated: C 46.79%; H 4.39%; Cl 16.25%; N 3.21%; S 14.70%.

Found: C 46.88%; H 4.40%; Cl 16.14%; N 3.30%; S 14.52%.

Example 106

3-[6-(tert-Butyldimethylsilyloxy)-1-[(4-chlorophenyl)sulfonyl]hexyl]-2-chloropyridine

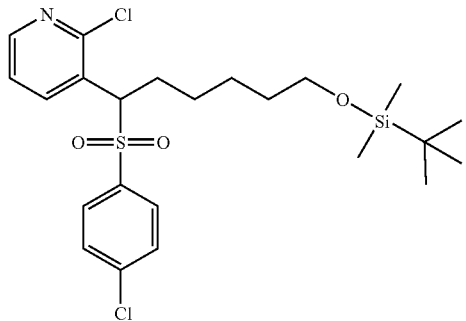

A toluene (5 ml) solution of the 2-chloro-3-(4-chlorophenylsulfonylmethyl)pyridine (200 mg, 0.662 mmol) obtained in Example 98, 5-(tert-butyldimethylsilyloxy)pentanol (288 mg, 1.32 mmol) and cyanomethylenetri-n-butylphosphorane (318 mg, 1.32 mmol) was heated under reflux for 22 hours under an argon atmosphere. After cooling to room temperature, the reaction mixture was concentrated under reduced pressure. The residue was subjected to flash chromatography on a silica gel column, and the fraction obtained from the 15% ethyl acetate/hexane eluate was concentrated under reduced pressure, whereby the title compound (307 mg, 92%) was obtained as a colorless oil.

IR (ATR) ν: 2929, 2856, 1581, 1562, 1473, 1409, 1394, 1359, 1321, 1278, 1253, 1184, 1149, 1083, 1058, 1012, 985, 921, 833, 775, 752, 734, 690, 626, 570, 534, 466 cm$^{-1}$.

$^1$H-NMR (400 MHz, CDCl$_3$) δ: 0.01(6H,s), 0.86(9H,s), 1.12-1.50(6H,m), 2.07-2.20(1H,m), 2.45-2.57(1H,m), 3.53 (2H,t,J=6.1 Hz), 4.78(1H,dd,J=11.4, 3.8 Hz), 7.31-7.40(3H, m), 8.79(2H,d,J=7.5 Hz), 8.03(1H,dd,J=7.8, 2.0 Hz), 8.34 (1H,dd,J=4.6, 2.0 Hz).

MS (m/z): 502 (M$^+$+H).

Example 107

6-(4-Chlorophenylsulfonyl)-6-(2-chloropyridin-3-yl)-1-hexanol

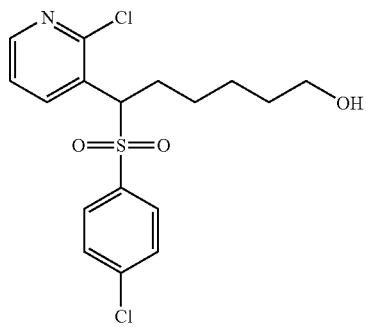

Under ice cooling, tetrabutylammonium fluoride (a 1 mol/l tetrahydrofuran solution; 0.70 ml) was added to a tetrahydrofuran (10 ml) solution of 3-[6-(tert-butyldimethylsilyloxy)-1-[(4-chlorophenyl)sulfonyl]hexyl]-2-chloropyridine (294 mg, 0.585 mmol). The resulting mixture was stirred at room temperature for 24 hours. The reaction mixture was concentrated under reduced pressure. Ethyl acetate was added to the residue, and the mixture was washed successively with water and brine, and dried over anhydrous sodium sulfate. After filtration, the filtrate was concentrated under reduced pressure. The residue was subjected to chromatography on a silica gel column. The fraction obtained from the hexane:ethyl acetate (=1:1) eluate was concentrated under reduced pressure, whereby the title compound (212 mg, 93%) was obtained as a colorless oil.

IR (ATR) ν: 3400, 2933, 2859, 1579, 1562, 1475, 1407, 1394, 1315, 1278, 1184, 1145, 1083, 1058, 1012, 821, 752, 734, 690, 626, 605, 570, 534, 466, 412 cm$^{-1}$.

$^1$H-NMR (400 MHz, CDCl$_3$) δ: 1.15-1.65(8H,m), 2.07-2.20(1H,m), 2.47-2.58(1H,m), 3.59(2H,t,J=6.4 Hz), 4.79 (1H,dd,J=11.4, 3.8 Hz), 7.30-7.42(3H,m), 7.48(2H,d,J=8.8 Hz), 8.03(1H,dd,J=7.8, 2.0 Hz), 8.34(1H,dd,J=4.1, 1.7 Hz).

MS (m/z): 388 (M$^+$+H).

HRMS (FAB) for $C_{17}H_{20}O_3NCl_2S$ (M$^+$+H)

Calculated: 388.0541

Found: 388.0561

Example 108

2-Chloro-3-[1-(4-chlorophenylsulfonyl)cycloheptyl]pyridine

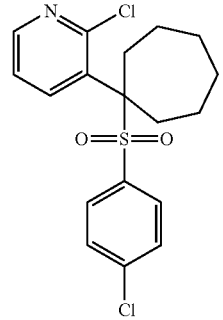

At −78° C., butyl lithium (a 1.57M hexane solution; 0.62 ml, 0.966 mmol) was added dropwise to a dimethoxyethane (5 ml) solution of the 2-chloro-3-(4-chlorophenylsulfonylmethyl)pyridine (146 mg, 0.483 mmol) obtained in Example 98. At −78° C., the resulting mixture was stirred for 20 minutes, followed by the addition of 1,6-diiodohexane (0.095 ml, 0.580 mmol). The temperature of the reaction mixture was gradually raised to room temperature, at which stirring was performed for 4 hours. Water was added to the reaction mixture, followed by extraction with ethyl acetate. The organic layer was washed with brine and then dried over anhydrous sodium sulfate. After filtration, the filtrate was concentrated under reduced pressure. The residue was subjected to flash chromatography on a silica gel column, and the fraction obtained from the 15% ethyl acetate/hexane eluate was concentrated under reduced pressure. The residue thus obtained was purified by high performance liquid chromatography (using a mixed solvent of water/acetonitrile/formic acid) to yield the title compound (60 mg, 32%) as a white solid. The resulting solid was washed with hexane-ether and then collected by filtration, whereby the title compound was obtained as a white powder.

Melting point: 168-169° C.

IR (ATR) ν: 2929, 2861, 1573, 1558, 1473, 1454, 1394, 1303, 1276, 1139, 1083, 1066, 1008, 840, 800, 748, 711, 646, 613, 574, 522, 470, 412 cm$^{-1}$.

$^1$H-NMR (400 MHz, CDCl$_3$) δ: 1.30-1.50(4H,m), 1.50-1.66(2H,m), 1.85-1.98(2H,m), 2.33-2.48(2H,m), 2.94-3.10(2H,m), 7.28-7.37(3H,m), 7.40(2H,d,J=8.8 Hz), 7.93(1H,dd, J=8.1, 1.7 Hz), 8.38(1H,dd,J=4.5, 1.8 Hz).

MS (m/z): 384 (M$^+$+H).

Elemental Analysis for C$_{18}$H$_{19}$Cl$_2$NO$_2$S
    Calculated: C 56.25%; H 4.98%; Cl 18.45%; N 3.64%; S 8.34%.
    Found: C 56.20%; H 4.85%; Cl 18.50%; N 3.73%; S 8.46%.

Example 109

2-Chloro-3-[1-(4-chlorophenylsulfonyl) cyclohexyl]pyridine

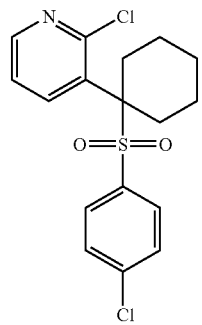

At −78° C., butyl lithium (a 1.57M hexane solution; 0.66 ml, 1.03 mmol) was added dropwise to a dimethoxyethane (5 ml) solution of the 2-chloro-3-(4-chlorophenylsulfonylmethyl)pyridine (156 mg, 0.516 mmol) obtained in Example 98. At −78° C., the resulting mixture was stirred for 20 minutes, followed by the addition of 1,5-diiodopentane (0.092 ml, 0.619 mmol). The temperature of the reaction mixture was gradually elevated to room temperature, at which stirring was performed for 15 hours. Water was added to the reaction mixture, followed by extraction with ethyl acetate. The organic layer was washed with brine and then dried over anhydrous sodium sulfate. After filtration, the filtrate was concentrated under reduced pressure. The residue was subjected to flash chromatography on a silica gel column, and the fraction obtained from the 15% ethyl acetate/hexane eluate was concentrated under reduced pressure. The residue thus obtained was purified by high performance liquid chromatography (using a mixed solvent of water/acetonitrile/formic acid) to give the title compound (72 mg, 38%) as a white solid. The resulting solid was washed with hexane-ether and then collected by filtration, whereby the title compound was obtained as a white powder.

Melting point: 129-131° C.

IR (ATR) ν: 2929, 2861, 1575, 1558, 1475, 1446, 1392, 1303, 1278, 1143, 1130, 1083, 1054, 1010, 910, 875, 833, 809, 754, 742, 742, 732, 703, 646, 617, 580, 495, 458 cm$^{-1}$.

$^1$H-NMR (400 MHz, CDCl$_3$) δ: 1.05-1.30(2H,m), 1.33-1.50(1H,m), 1.52-1.70(1H,m), 1.75-1.90(2H,m), 2.02-2.30(2H,m), 2.65-3.60(2H,m), 7.29-7.39(3H,m), 7.41(2H,d, J=8.8 Hz), 8.05(1H,dd,J=8.1, 1.7 Hz), 8.39(1H,dd,J=4.5, 1.8 Hz).

MS (m/z): 370 (M$^+$+H).

Elemental Analysis for C$_{17}$H$_{17}$Cl$_2$NO$_2$S
    Calculated: C 55.14%; H 4.63%; Cl 19.15%; N 3.78%; S 8.66%.
    Found: C 55.06%; H 4.55%; Cl 19.15%; N 3.87%; S 8.76%.

Example 110

4-Chloro-3-[1-(4-chlorophenylsulfonyl) cyclohexyl]pyridine

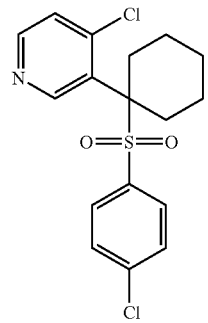

At −78° C., butyl lithium (a 1.57M hexane solution; 0.58 ml, 0.913 mmol) was added dropwise to a dimethoxyethane (5 ml) solution of the 4-chloro-3-(4-chlorophenylsulfonylmethyl)pyridine (138 mg, 0.457 mmol) obtained in Example 104. At −78° C., the resulting mixture was stirred for 20 minutes and then 1,5-diiodopentane (0.068 ml, 0.457 mmol) was added thereto. The temperature of the reaction mixture was gradually raised to room temperature, at which stirring was performed for 17 hours. Water was added to the reaction mixture, followed by extraction with ethyl acetate. The organic layer was washed with brine and then dried over anhydrous sodium sulfate. After filtration, the filtrate was concentrated under reduced pressure. The residue was subjected to flash chromatography on a silica gel column, and the fraction obtained from the hexane:ethyl acetate (=2:1) eluate was concentrated under reduced pressure. The residue thus obtained was purified by high performance liquid chromatography (using a mixed solvent of water/acetonitrile/formic acid) to give the title compound (30 mg, 18%) as a white solid. The resulting solid was washed with ether and then collected by filtration, whereby the title compound was obtained as a white powder.

Melting point: 145-147° C.

IR (ATR) ν: 2929, 2863, 1579, 1469, 1452, 1392, 1346, 1305, 1280, 1270, 1211, 1143, 1081, 1012, 975, 937, 910, 871, 823, 794, 754, 725, 680, 617, 582, 563, 547, 507, 468 cm$^{-1}$.

$^1$H-NMR (400 MHz, CDCl$_3$) δ: 1.10-1.30(2H,m), 1.32-1.50(1H,m), 1.60-1.69(1H,m), 1.78-1.89(2H,m), 2.01-2.22(2H,m), 2.70-3.00(1H,m), 3.30-3.70(1H,m), 7.23(1H,d, J=5.4 Hz), 7.35(2H,d,J=8.8 Hz), 7.40(2H,d,J=8.8 Hz), 8.41(1H,d,J=5.1 Hz), 8.57(1H,s).

MS (m/z): 370 (M$^+$+H).

Elemental Analysis for C$_{17}$H$_{17}$Cl$_2$NO$_2$S
    Calculated: C 55.14%; H 4.63%; Cl 19.15%; N 3.78%; S 8.66%.
    Found: C 54.99%; H 4.61%; Cl 19.06%; N 3.89%; S 8.72%.

Example 111

4-(4-Chlorophenylsulfonylmethyl)thiazole

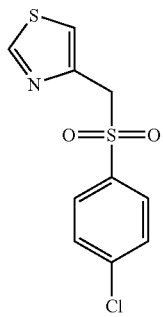

To 1-propanol (10 ml) were added sodium 4-chlorobenzenesulfinate (359 mg, 1.81 mmol), 4-(chloromethyl)thiazole hydrochloride (307 mg, 1.81 mmol) and potassium acetate (354 mg, 3.61 mmol) and the mixture was stirred at 70° C. for 21 hours. After cooling the reaction mixture to room temperature, the solvent was concentrated under reduced pressure. Ethyl acetate was added to the residue. The mixture was washed successively with water and brine and then dried over anhydrous sodium sulfate. After filtration, the filtrate was concentrated under reduced pressure. The residue was subjected to flash chromatography on a silica gel column, and the fraction obtained from the hexane:ethyl acetate eluate (=3:2) was concentrated under reduced pressure. The resulting solid was washed with hexane-ether and then collected by filtration, whereby the title compound (154 mg, 31%) was obtained as a white powder.

IR (ATR) ν: 3102, 2969, 2917, 1575, 1504, 1473, 1413, 1396, 1334, 1309, 1257, 1220, 1159, 1122, 1081, 1012, 948, 898, 875, 831, 821, 784, 723, 657, 593, 561, 541, 478, 451, 418 cm$^{-1}$.

$^1$H-NMR (400 MHz, CDCl$_3$) δ: 4.64(2H,s), 7.40-7.50(3H,m), 7.62(2H,d,J=8.8 Hz), 8.66(1H,s).

MS (m/z): 274 (M$^+$+H).

Example 112

4-[1-(4-Chlorophenylsulfonyl)-5-(methylsulfonyl)pentyl]thiazole

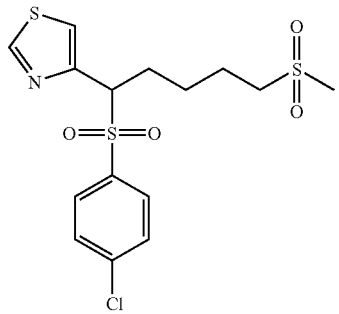

To butanol (5 ml) were added sodium 4-chlorobenzenesulfinate (113 mg, 0.569 mmol), 4-(chloromethyl)thiazole hydrochloride (97 mg, 0.569 mmol) and potassium acetate (112 mg, 1.14 mmol) and the resulting mixture was stirred at 70° C. for 11 hours. After cooling the reaction mixture to room temperature, the solvent was concentrated under reduced pressure. Ethyl acetate was added to the residue. The resulting mixture was washed with a saturated aqueous solution of sodium bicarbonate and then, dried over anhydrous sodium sulfate. After filtration, the filtrate was concentrated under reduced pressure. A toluene (10 ml) solution of the resulting residue, the 4-(methylsulfonyl)-1-butanol (130 mg, 0.853 mmol) obtained in Referential Example 3 and cyanomethylenetri-n-butylphosphorane (206 mg, 0.853 mmol) was heated under reflux for 15 hours under an argon atmosphere. After cooling to room temperature, the reaction mixture was concentrated under reduced pressure. The residue was subjected to flash chromatography on a silica gel column, and the fraction obtained from the hexane:ethyl acetate (=1:3) eluate was concentrated under reduced pressure to give the title compound (111 mg, 48%) as a white solid. The white solid was washed with hexane-ether and then collected by filtration, whereby the title compound was obtained as a white powder.

Melting point: 123-125° C.

IR (ATR) ν: 3102, 2937, 1581, 1508, 1475, 1421, 1392, 1311, 1295, 1274, 1234, 1197, 1145, 1130, 1085, 1014, 964, 931, 877, 850, 821, 767, 750, 709, 665, 557, 530, 487, 455, 420 cm$^{-1}$.

$^1$H-NMR (400 MHz, CDCl$_3$) δ: 1.35-1.55(2H,m), 1.80-1.98(2H,m), 2.24-2.39(1H,m), 2.39-2.50(1H,m), 2.87(3H,s), 2.91-3.01(2H,m), 4.48(1H,dd,J=11.2, 3.9 Hz), 7.38-7.45(3H, m), 7.47(2H,d,J=8.6 Hz), 8.65(1H,s).

MS (m/z): 408 (M$^+$+H).

Elemental Analysis for C$_{15}$H$_{18}$ClNO$_4$S$_3$

Calculated: C 44.16%; H 4.45%; Cl 8.69%; N 3.43%; S 23.58%.

Found: C 44.25%; H 4.34%; Cl 8.58%; N 3.54%; S 23.82%.

Example 113

5-(4-Chlorophenylsulfonylmethyl)thiazole

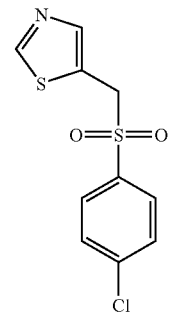

A carbon tetrachloride (15 ml) suspension of 5-methylthiazole (380 mg, 3.83 mmol), N-chlorosuccinic imide (511 mg, 3.83 mmol), 2,2'-azobis(2-methylpropionitrile) (62 mg, 0.380 mmol) and acetic acid (0.22 ml, 3.83 mmol) was heated under reflux for 18 hours under a nitrogen atmosphere. The reaction mixture was cooled to room temperature and then, concentrated under reduced pressure. The resulting residue was dissolved in butanol (10 ml). To the resulting solution were added sodium 4-chlorophenylsulfinate (761 mg, 3.83 mmol) and potassium acetate (376 mg, 3.83 mmol), followed by stirring at 70° C. for 23 hours. After cooling to room temperature, the reaction mixture was concentrated under reduced pressure. Ethyl acetate was added to the residue. The mixture was washed successively with water and brine and then dried over anhydrous sodium sulfate. After filtration, the filtrate was concentrated under reduced pressure. The residue was subjected to chromatography on a silica gel column. The fraction obtained from the hexane:ethyl acetate (=1:1) eluate was concentrated under reduced pressure, whereby the title compound (76 mg, 7.2%) was obtained as a pale yellow solid.

IR (ATR) ν: 3085, 2975, 2915, 1671, 1577, 1521, 1473, 1392, 1313, 1253, 1193, 1143, 1081, 1012, 968, 894, 873, 836, 773, 728, 705, 651, 620, 605, 565, 543, 476, 443 cm$^{-1}$.

$^1$H-NMR (400 MHz, CDCl$_3$) δ: 4.57(2H,s), 7.49(2H,d, J=8.8 Hz), 7.57(1H,s), 7.65(2H,d,J=8.6 Hz), 8.81(1H,s).

MS (m/z): 274 (M$^+$+H).

Example 114

5-[1-[(4-Chlorophenyl)sulfonyl]-5-(methylsulfonyl)pentyl]thiazole

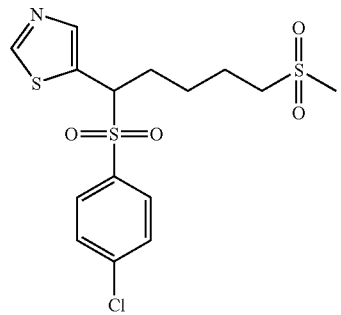

A toluene (10 ml) solution of 5-(4-chlorophenylsulfonylmethyl)thiazole (51 mg, 0.186 mmol), the 4-(methylsulfonyl)-1-butanol (57 mg, 0.372 mmol) obtained in Referential Example 3 and cyanomethylenetri-n-butylphosphorane (90 mg, 0.372 mol) was heated under reflux for 21 hours under an argon atmosphere. After cooling to room temperature, the reaction mixture was concentrated under reduced pressure. The residue was subjected to flash chromatography on a silica gel column. The fraction obtained from the methylene chloride:ethyl acetate (=1:2) eluate was concentrated under reduced pressure to give the title compound (53 mg, 70%) as a white solid. The resulting white solid was washed with hexane-ether, and then filtered, whereby the title compound was obtained as a white powder.

Melting point: 95-96° C.

IR (ATR) ν: 3099, 3021, 2942, 1575, 1513, 1473, 1392, 1351, 1299, 1272, 1240, 1201, 1174, 1137, 1085, 1012, 966, 914, 873, 827, 777, 746, 703, 634, 613, 566, 528, 470 cm$^{-1}$.

$^1$H-NMR (400 MHz, CDCl$_3$) δ: 1.445-1.60(2H,m), 1.81-1.99(2H,m), 2.00-2.12(1H,m), 2.50-2.61(1H,m), 2.89(3H,s), 2.92-3.01(2H,m), 4.41(1H,dd,J=11.1, 3.5 Hz), 7.43(2H,d, J=8.5 Hz), 7.47(1H,s), 7.52(2H,d,J=8.5 Hz), 8.82(1H,s).

MS (m/z): 408 (M$^+$+H).

Elemental Analysis for $C_{15}H_{18}ClNO_4S_3$

Calculated: C 44.16%; H 4.45%; Cl 8.69%; N 3.43%; S 23.58%.

Found: C 44.44%; H 4.38%; Cl 8.75%; N 3.53%; S 23.41%.

Referential Example 12

Thiazole-2-methanol

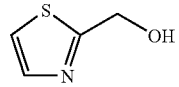

While stirring under ice cooling, sodium borohydride (242 mg, 6.40 mmol) was added to a methanol (10 ml) solution of 2-formylthiazole (483 mg, 4.27 mmol). After completion of the reaction was confirmed, water was added to the reaction mixture. The resulting mixture was concentrated under reduced pressure. Water and ethyl acetate were added to the residue to separate the organic layer. The organic layer was washed with brine and then dried over anhydrous sodium sulfate. After filtration, the filtrate was concentrated under reduced pressure. The residue was subjected to chromatography on a silica gel column. The fraction obtained from the hexane:ethyl acetate (=1:1) eluate was concentrated under reduced pressure, whereby the title compound (324 mg, 66%) was obtained as a white solid.

$^1$H-NMR (400 MHz, CDCl$_3$) δ: 3.30-3.70(1H,m), 5.14 (2H,s), 7.32(1H,d,J=3.4 Hz), 7.74(1H,d,J=3.2 Hz).

MS (m/z): 116 (M$^+$+H).

Example 115

2-(4-Chlorophenylsulfonylmethyl)thiazole

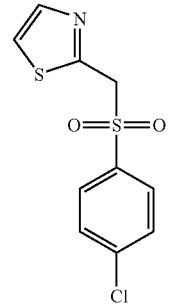

To a chloroform (15 ml) solution of thiazole-2-methanol (171 mg, 1.49 mmol) was added thionyl chloride (0.33 ml, 4.47 mmol) and the resulting mixture was stirred at 50° C. for 11 hours. After cooling to room temperature, the reaction mixture was concentrated under reduced pressure. The residue was dissolved in butanol (10 ml). To the resulting solution were added sodium 4-chlorobenzenesulfinate (296 mg, 1.49 mmol) and potassium acetate (292 mg, 2.98 mmol). The mixture was stirred at 70° C. for 24 hours. After cooling to room temperature, the reaction mixture was concentrated under reduced pressure. Ethyl acetate was added to the residue. The mixture was washed successively with water and brine and then, dried over anhydrous sodium sulfate. After filtration, the filtrate was concentrated under reduced pressure. The residue was subjected to chromatography on a silica gel column. The fraction obtained from the hexane:ethyl acetate (=1:1) eluate was concentrated under reduced pressure, whereby the title compound (169 mg, 41%) was obtained as a pale yellow solid.

IR (ATR) ν: 2967, 2913, 1573, 1498, 1475, 1394, 1317, 1280, 1218, 1184, 1147, 1081, 1062, 1012, 966, 887, 825, 775, 763, 730, 700, 630, 599, 563, 549, 478, 447 cm$^{-1}$.

$^1$H-NMR (400 MHz, CDCl$_3$) δ: 4.79(2H,s), 7.42(1H,d, J=3.2 Hz), 7.47(2H,d,J=8.6 Hz), 7.64(2H,d,J=8.8 Hz), 7.72 (1H,d,J=3.4 Hz).

MS (m/z): 274 (M$^+$+H).

Example 116

2-[1-[(4-Chlorophenyl)sulfonyl]-5-(methylsulfonyl) pentyl]thiazole

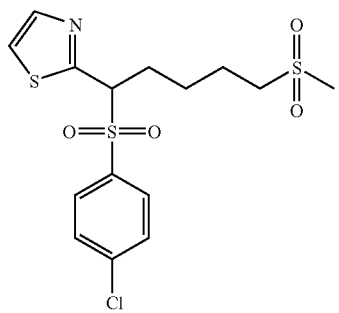

A toluene (10 ml) solution of 2-(4-chlorophenylsulfonyl-methyl)thiazole (75 mg, 0.274 mmol), the 4-(methylsulfonyl)-1-butanol (83 mg, 0.548 mmol) obtained in Referential Example 3 and cyanomethylenetri-n-butylphosphorane (132 mg, 0.548 mol) was heated under reflux for 20 hours under an argon atmosphere. After cooling to room temperature, the reaction mixture was concentrated under reduced pressure. The residue was subjected to flash chromatography on a silica gel column. The fraction obtained from the methylene chloride:ethyl acetate (=1:2) eluate was concentrated under reduced pressure to give the title compound (87 mg, 78%) as a white solid. The resulting solid was washed with ether and then, collected by filtration, whereby the title compound was obtained as a white powder.

Melting point: 118-119° C.

IR (ATR) ν: 3137, 3006, 2913, 1583, 1496, 1471, 1388, 1357, 1315, 1284, 1238, 1203, 1135, 1083, 1043, 1010, 975, 877, 842, 804, 765, 736, 705, 642, 601, 572, 526, 468, 439 cm$^{-1}$.

$^1$H-NMR (400 MHz, CDCl$_3$) δ: 1.40-1.62(2H,m), 1.80-1.99(2H,m), 2.22-2.35(1H,m), 2.48-2.58(1H,m), 2.88(3H,s), 2.92-3.00(2H,m), 4.61(1H,dd,J=11.2, 3.7 Hz), 7.39-7.47(3H, m), 7.51(2H,d,J=8.5 Hz), 7.68(1H,d,J=3.4 Hz).

MS (m/z): 408 (M$^+$+H).

Elemental Analysis for C$_{15}$H$_{18}$ClNO$_4$S$_3$

Calculated: C 44.16%; H 4.45%; Cl 8.69%; N 3.43%; S 23.58%.

Found: C 44.32%; H 4.40%; Cl 8.74%; N 3.54%; S 24.04%.

Example 117

5-(4-Chlorophenylsulfonylmethyl)oxazole

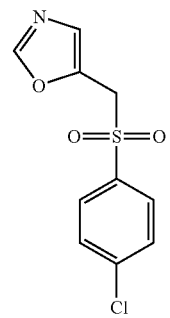

Thionyl chloride (188 μl, 2.57 mmol) was added to a chloroform (10 ml) solution of oxazol-5-ylmethanol (85 mg, 0.858 mmol). The resulting mixture was stirred at 50° C. for 1.5 hours. After cooling to room temperature, the reaction mixture was concentrated under reduced pressure. The residue thus obtained was dissolved in butanol (10 ml). To the resulting solution were added sodium 4-chlorobenzenesulfinate (170 mg, 0.858 mmol), potassium acetate (252 mg, 2.57 mmol) and tetrabutylammonium iodide (15 mg), followed by stirring at 70° C. for 3 days. After cooling to room temperature, the reaction mixture was concentrated under reduced pressure. Ethyl acetate was added to the residue. The mixture was washed successively with water and brine and then, dried over anhydrous sodium sulfate. After filtration, the filtrate was concentrated under reduced pressure. The residue was subjected to flash chromatography on a silica gel column, and the fraction obtained from the hexane:ethyl acetate (=1:1) fraction was concentrated under reduced pressure, whereby the title compound (81 mg, 37%) was obtained as a white solid.

IR (ATR) ν: 3141, 3085, 2983, 2921, 1475, 1506, 1490, 1475, 1396, 1319, 1284, 1263, 1213, 1178, 1151, 1110, 968, 923, 869, 823, 769, 746, 700, 644, 559, 541, 482, 455, 422 cm$^{-1}$.

$^1$H-NMR (400 MHz, CDCl$_3$) δ: 4.47(2H,s), 7.02(1H,s), 7.52(2H,d,J=8.8 Hz), 7.70(2H,d,J-8.8 Hz), 7.82(1H,s).

MS (m/z): 258 (M$^+$+H).

Example 118

5-[1-(4-Chlorophenylsulfonyl)-5-(methylsulfonyl) pentyl]oxazole

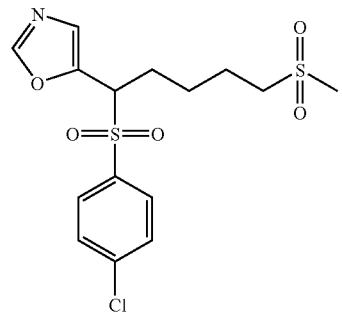

A toluene (10 ml) solution of 5-(4-chlorophenylsulfonylmethyl)oxazole (65 mg, 0.252 mmol), the 4-(methylsulfonyl)-1-butanol (77 mg, 0.504 mmol) obtained in Referential Example 3 and cyanomethylenetri-n-butylphosphorane (122 mg, 0.504 mmol) was heated under reflux for 15 hours under an argon atmosphere. After cooling to room temperature, the reaction mixture was added with the 4-(methylsulfonyl)-1-butanol (77 mg, 0.504 mmol) obtained in Referential Example 3 and cyanomethylenetri-n-butylphosphorane (122 mg, 0.504 mmol), followed by heating under reflux for 25 hours under an argon atmosphere. After cooling to room temperature, the reaction mixture was concentrated under reduced pressure. The residue was subjected to flash chromatography on a silica gel column, and the fraction obtained from the hexane:ethyl acetate (=1:3) eluate was concentrated under reduced pressure to give the title compound (82 mg, 83%) as a white solid. The resulting white solid was washed with hexane and then, collected by filtration, whereby the title compound was obtained as a white powder.

Melting point: 164-166° C.

IR (ATR) ν: 3139, 2937, 1583, 1504, 1475, 1394, 1311, 1276, 1193, 1147, 1128, 1108, 1085, 1054, 1012, 968, 946, 919, 871, 854, 831, 771, 754, 707, 649, 622, 553, 532, 491, 462 cm$^{-1}$.

$^1$H-NMR (400 MHz, CDCl$_3$) δ: 1.43-1.60(2H,m), 1.80-1.99(2H,m), 2.06-2.20(1H,m), 2.39-2.49(1H,m), 2.89(3H,s), 2.94-3.01(2H,m), 4.29(1H,dd,J=11.1, 4.0 Hz), 6.96(1H,s), 7.48(2H,d,J=8.3 Hz), 7.57(2H,d,J=8.6 Hz), 7.79(1H,s).

MS (m/z): 392 (M$^+$+H).

Elemental Analysis for C$_{15}$H$_{18}$ClNO$_5$S$_2$

Calculated: C 45.97%; H 4.63%; Cl 9.05%; N 3.57%; S 16.36%.

Found: C 45.98%; H 4.79%; Cl 8.96%; N 3.66%; S 16.29%.

Example 119

4-(4-Chlorophenylsulfonylmethyl)pyridine

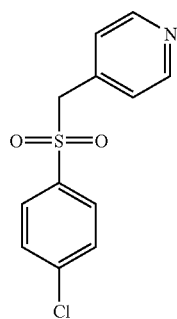

Under heating, a 1-propanol (50 ml) solution of 4-chloromethylpyridine hydrochloride (1.26 g, 7.65 mmol), sodium 4-chlorobenzenesulfinate (1.52 g, 7.65 mmol) and potassium acetate (1.50 g, 15.3 mmol) was stirred at 70° C. for 8 hours. After cooling to room temperature, the reaction mixture was concentrated under reduced pressure. The residue was filtered through a short column (silica gel, ethyl acetate) and the eluate was concentrated under reduced pressure. The residue was subjected to chromatography on a silica gel column, and the fraction obtained from the hexane:ethyl acetate (=2:3) eluate was concentrated under reduced pressure, whereby the title compound (1.26 g, 62%) was obtained as a white solid.

$^1$H-NMR (400 MHz, CDCl$_3$) δ: 4.29(2H,s), 7.06(2H,d, J=6.1 Hz), 7.47(2H,d,J=8.8 Hz), 7.59(2H,d,J=8.5 Hz), 8.57 (2H,d,J=6.1 Hz).

MS (m/z): 268 (M$^+$+H).

Example 120

4-[1-(4-Chlorophenylsulfonyl)pentyl]pyridine

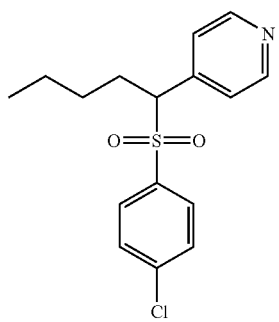

At −78° C., butyl lithium (a 1.57M hexane solution; 0.29 ml, 0.448 mmol) was added dropwise to a tetrahydrofuran (5 ml) solution of 4-(4-chlorophenylsulfonylmethyl)pyridine (100 mg, 0.374 mmol). At −78° C., the resulting mixture was stirred for 10 minutes. Iodobutane (51 μl, 0.448 mmol) was then added thereto. The temperature of the reaction mixture was gradually elevated to room temperature, at which stirring was performed for 16 hours. Water was added to the reaction mixture, followed by extraction with ethyl acetate. The organic layer was washed with brine and then dried over anhydrous sodium sulfate. After filtration, the filtrate was concentrated under reduced pressure. The residue was subjected to flash chromatography on a silica gel column. The fraction obtained from the hexane:ethyl acetate (=2:1) eluate was concentrated under reduced pressure to give the title compound (76 mg, 63%) as a white solid. The resulting solid was washed with hexane-ether and then collected by filtration, whereby the title compound was obtained as a white powder.

Melting point: 109-111° C.

IR (ATR) ν: 2933, 2859, 1596, 1575, 1558, 1473, 1415, 1392, 1322, 1280, 1238, 1209, 1172, 1145, 1083, 1010, 991, 970, 885, 844, 821, 767, 754, 730, 703, 667, 630, 599, 565, 520, 466, 410 cm$^{-1}$.

$^1$H-NMR (400 MHz, CDCl$_3$) δ: 0.84(3H,t,J=7.3 Hz), 1.09-1.40(4H,m), 2.07-2.10(1H,m), 2.37-2.49(1H,m), 3.98(1H, dd,J=11.6,3.5 Hz), 7.06(1H,d,J=6.1 Hz), 7.39(2H,d,J=8.8 Hz), 7.48(2H,d,J=8.6 Hz), 8.53(2H,d,J=6.1 Hz).

MS (m/z): 324 (M$^+$+H).

Elemental Analysis for C$_{16}$H$_{18}$ClNO$_2$S

Calculated: C 59.34%; H 5.60%; Cl 10.95%; N 4.33%; S 9.90%.

Found: C 59.41%; H 5.54%; Cl 11.18%; N 4.47%; S 10.09%.

Example 121

4-[(4-Chlorophenylsulfonyl)(cyclopentyl)methyl]pyridine

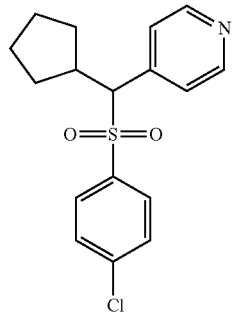

A toluene (5 ml) solution of the 4-(4-chlorophenylsulfonylmethyl)pyridine (70 mg, 0.261 mmol) obtained in Example 119, cyclopentanol (49 μl, 0.538 mmol) and cyanomethylenetri-n-butylphosphorane (129 mg, 0.538 mol) was heated under reflux for 3 days under an argon atmosphere. After cooling to room temperature, the reaction mixture was added with cyclopentanol (49 μl, 0.538 mmol) and cyanomethylenetri-n-butylphosphorane (129 mg, 0.538 mol). The mixture was heated under reflux for 22 hours under an argon atmosphere. After cooling to room temperature, the reaction mixture was concentrated under reduced pressure. The residue was subjected to flash chromatography on a silica gel column, and the fraction obtained from the hexane:ethyl acetate (=2:1) eluate was concentrated under reduced pressure to give the title compound (77 mg, 88%) as a white solid. The resulting solid was washed with hexane-ether and collected by filtration, whereby the title compound was obtained as a white powder.

Melting point: 133-135° C.

IR (ATR) ν: 2960, 2867, 1594, 1577, 1558, 1473, 1415, 1392, 1342, 1319, 1278, 1224, 1143, 1083, 1010, 993, 954, 902, 840, 821, 767, 750, 705, 642, 592, 551, 507, 464 cm$^{-1}$.

$^1$H-NMR (400 MHz, CDCl$_3$) δ: 0.92-1.08(1H,m), 1.44-1.83(6H,m), 2.33-2.45(1H,m), 2.78-2.90(1H,m), 3.88(1H,d, J=10.3 Hz), 7.03(2H,d,J=5.1 Hz), 7.32(2H,d,J=8.6 Hz), 7.43(2H,d,J=8.6 Hz), 8.46(2H,d,J=5.6 Hz).

MS (m/z): 336 (M$^+$+H).

Elemental Analysis for C$_{17}$H$_{18}$ClNO$_2$S

Calculated: C 60.80%; H 5.40%; Cl 10.56%; N 4.17%; S 9.55%.

Found: C 60.76%; H 5.44%; Cl 10.68%; N 4.20%; S 9.61%.

Example 122

4-[(4-Chlorophenylsulfonyl)(tetrahydropyran-4-yl)methyl]pyridine

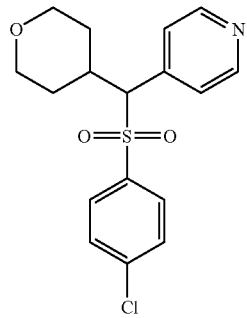

A toluene (5 ml) solution of the 4-(4-chlorophenylsulfonylmethyl)pyridine (70 mg, 0.261 mmol) obtained in Example 119, tetrahydropyran-4-ol (51 μl, 0.538 mmol) and cyanomethylenetri-n-butylphosphorane (129 mg, 0.538 mol) was heated under reflux for 3 days under an argon atmosphere. After cooling to room temperature, the reaction mixture was added with tetrahydropyran-4-ol (51 μl, 0.538 mmol) and cyanomethylenetri-n-butylphosphorane (129 mg, 0.538 mol), followed by heating under reflux for 22 hours under an argon atmosphere. After cooling to room temperature, the reaction mixture was concentrated under reduced pressure. The residue was subjected to flash chromatography on a silica gel column, and the fraction obtained from the hexane:ethyl acetate (=1:2) eluate was concentrated under reduced pressure to give the title compound (65 mg, 71%) as a white solid. The resulting solid was washed with hexane-ether and collected by filtration, whereby the title compound was obtained as a white powder.

Melting point: 208-209° C.

IR (ATR) ν: 2846, 1594, 1573, 1560, 1475, 1440, 1417, 1394, 1371, 1315, 1278, 1245, 1211, 1180, 1143, 1083, 989, 877, 835, 773, 752, 703, 630, 603, 565, 524, 478, 451 cm$^{-1}$.

$^1$H-NMR (400 MHz, CDCl$_3$) δ: 1.22-1.42(2H,m), 1.60-1.75(1H,m), 2.30-2.40(1H,m), 2.78-3.01(1H,m), 3.41(1H,td, J=11.7, 2.4 Hz), 3.51(1H,td,J=11.9, 2.0 Hz), 3.80-3.93(1H,m), 3.87(1H,d,J=8.6 Hz), 3.98-4.06(1H,m), 7.00-7.12(2H,m), 7.30(2H,d,J=8.8 Hz), 7.43(2H,d,J=8.6 Hz), 8.47(2H,d, J=5.4 Hz).

MS (m/z): 352 (M$^+$+H).

Example 123

4-[(1-Benzylpiperidin-4-yl)(4-chlorophenylsulfonyl)methyl]pyridine

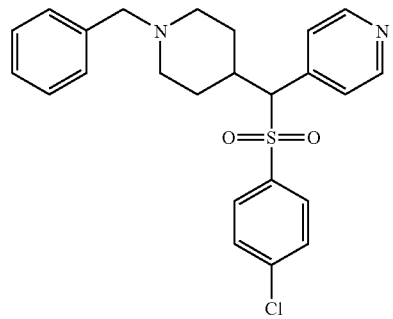

A toluene (5 ml) solution of the 4-(4-chlorophenylsulfonylmethyl)pyridine (70 mg, 0.261 mmol) obtained in Example 119, 1-benzylpiperidin-4-ol (103 mg, 0.538 mmol) and cyanomethylenetri-n-butylphosphorane (129 mg, 0.538 mol) was heated under reflux for 3 days under an argon atmosphere. After cooling to room temperature, the reaction mixture was added with 1-benzylpiperidin-4-ol (103 mg, 0.538 mmol) and cyanomethylenetri-n-butylphosphorane (129 mg, 0.538 mol), followed by heating under reflux for 22 hours under an argon atmosphere. After cooling to room temperature, the reaction mixture was concentrated under reduced pressure. The residue was subjected to flash chromatography on a silica gel column. The fraction obtained from the methanol:methylene chloride (=1:10) eluate was concentrated under reduced pressure. The residue thus obtained was purified by high performance liquid chromatography (using a mixed solvent of water/acetonitrile/formic acid), whereby the title compound (40 mg, 35%) was obtained as an amorphous substance.

IR (ATR) ν: 2938, 2803, 2763, 1594, 1560, 1475, 1452, 1415, 1367, 1317, 1280, 1218, 1176, 1143, 1085, 1012, 975, 825, 750, 742, 698, 617, 566, 536, 464 cm$^{-1}$.

$^1$H-NMR (400 MHz, CDCl$_3$) δ: 1.21-1.37(2H,m), 1.49-1.70(1H,m), 1.92-2.01(1H,m), 2.03-2.14(1H,m), 2.25-2.35(1H,m), 2.52-2.65(1H,m), 2.79-2.85(1H,m), 2.90-3.00(1H,m), 3.47(2H,s), 3.86(1H,d,J=8.1 Hz), 7.02-7.12(2H,m), 7.20-7.38(7H,m), 7.43(2H,d,J=8.5 Hz), 8.45(2H,d,J=5.4 Hz).

MS (m/z): 441 (M$^+$+H).

HRMS (FAB): as C$_{24}$H$_{26}$O$_2$N$_2$ClS (M$^+$+H)

Calculated: 441.1404

Found: 441.1387

Example 124

4-[(4-Chlorophenylsulfonyl)(1-methylpiperidin-4-yl)methyl]pyridine

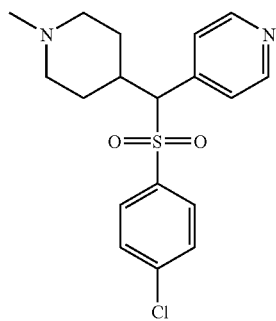

A toluene (5 ml) solution of the 4-(4-chlorophenylsulfonylmethyl)pyridine (70 mg, 0.261 mmol) obtained in Example 119, 1-methylpiperidin-4-ol (62 μl, 0.538 mmol) and cyanomethylenetri-n-butylphosphorane (62 μl, 0.538 mol) was heated under reflux for 3 days under an argon atmosphere. After cooling to room temperature, the reaction mixture was added with 1-methylpiperidin-4-ol (62 μl, 0.538 mmol) and cyanomethylenetri-n-butylphosphorane (129 mg, 0.538 mol), followed by heating under reflux for 22 hours under an argon atmosphere. After cooling to room temperature, the reaction mixture was concentrated under reduced pressure. The residue was subjected to silica gel column chromatography, and the fraction obtained from the methanol:methylene chloride (=1:50) eluate was concentrated under reduced pressure. The residue thus obtained was purified by high performance liquid chromatography (using a mixed solvent of water/acetonitrile/formic acid) to give the title compound (31 mg, 33%) as a white solid. The resulting solid was washed with hexane-ether and then, collected by filtration, whereby the title compound was obtained as a white powder.

Melting point: 176-177° C.

IR (ATR) ν: 3077, 2935, 2856, 2786, 2740, 1594, 1556, 1465, 1450, 1413, 1380, 1346, 1315, 1280, 1241, 1145, 1085, 1008, 973, 850, 835, 798, 750, 705, 617, 561, 528, 476, 464, 424 cm$^{-1}$.

$^1$H-NMR (400 MHz, CDCl$_3$) δ: 1.22-1.38(2H,m), 1.50-1.68(1H,m), 1.88-1.99(1H,m), 2.00-2.10(1H,m), 2.25(3H,s), 2.30-2.40(1H,m), 2.50-2.63(1H,m), 2.74-2.83(1H,m), 2.89-2.95(1H,m), 3.86(1H,d,J=8.3 Hz), 7.08(2H,d,J=4.6 Hz), 7.30(2H,d,J=8.6 Hz), 7.44(2H,d,J=8.6 Hz), 8.46(2H,d,J=5.6 Hz).

MS (m/z): 365 (M$^+$+H).

Elemental Analysis for C$_{18}$H$_{21}$ClN$_2$O$_2$S

Calculated: C 59.25%; H 5.80%; Cl 9.72%; N 7.68%; S 8.79%.

Found: C 59.00%; H 5.76%; Cl 9.75%; N 7.61%; S 8.77%.

Example 125

4-(4-Chlorophenylsulfonyl)-N,N-dimethyl-4-(pyridin-4-yl)butylamine

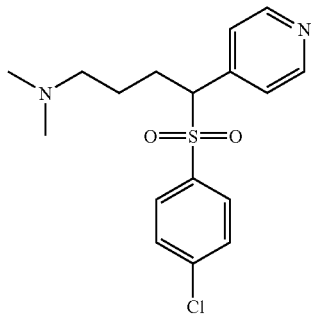

A toluene (5 ml) solution of the 4-(4-chlorophenylsulfonylmethyl)pyridine (70 mg, 0.261 mmol) obtained in Example 119, 3-dimethylamino-1-propanol (62 μl, 0.538 mmol) and cyanomethylenetri-n-butylphosphorane (129 mg, 0.538 mol) was heated under reflux for 3 days under an argon atmosphere. After cooling to room temperature, the reaction mixture was added with 3-dimethylamino-propan-1-ol (62 μl, 0.538 mmol) and cyanomethylenetri-n-butylphosphorane (129 mg, 0.538 mol), followed by heating under reflux for 22 hours under an argon atmosphere. After cooling to room temperature, the reaction mixture was concentrated under reduced pressure. The residue was subjected to chromatography on a silica gel column, and the fraction obtained from the methanol:methylene chloride (=1:10) eluate was concentrated under reduced pressure. The residue thus obtained was purified by high performance liquid chromatography (using a mixed solvent of water/acetonitrile/formic acid) to give the title compound (44 mg, 48%) as a white solid. The resulting solid was washed with hexane-ether and then, collected by filtration, whereby the title compound was obtained as a white powder.

Melting point: 78-80° C.

IR (ATR) ν: 3089, 2985, 2937, 2809, 2757, 2596, 1587, 1455, 1413, 1392, 1322, 1278, 1203, 1145, 1083, 1041, 1010, 991, 962, 846, 821, 767, 754, 703, 628, 578, 539, 514, 472 cm$^{-1}$.

$^1$H-NMR (400 MHz, CDCl$_3$) δ: 1.38-1.43(2H,m), 2.05-2.29(3H,m), 2.11(6H,s), 2.39-2.50(1H,m), 4.05-4.13(1H,m), 7.07(2H,d,J=6.1 Hz), 7.40(2H,d,J=8.5 Hz), 7.48(2H,d,J=8.6 Hz), 8.53(2H,d,J=6.1 Hz).

MS (m/z): 353 (M$^+$+H).

Elemental Analysis for C$_{17}$H$_{21}$ClN$_2$O$_2$S

Calculated: C 57.86%; H 6.00%; Cl 10.05%; N 7.94%; S 9.09%.

Found: C 57.62%; H 5.92%; Cl 9.89%; N 7.91%; S 9.12%.

Example 126

3-(4-Chlorophenylsulfonyl)-N,N-dimethyl-3-(pyridin-4-yl)propylamine

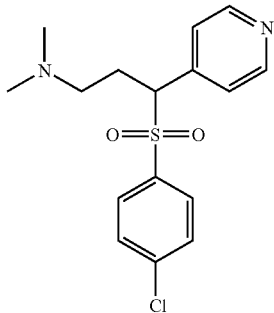

A toluene (5 ml) solution of the 4-(4-chlorophenylsulfonylmethyl)pyridine (70 mg, 0.261 mmol) obtained in Example 119, 2-dimethylaminoethanol (54 μl, 0.538 mmol) and cyanomethylenetri-n-butylphosphorane (129 mg, 0.538 mol) was heated under reflux for 3 days under an argon atmosphere. After cooling to room temperature, the reaction mixture was added with 2-dimethylaminoethanol (54 μl, 0.538 mmol) and cyanomethylenetri-n-butylphosphorane (129 mg, 0.538 mol), followed by heating under reflux for 22 hours under an argon atmosphere. After cooling to room temperature, the reaction mixture was concentrated under reduced pressure. The residue was subjected to chromatography on a silica gel column, and the fraction obtained from the methanol:methylene chloride (=1:10) eluate was concentrated under reduced pressure. The residue thus obtained was purified by high performance liquid chromatography (using a mixed solvent of water/acetonitrile/formic acid) to give the title compound (49 mg, 55%) as a white solid. The resulting solid was washed with hexane-ether and then, collected by filtration, whereby the title compound was obtained as a white powder.

Melting point: 91-92° C.

IR (ATR) ν: 3031, 2975, 2940, 2857, 2821, 2790, 1587, 1575, 1554, 1459, 1413, 1384, 1313, 1280, 1249, 1143, 1083, 1045, 1008, 991, 842, 821, 759, 723, 703, 630, 570, 526, 468 cm$^{-1}$.

$^1$H-NMR (400 MHz, CDCl$_3$) δ: 2.05-2.20(2H,m), 2.11 (6H,s), 2,59-2.70(1H,m), 4.35(1H,dd,J=10.5, 3.2 Hz), 7.11 (2H,d,J=6.1 Hz), 7.39(2H,d,J=8.6 Hz), 7.59(2H,d,J=8.6 Hz), 8.53(2H,d,J=6.1 Hz).

MS (m/z): 339 (M$^+$+H).

Elemental Analysis for C$_{16}$H$_{19}$ClN$_2$O$_2$S

Calculated: C 56.71%; H 5.65%; Cl 10.46%; N 8.27%; S 9.46%.

Found: C 56.64%; H 5.61%; Cl 10.51%; N 8.26%; S 9.57%.

Referential Example 13

2-[(2,5-Difluorophenyl)-hydroxymethyl]pyridine

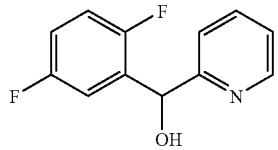

Under an argon atmosphere, a hexane solution of n-butyl lithium (1.53M, 3.92 ml, 6 mmol) was added dropwise to a tetrahydrofuran (10 ml) solution of 2-bromopyridine (572 μl, 6 mmol) at −78° C. and the mixture was stirred for 30 minutes. To the resulting brown solution, 2,5-difluorobenzaldehyde (655 μl, 6 mmol) was added dropwise and the temperature of the mixture was gradually raised to room temperature. Water was added to the reaction mixture, followed by extraction with ethyl acetate. After drying the solvent, the residue obtained by concentration under reduced pressure was purified by silica gel chromatography, whereby the title compound (120 mg, 9%) was obtained as a white solid.

$^1$H-NMR (400 MHz, CDCl$_3$) δ:5.45(1H,br), 6.08 (1H,s), 6.87-7.15(3H,m), 7.2-7.3(2H,m), 7.65(1H,m), 8.56(1H,m).

mp: 65-66° C.

Referential Example 14

2-[Chloro-(2,5-difluorophenyl)methyl]-3-methylpyridine hydrochloride

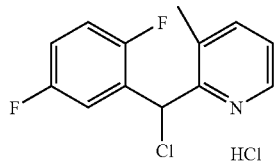

Under an argon atmosphere, a tetrahydrofuran solution (1.5 ml, 3 mmol) of isopropylmagnesium chloride was added dropwise to a tetrahydrofuran (2.0 ml) solution of 2-bromo-3-methylpyridine (510 mg, 3 mmol) under ice cooling and the mixture was stirred at room temperature for 60 minutes. Under ice cooling, 2,5-difluorobenzaldehyde (328 μl, 3 mmol) was added dropwise to the resulting brown solution. The temperature of the reaction mixture was then raised gradually to room temperature. After addition of a saturated aqueous solution of ammonium chloride, the resulting mixture was extracted with ethyl acetate. After drying the solvent, the residue obtained by concentration under reduced pressure was purified by silica gel chromatography (hexane:ethyl acetate=8:1) to yield a mixture containing the title compound. To the resulting mixture were added thionyl chloride (2.0 ml) and a drop of dimethylformamide, followed by stirring at room temperature for 14 hours. Distillation of excess thionyl chloride under reduced pressure yielded a white precipitate. The resulting white precipitate was triturated with hexane and diethyl ether, whereby the title compound (101 mg, 12%) was obtained.

¹H-NMR (400 MHz, CDCl₃) δ: 2.37(3H,s), 6.95-7.10(2H, m), 7.28 (1H,s), 7.7-7.8(2H,m), 8.11(1H,d,J=6.3 Hz), 8.72 (1H,d,J=4.9 Hz).
IR (ATR) cm⁻¹: 1612, 1496, 1294, 1232, 821.
mp: 118-119° C.
MS m/z: 254 (M⁺+H).

Referential Example 15

2-[(2,5-Difluorophenyl)-hydroxymethyl]-5-methylpyridine

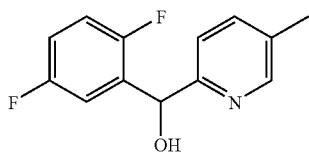

Under an argon atmosphere, a tetrahydrofuran solution (1.5 ml, 3 mmol) of isopropylmagnesium chloride was added dropwise to a tetrahydrofuran (2 ml) solution of 2-bromo-5-methylpyridine (510 mg, 3 mmol) under ice cooling and the mixture was stirred at room temperature for 60 minutes. Under ice cooling, 2,5-difluorobenzaldehyde (328 μl, 3 mmol) was added dropwise to the resulting brown solution. The temperature of the reaction mixture was raised gradually to room temperature. A saturated aqueous solution of ammonium chloride was added and the mixture was extracted with ethyl acetate. After drying the solvent, the residue obtained by concentration under reduced pressure was purified by silica gel chromatography (hexane:ethyl acetate=5:1), whereby the title compound (130 mg, 18%) was obtained as an oil.
¹H-NMR (400 MHz, CDCl₃) δ: 2.31(3H,s), 5.38(1H,br), 6.04(1H,s), 6.83-7.18(4H,m), 7.44(1H,dd,J=2.0, 8.0 Hz), 8.37(1H,m).
IR (ATR) cm⁻¹: 1485, 1178, 1132, 814.
MS m/z: 236 (M⁺+H).

Referential Example 16

2-[(2,5-Difluorophenyl)-hydroxymethyl]-4-methylpyridine

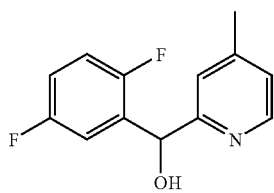

Under an argon atmosphere, a tetrahydrofuran solution (1.5 ml, 3 mmol) of isopropylmagnesium chloride was added dropwise to a tetrahydrofuran (2 ml) solution of 2-bromo-4-methylpyridine (334 μl, 3 mmol) under ice cooling and the mixture was stirred at room temperature for 60 minutes. Under ice cooling, 2,5-difluorobenzaldehyde (328 μl, 3 mmol) was added dropwise to the resulting brown solution. The temperature of the reaction mixture was raised gradually to room temperature. To the reaction mixture was added a saturated aqueous solution of ammonium chloride, followed by extraction with ethyl acetate. After drying the solvent, the residue obtained by concentration under reduced pressure was purified by silica gel chromatography (hexane:ethyl acetate=5:1), whereby the title compound (456 mg, 65%) was obtained as needle crystals.
¹H-NMR (400 MHz, CDCl₃) δ: 2.30(3H,s), 5.48(1H,br-s), 6.02(1H,s), 6.83-7.13(5H,m), 8.38(1H,m).
IR (ATR) cm⁻¹: 3162, 1610, 1481, 1054, 825.
mp: 105-106° C.
MS m/z: 236 (M⁺+H).

Referential Example 17

2-Bromo-3-methoxypyridine

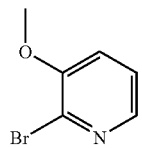

Under a nitrogen atmosphere, 60% oil sodium hydride (605 mg, 15.1 mmol) was added in portions to methanol (10 ml) under ice cooling. Twenty minutes later, a dimethylformamide (20 ml) solution of 2-bromo-3-hydroxypyridine (2.5 g, 14.4 mmol) was added to the resulting mixture. The reaction mixture was distilled under reduced pressure to remove methanol and to the residue was added methyl iodide (0.94 ml, 15.1 mmol). The mixture was stirred at room temperature for 3 hours.
After the reaction mixture was concentrated to dryness, water (50 ml) and ether (50 ml) were added to the residue. The organic layer obtained by separation was washed with a saturated aqueous solution of sodium bicarbonate and brine. The extract was dried over anhydrous magnesium sulfate and concentrated under reduced pressure. The residue was then purified by silica gel chromatography (hexane:ethyl acetate=8:1), whereby the title compound (1.51 g, 56%) was obtained as colorless needle crystals.
¹H-NMR (400 MHz, CDCl₃) δ: 3.90(3H,s), 7.12(1H,m), 7.21(1H,dd,J=4.8, 8.0 Hz), 7.97(1H,m).
IR (ATR) cm⁻¹: 1556, 1410, 1076, 1049, 788.
mp: 34° C.

Referential Example 18

3-Allyloxy-2-bromopyridine

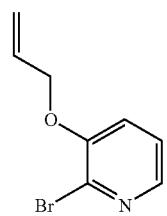

In a similar manner to that employed for the synthesis of 2-bromo-3-methoxypyridine, the title compound (2.35 g, 76%) was obtained as an oil.

¹H-NMR (400 MHz, CDCl₃) δ: 4.62(2H,m), 5.33(1H,dd, J=1.2, 10.4 Hz), 5.47(1H,dd,J=1.2, 17.6 Hz), 6.06(1H,m), 7.11(1H,dd,J=1.2 Hz,8.0 Hz), 7.18(1H,dd,J=4.8, 8.0 Hz), 7.98(1H,m).
IR (ATR) cm⁻¹: 1562, 1408, 1282, 1052, 790.
MS m/z: 215 (M⁺+H).

Referential Example 19

2-[(2,5-Difluorophenyl)-hydroxymethyl]-3-methoxypyridine

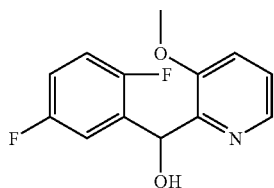

Under an argon atmosphere, a tetrahydrofuran solution (1.5 ml, 3 mmol) of isopropylmagnesium chloride was added dropwise to a tetrahydrofuran (2 ml) solution of 2-bromo-3-methoxypyridine (564 mg, 3 mmol) under ice cooling. The resulting mixture was stirred at room temperature for 60 minutes. Under ice cooling, 2,5-difluorobenzaldehyde (328 μl, 3 mmol) was added dropwise to the resulting brown solution. The temperature of the reaction mixture was raised gradually to room temperature. To the reaction mixture was added a saturated aqueous solution of ammonium chloride, followed by extraction with ethyl acetate. The solvent was dried, followed by concentration under reduced pressure to yield needle crystals. The resulting needle crystals were triturated with hexane, whereby the title compound (660 mg, 88%) was obtained.
¹H-NMR (400 MHz, CDCl₃) δ: 3.71(3H,s), 5.56(1H,br, J=6.0 Hz), 6.16(1H,d,J=6.0 Hz), 6.75-7.00(3H,m), 7.14(1H, m), 7.26(1H,m), 8.18(1H,m).
IR (ATR) cm⁻¹: 3384, 1577, 1488, 1284, 810.
mp: 94-95° C.
MS m/z: 252 (M⁺+H).

Referential Example 20

3-Allyloxy-2-[(2,5-difluorophenyl)-hydroxymethyl]pyridine

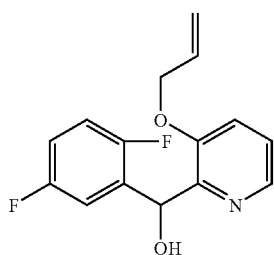

Under an argon atmosphere, a tetrahydrofuran solution (1.5 ml, 3 mmol) of isopropylmagnesium chloride was added dropwise to a tetrahydrofuran (2 ml) solution of 3-allyloxy-2-bromopyridine (642 mg, 3 mmol) under ice cooling. The resulting mixture was stirred at room temperature for 60 minutes. Under ice cooling, 2,5-difluorobenzaldehyde (328 μl, 3 mmol) was added dropwise to the resulting brown solution. The temperature of the reaction mixture was raised gradually to room temperature. A saturated aqueous solution of ammonium chloride was added and then, the mixture was extracted with ethyl acetate. The solvent was dried, followed by concentration under reduced pressure. The residue thus obtained was purified by silica gel chromatography (hexane: ethyl acetate=4:1), whereby the title compound (375 mg, 45%) was obtained as an oil.
¹H-NMR (400 MHz, CDCl₃) δ: 4.38(1H,m), 4.44(1H,m), 5.16(1H,m), 5.18(1H,m), 5.61(1H,br,J=6.4 Hz), 5.78(1H,m), 6.17(1H,d,J=6.0 Hz), 6.73-6.96(3H,m), 7.10(1H,m), 7.22(1H,m), 8.19(1H,m).
IR (ATR) cm⁻¹: 3367, 1575, 1490, 1276, 1180, 795.
MS m/z: 278 (M⁺+H).

Referential Example 21

3-[(2,5-difluorophenyl)-hydroxymethyl]pyridine

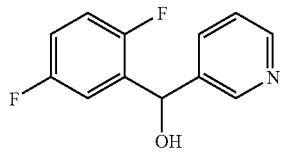

Under an argon atmosphere, a tetrahydrofuran solution (1.5 ml, 3 mmol) of isopropylmagnesium chloride was added dropwise to a tetrahydrofuran (2 ml) solution of 3-bromopyridine (286 μl, 3 mmol) under ice cooling. The resulting mixture was stirred at room temperature for 60 minutes. Under ice cooling, 2,5-difluorobenzaldehyde (328 μl, 3 mmol) was added dropwise to the resulting brown solution. The temperature of the reaction mixture was raised gradually to room temperature. To the reaction mixture was added a saturated aqueous solution of ammonium chloride and then, the mixture was extracted with ethyl acetate. The solvent was dried, followed by concentration under reduced pressure. The residue thus obtained was purified by silica gel chromatography (hexane:ethyl acetate=1:1), whereby the title compound (296 mg, 45%) was obtained as needle crystals.
¹H-NMR (400 MHz, CDCl₃) δ: 3.76(1H,br), 6.10(1H,s), 6.88-6.98(2H,m), 7.20-7.30(2H,m), 7.70(1H,m), 8.42(1H,d, J=4.8 Hz), 8.53(1H,m).
IR (ATR) cm⁻¹: 1486, 1429, 1178, 1130, 739, 707.
mp: 79-80° C.

Referential Example 22

4-[(2,5-Difluorophenyl)-hydroxymethyl]pyridine

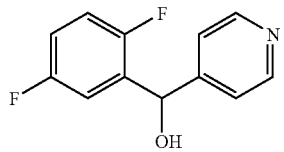

In a similar manner to Referential Example 21 except for the use of 4-bromopyridine, the title compound (79 mg, 8%) was obtained as needle crystals.

¹H-NMR (400 MHz, CDCl₃) δ: 6.08(1H,s), 6.90-7.00(2H, m), 7.15(1H,m), 7.32(1H,dd,J=1.6, 8.4 Hz), 8.48(1H,dd, J=1.6, 8.4 Hz).
IR (ATR) cm⁻¹: 1602, 1489, 1415, 1174, 1049, 711.
mp: 120-121° C.
MS m/z: 221 (M⁺)

Referential Example 23

5-[(2,5-Difluorophenyl)-hydroxymethyl]pyrimidine

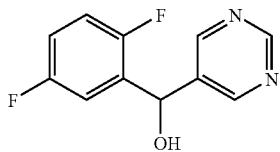

In a similar manner to Referential Example 21 except for the use of 5-bromopyrimidine, the title compound (117 mg, 18%) was obtained as an oil.
¹H-NMR (400 MHz, CDCl₃) δ: 6.12(1H,s), 6.90-7.02(2H, m), 7.26(1H,m), 8.70(2H,s), 9.04(1H,s).
IR (ATR) cm⁻¹: 3219, 1566, 1489, 1408, 1180, 715.
MS m/z: 205 (M⁺—OH)

Example 127

2-[[(4-Chlorophenyl)thio]-(2,5-difluorophenyl)methyl]pyridine

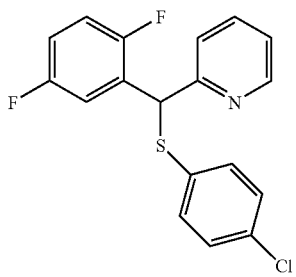

The 2-[(2,5-difluorophenyl)-hydroxymethyl]pyridine (88 mg, 0.40 mmol) obtained in Referential Example 13 was dissolved in thionyl chloride (2.0 ml). To the resulting solution was added a catalytic amount of dimethylformamide, followed by stirring for 15 hours.

The reaction mixture was concentrated under reduced pressure. To the residue was added dioxane and the mixture was concentrated further. The residue was dissolved in dimethylformamide (5 ml), followed by the addition of 4-chlorobenzenethiol (79 mg, 0.55 mmol) and potassium carbonate (226 mg, 1.64 mmol) under a nitrogen atmosphere. The resulting mixture was stirred at 50° C. for 1 hour. After cooling to room temperature, diethyl ether (50 ml) was added to the reaction mixture. The mixture was washed with water and brine. The organic layer was dried over magnesium sulfate and concentrated under reduced pressure. The residue was subjected to silica gel chromatography (hexane:ethyl acetate=10:1), whereby the title compound (128 mg, 92%) was obtained as an oil.

¹H-NMR (400 MHz, CDCl₃) δ: 5.89(1H,s), 6.80-7.27(7H, m), 7.38(1H,d,J=7.6 Hz), 7.48(1H,m), 7.65(1H,m), 8.63(1H, m).
IR (ATR) cm⁻¹: 1585, 1488, 1432, 1093, 810.
MS m/z: 348 (M⁺+H).

Example 128

2-[[(4-Chlorophenyl)thio]-(2,5-difluorophenyl)methyl]-3-methylpyridine

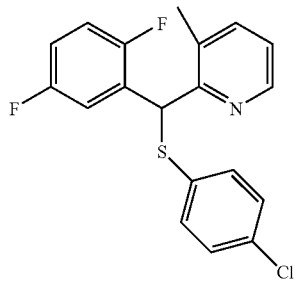

To a dimethylformamide (5 ml) solution of the 2-[chloro-(2,5-difluorophenyl)methyl]-3-methylpyridine hydrochloride (94 mg, 0.32 mmol) obtained in Referential Example 14 were added 4-chlorobenzenethiol (70 mg, 0.49 mmol) and potassium carbonate (265 mg, 1.92 mmol) under a nitrogen atmosphere. The resulting mixture was stirred at 50° C. for 1 hour. After cooling to room temperature, diethyl ether (50 ml) was added to the reaction mixture. The resulting mixture was washed with water and brine. The organic layer was dried over magnesium sulfate and concentrated under reduced pressure. The residue was subjected to silica gel chromatography (hexane:ethyl acetate 10:1), whereby the title compound (103 mg, 89%) was obtained as an oil.
¹H-NMR (400 MHz, CDCl₃) δ: 2.21(3H,s), 5.87(1H,s), 6.77(1H,m), 7.00-7.19(5H,m), 7.36(1H,m), 7.45(1H,m), 8.45(1H,dd,J=1.2, 4.8 Hz).
IR (ATR) cm⁻¹: 1572, 1489, 1093, 810.
MS m/z: 362 (M⁺+H).

Example 129

2-[[(4-Chlorophenyl)thio]-(2,5-difluorophenyl)methyl]-5-methylpyridine

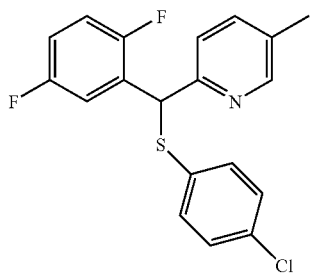

The 2-[(2,5-difluorophenyl)-hydroxymethyl]-5-methylpyridine (125 mg, 0.53 mmol) obtained in Referential Example 15 was dissolved in thionyl chloride (1.0 ml). To the resulting solution was added a catalytic amount of dimethylformamide and the mixture was stirred for 14 hours.

The reaction mixture was concentrated under reduced pressure. Dioxane was added to the residue and the mixture was concentrated further. The resulting residue was dissolved in dimethylformamide (5 ml), followed by the addition of 4-chlorobenzenethiol (115 mg, 0.80 mmol) and potassium carbonate (438 mg, 3.18 mmol) under a nitrogen atmosphere. The mixture was stirred at 50° C. for 1 hour. After cooling to room temperature, diethyl ether (50 ml) was added to the reaction mixture. The mixture was washed with water and brine. The organic layer was dried over magnesium sulfate and concentrated under reduced pressure. The residue was subjected to silica gel chromatography (hexane:ethyl acetate=10:1), whereby the title compound (120 mg, 66%) was obtained as an oil.

$^1$H-NMR (400 MHz, CDCl$_3$) δ: 2.29 (3H,s), 5.83(1H,s), 6.80-6.93(2H,m), 7.16(2H,m), 7.20(2H,m), 7.28(1H,m), 7.43(1H,m), 8.41 (1H,d,J=0.8 Hz).

IR (ATR) cm$^{-1}$: 1475, 1095, 814.

MS m/z: 362 (M$^+$+H).

Example 130

2-[[(4-Chlorophenyl)thio]-(2,5-difluorophenyl)methyl]-4-methylpyridine

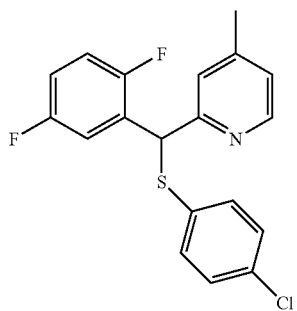

The 2-[(2,5-difluorophenyl)-hydroxymethyl]-4-methylpyridine (235 mg, 0.53 mmol) obtained in Referential Example 16 was dissolved in thionyl chloride (2.0 ml). To the resulting solution was added a catalytic amount of dimethylformamide and the mixture was stirred for 16 hours. The reaction mixture was concentrated under reduced pressure. Dioxane was added to the residue and the mixture was concentrated further.

The residue was dissolved in dimethylformamide (10 ml), followed by the addition of 4-chlorobenzenethiol (217 mg, 1.5 mmol) and potassium carbonate (828 mg, 6.0 mmol) under a nitrogen atmosphere. The mixture was stirred at 50° C. for 1 hour. After cooling to room temperature, diethyl ether (50 ml) was added and the mixture was washed with water and brine. The organic layer was dried over magnesium sulfate and concentrated under reduced pressure. The residue was subjected to silica gel chromatography (hexane:ethyl acetate=10:1), whereby the title compound (290 mg, 80%) was obtained as an oil.

$^1$H-NMR (400 MHz, CDCl$_3$) δ: 2.31(3H,s), 5.82(1H,s), 6.80-7.0(3H,m), 7.15(2H,d,J=8.8 Hz), 7.16(1H,m), 7.21(2H, d,J=8.8 Hz), 7.45(1H,m), 8.45(1H,d,J=5.6 Hz).

IR (ATR) cm$^{-1}$: 1600, 1489, 1475, 1093, 812.

MS m/z: 362 (M$^+$+H).

Example 131

2-[[(4-Chlorophenyl)thio]-(2,5-difluorophenyl)methyl]-3-methoxypyridine

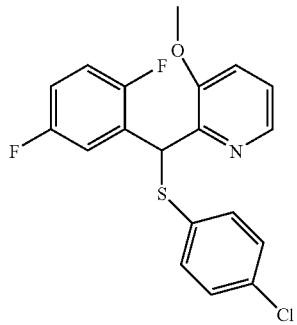

The 2-[(2,5-difluorophenyl)-hydroxymethyl]-3-methoxypyridine (251 mg, 1.0 mmol) obtained in Referential Example 19 was dissolved in thionyl chloride (2.0 ml). To the resulting solution was added a catalytic amount of dimethylformamide and the mixture was stirred for 16 hours.

The reaction mixture was concentrated under reduced pressure. Dioxane was added to the residue and the mixture was concentrated further.

The residue was dissolved in dimethylformamide (10 ml), followed by the addition of 4-chlorobenzenethiol (289 mg, 2.0 mmol) and potassium carbonate (1.10 g, 8.0 mmol) under a nitrogen atmosphere. The resulting mixture was stirred at 50° C. for 1 hour. After cooling to room temperature, diethyl ether (50 ml) was added, and the mixture was washed with water and brine. The organic layer was dried over magnesium sulfate and concentrated under reduced pressure. The residue was subjected to silica gel chromatography (hexane:ethyl acetate=10:1), whereby the title compound (256 mg, 58%) was obtained as an oil.

$^1$H-NMR (400 MHz, CDCl$_3$) δ: 3.77(3H,s), 6.25(1H,s), 6.82 (2H,m), 7.15(2H,d,J=8.4 Hz), 7.10-7.20(2H,m), 7.25 (2H,d,J=8.8 Hz), 7.52(1H,m), 8.24(1H,m).

IR (ATR) cm$^{-1}$: 1489, 1423, 1273, 1091, 831.

MS m/z: 378 (M$^+$+H).

Example 132

3-Allyloxy-2-[[(4-chlorophenyl)thio]-(2,5-difluorophenyl)methyl]pyridine

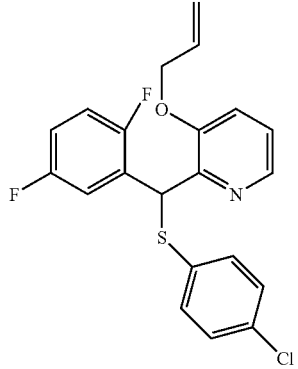

The 3-allyloxy-2-[(2,5-difluorophenyl)-hydroxymethyl] pyridine (370 mg, 1.33 mmol) obtained in Referential Example 20 was dissolved in thionyl chloride (2.0 ml). To the resulting solution was added a catalytic amount of dimethylformamide and the mixture was stirred for 16 hours.

The reaction mixture was concentrated under reduced pressure. Dioxane was added to the residue and the mixture was concentrated further.

The residue was dissolved in dimethylformamide (10 ml), followed by the addition of 4-chlorobenzenethiol (217 mg, 1.5 mmol) and potassium carbonate (828 mg, 6.0 mmol) under a nitrogen atmosphere. The mixture was stirred at 50° C. for 1 hour. After cooling to room temperature, diethyl ether (50 ml) was added, and the mixture was washed with water and brine. The organic layer was dried over magnesium sulfate and concentrated under reduced pressure. The residue was subjected to silica gel chromatography (hexane:ethyl acetate=10:1), whereby the title compound (256 mg, 68%) was obtained as an oil.

$^1$H-NMR (400 MHz, CDCl$_3$) δ: 4.46(2H,m), 5.24(1H,d, J=10.6 Hz), 5.28(1H,d,J=17.2 Hz), 5.90(1H,m), 6.29(1H,d, J=1.2 Hz), 6.82(2H,m), 7.15(2H,d,J=8.4 Hz), 7.06-7.20(2H, m), 7.24(2H,d,J=8.4 Hz), 7.50(1H,m), 8.24(1H,m).

IR (ATR) cm$^{-1}$: 1572, 1489, 1438, 1276, 1093, 814.

MS m/z: 404 (M$^+$+H).

Example 133

3-[[(4-Chlorophenyl)thio]-(2,5-difluorophenyl)methyl]pyridine

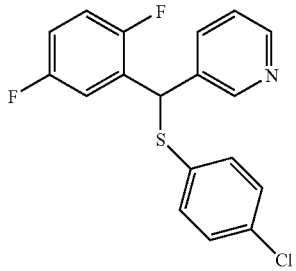

The 3-[(2,5-difluorophenyl)-hydroxymethyl]pyridine (87 mg, 0.39 mmol) obtained in Referential Example 21 was dissolved in thionyl chloride (1.0 ml). To the resulting solution was added a catalytic amount of dimethylformamide and the mixture was stirred for 14 hours.

The reaction mixture was concentrated under reduced pressure. Dioxane was added to the residue and the mixture was concentrated further.

The residue thus obtained was dissolved in dimethylformamide (5 ml), followed by the addition of 4-chlorobenzenethiol (84 mg, 0.58 mmol) and potassium carbonate (323 mg, 2.34 mmol) under a nitrogen atmosphere. The mixture was stirred at 50° C. for 1 hour. After cooling to room temperature, diethyl ether (50 ml) was added, and the mixture was washed with water and brine. The organic layer was dried over magnesium sulfate and concentrated under reduced pressure. The residue was subjected to silica gel chromatography (hexane:ethyl acetate=1:1), whereby the title compound (131 mg, 96%) was obtained as an oil.

$^1$H-NMR (400 MHz,CDCl$_3$) δ: 5.73(1H,s), 6.84-6.96(2H, m), 7.18(2H,m), 7.19(2H,m), 7.15-7.22(2H,m), 7.71(1H,m), 8.49(1H,dd,J=1.6, 4.8 Hz), 8.58(1H,d,J=2.0 Hz).

IR (ATR) cm$^{-1}$: 1489, 1093, 814, 710.

MS m/z: 348 (M$^+$+H).

Example 134

5-[[(4-Chlorophenyl)thio]-(2,5-difluorophenyl)methyl]pyrimidine

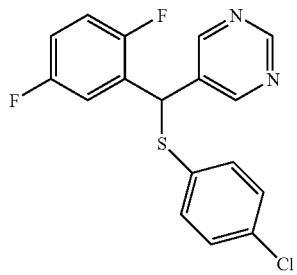

The 5-[(2,5-difluorophenyl)-hydroxymethyl]pyrimidine (111 mg, 0.5 mmol) obtained in Referential Example 23 was dissolved in thionyl chloride (1.0 ml). To the resulting solution was added a catalytic amount of dimethylformamide and the mixture was stirred for 16 hours.

The reaction mixture was concentrated under reduced pressure. Dioxane was added to the residue and the mixture was concentrated further.

The residue was dissolved in dimethylformamide (5 ml), followed by the addition of 4-chlorobenzenethiol (108 mg, 0.75 mmol) and potassium carbonate (414 mg, 3.0 mmol) under a nitrogen atmosphere. The mixture was stirred at 50° C. for 1 hour. After cooling to room temperature, diethyl ether (50 ml) was added, and the mixture was washed with water and brine. The organic layer was dried over magnesium sulfate and concentrated under reduced pressure. The residue was subjected to silica gel chromatography (hexane:ethyl acetate=4:1), whereby a mixture (202 mg) of the title compound and an unidentified compound was obtained as an oil.

$^1$H-NMR (400 MHz, CDCl$_3$) δ: 5.66(1H,s), 6.96(2H,m), 7.17-7.34(5H,d), 8.70(2H,s), 9.09(1H,s).

MS m/z: 349 (M$^+$+H).

Example 135

2-[[(4-Chlorophenyl)sulfonyl]-(2,5-difluorophenyl) methyl]pyridine

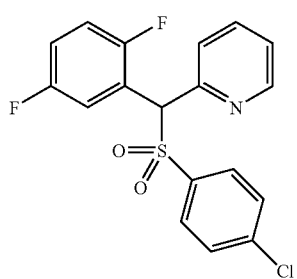

To a methanol (12 ml) solution of the 2-[[(4-chlorophenyl) thio]-(2,5-difluorophenyl)methyl]pyridine (120 mg, 0.345 mmol) obtained in Example 127 was added hexaammonium heptamolybdate tetrahydrate (80 mg), followed by the addition of 30% aqueous hydrogen peroxide (6 ml). The resulting mixture was stirred for 24 hours. The precipitate thus obtained was collected by filtration and recrystallized from ethanol, whereby the title compound (96 mg, 73%) was obtained as colorless needle crystals.

¹H-NMR (400 MHz, CDCl₃) δ: 5.93(1H,s), 6.87-7.00(2H,m), 7.28(1H,m), 7.37(2H,d,J=8.8 Hz), 7.53(2H,d,J=8.8 Hz), 7.60(1H,d,J=8.0 Hz), 7.71(1H,m), 8.00(1H,m), 8.59(1H,m).
IR (ATR) cm⁻¹: 1585, 1484, 1434, 1321, 1147, 817.
mp: 171-172° C.
MS m/z: 380 (M⁺+H).
Anal. calcd for $C_{18}H_{12}ClF_2NO_2S$: C 56.92%; H 3.18%; N 3.69%; S 8.44%; Cl 9.33%; F 10.00%. Found: C 56.76%; H 3.19%; N 3.77%; S 8.55%; Cl 9.27%; F 10.02%.
Fab-MS: 380.0309 (Calcd for $C_{18}H_{13}ClF_2NO_2S$: 380.0324).

Example 136

2-[[(4-Chlorophenyl)sulfonyl]-(2,5-difluorophenyl)methyl]-3-methylpyridine

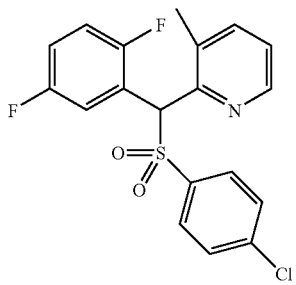

In a similar manner to Example 135, the title compound (35 mg, 35%) was obtained as colorless needle crystals by using the 2-[[(4-chlorophenyl)thio]-(2,5-difluorophenyl)methyl]-3-methylpyridine obtained in Example 128 and purifying by silica gel chromatography (hexane:ethyl acetate=5:1).
¹H-NMR (400 MHz, CDCl₃) δ: 2.36(3H,s), 6.18(1H,s), 6.89-7.02(2H,m), 7.17(1H,m), 7.37(2H,d,J=8.4 Hz), 7.46 (1H,d,J=7.2 Hz), 7.53(2H,d,J=8.4 Hz), 8.06(1H,m), 8.53 (1H,d, J=4.0 Hz).
IR (ATR) cm⁻¹: 1571, 1477, 1321, 1151, 1080, 816.
mp: 142-143° C.
MS m/z: 394 (M⁺+H).
Anal. calcd for $C_{19}H_{14}ClF_2NO_2S$: C 57.94%; H 3.58%; N 3.56%; S 8.12%; Cl 9.00%; F 9.65%. Found: C 58.03%; H 3.66%; N 3.78%; S 8.12%; Cl 9.13%; F 9.59%.

Example 137

2-[[(4-Chlorophenyl)sulfonyl]-(2,5-difluorophenyl)methyl]-5-methylpyridine

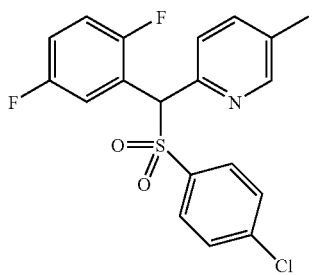

In a similar manner to Example 135 except for the use of the 2-[[(4-chlorophenyl)thio]-(2,5-difluorophenyl)methyl]-5-methylpyridine obtained in Example 129, the title compound (91 mg, 73%) was obtained as colorless needle crystals.

¹H-NMR (400 MHz, CDCl₃) δ: 2.33(3H,s), 5.89(1H,s), 6.88-7.01(2H,m), 7.37(2H,d,J=8.8 Hz), 7.48-7.56(2H,m), 7.53(2H,d,J=8.8 Hz), 7.99(1H,m), 8.42(1H,s).
IR (ATR) cm⁻¹: 1574, 1477, 1319, 1147, 1093, 822.
mp: 159-160° C.
MS m/z: 394(M⁺+H).
Anal. calcd for $C_{19}H_{14}ClF_2NO_2S$: C 57.94%; H 3.58%; N 3.56%; S 8.12%; Cl 9.00%; F 9.56%. Found: C 57.88%; H 3.61%; N 3.68%; S 8.27%; Cl 9.11%; F 9.70%.

Example 138

2-[[(4-Chlorophenyl)sulfonyl]-(2,5-difluorophenyl)methyl]-4-methylpyridine

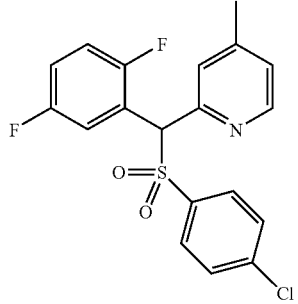

In a similar manner to Example 135, the title compound (140 mg, 95%) was obtained as colorless needle crystals by using the 2-[[(4-chlorophenyl)thio]-(2,5-difluorophenyl)methyl]-4-methylpyridine obtained in Example 130 and purifying by silica gel chromatography (hexane:ethyl acetate=3:1).
¹H-NMR (400 MHz, CDCl₃) δ: 2.36(3H,s), 5.88(1H,s), 6.88-7.02(2H,m), 7.09(1H,d,J=5.2 Hz), 7.37(2H,d,J=8.8 Hz), 7.41(1H,m), 7.52(2H,d,J=8.8 Hz), 7.97(1H,m), 8.43 (1H,d,J=5.2 Hz).
IR (ATR) cm⁻¹: 1600, 1484, 1322, 1149, 1080, 827.
mp: 116-117° C.
MS m/z: 394(M⁺+H).
Anal. calcd for $C_{19}H_{14}ClF_2NO_2S$: C 57.94%; H 3.5.8%; N 3.56%; S 8.12%; Cl 9.00%; F 9.65%. Found: C 57.80%; H 3.66%; N 3.72%; S 8.29%; Cl 9.05%; F 9.71%.

Example 139

2-[[(4-Chlorophenyl)sulfonyl]-(2,5-difluorophenyl)methyl]-3-methoxypyridine

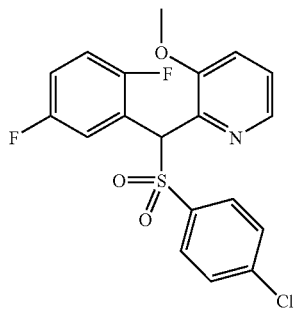

In a similar manner to Example 135, the title compound (71 mg, 87%) was obtained as colorless columnar crystals by using the 2-[[(4-chlorophenyl)thio]-(2,5-difluorophenyl)methyl]-3-methoxypyridine obtained in Example 131 and recrystallizing from ethanol.

$^1$H-NMR (400 MHz, CDCl$_3$) δ: 3.72(3H,s), 6.62(1H,s), 6.90-7.04(2H,m), 7.09(1H,m), 7.24(1H,m), 7.35(2H,d,J=8.8 Hz), 7.53(2H,d,J=8.8 Hz), 8.18(1H,m), 8.30(1H,m).

IR (ATR) cm$^{-1}$: 1576, 1491, 1429, 1323, 1281, 1147, 796.
mp: 184-185° C.
MS m/z: 410 (M$^+$+H).
Anal. calcd for C$_{19}$H$_{14}$ClF$_2$NO$_3$S: C 55.68%; H 3.44%; N 3.42%; S 7.82%; Cl 8.65%; F 9.27%. Found: C 55.68%; H 3.45%; N 3.60%; S 7.98%; Cl 8.74%; F 9.23%.

Example 140

3-Allyloxy-2-[[(4-chlorophenyl)sulfonyl]-(2,5-difluorophenyl)methyl]pyridine

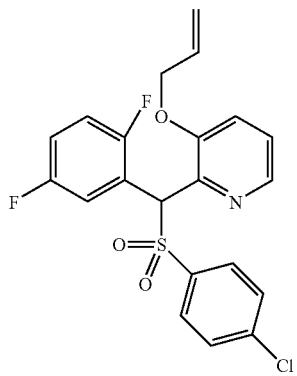

In a similar manner to Example 135, the title compound (135 mg, 80%) was obtained as colorless needle crystals by synthesizing using the 3-allyloxy-2-[[(4-chlorophenyl)thio]-(2,5-difluorophenyl)methyl]pyridine obtained in Example 132 and crystallizing from ethanol.

$^1$H-NMR (400 MHz, CDCl$_3$) δ: 4.38(1H,m), 4.46(1H,m), 5.29(1H,dd,J=1.2, 10.4 Hz), 5.35(1H,dd,J=1.2, 17.2 Hz), 5.93(1H,m), 6.68(1H,s), 6.91-7.04(2H,m), 7.08(1H,m), 7.22 (1H,dd,J=4.8, 8.4 Hz), 7.34(2H,d,J=8.8 Hz), 7.53(2H,d, J=8.8 Hz), 8.17(1H,m), 8.31(1H,m).

IR (ATR) cm$^{-1}$: 1577, 1493, 1319, 1151, 822.
mp: 119-120° C.
MS m/z: 436(M$^+$+H).
Anal. calcd for C$_{21}$H$_{16}$ClF$_2$NO$_3$S: C 57.87%; H 3.70%; N 3.21%; S 7.36%; Cl 8.13%; F 8.72%. Found: C 57.90%; H 3.75%; N 3.37%; S 7.51%; Cl 8.20%; F 8.73%.

Example 141

3-[[(4-Chlorophenyl)sulfonyl]-(2,5-difluorophenyl)methyl]pyridine

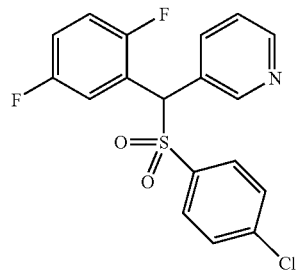

In a similar manner to Example 135, the title compound (118 mg, 86%) was obtained as colorless needle crystals by synthesizing using the 3-[[(4-chlorophenyl)thio]-(2,5-difluorophenyl)methyl]pyridine obtained in Example 133 and purifying through silica gel chromatography (hexane:ethyl acetate=4:1).

$^1$H-NMR (400 MHz, CDCl$_3$) δ: 5.68(1H,s), 6.91-7.07(2H, m), 7.34(1H,m), 7.40(2H,d,J=8.4 Hz), 7.57(2H,d,J=8.4 Hz), 7.76(1H,m), 8.04(1H,m), 8.53(1H,d,J=2.0 Hz), 8.59(1H,m).

IR (ATR) cm$^{-1}$: 1574, 1491, 1421, 1327, 1144, 816.
mp: 130-131° C.
MS m/z: 380(M$^+$+H).
Anal. calcd for C$_{18}$H$_{12}$ClF$_2$NO$_2$S: C 56.92%; H 3.18%; N 3.69%; S 8.44%; Cl 9.33%; F 10.00%. Found: C 56.87%; H 3.16%; N 3.74%; S 8.51%; Cl 9.34%; F 10.00%.

Example 142

4-[[(4-Chlorophenyl)sulfonyl]-(2,5-difluorophenyl)methyl]pyridine

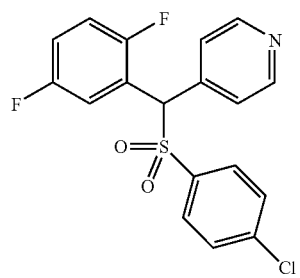

The 4-[(2,5-difluorophenyl)-hydroxymethyl]pyridine (75 mg, 0.34 mmol) obtained in Referential Example 22 was dissolved in thionyl chloride (1.0 ml). To the resulting solution was added a catalytic amount of dimethylformamide. The resulting mixture was stirred for 14 hours.

The reaction mixture was concentrated under reduced pressure. Dioxane was added to the residue and the mixture was concentrated further.

The residue was dissolved in dimethylformamide (5 ml), followed by the addition of 4-chlorobenzenethiol (74 mg, 0.51 mmol) and potassium carbonate (281 mg, 2.04 mmol) under a nitrogen atmosphere. The mixture was stirred at 50° C. for 1 hour. After cooling to room temperature, diethyl ether (50 ml) was added, and the mixture was washed with water and brine. The organic layer was dried over magnesium sulfate and concentrated under reduced pressure. The residue was subjected to silica gel chromatography (hexane:ethyl acetate=1:1), whereby a mixture containing 4-[(4-chlorophenyl)thio]-(2,5-diflurophenyl)]pyridine was obtained.

To a methanol (12 ml) solution of the resulting compound was added hexaammonium heptamolybdate tetrahydrate (60 mg), followed by the addition of 30% aqueous hydrogen peroxide (6 ml). The resulting mixture was stirred for 65 hours. Ethyl acetate (80 ml) was added to the reaction mixture. The mixture was washed with water and brine, and then dried over anhydrous magnesium sulfate. The mixture was concentrated under reduced pressure to remove the solvent. The residue was purified by silica gel chromatography (hexane:ethyl acetate=4:1-1:1), whereby the title compound (51 mg, 39%) was obtained. The compound was recrystallized from ethanol to give colorless needle crystals.

$^1$H-NMR (400 MHz, CDCl$_3$) δ: 5.64(1H,s), 6.91-7.06(2H, m), 7.40(2H,d,J=8.0 Hz), 7.45(2H,d,J=4.8 Hz), 7.58(2H,d, J=8.0 Hz), 7.70(1H,s), 8.61(2H,d,J=4.8 Hz).

IR (ATR) cm$^{-1}$: 1595, 1493, 1315, 1147, 1082, 823.

mp: 126-127° C.

MS m/z: 380 (M$^+$+H).

Anal. calcd for C$_{18}$H$_{12}$ClF$_2$NO$_2$S: C 56.92%; H 3.18%; N 3.69%; S 8.44%; Cl 9.33%; F 10.00%. Found: C 56.66%; H 3.16%; N 3.83%; S 8.58%; Cl 9.32%; F 9.99%.

Example 143

2-[[(4-Chlorophenyl)sulfonyl]-(2,5-difluorophenyl)methyl]pyrimidine

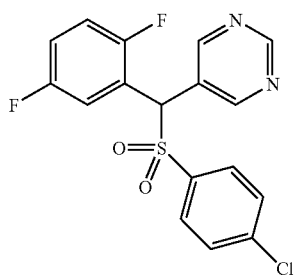

In a similar manner to Example 135, the title compound (71 mg, 87%, yield: two steps from the 5-[(2,5-difluorophenyl)-hydroxymethyl]pyrimidine of Referential Example 23) was obtained as colorless columnar crystals by using the 2-[[(4-chlorophenyl)thio]-(2,5-difluorophenyl)methyl]pyrimidine obtained in Example 134, and purifying through silica gel chromatography (hexane:ethyl acetate=5:1).

$^1$H-NMR (400 MHz, CDCl$_3$) δ: 5.65(1H,s), 6.93-7.10(2H, m), 7.43(2H,d,J=8.8 Hz), 7.61(2H,d,J=8.8 Hz), 7.73(1H,m), 8.90(2H,s), 9.21(1H,s).

IR (ATR) cm$^{-1}$: 1560, 1490, 1141, 1080, 825.

mp: 136-137° C.

MS m/z: 381 (M$^+$+H).

Anal. calcd for C$_{17}$H$_{11}$ClF$_2$N$_2$O$_2$S: C 53.62%; H 2.91%; N 7.36%; S 8.42%; Cl 9.31%; F 9.98%. Found: C 53.64%; H 2.83%; N 7.44%; S 8.61%; Cl 9.34%; F 9.96%.

Example 144

3-[[(4-Chlorophenyl)thio]-(2,5-difluorophenyl)methyl]-4-hydroxychromen-2-one

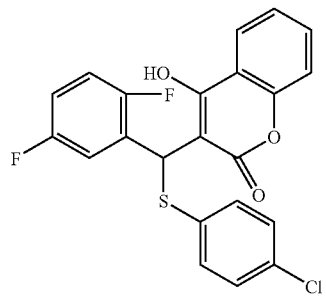

At room temperature, glacial acetic acid (60 mg, 1 mmol) and pyridine (80.5 µl, 1 mmol) were added to an ethanol (4 ml) solution of 2,5-difluorobenzaldehyde (109 µl, 1 mmol), 4-hydroxycoumarin (162 mg, 1 mmol) and 4-chlorothiophenol (144.6 mg, 1 mmol) and the mixture was stirred for 24 hours. The precipitate thus formed was collected by filtration and washed with a small amount of ethanol, whereby the title compound (345 mg, 80%) was obtained as a white solid.

$^1$H-NMR (400 MHz, CDCl$_3$) δ: 6.16(1H,s), 6.95-7.12(3H, m), 7.24-7.27(1H,m), 7.27(2H,d,J=8.8 Hz), 7.32(1H,t,J=7.6 Hz), 7.43(2H, d,J=8.8 Hz), 7.56(1H,m), 7.94(1H,dd,J=1.6, 7.6 Hz).

IR (ATR) cm$^{-1}$: 1668, 1620, 1481, 1194, 818.

mp: 146-147° C.

MS m/z: 431 (M$^+$+H).

Example 145

3-[[(4-Chlorophenyl)sulfonyl]-(2,5-difluorophenyl)methyl]-4-methoxychromen-2-one (Compound A) and 3-[[(4-chlorophenyl)sulfonyl]-(2,5-difluorophenyl)methyl]-2-methoxychromen-4-one (Compound B)

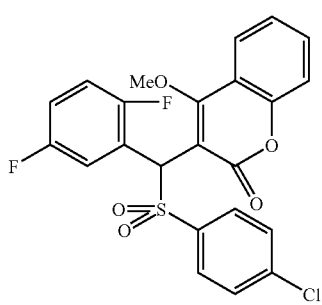

Compound A

-continued

Compound B

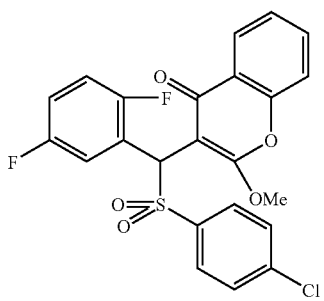

To a benzene-methanol (10:1) solution of 3-[[(4-chlorophenyl)thio]-(2,5-difluorophenyl)methyl]-4-hydroxychromen-2-one (118 mg, 0.274 mmol) was added a hexane solution (0.41 ml, 0.822 mmol) of 2N trimethylsilyldiazomethane in portions at room temperature and the mixture was stirred for 5 minutes. Acetic acid was added to the reaction mixture until the solution became colorless. The reaction mixture was then concentrated under reduced pressure.

The residue was dissolved in methanol (12 ml), followed by the addition of 30% aqueous hydrogen peroxide (6 ml) and hexaammonium heptamolybdate tetrahydrate (60 mg). The resulting mixture was stirred for 20 hours. Ethyl acetate (50 ml) was added to the reaction mixture. The mixture was washed with water and brine, dried over anhydrous magnesium sulfate, and concentrated under reduced pressure. The residue was purified by silica gel chromatography (hexane: ethyl acetate=5:1-3:1) to yield a non polar compound (22 mg, 17%) as needle crystals, and a polar compound (9.0 mg, 7%) as a white solid after solidification with hexane. As a result of the NOE (Nuclear Overhauser effect) test, in the nonpolar compound, NOE was observed between the methoxy and the 5-hydrogen of chromenone. In the polar compound, on the other hand, NOE was not observed between the methoxy and the hydrogen on the aromatic ring of the chromenone, but was observed between the methoxy and the 6-hydrogen on the difluorobenzene ring. The structures of the nonpolar compound and the polar compound were therefore determined as 3-[[(4-chlorophenyl)sulfonyl]-(2,5-difluorophenyl)methyl]-4-methoxychromen-2-one (Compound A) and 3-[[(4-chlorophenyl)sulfonyl]-(2,5-difluorophenyl)methyl]-2-methoxychromen-4-one (Compound B), respectively.

Compound A $^1$H-NMR (400 MHz, CDCl$_3$) δ: 4.13(3H,s), 6.39(1H,s), 6.88(1H,m), 6.98(1H,m), 7.3-7.4(2H,m), 7.43(2H,d,J=8.8 Hz), 7.58(1H,m), 7.70(2H,d,J=8.8 Hz), 7.73(1H,m), 8.09(1H,m).

IR (ATR) cm$^{-1}$: 1726, 1606, 1493, 1360, 1184, 1085, 768.

mp: 178-179° C.

MS m/z: 477 (M$^+$+H).

Anal. calcd for C$_{23}$H$_{15}$ClF$_2$O$_3$S: C 57.93%; H 3.17%; S 6.72%; Cl 7.43%; F 7.97%. Found: C 57.59%; H 3.14%; S 6.85%; Cl 7.52%; F 8.01%.

FAB-MS: 477.0393 (Calcd for C$_{23}$H$_{16}$ClF$_2$O$_5$S: 477.0375).

Compound B $^1$H-NMR (400 MHz, CDCl$_3$) δ: 4.23(3H,s), 6.54(1H,s), 6.89(1H,m), 6.96(1H,m), 7.41(2H,d,J=8.4 Hz), 7.4-7.46(2H, m), 7.63(1H,m), 7.73(2H,d,J=8.4 Hz), 8.02(1H,m), 8.14(1H, dd,J=1.6, 8.0 Hz).

IR (ATR) cm$^{-1}$: 1621, 1565, 1461, 1384, 1141, 980.

mp: 162-163° C.

MS m/z: 477 (M$^+$+H).

FAB-MS: 477.0366 (Calcd for C$_{23}$H$_{16}$ClF$_2$O$_5$S: 477.0375).

Referential Example 24

2-[(tert-Butoxycarbonyloxy)-(2,5-difluorophenyl) methyl]-1-methyl-1H-benzimidazole

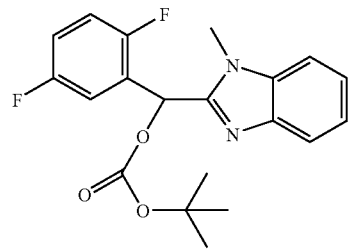

An acetonitrile (3 ml) solution of 2,5-difluorobenzaldehyde (164 μl, 1.5 mmol), 1-methylbenzimidazole (132 mg, 1 mmol), di-tert-butyl dicarbonate (252 μl, 1.1 mmol) was stirred at room temperature for 20 hours. The precipitate thus formed was collected by filtration, and triturated with hexane, whereby the title compound (310 mg, 83%) was obtained as a white solid.

$^1$H-NMR (400 MHz, CDCl$_3$) δ: 1.45(9H,s), 3.86(3H,s), 6.9-7.0(2H,m), 7.12(1H,s), 7.22-7.35(3H,m), 7.45(1H,m), 7.77(1H, d,J=8.0 Hz).

IR (ATR) cm$^{-1}$: 1733, 1492, 1270, 1257, 1137, 852.

mp: 163-164° C.

MS m/z: 375 (M$^+$+H).

Referential Example 25

2-[(tert-Butoxycarbonyloxy)-(2,5-difluorophenyl) methyl]-1-methyl-5-chloro-1H-benzimidazole

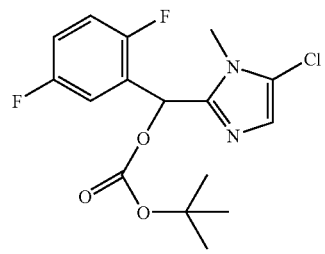

An acetonitrile (6 ml) solution of 2,5-difluorobenzaldehyde (327 μl, 3 mmol), 5-chloro-1-methylimidazole (187 μg, 2 mmol), and di-tert-butyl dicarbonate (504 μl, 2.2 mmol) was stirred at room temperature for 20 hours. The precipitate thus formed was collected by filtration and triturated with hexane, whereby the title compound (472 mg, 66%) was obtained as a white solid.

$^1$H-NMR (400 MHz, CDCl$_3$) δ: 1.48(9H,s), 3.67(3H,s), 6.88-7.1(4H,m), 7.39(1H,m).

IR (ATR) cm$^{-1}$: 1739, 1496, 1257, 1149, 1080, 858.

mp: 125-126° C.

MS m/z: 359 (M$^+$+H).

147

Referential Example 26

2-[(2,5-Difluorophenyl)-hydroxymethyl]thiazole

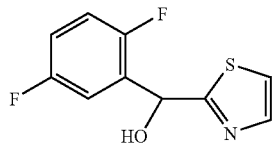

To a tetrahydrofuran (10 ml) solution of 2-bromothiazole (180 μg, 2 mmol) was added dropwise a hexane solution of n-butyl lithium (1.57M, 1.40 ml, 2.2 mmol) at −78° C. After stirring for 10 minutes, 2,5-difluorobenzaldehyde (238 μl, 2.2 mmol) was added and while stirring, the temperature of the mixture was gradually raised to 0° C. The reaction was then quenched by the addition of an aqueous solution of ammonium chloride, followed by the addition of ether. The ether layer was washed with water and brine, and then, dried over anhydrous magnesium sulfate. After filtration, the filtrate was concentrated under reduced pressure. The residue was purified by silica gel chromatography (hexane:ethyl acetate=1:1), whereby the title compound (358 mg, 79%) was obtained as an oil.

$^1$H-NMR (400 MHz, CDCl$_3$) δ: 3.77(1H, d, J=4.0 Hz), 6.33(1H, d,J=4.0 Hz), 6.95-7.10(2H,m), 7.24 (1H,m), 7.34 (1H, d,J=3.6Hz), 7.75(1H, d,J=3.6Hz).

IR (ATR) cm$^{-1}$: 3224, 1489, 1238, 1172, 1128, 818.

MS m/z: 228 (M$^+$+H).

Referential Example 27

2-[(tert-Butoxycarbonyloxy)-(2,5-difluorophenyl)methyl]-1-(4-methoxyphenyl)-1H-benzimidazole

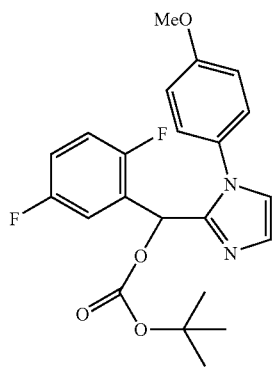

148

An acetonitrile (6 ml) solution of 2,5-difluorobenzaldehyde (327 μl, 3 mmol), 1-(4-methoxyphenyl)imidazole (348 mg, 2 mmol) and di-tert-butyl dicarbonate (504 μl, 2.2 mmol) was stirred at room temperature for 20 hours. The reaction mixture was concentrated and then, the residue was purified by silica gel chromatography (hexane:ethyl acetate=5:1-1:1), whereby the title compound (774 mg, 93%) was obtained as an oil.

$^1$H-NMR (400 MHz, CDCl$_3$) δ: 1.40(9H,s), 3.86(3H,s), 6.76(1H,s), 6.90-7.00(4H,m), 7.02(1H,s), 7.11(1H,s), 7.26 (2H,m), 7.33(1H,m).

IR (ATR) cm$^{-1}$: 1741, 1513, 1494, 1243, 1155, 858, 835.

MS m/z: 417 (M$^+$+H).

Example 146

2-[[(4-Chlorophenyl)thio]-(2,5-difluorophenyl)methyl]-1-methyl-1H-benzimidazole

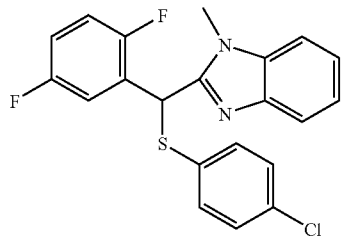

Trifluoroacetic acid (2.0 ml) was added to the 2-[(tert-butoxycarbonyloxy)-(2,5-difluorophenyl)methyl]-1-methyl-1H-benzimidazole (204 mg, 0.545 mmol) obtained in Referential Example 24 and the mixture was stirred at room temperature for 30 minutes. The reaction mixture was concentrated under reduced pressure. Dioxane was added to the residue, followed by concentration under reduced pressure.

The residue was dissolved in thionyl chloride (1.0 ml). To the resulting solution was added a drop of dimethylformamide and the mixture was stirred at room temperature for 16 hours. The reaction mixture was concentrated under reduced pressure. Dioxane was added to the residue, followed by concentration under reduced pressure.

The residue was dissolved in dimethylformamide (5.0 ml). To the resulting solution were added 4-chlorobenzenethiol (118 mg, 0.82 mmol) and potassium carbonate (451 mg, 3.27 mmol) and the mixture was stirred at 50° C. for 2 hours. The reaction mixture was allowed to stand until it became room temperature. Then, ethyl ether (60 ml) was added to the reaction mixture. The mixture was washed with water and brine, dried over anhydrous magnesium sulfate and concentrated under reduced pressure. The residue was purified by silica gel chromatography (hexane:ethyl acetate=10:1-5:1), whereby the title compound (195 mg, 89%) was obtained as a colorless oil.

$^1$H-NMR (400 MHz, CDCl$_3$) δ: 3.67(3H,s), 5.91(1H,s), 6.87-6.93 (2H,m), 7.19(2H,d,J=8.8 Hz), 7.27(2H,d,J=8.8 Hz), 7.25-7.33(3H,m), 7.60(1H,m), 7.85(1H,m).

IR (ATR) cm$^{-1}$: 1492, 1388, 1238, 193, 820.

MS m/z: 401 (M$^+$+H).

Example 147

2-[[(4-Chlorophenyl)thio]-(2,5-difluorophenyl)methyl]-1-methyl-5-chloro-1H-imidazole

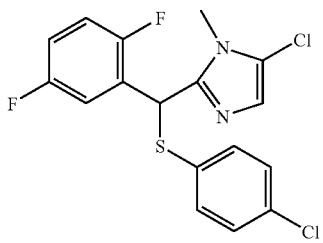

Trifluoroacetic acid (10 ml) was added to the 2-[(tert-butoxycarbonyloxy)-(2,5-difluorophenyl)methyl]-1-methyl-5-chloro-1H-imidazole (404 mg, 1.13 mmol) obtained in Referential Example 25 and the mixture was stirred at room temperature for 3 hours. The reaction mixture was concentrated under reduced pressure. Dioxane was added to the residue, followed by concentration under reduced pressure.

The residue was dissolved in thionyl chloride (2.0 ml). To the resulting solution was added a drop of dimethylformamide and the mixture was stirred at room temperature for 17 hours. The reaction mixture was concentrated under reduced pressure. Dioxane was added to the residue, followed by concentration under reduced pressure.

The residue was dissolved in dimethylformamide (5.0 ml). To the resulting solution were added 4-chlorobenzenethiol (244 mg, 1.69 mmol) and potassium carbonate (936 mg, 6.78 mmol). The mixture was stirred at 50° C. for 2 hours. After the reaction mixture was allowed to stand until it became room temperature, ethyl ether (60 ml) was added thereto. The mixture was washed with water and brine, dried over anhydrous magnesium sulfate and concentrated under reduced pressure. The residue was purified by silica gel chromatography (hexane:ethyl acetate=10:1-5:1), whereby the title compound (195 mg, 89%) was obtained as a colorless oil.

$^1$H-NMR (400 MHz, CDCl$_3$) δ: 3.57(3H,s), 5.67(1H,s), 6.89-6.95(2H,m), 6.97(1H,s), 7.20(2H,d,J=8.4 Hz), 7.21(2H, d, J=8.4 Hz), 7.54(1H,m).

IR (ATR) cm$^{-1}$: 1490, 1473, 1162, 1012, 821, 806.
MS m/z: 386 (M$^+$+H).

Example 148

2-[[(4-Chlorophenyl)thio]-(2,5-difluorophenyl)methyl]thiazole

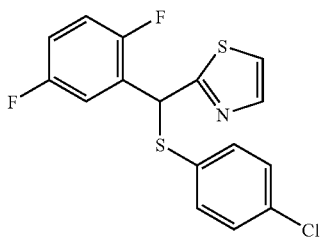

In thionyl chloride (1.5 ml) was dissolved the 2-[(2,5-difluorophenyl)-hydroxymethyl]thiazole (348 mg, 1.53 mmol) obtained in Referential Example 26. To the resulting solution was added a drop of dimethylformamide and the mixture was stirred at room temperature for 14 hours. The reaction mixture was concentrated under reduced pressure. Dioxane was added to the residue, followed by concentration under reduced pressure.

The residue was dissolved in dimethylformamide (10.0 ml). To the resulting solution were added 4-chlorobenzenethiol (332 mg, 2.3 mmol) and potassium carbonate (845 mg, 6.12 mmol) and the mixture was stirred at 50° C. for 2 hours. After the reaction mixture was allowed to stand until it became room temperature, ethyl ether (60 ml) was added thereto. The mixture was washed with water and brine, dried over anhydrous magnesium sulfate and concentrated under reduced pressure. The residue was purified by silica gel chromatography (hexane:ethyl acetate=10:1-6:1), whereby the title compound (130 mg, 24%) was obtained as a colorless oil.

$^1$H-NMR (400 MHz, CDCl$_3$) δ: 6.04(1H,s), 6.90-7.06(2H, m), 7.22(2H,d,J=8.4 Hz), 7.30(2H,d,J=8.4 Hz), 7.15-7.35 (2H,m), 7.76(1H,d,J=3.2 Hz).

IR (ATR) cm$^{-1}$: 1489, 1475, 1093, 1012, 817, 725.
MS m/z: 354 (M$^+$+H).

Example 149

2-[[(4-Chlorophenyl)thio]-(2,5-difluorophenyl)methyl]-1-(4-methoxyphenyl)-1H-imidazole

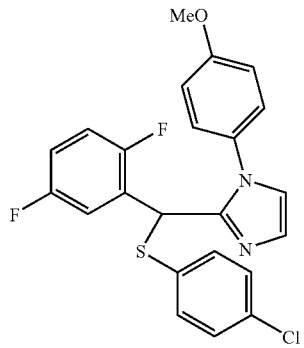

Trifluoroacetic acid (10 ml) was added to the 2-[(tert-butoxycarbonyloxy)-(2,5-difluorophenyl)methyl]-1-(4-methoxyphenyl)-1H-imidazole (667 mg, 1.6 mmol) obtained in Referential Example 27. The mixture was stirred at room temperature for 3 hours. The reaction mixture was concentrated under reduced pressure. Dioxane was added to the residue, followed by concentration under reduced pressure.

The residue was dissolved in thionyl chloride (2.0 ml) and a drop of dimethylformamide was added to the resulting solution. The mixture was stirred at room temperature for 17 hours. The reaction mixture was then concentrated under reduced pressure. Dioxane was added to the residue, followed by concentration under reduced pressure.

The residue was dissolved in dimethylformamide (5.0 ml), and 4-chlorobenzenethiol (347 mg, 2.4 mmol) and potassium carbonate (1.32 g, 9.6 mmol) were added to the resulting solution. The mixture was stirred at 50° C. for 2 hours. After the reaction mixture was allowed to stand until it became room temperature, ethyl ether (60 ml) was added thereto. The mixture was washed with water and brine, dried over anhydrous magnesium sulfate and concentrated under reduced pressure. The residue was purified by silica gel chromatography (hexane:ethyl acetate=10:1-5:1) and crystallized from ethanol, whereby the title compound (535 mg, 75%) was obtained as colorless needle crystals.

$^1$H-NMR (400 MHz, CDCl$_3$) δ: 3.86(3H,s), 5.57(1H,s), 6.8-6.9(3H,m), 6.91(2H,d,J=8.4 Hz), 7.00(2H,d,J=8.4 Hz), 7.06(2H, d,J=6.8 Hz), 7.11(2H,d,J=6.8 Hz), 7.16(1H,s), 7.81 (1H,m).

IR (ATR) cm$^{-1}$: 1513, 1475, 1240, 1037, 821.

MS m/z: 443 (M$^+$+H).

Example 150

2-[[(4-Chlorophenyl)sulfonyl]-(2,5-difluorophenyl) methyl]-1-methyl-1H-benzimidazole (Compound A) and 2-[[(4-chlorophenyl)sulfinyl]-(2,5-difluorophenyl)methyl]-1-methyl-1H-benzimidazole (Compound B)

Compound A

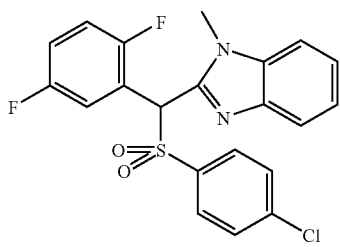

Compound B

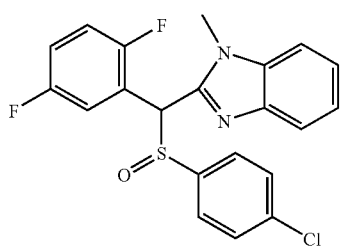

Hexaammonium heptamolybdate tetrahydrate (60 mg) was added to a methanol (12 ml) solution of the 2-[[(4-chlorophenyl)thio]-(2,5-difluorophenyl)methyl]-1-methyl-1H-benzimidazole (190 mg, 0.474 mmol) obtained in Example 146. To the resulting mixture was added 30% aqueous hydrogen peroxide (6 ml), followed by stirring for 17 hours. Ethyl acetate (60 ml) was added to the reaction mixture. The resulting mixture was washed with water and brine, dried over anhydrous magnesium sulfate and then concentrated under reduced pressure. The residue was purified by silica gel chromatography (hexane:ethyl acetate=6:1-4:1), whereby a nonpolar compound (Compound A) (48 mg, 23%) was obtained as needle crystals and a polar compound (Compound B) (23 mg, 12%) was obtained as a white solid.

Compound A $^1$H-NMR (400 MHz, CDCl$_3$) δ: 3.90(3H,s), 6.14(1H,s), 6.9-7.1(2H,m), 7.26-7.42(3H,m), 7.39(2H,d,J=8.8 Hz), 7.46 (2H,d,J=8.8 Hz), 7.81(1H,d,J=8.0 Hz), 8.16(1H,m).

IR (ATR) cm$^{-1}$: 1726, 1606, 1493, 1360, 1184, 1085, 768.

mp: 213-214° C.

MS m/z: 433 (M$^+$+H).

Anal. calcd for C$_{21}$H$_{15}$ClF$_2$N$_2$OS: C 58.27%; H 3.49%; N 6.47%; S 7.41%; Cl 8.19%; F 8.78%. Found: C 58.08%; H 3.62%; N 6.53%; S 7.35%; Cl 8.10%; F 8.74%.

Compound B $^1$H-NMR (400 MHz, CDCl$_3$) δ: 3.35(½*3H,s), 3.78(½*3H,s), 5.52(½*1H,s), 5.57(½*1H,s), 6.78-7.1(2H, m), 7.2-7.4(7H,m), 7.76-7.95(2H,m).

IR (ATR) cm$^{-1}$: 1490, 1238, 1054, 820, 731.

mp: 130-131° C.

MS m/z: 417 (M$^+$+H).

FAB-MS: 477.0646 (Calcd for C$_{21}$H$_{16}$ClF$_2$N$_2$OS: 477.0640).

Example 151

2-[[(4-Chlorophenyl)sulfonyl]-(2,5-difluorophenyl) methyl]-1-methyl-5-chloro-1H-imidazole

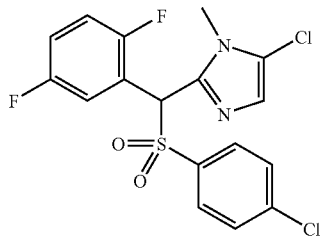

To a methanol (12 ml) solution of the 2-[[(4-chlorophenyl)thio]-(2,5-difluorophenyl)methyl]-1-methyl-5-chloro-1H-imidazole (141 mg, 0.37 mmol) obtained in Example 147 was added hexaammonium heptamolybdate tetrahydrate (60 mg). To the resulting mixture was added 30% aqueous hydrogen peroxide (6 ml), followed by stirring for 64 hours. Ethyl acetate (60 ml) was added and the mixture was washed with water and brine, dried over anhydrous magnesium sulfate and concentrated under reduced pressure. The residue was then crystallized from ethanol, whereby the title compound (103 mg, 67%) was obtained as colorless needle crystals.

$^1$H-NMR (400 MHz, CDCl$_3$) δ: 3.71(3H,s), 5.88(1H,s), 6.93-7.08(2H,m), 7.03(1H,s), 7.43(4H,s), 7.98(1H,m).

IR (ATR) cm$^{-1}$: 1490, 1467, 1313, 1149, 1079, 818, 729.

mp: 179-180° C.

MS m/z: 417 (M$^+$+H).

Anal. calcd for C$_{17}$H$_{12}$Cl$_2$F$_2$N$_2$O$_2$S: C 48.90%; H 2.93%; N 6.71%; S 7.68%; Cl 16.99%; F 9.11%. Found: C 48.90%; H 2.93%; N 6.77%; S 7.80%; Cl 17.02%; F 9.19%.

Example 152

2-[[(4-Chlorophenyl)sulfonyl]-(2,5-difluorophenyl) methyl]thiazole

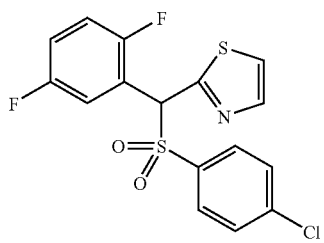

To a methanol (6.0 ml) solution of the 2-[[(4-chlorophenyl)thio]-(2,5-difluorophenyl)methyl]thiazole (124 mg, 0.35 mmol) obtained in Example 148 was added hexaammonium

Example 153

2-[[(4-Chlorophenyl)sulfonyl]-(2,5-difluorophenyl)methyl]-1-(4-methoxyphenyl)-1H-imidazole

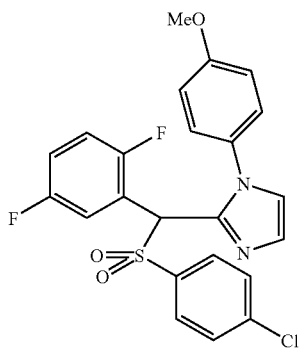

To a methanol (12 ml) solution of the 2-[[(4-chlorophenyl)thio]-(2,5-difluorophenyl)methyl]-1-(4-methoxyphenyl)-1H-benzimidazole (118 mg, 0.27 mmol) obtained in Example 149 was added hexaammonium heptamolybdate tetrahydrate (60 mg). To the resulting mixture was added 30% aqueous hydrogen peroxide (6 ml), followed by stirring for 64 hours. Ethyl acetate (60 ml) was added, and the mixture was washed with water and brine, dried over anhydrous magnesium sulfate and concentrated under reduced pressure. The residue was crystallized from ethanol, whereby the title compound (76 mg, 60%) was obtained as colorless needle crystals.

$^1$H-NMR (400 MHz, CDCl$_3$) δ: 3.89(3H,s), 5.83(1H,s), 6.93-7.05(4H,m), 6.97(2H,d,J=8.8 Hz), 7.01(2H,d,J=8.8 Hz), 7.38(2H,d,J=8.8 Hz), 7.41(2H,d,J=8.8 Hz), 8.15(1H,m).

IR (ATR) cm$^{-1}$: 1513, 1492, 1332, 1155, 836.

mp: 150-151° C.

MS m/z: 475 (M$^+$+H).

Anal. calcd for C$_{23}$H$_{17}$ClF$_2$N$_2$O$_3$S: C 58.13%; H 3.61%; N 5.90%; S 6.75%; Cl 7.47%; F 8.00%. Found: C 58.09%; H 3.51%; N 5.99%; S 6.88%; Cl 7.48%; F 8.06%.

Referential Example 28

5-(Methylsulfonyl)-1-pentanol

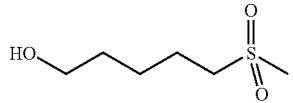

To a dichloromethane (25 ml) solution of 5-(methylthio)-1-pentanol (682 mg, 5.08 mmol) was added 3-chloroperbenzoic acid (2.10 g, 12.2 mmol) and the resulting mixture was stirred at room temperature for 2 hours. After concentration under reduced pressure, diethyl ether was added to the residue and the mixture was extracted with water. After the organic layer was extracted twice with water, the water layers were combined and concentrated under reduced pressure. The residue thus obtained was subjected to flash silica gel chromatography, and the fraction obtained from the dichloromethane:methanol=19:1 eluate was concentrated under reduced pressure, whereby the title compound (517 mg, 3.11 mmol, 61%) was obtained as a colorless oil.

$^1$H-NMR (400 MHz, CDCl$_3$) δ: 1.50-1.67(4H,m), 1.84-1.94(2H,m), 2.90(3H,s), 3.03(2H,t,J=8.0 Hz), 3.68(2H,t, J=6.1 Hz).

Referential Example 29

5-(Methylsulfonyl)pentanal

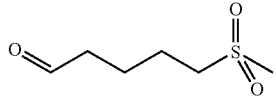

To a dichloromethane (15 ml) solution of 5-(methylsulfonyl)-1-pentanol (344 mg, 2.07 mmol), dimethylsulfoxide (0.441 ml, 6.21 mmol) and triethylamine (1.15 ml, 8.28 ml) was added a sulfur trioxide pyridine complex (659 mg, 4.14 mmol) at 0° C. and the mixture was stirred at room temperature for 3 hours. After the reaction mixture was washed with water, the organic layer was dried over anhydrous sodium sulfate. After filtration, the filtrate was concentrated under reduced pressure. The residue was subjected to flash silica gel chromatography, and the fraction obtained from the ethyl acetate eluate was concentrated under reduced pressure, whereby the title compound (183 mg, 1.11 mmol, 54%) was obtained as a colorless oil.

$^1$H-NMR (400 MHz, CDCl$_3$) δ: 1.76-1.97(4H,m), 2.55 (2H,t,J=7.1 Hz), 2.91(3H,s), 3.04(2H,t,J=7.8 Hz), 9.79(1H, s).

Referential Example 30

1-(2,5-Difluorophenyl)-5-(methylsulfonyl)-1-pentanol

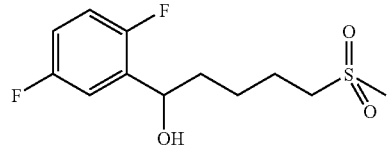

A tetrahydrofuran (5 ml) solution of 1-bromo-2,5-difluorobenzene (0.151 ml, 1.34 mmol) was stirred at −78° C. To the resulting mixture was added a hexane solution (0.843 ml, 1.34 mmol) of n-butyl lithium. The reaction mixture was added to a tetrahydrofuran (5 ml) solution of 5-(methylsulfonyl)pentanal (183 mg, 1.11 mmol) at −78° C. and at the same temperature, stirring was conducted for 30 minutes. After elevating the temperature of the reaction mixture to room temperature, diethyl ether was added thereto. The resulting mixture was washed successively with a saturated aqueous solution of ammonium chloride and a saturated aqueous solution of sodium bicarbonate. The organic layer was then dried over anhydrous sodium sulfate. After filtration, the filtrate was concentrated under reduced pressure. The residue was subjected to flash silica gel chromatography, and the fraction obtained from the hexane:ethyl acetate=1:2 eluate was concentrated under reduced pressure, whereby the title compound (116 mg, 0.42 mmol, 37%) was obtained as a colorless oil.

$^1$H-NMR (400 MHz, CDCl$_3$) δ: 1.49-1.69(2H,m), 1.71-1.97(4H,m), 2.89(3H,s), 3.01(2H,t,J=8.1 Hz), 5.02(1H,t, J=6.2 Hz), 6.88-7.01(2H,m), 7.16-7.22(1H,m).

MS m/z: 296 (M$^+$+NH$_4$).

Referential Example 31

1-(2,5-Difluorophenyl)-5-(methylsulfonyl)pentyl=methanesulfonate

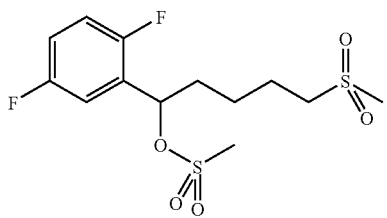

To a dichloromethane (5 ml) solution of 1-(2,5-difluorophenyl)-5-(methylsulfonyl)-1-pentanol (278 mg, 1.00 mmol) were successively added triethylamine (0.209 ml, 1.50 mmol) and methanesulfonyl chloride (0.115 ml, 1.50 mmol) at 0° C. The resulting mixture was stirred at room temperature for 3 hours. The reaction mixture was washed with a saturated aqueous solution of sodium bicarbonate. Then, the organic layer was dried over anhydrous sodium sulfate. After filtration, the filtrate was concentrated under reduced pressure. The residue was subjected to flash silica gel chromatography, and the fraction obtained from the hexane:ethyl acetate=1:1 eluate was concentrated under reduced pressure, whereby the title compound (278 mg, 0.78 mmol, 78%) was obtained as a colorless oil.

$^1$H-NMR (400 MHz, CDCl$_3$) δ: 1.48-1.71(2H,m), 1.85-1.98(3H,m), 2.03-2.13(1H,m), 2.90(3H,s), 2.90(3H,s), 3.02 (2H,t,J=7.8 Hz), 5.82(1H,dd,J=8.6, 5.1 Hz), 7.01-7.19(3H, m).

MS m/z: 374 (M$^+$+NH$_4$).

Example 154

1,4-Difluoro-2-[1-[(4-methoxyphenyl) sulfonyl]-5-(methylsulfonyl)pentyl]benzene

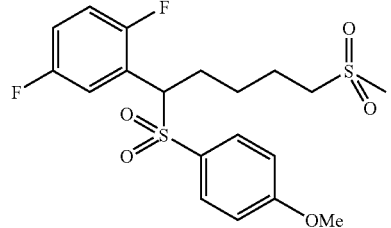

To an N,N-dimethylformamide (2 ml) solution of 1-(2,5-difluorophenyl)-5-(methylsulfonyl) pentyl=methanesulfonate (139 mg, 0.39 mmol) were successively added 4-methoxybenzenethiol (0.058 ml, 0.47 mmol) and potassium carbonate (81 mg, 0.59 mmol). The resulting mixture shaken at room temperature for 15 hours. Ethyl acetate was added to the residue. The mixture was washed with a saturated aqueous solution of ammonium chloride. Then, the organic layer was dried over anhydrous sodium sulfate. After filtration, the filtrate was concentrated under reduced pressure.

The residue thus obtained was dissolved in methanol (2 ml), followed by the addition of a water (2 ml) solution of Oxone (potassium peroxymonosulfate compound, 2 KHSO$_5$.KHSO$_4$.K$_2$SO$_4$) (480 mg, 0.78 mmol) at 0° C. After shaking at room temperature for 3 hours, dichloromethane was added and the mixture was washed with water. The organic layer was dried over anhydrous sodium sulfate. After filtration, the filtrate was concentrated under reduced pressure. The residue was purified by preparative high performance liquid chromatography (using a mixed solvent of water/acetonitrile/formic acid). The resulting solid was washed with diethyl ether and then, collected by filtration, whereby the title compound (86 mg, 0.20 mmol, 51%) was obtained as a white powder.

$^1$H-NMR (400 MHz, CDCl$_3$) δ: 1.34-1.52(2H,m), 1.79-1.95(2H,m), 2.05-2.16(1H,m), 2.42-2.52(1H,m), 2.87(3H,s), 2.92-2.99(2H,m), 3.85(3H,s), 4.48(1H,dd,J=11.0, 2.9 Hz), 6.80-6.89(1H,m), 6.87(2H,d,J=8.8 Hz), 6.94-7.00(1H,m), 7.19-7.25(1H,m), 7.51(2H,d,J=8.8 Hz).

IR (ATR) cm$^{-1}$: 2951, 1595, 1496, 1271, 1132, 1084, 1022, 970.

Anal. Calcd for C$_{19}$H$_{22}$F$_2$O$_5$S$_2$: C, 52.76; H, 5.13; F, 8.79. Found: C, 52.57; H, 5.13; F, 8.71.

MS m/z: 433 (M$^+$+H).

Example 155

1,4-Difluoro-2-[5-(methylsulfonyl)-1-(phenylsulfonyl)pentyl]benzene

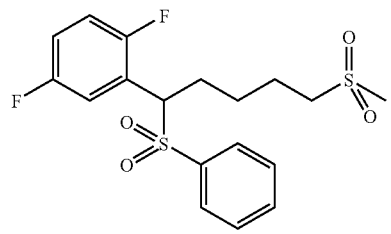

In a similar manner to Example 154 except for the use of 1-(2,5-difluorophenyl)-5-(methylsulfonyl)pentyl=methanesulfonate (127 mg, 0.36 mmol) and thiophenol (0.037 ml, 0.36 mmol), the title compound (83 mg, 0.21 mmol, 58%) was obtained as a white powder.

$^1$H-NMR (400 MHz, CDCl$_3$) δ: 1.34-1.52(2H,m), 1.79-1.97(2H,m), 2.07-2.20(1H,m), 2.44-2.55(1H,m), 2.87(3H,s), 2.90-3.01(2H,m), 4.51(1H,dd,J=10.9, 3.6 Hz), 6.75-6.84(1H, m), 6.92-7.00(1H,m), 7.19-7.27(1H,m), 7.38-7.46(2H,m), 7.55-7.65(3H,m).

MS m/z: 420 (M$^+$+NH$_4$).

Example 156

1,4-Difluoro-2-[1-[(4-methylphenyl)sulfonyl]-5-(methylsulfonyl)pentyl]benzene

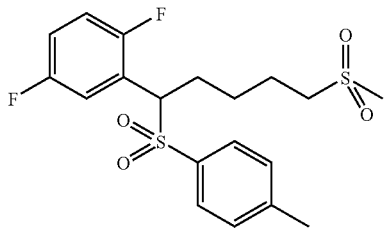

In a similar manner to Example 154 except for the use of 1-(2,5-difluorophenyl)-5-(methylsulfonyl)pentyl=methanesulfonate (139 mg, 0.39 mmol) and p-toluenethiol (58 mg, 0.47 mmol), the title compound (65 mg, 0.16 mmol, 40%) was obtained as a white powder.

$^1$H-NMR (400 MHz, CDCl$_3$) δ: 1.33-1.51(2H,m), 1.77-1.96(2H,m), 2.03-2.16(1H,m), 2.37-2.51(1H,m), 2.40(3H,s), 2.87(3H,s), 2.90-3.00(2H,m), 4.49(1H,dd,J=11.1, 3.8 Hz), 6.79-6.88(1H,m), 6.94-7.02(1H,m), 7.19-7.26(1H,m), 7.21(2H,d,J=7.8 Hz), 7.48 (2H,d,J=7.8 Hz).

IR (ATR) cm$^{-1}$: 2943, 1597, 1498, 1269, 1142, 1084, 957, 868.

Anal. Calcd for C$_{19}$H$_{22}$F$_2$O$_4$S$_2$: C, 54.79; H, 5.32; F, 9.12. Found: C, 54.67; H, 5.30; F, 9.10.

MS m/z: 417 (M$^+$+H).

Example 157

2-[1-[(3-Chlorophenyl)sulfonyl]-5-(methylsulfonyl)pentyl]-1,4-difluorobenzene

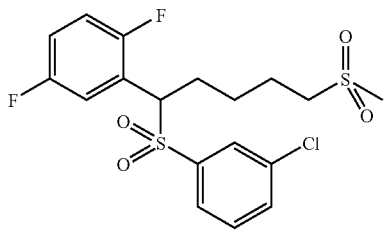

In a similar manner to Example 154 except for the use of 1-(2,5-difluorophenyl)-5-(methylsulfonyl)pentyl=methanesulfonate (127 mg, 0.36 mmol) and 3-chlorobenzenethiol (0.041 ml, 0.36 mmol), the title compound (6.3 mg, 0.014 mmol, 4%) was obtained as a white powder.

$^1$H-NMR (400 MHz, CDCl$_3$) δ: 1.34-1.54(2H,m), 1.79-1.97(2H,m), 2.08-2.21(1H,m), 2.41-2.56(1H,m), 2.88(3H,s), 2.90-3.03(2H,m), 4.51(1H,dd,J=10.6, 3.4 Hz), 6.78-6.90(1H, m), 6.95-7.06(1H,m), 7.19-7.29(1H,m), 7.36(1H,t,J=7.8 Hz), 7.49(1H,d,J=7.8 Hz), 7.55(1H,d,J=7.8 Hz), 7.56(1H,s).

MS m/z: 437 (M$^+$+H).

Example 158

1,4-Difluoro-2-[1-[(3-methylphenyl)sulfonyl]-5-(methylsulfonyl)pentyl]benzene

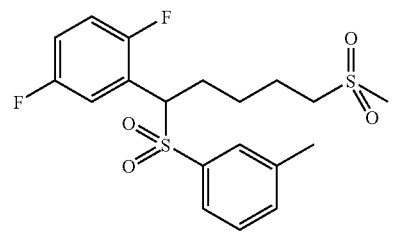

In a similar manner to Example 154 except for the use of 1-(2,5-difluorophenyl)-5-(methylsulfonyl)pentyl=methanesulfonate (127 mg, 0.36 mmol) and m-toluenethiol (0.043 ml, 0.36 mmol), the title compound (26 mg, 0.062 mmol, 17%) was obtained as a white powder.

$^1$H-NMR (400 MHz, CDCl$_3$) δ: 1.33-1.52(2H,m), 1.78-1.96(2H,m), 2.03-2.19(1H,m), 2.34(3H,s), 2.39-2.51(1H,m), 2.87(3H,s), 2.91-2.99(2H,m), 4.50(1H,dd,J=11.0, 3.4 Hz), 6.78-6.86(1H,m), 6.93-7.02(1H,m), 7.19-7.33(2H,m), 7.36-7.44(3H,m).

MS m/z: 417 (M$^+$+H).

Example 159

1,4-Difluoro-2-[1-[(3-methoxyphenyl) sulfonyl]-5-(methylsulfonyl)pentyl]benzene

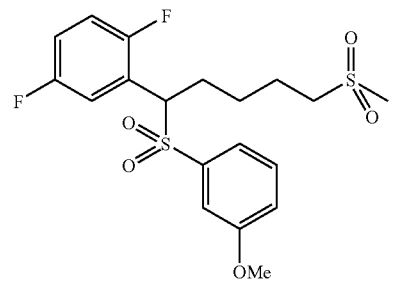

In a similar manner to Example 154 except for the use of 1-(2,5-difluorophenyl)-5-(methylsulfonyl)pentyl=methanesulfonate (127 mg, 0.36 mmol) and 3-methoxybenzenethiol (0.044 ml, 0.36 mmol), the title compound (25 mg, 0.059 mmol, 16%) was obtained as a white powder.

$^1$H-NMR (400 MHz, CDCl$_3$) δ: 1.34-1.51(2H,m), 1.79-1.95(2H,m), 2.06-2.18(1H,m), 2.42-2.52(1H,m), 2.87(3H,s), 2.90-3.00(2H,m), 3.75(3H,s), 4.51(1H,dd,J=11.5, 4.6 Hz), 6.80-6.87(1H,m), 6.94-7.01(1H,m), 7.05(1H,s), 7.10(1H,d, J=8.1 Hz), 7.21(1H,d,J=8.1 Hz), 7.21-7.29(1H,m), 7.32(1H, t,J=8.1 Hz).

MS m/z: 433 (M$^+$+H).

Example 160

1,4-Difluoro-2-[1-[(4-fluorophenyl) sulfonyl]-5-(methylsulfonyl)pentyl]benzene

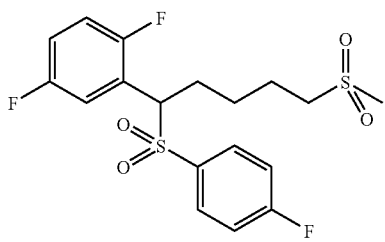

In a similar manner to Example 154 except for the use of 1-(2,5-difluorophenyl)-5-(methylsulfonyl) pentyl=methanesulfonate (127 mg, 0.36 mmol) and 4-fluorobenzenethiol (0.038 ml, 0.36 mmol), the title compound (35 mg, 0.083 mmol, 23%) was obtained as a white powder.

$^1$H-NMR (400 MHz, CDCl$_3$) δ: 1.38-1.53(2H,m), 1.82-1.97(2H,m), 2.08-2.20(1H,m), 2.47-2.57(1H,m), 2.88(3H,s), 2.92-3.02(2H,m), 4.50(1H,dd,J=11.0, 4.4 Hz), 6.78-6.88(1H, m), 6.95-7.02(1H,m), 7.05-7.13(2H,m), 7.22-7.32(1H,m), 7.57-7.64(2H,m).

MS m/z: 438 (M$^+$+NH$_4$).

Example 161

4-[[1-(2,5-Difluorophenyl)-5-(methylsulfonyl)pentyl]sulfonyl]phenol

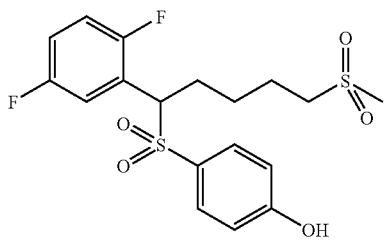

In a similar manner to Example 154 except for the use of 1-(2,5-difluorophenyl)-5-(methylsulfonyl) pentyl=methanesulfonate (127 mg, 0.36 mmol) and 4-mercaptophenol (45 mg, 0.36 mmol), the title compound (63 mg, 0.15 mmol, 42%) was obtained as a white powder.

$^1$H-NMR (400 MHz, CDCl$_3$) δ: 1.34-1.52(2H,m), 1.80-1.93(2H,m), 2.03-2.18(1H,m), 2.42-2.52(1H,m), 2.88(3H,s), 2.90-3.00(2H,m), 4.47(1H,dd,J=10.8, 3.2 Hz), 5.44(1H,s), 6.78-6.87(1H,m), 6.81(2H,d,J=8.8 Hz), 6.94-7.01(1H,m), 7.19-7.28(1H,m), 7.48(2H,d,J=8.8 Hz).

MS m/z: 419 (M$^+$+H).

Example 162

1-[[1-(2,5-Difluorophenyl)-5-(methylsulfonyl)pentyl]sulfonyl]naphthalene

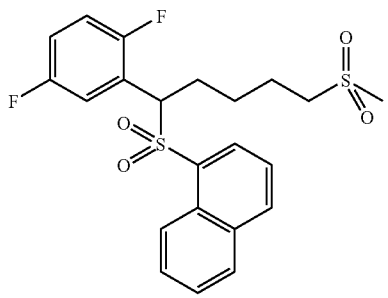

In a similar manner to Example 154 except for the use of 1-(2,5-difluorophenyl)-5-(methylsulfonyl) pentyl=methanesulfonate (127 mg, 0.36 mmol) and 1-naphthalenethiol (57 mg, 0.36 mmol), the title compound (48 mg, 0.11 mmol, 29%) was obtained as a white powder.

$^1$H-NMR (400 MHz, CDCl$_3$) δ: 1.29-1.46(2H,m), 1.72-1.90(2H,m), 2.13-2.26(1H,m), 2.29-2.40(1H,m), 2.83(3H,s), 2.82-2.93(2H,m), 4.79(1H,dd,J=11.3, 3.9 Hz), 6.66-6.75(1H, m), 6.87-6.94(1H,m), 7.24-7.31(1H,m), 7.45(1H,t,J=7.6 Hz), 7.58-7.62(2H,m), 7.94(1H,d,J=8.1 Hz), 8.01(1H,d,J=7.6 Hz), 8.08(1H,d,J=8.1 Hz), 8.73(1H,d,J=8.6 Hz).

MS m/z: 453 (M$^+$+H).

Example 163

2-[[1-(2,5-Difluorophenyl)-5-(methylsulfonyl)pentyl]sulfonyl]-1H-benzimidazole

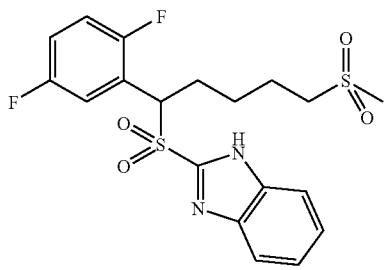

In a similar manner to Example 154 except for the use of 1-(2,5-difluorophenyl)-5-(methylsulfonyl) pentyl=methanesulfonate (127 mg, 0.36 mmol) and 2-mercaptobenzimidazole (54 mg, 0.36 mmol), the title compound (62 mg, 0.14 mmol, 39%) was obtained as a white powder.

$^1$H-NMR (400 MHz, CDCl$_3$) δ: 1.28-1.53(2H,m), 1.78-1.96(2H,m), 2.17-2.30(1H,m), 2.42-2.53(1H,m), 2.86(3H,s), 2.88-3.02(2H,m), 5.03(1H,dd,J=11.3, 3.9 Hz), 6.90-7.04(2H, m), 7.13-7.20(1H,m), 7.39-7.47(2H,m), 7.50(1H,br s), 7.90 (1H,br s), 10.08(1H,br s).

MS m/z: 443 (M$^+$+H).

Example 164

4-[[1-(2,5-Difluorophenyl)-5-(methylsulfonyl)pentyl]sulfonyl]pyridine

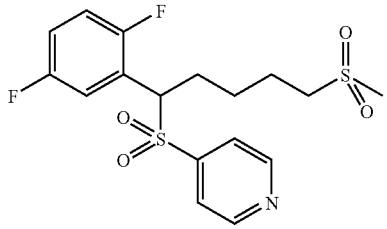

In a similar manner to Example 154 except for the use of 1-(2,5-difluorophenyl)-5-(methylsulfonyl) pentyl=methanesulfonate (127 mg, 0.36 mmol) and 4-mercaptopyridine (40 mg, 0.36 mmol), the title compound (38 mg, 0.093 mmol, 26%) was obtained as a white powder.

$^1$H-NMR (400 MHz, CDCl$_3$) δ: 1.27-1.60(2H,m), 1.70-1.90(2H,m), 2.00-2.13(1H,m), 2.35-2.48(1H,m), 2.88(3H,s), 2.90-3.04(2H,m), 4.56(1H,dd,J=10.6, 4.3 Hz), 6.78-6.85(1H,m), 6.95-7.03(1H,m), 7.22-7.30(1H,m), 7.45(2H,d,J=5.2 Hz), 8.75(2H,d,J=5.2 Hz).

MS m/z: 404 (M$^+$+H).

Example 165

2-[[1-(2,5-Difluorophenyl)-5-(methylsulfonyl)pentyl]sulfonyl]pyridine

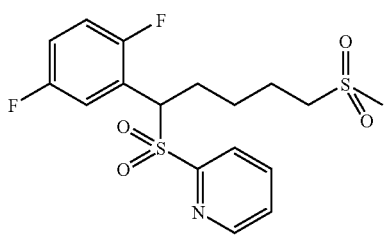

In a similar manner to Example 154 except for the use of 1-(2,5-difluorophenyl)-5-(methylsulfonyl) pentyl=methanesulfonate (127 mg, 0.36 mmol) and 2-mercaptopyridine (40 mg, 0.36 mmol), the title compound (72 mg, 0.18 mmol, 50%) was obtained as a white powder.

$^1$H-NMR (400 MHz, CDCl$_3$) δ: 1.36-1.52(2H,m), 1.78-1.96(2H,m), 2.10-2.21(1H,m), 2.35-2.46(1H,m), 2.87(3H,s), 2.90-3.03(2H,m), 5.11(1H,dd,J=10.9, 3.8 Hz), 6.82-6.91(1H,m), 6.92-6.98(1H,m), 7.24-7.31(1H,m), 7.48-7.54(1H,m), 7.79-7.87(2H,m), 8.75(1H,d,J=4.6 Hz).

MS m/z: 404 (M$^+$+H).

Example 166

2-[[1-(2,5-Difluorophenyl)-5-(methylsulfonyl)pentyl]sulfonyl]quinoline

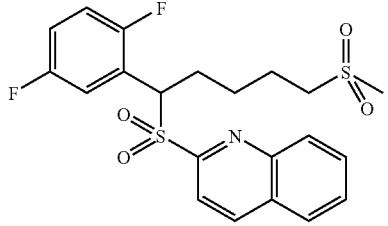

In a similar manner to Example 154 except for the use of 1-(2,5-difluorophenyl)-5-(methylsulfonyl) pentyl=methanesulfonate (127 mg, 0.36 mmol) and 2-quinolinethiol (58 mg, 0.36 mmol), the title compound (90 mg, 0.20 mmol, 55%) was obtained as a colorless foam.

$^1$H-NMR (400 MHz, CDCl$_3$) δ: 1.39-1.59(2H,m), 1.80-1.99(2H,m), 2.13-2.26(1H,m), 2.42-2.53(1H,m), 2.86(3H,s), 2.91-3.02(2H,m), 5.33(1H,dd,J=11.1, 3.1 Hz), 6.74-6.82(1H,m), 6.88-6.96(1H,m), 7.31-7.36(1H,m), 7.72(1H,t,J=7.1 Hz), 7.86-7.92(3H,m), 8.24(1H,d,J=8.5 Hz), 8.29(1H,d,J=8.8 Hz).

MS m/z: 454 (M$^+$+H).

Example 167

2-[[1-(2,5-Difluorophenyl)-5-(methylsulfonyl)pentyl]sulfonyl]pyrimidine

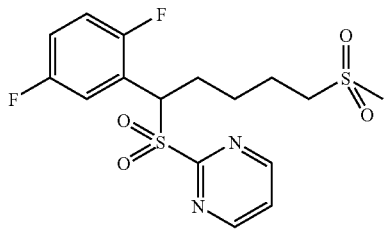

In a similar manner to Example 154 except for the use of 1-(2,5-difluorophenyl)-5-(methylsulfonyl) pentyl=methanesulfonate (127 mg, 0.36 mmol) and 2-mercaptopyrimidine (40 mg, 0.36 mmol), the title compound (55 mg, 0.14 mmol, 38%) was obtained as a colorless oil.

$^1$H-NMR (400 MHz, CDCl$_3$) δ: 1.38-1.60(2H,m), 1.79-1.98(2H,m), 2.11-2.25(1H,m), 2.37-2.47(1H,m), 2.88(3H,s), 2.90-3.02(2H,m), 5.31(1H,dd,J=10.5, 3.4 Hz), 6.89-7.02(2H,m), 7.33-7.39(1H,m), 7.52(1H,t,J=4.9 Hz), 8.91(2H,d,J=4.9 Hz).

MS m/z: 405 (M$^+$+H).

Example 168

5-[[1-(2,5-Difluorophenyl)-5-(methylsulfonyl)pentyl]sulfonyl]-1-methyl-1H-tetrazole

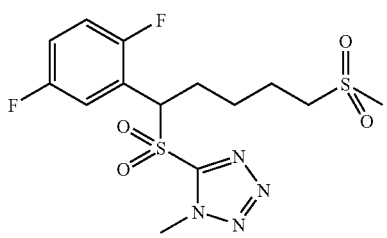

In a similar manner to Example 154 except for the use of 1-(2,5-difluorophenyl)-5-(methylsulfonyl)pentyl=methanesulfonate (127 mg, 0.36 mmol) and 1-methyl-5-mercapto-1,2,3,4-tetrazole (42 mg, 0.36 mmol), the title compound (75 mg, 0.18 mmol, 52%) was obtained as a colorless oil.

$^1$H-NMR (400 MHz, CDCl$_3$) δ: 1.43-1.65(2H,m), 1.82-2.01(2H,m), 2.18-2.31(1H,m), 2.49-2.60(1H,m), 2.90(3H,s), 2.92-3.06(2H,m), 4.10(3H,s), 5.12(1H,dd,J=11.0, 3.7 Hz), 7.03-7.22(3H,m).

MS m/z: 409 (M$^+$+H).

Example 169

2-[[1-(2,5-Difluorophenyl)-5-(methylsulfonyl)pentyl]sulfinyl]-1-methyl-1H-imidazole (Compound A) and 2-[[1-(2,5-difluorophenyl)-5-(methylsulfonyl)pentyl]sulfonyl]-1-methyl-1H-imidazole (Compound B)

Compound A

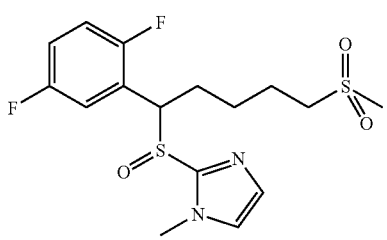

Compound B

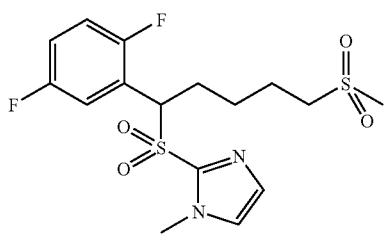

In a similar manner to Example 154 except for the use of 1-(2,5-difluorophenyl)-5-(methylsulfonyl)pentyl=methanesulfonate (127 mg, 0.36 mmol) and 2-mercapto-1-methylimidazole (41 mg, 0.36 mmol), the title compound A (45 mg, 0.12 mmol, 32%) and the title compound B (47 mg, 0.11 mmol, 32%) were obtained as a yellow oil and as a colorless oil, respectively.

Compound A $^1$H-NMR (400 MHz, CDCl$_3$) δ: 1.45-1.67(2H,m), 1.82-2.02(2H,m), 2.09-2.21(1H,m), 2.41-2.52(1H,m), 2.89(3H,s), 2.92-3.08(2H,m), 3.66(3H,s), 4.91(1H,dd,J=11.1, 4.5 Hz), 6.78-6.84(1H,m), 6.90(1H,s), 6.93-7.01(2H,m), 7.12(1H,s).

MS m/z: 391 (M$^+$+H).

Compound B $^1$H-NMR (400 MHz, CDCl$_3$) δ: 1.37-1.66(2H,m), 1.81-1.96(2H,m), 2.12-2.23(1H,m), 2.45-2.56(1H,m), 2.88(3H,s), 2.91-3.03(2H,m), 3.59(3H,s), 4.89(1H,dd,J=10.9, 4.0 Hz), 6.93(1H,d, J=0.7 Hz), 6.97-7.08(3H,m), 7.19(1H,d,J=0.7 Hz).

MS m/z: 407 (M$^+$+H).

Example 170

2-[[1-(2,5-Difluorophenyl)-5-(methylsulfonyl)pentyl]sulfinyl]-1,3-benzothiazole

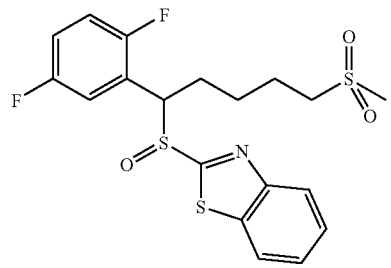

In a similar manner to Example 154 except for the use of 1-(2,5-difluorophenyl)-5-(methylsulfonyl)pentyl=methanesulfonate (127 mg, 0.36 mmol) and 2-mercaptobenzothiazole (60 mg, 0.36 mmol), the title compound (78 mg, 0.18 mmol, 49%) was obtained as a white powder.

$^1$H-NMR (400 MHz, CDCl$_3$) δ: 1.37-1.48 (2H,m), 1.72-1.91 (2H,m), 2.09-2.29(2H,m), 2.83(3H,s), 2.85-2.95(2H,m), 4.66(1H,dd,J=10.5,4.1 Hz), 7.01-7.08(3H,m), 7.48-7.50 (2H,m), 7.87-8.08(2H,m).

MS m/z: 444 (M$^+$+H).

Example 171

2-[1-[(2-Chlorophenyl)sulfonyl]-5-(methylsulfonyl)pentyl]-1,4-difluorobenzene

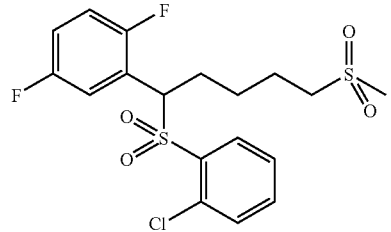

To an N,N-dimethylformamide (2 ml) solution of the 1-(2,5-difluorophenyl)-5-(methylsulfonyl)pentyl=methanesulfonate (127 mg, 0.36 mmol) obtained in Referential Example 31 were successively added 2-chlorobenzenethiol (0.041 ml, 0.36 mmol) and potassium carbonate (62 mg, 0.45 mmol). At room temperature, the resulting mixture was shaken for 4 hours. Ethyl acetate was added to the reaction mixture. The mixture was washed with water and then, the organic layer was dried over anhydrous sodium sulfate. After filtration, the filtrate was concentrated under reduced pressure.

The residue thus obtained was dissolved in methanol (2 ml), followed by the addition of a water (2 ml) solution of Oxone (potassium peroxymonosulfate compound, 2 $KHSO_5 \cdot KHSO_4 \cdot K_2SO_4$) (439 mg, 0.71 mmol) at 0° C. After shaking at room temperature for 14 hours, the reaction mixture was added with dichloromethane and the mixture was washed with water. The organic layer was dried over anhydrous sodium sulfate. After filtration, the filtrate was concentrated under reduced pressure.

The residue thus obtained was dissolved in dichloromethane (4 ml) and at 0° C., 3-chloroperbenzoic acid (95 mg, 0.36 mmol) was added to the resulting solution. The reaction mixture was shaken at room temperature for 4 hours, and then washed with a 1N sodium hydroxide solution. The organic layer was dried over anhydrous sodium sulfate. After filtration, the filtrate was concentrated under reduced pressure. The residue was purified by preparative high performance liquid chromatography (using a mixed solvent of water/acetonitrile/formic acid). The resulting solid was washed with diethyl ether and then, collected by filtration, whereby the title compound (59 mg, 0.14 mmol, 38%) was obtained as a white powder.

$^1$H-NMR (400 MHz, $CDCl_3$) δ: 1.39-1.60(2H,m), 1.82-1.97(2H,m), 2.10-2.22(1H,m), 2.37-2.48(1H,m), 2.87(3H,s), 2.91-3.02(2H,m), 5.13(1H,dd,J=10.7, 3.7 Hz), 6.79-6.87(1H, m), 6.90-6.97(1H,m), 7.23-7.33(2H,m), 7.46-7.55(2H,m), 8.75 (1H,dd,J=7.9, 1.6 Hz).

MS m/z: 437 ($M^+$+H).

Example 172

1,4-Difluoro-2-[1-[(2-fluorophenyl)sulfonyl]-5-(methylsulfonyl)pentyl]benzene

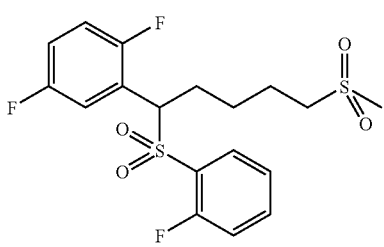

In a similar manner to Example 171 except for the use of 1-(2,5-difluorophenyl)-5-(methylsulfonyl)pentyl=methanesulfonate (127 mg, 0.36 mmol) and 2-fluorobenzenethiol (0.040 ml, 0.36 mmol), the title compound (71 mg, 0.17 mmol, 47%) was obtained as a white powder.

$^1$H-NMR (400 MHz, $CDCl_3$) δ: 1.39-1.60(2H,m), 1.80-1.98(2H,m), 2.10-2.22(1H,m), 2.44-2.54(1H,m), 2.88(3H,s), 2.96(2H,t,J=7.4 Hz), 4.84(1H,dd,J=10.7, 4.4 Hz), 6.78-6.85 (1H,m), 6.90-6.96(1H,m), 7.10-7.21(2H,m), 7.22-7.29(1H, m), 7.52-7.60(2H,m).

MS m/z: 421 ($M^+$+H).

Example 173

1,4-Difluoro-2-[1-[(2-methylphenyl)sulfonyl]-5-(methylsulfonyl)pentyl]benzene

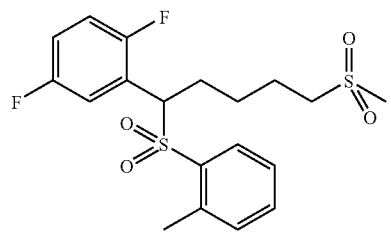

In a similar manner to Example 171 except for the use of 1-(2,5-difluorophenyl)-5-(methylsulfonyl)pentyl=methanesulfonate (127 mg, 0.36 mmol) and o-toluenethiol (0.042 ml, 0.36 mmol), the title compound (38 mg, 0.091 mmol, 25%) was obtained as a white powder.

$^1$H-NMR (400 MHz, $CDCl_3$) δ: 1.33-1.55(2H,m), 1.79-1.95(2H,m), 2.09-2.21(1H,m), 2.37-2.47(1H,m), 2.63(3H,s), 2.87(3H,s), 2.92-2.98(2H,m), 4.61(1H,dd,J=11.2, 3.4 Hz), 6.75-6.82(1H,m), 6.89-6.97(1H,m), 7.16(1H,t,J=7.6 Hz), 7.22-7.31(2H,m), 1.43(1H,t,J=7.6 Hz), 7.43(1H,t,J=8.0 Hz).

MS m/z: 417 ($M^+$+H).

Example 174

1,4-Difluoro-2-[1-[(2-methoxyphenyl) sulfonyl]-5-(methylsulfonyl)pentyl]benzene

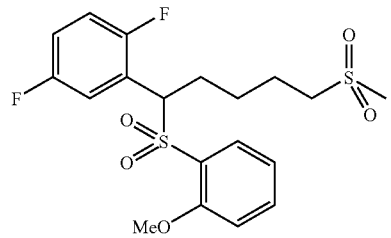

In a similar manner to Example 171 except for the use of 1-(2,5-difluorophenyl)-5-(methylsulfonyl)pentyl=methanesulfonate (127 mg, 0.36 mmol) and 2-methoxybenzenethiol (0.044 ml, 0.36 mmol), the title compound (52 mg, 0.12 mmol, 33%) was obtained as a white powder.

$^1$H-NMR (400 MHz, $CDCl_3$) δ: 1.33-1.55(2H,m), 1.78-1.96(2H,m), 2.06-2.17(1H,m), 2.36-2.47(1H,m), 2.87(3H,s), 2.90-3.00(2H,m), 4.00(3H,s), 5.13(1H,dd,J=11.2, 3.2 Hz), 6.78-6.95(3H,m), 6.98(1H,d,J=7.8 Hz), 7.27-7.33(1H,m), 7.46-7.53(1H,m), 7.63 (1H,dd,J=8.0, 1.7 Hz).

MS m/z: 433 ($M^+$+H).

Example 175

2-[1-[(4-Chlorophenyl)sulfonyl]-6-(methylsulfonyl)hexyl]-1,4-difluorobenzene

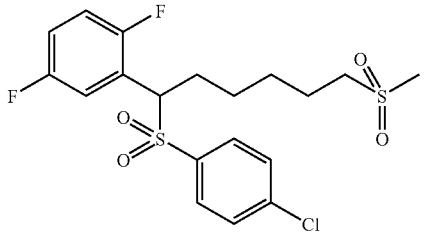

To a toluene (2 ml) solution of the 2-[(4-chlorophenyl)sulfonylmethyl]-1,4-difluorobenzene (100 mg, 0.33 mmol) obtained in Example 5 and the 5-(methylsulfonyl)-1-pentanol (110 mg, 0.66 mmol) obtained in Referential Example 28 was added a toluene (1 ml) solution of cyanomethylenetri-n-butylphosphorane (177 mg, 0.66 mmol). The resulting mixture was heated under reflux for 16 hours. After cooling the reaction mixture to room temperature, it was concentrated under reduced pressure. The residue thus obtained was subjected to flash chromatography on a silica gel column, and the fraction obtained from the hexane:ethyl acetate=3:2 eluate was concentrated under reduced pressure. The resulting solid was washed with diethyl ether and then, collected by filtration, whereby the title compound (140 mg, 0.31 mmol, 94%) was obtained as a white powder.

$^1$H-NMR (400 MHz, CDCl$_3$) δ: 1.22-1.38(2H,m), 1.39-1.56(2H,m), 1.73-1.86(2H,m), 2.03-2.16(1H,m), 2.41-2.52(1H,m), 2.88(3H,s), 2.95(2H,t,J=7.9 Hz), 4.50(1H,dd, J=11.5, 3.2 Hz), 6.80-6.89(1H,m), 6.95-7.04(1H,m), 7.22-7.28(1H,m), 7.38(2H, d, J=8.5 Hz), 7.52(2H,d,J=8.5 Hz).

IR (ATR) cm$^{-1}$: 2949, 1500, 1475, 1317, 1294, 1275, 1136, 1084, 964, 752.

Anal. Calcd for C$_{19}$H$_{21}$ClF$_2$O$_4$S$_2$: C, 50.61; H, 4.69; Cl, 7.86; F, 8.43; S, 14.22. Found: C, 50.59; H, 4.67; Cl, 8.04; F, 8.39; S, 14.15.

Referential Example 32

5-Chloro-2-pyridinethiol

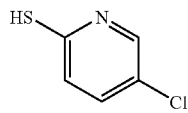

After addition of thiourea (152 mg, 2.00 mmol) to an ethanol (4 ml) solution of 2,5-dichloropyridine (296 mg, 2.00 mmol), the resulting mixture was heated under reflux for 18 hours. The reaction mixture was cooled to room temperature, followed by the addition of a water (1 ml) solution of potassium hydroxide (198 mg, 3.00 mmol). The resulting mixture was heated under reflux for 3 hours. After cooling to room temperature, to the reaction mixture was added water and then the mixture was washed with dichloromethane. The water layer was made acidic with acetic acid, followed by extraction with dichloromethane. The organic layer was dried over anhydrous sodium sulfate. After filtration, the filtrate was concentrated under reduced pressure. The resulting solid was washed with diethyl ether and then collected by filtration, whereby the title compound (83 mg, 0.57 mmol, 29%) was obtained as yellow powder.

$^1$H-NMR (400 MHz, CDCl$_3$) δ: 7.35(1H,dd,J=9.3, 2.4 Hz), 7.46(1H,d, J=9.3 Hz), 7.64(1H,d, J=2.4 Hz).

MS m/z: 146 (M$^+$+H).

Example 176

5-Chloro-2-[[1-(2,5-difluorophenyl)-5-(methylsulfonyl)pentyl]thio]pyridine

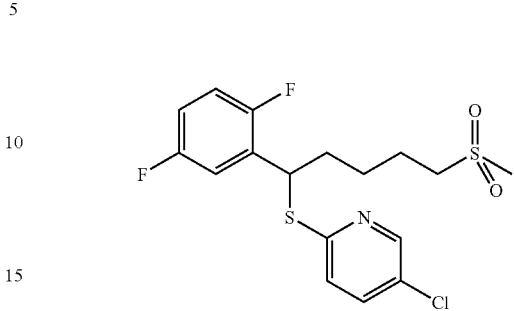

To a dichloromethane (5 ml) solution of the 1-(2,5-difluorophenyl)-5-(methylsulfonyl)-1-pentanol (100 mg, 0.36 mmol) obtained in Referential Example 30 were successively added triethylamine (0.060 ml, 0.43 mmol) and methanesulfonyl chloride (0.033 ml, 0.43 mmol) at 0° C. The resulting mixture was stirred at room temperature for 3 hours. The reaction mixture was washed with water, and the organic layer was dried over anhydrous sodium sulfate. After filtration, the filtrate was concentrated under reduced pressure.

To an N,N-dimethylformamide (4 ml) solution of the resulting residue were successively added 5-chloro-2-pyridinethiol (52 mg, 0.36 mmol) and potassium carbonate (62 mg, 0.45 mmol). The resulting mixture was stirred at room temperature for 3 hours. Ethyl acetate was added to the reaction mixture. After washing with water, the organic layer was dried over anhydrous sodium sulfate. After filtration, the filtrate was concentrated under reduced pressure. The residue was subjected to flash chromatography on a silica gel column, and the fraction obtained from the hexane:ethyl acetate=1:1 eluate was concentrated under reduced pressure, whereby the title compound (116 mg, 0.29 mmol, 79%) was obtained as a colorless oil.

$^1$H-NMR (400 MHz, CDCl$_3$) δ: 1.39-1.64(2H,m), 1.83-2.17(4H,m), 2.88(3H,s), 2.92-3.06(2H,m), 5.20(1H,t,J=7.6 Hz), 6.84-6.92(1H,m), 6.96-7.02(1H,m), 7.05(1H,dd,J=8.6, 0.7 Hz), 7.11-7.18(1H,m), 7.43(1H,dd,J=8.6, 2.5 Hz), 8.37 (1H,dd,J=2.5, 0.7 Hz).

MS m/z: 406 (M$^+$+H).

Example 177

5-Chloro-2-[[1-(2,5-difluorophenyl)-5-(methylsulfonyl)pentyl]sulfonyl]pyridine

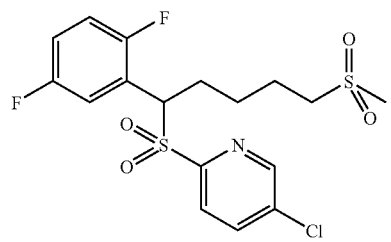

To a methanol (2 ml) solution of 5-chloro-2-[[1-(2,5-difluorophenyl)-5-(methylsulfonyl)pentyl]thio]pyridine (100 mg, 0.25 mmol) was added a water (2 ml) solution of Oxone (potassium peroxymonosulfate compound, 2 KHSO$_5$·KHSO$_4$·K$_2$SO$_4$) (303 mg, 0.49 mmol) at 0° C. After shaking at room temperature for 22 hours, the reaction mixture was added with dichloromethane and the mixture was washed with water. The organic layer was dried over anhydrous sodium sulfate. After filtration, the filtrate was concentrated under reduced pressure. The residue was subjected to flash chromatography on a silica gel column, and the fraction obtained from the hexane:ethyl acetate=1:1 eluate was concentrated under reduced pressure, whereby the title compound (61 mg, 0.14 mmol, 56%) was obtained as a colorless foam.

$^1$H-NMR (400 MHz, CDCl$_3$) δ: 1.37-1.53(2H,m), 1.80-1.97(2H,m), 2.09-2.20(1H,m), 2.36-2.48(1H,m), 2.88(3H,s), 2.96(2H,t,J=7.5 Hz), 5.07(1H,dd,J=11.1, 3.8 Hz), 6.86-7.02 (2H,m), 7.23-7.31(1H,m), 7.74(1H,d,J=8.3 Hz), 7.79(1H,dd, J=8.3, 2.2 Hz), 8.67(1H,d,J=2.2 Hz).

Anal. Calcd for C$_{17}$H$_{18}$ClF$_2$NO$_4$S$_2$·0.25H$_2$O: C, 46.15; H, 4.21; F, 8.59; N, 3.17; S, 14.50. Found: C, 46.38; H, 4.11; F, 8.40; N, 3.20; S, 14.22.

MS m/z: 438 (M$^+$+H).

Referential Example 33

S-(6-Chloro-3-pyridyl) O-ethyl dithiocarbonate

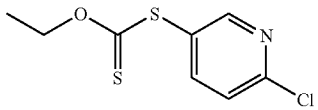

In 1N hydrochloric acid (10 ml) was dissolved 5-amino-2-chloropyridine (643 mg, 3.00 mmol). A water (1 ml) solution of sodium nitrite (207 mg, 3.00 mmol) was added dropwise to the resulting solution at −5° C. After the reaction mixture was stirred at 60° C. for 30 minutes, a water (1 ml) solution of potassium O-ethyl dithiocarbonate (481 mg, 3.00 mmol) was added dropwise thereto at the same temperature. The reaction mixture was then stirred at 80° C. for 1 hour, followed by cooling to room temperature. Ethyl acetate was added, and the resulting mixture was washed with a saturated aqueous solution of sodium bicarbonate. The organic layer was dried over anhydrous sodium sulfate. After filtration, the filtrate was concentrated under reduced pressure. The residue was subjected to flash chromatography on a silica gel column, and the fraction obtained from the hexane:ethyl acetate=49:1 eluate was concentrated under reduced pressure, whereby the title compound (148 mg, 0.63 mmol, 21%) was obtained as a yellow oil.

$^1$H-NMR (400 MHz, CDCl$_3$) δ: 1.37(3H,t,J=7.1 Hz), 4.63 (2H,t,J=7.1 Hz), 7.41(1H,d,J=8.3 Hz), 7.76(1H,dd,J=8.3, 2.4 Hz), 8.45(1H,d, J=2.4 Hz).

MS m/z: 234 (M$^+$+H).

Example 178

2-Chloro-5-[[1-(2,5-difluorophenyl)-5-(methylsulfonyl)pentyl]sulfonyl]pyridine

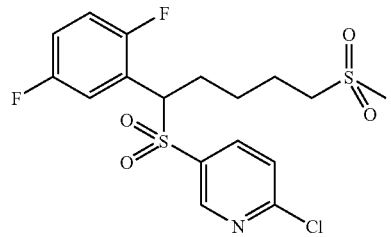

To an ethanol (3 ml) solution of S-(6-chloro-3-pyridyl) O-ethyl dithiocarbonate (145 mg, 0.62 mmol) was added a 1N aqueous solution (3 ml) of sodium hydroxide, followed by stirring at 80° C. for 2 hours. After cooling to room temperature, the reaction mixture was added with water and the mixture was then washed with dichloromethane. The water layer was made acidic with acetic acid and then, was extracted with dichloromethane. The organic layer was dried over anhydrous sodium sulfate. After filtration, the filtrate was concentrated under reduced pressure, whereby 6-chloro-3-pyridinethiol was obtained as a yellow solid.

To a dichloromethane (5 ml) solution of the 1-(2,5-difluorophenyl)-5-(methylsulfonyl)-1-pentanol (173 mg, 0.62 mmol) obtained in Referential Example 30 were successively added triethylamine (0.130 ml, 0.93 mmol) and methanesulfonyl chloride (0.060 ml, 0.78 mmol) at 0° C. The resulting mixture was stirred at room temperature for 2 hours. The reaction mixture was washed with a saturated aqueous solution of sodium bicarbonate. The organic layer was dried over anhydrous sodium sulfate. After filtration, the filtrate was concentrated under reduced pressure.

To an N,N-dimethylformamide (6 ml) solution of the residue were successively added 6-chloro-3-pyridinethiol and potassium carbonate (107 mg, 0.78 mmol). The resulting mixture was stirred at room temperature for 2 hours. After addition of ethyl acetate and washing with water, the organic layer was dried over anhydrous sodium sulfate. After filtration, the filtrate was concentrated under reduced pressure.

The residue was dissolved in dichloromethane (5 ml), followed by the addition of 3-chloroperbenzoic acid (214 mg, 1.24 mmol) at 0° C. The mixture was stirred at room temperature for 2 hours. The reaction mixture was washed with a 1N aqueous solution of sodium hydroxide and then, the organic layer was dried over anhydrous sodium sulfate. After filtration, the filtrate was concentrated under reduced pressure. The residue was subjected to flash silica gel chromatography, and the fraction obtained from the hexane:ethyl acetate=2:1 eluate was concentrated under reduced pressure. The resulting solid was washed with diethyl ether and then, collected by filtration, whereby the title compound (187 mg, 0.43 mmol, 69%) was obtained as a white powder.

$^1$H-NMR (400 MHz, CDCl$_3$) δ: 1.40-1.57(2H,m), 1.84-1.98(2H,m), 2.11-2.22(1H,m), 2.50-2.60(1H,m), 2.89(3H,s), 2.93-3.02(2H,m), 4.48(1H,dd,J=10.4, 3.8 Hz), 6.82-6.91(1H, m), 7.00-7.07(1H,m), 7.24-7.29(1H,m), 7.38(1H,d,J=8.3 Hz), 7.79(1H,dd,J=8.3, 2.4 Hz), 8.48(1H,d,J=2.4 Hz).

IR (ATR) cm$^{-1}$: 3059, 1566, 1495, 1446, 1279, 1161, 1107, 829.

Example 179

2-[1-(Cyclohexylsulfonyl)-5-(methylsulfonyl)pentyl]-1,4-difluorobenzene

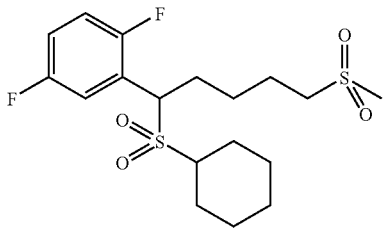

To a dichloromethane (3 ml) solution of the 1-(2,5-difluorophenyl)-5-(methylsulfonyl)-1-pentanol (100 mg, 0.36 mmol) obtained in Referential Example 30 were successively added triethylamine (0.072 ml, 0.52 mmol) and methanesulfonyl chloride (0.033 ml, 0.43 mmol) at 0° C. The resulting mixture was stirred at room temperature for 1 hour. The reaction mixture was washed with a saturated aqueous solution of sodium bicarbonate. The organic layer was dried over anhydrous sodium sulfate. After filtration, the filtrate was concentrated under reduced pressure.

To an acetonitrile (3 ml) solution of the resulting residue were successively added cyclohexanethiol (0.066 ml, 0.54 mmol) and cesium carbonate (176 mg, 0.54 mmol). The resulting mixture was stirred at room temperature for 2 hours. The reaction mixture added with dichloromethane was washed with brine and then, the organic layer was dried over anhydrous sodium sulfate. After filtration, the filtrate was concentrated under reduced pressure. The residue was subjected to flash silica gel chromatography, and the fraction obtained from the hexane:ethyl acetate=2:1 eluate was concentrated under reduced pressure.

The residue was dissolved in dichloromethane (3 ml), followed by the addition of 3-chloroperbenzoic acid (113 mg, 0.43 mmol) at 0° C. and the mixture was stirred at room temperature for 2 hours. The reaction mixture was washed with a 1N aqueous solution of sodium hydroxide and then, the organic layer was dried over anhydrous sodium sulfate. After filtration, the filtrate was concentrated under reduced pressure. The residue was subjected to flash silica gel chromatography, and the fraction obtained from the hexane:ethyl acetate=3:2 eluate was concentrated under reduced pressure. The resulting solid was washed with diethyl ether and collected by filtration, whereby the title compound (53 mg, 0.13 mmol, 36%) was obtained as a white powder.

$^1$H-NMR (400 MHz, CDCl$_3$) δ: 1.03-1.27(3H,m), 1.30-1.70(5H,m), 1.78-2.10(7H,m), 2.40-2.60(2H,m), 2.88(3H,s), 2.90-3.02(2H,m), 4.54(1H,dd,J=11.1, 2.6 Hz), 7.04-7.15(2H,m), 7.36-7.42(1H,m).

IR (ATR) cm$^{-1}$: 2931, 1495, 1273, 1126, 1117, 976.

Anal. Calcd for $C_{18}H_{26}F_2O_4S_2$: C, 52.92; H, 6.41; F, 9.30; S, 15.70. Found: C, 52.85; H, 6.31; F, 9.34; S, 15.53.

MS m/z: 409 (M$^+$+H).

Example 180

4-[4-[[1-(2,5-Difluorophenyl)-5-(methylsulfonyl)pentyl]sulfonyl]phenyl]morpholine

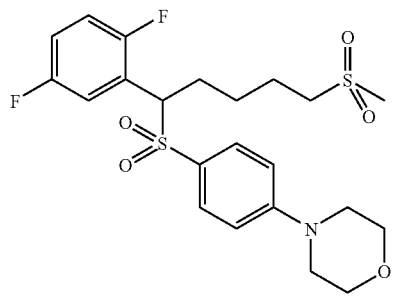

To a dimethylsulfoxide (0.5 ml) solution of the 1,4-difluoro-2-[1-[(4-fluorophenyl)sulfonyl]-5-(methylsulfonyl)pentyl]benzene (40 mg, 0.095 mmol) obtained in Example 160 were successively added morpholine (0.012 ml, 0.14 mmol) and 1-methylpiperidine (0.017 ml, 0.14 mmol). The resulting mixture was allowed to stand at 80° C. for 24 hours. The reaction mixture was purified by preparative high performance liquid chromatography (using a mixed solvent of water/acetonitrile/formic acid). The resulting solid was washed with diethyl ether and collected by filtration, whereby the title compound (43 mg, 0.088 mmol, 92%) was obtained as a white powder.

$^1$H-NMR (400 MHz, CDCl$_3$) δ: 1.31-1.51(2H,m), 1.77-1.94(2H,m), 2.02-2.14(1H,m), 2.38-2.50(1H,m), 2.88(3H,s), 2.90-3.00(2H,m), 3.28(4H,t,J=4.9 Hz), 3.85(4H,t,J=4.9 Hz), 4.47(1H,dd,J=10.6, 3.5 Hz), 6.78(2H,d,J=9.0 Hz), 6.83-6.90 (1H,m), 6.94-7.01(1H,m), 7.19-7.24(1H,m), 7.44(2H,d, J=9.0 Hz).

IR (ATR) cm$^{-1}$: 2962, 1591, 1498, 1271, 1131, 1090, 976, 926.

Anal. Calcd for $C_{22}H_{27}F_2NO_5S_2$: C, 54.19; H, 5.58; F, 7.79; N, 2.87; S, 13.15. Found: C, 53.93; H, 5.53; F, 7.90; N, 2.87; S, 13.17.

MS m/z: 488 (M$^+$+H).

Example 181

1-[4-[[1-(2,5-Difluorophenyl)-5-(methylsulfonyl)pentyl]sulfonyl]phenyl]piperidine

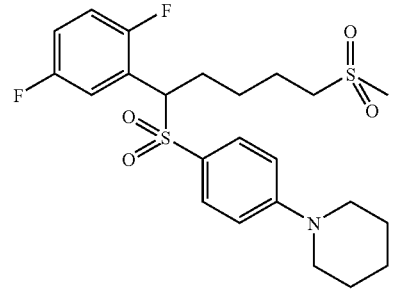

In a similar manner to Example 180 except for the use of 1,4-difluoro-2-[1-[(4-fluorophenyl)sulfonyl]-5-(methylsulfonyl)pentyl]benzene (100 mg, 0.24 mmol) and piperidine (0.035 ml, 0.36 mmol), the title compound (83 mg, 0.17 mmol, 71%) was obtained as a white powder.

$^1$H-NMR (400 MHz, CDCl$_3$) δ: 1.30-1.51(2H,m), 1.56-1.72(6H,m), 1.76-1.93(2H,m), 2.01-2.13(1H,m), 2.36-2.48(1H,m), 2.87(3H,s), 2.88-3.00(2H,m), 3.34(4H,br s), 4.45(1H,dd,J=11.5, 3.4 Hz), 6.75(2H,d,J=9.0 Hz), 6.82-6.90(1H,m), 6.92-7.00(1H,m), 7.16-7.23(1H,m), 7.38(2H,d,J=9.0 Hz).

IR (ATR) cm$^{-1}$: 2935, 1591, 1495, 1282, 1122, 1090.

Anal. Calcd for C$_{23}$H$_{29}$F$_2$NO$_4$S$_2$: C, 56.89; H, 6.02; F, 7.82; N, 2.88; S, 13.21. Found: C, 56.73; H, 5.99; F, 7.88; N, 2.93; S, 13.22.

MS m/z: 486 (M$^+$+H).

Example 182

4-[1-(2,5-Difluorophenyl)-5-methylsulfonylpentylsulfonyl]-N,N-dimethylaniline

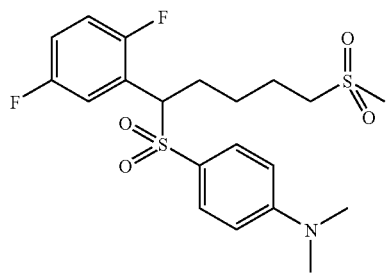

In a similar manner to Example 180 except for the use of 1,4-difluoro-2-[1-[(4-fluorophenyl)sulfonyl]-5-(methylsulfonyl)pentyl]benzene (100 mg, 0.24 mmol) and dimethylamine hydrochloride (58 mg, 0.71 mmol), the title compound (83 mg, 0.19 mmol, 78%) was obtained as a white powder.

$^1$H-NMR (400 MHz, CDCl$_3$) δ: 1.30-1.50(2H,m), 1.76-1.93(2H,m), 2.01-2.12(1H,m), 2.36-2.48(1H,m), 2.87(3H,s), 2.88-3.00(2H,m), 3.03(6H,s), 4.45(1H,dd,J=11.2, 2.9 Hz), 6.55(2H, d,J=9.0 Hz), 6.82-6.91(1H,m), 6.93-7.01(1H,m), 7.18-7.24(1H,m), 7.38(2H,d,J=9.0 Hz).

IR (ATR) cm$^{-1}$: 2941, 1603, 1496, 1284, 1269, 1230, 1138, 1088.

Anal. Calcd for C$_{20}$H$_{25}$F$_2$NO$_4$S$_2$: C, 53.91; H, 5.66; F, 8.53; N, 3.14; S, 14.39. Found: C, 53.61; H, 5.61; F, 8.51; N, 3.06; S, 14.35.

MS m/z: 446 (M$^+$+H).

Example 183

1-[4-[[1-(2,5-Difluorophenyl)-5-(methylsulfonyl)pentyl]sulfonyl]phenyl]-4-methylpiperazine

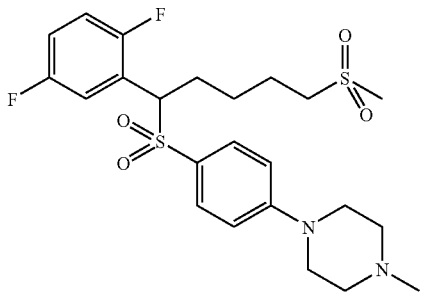

In a similar manner to Example 180 except for the use of 1,4-difluoro-2-[1-[(4-fluorophenyl)sulfonyl]-5-(methylsulfonyl)pentyl]benzene (100 mg, 0.24 mmol) and 1-methylpiperazine (0.040 ml, 0.36 mmol), the title compound (68 mg, 0.14 mmol, 57%) was obtained as a white powder.

$^1$H-NMR (400 MHz, CDCl$_3$) δ: 1.31-1.51(2H,m), 1.77-1.94(2H,m), 2.02-2.13(1H,m), 2.35(3H,s), 2.36-2.48(1H,m), 2.53(4H,t,J=5.1 Hz), 2.87(3H,s), 2.88-3.00(2H,m), 3.34(4H, t, J=5.1 Hz), 4.46(1H,dd,J=11.0, 3.7 Hz), 6.77(2H,d,J=9.0 Hz), 6.82-6.90(1H,m), 6.92-7.01(1H,m), 7.18-7.23(1H,m), 7.41(2H,d,J=9.0 Hz).

IR (ATR) cm$^{-1}$: 1595, 1495, 1292, 1134, 1090, 1003, 968.

Anal. Calcd for C$_{23}$H$_{30}$F$_2$N$_2$O$_4$S$_2$: C, 55.18; H, 6.04; F, 7.59; N, 5.60; S, 12.81. Found: C, 54.92; H, 5.92; F, 7.66; N, 5.60; S, 12.80.

MS m/z: 501 (M$^+$+H).

Example 184

N-Benzyl-4-[1-(2,5-difluorophenyl)-5-methylsulfonylpentylsulfonyl]-N-methylaniline

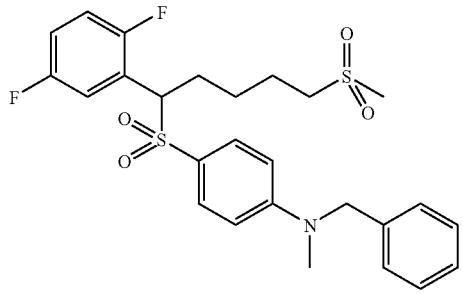

In a similar manner to Example 180 except for the use of 1,4-difluoro-2-[1-[(4-fluorophenyl)sulfonyl]-5-(methylsulfonyl)pentyl]benzene (100 mg, 0.24 mmol) and N-benzylmethylamine (0.046 ml, 0.36 mmol), the title compound (34 mg, 0.065 mmol, 27%) was obtained as a white powder.

$^1$H-NMR (400 MHz, CDCl$_3$) δ: 1.30-1.50(2H,m), 1.76-1.93(2H,m), 2.01-2.13(1H,m), 2.36-2.48(1H,m), 2.87(3H,s), 2.88-3.00(2H,m), 3.11(3H,s), 4.46(1H,dd,J=11.4, 3.5 Hz), 4.58(1H,d, J=17.5 Hz), 4.63(1H,d,J=17.5 Hz), 6.60(2H,d, J=9.0 Hz), 6.78-6.86(1H,m), 6.89-6.98(1H,m), 7.12(2H,d, J=7.1 Hz), 7.13-7.20(1H,m), 7.24-7.35(3H,m), 7.35(2H,d, J=9.0 Hz).

IR (ATR) cm$^{-1}$: 1593, 1493, 1390, 1281, 1124, 1088.

Anal. Calcd for C$_{26}$H$_{29}$F$_2$NO$_4$S$_2$: C, 59.86; H, 5.60; F, 7.28; N, 2.69; S, 12.29. Found: C, 59.74; H, 5.52; F, 7.35; N, 2.76; S, 12.44.

MS m/z: 522 (M$^+$+H).

Example 185

N-Benzyl-4-[1-(2,5-difluorophenyl)-5-methylsulfonylpentylsulfonyl]aniline

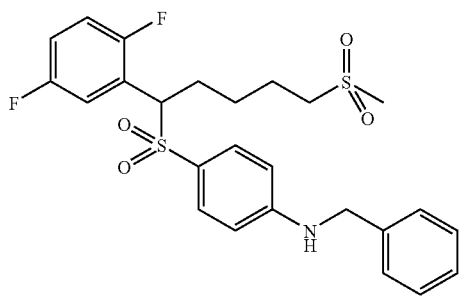

In a similar manner to Example 180 except for the use of 1,4-difluoro-2-[1-[(4-fluorophenyl)sulfonyl]-5-(methylsulfonyl)pentyl]benzene (100 mg, 0.24 mmol) and benzylamine (0.039 ml, 0.36 mmol), the title compound (49 mg, 0.097 mmol, 41%) was obtained as a white powder.

$^1$H-NMR (400 MHz, CDCl$_3$) δ: 1.31-1.50(2H,m), 1.78-1.93(2H,m), 2.01-2.13(1H,m), 2.37-2.48(1H,m), 2.87(3H,s), 2.89-3.00(2H,m), 4.36(2H,br d,J=3.7 Hz), 4.46(1H,dd, J=11.2, 3.2 Hz), 4.61(1H,br s), 6.51(2H,d,J=9.0 Hz), 6.80-6.87(1H,m), 6.90-6.98(1H,m), 7.15-7.22(1H,m), 7.29-7.40 (5H,m), 7.34(2H,d,J=9.0 Hz).

IR (ATR) cm$^{-1}$: 3411, 1597, 1495, 1282, 1142, 1086, 870.

Anal. Calcd for C$_{25}$H$_{27}$F$_2$NO$_4$S$_2$.0.25H$_2$O: C, 58.63; H, 5.41; F, 7.42; N, 2.74; S, 12.52. Found: C, 58.59; H, 5.27; F, 7.49; N, 2.78; S, 12.61.

MS m/z: 508 (M$^+$+H).

Referential Example 34

6-(t-Butyl-diphenylsilyloxy)-1-(2,5-difluorophenyl)-1-hexanol

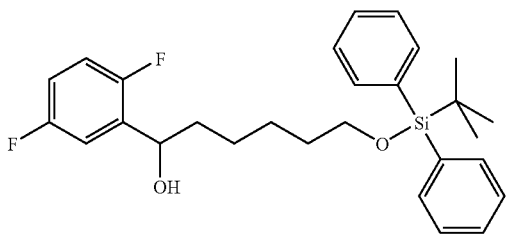

A tetrahydrofuran (30 ml) solution of 1-bromo-2,5-difluorobenzene (0.956 ml, 8.46 mmol) was stirred at −78° C. To the reaction mixture was added a hexane solution (6.46 ml, 10.2 mmol) of n-butyl lithium. The reaction mixture was added to a tetrahydrofuran (20 ml) solution of 6-(t-butyldiphenylsilyloxy)hexanal (2.50 g, 7.05 mmol) at −78° C. and the mixture was stirred at the same temperature for 30 minutes. After the temperature of the reaction mixture was elevated to room temperature, diethyl ether was added thereto. The mixture was washed with a saturated aqueous solution of ammonium chloride and the organic layer was dried over anhydrous sodium sulfate. After filtration, the filtrate was concentrated under reduced pressure. The residue was subjected to flash silica gel chromatography, and the fraction obtained from the hexane:ethyl acetate=9:1 eluate was concentrated under reduced pressure, whereby the title compound (2.92 g, 4.65 mmol, 88%) was obtained as a colorless oil.

$^1$H-NMR (400 MHz, CDCl$_3$) δ: 1.04(9H,m), 1.21-1.90 (8H,m), 3.64(2H,t,J=6.3 Hz), 4.96(1H,t,J=6.5 Hz), 6.86-7.01 (2H,m), 7.13-7.20(1H,m), 7.32-7.45(6H,m), 7.62-7.70(4H, m).

Example 186

6-[(5-Chloro-2-pyridyl)sulfonyl]-(2,5-difluorophenyl)-1-hexanol

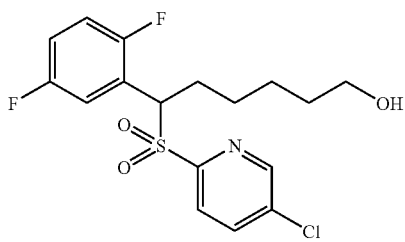

To a dichloromethane (20 ml) solution of 6-(t-butyldiphenylsilyl)oxy-1-(2,5-difluorophenyl)-1-hexanol (1.04 g, 2.22 mmol) were successively added triethylamine (0.619 ml, 4.44 mmol) and methanesulfonyl chloride (0.258 ml, 3.33 mmol) at 0° C. The mixture was stirred at room temperature for 2 hours. The reaction mixture was washed with a saturated aqueous solution of sodium bicarbonate and the organic layer was dried over anhydrous sodium sulfate. After filtration, the filtrate was concentrated under reduced pressure.

To an N,N-dimethylformamide (20 ml) solution of the residue were successively added the 5-chloro-2-pyridinethiol (323 mg, 2.22 mmol) obtained in Referential Example 32 and potassium carbonate (368 mg, 2.66 mmol). The mixture was stirred at room temperature for 3 hours. Ethyl acetate was added to the reaction mixture. After washing with water, the organic layer was dried over anhydrous sodium sulfate. After filtration, the filtrate was concentrated under reduced pressure.

The residue thus obtained was dissolved in dichloromethane (20 ml) and at 0° C., 3-chloroperbenzoic acid (1.18 g, 4.44 mmol) was added to the resulting solution. The mixture was stirred at room temperature for 3 hours. The reaction mixture was washed with a 1N aqueous solution of sodium hydroxide. The organic layer was then dried over anhydrous sodium sulfate. After filtration, the filtrate was concentrated under reduced pressure.

A tetrahydrofuran (10 ml) solution of the residue was added with a tetrahydrofuran solution (3.33 ml, 3.33 mmol) of tetrabutylammonium fluoride, and the mixture was stirred at room temperature for 8 hours. After concentration of the reaction mixture under reduced pressure, the residue was dissolved in ethyl acetate, followed by washing with water. The organic layer was dried over anhydrous sodium sulfate. After filtration, the filtrate was concentrated under reduced pressure. The residue was subjected to flash silica gel chromatography and the fraction obtained from the hexane:ethyl acetate=7:3 eluate was concentrated under reduced pressure, whereby the title compound (477 mg, 1.22 mmol, 55%) was obtained as a colorless oil.

$^1$H-NMR (400 MHz, CDCl$_3$) δ: 1.17-1.59(6H,m), 2.04-2.17(1H,m), 2.30-2.42(1H,m), 3.59(2H,t,J=6.3 Hz), 5.07

(1H,dd,J=11.6, 2.8 Hz), 6.84-6.92(1H,m), 6.93-7.01(1H,m), 7.26-7.32(1H,m), 7.74(1H,dd,J=8.3, 0.7 Hz), 7.78(1H,dd, J=8.3, 2.2 Hz), 8.67(1H,dd,J=2.2, 0.7 Hz). MS m/z: 390 (M⁺+H).

Example 187

5-Chloro-2-[[1-(2,5-difluorophenyl)cyclohexyl]sulfonyl]pyridine

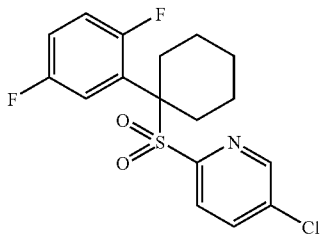

To a toluene (5 ml) solution of 6-[(5-chloro-2-pyridyl)sulfonyl]-(2,5-difluorophenyl)-1-hexanol (308 mg, 0.79 mmol) was added a toluene (3 ml) solution of cyanomethylenetri-n-butylphosphorane (424 mg, 1.58 mmol). The resulting mixture was heated under reflux for 16 hours. After cooling to room temperature, the reaction mixture was concentrated under reduced pressure. The residue thus obtained was subjected to flash chromatography on a silica gel column and the fraction obtained from the hexane:ethyl acetate=9:1 eluate was concentrated under reduced pressure. The resulting solid was washed with diethyl ether and then collected by filtration, whereby the title compound (96 mg, 0.26 mmol, 33%) was obtained as a white powder.

$^1$H-NMR (400 MHz, CDCl$_3$) δ: 1.12-1.42(3H,m), 1.58-1.66(1H,m), 1.77-1.86(2H,m), 2.11-2.25 (2H,m), 2.91(2H,br s), 6.79-6.89(1H,m), 6.97-7.04(1H,m), 7.06-7.13(1H,m), 7.50(1H,d,J=8.3 Hz), 7.72(1H,dd,J=8.3, 2.4 Hz), 8.65(1H, dd,J=2.4 Hz).

IR (ATR) cm$^{-1}$: 2933, 2862, 1493, 1302, 1190, 1153, 1107, 1012.

Anal. Calcd for C$_{17}$H$_{16}$ClF$_2$NO$_2$S: C, 54.91; H, 4.34; Cl, 9.53; F, 10.22; N, 3.77; S, 8.62. Found: C, 54.88; H, 4.50; Cl, 9.65; F, 10.35; N, 3.80; S, 8.76.

MS m/z: 372 (M⁺+H).

Referential Example 35

7-(t-Butyldiphenylsilyloxy)-1-(2,5-difluorophenyl)-1-heptanol

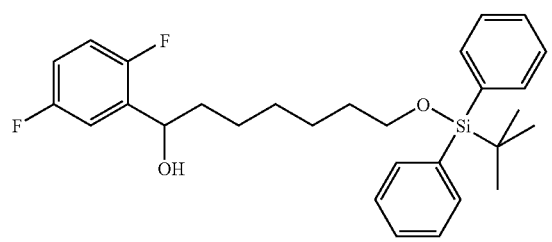

A tetrahydrofuran (40 ml) solution of 1-bromo-2,5-difluorobenzene (1.21 ml, 10.7 mmol) was stirred at −78° C., followed by the addition of a hexane solution (8.50 ml, 13.4 mmol) of n-butyl lithium. The reaction mixture was added to a tetrahydrofuran (20 ml) solution of 7-(t-butyldiphenylsilyloxy)heptanal (3.28 g, 8.90 mmol) at −78° C. and the mixture was stirred at the same temperature for 30 minutes. After the temperature of the reaction mixture was elevated to room temperature, diethyl ether was added thereto. The mixture was washed with a saturated aqueous solution of ammonium chloride. The organic layer was then dried over anhydrous sodium sulfate. After filtration, the filtrate was concentrated under reduced pressure. The residue was subjected to flash silica gel chromatography, and the fraction obtained from the hexane:ethyl acetate=9:1 eluate was concentrated under reduced pressure, whereby the title compound (3.88 g, 8.04 mmol, 90%) was obtained as a colorless oil.

$^1$H-NMR (400 MHz, CDCl$_3$) δ: 1.04(9H,m), 1.21-1.92 (10H,m), 3.64(2H,t,J=6.5 Hz), 4.97(1H,t,J=6.5 Hz), 6.86-7.00(2H,m), 7.13-7.20(1H,m), 7.33-7.44(6H,m), 7.62-7.70 (4H,m).

Example 188

7-[(5-Chloro-2-pyridyl)sulfonyl]-(2,5-difluorophenyl)-1-heptanal

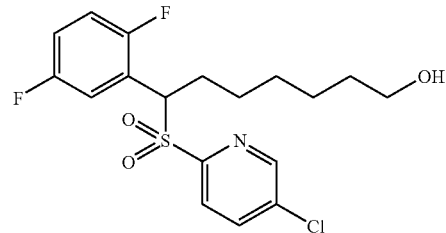

To a dichloromethane (20 ml) solution of 7-(t-butyldiphenylsilyloxy)-1-(2,5-difluorophenyl)-1-heptanol (1.04 g, 2.15 mmol) were successively added triethylamine (0.601 ml, 4.31 mmol) and methanesulfonyl chloride (0.250 ml, 3.23 mmol) at 0° C. The resulting mixture was stirred at room temperature for 2 hours. The reaction mixture was washed with a saturated aqueous solution of sodium bicarbonate and then, the organic layer was dried over anhydrous sodium sulfate. After filtration, the filtrate was concentrated under reduced pressure.

To an N,N-dimethylformamide (20 ml) solution of the residue were successively added the 5-chloro-2-pyridinethiol (314 mg, 2.15 mmol) obtained in Referential Example 32 and potassium carbonate (357 mg, 2.59 mmol) and the resulting mixture was stirred at room temperature for 3 hours. Ethyl acetate was added and the mixture was washed with water. The organic layer was then dried over anhydrous sodium sulfate. After filtration, the filtrate was concentrated under reduced pressure.

To a dichloromethane (20 ml) solution of the resulting residue was added 3-chloroperbenzoic acid (1.14 g, 4.31 mmol) at 0° C. and the mixture was stirred at room temperature for 2 hours. The reaction mixture was washed with a 1N aqueous solution of sodium hydroxide. The organic layer was then dried over anhydrous sodium sulfate. After filtration, the filtrate was concentrated under reduced pressure.

The resulting residue was dissolved in tetrahydrofuran (10 ml), followed by the addition of a tetrahydrofuran solution (3.23 ml, 3.23 mmol) of tetrabutylammonium fluoride. The resulting mixture was stirred at room temperature for 8 hours.

After concentration of the reaction mixture under reduced pressure, the residue was dissolved in ethyl acetate and the solution was washed with water. The organic layer was dried over anhydrous sodium sulfate. After filtration, the filtrate was concentrated under reduced pressure. The residue was subjected to flash silica gel chromatography, and the fraction obtained from the hexane:ethyl acetate=7:3 eluate was concentrated under reduced pressure, whereby the title compound (595 mg, 1.47 mmol, 69%) was obtained as a colorless oil.

$^1$H-NMR (400 MHz, CDCl$_3$) δ: 1.14-1.66(8H,m), 2.03-2.17(1H,m), 2.29-2.40(1H,m), 3.60(2H,t,J=6.6 Hz), 5.06 (1H,dd,J=11.6, 3.1 Hz), 6.84-6.91(1H,m), 6.92-7.00(1H,m), 7.25-7.31(1H,m), 7.74(1H,dd,J=8.3 Hz), 7.78(1H,dd,J=8.3, 2.2 Hz), 8.67(1H,dd,J=2.2 Hz).

MS m/z: 404 (M$^+$+H).

Example 189

5-Chloro-2-[[1-(2,5-difluorophenyl)cycloheptyl]sulfonyl]pyridine

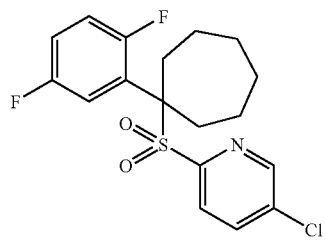

To a toluene (8 ml) solution of 7-[(5-chloro-2-pyridyl)sulfonyl]-(2,5-difluorophenyl)-1-heptanol (436 mg, 1.08 mmol) was added a toluene (3 ml) solution of cyanomethylenetri-n-butylphosphorane (579 mg, 2.16 mmol). The resulting mixture was heated under reflux for 16 hours. The reaction mixture was cooled to room temperature and then, was concentrated under reduced pressure. The residue thus obtained was subjected to flash chromatography on a silica gel column and the fraction obtained from the hexane:ethyl acetate=9:1 eluate was concentrated under reduced pressure. The resulting solid was washed with diethyl ether and then collected by filtration, whereby the title compound (79 mg, 0.20 mmol, 19%) was obtained as a white powder.

$^1$H-NMR (400 MHz, CDCl$_3$) δ: 1.32-1.63(6H,m), 1.82-1.94(2H,m), 2.42-2.52(2H,m), 2.79-2.90(2H,m), 6.81-6.90 (1H,m), 6.97-7.07(2H,m), 7.48(1H,d,J=8.6 Hz), 7.71(1H,dd, J=8.6, 2.5 Hz), 8.65(1H,dd,J=2.5 Hz).

IR (ATR) cm$^{-1}$: 2933, 2864, 1493, 1308, 1188, 1159, 1107, 1011.

Anal. Calcd for C$_{18}$H$_{18}$ClF$_2$NO$_2$S: C, 56.03; H, 4.70; Cl, 9.19; F, 9.85; N, 3.63; S, 8.31. Found: C, 55.92; H, 4.77; Cl, 9.23; F, 9.90; N, 3.67; S, 8.41.

MS m/z: 386 (M$^+$+H).

Referential Example 36

2,5-Difluorophenyl-4-pyridylmethanol

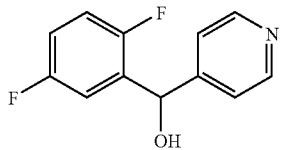

A tetrahydrofuran (30 ml) solution of 1-bromo-2,5-difluorobenzene (1.08 ml, 9.60 mmol) was stirred at −78° C., followed by the addition of a hexane solution (7.32 ml, 11.5 mmol) of n-butyl lithium. To the resulting mixture was added a tetrahydrofuran (10 ml) solution of 4-pyridinecarboxyaldehyde (0.764 ml, 8.00 mmol) at −78° C. and the mixture was stirred at the same temperature for 30 minutes. After the temperature of the reaction mixture was raised to room temperature, diethyl ether was added thereto. The mixture was washed with a saturated aqueous solution of sodium bicarbonate. The organic layer was then dried over anhydrous sodium sulfate. After filtration, the filtrate was concentrated under reduced pressure. The residue was subjected to flash silica gel chromatography, and the fraction obtained from the hexane:ethyl acetate=7:3 eluate was concentrated under reduced pressure. The resulting solid was washed with diisopropyl ether and then collected by filtration, whereby the title compound (1.15 g, 5.20 mmol, 65%) was obtained as a white powder.

$^1$H-NMR (400 MHz, CDCl$_3$) δ: 4.25(1H,br s), 6.09(1H,s), 6.89-7.05(2H,m), 7.14-7.23(1H,m), 7.34(2H,d,J=5.4 Hz), 8.44(2H,d,J=5.4 Hz).

Example 190

5-Chloro-2-[(2,5-difluorophenyl-4-pyridylmethyl)thio]pyridine

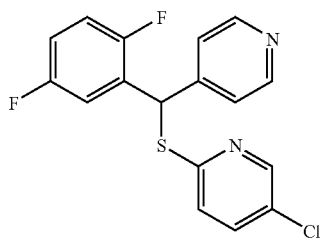

To a dichloromethane (10 ml) solution of 2,5-difluorophenyl-4-pyridylmethanol (221 mg, 1.00 mmol) were successively added triethylamine (0.279 ml, 2.00 mmol) and methanesulfonyl chloride (0.116 ml, 1.50 mmol) at 0° C. The resulting mixture was stirred at room temperature for 3 hours. The reaction mixture was washed with a saturated aqueous solution of sodium bicarbonate and then, the organic layer was dried over anhydrous sodium sulfate. After filtration, the filtrate was concentrated under reduced pressure.

To an N,N-dimethylformamide (10 ml) solution of the resulting residue were successively added 5-chloro-2-pyridinethiol (145 mg, 1.00 mmol) obtained in Referential Example 32 and potassium carbonate (166 mg, 1.20 mmol). The resulting mixture was stirred at room temperature for 2 hours. Ethyl acetate was added and the mixture was washed with water. The organic layer was then dried over anhydrous sodium sulfate. After filtration, the filtrate was concentrated under reduced pressure. The residue was subjected to flash silica gel chromatography and the fraction obtained from the hexane: ethyl acetate=17:3 eluate was concentrated under reduced pressure, whereby the title compound (267 mg, 0.77 mmol, 77%) was obtained as a yellow solid.

$^1$H-NMR (400 MHz, CDCl$_3$) δ: 6.52(1H,s), 6.92-6.98(1H, m), 6.99-7.06(1H,m), 7.48(1H,dd,J=8.5, 0.7 Hz), 7.17-7.23 (1H,m), 7.34(2H,d,J=6.1 Hz), 7.47(1H,dd,J=8.5, 2.4 Hz), 8.33(1H,dd,J=2.4, 0.7 Hz), 8.54(2H,d,J=6.1 Hz).

MS m/z: 349 (M$^+$+H).

Example 191

5-Chloro-2-[(2,5-difluorophenyl-4-pyridylmethyl)sulfonyl]pyridine

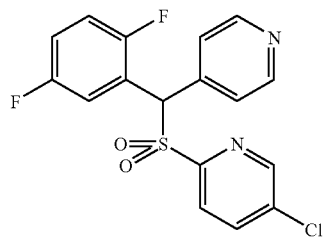

To a methanol (6 ml) solution of 5-chloro-2-[(2,5-difluorophenyl-4-pyridylmethyl)thio]pyridine (239 mg, 0.68 mmol) was added a water (12 ml) solution of Oxone (potassium peroxymonosulfate compound, 2 KHSO$_5$·KHSO$_4$·K$_2$SO$_4$) (631 mg, 1.03 mmol) at 0° C. After stirring at room temperature for 3 days, to the reaction mixture was added dichloromethane and the mixture was washed with a saturated aqueous solution of sodium bicarbonate. The organic layer was dried over anhydrous sodium sulfate. After filtration, the filtrate was concentrated under reduced pressure. The residue was purified by preparative high performance liquid chromatography (using a mixed solvent of water/acetonitrile/formic acid). The resulting solid was washed with hexane/diisopropyl ether and then, collected by filtration, whereby the title compound (67 mg, 0.18 mmol, 26%) was obtained as a white powder.

$^1$H-NMR (400 MHz, CDCl$_3$) δ: 6.44(1H,s), 6.96-7.08(2H, m), 7.48(2H,d,J=6.3 Hz), 7.70-7.77(1H,m), 7.79(1H,dd, J=8.3, 2.2 Hz), 7.84(1H,dd,J=8.3, 0.7 Hz), 8.61(2H, d,J=6.3 Hz), 8.67(1H,dd,J=2.2, 0.7 Hz).

IR (ATR) cm$^{-1}$: 1591, 1493, 1329, 1161, 1107, 1014.

Anal. Calcd for C$_{17}$H$_{11}$ClF$_2$N$_2$O$_2$S: C, 53.62; H, 2.91; F, 9.98; N, 7.36; S, 8.42. Found: C, 53.55; H, 2.87; F, 10.10; N, 7.40; S, 8.55.

MS m/z: 381 (M$^+$+H).

Example 192

5-(4-Chlorobenzenesulfonylmethyl)-1H-tetrazole

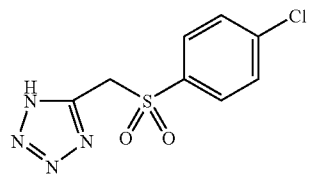

To an N,N-dimethylformamide (100 ml) solution of 4-chlorophenylsulfonylacetonitrile (2.81 g, 13.0 mmol) and triethylamine hydrochloride (4.24 g, 65.2 mmol) was added sodium azide (10.8 g, 78.2 mmol) and the mixture was stirred at 80° C. for 16 hours. The reaction mixture was then cooled to room temperature. Ethyl acetate was added and the mixture was washed with a saturated aqueous solution of ammonium chloride. The organic layer was dried over anhydrous sodium sulfate. After filtration, the filtrate was concentrated under reduced pressure. The resulting solid was washed with diethyl ether and then, collected by filtration, whereby the title compound (2.53 g, 9.78 mmol, 75%) was obtained as a white solid.

$^1$H-NMR (400 MHz, CD$_3$OD) δ: 5.02(2H,s), 7.62(1H,d, J=8.6 Hz), 7.73(2H,d,J=8.6 Hz).

MS m/z: 300 (M$^+$+H+CH$_3$CN).

Example 193

1-Benzyl-5-(4-chlorobenzenesulfonylmethyl)-1H-tetrazole (Isomer 193-A) and 2-benzyl-5-(4-chlorobenzenesulfonylmethyl)-2H-tetrazole (Isomer 193-B)

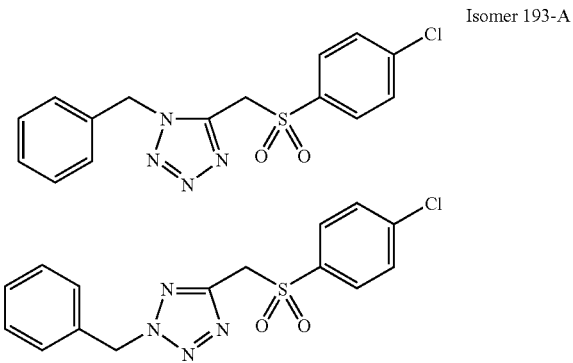

To a dichloromethane/tetrahydrofuran (1:1) (20 ml) solution of 5-(4-chlorophenylsulfonylmethyl)-1H-tetrazole (837 mg, 3.24 mmol) and benzyl alcohol (0.335 ml, 3.24 mmol) was added triphenylphosphine (849 mg, 3.24 mmol) under ice cooling. Then, diethyl azodicarboxylate (0.510 ml, 3.24 mmol) was added dropwise at the same temperature. The reaction mixture was stirred at room temperature for 16 hours, followed by concentration under reduced pressure. The residue was subjected to flash silica gel chromatography and the fraction obtained from the hexane:ethyl acetate=4:1 eluate was concentrated under reduced pressure, whereby the title Isomer 193-A (406 mg, 1.16 mmol, 36%) and the title Isomer 193-B (317 mg, 0.91 mmol, 28%) were obtained, each as a white solid.

Based on the NOE (Nuclear Overhauser Effect) test, the structure of each of Isomer 193-A and Isomer 193-B was determined.

Isomer 193-A $^1$H-NMR (400 MHz, CDCl$_3$) δ: 4.46(2H,s), 5.88(2H,s), 7.22-7.43(5H,m), 7.51(2H,d,J=8.7 Hz), 7.57(2H,d,J=8.7 Hz).

MS m/z: 349 (M$^+$+H).

Isomer 193-B $^1$H-NMR (400 MHz, CDCl$_3$) δ: 4.68(2H,s), 5.72(2H,s), 7.22-7.45(5H,m), 7.33(2H,d,J=8.6 Hz), 7.55(2H,d,J=8.6 Hz).

MS m/z: 349 (M$^+$+H).

Example 194

6-(1-Benzyl-1H-tetrazol-5-yl)-6-[(4-chlorophenyl)sulfonyl]-1-hexanol

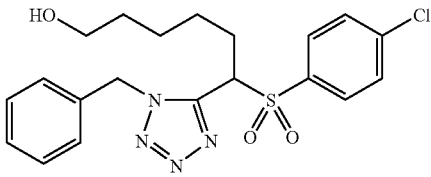

To a toluene (5 ml) solution of 1-benzyl-5-(4-chlorobenzenesulfonylmethyl)-1H-tetrazole (Isomer 193-A) (174 mg, 0.50 mmol) and 5-(t-butyldimethylsilyloxy)-1-pentanol (146 mg, 0.60 mmol) was added cyanomethylenetri-n-butylphosphorane (161 mg, 0.60 mmol). The resulting mixture was heated under reflux for 8 hours. After cooling to room temperature, the reaction mixture was concentrated under reduced pressure. The residue was subjected to flash silica gel chromatography and the fraction obtained from the hexane:ethyl acetate=87:13 eluate was concentrated under reduced pressure.

The residue was dissolved in tetrahydrofuran (5 ml), followed by the addition of a tetrahydrofuran solution (0.410 ml, 0.41 mmol) of tetra-n-butylammonium fluoride. The resulting mixture was stirred at room temperature for 4 hours. After concentration of the reaction mixture under reduced pressure, ethyl acetate was added to the residue. The mixture was washed with a saturated aqueous solution of ammonium chloride. The organic layer was dried over anhydrous sodium sulfate. After filtration, the filtrate was concentrated under reduced pressure. The residue was subjected to flash silica gel chromatography and the fraction obtained from the hexane:ethyl acetate=1:1 eluate was concentrated under reduced pressure, whereby the title compound (115 mg, 0.26 mmol, 54%) was obtained as a colorless oil.

$^1$H-NMR (400 MHz, CDCl$_3$) δ: 0.54-0.67(1H,m), 0.79-1.02(3H,m), 1.08(1H,t,J=5.9 Hz), 1.19-1.32(2H,m), 1.94-2.05(1H,m), 2.06-2.16(1H,m), 3.43(2H,q,J=5.9 Hz), 4.21 (1H,dd,J=11.5, 3.4 Hz), 5.72(1H,d,J=15.5 Hz), 6.04(1H,d,J=15.5 Hz), 7.21-7.28(2H,m), 7.37-7.44(3H,m), 7.42(2H,d,J=8.5 Hz), 7.50(2H,d,J=8.5 Hz).

IR (ATR) cm$^{-1}$: 3402, 2935, 1581, 1456, 1321, 1151, 1084, 1012, 725.

MS m/z: 435 (M$^+$+H).

FAB-MS: 435.1240 (Calcd for C$_{20}$H$_{24}$ClN$_4$O$_3$S: 435.1258).

Example 195

1-Benzyl-5-[1-(4-chlorobenzenesulfonyl)cyclohexyl]-1H-tetrazole

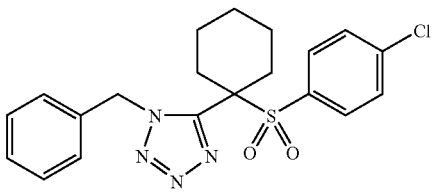

To a toluene (3 ml) solution of 6-(1-benzyl-1H-tetrazol-5-yl)-6-[(4-chlorophenyl)sulfonyl]-1-hexanol (104 mg, 0.24 mmol) was added a toluene (2 ml) solution of cyanomethylenetri-n-butylphosphorane (128 mg, 0.48 mmol). The resulting mixture was heated under reflux for 7 hours. After cooling to room temperature, the reaction mixture was concentrated under reduced pressure. The residue was subjected to flash silica gel chromatography and the fraction obtained from the hexane:ethyl acetate=4:1 eluate was concentrated under reduced pressure. The resulting solid was washed with hexane/diethyl ether and then, collected by filtration, whereby the title compound (51 mg, 0.12 mmol, 51%) was obtained as a white solid.

$^1$H-NMR (400 MHz, CDCl$_3$) δ: 0.45-0.93(2H,m), 1.07-1.21(1H,m), 1.31-1.50(3H,m), 2.07-2.20(2H,m), 2.58-2.68 (2H,m), 6.13(2H,s), 7.21(2H,d,J=8.8 Hz), 7.28-7.39(5H,m), 7.41(2H,d,J=8.8 Hz).

IR (ATR) cm$^{-1}$: 2941, 1574, 1460, 1392, 1302, 1282, 1142, 1080, 1011, 831.

MP: 154-155° C.

Anal. Calcd for C$_{20}$H$_{21}$ClN$_4$O$_2$S: C, 57.62; H, 5.08; Cl, 8.50; N, 13.44. Found: C, 57.47; H, 5.07; Cl, 8.53; N, 13.45.

MS m/z: 417 (M$^+$+H).

Example 196

6-(2-Benzyl-2H-tetrazol-5-yl)-6-[(4-chlorophenyl)sulfonyl]-1-hexanol

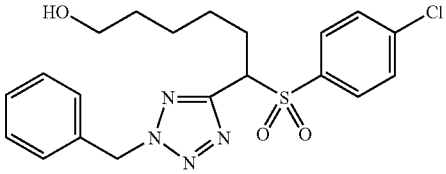

To a toluene (5 ml) solution of the 2-benzyl-5-(4-chlorobenzenesulfonylmethyl)-2H-tetrazole (Isomer 193-B) (174 mg, 0.50 mmol) obtained in Example 193 and 5-(t-butyldimethylsilyloxy)-1-pentanol (146 mg, 0.60 mmol) was added cyanomethylenetri-n-butylphosphorane (161 mg, 0.60 mmol). The resulting mixture was heated under reflux for 8 hours. After cooling to room temperature, the reaction mixture was concentrated under reduced pressure. The residue was subjected to flash silica gel chromatography and the fraction obtained from the hexane:ethyl acetate=17:3 eluate was concentrated under reduced pressure.

The residue thus obtained was dissolved in tetrahydrofuran (5 ml), followed by the addition of a tetrahydrofuran (0.574 ml, 0.57 mmol) solution of tetra-n-butylammonium fluoride and the mixture was stirred at room temperature for 4 hours. After concentration of the reaction mixture under reduced pressure, ethyl acetate was added to the residue. The resulting mixture was washed with a saturated aqueous solution of ammonium chloride. The organic layer was dried over anhydrous sodium sulfate. After filtration, the filtrate was concentrated under reduced pressure. The residue was subjected to flash silica gel chromatography and the fraction obtained from the hexane:ethyl acetate=1:1 eluate was concentrated under reduced pressure, whereby the title compound (155 mg, 0.36 mmol, 71%) was obtained as a colorless oil.

$^1$H-NMR (400 MHz, CDCl$_3$) δ: 1.12-1.64(7H,m), 2.22-2.34(1H,m), 2.36-2.48(1H,m), 3.56(2H,br s), 4.21(1H,dd, J=11.4, 3.8 Hz), 5.69(1H,d,J=14.4 Hz), 5.73(1H,d,J=14.4 Hz), 7.20(2H,d,J=8.3 Hz), 7.28-7.48(5H,m), 7.37(2H,d, J=8.3 Hz).

IR (ATR) cm$^{-1}$: 3543, 2933, 1581, 1475, 1394, 1321, 1149, 1088, 1012, 723.

MS m/z: 435 (M$^+$+H).

FAB-MS: 435.1252 (Calcd for C$_{20}$H$_{24}$ClN$_4$O$_3$S: 435.1258).

Example 197

2-Benzyl-5-[1-(4-chlorobenzenesulfonyl)cyclohexyl]-2H-tetrazole

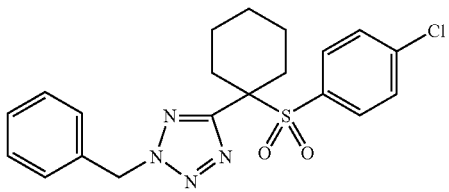

To a toluene (3 ml) solution of 6-(2-benzyl-2H-tetrazol-5-yl)-6-[(4-chlorophenyl)sulfonyl]-1-hexanol (145 mg, 0.33 mmol) was added a toluene (3 ml) solution of cyanomethylenetri-n-butylphosphorane (179 mg, 0.67 m=ol). The resulting mixture was heated under reflux for 7 hours. After cooling to room temperature, the reaction mixture was concentrated under reduced pressure. The residue was subjected to flash silica gel chromatography and the fraction obtained from the hexane:ethyl acetate=4:1 eluate was concentrated under reduced pressure. The resulting solid was washed with hexane/diethyl ether and collected by filtration, whereby the title compound (78 mg, 0.19 mmol, 56%) was obtained as a white solid.

$^1$H-NMR (400 MHz, CDCl$_3$) δ: 0.99-1.14(2H,m), 1.21-1.36(1H,m), 1.52-1.62(1H,m), 1.75-1.82(2H,m), 2.15-2.25 (2H,m), 2.69-2.76(2H,m), 5.72(2H,s), 7.07(2H,d,J=8.8 Hz), 7.11(2H,d,J=8.8 Hz), 7.34-7.47 (5H,m).

IR (ATR) cm$^{-1}$: 2939, 1579, 1477, 1396, 1317, 1144, 1084, 1012, 756.

MP: 133-134° C.

Anal. Calcd for C$_{20}$H$_{21}$ClN$_4$O$_2$S: C, 57.62; H, 5.08; Cl, 8.50; N, 13.44. Found: C, 57.74; H, 5.14; Cl, 8.51; N, 13.37.

MS m/z: 417 (M$^+$+H).

Example 198

3-[(4-Chlorophenyl)sulfonyl]-3-(2,5-difluorophenyl)-1-(1-pyrrolildinyl)-1-propanone

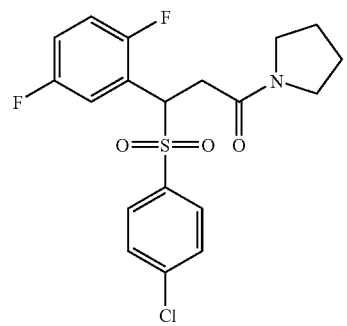

In dichloromethane (6 ml) was dissolved the 3-[(4-chlorophenyl)sulfonyl]-3-(2,5-difluorophenyl)propionic acid (200 mg, 0.554 mmol) obtained in Example 62. To the resulting solution was added thionyl chloride (162 μl, 2.22 mmol). The resulting mixture was stirred at room temperature for 24 hours. The reaction mixture was then concenterated to dryness. The residue thus obtained was dissolved in dichloromethane (6 ml) and to the resulting solution were added pyrrolidine (185 μl, 2.22 mmol) and triethylamine (309 μl, 2.22 mmol). The resulting mixture was stirred at room temperature for 2 hours. The reaction mixture was diluted with dichloromethane, washed successively with water, a saturated aqueous ammonium chloride solution and brine, dried over magnesium sulfate and then concentrated. The residue thus obtained was subjected to flash chromatography on a silica gel column, and the fraction obtained from the hexane:ethyl acetate=1:1 eluate was concentrated. The colorless solid thus obtained was recrystallized from ethyl acetate-hexane, whereby the title compound (192 mg, 0.463 mmol, 84%) was obtained as colorless needle crystals.

$^1$H-NMR (CDCl$_3$) δ: 1.80-1.90(2H,m), 1.96-2.03(2H,m), 3.06(1H,dd,J=16.4, 9.8 Hz), 3.28-3.57(5H,m), 5.25(1H,dd, J=9.8, 3.7 Hz), 6.81(1H,td,J=9.1, 4.4 Hz), 6.91-6.98(1H,m), 7.18(1H,ddd,J=8.6,5.4,3.2 Hz), 7.38(2H,d,J=8.6 Hz), 7.53 (2H,d,J=8.6 Hz).

IR (ATR) cm$^{-1}$: 2949, 1633, 1583, 1495, 1442, 1396, 1346, 1308, 1277, 1211, 1147, 1014, 822, 769, 708, 615, 536, 472.

mp: 122-125° C.

MS m/z: 414 (M$^+$+H).

FAB-MS: 414.0769 (Calcd for C$_{19}$H$_{19}$ClF$_2$NO$_3$S: 414.0742)

Anal. calcd for C$_{19}$H$_{18}$ClF$_2$NO$_3$S: C, 55.14; H, 4.38; Cl, 8.57; F, 9.18; N, 3.38; S, 7.75. Found: C, 55.22; H, 4.50; Cl, 8.44; F, 9.00; N, 3.39; S, 7.78.

Example 199 t-Butyl 4-[(4-chlorophenyl)sulfonyl]-4-(2,5-difluorophenyl)butyrate

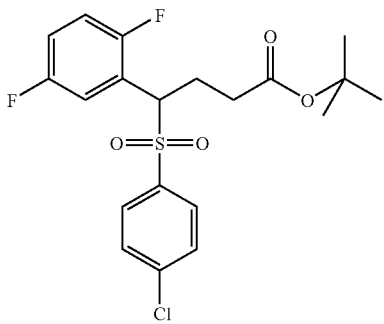

In N,N-dimethylformamide (4 ml) was dissolved the 2-[(4-chlorophenyl)sulfonylmethyl]-1,4-difluorobenzene (101 mg, 0.333 mmol) obtained in Example 5. After addition thereto of t-butyl acrylate (146 μl, 1.00 mmol) and 1,8-diazabicyclo[5,4,0]undece-7-en (151 μl, 1.00 mmol), stirring was conducted at room temperature for 1 week. The reaction mixture was then concentrated. The residue thus obtained was subjected to flash chromatoraphy on a silica gel column, and the fraction obtained from the hexane:ethyl acetate=4:1 eluate was concentrated, whereby the title compound (142 mg, 0.329 mmol, 99%) was obtained as a colorless oil.

$^1$H-NMR (400 MHz, CDCl$_3$) δ: 1.40(9H,s), 2.10-2.20(1H, m), 2.23-2.35(2H,m), 2.65-2.76(1H,m), 4.67(1H,dd,J=10.3, 4.4 Hz), 6.85(1H,td,J=10.3, 4.4 Hz), 6.96-7.03(1H,m), 7.24 (1H,ddd,J=8.6,5.4,3.2 Hz), 7.40(2H,d,J=8.3 Hz), 7.56(2H,d, J=8.3 Hz).

IR (ATR) cm$^{-1}$: 2978, 1724, 1583, 1496, 1367, 1321, 1232, 1146, 1084, 1014, 829, 756, 710, 642, 629, 555, 471.

MS m/z: 431 (M$^+$+H).

FAB-MS: 431.0904 (Calcd for C$_{20}$H$_{22}$ClF$_2$O$_4$S: 431.0895)

Example 200

4-[(4-Chlorophenyl)sulfonyl]-4-(2,5-difluorophenyl) butyric Acid

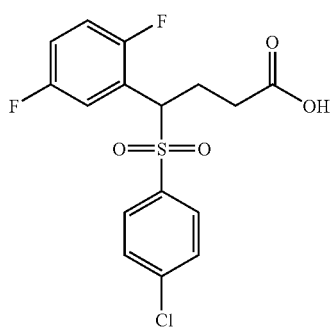

To a dichloromethane solution (10 ml) of t-butyl 4-[(4-chlorophenyl)sulfonyl]-4-(2,5-difluorophenyl)butyrate (1.25 g, 3.33 mmol) was added trifluoroacetic acid (5 ml). The resulting mixture was stirred at room temperature for 4 hours. The solid obtained by concentrating the reaction mixture was recrystallized from ethyl acetate, whereby the title compound (595 mg, 1.59 mmol, 48%) was obtained as colorless needle crystals.

$^1$H-NMR (400 MHz, CDCl$_3$) δ: 2.32-2.50(3H,m), 2.71-2.81(1H,m), 4.68(1H,dd,J=9.3, 4.9 Hz), 6.86(1H,td,J=9.3, 4.4 Hz), 6.97-7.04(1H,m), 7.21-7.27(1H,m), 7.40(2H,d, J=8.6 Hz), 7.56(2H,d,J=8.6 Hz).

IR (ATR) cm$^{-1}$: 2942, 1710, 1571, 1495, 1427, 1327, 1240, 1151, 1084, 1012, 916, 831, 789, 752, 710, 636, 555, 528, 463, 417.

mp: 157-158° C.

MS m/z: 375 (M$^+$+H).

Anal. calcd for C$_{16}$H$_{13}$ClF$_2$O$_4$S: C, 51.27; H, 3.50; Cl, 9.46; F, 10.14; S, 8.56. Found: C, 51.18; H, 3.47; Cl, 9.45; F, 10.32; S, 8.60.

Example 201

4-[(4-Chlorophenyl)sulfonyl]-4-(2,5-difluorophenyl)-1-(1-pyrrolildinyl)-1-butanone

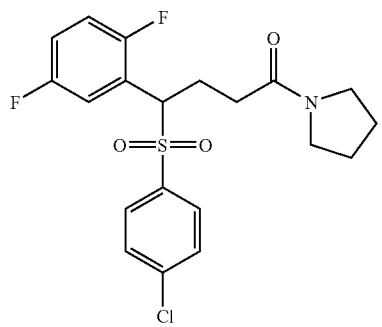

To a tetrahydrofuran solution (4 ml) of 4-[(4-chlorophenyl) sulfonyl]-4-(2,5-difluorophenyl)butyric acid (150 mg, 0.400 mmol) were added pyrrolidine (40.1 μl, 0.480 mmol), triethylamine (61.2 μl, 0.440 mmol), 4-dimethylaminopyridine (10.0 mg, 0.0820 mmol) and 1-ethyl-3-(3-dimethylaminopropyl)carbodiimide hydrochloride (84.5 mg, 0.440 mmol). The resulting mixture was stirred at room temperature for 18 hours. The solvent was distilled off. The residue thus obtained was dissolved in ethyl acetate. The resulting solution was washed with a saturated aqueous ammonium chloride solution and brine, dried over magnesium sulfate and then, concentrated. The residue thus obtained was subjected to flash chromatoraphy on a silica gel column, and the fraction obtained from the hexane:ethyl acetate=3:7 eluate was concentrated. The resulting solid was recrystallized from ethyl acetate-hexane, whereby the title compound (97.0 mg, 0.227 mmol, 57%) was obtained as colorless plate crystals.

$^1$H-NMR (400 MHz, CDCl$_3$) δ: 1.78-1.93(4H,m), 2.20-2.43(3H,m), 2.69-2.78(1H,m), 3.15-3.21(1H,m), 3.25-3.30 (1H,m), 3.41(2H,t,J=6.8 Hz), 4.84(1H,dd,J=8.5, 5.6 Hz), 6.86(1H,td,J=9.0, 4.6 Hz), 6.95-7.02(1H,m), 7.24(1H,ddd, J=8.8,5.6,3.4 Hz), 7.40(2H,d,J=8.5 Hz), 7.59 (2H, d,J=8.5 Hz).

IR (ATR) cm$^{-1}$: 3072, 2973, 2875, 1635, 1496, 1444, 1421, 1317, 1234, 1173, 1146, 1082, 1011, 877, 760, 737, 619, 559, 509, 469.

mp: 134-135° C.

MS m/z: 428 (M$^+$+H).

Anal. calcd for $C_{20}H_{20}ClF_2NO_3S$: C, 56.14; H, 4.71; Cl, 8.29; F, 8.88; N, 3.27; S, 7.49. Found: C, 56.01; H, 4.68; Cl, 8.03; F, 8.64; N, 3.35; S, 7.63.

Example 202

5-[(4-chlorophenyl)sulfonyl]-5-(2,5-difluorophenyl)-1-valeric Acid

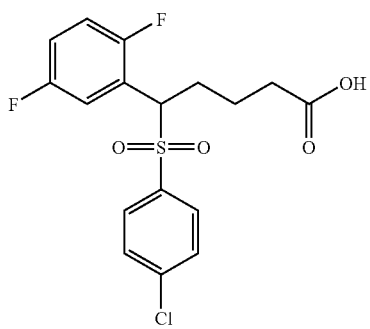

Under an argon atmosphere and at −78° C., n-butyl lithium (a 1.57 M hexane solution, 578 μl, 0.908 mmol) was added to a dimethoxyethane solution (5 ml) of the 2-[(4-chlorophenyl)sulfonylmethyl]-1,4-difluorobenzene (250 mg, 0.825 mmol) obtained in Example 5. After the temperature of the reaction mixture was elevated to room temperature, it was cooled again to −78° C. Ethyl 4-bromobutyrate (142 mg, 0.990 mmol) was added and the mixture was stirred at room temperature for 5 hours. Water was added to the reaction mixture, followed by extraction with dichloromethane. The extracts were combined, washed with water and brine, dried over magnesium sulfate and then, concentrated. The residue thus obtained was dissolved in tetrahydrofuran (4 ml). An aqueous solution (2 ml) of lithium hydroxide (19.8 mg, 0.825 mmol) was added to the resulting solution. The mixture was stirred at room temperature for 15 hours. After 1N hydrochloric acid was added to make the mixture to acidic, it was extracted with dichloromethane. The extracts were combined, washed with brine, dried over magnesium sulfate and then concentrated. The resulting solid was recrystallized from ethyl acetate-hexane, whereby the title compound (139 mg, 0.357 mmol, 43%) was obtained as a colorless solid.

$^1$H-NMR (400 MHz, CDCl$_3$) δ: 1.53-1.55(2H,m), 2.12-2.23(1H,m), 2.32-2.54(3H,m), 4.52(1H,dd,J=11.5, 3.7 Hz), 6.84(1H,td,J=9.0, 4.4 Hz), 6.96-7.02(1H,m), 7.23-7.28(1H, m), 7.38(2H,d,J=8.3 Hz), 7.53(2H,d,J=8.3 Hz).

IR (ATR) cm$^{-1}$: 2945, 1693, 1585, 1495, 1427, 1323, 1296, 1238, 1211, 1153, 1086, 1012, 949, 829, 750, 708, 628, 542, 463.

mp: 151-152° C.

MS m/z: 389 (M$^+$+H).

Anal. calcd for $C_{17}H_{15}ClF_2O_4S$: C, 52.51; H, 3.89; Cl, 9.12; F, 9.77; S, 8.25. Found: C, 52.36; H, 3.88; Cl, 9.14; F, 9.75; S, 8.37.

Example 203

5-[(4-Chlorophenyl)sulfonyl]-5-(2,5-difluorophenyl)-1-(1-pyrrolildinyl)-1-pentanone

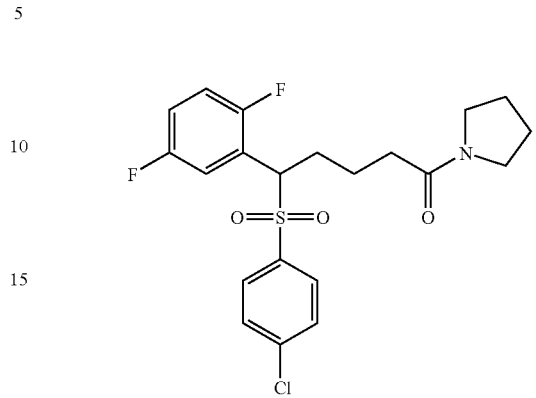

Under an argon atmosphere and at −15° C., N-methylmorpholine (38.5 μl, 0.351 mmol) and isobutyl chloroformate (45.8 μl, 0.351 mmol) were added to a tetrahydrofuran solution (4 ml) of 5-[(4-chlorophenyl)sulfonyl]-5-(2,5-difluorophenyl)-1-valeric acid (130 mg, 0.334 mmol). The mixture was stirred for 5 minutes at −15° C. Pyrrolidine (33.5 μl, 0.401 mmol) was added and the mixture was stirred at room temperature for 1 hour. The reaction mixture was diluted with dichloromethane, washed with a saturated aqueous ammonium chloride solution and brine, dried over magnesium sulfate and then concentrated. The residue thus obtained was subjected to flash chromatoraphy on a silica gel column, and the fraction obtained from the hexane:ethyl acetate=1:2 eluate was concentrated. The resulting solid was recrystallized from ethyl acetate-hexane, whereby the title compound (128 mg, 0.290 mmol, 87%) was obtained as colorless needle crystals.

$^1$H-NMR (400 MHz, CDCl$_3$) δ: 1.52-1.66(2H,m), 1.80-1.88(2H,m), 1.91-1.98(2H,m), 2.15-2.34(3H,m), 2.41-2.50 (1H,m), 3.34(2H,td,J=6.8, 2.4 Hz), 3.41(2H,t,J=6.8 Hz), 4.55 (1H,dd,J=11.7, 2.9 Hz), 6.81(1H,td,J=9.0, 4.4 Hz), 6.93-7.00 (1H,m), 7.22-7.28(1H,m), 7.38(2H,d,J=8.5 Hz), 7.52(2H,d, J=8.5 Hz).

IR (ATR) cm$^{-1}$: 2941, 2883, 1635, 1583, 1496, 1441, 1315, 1277, 1244, 1215, 1180, 1146, 1082, 1038, 1014, 829, 787, 752, 710, 631, 548, 519, 480, 440.

mp: 125-126° C.

MS m/z: 442(M$^+$+H).

Anal. calcd for $C_{21}H_{22}ClF_2NO_3S$: C, 57.07; H, 5.02; Cl, 8.02; F, 8.60; N, 3.17; S, 7.26. Found: C, 57.04; H, 5.13; Cl, 8.03; F, 8.64; N, 3.29; S, 7.39.

Referential Example 37

5-Bromo-1-(1-pyrrolildinyl)-1-pentanone

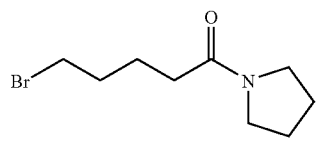

Under an argon atmosphere, N-methylmorpholine (606 μl, 5.52 mmol) and isobutyl chloroformate (757 μl, 5.80 mmol)

were added to a tetrahydrofuran solution (35 ml) of 6-bromovaleric acid (1.00 g, 5.52 mmol) at −15° C. The resulting mixture was stirred for 5 minutes at −15° C. Pyrrolidine (484 µl, 5.80 mmol) was added and the resulting mixture was stirred at −15° C. for 5 minutes and then, at room temperature for 1 hour. Ice water was added and the mixture was extracted with dichloromethane. The extract was washed with brine, dried over magnesium sulfate and then, concentrated. The residue thus obtained was subjected to flash chromatography on a silica gel column, and the fraction obtained from the hexane:ethyl acetate=1:2 eluate was concentrated, whereby the title compound (1.18 g, 5.04 mmol, 91%) was obtained as a colorless oil.

$^1$H-NMR (400 MHz, CDCl$_3$) δ: 1.77-2.00(8H,m), 2.29 (2H,t,J=7.3 Hz), 3.39-3.48(6H,m).

MS m/z: 234 (M$^+$+H).

Example 204

6-[(4-Chlorophenyl)sulfonyl]-6-(2,5-difluorophenyl)-1-hexanone

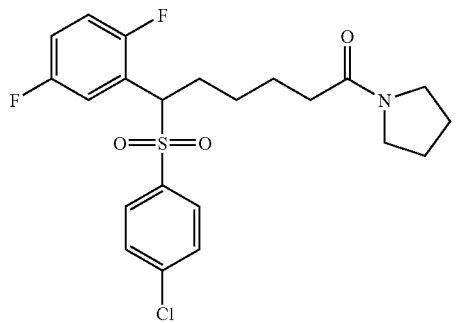

Under an argon atmosphere and at −78° C., n-butyl lithium (a 1.57 M hexane solution, 701 µl, 1.10 mmol) was added to a dimethoxyethane solution (6 ml) of the 2-[(4-chlorophenyl)sulfonylmethyl]-1,4-difluorobenzene (303 mg, 1.00 mmol) obtained in Example 5. After the temperature of the reaction mixture was elevated to room temperature, it was cooled again to −78° C. After addition of 5-bromo-1-(1-pyrrolildinyl)-1-pentanone (281 mg, 1.20 mmol), the resulting mixture was stirred at room temperature for 20 hours. The reaction mixture was added with water, and then, diluted with dichloromethane. The solution thus obtained was washed successively with water and brine, dried over magnesium sulfate and then, concentrated. The residue thus obtained was subjected to flash chromatography on a silica gel column, and the fraction obtained from the hexane:ethyl acetate=1:2 eluate was concentrated. The resulting solid was recrystallized from ethyl acetate-hexane, whereby the title compound (385 mg, 0.844 mmol, 84%) was obtained as a colorless solid.

$^1$H-NMR (400 MHz, CDCl$_3$) δ: 1.25-1.37(2H,m), 1.58-1.75(2H,m), 1.80-1.88(2H,m), 1.91-1.97(2H,m), 2.07-2.16 (1H,m), 2.20(2H,td,J=7.6, 3.2 Hz), 2.41-2.50(1H,m), 3.35 (2H,t,J=6.8 Hz), 3.43(2H,t,J=6.8 Hz), 4.50-4.56(1H,m), 6.83 (1H,td,J=9.0, 4.4 Hz), 6.94-7.01(1H,m), 7.24(1H,ddd,J=8.8, 5.4,3.2 Hz), 7.38(2H,d,J=8.8 Hz), 7.53(2H,d,J=8.8 Hz).

IR (ATR) cm$^{-1}$: 2952, 1626, 1493, 1441, 1321, 1232, 1149, 1086, 1014, 820, 768, 631, 528, 469.

mp: 135-136° C.

MS m/z: 456 (M$^+$+H).

Anal. calcd for C$_{22}$H$_{24}$ClF$_2$NO$_3$S: C, 57.95; H, 5.31; Cl, 7.78; F, 8.33; N, 3.07; S, 7.03. Found: C, 57.73; H, 5.20; Cl, 7.76; F, 8.31; N, 3.13; S, 7.14.

Example 205

7-[(4-Chlorophenyl)sulfonyl]-7-(2,5-difluorophenyl) heptanoic Acid

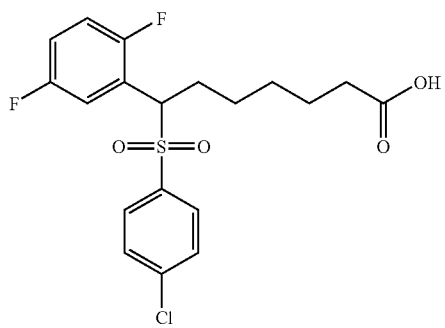

Under an argon atmosphere and at −78° C., n-butyl lithium (a 1.57 M hexane solution, 2.31 ml, 3.63 mmol) was added to a dimethoxyethane solution (20 ml) of the 2-[(4-chlorophenyl)sulfonylmethyl]-1,4-difluorobenzene (1.00 g, 3.30 mmol) obtained in Example 5. After the temperature of the reaction mixture was elevated to room temperature, it was cooled again to −78° C. To the reaction mixture was added ethyl 6-bromohexanoate (706 µl, 3.96 mmol), followed by stirring at room temperature for 18 hours. The reaction mixture was added with water and then the mixture was extracted with dichloromethane. The extracts were combined, washed with brine, dried over magnesium sulfate and then, concentrated, whereby an ester compound was obtained as a crude product. The resulting ester compound was dissolved in tetrahydrofuran (20 ml). To the resulting solution was added an aqueou solution (6 ml) of lithium hydroxide (96.0 mg, 4.00 mmol). The mixture was stirred at room temperature for 18 hours. After the reaction mixture was made acidic with 1N hydrochloric acid, the acid mixture was extracted with dichloromethane. The extracts were combined, washed with brine, dried over magnesium sulfate and then concentrated. The resulting solid was recrystallized from ethyl acetate-hexane, whereby the title compound (931 mg, 2.23 mmol, 68%) was obtained as a colorless solid.

$^1$H-NMR (400 MHz, CDCl$_3$) δ: 1.22-1.90(7H,m), 2.30 (2H,t,J=7.3 Hz), 2.40-2.48(1H,m), 4.51(1H,dd,J=11.7, 2.9 Hz), 6.83(1H,td,J=9.0, 4.4 Hz), 6.94-7.01(1H,m), 7.22-7.26 (1H,m), 7.38(2H,d,J=8.5 Hz), 7.53(2H,d,J=8.5 Hz).

IR (ATR) cm$^{-1}$: 3487, 2941, 2860, 1728, 1496, 1414, 1321, 1217, 1176, 1149, 1086, 1014, 818, 787, 756, 633, 536, 478.

mp: 72-76° C.

MS m/z: 417 (M$^+$+H).

Anal. calcd for C$_{19}$H$_{19}$ClF$_2$O$_4$S 0.5H$_2$O: C, 53.59; H, 4.73; Cl, 8.32; F, 8.92; S, 7.53. Found: C, 53.83; H, 4.67; Cl, 8.39; F, 8.94; S, 7.72.

Example 206

7-[(4-Chlorophenyl)sulfonyl]-7-(2,5-difluorophenyl)-1-(1-pyrrolildinyl)-1-heptanone

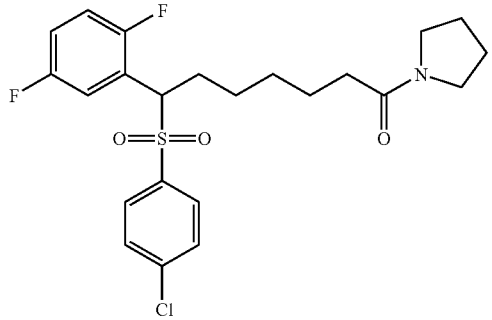

Under an argon atmosphere and at −15° C., N-methylmorpholine (53.9 µl, 0.491 mmol) and isobutyl chloroformate (64.1 µl, 0.491 mmol) were added to a tetrahydrofuran solution (5 ml) of 7-[(4-chlorophenyl)sulfonyl]-7-(2,5-difluorophenyl)heptanoic acid (195 mg, 0.468 mmol). The resulting mixture was stirred at −15° C. for 5 minutes. Pyrrolidine (46.9 µl, 0.562 mmol) was added and the mixture was stirred at room temperature for 1 hour. The reaction mixture was diluted with dichloromethane, washed successively with a saturated aqueous solution of sodium bicarbonate, water and brine, dried over magnesium sulfate and then concentrated. The residue thus obtained was subjected to flash chromatoraphy on a silica gel column, and the fraction obtained from the hexane:ethyl acetate=3:7 eluate was concentrated. The resulting solid was recrystallized from ethyl acetate-hexane, whereby the title compound (171 mg, 0.364 mmol, 78%) was obtained as a white solid.

$^1$H-NMR (400 MHz, CDCl$_3$) δ: 1.21-1.43(4H,m), 1.54-1.67(2H,m), 1.80-1.98(4H,m), 2.03-2.15(1H,m), 2.19(2H,t, J=7.6 Hz), 2.38-2.46(1H,m), 3.36(2H,t,J=6.8 Hz), 3.44(2H, t,J=6.8 Hz), 4.51(1H,dd,J=11.5, 2.9 Hz), 6.83(1H,td,J=9.0, 4.4 Hz), 6.94-7.01(1H,m), 7.23(1H,ddd,J=8.8,5.4,3.2 Hz), 7.38(2H,d,J=8.8 Hz), 7.53(2H,d,J=8.8 Hz).

IR (ATR) cm$^{-1}$: 2960, 1630, 1583, 1496, 1442, 1315, 1228, 1196, 1149, 1086, 1011, 872, 841, 822, 787, 756, 633, 536, 467.

mp: 106-106° C.

MS m/z: 470 (M$^+$+H).

Anal. calcd for C$_{23}$H$_{26}$ClF$_2$NO$_3$S: C, 58.78; H, 5.58; Cl, 7.54; F, 8.08; N, 2.98; S, 6.82. Found: C, 58.53; H, 5.49; Cl, 7.66; F, 8.19; N, 3.06; S, 8.82.

Example 207

3-[(4-Chlorophenyl)sulfonyl]-3-(2,5-difluorophenyl)-1-propanol

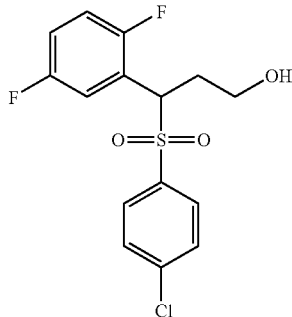

Process 1: At 0° C., lithium aluminum hydride (a 1.0M tetrahydrofuran solution, 6.74 ml, 6.74 mmol) was added dropwise to a tetrahydrofuran solution (10 ml) of the ethyl 3-[(4-chlorophenyl)sulfonyl]-3-(2,5-difluorophenyl)propionate (1.31 g, 3.37 mmol) obtained in Example 25. The mixture was then was stirred at room temperature for 3 hours. After cooling the reaction mixture to 0° C., and addition of a saturated aqueous ammonium chloride solution, the mixture was stirred at room temperature for 15 hours. The solid thus precipitated was filtered off. The solution thus obtained was diluted with ether, washed with brine, dried over magnesium sulfate and then, concentrated. The residue thus obtained was recrystallized from ethyl acetate-hexane, whereby the title compound (397 mg, 1.14 mmol, 34%) was obtained as a colorless solid.

Process 2: Under an argon atmosphere and at −78° C., n-butyl lithium (a 1.57M hexane solution, 4.62 ml, 7.26 mmol) was added to a dimethoxyethane solution (50 ml) of the 2-[(4-chlorophenyl)sulfonylmethyl]-1,4-difluorobenzene (2.00 g, 6.60 mmol) obtained in Example 5. The temperature of the resulting mixture was elevated to room temperature, and stirring was performed for 15 minutes. After cooling the reaction mixture to −78° C., a dimethoxyethane solution (5 ml) of t-butyl-(2-iodoethyloxy)dimethylsilane (2.08 g, 7.26 mmol) was added thereto. The resulting mixture was stirred at room temperature for 15 hours. Water was added to the reaction mixture, followed by extraction with ether. The extracts were combined, washed successively with water and brine, dried over magnesium sulfate and then, concentrated. The residue thus obtained was subjected to short silica gel chromatography (hexane:ethyl acetate=7:1) to remove high-polarity impurities. The resulting oil was dissolved in tetrahydrofuran (50 ml), and to the resulting solution was added tetrabutylammonium fluoride (a 1M tetrahydrofuran solution, 14.5 ml, 14.5 mmol). After stirring for 2 days, the solvent was distilled off. The residue thus obtained was dissolved in dichloromethane, followed by successive washing with 1N hydrochloric acid, water, and brine, driying over magnesium sulfate and concentration. The residue thus obtained was subjected to chromatography on a silica gel column, and the fraction obtained from the hexane:ethyl acetate=1:1 eluate was concentrated, whereby the title compound (2.07 g, 5.82 mmol, 88%) was obtained as a colorless solid.

$^1$H-NMR (CDCl$_3$) δ 2.27(1H,ddd,J=19.3,10.3,5.1 Hz), 2.72(1H,ddd,J=19.3,9.0,3.9 Hz), 3.48(1H,td,J=10.5, 4.4 Hz), 3.85(1H,td,J=10.5, 5.1 Hz), 4.85(1H,dd,J=10.3, 3.9 Hz), 6.84 (1H,td,J=9.0, 4.4 Hz), 6.95-7.02(1H,m), 7.23-7.27(1H,m), 7.31(2H,d,J=8.5 Hz), 7.55(2H,d,J=8.5 Hz).

IR (ATR) cm$^{-1}$: 3519, 3043, 2964, 2922, 2875, 1576, 1495, 1427, 1396, 1308, 1186, 1147, 1084, 1036, 957, 895, 818, 786, 752, 708, 625, 521, 467.

mp: 147-149° C.

MS m/z: 347(M$^+$+H).

Anal. calcd for C$_{15}$H$_{13}$ClF$_2$O$_3$S: C, 51.95; H, 3.78; Cl, 10.22; F, 10.96; S, 9.25. Found: C, 51.89; H, 3.75; Cl, 10.15; F, 10.90; S, 9.36.

Example 208

3-[(4-Chlorophenyl)sulfonyl]-3-(2,5-difluorophenyl)propyl=1-pyrrolidinecarboxylate

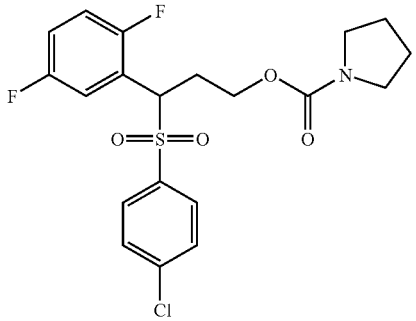

In dichloromethane (4 ml) was dissolved 3-[(4-chlorophenyl)sulfonyl]-3-(2,5-difluorophenyl)-1-propanol (150 mg, 0.432 mmol), followed by the addition of triethylamine (63.2 µl, 0.454 mmol) and 4-nitrophenyl chloroformate (91.7 mg, 0.454 mmol). The resulting mixture was stirred at room temperature for 20 hours. Pyrrolidine (43.2 µl, 0.518 mmol) and triethylamine (72.1 µl, 0.518 mmol) were added and the mixture was stirred at room temperature for 18 hours. The reaaction mixture was concentrated. The residue thus obtained was subjected to flash chromatography on a silica gel column, and the fraction obtained from the hexane:ethyl acetate=3:2 eluate was concentrated. The resulting colorless solid was recrystallized from hexane, whereby the title compound (84.0 mg, 0.189 mmol, 44%) was obtained as colorless needle crystals.

$^1$H-NMR (400 MHz, CDCl$_3$) δ: 1.77-1.88(4H,m), 2.37-2.47(1H,m), 2.75-3.84(1H,m), 3.09-3.20(2H,m), 3.28-3.34(2H,m), 3.89(1H,ddd,J=11.3,8.3,4.4 Hz), 4.22(1H,dt,J=11.3, 5.6 Hz), 4.70(1H,dd,J=11.3, 3.6 Hz), 6.83(1H,td,J=9.1, 4.4 Hz), 6.95-7.02(1H,m), 7.20-7.26(1H,m), 7.39(2H,d,J=8.6 Hz), 7.54(2H,d,J=8.6 Hz).

IR (ATR) cm$^{-1}$: 2974, 2879, 1685, 1585, 1496, 1427, 1373, 1306, 1178, 1149, 1091, 816, 766, 754, 710, 631, 553, 523, 467, 444.

mp: 109-110° C.

MS m/z: 444 (M$^+$+H).

Anal. calcd for C$_{20}$H$_{20}$ClF$_2$NO$_4$S: C, 54.12; H, 4.54; Cl, 7.99; F, 8.56; N, 3.16; S, 7.37. Found: C, 53.93; H, 4.49; Cl, 8.00; F, 8.50; N, 3.22; S, 7.37.

Example 209

3-[(4-Chlorophenyl)sulfonyl]-3-(2,5-difluorophenyl)propyl=4-benzyl-1-piperazinecarboxylate Hydrochloride

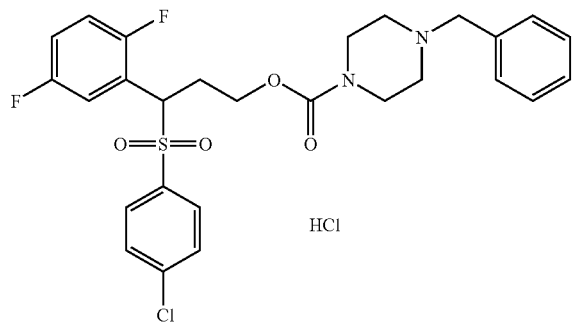

The 3-[(4-chlorophenyl)sulfonyl]-3-(2,5-difluorophenyl)-1-propanol (150 mg, 0.432 mmol) obtained in Example 207 was dissolved in dichloromethane (4 ml), followed by the addition of triethylamine (63.2 µl, 0.454 mmol) and 4-nitrophenyl chloroformate (91.7 mg, 0.454 mmol). The resulting mixture was stirred at room temperature for 18 hours. To the reaction mixture were added N-benzylpiperazine (90.3 µl, 0.518 mmol) and triethylamine (72.1 µl, 0.518 mmol) and the mixture was stirred at room temperature for 24 hours. The reaction mixture was then concentrated. The residue thus obtained was subjected to flash chromatography on a silica gel column, and the fraction obtained from the hexane:ethyl acetate=1:1 eluate was concentrated. The resulting colorless solid was dissolved in ethanol, followed by the addition of 1N hydrochloric acid (0.5 ml). The mixture was then concentrated to dryness. The resulting solid was recrystallized from ethanol, whereby the title compound (132 mg, 0.226 mmol, 52%) was obtained as a colorless solid.

$^1$H-NMR (400 MHz, CDCl$_3$) δ: 2.35-2.45(1H,br m), 2.56-2.72(2H,br m), 2.79-2.88(1H,m), 3.28-3.40(2H,m), 3.63-4.28(8H,m), 4.60(1H,dd,J=10.8, 3.9 Hz), 6.82(1H,td,J=9.1, 4.4 Hz), 6.96-7.02(1H,m), 7.18-7.26(1H,br m), 7.39(2H,d, J=8.6 Hz), 7.45-7.53(5H,m), 7.58-7.64(2H, br).

IR (ATR) cm$^{-1}$: 2958, 2708, 2675, 1701, 1583, 1495, 1423, 1321, 1255, 1217, 1153, 1142, 1092, 951, 827, 752, 700, 627, 555, 525, 468.

mp: 184-189° C.

MS m/z: 549 (M$^+$+H).

Anal. calcd for C$_{27}$H$_{27}$ClF$_2$N$_2$O$_4$S.HCl: C, 55.39; H, 4.82; Cl, 12.11; F, 6.49; N, 4.78; S, 5.48. Found: C, 55.11; H, 4.80; Cl, 11.92; F, 6.36; N, 4.85; S, 5.54.

Example 210

3-[(4-Chlorophenyl)sulfonyl]-3-(2,5-difluorophenyl)propyl=N-(2-hydroxyethyl)-N-methylcarbamate

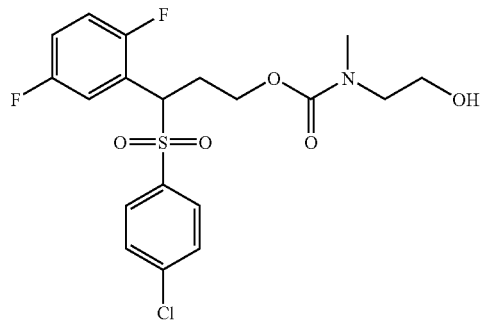

In dichloromethane (4 ml) was dissolved the 3-[(4-chlorophenyl)sulfonyl]-3-(2,5-difluorophenyl)-1-propanol (150 mg, 0.432 mmol) obtained in Example 207, followed by the addition of triethylamine (63.2 µl, 0.454 mmol) and 4-nitrophenyl chloroformate (91.7 mg, 0.454 mmol). The resulting mixture was stirred at room temperature for 20 hours. To the reaction mixture were added N-methylethanolamine (41.6 µl, 0.518 mmol) and triethylamine (72.1 µl, 0.518 mmol) and the resulting mixture was stirred at room temperature for 24 hours. The reaction mixture was then concentrated. The residue thus obtained was subjected to flash chromatography on a silica gel column, and the fraction obtained from the hexane:ethyl acetate=1:2 eluate was concentrated, whereby the title compound (136 mg, 0.304 mmol, 70%) was obtained as a colorless oil.

¹H-NMR (400 MHz, CDCl₃) δ: 2.33-2.48(1H,br m), 2.77-2.97(4H,m), 3.27-3.43(2H,br m), 3.68-3.78(2H,br s), 3.87-3.98(1H,br m), 4.19-4.30(1H,br m), 4.65-4.77(1H,br m), 6.84(1H,td,J=9.1, 4.4 Hz), 6.95-7.02(1H,m), 7.21-7.26(1H, m), 7.39(2H,d,J=8.8 Hz), 7.54(2H,d,J=8.8 Hz).

IR (ATR) cm⁻¹: 3423, 2943, 1685, 1583, 1495, 1317, 1279, 1215, 1147, 1080, 1012, 827, 754, 708, 627, 555, 467.

MS m/z: 448 (M⁺+H).

EI-MS: 447.0699(Calcd for C₁₉H₂₀ClF₂NO₅S: 447.0719)

Example 211

3-[(4-Chlorophenyl)sulfonyl]-3-(2,5-difluorophenyl)propyl=4-morpholinecarboxylate

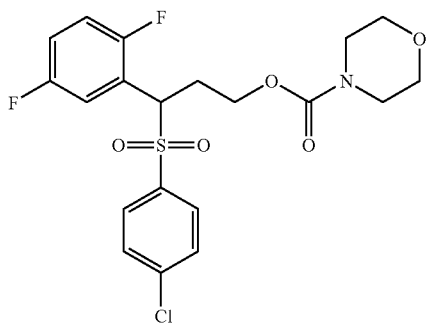

In dichloromethane (4 ml) was dissolved the 3-[(4-chlorophenyl)sulfonyl]-3-(2,5-difluorophenyl)-1-propanol (150 mg, 0.432 mmol) obtained in Example 207, followed by the addition of triethylamine (63.2 μl, 0.454 mmol) and 4-nitrophenyl chloroformate (91.7 mg, 0.454 mmol). The resulting mixture was stirred at room temperature for 20 hours. To the reaction mixture were added morpholine (45.1 μl, 0.518 mmol) and triethylamine (72.1 μl, 0.518 mmol). The resulting mxiture was stirred at room temperature for 2 hours. The reaction mixture was diluted with dichloromethane, washed successively with a saturated aqueous solution of sodium bicarbonate and brine, dried over magnesium sulfate and then, concentrated. The residue thus obtained was subjected to flash chromatography on a silica gel column, and the fraction obtained from the hexane:ethyl acetate=3:2 eluate was concentrated. The solid thus obtained was recrystallized from ethyl acetate-hexane, whereby the title compound (123 mg, 0.267 mmol, 62%) was obtained as colorless needle crystals.

¹H-NMR (400 MHz, CDCl₃) δ: 2.39-2.48(1H,m), 2.79-2.88(1H,m), 3.19-3.47(4H,br), 3.52-3.70(4H,br s), 3.97(1H, ddd,J=11.2,8.3,5.1 Hz), 4.23(1H,dt,J=11.2, 5.6 Hz), 4.65 (1H,dd,J=11.2, 3.4 Hz), 6.84(1H,td,J=9.0, 4.6 Hz), 6.97-7.03 (1H,m), 7.22-7.26(1H,m), 7.40(2H,d,J=8.5 Hz), 7.53 (2H,d, J=8.5 Hz).

IR (ATR) cm⁻¹: 3086, 2864, 1684, 1576, 1498, 1469, 1427, 1311, 1281, 1240, 1221, 1178, 1142, 1080, 837, 773, 752, 710, 633, 557, 528, 471.

mp: 140-141° C.

MS m/z: 460 (M⁺+H).

Anal. calcd for C₂₀H₂₀ClF₂NO₅S: C, 52.23; H, 4.38; Cl, 7.71; F, 8.26; N, 3.05; S, 6.97. Found: C, 51.95; H, 4.29; Cl, 7.80; F, 8.32; N, 3.12; S, 7.12.

Example 212

3-[(4-Chlorophenyl)sulfonyl]-3-(2,5-difluorophenyl)propyl=4-phenyl1-piperazinecarboxylate

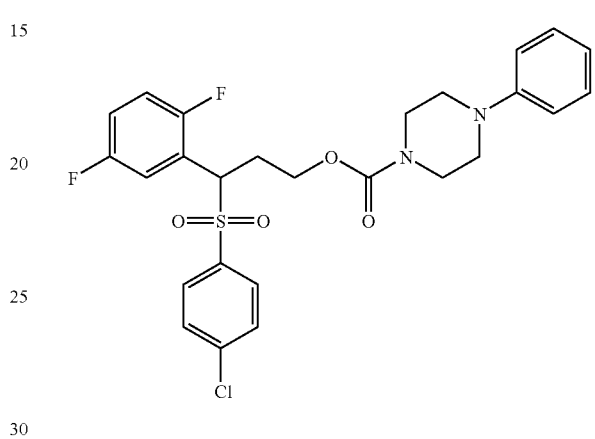

The 3-[(4-chlorophenyl)sulfonyl]-3-(2,5-difluorophenyl)-1-propanol (150 mg, 0.432 mmol) obtained in Example 207 was dissolved in dichloromethane (6 ml), followed by the addition of triethylamine (63.2 μl, 0.454 mmol) and 4-nitrophenyl chloroformate (91.7 mg, 0.454 mmol). The resulting mixture was stirred at room temperature for 18 hours. After N-phenylpiperazine (79.1 μl, 0.518 mmol) and triethylamine (72.1 μl, 0.518 mmol) were added, the mixture was stirred at room temperature for 4 hours. The reaction mixture was diluted with dichloromethane, washed successively with a saturated aqueous solution of sodium bicarbonate and brine, dried over magnesium sulfate and then, concentrated. The residue thus obtained was subjected to flash chromatography on a silica gel column, and the fraction obtained from the hexane:ethyl acetate=4:1 eluate was concentrated. The solid thus obtained was recrystallized from ethyl acetate-hexane, whereby the title compound (158 mg, 0.295 mmol, 68%) was obtained as colorless needle crystals.

¹H-NMR (400 MHz, CDCl₃) δ: 2.40-2.50(1H,m), 2.80-2.89(1H,m), 3.00-3.15(4H,br s), 3.37-3.65(4H,m), 3.98(1H, ddd,J=11.2,8.3,5.1 Hz), 4.24(1H,dt,J=11.2, 5.6 Hz), 4.67 (1H,dd,J=11.2, 3.9 Hz), 6.84(1H,td,J=9.0, 4.6 Hz), 6.89-6.93 (3H,m), 6.95-7.03(1H,m), 7.23-7.32(3H,m), 7.39(2H,d, J=8.3 Hz), 7.54(2H,d,J=8.3 Hz).

IR (ATR) cm⁻¹: 2829, 1687, 1599, 1581, 1495, 1437, 1321, 1223, 1151, 1130, 1084, 1001, 930, 814, 758, 692, 634, 552, 469.

mp: 127-129° C.

MS m/z: 535 (M⁺+H).

Anal. calcd for C₂₆H₂₅ClF₂N₂O₄S: C, 58.37; H, 4.71; Cl, 6.63; F, 7.10; N, 5.24; S, 5.99. Found: C, 58.28; H, 4.86; Cl, 6.56; F, 7.17; N, 5.30; S, 6.13.

Example 213

3-[(4-Chlorophenyl)sulfonyl]-3-(2,5-difluorophenyl)propyl=4-methyl-1-piperazinecarboxylate Hydrochloride

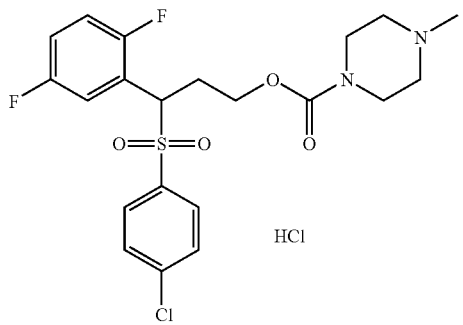

The 3-[(4-chlorophenyl)sulfonyl]-3-(2,5-difluorophenyl)-1-propanol (150 mg, 0.432 mmol) obtained in Example 207 was dissolved in dichloromethane (4 ml), followed by the addition of triethylamine (63.2 μl, 0.454 mmol) and 4-nitrophenyl chloroformate (91.7 mg, 0.454 mmol). The resulting mixture was stirred at room temperature for 18 hours. After addition of N-methylpiperazine (57.4 μl, 0.518 mmol) and triethylamine (72.1 μl, 0.518 mmol), the mixture was stirred at room temperature for 24 hours. The reaction mixture was diluted with dichloromethane, washed successively with a saturated aqueous solution of sodium bicarbonate and brine, dried over sodium sulfate and then, concentrated. The residue thus obtained was subjected to flash chromatography on a silica gel column, and the fraction obtained from the dichloromethane:methanol=30:1 eluate was concentrated. The solid thus obtained was dissolved in ethanol. After addition of 1N hydrochloric acid-ethanol (2 ml), the resulting mixture was concentrated to dryness. The solid thus obtained was washed with ethyl acetate, whereby the title compound (96.9 mg, 0.189 mmol, 44%) was obtained as a pale yellow solid.

$^1$H-NMR (400 MHz, CDCl$_3$) δ: 2.37-2.47(1H,m), 2.60-2.92(8H,m), 3.20-4.30(6H,m), 4.62(1H,dd,J=10.0, 3.4 Hz), 6.85(1H,td,J=9.0, 4.4 Hz), 6.98-7.05(1H,m), 7.19-7.28(1H, m), 7.39(2H,d,J=8.8 Hz), 7.51(2H,d,J=8.8 Hz).

IR (ATR) cm$^{-1}$: 2387, 1699, 1583, 1496, 1473, 1425, 1317, 1255, 1232, 1176, 1149, 1084, 978, 829, 758, 710, 629, 555, 467.

MS m/z: 473 (M$^+$+H).

Anal. calcd for C$_{21}$H$_{23}$ClF$_2$N$_2$O$_4$S.HCl.0.25H$_2$O: C, 49.08; H, 4.81; Cl, 13.80; F, 7.39; N, 5.45; S, 6.24. Found: C, 49.03; H, 5.01; Cl, 13.31; F, 7.31; N, 5.54; S, 6.28.

Example 214

3-[(4-Chlorophenyl)sulfonyl]-3-(2,5-difluorophenyl)propyl=carbamate

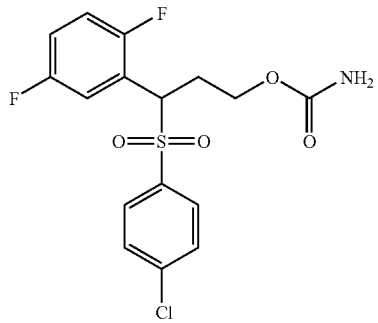

The 3-[(4-chlorophenyl)sulfonyl]-3-(2,5-difluorophenyl)-1-propanol (200 mg, 0.576 mmol) obtained in Example 207 was dissolved in dichloromethane (4 ml), followed by the addition of triethylamine (84.2 μl, 0.605 mmol) and 4-nitrophenyl chloroformate (122 mg, 0.605 mmol). The resulting mxiture was stirred at room temperature for 18 hours. Concenterated aqueous ammonia (2.5 ml) was added and the mixture was vigorously stirred at room temperature for 3 hours. After separation of the water layer, the organic layer was washed with water and brine, dried over sodium sulfate and then, concentrated. The residue thus obtained was subjected to flash chromatography on a silica gel column, and the fraction obtained from the hexane:ethyl acetate=1:1 eluate was concentrated. The solid thus obtained was recrystallized from ethyl acetate-hexane, whereby the title compound (156 mg, 0.353 mmol, 61%) was obtained as colorless needle crystals.

$^1$H-NMR (400 MHz, CDCl$_3$) δ: 2.34-2.44(1H,m), 2.77-2.86(1H,m), 3.89(1H,ddd,J=11.0,9.0,5.1 Hz), 4.19(1H,dt, J=11.0, 5.6 Hz), 4.53(2H,br s), 4.69(1H,dd,J=11.0, 3.9 Hz), 6.84(1H,td,J=9.0, 4.4 Hz), 6.97-7.03(1H,m), 7.24(1H,ddd, J=8.8,5.4,3.2 Hz), 7.40(2H,d,J=8.5 Hz), 7.54(2H,d,J=8.5 Hz).

IR (ATR) cm$^{-1}$: 3452, 3263, 1734, 1606, 1493, 1396, 1313, 1230, 1144, 1080, 1051, 957, 829, 795, 752, 623, 553, 465.

mp: 139-140° C.

MS m/z: 390 (M$^+$+H).

Anal. calcd for C$_{16}$H$_{14}$ClF$_2$NO$_4$S: C, 49.30; H, 3.62; Cl, 9.10; F, 9.75; N, 3.59; S, 8.23. Found: C, 49.13; H, 3.53; Cl, 9.19; F, 9.86; N, 3.68; S, 8.35.

Example 215

3-[(4-Chlorophenyl)sulfonyl]-3-(2,5-difluorophenyl)propyl N-methylcarbamate

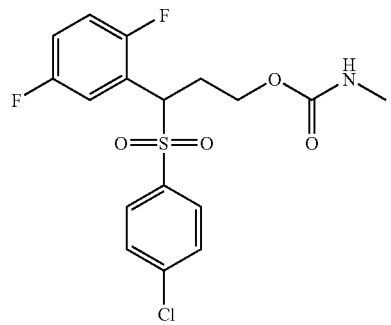

The 3-[(4-chlorophenyl)sulfonyl]-3-(2,5-difluorophenyl)-1-propanol (200 mg, 0.576 mmol) obtained in Example 207 was dissolved in dichloromethane (4 ml), followed by the addition, of triethylamine (84.2 μl, 0.605 mmol) and 4-nitrophenyl chloroformate (122 mg, 0.605 mmol). The resulting mixture was stirred at room temperature for 15 hours. After addition of methylamine (a 2.00M tetrahydrofuran solution, 2.0 ml, 4.00 mmol), the mixture was stirred at room temperature for 24 hours. Methylamine (a 2.00M tetrahydrofuran solution, 3.0 ml, 4.00 mmol) was added and the mixture was stirred at room temperature for 5 hours. The reaction mixture was diluted with dichloromethane, washed successively with a saturated aqueous solution of sodium bicarbonate, water and brine, dried over magnesium sulfate and then, concentrated. The residue thus obtained was subjected to flash chromatography on a silica gel column, and the fraction obtained from the hexane:ethyl acetate=3:2 eluate was concentrated. The concentrate was purified further by high performance liquid chromatography (using a mixed solvent of water/acetonitrile/formic acid) to yield the title compound (62.1 mg, 0.154 mmol, 27%) as a colorless oil.

$^1$H-NMR (400 MHz, CDCl$_3$) δ: 2.32-2.45(1H,m), 2.60-2.85(4H,m), 3.83-3.90(1H,m), 4.19(1H,dt,J=11.0, 5.4 Hz), 4.49(1H,br s), 4.68(1H,m), 6.84(1H,td,J=9.0, 4.4 Hz), 6.96-7.02(1H,m), 7.20-7.26(1H,m), 7.39(2H,d,J=8.5 Hz), 7.54 (2H,d,J=8.5 Hz).

IR (ATR) cm$^{-1}$: 3403, 1709, 1527, 1496, 1477, 1317, 1248, 1147, 1086, 1012, 827, 754, 629, 555, 467.

MS m/z: 404 (M$^+$+H).

FAB-MS: 404.0551 (calcd for C$_{17}$H$_{17}$ClF$_2$NO$_4$S: 404.0535)

Example 216

3-[(4-Chlorophenyl)sulfonyl]-3-(2,5-difluorophenyl) propyl=N,N-dimethylcarbamate

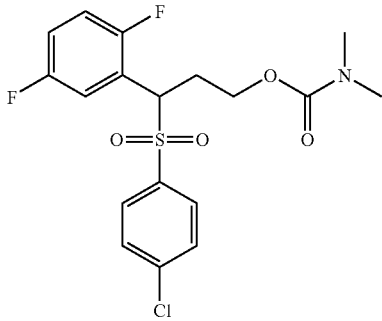

The 3-[(4-chlorophenyl)sulfonyl]-3-(2,5-difluorophenyl)-1-propanol (200 mg, 0.576 mmol) obtained in Example 207 was dissolved in dichloromethane (4 ml), followed by the addition of triethylamine (84.2 μl, 0.605 mmol) and 4-nitrophenyl chloroformate (122 mg, 0.605 mmol). The resulting mixture was stirred at room temperature for 6 hours. To the reaction mixture was added a 50% aqueous dimethylamine solution (2 ml). The mixture was stirred at room temperature for 15 hours. After further addition of a 50% aqueous dimethylamine solution (1 ml), stirring was conducted at room temperature for 1 hour. The reaction mixture was diluted with dichloromethane, washed with 1N potassium hydroxide, water and brine, dried over magnesium sulfate and then, concentrated. The residue thus obtained was subjected to flash chromatography on a silica gel column, and the fraction obtained from the hexane:ethyl acetate=3:2 eluate was concentrated, whereby the title compound (151 mg, 0.362 mmol, 63%) was obtained as a colorless oil.

$^1$H-NMR (400 MHz, CDCl$_3$) δ: 2.38-2.46(1H,m), 2.70-2.88(7H,m), 3.89(1H,ddd,J=11.2,8.3,4.9 Hz), 4.21(1H,dt, J=11.2, 5.6 Hz), 4.69(1H,dd,J=11.2, 3.9 Hz), 6.83(1H,td, J=9.0, 4.4 Hz), 6.95-7.02(1H,m), 7.23(1H,ddd,J=8.8,5.4,3.4 Hz), 7.39(2H,d,J=8.5 Hz), 7.54(2H,d,J=8.5 Hz).

IR (ATR) cm$^{-1}$: 2943, 1697, 1583, 1495, 1402, 1319, 1279, 1223, 1180, 1147, 1082, 1012, 829, 754, 710, 623, 555, 525, 467.

MS m/z: 418 (M$^+$+H).

FAB-MS: 418.0692 (calcd for C$_{18}$H$_{19}$ClF$_2$NO$_4$S: 418.0691)

Example 217

2-[1-[(4-Chlorophenyl)sulfonyl]-2-phenylethyl]-1,4-difluorobenzene

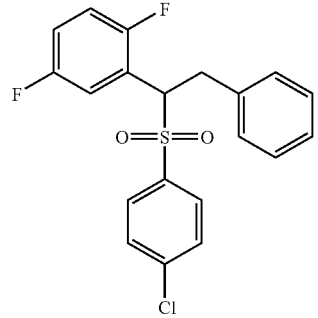

Under an argon atmosphere and at −78° C., n-butyl lithium (a 1.60 M hexane solution, 459 μl, 0.734 mmol) was added to a dimethoxyethane solution (50 ml) of the 2-[(4-chlorophenyl)sulfonylmethyl]-1,4-difluorobenzene (202 mg, 0.667 mmol) obtained in Example 5. The temperature of the resulting mxiture was then elevated to room temperature. After the reaction mixture was cooled to −78° C., benzylbromide (87.2 μl, 0.734 mmol) was added dropwise thereto. While elevating the temperature of the reaction mixture to room temperature, stirring was conducted for 15 hours. Water was added to the reaction mixture, followed by extraction with ethyl acetate. The extracts were combined, washed with brine, dried over magnesium sulfate and then, concentrated. The residue thus obtained was subjected to flash chromatography on a silica gel column, and the fraction obtained from the hexane:ethyl acetate=6:1 eluate was concentrated. The solid thus obtained was recrystallized from ethyl acetate-hexane, whereby the title compound (125 mg, 0.318 mmol, 48%) was obtained as colorless needle crystals.

$^1$H-NMR (400 MHz, CDCl$_3$) δ: 3.32(1H,dd,J=13.9, 11.7 Hz), 3.84(1H,dd,J=13.9, 3.4 Hz), 4.81(1H,dd,J=11.7, 3.4 Hz), 6.69(1H,td,J=9.3, 4.4 Hz), 6.87-6.94(1H,m), 7.00-7.05 (2H,m), 7.12-7.20(3H,m), 7.38-7.43(3H,m), 7.57(2H,d, J=8.5 Hz).

IR (ATR) cm$^{-1}$: 1574, 1493, 1303, 1279, 1219, 1144, 1083, 1011, 879, 825, 785, 742, 698, 633, 555, 526, 467.

mp: 160-161° C.

MS m/z: 393 (M$^+$+H).

Anal. calcd for C$_{20}$H$_{15}$ClF$_2$NO$_2$S: C, 61.15; H, 3.85; Cl, 9.02; F, 9.67; S, 8.16. Found: C, 61.07; H, 3.87; Cl, 8.95; F, 9.95; S, 8.30.

Example 218

2-[2-[(4-Chlorophenyl)sulfonyl]-2-(2,5-difluorophenyl)ethyl]pyridine

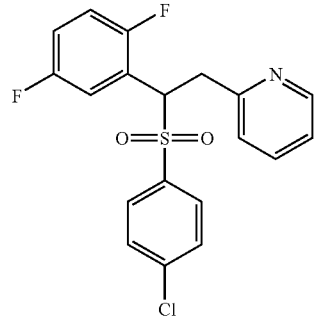

Under an argon atmosphere, the 2-[(4-chlorophenyl)sulfonylmethyl]-1,4-difluorobenzene (150 mg, 0.495 mmol) obtained in Example 5 and 2-pyridylmethanol (95.5 μl, 0.990 mmol) were dissolved in toluene (5 ml), followed by the addition of cyanomethylenetri-n-butylphosphorane (239 mg, 0.990 mmol). The resulting mixture was heated under reflux for 18 hours under an argon atmosphere. The reaction mixture was then concentrated. The residue thus obtained was subjected to flash chromatography on a silica gel column, and the fraction obtained from the hexane:ethyl acetate=1:1 eluate was concentrated. The solid thus obtained was recrystallized from ethyl acetate-hexane, whereby the title compound (96.6 mg, 0.245 mmol, 49%) was obtained as colorless needle crystals.

$^1$H-NMR (400 MHz, CDCl$_3$) δ: 3.49(1H,dd,J=14.7, 10.7 Hz), 3.95(1H,dd,J=14.7, 4.6 Hz), 5.37(1H,dd,J=11.0, 4.2 Hz), 6.73(1H,td,J=9.0, 4.4 Hz), 6.86-6.94(1H,m), 7.03-7.07 (2H,m), 7.33(1H,ddd,J=8.8,5.4,3.2 Hz), 7.39(2H,d,J=8.5 Hz), 7.49(1H,td,J=7.8, 1.7 Hz), 7.60(2H,d,J=8.5 Hz), 8.41 (1H,d,J=4.4 Hz).

IR (ATR) cm$^{-1}$: 3041, 1585, 1496, 1433, 1321, 1277, 1149, 1086, 910, 825, 779, 746, 644, 536, 461, 436.

mp: 105-107° C.

MS m/z: 394 (M$^+$+H).

Anal. calcd for C$_{19}$H$_{14}$ClF$_2$NO$_2$S: C, 57.94; H, 3.58; Cl, 9.00; F, 9.65; N, 3.56; S, 8.14. Found: C, 57.85; H, 3.59; Cl, 8.97; F, 9.52; N, 3.69; S, 8.28.

Example 219

3-[2-[(4-Chlorophenyl)sulfonyl]-2-(2,5-difluorophenyl)ethyl]pyridine

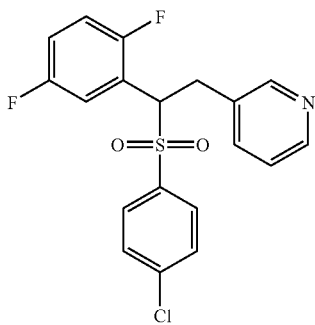

Under an argon atmosphere, the 2-[(4-chlorophenyl)sulfonylmethyl]-1,4-difluorobenzene (120 mg, 0.396 mmol) obtained in Example 5 and 3-pyridylmethanol (50.1 μl, 0.515 mmol) were dissolved in toluene (4 ml), followed by the addition of cyanomethylenetri-n-butylphosphorane (124 mg, 0.515 mmol). The resulting mixture was heated under reflux for 18 hours under an argon atmosphere. The reaction mixture was then concentrated. The residue thus obtained was subjected to flash chromatography on a silica gel column, and the fraction obtained from the hexane:ethyl acetate=3:7 eluate was concentrated. The solid thus obtained was recrystallized from ethyl acetate-hexane, whereby the title compound (90.3 mg, 0.229 mmol, 58%) was obtained as colorless columnar crystals.

$^1$H-NMR (400 MHz, CDCl$_3$) δ: 3.35(1H,dd,J=14.4, 11.7 Hz), 3.85(1H,dd,J=14.4, 3.9 Hz), 4.77(1H,dd,J=11.7, 3.2 Hz), 6.71(1H,td,J=9.0, 4.4 Hz), 6.90-6.97(1H,m), 7.13(1H, dd,J=8.1, 4.9 Hz), 7.37-7.45(4H,m), 7.57(2H,d,J=8.8 Hz), 8.30(1H,d,J=2.0 Hz), 8.41(1H,dd,J=4.9, 1.5 Hz).

IR (ATR) cm$^{-1}$: 3078, 1577, 1495, 1427, 1313, 1279, 1217, 1144, 1082, 1012, 823, 775, 752, 706, 646, 557, 532, 464.

mp: 162-163° C.

MS m/z: 394 (M$^+$+H).

Anal. calcd for C$_{19}$H$_{14}$ClF$_2$NO$_2$S: C, 57.94; H, 3.58; Cl, 9.00; F, 9.65; N, 3.56; S, 8.14. Found: C, 57.80; H, 3.51; Cl, 9.06; F, 9.53; N, 3.71; S, 8.22.

Example 220

4-[2-[(4-Chlorophenyl)sulfonyl]-2-(2,5-difluorophenyl)ethyl]pyridine

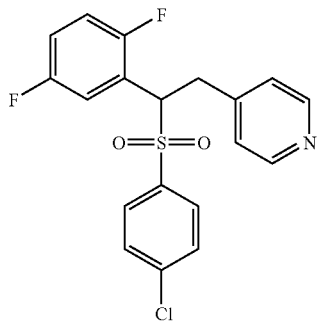

Under an argon atmosphere, the 2-[(4-chlorophenyl)sulfonylmethyl]-1,4-difluorobenzene (200 mg, 0.660 mmol) obtained in Example 5 and 4-pyridylmethanol (144 mg, 1.32 mmol) were dissolved in toluene (6 ml), followed by the addition of cyanomethylenetri-n-butylphosphorane (318 mg, 1.32 mmol). The resulting mixture was heated under reflux for 15 hours under an argon atmosphere. The reaction mixture was then concentrated. The residue thus obtained was subjected to flash chromatography on a silica gel column, and the fraction obtained from the hexane:ethyl acetate=1:2 elulate was concentrated. The solid thus obtained was recrystallized from ethyl acetate, whereby the title compound (81.4 mg, 0.207 mmol, 31%) was obtained as colorless needle crystals.

$^1$H-NMR (400 MHz, CDCl$_3$) δ: 3.34(1H,dd,J=14.2, 12.0 Hz), 3.84(1H,dd,J=14.2, 3.4 Hz), 4.81(1H,dd,J=12.0, 3.4 Hz), 6.72(1H,td,J=9.0, 4.6 Hz), 6.91-6.96(1H,m), 6.97(2H,d, J=6.1 Hz), 7.34-7.39(1H,m), 7.40(2H,d,J=8.5 Hz), 7.56(2H, d,J=8.5 Hz), 8.42(2H,dd,J=4.4, 1.5 Hz).

IR (ATR) cm$^{-1}$: 1597, 1493, 1417, 1301, 1277, 1219, 1174, 1144, 1082, 1012, 985, 883, 850, 808, 754, 706, 631, 606, 557, 524, 469.

mp: 129° C.

MS m/z: 394 (M$^+$+H).

Anal. calcd for C$_{19}$H$_{14}$ClF$_2$NO$_2$S: C, 57.94; H, 3.58; Cl, 9.00; F, 9.65; N, 3.56; S, 8.14. Found: C, 57.67; H, 3.45; Cl, 9.00; F, 9.78; N, 3.64; S, 8.31.

Example 221

2-[3-(4-Chlorophenylsulfonyl)-3-(2,5-difluorophenyl)propyl]thiophene

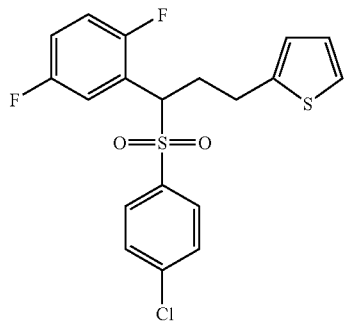

Under an argon atmosphere, the 2-[(4-chlorophenyl)sulfonylmethyl]-1,4-difluorobenzene (100 mg, 0.330 mmol) obtained in Example 5 and 2-(2-thienyl)ethanol (144 mg, 1.32 mmol) were dissolved in toluene (3 ml), followed by the addition of cyanomethylenetri-n-butylphosphorane (159 mg, 0.660 mmol). The resulting mixture was heated under reflux for 15 hours under a nitrogen atmosphere. The reaction mixture was then concentrated. The residue thus obtained was subjected to flash chromatography on a silica gel column, and the fraction obtained from the hexane:ethyl acetate=12:1 eluate was concentrated, whereby the title compound (90.0 mg, 0.218 mmol, 53%) was obtained as a colorless oil.

$^1$H-NMR (400 MHz, CDCl$_3$) δ: 2.42-2.52(1H,m), 2.68-2.83(2H,m), 2.85-2.92(1H,m), 4.54(1H,dd,J=11.2, 2.4 Hz), 6.70(1H,d,J=2.7 Hz), 6.86(1H,td,J=9.0, 4.4 Hz), 6.90(1H,dd, J=5.1, 3.4 Hz), 6.97-7.05(1H,m), 7.14(1H,dd,J=5.1, 1.2 Hz), 7.24-7.29(1H,m), 7.38(2H,d,J=8.5 Hz), 7.51(2H,d,J=8.5 Hz).

IR (ATR) cm$^{-1}$: 3086, 1583, 1495, 1425, 1394, 1317, 1277, 1147, 1084, 1012, 827, 754, 694, 627, 555, 465.

MS m/z: 413 (M$^+$+H).

FAB-MS: 413.0251 (Calcd for C$_{19}$H$_{16}$ClF$_2$O$_2$S: 413.0248).

Example 222

Ethyl N-[3-[(4-chlorophenyl)sulfonyl]-3-(2,5-difluorophenyl)propyl]carbamate

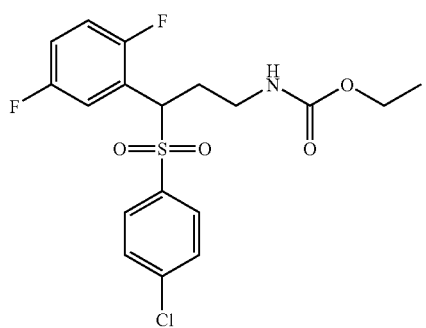

Under a nitrogen atmosphere and at 0° C., triethylamine (81.5 μl, 0.586 mmol) and diphenylphosphoric azide (126 μl, 0.586 mmol) were added to a toluene solution (5 ml) of the 4-[(4-chlorophenyl)sulfonyl]-4-(2,5-difluorophenyl)butyric acid (200 mg, 0.533 mmol) obtained in Example 200, followed by stirring at 0° C. for 2 hours. The reaction mixture was heated under reflux for 3 hours. After cooling to room temperature and addition of ethanol (2 ml), the mixture was heated under reflux for further 2 hours. The reaction mixture was then concentrated. The residue thus obtained was dissolved in dichloromethane. The resulting solution was washed successively with a saturated aqueous solution of potassium bicarbonate, water and brine, dried over magnesium sulfate and then, concentrated. The residue thus obtained was subjected to flash chromatography on a silica gel column, and the fraction obtained from the hexane:ethyl acetate=1:3 eluate was concentrated. The solid thus obtained was recrystallized from ethyl acetate-hexane, whereby the title compound (129 mg, 0.309 mmol, 58%) was obtained as a white solid.

$^1$H-NMR (400 MHz, CDCl$_3$) δ: 1.21(3H,t,J=7.1 Hz), 2.24-2.36(1H,m), 2.60-2.70(1H,m), 3.10-3.33(2H,m), 4.06(2H,q, J=7.1 Hz), 4.60(1H,dd,J=11.0, 4.6 Hz), 4.70(1H,br s), 6.83 (1H,td,J=9.0, 4.4 Hz), 6.95-7.02(1H,m), 7.21-7.26(1H,m), 7.38(2H,d,J=8.3 Hz), 7.52(2H,d,J=8.3 Hz).

IR (ATR) cm$^{-1}$: 3394, 1691, 1576, 1525, 1496, 1396, 1304, 1281, 1250, 1225, 1149, 1086, 1028, 1012, 974, 885, 829, 791, 766, 752, 629, 553, 465.

mp: 121-122° C.

MS m/z: 418 (M$^+$+H).

Anal. calcd for C$_{18}$H$_{18}$ClF$_2$NO$_4$S: C, 51.74; H, 4.34; Cl, 8.48; F, 9.09; N, 3.35; S, 7.67. Found: C, 51.49; H, 4.43; Cl, 8.55; F, 9.13; N, 3.61; S, 7.75.

Example 223

Ethyl N-[3-[(4-chlorophenyl)sulfonyl]-3-(2,5-difluorophenyl)propyl]-N-methylcarbamate

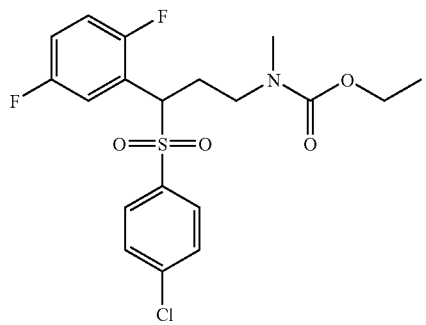

In tetrahydrofuran (4 ml) was dissolved ethyl N-[3-[(4-chlorophenyl)sulfonyl]-3-(2,5-difluorophenyl)propyl]carbamate (100 mg, 0.239 mmol), followed by the addition of sodium hydride (60% dispersion in mineral oil, 11.5 mg, 0.287 mmol). The resulting mixture was stirred at room temperature for 3 hours. Iodomethane (17.8 μl, 0.287 mmol) was added and the mixture was stirred at room temperature for 15 hours. Sodium hydride (60% dispersion in mineral oil, 5.00 mg, 0.125 mmol) and iodomethane (10.0 μl, 0.161 mmol) were added, followed by stirring at room temperature for 24 hours. Water (5 ml) was added, and the mixture was concentrated. The residue thus obtained was extracted with ethyl acetate. The extract was washed with brine, dried over magnesium sulfate and then concentrated. The residue thus obtained was subjected to flash chromatography on a silica gel column, and the fraction obtained from the hexane:ethyl acetate=3:1 eluate was concentrated, whereby the title compound (83.2 mg, 0.193 mmol, 81%) was obtained as a colorless oil.

$^1$H-NMR (400 MHz, CDCl$_3$) δ: 1.11-1.27(3H,br m), 2.20-2.35(1H,br m), 2.68-2.90(4H,m), 3.18-3.35(2H,m), 3.93-4.12(2H,br m), 4.51(1H,br s), 6.82(1H,td,J=9.0, 4.6 Hz), 6.96-7.04(1H,br m), 7.21-7.27(1H,br m), 7.38(2H,d,J=8.5 Hz), 7.51 (2H,d,J=8.5 Hz).

IR (ATR) cm$^{-1}$: 2983, 1693, 1583, 1495, 1319, 1182, 1147, 1084, 1012, 883, 827, 754, 710, 629, 555, 467.

MS m/z: 432 (M$^+$+H).

FAB-MS: 432.0838 (calcd for C$_{19}$H$_{21}$ClF$_2$NO$_4$S: 432.0848)

Example 224

2-Iodoethyl N-[4-[(4-chlorophenyl)sulfonyl]-4-(2,5-difluorophenyl)butyl]carbamate

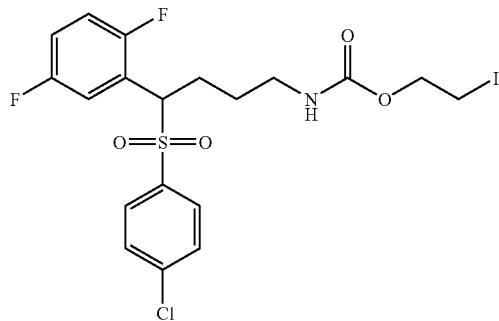

Under a nitrogen atmosphere and at 0° C., triethylamine (157 μl, 1.13 mmol) and diphenylphosphoric azide (243 μl, 1.13 mmol) were added to a toluene solution (5 ml) of the 5-[(4-chlorophenyl)sulfonyl]-5-(2,5-difluorophenyl)valeric acid (400 mg, 1.03 mmol) obtained in Example 202. The resulting mixture was stirred at room temperature for 2 hours. The reaction mixture was heated under reflux for 3 hours. After cooling to room temperature and addition of 2-iodoethanol (160 μl, 2.06 mmol), the mixture was heated under reflux for further 1.5 hours. The reaction mixture diluted with ethyl acetate was then washed successively with a saturated aqueous solution of sodium bicarbonate, water, and brine, dried over magnesium sulfate and then, concentrated. The residue thus obtained was subjected to flash chromatography on a silica gel column, and the fraction obtained from the hexane:ethyl acetate=3:1 eluate was concentrated. The solid thus obtained was recrystallized from ethyl acetate-hexane, whereby the title compound (300 mg, 0.538 mmol, 52%) was obtained as colorless needle crystals.

$^1$H-NMR (400 MHz, CDCl$_3$) δ: 1.44-1.60(2H,m), 2.05-2.17(1H,m), 2.44-2.55(1H,m), 3.19(2H,q,J=6.4 Hz), 3.28 (2H,t,J=6.8 Hz), 4.29(2H,t,J=6.8 Hz), 4.57(1H,br m), 4.76 (1H,br s), 6.84(1H,td,J=9.0, 4.4 Hz), 6.95-7.02(1H,m), 7.23-7.28(1H,m), 7.39(2H,d,J=8.5 Hz), 7.53(2H,d,J=8.5 Hz).

IR (ATR) cm$^{-1}$: 3406, 1722, 1585, 1516, 1493, 1306, 1238, 1147, 1009, 872, 822, 781, 752, 708, 627, 546, 525, 463.

mp: 100-101° C.

MS m/z: 558 (M$^+$+H).

Anal. calcd for C$_{19}$H$_{19}$ClF$_2$INO$_4$S: C, 40.91; H, 3.43; Cl, 6.36; F, 6.81; N, 2.51; S, 5.75. Found: C, 40.79; H, 3.40; Cl, 6.41; F, 6.96; N, 2.61; S, 5.85.

Example 225

3-[4-[(4-Chlorophenyl)sulfonyl]-4-(2,5-difluorophenyl)butyl]-2-oxazolidinone

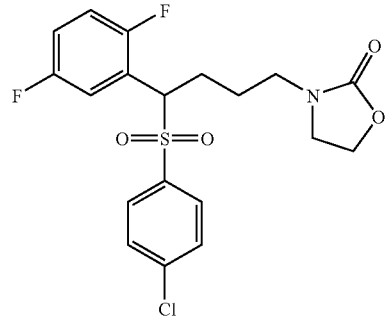

Under a nitrogen atmosphere and at 0° C., sodium hydride (60% dispersion in mineral oil, 13.6 mg, 0.340 mmol) was added to a tetrahydrofuran solution (5 ml) of 2-iodoethyl N-[4-[(4-chlorophenyl)sulfonyl]-4-(2,5-difluorophenyl)butyl]carbamate (158 mg, 0.283 mmol). The resulting mixture was stirred at room temperature for 18 hours. Water was added to the reaction mixture, followed by extraction wth ethyl acetate. The extract was washed with brine, dried over magnesium sulfate and then concentrated. The residue thus obtained was subjected to flash chromatography on a silica gel column, and the fraction obtained from the hexane:ethyl acetate=1:2 eluate was concentrated. The solid thus obtained was recrystallized from ethyl acetate-hexane, whereby the title compound (52.1 mg, 0.121 mmol, 43%) was obtained as colorless needle crystals.

$^1$H-NMR (400 MHz, CDCl$_3$) δ: 1.52-1.63(2H,m), 2.05-2.16(1H,m), 2.42-2.51(1H,m), 3.18-3.35(2H,m), 3.50(2H,t, J=8.3 Hz), 4.31(2H,dd,J=8.8, 7.1 Hz), 4.60(1H,dd,J=10.3, 4.9 Hz), 6.85(1H,td,J=9.0, 4.4 Hz), 6.96-7.02(1H,m), 7.22-7.28(1H,m), 7.39(2H,d,J=8.5 Hz), 7.54(2H,d,J=8.5 Hz).

IR (ATR) cm$^{-1}$: 2918, 1734, 1583, 1487, 1425, 1308, 1265, 1182, 1130, 1086, 1012, 895, 804, 758, 708, 594, 577, 538, 478, 444.

mp: 156-159° C.

MS m/z: 430 (M$^+$+H).

Anal. calcd for C$_{19}$H$_{18}$ClF$_2$NO$_4$S: C, 53.09; H, 4.22; Cl, 8.25; F, 8.84; N, 3.26; S, 7.46. Found: C, 52.84; H, 4.15; Cl, 8.40; F, 8.96; N, 3.33; S, 7.58.

Example 226 t-Butyl N-[4-[(4-chlorophenyl)sulfonyl]-4-(2,5-difluorophenyl)butyl]carbamate

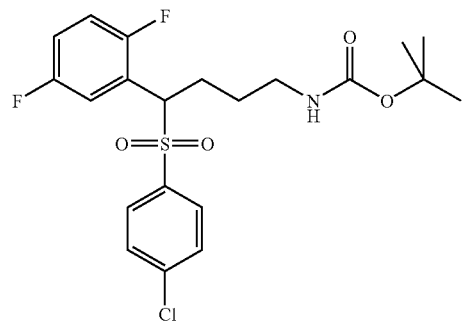

Under a nitrogen atmosphere, triethylamine (126 μl, 0.907 mmol) and diphenylphosphoric azide (195 μl, 0.907 mmol) were added to a toluene solution (6 ml) of the 5-[(4-chlorophenyl)sulfonyl]-5-(2,5-difluorophenyl)valeric acid (294 mg, 0.533 mmol) obtained in Example 202. The resulting mixture was stirred at room temperature for 3 hours. The reaction mixture was heated under reflux for 3 hours. After cooling to room temperature and addition of 2-methyl-2-propanol (1 ml), the mixture was stirred at 80° C. for further 18 hours. The reaction mixture was then concentrated and the residue thus obtained was dissolved in dichloromethane. The resulting solution was washed successively with a saturated aqueous solution of potassium bicarbonate, water and brine, dried over magnesium sulfate and then, concentrated. The residue thus obtained was subjected to flash chromatography on a silica gel column, and the fraction obtained from the hexane:ethyl acetate=4:1 eluate was concentrated to yield the title compound (171 mg, 0.383 mmol, 51%) as a white solid. The solid thus obtained was recrystallized from ethyl acetate-hexane, whereby colorless needle crystals were obtained.

$^1$H-NMR (400 MHz, CDCl$_3$) δ: 1.40-1.49(11H,s), 2.05-2.14(1H,m), 2.43-2.52(1H,m), 3.07-3.17(2H,m), 4.48-4.60 (2H,m), 6.83(1H,td,J=9.0, 4.4 Hz), 6.94-7.01(1H,m), 7.24 (1H,ddd,J=8.8,5.4,3.2 Hz), 7.38(2H,d,J=8.5 Hz), 7.53(2H,d, J=8.5 Hz).

IR (ATR) cm$^{-1}$: 3392, 2960, 1695, 1583, 1514, 1493, 1365, 1313, 1248, 1174, 1147, 1084, 999, 827, 752, 644, 548, 528, 451.

mp: 119-120° C.

MS m/z: 460 (M$^+$+H).

Anal. calcd for C$_{21}$H$_{24}$ClF$_2$NO$_4$S: C, 54.84; H, 5.26; Cl, 7.71; F, 8.26; N, 3.05; S, 6.97. Found: C, 54.84; H, 5.31; Cl, 7.06; F, 8.36; N, 3.16; S, 7.14.

Example 227

4-[(4-Chlorophenyl)sulfonyl]-4-(2,5-difluorophenyl) butylamine Hydrochloride

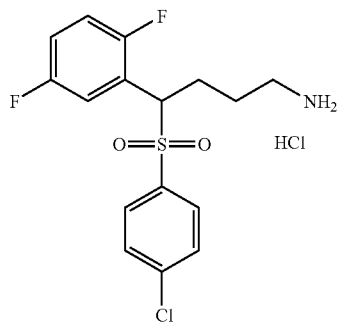

Concentrated hydrochloric acid (2 ml) was added to an ethanol solution (2 ml) of t-butyl N-[4-[(4-chlorophenyl)sulfonyl]-4-(2,5-difluorophenyl)butyl]carbamate (104 mg, 0.226 mmol), followed by stirring at room temperature for 2 hours. The reaction mixture was then concentrated. The residue thus obtained was recrystallized from ethanol-ethyl acetate, whereby the title compound (78.9 mg, 0.199 mmol, 88%) was obtained as colorless needle crystals.

$^1$H-NMR (400 MHz, CDCl$_3$) δ: 1.51-1.60(1H,m), 1.63-1.75(1H,m), 2.18-2.28(1H,m), 2.45-2.54(1H,m), 2.95(2H, ddd,J=8.5,6.8,3.2 Hz), 4.76(1H,dd,J=11.0, 4.6 Hz), 6.98(1H, td,J=9.3, 4.4 Hz), 7.09-7.17(1H,m), 7.32(1H,ddd,J=9.0,5.6, 3.4 Hz), 7.52(2H,d,J=8.8 Hz), 7.60(2H,d,J=8.8 Hz).

IR (ATR) cm$^{-1}$: 2951, 2871, 1583, 1496, 1427, 1396, 1311, 1279, 1219, 1147, 1081, 1011, 870, 825, 742, 706, 629, 536, 463.

mp: 232-233° C.

MS m/z: 360 (M$^+$+H).

Anal. calcd for C$_{16}$H$_{16}$ClF$_2$NO$_2$S.HCl: C, 48.49; H, 4.32; Cl, 17.89; F, 9.59; N, 3.53; S, 8.09. Found: C, 48.20; H, 4.27; Cl, 17.84; F, 9.61; N, 3.63; S, 8.15.

Example 228

N-[4-[(4-Chlorophenyl)sulfonyl]-4-(2,5-difluorophenyl)butyl]nicotinamide Hydrochloride

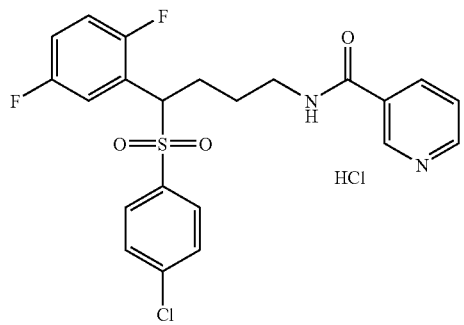

Under a nitrogen atmosphere and 0° C., N-methylmorpholine (44.6 μl, 0.406 mmol) and nicotinic acid chloride hydrochloride (36.1 mg, 0.203 mmol) were added to a dichloromethane solution (4 ml) of 4-[(4-chlorophenyl)sulfonyl]-4-(2,5-difluorophenyl)butylamine hydrochloride (67.0 mg, 0.169 mmol). After stirring at room temperature for 3 hours, the reaction mixture was diluted with dichloromethane, washed successively with a saturated aqueous solution of ammonium chloride, water and brine, dried over magnesium sulfate and then, concentrated. The residue thus obtained was subjected to flash chromatography on a silica gel column, and the fraction obtained from the hexane:ethyl acetate=1:3 eluate was concentrated. The resulting solid was dissolved in ethanol. To the resulting solution was added 1N hydrochloric acid-ethanol (0.5 ml), followed by concentration. The solid thus obtained was recrystallized from ethanol-ethyl acetate, whereby the title compound (67.1 mg, 0.134 mmol, 79%) was obtained as a white solid.

$^1$H-NMR (400 MHz, CD$_3$OD) δ: 1.58-1.67(2H,m), 2.18-2.28(1H,m), 2.42-2.52(1H,m), 3.40(1H,dt,J=13.7, 6.6 Hz), 3.51(1H,dt,J=13.7, 6.8 Hz), 4.81(1H,m), 6.98(1H,td,J=9.3, 4.4 Hz), 7.08-7.15(1H,m), 7.30(1H,ddd,J=9.0,5.6,3.4 Hz), 7.50(2H,d,J=8.8 Hz), 7.62(2H,d,J=8.8 Hz), 8.18(1H,dd, J=8.1, 5.9 Hz), 8.92(1H,dd,J=8.1, 1.5 Hz), 8.99(1H,d,J=5.9 Hz), 9.22(1H,d,J=1.2 Hz).

IR (ATR) cm$^{-1}$: 3282, 2457, 2096, 1977, 1666, 1547, 1493, 1302, 1234, 1173, 1147, 1092, 1016, 883, 829, 760, 733, 673, 623, 528.

mp: 154-157° C.

MS m/z: 465 (M$^+$+H).

Anal. calcd for C$_{22}$H$_{19}$ClF$_2$N$_2$O$_3$S.HCl: C, 52.70; H, 4.02; Cl, 14.14; F, 7.58; N, 5.59; S, 6.40. Found: C, 52.59; H, 4.01; Cl, 14.19; F, 7.72; N, 5.73; S, 6.56.

Example 229

1-[4-(4-Chlorophenylsulfonyl)-4-(2,5-difluorophenyl)butyl]-2-pyrrolidinone

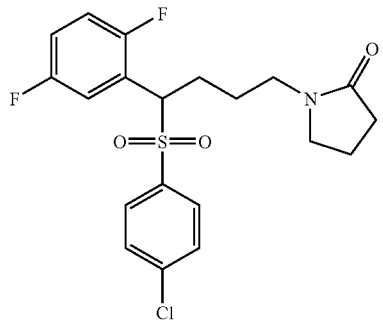

To a dichloromethane solution (6 ml) of the 4-[(4-chlorophenyl)sulfonyl]-4-(2,5-difluorophenyl)butylamine hydrochloride (120 mg, 0.303 mmol) obtained in Example 227 were added N-methylmorpholine (250 μl, 2.69 mmol) and 4-chlorobutyric acid chloride (40.7 μl, 0.364 mmol). After stirring at room temperature for 1 hour, the reaction mixture was diluted with dichloromethane, washed successively with a saturated aqueous solution of ammonium chloride, water and brine, dried over magnesium sulfate and then, concentrated. The residue thus obtained was dissolved in tetrahydrofuran (5 ml), followed by the addition of sodium hydride (60% dispersion in mineral oil, 14.2 mg, 0.356 mmol) and N,N-dimethylformamide (2 drops). The resulting mixture was stirred at room temperature for 24 hours. Water was added and the resulting mixture was extracted with ethyl acetate. The extracts were combined, washed with brine, dried over magnesium sulfate and then concentrated. The residue thus obtained was subjected to flash chromatography on a silica gel column, and the fraction obtained from the hexane:ethyl acetate=1:1 eluate was concentrated, whereby the title compound (105 mg, 0.245 mmol, 82%) was obtained as a colorless oil.

$^1$H-NMR (400 MHz, CDCl$_3$) δ: 1.43-1.65(2H,m), 1.97-2.12(3H,m), 2.32-2.43(3H,m), 3.16(1H,dt,J=13.7, 6.8 Hz), 3.28-3.42(3H,m), 4.67(1H,dd,J=10.9, 3.4 Hz), 6.84(1H,td, J=9.0, 4.4 Hz), 6.95-7.02(1H,m), 7.22-7.28(1H,m), 7.39(2H, d,J=8.5 Hz), 7.56(2H,d,J=8.5 Hz).

IR (ATR) cm$^{-1}$: 2941, 1676, 1583, 1495, 1425, 1394, 1319, 1279, 1147, 1084, 1012, 827, 754, 707, 625, 555, 467.

MS m/z: 428 (M$^+$+H)

FAB-MS: 428.0885 (Calcd for C$_{20}$H$_{21}$ClF$_2$NO$_3$S: 428.0899).

Example 230

N-[4-[(4-Chlorophenyl)sulfonyl]-4-(2,5-difluorophenyl)butyl]methanesulfonamide Under a nitrogen atmosphere, N-methylmorpholine (51.0 μl, 0.465 mmol) and methanesulfonyl chloride (18.8 μl, 0.242 mmol) were added to a dichloromethane solution (4 ml) of the 4-[(4-chlorophenyl)sulfonyl]-4-(2,5-difluorophenyl)butylamine hydrochloride (80.0 mg, 0.202 mmol) obtained in Example 227. After stirring at room temperature for 15 hours, N-methylmorpholine (156 μl, 1.42 mmol) and methanesulfonyl chloride (10.0 μl, 0.129 mmol) were added. The resulting mixture was stirred at room temperature for 2 hours. After dilution with dichloromethane, the mixture was successively washed with a saturated aqueous solution of ammonium chloride, water, and brine, dried over magnesium sulfate and then, concentrated. The residue thus obtained was subjected to flash chromatography on a silica gel column, and the fraction obtained from the hexane:ethyl acetate=1:1 eluate was concentrated. The solid thus obtained was recrystallized from ethyl acetate-hexane, whereby the title compound (71.5 mg, 0.163 mmol, 81%) was obtained as colorless plate crystals.

$^1$H-NMR (400 MHz, CDCl$_3$) δ: 1.50-1.67(2H,m), 2.09-2.20(1H,m), 2.50-2.59(1H,m), 2.95(3H,s), 3.12-3.21(2H,m), 4.30(1H,t,J=6.3 Hz), 4.56(1H,dd,J=10.7, 4.4 Hz), 6.84(1H, td,J=9.0, 4.6 Hz), 6.96-7.03(1H,m), 7.23-7.28(1H,m), 7.39 (2H,d,J=8.0 Hz), 7.53(2H,d,J=8.0 Hz).

IR (ATR) cm$^{-1}$: 3269, 1585, 1498, 1308, 1252, 1217, 1140, 1090, 1082, 976, 870, 787, 750, 627, 517, 467.

mp: 128° C.

MS m/z: 438 (M$^+$+H).

Anal. calcd for C$_{17}$H$_{18}$ClF$_2$NO$_4$S$_2$: C, 46.63; H, 4.14; Cl, 8.10; F, 8.68; N, 3.20; S, 14.64. Found: C, 46.62; H, 4.08; Cl, 8.15; F, 8.69; N, 3.27; S, 14.71.

Example 231

2-[1-(4-Chlorophenylsulfonyl)-5-fluoropentyl]-1,4-difluorobenzene

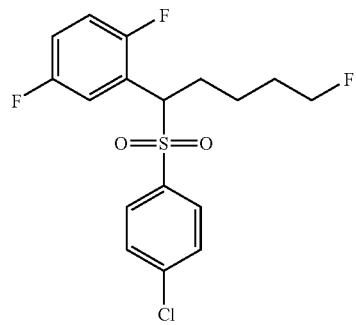

The 5-[(4-chlorophenyl)sulfonyl]-5-(2,5-difluorophenyl)-1-pentanol (152 mg, 0.404 mmol) obtained in Example 29 was dissolved in dichloromethane (4 ml), followed by the addition of N-methylmorpholine (58.0 μl, 0.528 mmol) and methanesulfonyl chloride (37.8 μl, 0.487 mmol) at 0° C. The resulting mixture was stirred at 0° C. for 2 hours, and then at room temperature for further 3 hours. After dilution with dichloromethane, the mixture was successively washed with a saturated aqueous solution of ammonium chloride, water and brine, dried over magnesium sulfate and then concentrated. The residue thus obtained was dissolved in tetrahydrofuran (4 ml). To the resulting solution was added a tetrahydrofuran solution (1.0M, 0.487 ml, 0.487 mmol) of tetrabutylammonium fluoride at room temperature. The resulting mixture was stirred at 60° C. for 4 hours. After cooling to room temperature and dilution with ethyl acetate, the mixture was washed with water and brine, dried over magnesium sulfate and then, concentrated. The residue thus obtained was subjected to flash chromatography on a silica gel column, and the fraction obtained from the hexane:ethyl acetate=9:1 eluate was concentrated. The solid thus obtained was recrystallized from hexane, whereby the title compound (30.3 mg, 0.0804 mmol, 20%) was obtained as colorless plate crystals.

$^1$H-NMR (400 MHz, CDCl$_3$) δ: 1.34-1.42(2H,m), 1.64-1.80(2H,m), 2.09-2.20(1H,m), 2.45-2.53(1H,m), 4.39(2H,dt, J=47.1, 5.9 Hz), 4.52(1H,dd,J=11.2, 2.9 Hz), 6.84(1H,td, J=9.0, 4.4 Hz), 6.96-7.02(1H,m), 7.23-7.28(1H,m), 7.38(2H, d,J=8.5 Hz), 7.53(2H,d,J=8.5 Hz) mp: 77-78° C.

IR (ATR) cm$^{-1}$: 2941, 1585, 1495, 1429, 1396, 1321, 1279, 1242, 1186, 1149, 1092, 1084, 962, 874, 829, 777, 752, 710, 633, 557, 536, 474.

MS m/z: 377 (M$^+$+H).

Anal. calcd for C$_{17}$H$_{16}$ClF$_3$O$_2$S: C, 54.19; H, 4.28; Cl, 9.41; F, 15.13; S, 8.51. Found: C, 54.27; H, 4.22; Cl, 9.44; F, 14.90; S, 8.68.

Example 232

2-[1-[(4-Chlorophenyl)sulfonyl]-1-methylethyl]-1,4-difluorobenzene

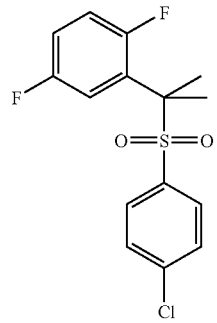

Under an argon atmosphere and at −78° C., n-butyl lithium (a 1.57M hexane solution, 450 μl, 0.707 mmol) was added to a tetrahydrofuran solution (4 ml) of the 2-[(4-chlorophenyl)sulfonylmethyl]-1,4-difluorobenzene (200 mg, 0.660 mmol) obtained in Example 0.5. After stirring for 5 minutes, iodomethane (103 μl, 1.65 mmol) was added. The resulting mixture was stirred for further 10 minute, and then, n-butyl lithium (a 1.57M hexane solution, 474 μl, 0.744 mmol) was added. After the temperature of the reaction mixture was elevated to room temperature, stirring was conducted for 2 hours. Water was added, followed by extraction with ethyl acetate. The extracts were combined, washed with brine, dried over magnesium sulfate and then, concentrated. The residue thus obtained was recrystallized from ethyl acetate-hexane, whereby the title compound (163 mg, 0.492 mmol, 75%) was obtained as colorless needle crystals.

$^1$H-NMR (400 MHz, CDCl$_3$) δ: 1.87(3H,s), 1.88(3H,s), 6.86(1H,ddd,J=11.9,9.0,4.9 Hz), 6.98-7.05(1H,m), 7.10(1H, ddd,J=9.8,6.6,3.4 Hz), 7.39(2H,d,J=8.5 Hz), 7.44(2H,d, J=8.5 Hz).

IR (ATR) cm$^{-1}$: 1574, 1489, 1475, 1412, 1304, 1219, 1184, 1155, 1124, 1068, 1011, 887, 867, 827, 756, 712, 660, 623, 600, 571, 532, 511, 474, 432.

mp: 147-148° C.

MS m/z: 331 (M$^+$+H).

Anal. calcd for C$_{15}$H$_{13}$ClF$_2$O$_2$S: C, 54.47; H, 3.96; Cl, 10.72; F, 11.49; S, 9.69. Found: C, 54.39; H, 3.92; Cl, 10.68; F, 11.51; S, 9.78.

Example 233

2-[1-[(4-Chlorophenyl)sulfonyl]cyclopropyl]-1,4-difluorobenzene

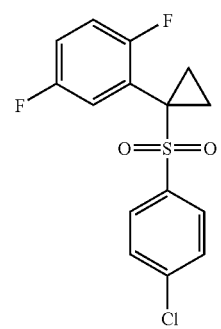

Under an argon atmosphere and at −78° C., n-butyl lithium (a 1.57M hexane solution, 600 μl, 0.942 mmol) was added to a tetrahydrofuran solution (4 ml) of the 3-[(4-chlorophenyl)sulfonyl]-3-(2,5-difluorophenyl)-1-propanol (300 mg, 0.865 mmol) obtained in Example 207. After stirring for 5 minutes, methanesulfonyl chloride (70.6 μl, 0.908 mmol) was added. The resulting solution was stirred for further 5 minutes and then, n-butyl lithium (a 1.57M hexane solution, 601 μl, 0.944 mmol) was added thereto. The temperature of the reaction mixture was elevated to room temperature, at which stirring was conducted for 18 hours. After cooling to −78° C., n-butyl lithium (a 1.57M hexane solution, 400 μl, 0.255 mmol) was added. The reaction mixture was stirred at room temperature for 3 hours. Water was added, followed by extraction with ethyl acetate. The extracts were combined, washed with brine, dried over magnesium sulfate and then, concentrated. The residue thus obtained was subjected to flash chromatography on a silica gel column, and the fraction obtained from the hexane:ethyl acetate=19:1 eluate was concentrated. The solid thus obtained was recrystallized from ethyl acetate-hexane, whereby the title compound (161 mg, 0.489 mmol, 57%) was obtained as colorless plate crystals.

$^1$H-NMR (400 MHz, CDCl$_3$) δ: 1.31(2H,dd,J=7.6, 5.1 Hz), 2.02(2H,dd,J=7.6, 5.1 Hz), 6.83(1H,td,J=9.0, 4.4 Hz), 6.97-7.03(1H,m), 7.06(1H,ddd,J=8.3,5.4,3.2 Hz), 7.41(2H,d, J=8.6 Hz), 7.49(2H,d,J=8.6 Hz).

IR (ATR) cm$^{-1}$: 3089, 1583, 1496, 1477, 1429, 1308, 1279, 1252, 1211, 1184, 1142, 1086, 1012, 893, 827, 769, 758, 737, 663, 625, 596, 559, 546, 492, 476, 451, 411.

mp: 177-179° C.

MS m/z: 329(M$^+$+H).

Anal. calcd for C$_{15}$H$_{11}$ClF$_2$O$_2$S: C, 54.80; H, 3.37; Cl, 10.78; F, 11.56; S, 9.75. Found: C, 54.72; H, 3.31; Cl, 10.71; F, 11.58; S, 9.87.

Referential Example 38

5-(t-Butyldimethylsilyloxy)pentanal

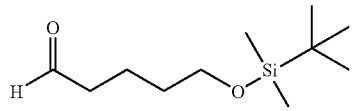

Under a nitrogen atmosphere and at 0° C., dimethylsulfoxide (7.81 ml, 110 mmol), triethylamine (9.60 ml, 69.0 mmol), and a sulfur trioxide-pyridine complex (4.39 g, 27.6 mmol) were added to a dichloromethane solution (80 ml) of 5-(t-butyldimethylsilyloxy)pentanol (3.00 g, 13.8 mmol). The resulting mixture was stirred at 0° C. for 30 minutes and then, at room temperature for further 3 hours. After cooling to 0° C., a saturated aqoeus ammonium chloride solution was added. Dichloromethane was distilled off under reduced pressure. To the residue was added ethyl acetate. After the water layer was separated, the organic layer was washed with water and brine, dried over magnesium sulfate and then, concentrated. The residue thus obtained was subjected to chromatography on a silica gel column, and the fraction obtained from the hexane:ethyl acetate=20:1 eluate was concentrated, whereby the title compound (2.42 g, 11.2 mmol, 81%) was obtained as a colorless oil.

$^1$H-NMR (400 MHz, CDCl$_3$) δ: 0.05(3H,s), 0.05(3H,s), 0.89(9H,s), 1.50-1.60(2H,m), 1.65-1.75(2H,m), 2.46(2H,t, J=6.8 Hz), 3.63(2H,t,J=6.3 Hz), 9.77(1H,s).

MS m/z: 217(M$^+$+H).

Example 234

6-(t-Butyldimethylsilyloxy)-1-[(4-chlorophenyl)sulfonyl]-1-(2,5-difluorophenyl)-2-hexanol (Isomer 234-A and Isomer 234-B)

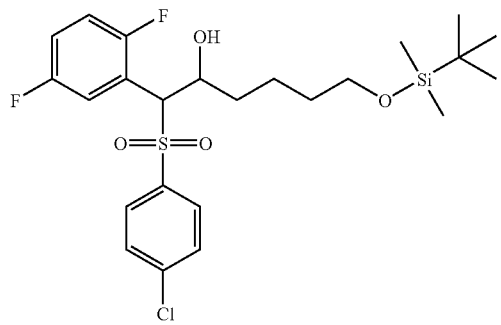

Under an argon atmosphere and at −78° C., n-butyl lithium (a 1.57M hexane solution, 1.40 ml, 2.20 mmol) was added to a dimethoxyethane solution (10 ml) of the 2-[(4-chlorophenyl)sulfonylmethyl]-1,4-difluorobenzene (606 mg, 2.00 mmol) obtained in Example 5. After dropwise addition of 5-(t-butyldimethylsilyloxy)pentanal (475 mg, 2.20 mmol), the resulting mixture was stirred at room temperature for 3 days. The reaction mixture was cooled to 0° C. To the resulting mixture were added water and then, ethyl acetate. After the water layer was separated, the organic layer was washed successively with an aqueous ammonium chloride solution, water and brine, dried over magnesium sulfate and then, concentrated. The residue thus obtained was subjected to flash chromatography on a silica gel column, and the fraction obtained from the hexane:ethyl acetate=10:1 eluate was concentrated, whereby the title Isomer 234-A (low polarity) (43.1 mg, 0.102 mmol, 5%) and the title Isomer 234-B (high polarity) (120 mg, 0.231 mmol, 12%) were obtained, each as a colorless oil.

Isomer 234-A $^1$H-NMR (400 MHz, CDCl$_3$) δ: 0.00(3H,s), 0.00(3H,s), 0.85(9H,s), 1.25-1.70(6H,m), 3.12(1H,d,J=3.2 Hz), 3.55(2H, t,J=5.9 Hz), 4.48(1H,s), 4.83-4.88(1H,m), 6.83(1H,td,J=9.0, 4.6 Hz), 6.95-7.02(1H,m), 7.39(2H,d,J=8.5 Hz), 7.57(2H,d, J=8.5 Hz), 7.84(1H,ddd,J=9.0,5.9,3.4 Hz).

MS m/z: 519(M$^+$+H).

Isomer 234-B $^1$H-NMR (400 MHz, CDCl$_3$) δ: −0.04(3H,s), −0.01(3H,s), 0.85(9H,s), 1.30-1.54(6H,m), 3.50-3.57(2H,m), 3.81(1H,br s), 4.58-4.80(2H,m), 6.84(1H,td,J=9.0, 4.6 Hz), 6.96-7.06 (1H,m), 7.15-7.27(1H,m), 7.39(2H,d,J=8.5 Hz), 7.52(2H,d, J=8.5 Hz).

MS m/z: 519 (M$^+$+H).

Example 235

6-[(4-Chlorophenyl)sulfonyl]-6-(2,5-difluorophenyl)-1,5-hexanediol

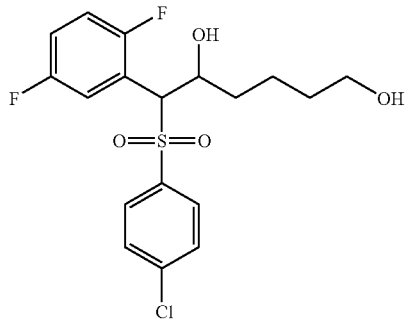

The 6-(t-butyldimethylsilyloxy)-1-[(4-chlorophenyl)sulfonyl]-1-(2,5-difluorophenyl)-2-hexanol (Isomer 234-A) (42.0 mg, 0.0809 mmol) obtained in Example 234 was dissolved in tetrahydrofuran (2 ml), followed by the addition of hydrogen fluoride-pyridine (0.2 ml). The resulting mixture was stirred at room temperature for 6 hours. The solution was diluted with ethyl acetate, washed with water and brine, dried over magnesium sulfate. The solid thus obtained was recrystallized from ethyl acetate-hexane, whereby the title compound (16.7 mg, 0.0412 mmol, 51%) was obtained as a white powder.

$^1$H-NMR (400 MHz, CDCl$_3$) δ: 1.25-1.70(7H,m), 3.15 (1H,s), 3.55-3.65(2H,m), 4.49(1H,s), 4.86-4.90(1H,m), 6.85 (1H,td,J=9.0, 4.4 Hz), 6.97-7.03(1H,m), 7.40(2H,d,J=8.8 Hz), 7.58(2H,d,J=8.8 Hz), 7.85(1H,ddd,J=9.0,5.9,3.4 Hz).

IR (ATR) cm$^{-1}$: 3232, 1576, 1491, 1396, 1306, 1236, 1217, 1147, 1093, 1012, 891, 814, 756, 719, 615, 548, 467.

mp: 108-109° C.

MS m/z: 405 (M$^+$+H).

FAB-MS: 405.0756 (Calcd for C$_{18}$H$_{19}$ClF$_2$O$_4$S: 405.0739).

Anal. calcd for C$_{18}$H$_{19}$ClF$_2$O$_4$S.0.5H$_2$O: C, 52.24; H, 4.87; S, 7.75. Found: C, 52.33; H, 4.84; S, 7.83.

Example 236

6-[(4-Chlorophenyl)sulfonyl]-6-(2,5-difluorophenyl)-1,5-hexanediol

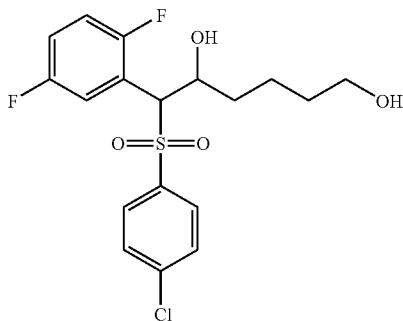

The 6-(t-butyldimethylsilyloxy)-1-[(4-chlorophenyl)sulfonyl]-1-(2,5-difluorophenyl)-2-hexanol (Isomer 234-B) (120 mg, 0.231 mmol) obtained in Example 234 was dissolved in tetrahydrofuran (5 ml), followed by the addition of hydrogen fluoride-pyridine (0.5 ml). The resulting mixture was stirred at room temperature for 20 hours. The reaction mixture was diluted with ethyl acetate, washed successively with water, a saturated aqueous solution of sodium bicarbonate, and brine, dried over magnesium sulfate and then, concentrated. The residue thus obtained was subjected to flash chromatography on a silica gel column, and the fraction obtained from the hexane:ethyl acetate=1:1 eluate was concentrated. The solid thus obtained was recrystallized from ethyl acetate-hexane, whereby the title compound (51.3 mg, 0.127 mmol, 55%) was obtained as a white powder.

$^1$H-NMR (400 MHz, CDCl$_3$) δ: 1.25-1.67(7H,m), 3.53-3.63(2H,m), 3.91(1H,br s), 4.59-4.78(2H,m), 6.85(1H,td, J=9.0, 4.4 Hz), 6.96-7.03(1H,m), 7.16-7.27(1H,br m), 7.39 (2H,d,J=80.5 Hz), 7.52 (2H, d,J=8.5 Hz).

IR (ATR) cm$^{-1}$: 3496, 2956, 1579, 1496, 1425, 1392, 1305, 1275, 1180, 1144, 1080, 1011, 966, 922, 833, 810, 756, 737, 650, 536, 521, 461.

mp: 105-107° C.

MS m/z: 405 (M$^+$+H).

Anal. calcd for C$_{18}$H$_{19}$ClF$_2$O$_4$S: C, 53.40; H, 4.73; Cl, 8.76; F, 9.39; S, 7.92. Found: C, 53.20; H, 4.61; Cl, 8.77; F, 9.20; S, 8.03.

Referential Example 39

4-(t-butyldimethylsilyloxy)-2-butanol

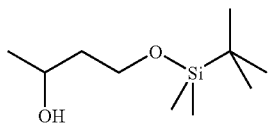

In N,N-dimethylformamide (30 ml) was dissolved 1,3-butanediol (3.00 g, 33.3 mmol), followed by the dropwise addition of an N,N-dimethylformamide solution (30 ml) of imidazole (2.72 g, 40.0 mmol) and t-butylchlorodimethylsilane (5.29 g, 35.0 mmol). After stirring at room temperature for 24 hours, ether was added to the reaction mixture and the white solid thus precipitated was filtered off. The resulting ether solution was washed with water and brine, dried over magnesium sulfate and then concentrated. The residue thus obtained was subjected to flash chromatography on a silica gel column, and the fraction obtained from the hexane:ethyl acetate=5:1 eluate was concentrated, whereby the title compound (5.43 g, 26.6 mmol, 80%) was obtained as a colorless oil.

$^1$H-NMR (400 MHz, CDCl$_3$) δ: 0.08(6H,s), 0.90(9H,d, J=1.0 Hz), 1.19(3H,d,J=6.4 Hz), 1.59-1.73(2H,m), 3.78-3.93 (2H,m), 3.98-4.07(1H,br m).

MS m/z: 205 (M$^+$+H).

Example 237

2-[4-(t-Butyldimethylsilyloxy)-1-[(4-chlorophenyl)sulfonyl]-2-methylbutyl]-1,4-difluorobenzene (Compound A (Isomer A) and Compound A (Isomer B)), and 2-[4-(t-butyldimethylsilyloxy)-1-[(4-chlorophenyl)sulfonyl]pentyl]-1,4-difluorobenzene (Compound B)

Compound A

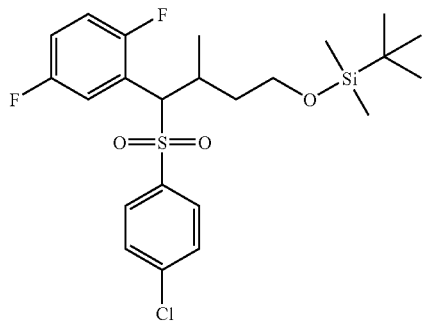

Compound B

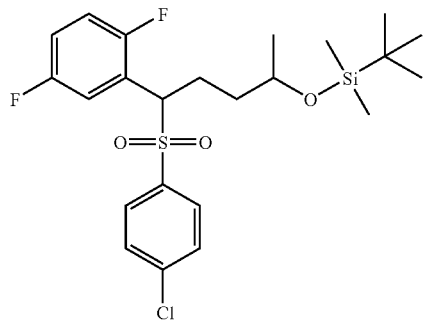

Under a nitrogen atmosphere, the 2-[(4-chlorophenyl)sulfonylmethyl]-1,4-difluorobenzene (303 mg, 1.00 mmol) obtained in Example 5 and 4-(tert-butyldimethylsilyloxy)-2-butanol (408 mg, 2.00 mmol) were dissolved in toluene (4 ml). After addition of cyanomethylenetri-n-butylphosphorane (482 mg, 2.00 mmol), the resulting mixture was heated under reflux for 15 hours under a nitrogen atmosphere. The reaction mixture was then concentrated. The residue thus obtained was separated and purified by flash chromatography on a silica gel column (hexane:ethyl acetate=50:1), whereby obtained were the title compound A (Isomer A) (low polarity) (109 mg, 0.222 mmol, 22%), the title compound A (Isomer B) (high polarity) (102 mg, 0.209 mmol, 21%), and the title compound B (234 mg, 0.479 mmol, 48%), each as as a colorless oil.

Compound A (Isomer A)

¹H-NMR (400 MHz, CDCl₃) δ: 0.05(3H,s), 0.05(3H,s), 0.89(9H,s), 1.14(3H, d,J=6.8 Hz), 1.38-1.47(1H,m), 1.79-1.89(1H,m), 2.91-3.02(1H,m), 3.63-3.73(2H,m), 4.56(1H,d, J=5.9 Hz), 6.81(1H,td,J=9.0, 4.6 Hz), 6.92-6.98(1H,m), 7.34 (2H,d,J=8.3 Hz), 7.51-7.57(1H,m), 7.55(2H,d,J=8.3 Hz).

MS m/z: 489 (M⁺+H).

Compound A (Isomer B)

¹H-NMR (400 MHz, CDCl₃) δ: −0.01(3H,s), 0.00(3H,s), 0.85-0.93(9H,m), 1.19-1.28(1H,m), 1.38(3H,d,J=6.6 Hz), 1.64-1.73(1H,m), 2.78-2.88(1H,m), 3.61(2H,dd,J=7.6, 4.9 Hz), 4.46(1H,d,J=9.0 Hz), 6.72(1H,td,J=9.0, 4.4 Hz), 6.87-6.93(1H,m), 7.30(2H,d,J=8.3 Hz), 7.34-7.41(1H,m), 7.49 (2H,d,J=8.3 Hz).

MS m/z: 489 (M⁺+H).

Compound B

¹H-NMR (400 MHz, CDCl₃) δ: −0.01(1.5H,s), 0.01(1.5H, s), 0.02(1.5H,s), 0.04(1.5H,s), 0.84(4.5H,m), 0.86(4.5H,m), 1.04-1.10(3H,m), 1.15-1.40(2H,m), 1.99-2.11(0.5H,m), 2.11-2.22(0.5H,m), 2.35-2.53(1H,m), 3.72-3.82(1H,m), 4.44-4.52(1H,m), 6.82-6.88(1H,m), 6.93-7.02(1H,m), 7.16-7.26(1H,m), 7.37-7.42(2H,m), 7.51-7.58(2H,m).

MS m/z: 489 (M⁺+H).

Example 238

4-(4-Chlorophenylsulfonyl)-4-(2,5-difluorophenyl)-3-methyl-1-butanol

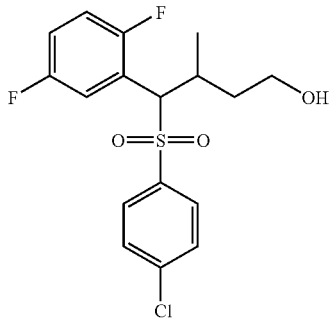

The 2-[4-(t-butyldimethylsilyloxy)-1-[(4-chlorophenyl)sulfonyl]-2-methylbutyl]-1,4-difluorobenzene (Compound A (Isomer A)) (109 mg, 0.223 mmol) obtained in Example 237 was dissolved in tetrahydrofuran (3 ml), followed by the addition of hydrogen fluoride-pyridine (0.5 ml). The resulting mixture was stirred at room temperature for 5 hours. The reaction mixture was diluted with ethyl acetate, washed with water, a saturated aqueous solution of sodium bicarbonate, and brine, and dried over magnesium sulfate. The solid thus obtained was recrystallized from ethyl acetate-hexane, whereby the title compound (61.1 mg, 0.163 mmol, 73%) was obtained as colorless columnar crystals.

¹H-NMR (400 MHz, CDCl₃) δ: 1.08(3H,d,J=7.1 Hz), 1.59-1.62(1H,m), 1.74-1.84(1H,m), 1.96-2.05(1H,m), 2.93-3.05(1H,m), 3.75-3.89(2H,m), 4.68(1H,d,J=6.8 Hz), 6.77 (1H,td,J=9.0, 4.6 Hz), 6.91-6.97(1H,m), 7.33(2H,d,J=8.3 Hz), 7.45-7.51(1H,m), 7.51(2H,d,J=8.3 Hz).

IR (ATR) cm⁻¹: 3527, 2935, 2897, 1583, 1487, 1315, 1267, 1232, 1188, 1144, 1086, 1068, 1049, 1012, 889, 864, 829, 789, 750, 715, 654, 611, 551, 490, 467.

mp: 111-112° C.

MS m/z: 375 (M⁺+H).

Anal. calcd for C₁₇H₁₇ClF₂O₃S: C, 54.47; H, 4.57; Cl, 9.46; F, 10.14; S, 8.55. Found: C, 54.44; H, 4.55; Cl, 9.44; F, 10.08; S, 8.75.

Example 239

4-(4-Chlorophenylsulfonyl)-4-(2,5-difluorophenyl)-3-methyl-1-butanol

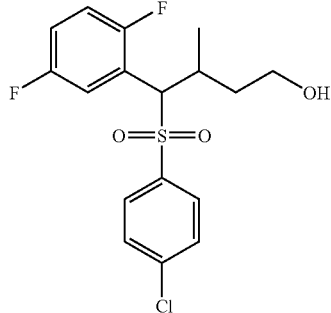

The 2-[4-(t-butyldimethylsilyloxy)-1-[(4-chlorophenyl)sulfonyl]-2-methylbutyl]-1,4-difluorobenzene (Compound A (Isomer B)) (102 mg, 0.209 mmol) obtained in Example 237 was dissolved in tetrahydrofuran (3 ml), followed by the addition of hydrogen fluoride-pyridine (0.5 ml). The resulting mixture was stirred at room temperature for 15 hours. The reaction mixture was diluted with ethyl acetate, washed with water and brine, and then dried over magnesium sulfate. The solid thus obtained was recrystallized from ethyl acetate-hexane, whereby the title compound (36.1 mg, 0.0963 mmol, 46%) was obtained as colorless columnar crystals.

¹H-NMR (400 MHz, CDCl₃) δ: 1.23-1.40(2H,m), 1.35 (3H,d,J=6.6 Hz), 1.81-1.90(1H,m), 2.84-2.93(1H,m), 3.63-3.78(2H,m), 4.51(1H,d,J=8.1 Hz), 6.75(1H,td,J=9.0, 4.6 Hz), 6.89-6.96(1H,m), 7.31(2H,d,J=8.5 Hz), 7.40-7.47(1H,m), 7.51(2H,d,J=8.5 Hz).

IR (ATR) cm⁻¹: 3525, 2954, 1655, 1493, 1477, 1427, 1394, 1306, 1279, 1240, 1180, 1144, 1080, 1055, 1014, 943, 887, 822, 754, 712, 665, 609, 559, 542, 453.

mp: 65-67° C.

MS m/z: 375 (M⁺+H).

Anal. calcd for C₁₇H₁₇ClF₂O₃S·0.5H₂O: C, 53.20; H, 4.73; Cl, 9.24; F, 9.90; S, 8.35. Found: C, 53.17; H, 4.86; Cl, 9.29; F, 10.00; S, 8.50.

Example 240

1-[(4-Chlorophenyl)sulfonyl-(2,5-difluorophenyl)]-4-pentanol (Isomer 240-A and Isomer 240-B)

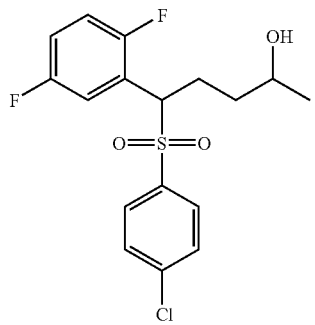

The 2-[4-(tert-butyldimethylsilyloxy)-1-(4-chlorophenylsulfonyl)pentyl]-1,4-difluorobenzene (Compound B) (230 mg, 0.470 mmol) obtained in Example 237 was dissolved in tetrahydrofuran (4 ml), followed by the addition of a tetrahydrofuran solution (1.0M, 0.564 ml, 0.564 mmol) of tetrabutylammonium fluoride. The resulting mixture was stirred at room temperature for 18 hours. The reaction mixture was diluted with ethyl acetate, washed with water and brine, dried over magnesium sulfate and then, concentrated. The residue thus obtained was separated and purified by flash chromatography on a silica gel column (hexane:ethyl acetate=2:1) to give a low-polarity isomer and a high-polarity isomer, each as a white solid. The resulting low-polarity isomer was recrystallized from hexane, whereby the title Isomer 240-A (low polarity) (48.0 mg, 0.128 mmol, 27%) was obtained as colorless needle crystals. On the other hand, the resulting high-polarity isomer was recrystallized from hexane, whereby the title Isomer 240-B (high polarity) (48.8 mg, 0.130 mmol, 28%) was obtained as colorless needle crystals.

Isomer 240-A $^1$H-NMR (400 MHz, CDCl$_3$) δ: 1.17(3H,d,J=6.1 Hz), 1.28-1.48(3H,m), 2.18-2.29(1H,m), 2.47-2.56(1H,m), 3.77-3.85(1H,m), 4.53-4.58(1H,m), 6.83(1H,td,J=9.0, 4.4 Hz), 6.95-7.01(1H,m), 7.22-7.28(1H,m), 7.38(2H,d,J=8.5 Hz), 7.53(2H,d,J=8.5 Hz).

IR (ATR) cm$^{-1}$: 3370, 3087, 2925, 1587, 1574, 1496, 1475, 1423, 1396, 1311, 1279, 1234, 1178, 1149, 1128, 1086, 1014, 949, 874, 827, 789, 760, 735, 710, 679, 631, 584, 559, 525, 469.

mp: 97-98° C.

MS m/z: 375 (M$^+$+H).

Anal. calcd for C$_{17}$H$_{17}$ClF$_2$NO$_3$S: C, 54.47; H, 4.57; Cl, 9.46; F, 10.14; S, 8.55. Found: C, 54.35; H, 4.69; Cl, 9.64; F, 10.31; S, 8.80.

Isomer 240-B $^1$H-NMR (400 MHz, CDCl$_3$) δ: 1.17(3H,d,J=6.1 Hz), 1.29-1.45(3H,m), 2.07-2.18(1H,m), 2.58-2.67(1H,m), 3.77-3.85(1H,m), 4.59(1H,dd,J=11.2, 2.9 Hz), 6.84(1H,td,J=9.0, 4.4 Hz), 6.95-7.02(1H,m), 7.23-7.27(1H,m), 7.38(2H,d, J=8.5 Hz), 7.54(2H,d,J=8.5 Hz).

IR (ATR) cm$^{-1}$: 3504, 3390, 2960, 2925, 1585, 1493, 1475, 1427, 1396, 1302, 1275, 1227, 1174, 1146, 1082, 1036, 1014, 823, 752, 723, 708, 625, 555, 530, 463.

mp: 89° C.

MS m/z: 375 (M$^+$+H).

Anal. calcd for C$_{17}$H$_{17}$ClF$_2$NO$_3$S: C, 54.47; H, 4.57; Cl, 9.46; F, 10.14; S, 8.55. Found: C, 54.25; H, 4.46; Cl, 9.51; F, 10.41; S, 8.66.

Example 241 t-butyl N-[5-[(4-Chlorophenyl)sulfonyl]-5-(2,5-difluorophenyl)pentyl]-N-methylsulfonylcarbamate

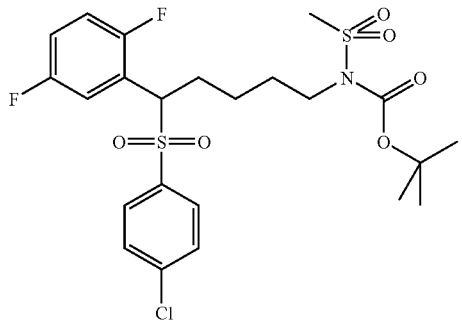

The 5-[(4-chlorophenyl)sulfonyl]-5-(2,5-difluorophenyl)-1-pentanol (115 mg, 0.307 mmol) obtained in Example 29, t-butyl N-methylsulfonylcarbamate (120 mg, 0.614 mmol), and triphenylphosphine (163 mg, 0.614 mmol) were dissolved in tetrahydrofuran (3 ml). At room temperature, diisopropyl azodicarboxylate (120 μl, 0.614 mmol) was added to the resulting solution. After stirring the resulting mixture for 18 hours at room temperature, the reaction mixture was diluted with ethyl acetate, washed with water and brine, dried over magnesium sulfate and then concentrated. The residue thus obtained was subjected to flash chromatography on a silica gel column, and the fraction obtained from the hexane:ethyl acetate=3:1 eluate was concentrated, whereby the title compound (168 mg, 0.304 mmol, 99%) was obtained as a colorless amorphous substance.

$^1$H-NMR (400 MHz, CDCl$_3$) δ: 1.22-1.35(2H,m), 1.50 (9H,m), 1.58-1.73(2H,m), 2.08-2.18(1H,m), 2.39-2.49(1H, m), 3.22(3H,s), 3.59(2H,ddd,J=8.1,6.6,3.9 Hz), 4.53(1H,dd, J=11.2, 2.9 Hz), 6.83(1H,td,J=9.0, 4.4 Hz), 6.95-7.01(1H,m), 7.22-7.27(1H,m), 7.39(2H,d,J=8.5 Hz), 7.54(2H,d,J=8.5 Hz).

IR (ATR) cm$^{-1}$: 1722, 1583, 1496, 1350, 1321, 1281, 1149, 1087, 1012, 966, 831, 754, 710, 629, 517.

MS m/z: 452 (M$^+$-Boc), 496 (M$^+$-t-Bu), 574 (M$^+$+Na).

FAB-MS: 574.0932 (Calcd for C$_{23}$H$_{28}$ClF$_2$NO$_6$S$_2$Na: 574.0912).

Example 242

N-[5-[(4-Chlorophenyl)sulfonyl]-5-(2,5-difluorophenyl)pentyl]methanesulfonamide

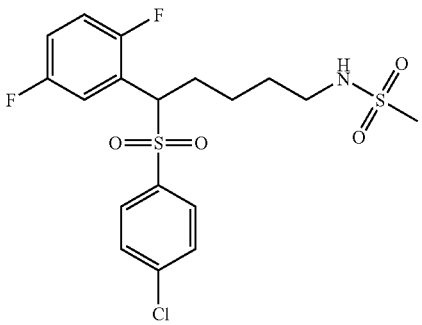

In dichloromethane (4 ml) was dissolved t-butyl N-[5-[(4-chlorophenyl)sulfonyl]-5(2,5-difluorophenyl)pentyl]-N-methylsulfonylcarbamate (108 mg, 0.196 mmol), followed by the addition of trifluoroacetic acid (1 ml) at room temperature. The resulting mixture was stirred at room temperature for 3 hours. The reaction mixture was diluted with dichloromethane, washed successively with water, a saturated aqueous solution of sodium bicarbonate, and brine, dried over magnesium sulfate and then concentrated. The residue thus obtained was subjected to flash chromatography on a silica gel column, and the fraction obtained from the hexane:ethyl acetate=1:1 eluate was concentrated, whereby the solid thus obtained was recrystallized from ethyl acetate-hexane, whereby the title compound (75.5 mg, 0.167 mmol, 85%) was obtained as a white powder.

$^1$H-NMR (400 MHz, CDCl$_3$) δ: 1.28-1.38(2H,m), 1.55-1.68(2H,m), 2.06-2.18(1H,m), 2.43-2.52(1H,m), 2.92(3H,s), 3.09(2H,dd,J=13.4, 6.8 Hz), 4.15-4.24(1H,m), 4.51(1H,dd,

J=11.5, 3.4 Hz), 6.84(1H,td,J=9.0, 4.4 Hz), 6.96-7.03(1H,m), 7.22-7.28(1H,m), 7.39(2H,d,J=8.5 Hz), 7.52(2H,d,J=8.5 Hz).

IR (ATR) cm$^{-1}$: 3219, 2871, 1583, 1495, 1425, 1300, 1248, 1167, 1144, 1084, 1068, 978, 893, 835, 752, 725, 706, 629, 545, 525, 471.

mp: 106-107° C.

MS m/z: 452 (M$^+$+H).

Anal. calcd for $C_{18}H_{21}ClF_2NO_4S_2$: C, 47.84; H, 4.46; Cl, 7.84; F, 8.41; N, 3.10; S, 14.19. Found: C, 47.75; H, 4.47; Cl, 7.94; F, 8.54; N, 3.14; S, 14.25.

Example 243 t-Butyl N-[4-[(4-chlorophenyl)sulfonyl]-4-(2,5-difluorophenyl)-3-methylbutyl]-N-methylsulfonylcarbamate

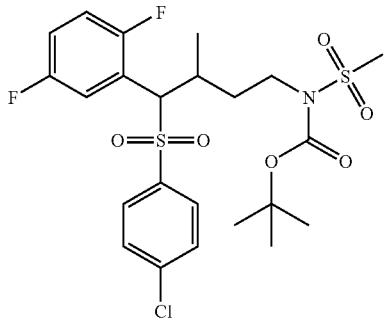

The 4-[(4-chlorophenyl)sulfonyl]-4-(2,5-difluorophenyl)-3-methyl-1-butanol (97.2 mg, 0.259 mmol) obtained in Example 239, t-butyl N-methylsulfonylcarbamate (101 mg, 0.518 mmol) and triphenylphosphine (138 mg, 0.518 mmol) were dissolved in tetrahydrofuran (3 ml), followed by the addition of diisopropyl azodicarboxylate (102 μl, 0.518 mmol) at room temperature. The reaction mixture was stirred at room temperature for 18 hours. The reaction mixture was diluted with ethyl acetate, washed with a saturated aqueous solution of ammonium chloride, water and brine, dried over magnesium sulfate and then concenetrated. The residue thus obtained was subjected to flash chromatography on a silica gel column, and the fraction obtained from the hexane:ethyl acetate=3:2 eluate was concentrated, whereby the title compound (136 mg, 0.246 mmol, 95%) was obtained as a colorless amorphous substance.

$^1$H-NMR (400 MHz, CDCl$_3$) δ: 1.33(3H,d,J=6.8 Hz), 1.35-1.45(1H,m), 1.52(9H,s), 1.99-2.08(1H,m), 2.70-2.78 (1H,m), 3.27(3H,s), 3.65-3.76(2H,m), 4.45(1H,d,J=7.6 Hz), 6.77(1H,td,J=9.0, 4.6 Hz), 6.91-6.97(1H,m), 7.32(2H,d, J=8.5 Hz), 7.38-7.45(1H,m), 7.50(2H,d,J=8.5 Hz).

MS m/z: 552 (M$^+$+H), 574 (M$^+$+Na).

FAB-MS: 552.1070 (Calcd for $C_{23}H_{29}ClF_2NO_6S_2$: 552.1093), 574.0875 (Calcd for $C_{23}H_{28}ClF_2NO_6S_2Na$: 574.0912).

Example 244

N-[4-[(4-Chlorophenyl)sulfonyl]-4-(2,5-difluorophenyl)-3-methylbutyl]methanesulfonamide

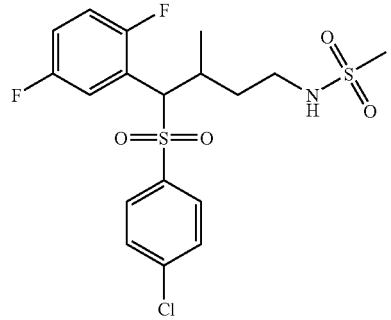

The t-butyl N-[4-[(4-chlorophenyl)sulfonyl]-4-(2,5-difluorophenyl)-3-methylbutyl]-N-methylsulfonylcarbamate (136 mg, 0.246 mmol) obtained in Example 243 was dissolved in dichloromethane (4 ml), followed by the addition of trifluoroacetic acid (1 ml) at room temperature. After stirring at room temperature for 6 hours, the reaction mixture was diluted with dichloromethane, washed successively with water, a saturated aqueous solution of sodium bicarbonate, and brine, dried over magnesium sulfate and then, concentrated. The solid thus obtained was recrystallized from ethyl acetate-hexane, whereby the title compound (99.5 mg, 0.220 mmol, 89%) was obtained as colorless needle crystals.

$^1$H-NMR (400 MHz, CDCl$_3$) δ: 1.27(3H,d,J=6.8 Hz), 1.35-1.44(1H,m), 1.95-2.05(1H,m), 2.82-2.88(1H,m), 2.95 (3H,s), 3.10-3.19(1H,m), 3.22-3.30(1H,m), 4.21-4.28(1H,br m), 4.49(1H,t,J=6.6 Hz), 6.81(1H,td,J=9.0, 4.4 Hz), 6.93-7.00(1H,m), 7.34(2H,d,J=8.5 Hz), 7.42-7.48(1H,m), 7.52 (2H,d,J=8.5 Hz).

IR (ATR) cm$^{-1}$: 3251, 3076, 1581, 1495, 1473, 1317, 1244, 1140, 881, 837, 781, 750, 729, 710, 665, 617, 553, 521, 465.

mp: 163° C.

MS m/z: 452 (M$^+$+H).

Anal. calcd for $C_{18}H_{20}ClF_2NO_4S_2$: C, 47.84; H, 4.46; Cl, 7.84; F, 8.41; N, 3.10; S, 14.19. Found: C, 47.88; H, 4.45; Cl, 7.91; F, 8.51; N, 3.16; S, 14.23.

Example 245

N-[3-(4-Chlorophenylsulfonyl)-3-(2,5-difluorophenyl)propyl]methanesulfonamide

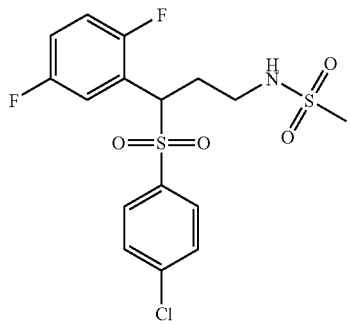

The 3-(4-chlorophenylsulfonyl)-3-(2,5-difluorophenyl)-1-propanol (120 mg, 0.307 mmol) obtained in Example 207, t-butyl N-methylsulfonylcarbamate (101 mg, 0.519 mmol), and triphenylphosphine (138 mg, 0.519 mmol) were dissolved in tetrahydrofuran (3 ml), followed by the addition of diisopropyl azodicarboxylate (102 μl, 0.519 mmol) at room temperature. The resulting mixture was stirred at room temperature for 18 hours. The reaction mixture was diluted with ethyl acetate, washed with water and brine, dried over magnesium sulfate and then, concentrated. The residue thus obtained was subjected to chromatography on a silica gel column (hexane:ethyl acetate=4:1) to remove the high-polarity byproduct. The crude product thus obtained was dissolved in dichloromethane (4 ml), followed by the addition of trifluoroacetic acid (2 ml). The resulting mixture was stirred at room temperature for 6 hours. The reaction mixture was diluted with dichloromethane, washed successively with water, a saturated aqueous solution of sodium bicarbonate, and brine, dried over magnesium sulfate and then, concentrated. The solid thus obtained was recrystallized from ethyl acetate-hexane, whereby the title compound (90.2 mg, 0.213 mmol, 62%) was obtained as colorless needle crystals.

$^1$H-NMR (400 MHz, CDCl$_3$) δ: 2.29-2.39(1H,m), 2.69-2.78(1H,m), 2.93(3H,s), 3.10-3.20(1H,m), 3.35-3.44(1H,m), 4.44-4.50(1H,br m), 4.74(1H,dd,J=9.0, 6.1 Hz), 6.84(1H,td, J=9.0, 4.6 Hz), 6.97-7.04(1H,m), 7.23(1H,ddd,J=8.5, 5.4,3.2 Hz), 7.39(2H,d,J=8.5 Hz), 7.52(2H,d,J=8.5 Hz).

IR (ATR) cm$^{-1}$: 3257, 3087, 2947, 1587, 1496, 1475, 1308, 1090, 1279, 1147, 1086, 1014, 962, 879, 827, 760, 737, 679, 621, 523, 463, 413.

mp: 131-134° C.

MS m/z: 424 (M$^+$+H).

Anal. calcd for C$_{16}$H$_{16}$ClF$_2$NO$_4$S$_2$: C, 45.34; H, 3.80; Cl, 8.36; F, 8.96; N, 3.30; S, 15.13. Found: C, 45.22; H, 3.67; Cl, 8.34; F, 8.98; N, 3.38; S, 15.16.

Referential Example 40

4-(t-Butyldiphenylsilyloxy)-2-buten-1-ol

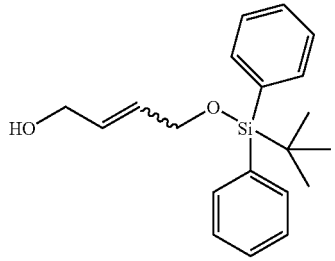

In a dichloromethane/N,N-dimethylformamide (200 ml/200 ml) mixture were dissolved 2-buten-1,4-diol (10.0 g, 113 mmol) and imidazole (4.70 g, 69.0 mmol), followed by the dropwise addition of t-butylchlorodiphenylsilane (30.0 ml, 115 mmol) at room temperature. After completion of the dropwise addition, the mixture was stirred at room temperature for 4 days. The residue obtained by concentrating the reaction mixture under reduced pressure was added with diethyl ether. From the resulting mixture, the insoluble matter was filtered off. The diethyl ether layer was washed with water and then, the organic layer was dried over anhydrous magnesium sulfate. After fitration, the filtrate was concentrated under reduced pressure. The residue was subjected to flash silica gel chromatography, and the fraction obtained from the hexane:ethyl acetate=2:1 eluate was concentrated under reduced pressure, whereby the title compound (15.3 g, 46.9 mmol, 42%) was obtained as a colorless oil.

$^1$H-NMR (400 MHz, CDCl$_3$) δ: 1.06(9H,s), 4.01(0.5H,br d,J=6.1 Hz), 4.15(1.5H,br d,J=4.9 Hz), 4.18-4.26(1.5H,m), 4.26(0.5H,dm,J=5.9 Hz), 5.60-5.75(1H,m), 5.78(3H,dm, J=15.4 Hz), 7.34-7.52(5H,m), 7.64-7.76(4H,m).

MS m/z: 327 (M$^+$+H).

Example 246

(Z)-2-[5-(t-Butyldiphenylsilyloxy)-1-[(4-chlorophenyl)sulfonyl]-3-pentenyl]-1,4-difluorobenzene (Isomer 246-A) and (E)-2-[5-(t-butyldiphenylsilyloxy)-1-[(4-chlorophenyl)sulfonyl]-3-pentenyl]-1,4-difluorobenzene (Isomer 246-B)

Isomer A

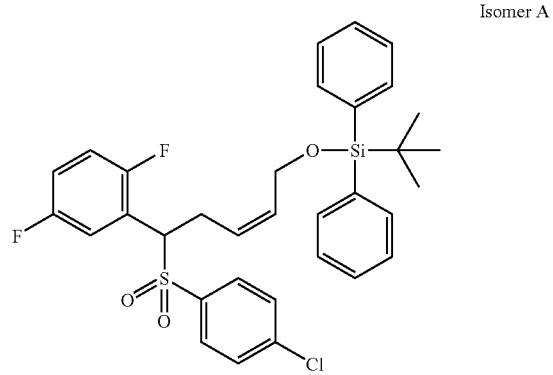

Isomer B

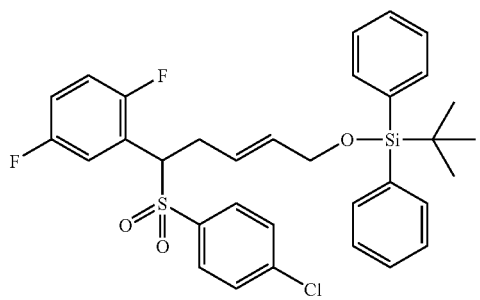

The 2-[(4-chlorophenyl)sulfonylmethyl]-1,4-difluorobenzene (400 mg, 1.32 mmol) obtained in Example 5 and 4-(t-butyldiphenylsilyloxy)-2-buten-1-ol (660 mg, 2.02 mmol) were dissolved in toluene (6 ml), followed by the addition of cyanomethylenetri-n-butylphosphorane (480 mg, 1.99 mmol). Under an argon atmosphere, the resulting mixture was heated under reflux for 6 hours. After the reaction mixture was allowed to cool down, the residue obtained by concenterating the reaction mixture under reduced pressure was separated and purified by flash silica gel chromatography (hexane:ethyl acetate=80:1) to give the Isomer 246-A (low polarity) (149 mg, 0.244 mmol, 18%) and the title Isomer 246-B (high polarity) (468 mg, 0.766 mmol, 58%), each as a colorless oil.

Isomer 246-A $^1$H-NMR (400 MHz, CDCl$_3$) δ: 1.04(9H,s), 2.64-2.78(1H, m), 2.95-3.08(1H,m), 4.09(1H,ddm,J=13.5, 5.6 Hz), 4.15 (1H,ddm,J=13.5, 6.3 Hz), 4.45(1H,ddm,J=11.0, 3.4 Hz), 5.12 (1H,dtm,J=11.0, 7.3 Hz), 5.62(1H,dtm,J=11.0, 6.3 Hz), 6.80-6.88(1H,m), 6.90-7.00(1H,m), 7.02-7.21(1H,m), 7.30-7.60 (10H,m), 7.60-7.72(4H,m).

IR (ATR) cm$^{-1}$: 2931, 2856, 1583, 1496, 1473, 1427, 1327, 1151, 1111, 1088, 823, 754, 702, 615, 505.

MS m/z: 611 (M$^+$+H), 633 (M$^+$+Na).

Isomer 246-B $^1$H-NMR (400 MHz, CDCl$_3$) δ: 0.93(9H,s), 2.80-2.92(1H, m), 3.14-3.26(1H,m), 3.98-4.05(2H,m), 4.01(1H,dd,J=11.5, 3.7 Hz), 5.43(1H,dtm,J=15.0, 7.3 Hz), 5.59(1H,dtm,J=15.0, 4.4 Hz), 6.75-6.88(1H,m), 6.92-7.01(1H,m), 7.22-7.50(9H, m), 7.50-7.65(6H,m).

IR (ATR) cm$^{-1}$: 2931, 2856, 1583, 1496, 1427, 1321, 1149, 1111, 1084, 1012, 822, 754, 700, 503.

MS m/z: 611 (M$^+$+H), 633 (M$^+$+Na).

Example 247

(Z)-5-[(4-Chlorophenyl)sulfonyl]-5-(2,5-difluorophenyl)-2-penten-1-ol

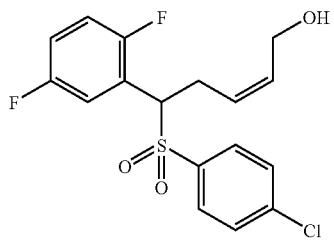

In tetrahydrofuran (5 ml) was dissolved (Z)-2-[5-(t-butyldiphenylsilyloxy)-1-[(4-chlorophenyl)sulfonyl]-3-pentenyl]-1,4-difluorobenzene (Isomer 246-A) (145 mg, 0.237 mmol). After dropwise addition of a tetrahydrofuran solution (1.0M, 0.5 ml, 0.5 mmol) of tetrabutylammonium fluoride, the mixture was stirred at room temperature for 2 hours. Water (0.2 ml) was added to the reaction mixture, followed by concentration under reduced pressure. The residue thus obtained was subjected to flash silica gel chromatography, and the fraction obtained from the hexane:ethyl acetate=2:1 eluate was concentrated under reduced pressure to give a white solid. The white solid was washed with hexane, whereby the title compound (51 mg, 0.137 mmol, 58%) was obtained as a white powder.

$^1$H-NMR (400 MHz, CDCl$_3$) δ: 1.35(1H,br s), 2.82-2.95 (1H,m), 3.22-3.32(1H,m), 4.08-4.18(1H,m), 4.18-4.28(1H, m), 4.56(1H,ddm,J=10.6, 4.5 Hz), 5.29(1H,dtm,J=11.0, 7.5 Hz), 5.67(1H,dtm,J=11.0, 6.6 Hz), 6.77-6.88(1H,m), 6.92-7.02(1H,m), 7.22-7.32(1H,m), 7.39(2H,d,J=8.7 Hz), 7.54 (2H,d,J=8.7 Hz).

IR (ATR) cm$^{-1}$: 3560, 3016, 1585, 1495, 1475, 1427, 1396, 1308, 1277, 1218, 879, 827, 789, 752, 708, 679, 627, 467, 420.

mp: 60-63° C.

MS m/z: 390 (M$^+$+NH$_4$).

Anal. Calcd for C$_{17}$H$_{15}$ClF$_2$O$_3$S: C, 54.77; H, 4.06; Cl, 9.51; F, 10.19; S, 8.60. Found: C, 54.57; H, 4.08; Cl, 9.41; F, 10.27; S, 8.74.

Example 248

(E)-5-[(4-Chlorophenyl)sulfonyl]-5-(2,5-difluorophenyl)-2-penten-1-ol

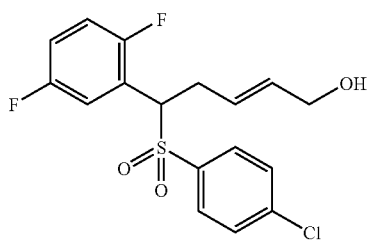

The (E)-2-[5-(t-butyldiphenylsilyloxy)-1-[(4-chlorophenyl)sulfonyl]-3-pentenyl]-1,4-difluorobenzene (Isomer 246-B) (465 mg, 0.761 mmol) obtained in Example 246 was dissolved in tetrahydrofuran (10 ml), followed by the dropwise addition of a tetrahydrofuran solution (1.0M, 1.5 ml, 1.5 mmol) of tetrabutylammonium fluoride. At room temperature, the mixture was stirred for 1 hour. After addition of water (0.2 ml), the residue obtained by concentrating the resulting mixture under reduced pressure was subjected to flash silica gel chromatography, and the fraction obtained from the hexane:ethyl acetate=2:1 eluate was concentrated under reduced pressure to give a white solid. The white solid was washed with hexane, whereby the title compound (225 mg, 0.605 mmol, 80%) was obtained as a white powder.

$^1$H-NMR (400 MHz, CDCl$_3$) δ: 1.21(1H,br t,J=5.5 Hz), 2.80-2.92(1H,m), 3.18-3.28(1H,m), 3.96-4.06(2H,m), 4.57 (1H,ddm,J=11.2, 3.9 Hz), 5.44(1H,dtm,J=15.2, 7.3 Hz), 5.70 (1H,dtm,J=15.2, 5.4 Hz), 6.78-6.88(1H,m), 6.95-7.03(1H, m), 7.22-7.30(1H,m), 7.39(2H,d,J=8.7 Hz), 7.54(2H,d,J=8.7 Hz).

IR (ATR) cm$^{-1}$: 3552, 3087, 1583, 1495, 1427, 1396, 1309, 1281, 1219, 1186, 1142, 1082, 1016, 984, 874, 831, 775, 756, 710, 619, 553, 534, 467.

mp: 108-109° C.

MS m/z: 395 (M$^+$+Na).

Anal. Calcd for C$_{17}$H$_{15}$ClF$_2$O$_3$S: C, 54.77; H, 4.06; Cl, 9.51; F, 10.19; S, 8.60. Found: C, 54.59; H, 4.03; Cl 9.53; F, 10.17; S, 8.71.

Referential Example 41

2-[2-(t-Butyldiphenylsilyloxy)ethylthio]ethanol

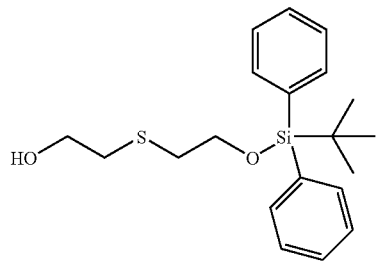

In dichloromethane (200 ml) were dissolved 2,2'-thiodiethanol (10.0 g, 81.8 mmol) and imidazole (4.70 g, 69.0 mmol), followed by the dropwise addition of t-butylchlorodiphenylsilane (15.0 ml, 57.7 mmol) at room temperature. After completion of the dropwise addition, the reaction mixture was stirred at room temperature for 14 hours. After concentration under reduced pressure, diethyl ether was added to the residue. Then, the insoluble matter was filtered off. The residue obtained by concentrating the filtrate under reduced pressure was subjected to flash silica gel chromatography, and the fraction obtained from the hexane:ethyl acetate=3:1 eluate was concentrated under reduced pressure, whereby the title compound (11.3 g, 31.3 mmol, 54%) was obtained as a colorless oil.

$^1$H-NMR (400 MHz, CDCl$_3$) δ: 1.06(9H,s), 2.19(1H,br s), 2.62-2.72(4H,m), 3.63(2H,br t,J=5.5 Hz), 3.80(2H,t,J=6.8 Hz), 7.32-7.52(6H,m), 7.66-7.75(4H,m).

IR (ATR) cm$^{-1}$: 3400, 2929, 2856, 1427, 1105, 822, 735, 700, 611, 503.

MS m/z: 383 (M$^+$+Na).

Example 249

2-[3-[2-(t-Butyldiphenylsilyloxy)ethylthio]-1-[(4-chlorophenyl)sulfonyl]propyl]-1,4-difluorobenzene

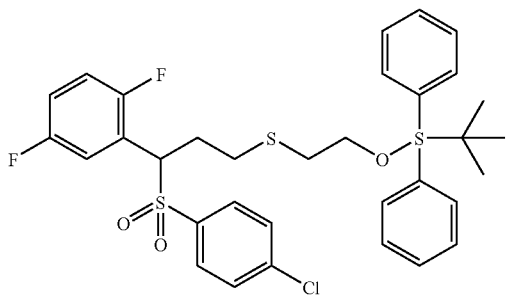

The 2-[(4-chlorophenyl)sulfonylmethyl]-1,4-difluorobenzene (900 mg, 2.97 mmol) obtained in Example 5 and 2-[2-(t-butyldiphenylsilyloxy)ethylthio]ethanol (1.64 g, 4.55 mmol) were dissolved in toluene (20 ml), followed by the addition of cyanomethylenetri-n-butylphosphorane (1.26 g, 5.22 mmol). Under an argon atmosphere, the resulting mixture was heated under reflux for 9 hours. After the reaction mixture was allowed to cool down, 2-[2-(t-butyldiphenylsilyloxy)ethylthio]ethanol (500 mg, 1.39 mmol) and cyanomethylenetri-n-butylphosphorane (400 mg, 1.66 mmol) were added thereto. Under an argon atmosphere, the mixture was heated under reflux for 14 hours. After the reaction mixture was allowed to cool down, it was concentrated under reduced pressure. The residue was subjected to flash silica gel chromatography, and the fraction obtained from the hexane:ethyl acetate=10:1 eluate was concentrated under reduced pressure, whereby the title compound (1.82 g, 2.82 mmol, 95%) was obtained as a pale yellowish brown oil.

$^1$H-NMR (400 MHz, CDCl$_3$) δ: 1.02(9H,s), 2.20-2.35(2H, m), 2.50-2.74(4H,m), 3.65-3.80(2H,m), 4.72-4.80(1H,m), 6.77-6.85(1H,m), 6.92-7.00(1H,m), 7.15-7.23(1H,m), 7.35-7.48(8H,m), 7.52(2H,d,J=8.8 Hz), 7.64(4H,d,J=8.1 Hz).

IR (ATR) cm$^{-1}$: 2931, 2858, 1583, 1496, 1323, 1149, 1105, 1084, 754, 700, 503.

MS m/z: 667 (M$^+$+Na).

Example 250

2-[3-[(4-Chlorophenyl)sulfonyl]-3-(2,5-difluorophenyl)propylthio]ethanol

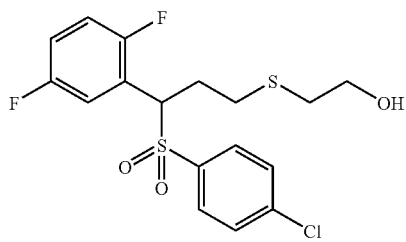

In tetrahydrofuran (30 ml) was dissolved 2-[3-[2-(t-butyldiphenylsilyloxy)ethylthiol-1-[(4-chlorophenyl)sulfonyl] propyl]-1,4-difluorobenzene (1.81 g, 2.80 mmol). Under ice cooling, a tetrahydrofuran solution (1.0M, 8.0 ml, 8.0 mmol) of tetrabutylammonium fluoride was added dropwise to the resulting solution, followed by stirring at room temperature for 2 hours. Water (3 ml) was added to the reaction mixture, followed by concentration under reduced pressure. The residue thus obtained was subjected to flash silica gel chromatography, and the fraction obtained from the hexane:ethyl acetate=2:1 eluate was concentrated under reduced pressure to give a white solid. The white solid was washed with hexane, whereby the title compound (977 mg, 2.40 mmol, 86%) was obtained as a white powder.

$^1$H-NMR (400 MHz, CDCl$_3$) δ: 1.97(1H,t,J=6.1 Hz), 2.30-2.45(2H,m), 2.60-2.80(4H,m), 3.60-3.78(2H,m), 4.81(1H, dd,J=9.6, 3.5 Hz), 6.80-6.90(1H,m), 6.96-7.05(1H,m), 7.20-7.30(1H,m), 7.39(2H,d,J=8.8 Hz), 7.54(2H,d,J=8.8 Hz).

IR (ATR) cm$^{-1}$: 3564, 3072, 1583, 1496, 1275, 1144, 1082, 835, 810, 762, 627, 534, 480.

mp: 108-110° C.

MS m/z: 424 (M$^+$+NH$_4$).

Anal. Calcd for C$_{17}$H$_{17}$ClF$_2$O$_3$S$_2$: C, 50.18; H, 4.21; Cl, 8.71; F, 9.34; S, 15.76. Found: C, 49.94; H, 4.20; Cl, 8.84; F, 9.41; S, 15.70.

Example 251

4-[(4-Chlorophenyl)sulfonyl]-4-(2,5-difluorophenyl) tetrahydrothiopyran

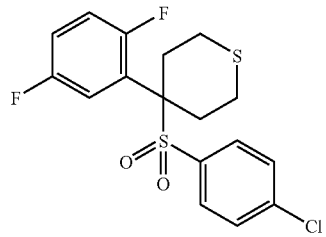

In toluene (50 ml) was dissolved 2-[3-[(4-chlorophenyl) sulfonyl]-3-(2,5-difluorophenyl)propylthio]ethanol (800 mg, 2.00 mmol), followed by the addition of cyanomethylenetri-n-butylphosphorane (1.50 g, 6.22 mmol). Under an argon atmosphere, the resulting mixture was heated under reflux for 14 hours. After the reaction mixture was allowed to cool

Example 252

4-[(4-Chlorophenyl)sulfonyl]-4-(2,5-difluorophenyl)tetrahydrothiopyran-1-on

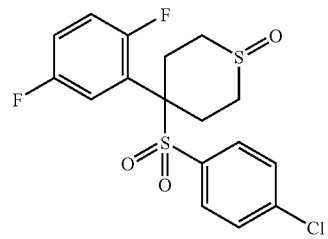

In dichloromethane (30 ml) was dissolved 4-[(4-chlorophenyl)sulfonyl]-4-(2,5-difluorophenyl)tetrahydrothiopyran (200 mg, 0.508 mmol). Under ice cooling, 3-chloroperbenzoic acid (106 mg, 0.614 mmol) was added. After stirring at room temperature for 14 hours, the reaction mixture was concentrated under reduced pressure. The residue thus obtained was subjected to flash silica gel chromatography, and the fraction obtained from the hexane:ethyl acetate=1:1 eluate was concentrated under reduced pressure to give a white solid. The white solid was washed with diethyl ether, whereby the title compound (163 mg, 0.403 mmol, 79%) was obtained as a white powder.

$^1$H-NMR (400 MHz, CDCl$_3$) δ: 2.30-3.55(8H,m), 6.85-7.04(1H,m), 7.05-7.20(2H,m), 7.33(0.8H,d,J=8.3 Hz), 7.40 (0.8H,d,J=8.3 Hz), 7.44(1.2H,d,J=8.8 Hz), 7.47(1.2H,d, J=8.8 Hz).

IR (ATR) cm$^{-1}$: 3095, 1576, 1491, 1308, 1279, 1146, 1082, 879, 818, 800, 752, 712, 621, 565, 474.

mp: 173-182° C.

MS m/z: 405 (M$^+$+H).

Anal. Calcd for C$_{17}$H$_{15}$ClF$_2$O$_3$S$_2$: C, 50.43; H, 3.73; Cl, 8.76; F, 9.38; S, 15.85. Found: C, 50.60; H, 3.76; Cl, 8.81; F, 9.48; S, 15.92.

Example 253

4-[(4-Chlorophenyl)sulfonyl]-4-(2,5-difluorophenyl)tetrahydrothiopyran-1,1-dioxide

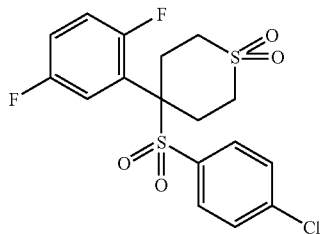

The 4-[(4-chlorophenyl)sulfonyl]-4-(2,5-difluorophenyl)tetrahydrothiopyran (100 mg, 0.254 mmol) obtained in Example 251 was dissolved in dichloromethane (15 ml), followed by the addition of 3-chloroperbenzoic acid (110 mg, 0.637 mmol) under ice cooling. After stirring at room temperature for 5 hours, diethyl ether was added. The resulting mixture was washed with a 1N aqueous solution of sodium hydroxide, and the organic layer was dried over anhydrous magnesium sulfate. After fitration, the filtrate was concentrated under reduced pressure. The residue thus obtained was subjected to flash silica gel chromatography, and the fraction obtained from the hexane:ethyl acetate=1:1 eluate was concentrated under reduced pressure to give a white solid. The white solid was washed with diethyl ether, whereby the title compound (89 mg, 0.211 mmol, 83%) was obtained as a white powder.

$^1$H-NMR (400 MHz, CDCl$_3$) δ: 2.80-3.02(4H,m), 3.02-3.24(4H,m), 6.91-7.01(1H,m), 7.06-7.13(1H,m), 7.14-7.22 (1H,m), 7.39(2H,d,J=8.7 Hz), 7.44(2H,d,J=8.7 Hz).

IR (ATR) cm$^{-1}$: 1577, 1496, 1473, 1415, 1311, 1201, 1149, 1122, 1080, 874, 854, 822, 754, 708, 623, 567, 474.

mp: 204-206° C.

MS m/z: 421 (M$^+$+H).

Anal. Calcd for C$_{17}$H$_{15}$ClF$_2$O$_4$S$_2$: C, 48.51; H, 3.59; Cl, 8.42; F, 9.03; S, 15.24. Found: C, 48.61; H, 3.60; Cl 8.44; F, 9.05; S, 15.21.

Example 254

2-[3-[(4-Chlorophenyl)sulfonyl]-3-(2,5-difluorophenyl)propylsulfinyl]ethanol

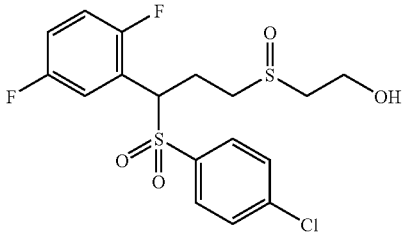

The 2-[3-[(4-chlorophenyl)sulfonyl]-3-(2,5-difluorophenyl)propylthio]ethanol (65 mg, 0.16 mmol) obtained in Example 250 was dissolved in dichloromethane (5 ml), followed by the addition of 3-chloroperbenzoic acid (33 mg, 0.19 mmol) under ice cooling. The resulting mixture was stirred at room temperature for 14 hours. The residue obtained by concentrating the reaction mixture under reduced pressure was subjected to flash silica gel chromatography, and the fraction obtained from the dichloromethane:methanol=30:1 eluate was concentrated under reduced pressure to give a white solid. The white solid was washed with diethyl ether, whereby the title, compound (50 mg, 0.12 mmol, 74%) was obtained as a white powder.

$^1$H-NMR (400 MHz, CDCl$_3$) δ: 2.52-2.65(2H,m), 2.80-3.02(5H,m), 4.11-4.22(2H,m), 4.68-4.78(1H,m), 6.80-6.90 (1H,m), 6.97-7.04(1H,m), 7.21-7.30(1H,m), 7.38-7.44(2H,m), 7.50-7.58(2H,m).

IR (ATR) cm$^{-1}$: 3421, 3259, 1585, 1496, 1319, 1147, 1086, 1028, 989, 833, 756, 555, 534, 480, 463.

mp: 124-132° C.

MS m/z: 423 (M$^+$+H).

Anal. Calcd for C$_{17}$H$_{17}$ClF$_2$O$_4$S$_2$: C, 48.28; H, 4.05; Cl, 8.42; F, 9.03; S, 15.24. Found: C, 48.03; H, 4.01; Cl, 8.33; F, 8.93; S, 15.06.

Example 255

2-[3-[(4-Chlorophenyl)sulfonyl]-3-(2,5-difluorophenyl)propylsulfonyl]ethanol

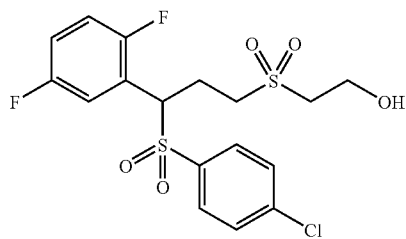

The 2-[3-[(4-chlorophenyl)sulfonyl]-3-(2,5-difluorophenyl)propylthio]ethanol (65 mg, 0.16 mmol) obtained in Example 250 was dissolved in dichloromethane (5 ml), followed by the addition of 3-chloroperbenzoic acid (66 mg, 0.38 mmol) under ice cooling. At room temperature, the mixture was stirred for 14 hours. The residue obtained by concentrating the reaction mixture under reduced pressure was subjected to flash silica gel chromatography, and the fraction obtained from the hexane:ethyl acetate=1:1 eluate was concentrated under reduced pressure to give a white solid. The white solid was washed with diethyl ether, whereby the title compound (53 mg, 0.12 mmol, 76%) was obtained as a white powder.

$^1$H-NMR (400 MHz, CDCl$_3$) δ: 2.19(1H,t,J=5.1 Hz), 2.56-2.70(1H,m), 2.97-3.10(1H,m), 3.12-3.28(4H,m), 4.12(2H,q, J=5.1 Hz), 4.77(1H,dd,J=9.4, 5.7 Hz), 6.82-6.92(1H,m), 6.98-7.07(1H,m), 7.20-7.30(1H,m), 7.41(2H,d,J=8.7 Hz), 7.54(2H,d,J=8.7 Hz).

IR (ATR) cm$^{-1}$: 3525, 3076, 1576, 1496, 1315, 1279, 1146, 1128, 1082, 1034, 1011, 997, 835, 758, 631, 559, 542, 523, 488, 467, 430.

mp: 111-113° C.

MS m/z: 439 (M$^+$+H).

Anal. Calcd for C$_{17}$H$_{17}$ClF$_2$O$_5$S$_2$: C, 46.52; H, 3.90; Cl, 8.08; F, 8.66; S, 14.61. Found: C, 46.46; H, 3.82; Cl, 8.15; F, 8.66; S, 14.55.

Referential Example 42 t-Butyl N-[2-(t-butyldiphenylsilyloxy)ethyl]-N-(2-hydroxyethyl)carbamate

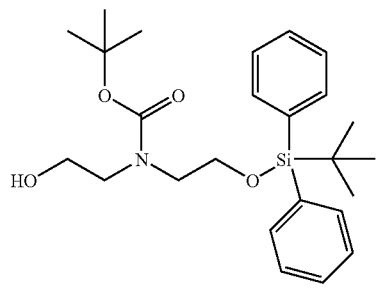

In a dichloromethane/N,N-dimethylformamide (70 ml/70 ml) mixture were dissolved t-butyl N,N-bis(2-hydroxyethyl)carbamate (9.00 g, 43.8 mmol) and imidazole (2.60 g, 38.2 mmol), followed by the dropwise addition of t-butylchlorodiphenylsilane (8.1 ml, 31 mmol) at room temperature. After completion of the dropwise addition, the reaction mixture was stirred at room temperature for 14 hours. The residue obtained by concentrating the reaction mixture under reduced pressure was added with diethyl ether. The resulting mixture was washed with water and the organic layer was dried over anhydrous magnesium sulfate. After filtration, the filtrate was concentrated under reduced pressure. The residue thus obtained was subjected to flash silica gel chromatography, and the fraction obtained from the hexane:ethyl acetate=2:1 eluate was concentrated under reduced pressure, whereby the title compound (7.41 g, 16.7 mmol, 54%) was obtained as a colorless oil.

$^1$H-NMR (400 MHz, CDCl$_3$) δ: 1.05(9H,s), 1.30-1.60(9H,m), 3.30-3.52(4H,m), 3.68-3.90(4H,m), 7.34-7.50(6H,m), 7.60-7.72(4H,m).

IR (ATR) cm$^{-1}$: 2931, 2858, 1693, 1670, 1408, 1365, 1171, 1144, 1105, 1051, 933, 822, 737, 700, 613, 501.

MS m/z: 444 (M$^+$+H).

Example 256 t-Butyl N-[2-(t-Butyldiphenylsilyloxy)ethyl]-N-[3-[(4-chlorophenyl)sulfonyl]-3-(2,5-difluorophenyl)propyl]carbamate

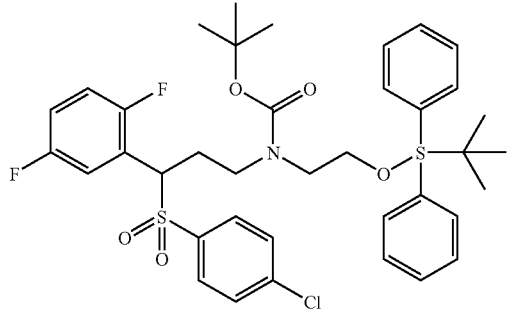

The 2-[(4-chlorophenyl)sulfonylmethyl]-1,4-difluorobenzene (500 mg, 1.65 mmol) obtained in Example 5 and t-butyl N-[2-(t-butyldiphenylsilyloxy)ethyl]-N-(2-hydroxyethyl)

carbamate (950 mg, 2.14 mmol) were dissolved in toluene (20 ml), followed by the addition of cyanomethylenetri-n-butylphosphorane (600 mg, 2.49 mmol). Under an argon atmosphere, the resulting mixture was heated under reflux for 9 hours. After the reaction mixture was allowed to cool down, t-butyl N-[2-(t-butyldiphenylsilyloxy)ethyl]-N-(2-hydroxyethyl)carbamate (500 mg, 1.13 mmol) and cyanomethylenetri-n-butylphosphorane (300 mg, 1.24 mmol) were added thereto. Under an argon atmosphere, the resulting mixture was heated under reflux for 14 hours. After the reaction mixture was allowed to cool down, the residue obtained by concentrating the reaction mixture under reduced pressure was subjected to flash silica gel chromatography, and the fraction obtained from the hexane:ethyl acetate=15:1 eluate was concentrated under reduced pressure, whereby the title compound (1.14 g, 1.57 mmol, 95%) was obtained as a pale yellowish browh foam.

$^1$H-NMR (400 MHz, CDCl$_3$) δ: 0.97(9H,s), 1.20-1.50(9H, m), 2.29(1H,br s), 2.62-2.78(1H,m), 3.05-3.50(4H,m), 3.66 (2H,br s), 4.40-4.60(1H,m), 6.81(1H,br s), 6.98(1H,br s), 7.18-7.70(15H,m).

IR (ATR) cm$^{-1}$: 2931, 1689, 1585, 1496, 1473, 1323, 1149, 1086, 737, 700, 613, 467, 426.

MS m/z: 726 (M$^+$+H).

Example 257 t-Butyl N-[3-[(4-chlorophenyl)sulfonyl]-3-(2,5-difluorophenyl)propyl]-N-(2-hydroxyethyl)carbamate

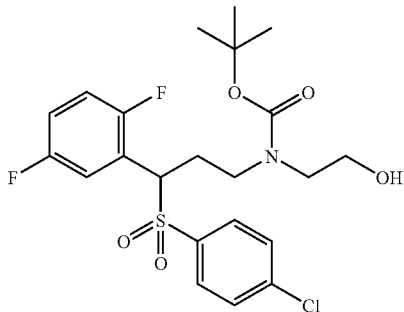

In tetrahydrofuran (20 ml) was dissolved t-butyl N-[2-(t-butyldiphenylsilyloxy)ethyl]-N-[3-[(4-chlorophenyl)sulfonyl]-3-(2,5-difluorophenyl)propyl]carbamate (1.13 g, 1.55 mmol). Under ice cooling, a tetrahydrofuran solution (1.0M, 5.0 ml, 5.0 mmol) of tetrabutylammonium fluoride was added dropwise. The resulting mixture was stirred at room temperature for 1 hour. Water (2 ml) was added to the reaction mixture. The residue obtained by concentrating the resulting mixture under reduced pressure was subjected to flash silica gel chromatography, and the fraction obtained from the hexane:ethyl acetate=1:1 eluate was concentrated under reduced pressure, whereby the title compound (651 mg, 1.32 mmol, 85%) was obtained as a white foam.

$^1$H-NMR (400 MHz, CDCl$_3$) δ: 1.39(9H,s), 2.28-2.42(1H, m), 2.70-2.80(1H,m), 3.15-3.32(3H,m), 3.40(1H,br s), 3.68-3.80(2H,m), 4.54(1H,br s), 6.78-6.88(1H,m), 6.95-7.03(1H, m), 7.20-7.31(1H,m), 7.39(2H,d,J=8.7 Hz), 7.52(2H,d,J=8.7 Hz).

IR (ATR) cm$^{-1}$: 3438, 2976, 2933, 1685, 1583, 1496, 1475, 1319, 1279, 1147, 1084, 1012, 827, 756, 710, 629, 555, 525, 467.

MS m/z: 490 (M$^+$+H), 512 (M$^+$+Na).

Anal. Calcd for C$_{22}$H$_{26}$ClF$_2$NO$_5$S.0.25H$_2$O: C, 53.44; H, 5.40; Cl, 7.17; F, 7.68; N, 2.83; S, 6.48. Found: C, 53.39; H, 5.45; Cl, 7.21; F, 7.48; N, 2.95; S, 6.51.

Example 258

2-[3-[(4-Chlorophenyl)sulfonyl]-3-(2,5-difluorophenyl)propylamino]ethanol Hydrochloride

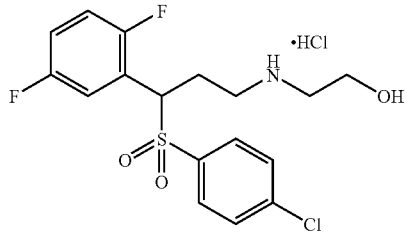

In dichloromethane (5 ml) was dissolved t-butyl N-[3-[(4-chlorophenyl)sulfonyl]-3-(2,5-difluorophenyl)propyl]-N-(2-hydroxyethyl)carbamate (300 mg, 0.607 mmol) and trifluoroacetic acid (0.5 ml) was added dropwise to the resulting solution under ice cooling. After stirring at room temperature for 2 hours, the reaction mixture was concentrated under reduced pressure. To the residue was added a 1N solution (5 ml) of hydrochloric acid in ethanol, followed by concentration under reduced pressure to give a white solid. The solid thus obtained was washed with diethyl ether, whereby the title compound (249 mg, 0.579 mmol, 95%) was obtained as a white powder.

$^1$H-NMR (400 MHz, CD$_3$OD) δ: 2.42-2.58(1H,m), 2.77-2.90(1H,m), 2.96(1H,td,J=11.8, 4.8 Hz), 3.06-3.15(2H,m), 3.22(1H,td,J=11.8, 5.1 Hz), 3.75(2H,dd,J=5.7, 4.5 Hz), 4.89 (1H,dd,J=9.6, 5.3 Hz), 6.98(1H,td,J=9.3, 4.4 Hz), 7.10-7.20 (1H,m), 7.26-7.34(1H,m), 7.54(2H,d,J=8.8 Hz), 7.61 (2H,d, J=8.8 Hz).

IR (ATR) cm$^{-1}$: 3535, 2956, 2902, 2677, 1576, 1496, 1306, 1232, 1192, 1146, 1084, 1016, 822, 754, 710, 633, 548, 521, 472, 442.

mp: 216-220° C.

MS m/z: 390 (M$^+$+H).

Anal. Calcd for C$_{17}$H$_{18}$ClF$_2$NO$_3$S.HCl.0.25H$_2$O: C, 47.40; H, 4.56; Cl, 16.46; F, 8.82; N, 3.25; S, 7.44. Found: C, 47.52; H, 4.47; Cl, 16.47; F, 9.06; N, 3.36; S, 7.58.

Example 259 t-Butyl 4-[(4-chlorophenyl)sulfonyl]-4-(2,5-difluorophenyl)-1-piperidinecarboxylate

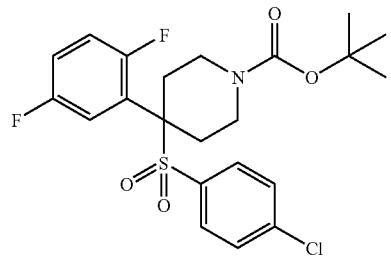

The t-butyl N-[3-[(4-chlorophenyl)sulfonyl]-3-(2,5-difluorophenyl)propyl]-N-(2-hydroxyethyl)carbamate (200 mg, 0.404 mmol) obtained in Example 257 was dissolved in toluene (10 ml), followed by the addition of cyanomethylenetri-n-butylphosphorane (200 mg, 0.829 mmol). Under an argon atmosphere, the resulting mixture was heated under reflux for 8 hours. After the reaction mixture was allowed to cool down, cyanomethylenetri-n-butylphosphorane (200 mg, 0.829 mmol) was added thereto. Under an argon atmosphere, the mixture was heated under reflux for 14 hours. After the reaction mixture was allowed to cool down, the residue obtained by concentrating the reaction mixture under reduced pressure was subjected to flash silica gel chromatography, and the fraction obtained from the hexane:ethyl acetate=4:1 eluate was concentrated under reduced pressure to give a white solid. The white solid was washed with diethyl ether, whereby the title compound (140 mg, 0.297 mmol, 74%) was obtained as a white powder.

$^1$H-NMR (400 MHz, CDCl$_3$) δ: 1.43(9H,s), 2.27(2H,br t,J=14.2 Hz), 2.67(4H,br s), 4.18(2H,br s), 6.82-6.92(1H,m), 7.03-7.16(2H,m), 7.36(2H,d,J=8.7 Hz), 7.40(2H,d,J=8.7 Hz).

IR (ATR) cm$^{-1}$: 2979, 1682, 1583, 1410, 1315, 1244, 1188, 1144, 1088, 831, 754, 623, 563, 534, 474.

mp: 101-106° C.

MS m/z: 472 (M$^+$+H).

Anal. Calcd for C$_{22}$H$_{24}$ClF$_2$NO$_4$S: C, 55.99; H, 5.13; Cl, 7.51; F, 8.05; N, 2.97; S, 6.79. Found: C, 55.89; H, 5.19; Cl, 7.35; F, 7.97; N, 3.02; S, 6.80.

Example 260

4-[(4-Chlorophenyl)sulfonyl]-4-(2,5-difluorophenyl)piperidine Hydrochloride

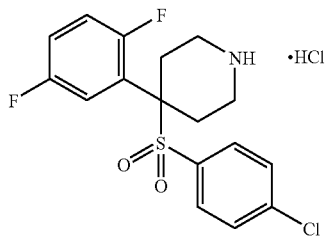

In dichloromethane (100 ml) was dissolved t-butyl 4-[(4-chlorophenyl)sulfonyl]-4-(2,5-difluorophenyl)-1-piperidinecarboxylate (3.17 g, 6.72 mmol), followed by the dropwise addition of trifluoroacetic acid (10.0 ml) under ice cooling. After stirring at room temperature for 2 hours, the reaction mixture was concentrated under reduced pressure. To the residue thus obtained was added a 1N solution (30 ml) of hydrochloric acid in ethanol. The resulting mixture was concentrated under reduced pressure to give a white solid. The white solid thus obtained was washed with diethyl ether, whereby the title compound (2.74 g, 6.71 mmol, quant.) was obtained as a white powder.

$^1$H-NMR (400 MHz, CD$_3$OD) δ: 2.57(2H,tm,J=14.1 Hz), 2.85(2H,tm,J=12.6 Hz), 2.98(2H,br s), 3.54(2H,dm,J=13.7 Hz), 7.02-7.12(1H,m), 7.22-7.31(2H,m), 7.43(2H,d,J=8.8 Hz), 7.55(2H,d,J=8.8 Hz).

IR (ATR) cm$^{-1}$: 3338, 2943, 2713, 1579, 1495, 1469, 1311, 1196, 1144, 1082, 1012, 893, 818, 750, 623, 567.

mp: 239-246° C. (decomp.).

MS m/z: 372 (M$^+$+H).

Anal. Calcd for C$_{17}$H$_{16}$ClF$_2$NO$_2$S.HCl.0.75H$_2$O: C, 48.41; H, 4.42; Cl, 16.81; F, 9.01; N, 3.32; S, 7.60. Found: C, 48.60; H, 4.31; Cl, 16.33; F, 9.16; N, 3.46; S, 7.80.

Example 261

4-[(4-Chlorophenyl)sulfonyl]-4-(2,5-difluorophenyl)-1-methylpiperidine

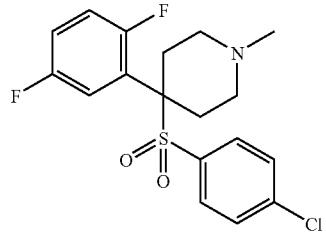

To dichloromethane (5 ml) were added 4-[(4-chlorophenyl)sulfonyl]-4-(2,5-difluorophenyl)piperidine hydrochloride (100 mg, 0.245 mmol), triethylamine (0.070 ml, 0.50 mmol) and a 37% aqueous formaldehyde solution (0.060 ml, 0.739 mmol), followed by the addition of sodium triacetoxyborohydride (220 mg, 1.04 mmol) at room temperature. After stirring at room temperature for 14 hours, a 1N aqueous sodium hydroxide solution (6.0 ml) was added. The mixture was stirred at room temperature for 30 minutes. To the reaction mixture was added diethyl ether and the mixture was washed with a 1N aqueous sodium hydroxide solution. The organic layer was dried over anhydrous sodium sulfate. After filtration, the filtrate was concentrated under reduced pressure. The residue thus obtained was subjected to flash silica gel chromatography, and the fraction obtained from the dichloromethane:methanol=30:1 eluate was concentrated under reduced pressure to give a white solid. The solid thus obtained was washed with diisopropyl ether, whereby the title compound (70 mg, 0.18 mmol, 74%) was obtained as a white powder.

$^1$H-NMR (400 MHz, CDCl$_3$) δ: 1.90(2H,tm,J=12.5 Hz), 2.17(3H,s), 2.42(2H,tm,J=11.8 Hz), 2.50-2.90(2H,m), 2.89 (2H,dt,J=12.0, 2.9 Hz), 6.82-6.92(1H,m), 7.03-7.16(2H,m), 7.38(2H,d,J=9.0 Hz), 7.42(2H,d,J=9.0 Hz).

IR (ATR) cm$^{-1}$: 3084, 3006, 2943, 2850, 2796, 1577, 1496, 1462, 1313, 1281, 1184, 1147, 1086, 814, 752, 712, 631, 571, 534, 474, 440.

mp: 172-175° C.

MS m/z: 386 (M$^+$+H).

Anal. Calcd for C$_{18}$H$_{18}$ClF$_2$NO$_2$S: C, 56.03; H, 4.70; Cl, 9.19; F, 9.85; N, 3.63; S, 8.31. Found: C, 55.92; H, 4.72; Cl, 9.10; F, 9.91; N, 3.67; S, 8.39.

Example 262

1-Benzyl-4-[(4-chlorophenyl)sulfonyl]-4-(2,5-difluorophenyl)piperidine

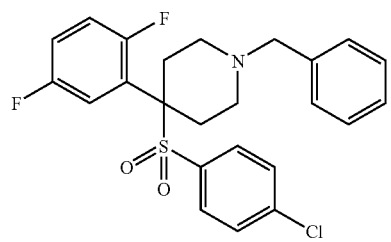

The 4-[(4-chlorophenyl)sulfonyl]-4-(2,5-difluorophenyl)piperidine hydrochloride (100 mg, 0.245 mmol) obtained in Example 260, triethylamine (0.070 ml, 0.50 mmol) and benzaldehyde (0.050 ml, 0.428 mmol) were added to dichloromethane (5 ml), followed by the addition of sodium triacetoxyborohydride (110 mg, 0.500 mmol) at room temperature. The resulting mixture was stirred at room temperature for 14 hours. A 1N aqueous sodium hydroxide solution (3.0 ml) was then added. The resulting mixture was stirred at room temperature for 30 minutes. After diethyl ether was added, the resulting mixture was washed with a 1N aqueous sodium hydroxide solution. The organic layer was dried over anhydrous sodium sulfate. After filtration, the filtrate was concentrated under reduced pressure. The residue thus obtained was subjected to flash silica gel chromatography, and the fraction obtained from the dichloromethane:methanol=50:1 eluate was concentrated under reduced pressure, whereby the title compound (87 mg, 0.19 mmol, 77%) was obtained as a white foam.

$^1$H-NMR (400 MHz, CDCl$_3$) δ: 1.93(2H,br t,J=12.5 Hz), 2.46(2H, br t,J=11.6 Hz), 2.65(2H,br s), 2.93(2H,dm,J=12.5 Hz), 3.36(2H,s), 6.81-6.94(1H,m), 7.00-7.15(2H,m), 7.20-7.34 (5H,m), 7.37 (4H,s).

IR (ATR) cm$^{-1}$: 2812, 2769, 1583, 1495, 1313, 1259, 1188, 1144, 1088, 810, 752, 698, 629, 571, 542, 469.

MS m/z: 462 (M$^+$+H).

Anal. Calcd for C$_{24}$H$_{22}$ClF$_2$NO$_2$S: C, 62.40; H, 4.80; Cl, 7.67; F, 8.23; N, 3.03; S, 6.94. Found: C, 62.50; H, 4.98; Cl, 7.50; F, 8.05; N, 3.04; S, 6.90.

Example 263

1-[4-[(4-Chlorophenyl)sulfonyl]-4-(2,5-difluorophenyl)piperidino]-1-ethanone

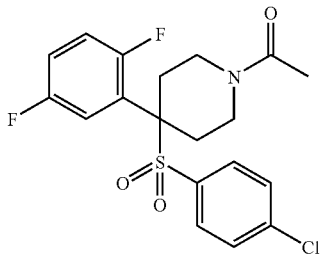

The 4-[(4-chlorophenyl)sulfonyl]-4-(2,5-difluorophenyl)piperidine hydrochloride (90 mg, 0.22 mmol) obtained in Example 260 and triethylamine (0.092 ml, 0.66 mmol) were dissolved in dichloromethane (4 ml), followed by the addition of acetyl chloride (0.024 ml, 0.34 mmol) at room temperature. After stirring at room temperature for 14 hours, a saturated aqueous solution of sodium bicarbonate (0.5 ml) was added. The residue obtained by concentrating the resulting mixture under reduced pressure was subjected to flash silica gel chromatography, and the fraction obtained from the dichloromethane:methanol=30:1 eluate was concentrated under reduced pressure to give a white solid. The solid thus obtained was washed with hexane, whereby the title compound (48 mg, 0.12 mmol, 53%) was obtained as a white powder.

$^1$H-NMR (400 MHz, CDCl$_3$) δ: 2.08(3H,s), 2.20-2.42(2H, m), 2.49(1H,br t,J=13.0 Hz), 2.60-2.75(1H,m), 2.75-2.90 (1H,m), 3.01(1H,br t,J=13.2 Hz), 3.92(1H,dm,J=13.4 Hz), 4.70(1H,dm,J=13.9 Hz), 6.85-6.94(1H,m), 7.50-7.60(2H,m), 7.36(2H,d,J=8.8 Hz), 7.40(2H,d,J=8.8 Hz).

IR (ATR) cm$^{-1}$: 3084, 1653, 1496, 1427, 1309, 1279, 1244, 1144, 1088, 993, 754, 627, 563, 474.

mp: 159-160° C.

MS m/z: 414 (M$^+$+H).

Anal. Calcd for C$_{19}$H$_{18}$ClF$_2$NO$_3$S: C, 55.14; H, 4.38; Cl, 8.57; F, 9.18; N, 3.38; S, 7.75. Found: C, 55.07; H, 4.49; Cl, 8.69; F, 9.30; N, 3.41; S, 7.77.

Example 264

[4-[(4-Chlorophenyl)sulfonyl]-4-(2,5-difluorophenyl)piperidino](4-pyridyl)methanone

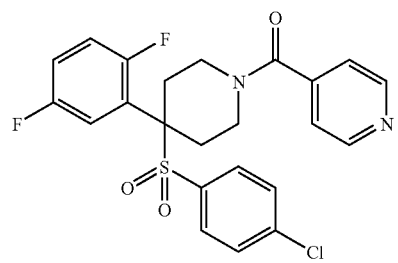

In a similar manner to Example 263 except for the use of the 4-[(4-chlorophenyl)sulfonyl]-4-(2,5-difluorophenyl)piperidine hydrochloride (80 mg, 0.20 mmol) obtained in Example 260 and isonicotinoyl chloride hydrochloride (60 mg, 0.34 mmol), the title compound (84 mg, 0.18 mmol, 90%) was obtained as a white powder.

$^1$H-NMR (400 MHz, CDCl$_3$) δ: 2.24-2.55(2H,m), 2.60-2.90(3H,m), 2.90-3.10(1H,m), 3.70-3.82(1H,m), 4.74-4.90 (1H,m), 6.84-6.92(1H,m), 7.04-7.14(2H,m), 7.18-7.25(2H, m), 7.34(2H,d,J=8.5 Hz), 7.39(2H,d,J=8.5 Hz), 8.70(2H,d, J=5.9 Hz).

IR (ATR) cm$^{-1}$: 3032, 1630, 1496, 1439, 1311, 1279, 1146, 1086, 1013, 810, 752, 625, 561, 505.

mp: 245-248° C.

MS m/z: 477 (M$^+$+H).

FAB-MS: 477.0839 (Calcd for C$_{23}$H$_{20}$ClF$_2$N$_2$O$_3$S: 477.0851).

Example 265

[4-[(4-Chlorophenyl)sulfonyl]-4-(2,5-difluorophenyl)piperidino](3-pyridyl)methanone

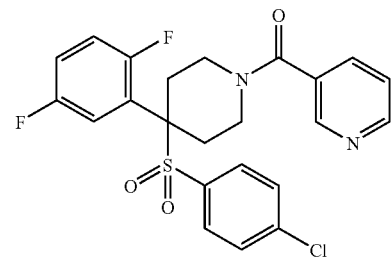

In a similar manner to Example 263 except for the use of the 4-[(4-chlorophenyl)sulfonyl]-4-(2,5-difluorophenyl)piperidine hydrochloride (90 mg, 0.22 mmol) obtained in Example 260 and niconitonyl chloride hydrochloride (60 mg, 0.34 mmol), the title compound (75 mg, 0.16 mmol, 71%) was obtained as a white powder.

$^1$H-NMR (400 MHz, CDCl$_3$) δ: 2.20-4.90(8H,m), 6.85-6.95(1H,m), 7.08-7.18(2H,m), 7.32-7.43(1H,m), 7.35(2H,d,J=8.9 Hz), 7.40(2H,d,J=8.9 Hz), 7.73(1H,dt,J=7.8, 2.0 Hz), 8.62(1H,dd,J=2.0, 1.0 Hz), 8.68(1H,dd,J=4.9, 2.0 Hz).

IR (ATR) cm$^{-1}$: 1631, 1585, 1493, 1444, 1315, 1144, 1088, 831, 756, 625, 557, 505, 474.

mp: 119-124° C.

MS m/z: 477 (M$^+$+H).

Anal. Calcd for C$_{23}$H$_{19}$ClF$_2$N$_2$O$_3$S: C, 57.92; H, 4.02; Cl, 7.43; F, 7.97; N, 5.87; S, 6.72. Found: C, 57.69; H, 4.08; Cl, 7.33; F, 7.97; N, 5.94; S, 6.78.

Example 266

[4-[(4-Chlorophenyl)sulfonyl]-4-(2,5-difluorophenyl)piperidino](2-pyridyl)methanone

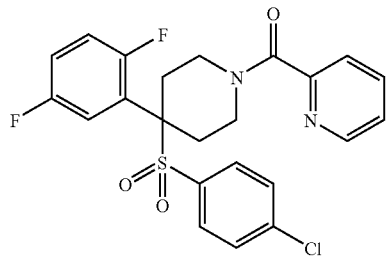

In a similar manner to Example 263 except for the use of 4-[(4-chlorophenyl)sulfonyl]-4-(2,5-difluorophenyl)piperidine hydrochloride (80 mg, 0.20 mmol) obtained in Example 260 and picolinoyl chloride hydrochloride (60 mg, 0.34 mmol), the title compound (77 mg, 0.16 mmol, 82%) was obtained as a white powder.

$^1$H-NMR (400 MHz, CDCl$_3$) δ: 2.35-2.52(2H,m), 2.60-2.90(3H,m), 3.09(1H,br t,J=13.1 Hz), 4.21(1H,dm,J=13.5 Hz), 4.83(1H,dm,J=14.0 Hz), 6.82-6.95(1H,m), 7.04-7.18(2H,m), 7.30-7.45(5H,m), 7.65(1H,dm,J=7.8 Hz), 7.80(1H,td,J=7.8, 1.7 Hz), 8.55(1H,dm,J=4.9 Hz).

IR (ATR) cm$^{-1}$: 3084, 1635, 1496, 1311, 1146, 1086, 1007, 843, 804, 752, 629, 555, 467.

mp: 193-196° C.

MS m/z: 477 (M$^+$+H).

Anal. Calcd for C$_{23}$H$_{19}$ClF$_2$N$_2$O$_3$S: C, 57.92; H, 4.02; Cl, 7.43; F, 7.97; N, 5.87; S, 6.72. Found: C, 57.94; H, 4.08; Cl, 7.48; F, 7.99; N, 5.92; S, 6.81.

Example 267

Methyl 4-[(4-chlorophenyl)sulfonyl]-4-(2,5-difluorophenyl)-1-piperidinecarboxylate

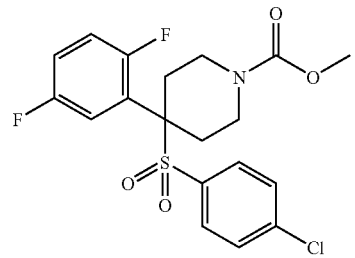

In a similar manner to Example 263 except for the use of 4-[(4-chlorophenyl)sulfonyl]-4-(2,5-difluorophenyl)piperidine hydrochloride (90 mg, 0.22 mmol) obtained in Example 260 and methyl chloroformate (0.026 ml, 0.34 mmol), the title compound (62 mg, 0.14 mmol, 65%) was obtained as a white powder.

$^1$H-NMR (400 MHz, CDCl$_3$) δ: 2.29(2H,tm,J=12.1 Hz), 2.55-2.85(4H,m), 3.68(3H,s), 4.22(2H,br s), 6.82-6.92(1H,m), 7.05-7.15(2H,m), 7.36(2H,d,J=8.8 Hz), 7.40(2H,d,J=8.8 Hz).

IR (ATR) cm$^{-1}$: 1695, 1493, 1450, 1400, 1248, 1188, 1142, 1090, 901, 825, 623, 565, 534, 474.

mp: 123-126° C.

MS m/z: 430 (M$^+$+H).

Anal. Calcd for C$_{19}$H$_{18}$ClF$_2$NO$_4$S: C, 53.09; H, 4.22; Cl, 8.25; F, 8.84; N, 3.26; S, 7.46. Found: C, 52.89; H, 4.20; Cl, 8.27; F, 8.90; N, 3.35; S, 7.58.

Example 268

N,N-dimethyl-4-[(4-chlorophenyl)sulfonyl]-4-(2,5-difluorophenyl)-1-piperidinecarboxamide

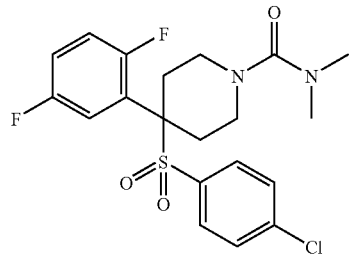

In a similar manner to Example 263 except for the use of 4-[(4-chlorophenyl)sulfonyl]-4-(2,5-difluorophenyl)piperidine hydrochloride (90 mg, 0.22 mmol) obtained in Example 260 and N,N-dimethylcarbamoyl chloride (0.031 ml, 0.34 mmol), the title compound (81 mg, 0.18 mmol, 83%) was obtained as a white powder.

$^1$H-NMR (400 MHz, CDCl$_3$) δ: 2.40(2H,br t,J=12.1 Hz), 2.60-2.80(4H,m), 2.81(6H,s), 3.72(2H,dm,J=13.7 Hz), 6.82-6.92(1H,m), 7.04-7.14(2H,m), 7.35(2H,d,J=9.0 Hz), 7.39 (2H,d,J=9.0 Hz).

IR (ATR) cm$^{-1}$: 1651, 1576, 1496, 1469, 1365, 1308, 1190, 1146, 1074, 1034, 914, 814, 758, 752, 617, 561, 474.

mp: 143-146° C.

MS m/z: 443 (M$^+$+H).

Anal. Calcd for C$_{20}$H$_{21}$ClF$_2$N$_2$O$_3$S: C, 54.24; H, 4.78; Cl, 8.00; F, 8.58; N, 6.32; S, 7.24. Found: C, 53.96; H, 4.73; Cl, 8.14; F, 8.64; N, 6.34; S, 7.32.

Example 269

4-[(4-Chlorophenyl)sulfonyl]-4-(2,5-difluorophenyl)-1-(methylsulfonyl)piperidine

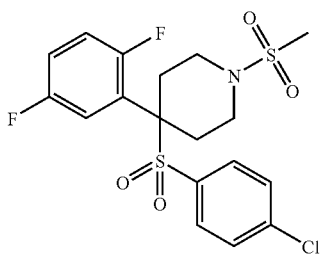

In a similar manner to Example 263 except for the use of the 4-[(4-chlorophenyl)sulfonyl]-4-(2,5-difluorophenyl)piperidine hydrochloride (90 mg, 0.22 mmol) obtained in Example 260 and methanesulfonyl chloride (0.026 ml, 0.34 mmol), the title compound (72 mg, 0.16 mmol, 73%) was obtained as a white powder.

$^1$H-NMR (400 MHz, CDCl$_3$) δ: 2.48(2H,br t,J=12.1 Hz), 2.60-2.90(4H,m), 2.72(3H,s), 3.88(2H,dm,J=12.9 Hz), 6.88-6.96(1H,m), 7.04-7.14(2H,m), 7.37(2H,d,J=8.9 Hz), 7.42 (2H,d,J=8.9 Hz).

IR (ATR) cm$^{-1}$: 1579, 1495, 1308, 1257, 1138, 966, 814, 752, 623, 565, 513.

mp: 176-178° C.

MS m/z: 450(M$^+$+H).

Anal. Calcd for C$_{18}$H$_{18}$ClF$_2$NO$_3$S: C, 48.05; H, 4.03; Cl, 7.88; F, 8.45; N, 3.11; S, 14.25. Found: C, 48.02; H, 4.00; Cl, 7.91; F, 8.52; N, 3.22; S, 14.28.

Example 270

N,N-Dimethyl-4-[(4-chlorophenyl)sulfonyl]-4-(2,5-difluorophenyl)-1-piperidinesulfonamide

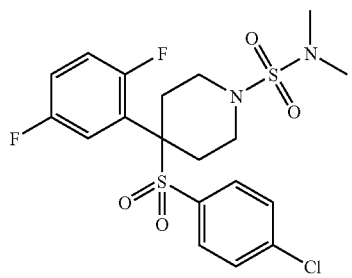

In a similar manner to Example 263 except for the use of the 4-[(4-chlorophenyl)sulfonyl]-4-(2,5-difluorophenyl)piperidine hydrochloride (90 mg, 0.22 mmol) obtained in Example 260 and N,N-dimethylsulfamoyl chloride (0.036 ml, 0.34 mmol), the title compound (84 mg, 0.18 mmol, 80%) was obtained as a white powder.

$^1$H-NMR (400 MHz, CDCl$_3$) δ: 2.45(2H,br t,J=12.5 Hz), 2.68-2.90(4H,m), 2.79(6H,s), 3.73(2H,dm,J=13.4 Hz), 6.80-6.92(1H,m), 7.05-7.14(2H,m), 7.34(2H,d,J=8.8 Hz), 7.40 (2H,d,J=8.8 Hz).

IR (ATR) cm$^{-1}$: 1576, 1493, 1469, 1315, 1144, 984, 904, 808, 742, 621, 553, 519, 472.

mp: 125-129° C.

MS m/z: 479 (M$^+$+H).

Anal. Calcd for C$_{19}$H$_{21}$ClF$_2$N$_2$O$_4$S$_2$: C, 47.65; H, 4.42; Cl, 7.40; F, 7.93; N, 5.85; S, 13.39. Found: C, 47.62; H, 4.40; Cl, 7.42; F, 8.03; N, 5.95; S, 13.43.

Example 271

1-[4-[(4-Chlorophenyl)sulfonyl]-4-(2,5-difluorophenyl)piperidino]-2-(dimethylamino)-1-ethanone

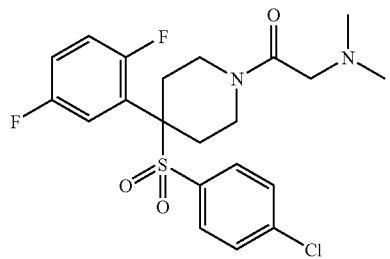

The 4-[(4-chlorophenyl)sulfonyl]-4-(2,5-difluorophenyl)piperidine hydrochloride (100 mg, 0.245 mmol) obtained in Example 260, N,N-dimethylglycine (40 mg, 0.39 mmol) and N-methylmorpholine (0.142 ml, 1.29 mmol) were dissolved in dichloromethane (5 ml), followed by the addition of 1-ethyl-3-(3-dimethylaminopropyl)carbodiimide hydrochloride (80 mg, 0.42 mmol) at room temperature. After stirring at room temperature for 14 hours, a saturated aqueous solution (0.5 ml) of sodium bicarbonate was added. The residue obtained by concentrating the reaction mixture under reduced pressure was subjected to flash silica gel chromatography, and the fraction obtained from the dichloromethane:methanol=30:1 eluate was concentrated under reduced pressure to give a white solid. The resulting solid was washed with diisopropyl ether, whereby the title compound (70 mg, 0.15 mmol, 62%) was obtained as a white powder.

$^1$H-NMR (400 MHz, CDCl$_3$) δ: 2.15-2.40(2H,m), 2.25 (6H,s), 2.50(1H,br t,J=12.9 Hz), 2.60-2.85(2H,m), 2.93(1H, br t,J=12.0 Hz), 3.03(1H,d,J=13.2 Hz), 3.13(1H,d,J=13.2 Hz), 4.32(1H,br d,J=14.4 Hz), 4.67(1H,br d,J=13.7 Hz), 6.83-6.93(1H,m), 7.02-7.16(2H,m), 7.36(2H,d,J=8.8 Hz), 7.40 (2H,d,J=8.8 Hz).

IR (ATR) cm$^{-1}$: 2829, 2773, 1635, 1460, 1313, 1142, 1090, 827, 806, 754, 625, 561, 523, 474.

mp: 88-92° C.

MS m/z: 457 (M$^+$+H).

Anal. Calcd for C$_{21}$H$_{23}$ClF$_2$N$_2$O$_3$S: C, 55.20; H, 5.07; Cl, 7.76; F, 8.32; N, 6.13; S, 7.02. Found: C, 55.15; H, 5.18; Cl, 7.76; F, 8.40; N, 6.13; S, 7.13.

Example 272

N-ethyl-4-[(4-chlorophenyl)sulfonyl]-4-(2,5-difluorophenyl)-1-piperidinecarboxamide

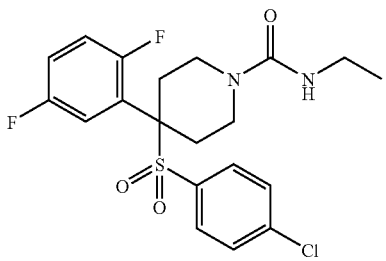

The 4-[(4-chlorophenyl)sulfonyl]-4-(2,5-difluorophenyl) piperidine hydrochloride (80 mg, 0.20 mmol) obtained in Example 260 and triethylamine (0.092 ml, 0.66 mmol) were dissolved in dichloromethane (4 ml), followed by the addition of ethyl isocyanate (0.027 ml, 0.34 mmol) at room temperature. After stirring at room temperature for 6 hours, a saturated aqueous solution of sodium bicarbonate (0.5 ml) was added. The residue obtained by concentrating the reaction mixture under reduced pressure was subjected to flash silica gel chromatography, and the fraction obtained from the dichloromethane:methanol=50:1 eluate was concentrated under reduced pressure to give a white solid. The resulting solid was washed with diisopropyl ether, whereby the title compound (74 mg, 0.17 mmol, 85%) was obtained as a white powder.

$^1$H-NMR (400 MHz, CDCl$_3$) δ: 1.12(3H,t,J=7.2 Hz), 2.33 (2H,br t,J=11.8 Hz), 2.72(4H,br t,J=12.0 Hz), 3.18-3.30(2H, m), 3.99(2H,dm,J=13.4 Hz), 4.30-4.40(1H,m), 6.84-6.95 (1H,m), 7.05-7.15(2H,m), 7.37(2H,d,J=8.8 Hz), 7.40(2H,d, J=8.8 Hz).

IR (ATR) cm$^{-1}$: 3286, 1622, 1496, 1309, 1265, 1144, 1090, 889, 825, 752, 629, 567, 542, 474.

mp: 172-174° C.

MS m/z: 443(M$^+$+H).

Anal. Calcd for C$_{20}$H$_{21}$ClF$_2$N$_2$O$_3$S: C, 54.24; H, 4.78; Cl, 8.00; F, 8.58; N, 6.32; S, 7.24. Found: C, 54.18; H, 4.76; Cl, 8.15; F, 8.70; N, 6.41; S, 7.39.

Example 273

2-[7-(t-Butyldiphenylsilyloxy)-1-[(4-chlorophenyl)sulfonyl]heptyl]-1,4-difluorobenzene

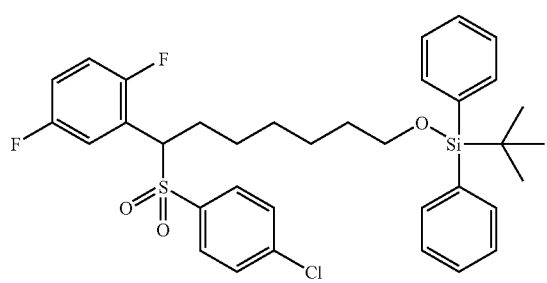

The 2-[(4-chlorophenyl)sulfonylmethyl]-1,4-difluorobenzene (470 mg, 1.55 mmol) obtained in Example 5 and 6-(t-butyldiphenylsilyloxy)-1-hexanol (740 mg, 2.08 mmol) were dissolved in toluene (20 ml), followed by the addition of cyanomethylenetri-n-butylphosphorane (500 mg, 2.07 mmol). Under an argon atmosphere, the resulting mixture was heated under reflux for 7 hours. After the reaction mixture was allowed to cool down, the residue obtained by concentrating the reaction mixture under reduced pressure was subjected to flash silica gel chromatography. The fraction obtained from the hexane:ethyl acetate=10:1 eluate was concentrated under reduced pressure, whereby the title compound (786 mg, 1.23 mmol, 79%) was obtained as a pale yellowish brown oil.

$^1$H-NMR (400 MHz, CDCl$_3$) δ: 1.02(9H,s), 1.10-1.40(6H, m), 1.42-1.55(2H,m), 2.00-2.14(1H,m), 2.35-2.48(1H,m), 3.60(2H,t,J=6.5 Hz), 4.49(1H,dd,J=11.6, 2.6 Hz), 6.76-6.89 (1H,m), 6.94-7.03(1H,m), 7.20-7.30(1H,m), 7.34-7.50(8H, m), 7.53(2H,d,J=8.6 Hz), 7.64(4H,dm,J=8.1 Hz).

IR (ATR) cm$^{-1}$: 2931, 2856, 1583, 1496, 1427, 1323, 1149, 1105, 1084, 822, 700, 627, 613, 503, 486, 467.

MS m/z: 641 (M$^+$+H).

Example 274

7-[(4-Chlorophenyl)sulfonyl]-7-(2,5-difluorophenyl)-1-heptanol

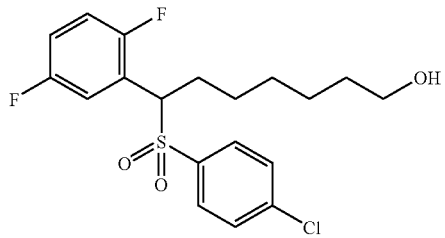

In tetrahydrofuran (20 ml) was dissolved 2-[7-(t-butyldiphenylsilyloxy)-1-[(4-chlorophenyl)sulfonyl]heptyl]-1,4-difluorobenzene (786 mg, 1.23 mmol), followed by the dropwise addition of a tetrahydrofuran solution (1.0M, 4.0 ml, 4.0 mmol) of tetrabutylammonium fluoride under ice cooling. The resulting mixture was stirred at room temperature for 14 hours. After addition of water (2 ml), the mixture was concentrated under reduced pressure. The residue thus obtained was subjected to flash silica gel chromatography, and the fraction obtained from the hexane:ethyl acetate=2:1 eluate was concentrated under reduced pressure to give a white solid. The white solid was washed with hexane, whereby the title compound (403 mg, 1.00 mmol, 81%) was obtained as a white powder.

$^1$H-NMR (400 MHz, CDCl$_3$) δ: 1.10-1.75(9H,m), 2.02-2.20(1H,m), 2.38-2.52(1H,m), 3.60(2H,t,J=6.4 Hz), 4.50 (1H,dd,J=11.7, 3.2 Hz), 6.78-6.90(1H,m), 6.92-7.05(1H,m), 7.20-7.35(1H,m), 7.38(2H,d,J=8.4 Hz), 7.53(2H,d,J=8.4 Hz).

IR (ATR) cm$^{-1}$: 3338, 2935, 2860, 1583, 1495, 1325, 1149, 1082, 1012, 752, 631, 542, 467.

mp: 77-79° C.

MS m/z: 403 (M$^+$+H), 420 (M$^+$+NH$_4$).

Anal. Calcd for C$_{19}$H$_{21}$ClF$_2$O$_3$S: C, 56.64; H, 5.25; Cl, 8.80; F, 9.43; S, 7.96. Found: C, 56.16; H, 5.18; Cl, 8.80; F, 9.36; S, 8.00.

Example 275

2-[1-[(4-Chlorophenyl)sulfonyl]cycloheptyl-1,4-difluorobenzene

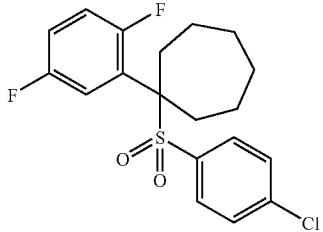

In toluene (5 ml) was dissolved 7-[(4-chlorophenyl)sulfonyl]-7-(2,5-difluorophenyl)-1-heptanol (200 mg, 0.496 mmol), followed by the addition of cyanomethylenetri-n-butylphosphorane (400 mg, 1.66 mmol). Under an argon atmosphere, the resulting mixture was heated under reflux for 14 hours. After the reaction mixture was allowed to cool down, the residue obtained by concentrating the reaction mixture under reduced pressure was subjected to flash silica gel chromatography. The fraction obtained from the hexane:ethyl acetate=10:1 eluate was concentrated under reduced pressure to give a white solid. The white solid was washed with hexane, whereby the title compound (111 mg, 0.288 mmol, 58%) was obtained as a white powder.

$^1$H-NMR (400 MHz, CDCl$_3$) δ: 1.34-1.50(4H,m), 1.50-1.68(2H,m), 1.82-1.98(2H,m), 2.36(2H,tm,J=12.5 Hz), 2.65-2.78(2H,m), 6.84-6.94(1H,m), 6.97-7.08(2H,m), 7.34(2H,d,J=9.0 Hz), 7.37(2H,d,J=9.0 Hz).

IR (ATR) cm$^{-1}$: 2931, 2856, 1577, 1493, 1473, 1308, 1277, 1186, 1140, 1086, 1012, 881, 818, 748, 710, 615, 559, 467.

mp: 101-103° C.

MS m/z: 402 (M$^+$+NH$_4$).

Anal. Calcd for C$_{19}$H$_{19}$ClF$_2$O$_2$S: C, 59.29; H, 4.98; Cl, 9.21; F, 9.87; S, 8.33. Found: C, 59.21; H, 4.86; Cl, 9.25; F, 9.96; S, 8.48.

Example 276

2-[2-[2-[(t-Butyldiphenylsilyloxy)methyl]phenyl]-1-[(4-chlorophenyl)sulfonyl]ethyl]-1,4-difluorobenzene

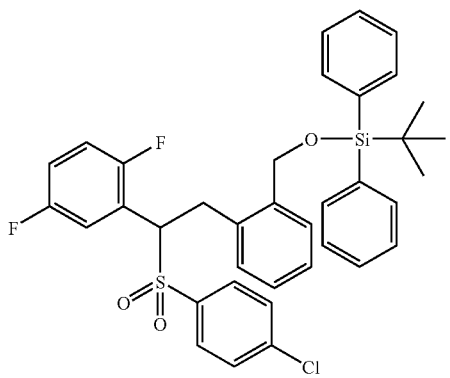

The 2-[(4-chlorophenyl)sulfonylmethyl]-1,4-difluorobenzene (600 mg, 1.98 mmol) obtained in Example 5 and [2-[(t-butyldiphenylsilyloxy)methyl]phenyl]methanol (1.00 g, 2.66 mmol) were dissolved in toluene (20 ml), followed by the addition of cyanomethylenetri-n-butylphosphorane (640 mg, 2.65 mmol). Under an argon atmosphere, the resulting mixture was heated under reflux for 14 hours. After the reaction mixture was allowed to cool down, 2-[(t-butyldiphenylsilyloxy)methyl]phenyl]methanol (400 mg, 1.06 mmol) and cyanomethylenetri-n-butylphosphorane (400 mg, 1.66 mmol) were added. Under an argon atmosphere, the resulting mixture was heated under reflux for 14 hours. After the reaction mixture was allowed to cool down, the residue obtained by concentrating the mixture under reduced pressure was subjected to flash silica gel chromatography. The fraction obtained from the hexane:ethyl acetate=15:1 eluate was concentrated under reduced pressure, whereby the title compound (1.13 g, 1.71 mmol, 86%) was obtained as a pale yellowish brown oil.

$^1$H-NMR (400 MHz, CDCl$_3$) δ: 1.09(9H,s), 3.30(1H,dd,J=14.7, 11.2 Hz), 3.80(1H,dd,J=14.7, 3.4 Hz), 4.65(1H,d,J=12.9 Hz), 4.70-4.85(2H,m), 6.64-6.74(1H,m), 6.82(1H,d,J=6.8 Hz), 6.85-6.94(1H,m), 7.03(1H,td,J=7.5, 1.4 Hz), 7.15(1H,td,J=7.5, 1.2 Hz), 7.20-7.55(12H,m), 7.65-7.76(4H,m).

IR (ATR) cm$^{-1}$: 2931, 2856, 1583, 1496, 1473, 1427, 1319, 1149, 1111, 1082, 822, 740, 700, 634, 501.

MS m/z: 661(M$^+$+H), 683(M$^+$+Na).

Example 277

[2-[2-[(4-Chlorophenyl)sulfonyl]-2-(2,5-difluorophenyl)ethyl]phenyl]methanol

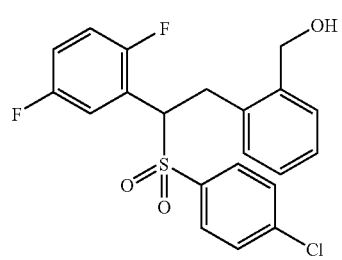

In tetrahydrofuran (20 ml) was dissolved 2-[2-[2-[(t-butyldiphenylsilyloxy)methyl]phenyl]-1-[(4-chlorophenyl)sulfonyl]ethyl]-1,4-difluorobenzene (1.10 g, 1.66 mmol), followed by the dropwise addition of a tetrahydrofuran solution (1.0M, 5.0 ml, 5.0 mmol) of tetrabutylammonium fluoride under ice cooling. The resulting mixture was stirred at room temperature for 14 hours. After addition of water (3 ml), the residue obtained by concentrating the resulting mixture under reduced pressure was subjected to flash silica gel chromatography. The fraction obtained from the hexane:ethyl acetate=1:1 eluate was concentrated under reduced pressure to give a white solid. The white solid was washed with diisopropyl ether, whereby the title compound (595 mg, 1.41 mmol, 85%) was obtained as a white powder.

$^1$H-NMR (400 MHz, CDCl$_3$) δ: 1.92(1H,dd,J=6.1, 4.9 Hz), 3.35(1H,dd,J=14.1, 10.0 Hz), 4.00(1H,dd,J=14.1, 3.4 Hz), 4.66(1H,dd,J=12.3, 4.9 Hz), 4.81(1H,dd,J=12.3, 6.1 Hz), 5.10(1H,dm,J=10.0 Hz), 6.66-6.75(1H,m), 6.82(1H,d,J=7.5 Hz), 6.89-6.98(1H,m), 7.06(1H,td,J=7.5, 1.5 Hz), 7.17(1H,td,J=7.5, 1.2 Hz), 7.29(1H,dd,J=7.5, 1.2 Hz), 7.38(2H,d,J=8.7 Hz), 7.50(1H,br s), 7.58(2H,d,J=8.7 Hz).

IR (ATR) cm$^{-1}$: 3506, 1576, 1493, 1313, 1279, 1213, 1144, 1080, 1014, 829, 750, 708, 634, 536, 471.
mp: 107-108° C.
MS m/z: 422 (M$^+$).
Anal. Calcd for $C_{21}H_{17}ClF_2O_3S$: C, 59.65; H, 4.05; Cl, 8.38; F, 8.99; S, 7.58. Found: C, 59.46; H, 3.97; Cl, 8.41; F, 9.05; S, 7.67.

Example 278

2-[(4-Chlorophenyl)sulfonyl]-2-(2,5-difluorophenyl)indane

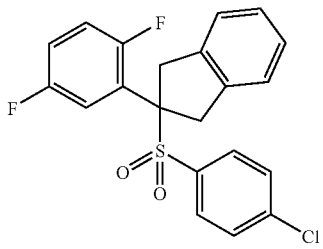

In toluene (5 ml) was dissolved 2-[2-[(4-chlorophenyl)sulfonyl]-2-(2,5-difluorophenyl)ethyl]phenyl]methanol (80 mg, 0.19 mmol), followed by the addition of cyanomethylenetri-n-butylphosphorane (140 mg, 0.580 mmol). Under an argon atmosphere, the resulting mixture was heated under reflux for 8 hours. After the reaction mixture was allowed to cool down, the residue obtained by concentrating it under reduced pressure was subjected to flash silica gel chromatography, and the fraction obtained from the hexane:ethyl acetate=5:1 eluate was concentrated under reduced pressure to give a white solid. The white solid was washed with diisopropyl ether, whereby the title compound (32 mg, 0.079 mmol, 42%) was obtained as a white powder.
$^1$H-NMR (400 MHz, CDCl$_3$) δ: 3.72(2H,dm,J=17.6 Hz), 4.18(2H,dd,J=17.6, 2.9 Hz), 6.95-7.04(1H,m), 7.04-7.12(4H, m), 7.12-7.21(1H,m), 7.21-7.30(1H,m), 7.23(2H,d,J=8.7 Hz), 7.45(2H,d,J=8.7 Hz).
IR (ATR) cm$^{-1}$: 1572, 1495, 1306, 1138, 1078, 821, 754, 656, 598, 571, 525, 478, 451.
mp: 209-210° C. (dec.).
MS m/z: 422 (M$^+$+NH$_4$).

Example 279

2-[1-[(4-Chlorophenyl)sulfonyl]-2-methylcyclopentyl]-1,4-difluorobenzene

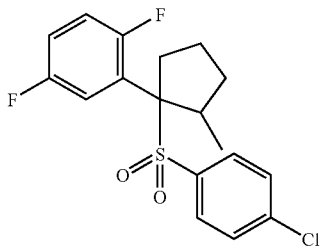

The 2-[5-(t-butyldiphenylsilyloxy)-1-[(4-chlorophenyl)sulfonyl]-2-methylpentyl]-1,4-difluorobenzene (isomer mixture) (1.40 g, 2.23 mmol) obtained in Example 38 was dissolved in tetrahydrofuran (30 ml), followed by the addition of a tetrahydrofuran solution (1.0M, 5.0 ml, 5.0 mmol) of tetrabutylammonium fluoride under ice cooling. The resulting mixture was stirred at room temperature for 14 hours. After addition of water (3 ml), the residue obtained by concentrating the resulting mixture under reduced pressure was subjected to flash silica gel chromatography. The fraction obtained from the hexane:ethyl acetate=2:1 eluate was concentrated under reduced pressure, whereby 5-[(4-chlorophenyl)sulfonyl]-5-(2,5-difluorophenyl)-4-methyl-1-pentanol (isomer mixture) (879 mg, quant.) was obtained as a colorless oil.

The resulting 5-[(4-chlorophenyl)sulfonyl]-5-(2,5-difluorophenyl)-4-methyl-1-pentanol (isomer mixture) was dissolved in toluene (10 ml), followed by the addition of cyanomethylenetri-n-butylphosphorane (1.00 g, 4.14 mmol). Under an argon atmosphere, the resulting mixture was heated under reflux for 14 hours. After the reaction mixture was allowed to cool down, the residue obtained by concentrating the reaction mixture under reduced pressure was subjected to flash silica gel chromatography. The fraction obtained from the hexane:ethyl acetate=20:1 eluate was concentrated under reduced pressure to give a white solid. The white solid was washed with hexane, whereby the title compound (423 mg, 1.14 mmol, 51%) was obtained as a white powder.
$^1$H-NMR (400 MHz, CDCl$_3$) δ: 0.85(1H,d,J=6.8 Hz), 1.50-1.80(1.67H,m), 1.72(2H,d,J=7.1 Hz), 1.84-2.50(3H,m), 2.62-3.05(2H,m), 3.30-3.45(0.33H,m), 6.72-6.92(1.33H,m), 6.92-7.06(1H,m), 7.12-7.22(0.67H,m), 7.27-7.40(4H,m).
IR (ATR) cm$^{-1}$: 1579, 1493, 1300, 1263, 1190, 1136, 1092, 1080, 1012, 839, 823, 756, 746, 712, 638, 600, 579, 546, 517, 472.
mp: 105-109° C.
MS m/z: 393 (M$^+$+Na).
Anal. Calcd for $C_{18}H_{17}ClF_2O_2S$: C, 58.30; H, 4.57; Cl, 9.71; F, 10.15; S, 8.79. Found: C, 58.27; H, 4.57; Cl, 9.71; F, 10.15; S, 8.79.

Referential Example 43

(2-Bromomethylbenzyloxy)-t-butyldiphenylsilane

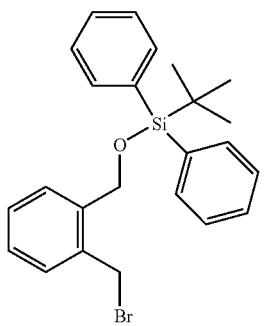

In dichloromethane (50 ml) were dissolved [2-[(t-butyldiphenylsilyloxy)methyl]phenyl]methanol (3.00 g, 7.97 mmol) and carbon tetrabromide (3.40 g, 10.3 mmol). Under ice cooling, a dichloromethane solution (5 ml) of triphenylphosphine (2.70 g, 10.3 mmol) was added dropwise. After stirring at room temperature for 14 hours, the reaction mixture was concentrated under reduced pressure. The residue thus obtained was subjected to silica gel chromatography.

The fraction obtained from the hexane:ethyl acetate=30:1 eluate was concentrated under reduced pressure, whereby the title compound (3.12 g, 7.10 mmol, 89%) was obtained as a colorless oil.

$^1$H-NMR (400 MHz, CDCl$_3$) δ: 1.05(9H,s), 4.51(2H,s), 4.88(2H,s), 7.20-7.51(10H,m), 7.68(4H,dd,J=7.6, 1.2 Hz).

IR (ATR) cm$^{-1}$: 2929, 2856, 1427, 1105, 1068, 822, 739, 698, 607, 501.

Example 280 t-Butyl [[2-[[(4-chlorophenyl)sulfonyl]methyl]benzyl]oxy]diphenylsilane

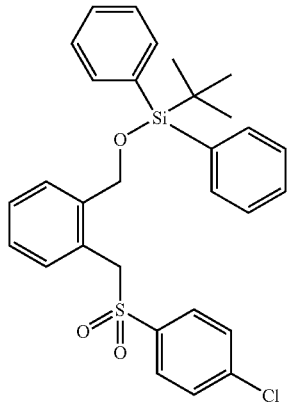

In propanol (20 ml) was dissolved (2-bromo methylbenzyloxy)-t-butyldiphenylsilane (3.10 g, 7.05 mmol), followed by the addition of sodium 4-chlorobenzenesulfinate (1.80 g, 9.06 mmol). At 90° C., the resulting mixture was stirred for 14 hours. After the reaction mixture was allowed to cool down, the residue obtained by concentrating the reaction mixture under reduced pressure was added with ethyl acetate. The resulting mixture was washed with water, and the organic layer was dried over anhydrous magnesium sulfate. After filtration, the filtrate was concentrated under reduced pressure, whereby the title compound (3.90 g, quant.) was obtained as a white solid.

$^1$H-NMR (400 MHz, CDCl$_3$) δ: 1.03(9H,s), 4.43(2H,s), 4.47(2H,s), 7.20-7.28(1H,m), 7.28-7.37(4H,m), 7.37-7.52 (9H,m), 7.60(4H,dd,J=7.8, 1.5 Hz).

MS m/z: 535 (M$^+$+H).

Example 281 t-Butyl [[2-[1-[(4-chlorophenyl)sulfonyl]-5-(methylsulfonyl)pentyl]benzyl]oxy]diphenylsilane

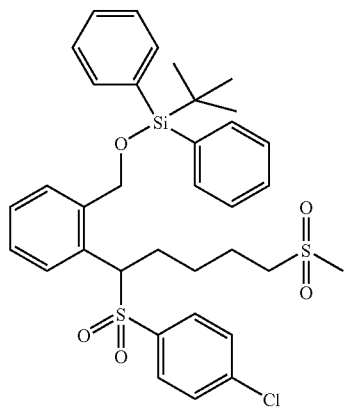

In toluene (5 ml) were dissolved t-butyl [[2-[[(4-chlorophenyl)sulfonyl]methyl]benzyl]oxy]diphenylsilane (350 mg, 0.654 mmol) and the 4-(methylsulfonyl)-1-butanol (200 mg, 1.31 mmol) obtained in Referential Example 3, followed by the addition of cyanomethylenetri-n-butylphosphorane (350 mg, 1.45 mmol). Under an argon atmosphere, the resulting mixture was heated under reflux for 14 hours. After the reaction mixture was allowed to cool down, cyanomethylenetri-n-butylphosphorane (300 mg, 1.24 mmol) was added thereto. Under an argon atmosphere, the resulting mixture was heated under reflux for 14 hours. The reaction mixture was then allowed to cool down. The residue obtained by concentrating the mixture under reduced pressure was subjected to flash silica gel chromatography, and the fraction obtained from the hexane:ethyl acetate=3:2 was concentrated under reduced pressure, whereby the title compound (175 mg, 0.261 mmol, 40%) was obtained as a pale yellowish brown oil.

$^1$H-NMR (400 MHz, CDCl$_3$) δ: 1.05(9H,s), 1.18-1.30(1H, m) 1.30-1.44(1H,m), 1.70-1.84(2H,m), 2.08-2.24(1H,m), 2.35-2.48(1H,m), 2.74-2.85(2H,m), 2.80(3H,s), 4.13(1H,d, J=12.7 Hz), 4.35(1H,d,J=12.7 Hz), 4.51(1H,dd,J=10.8, 4.4 Hz), 7.18-7.25(3H,m), 7.25-7.45(8H,m), 7.45-7.53(3H,m), 7.55-7.68(4H,m).

IR (ATR) cm$^{-1}$: 2929, 2856, 1583, 1473, 1321, 1147, 1105, 1088, 833, 775, 741, 702, 623, 569, 503.

MS m/z: 669 (M$^+$+H), 691 (M$^+$+Na).

Example 282

[2-[1-[(4-Chlorophenyl)sulfonyl]-5-(methylsulfonyl)pentyl]phenyl]methanol

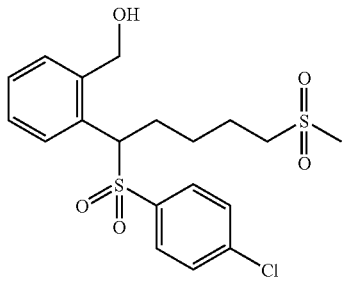

In tetrahydrofuran (5 ml) was dissolved t-butyl [[2-[1-[(4-chlorophenyl)sulfonyl]-5-(methylsulfonyl)pentyl]benzyl]oxy]diphenylsilane (175 mg, 0.261 mmol). Under ice cooling, a tetrahydrofuran solution (1.0M, 0.6 ml, 0.6 mmol) of tetrabutylammonium fluoride was added dropwise to the resulting solution. The resulting mixture was then stirred at room temperature for 1 hour. After addition of water (0.5 ml), the residue obtained by concentrating the resulting mixture under reduced pressure was subjected to flash silica gel chromatography. The fraction obtained from the dichloromethane:methanol=30:1 eluate was concentrated under reduced pressure, whereby the title compound (87 mg, 0.20 mmol, 61%) was obtained as a pale yellowish brown oil.

$^1$H-NMR (400 MHz, CDCl$_3$) δ: 1.20-1.60(2H,m), 1.65-1.95(2H,m), 2.10-2.40(3H,m), 2.70-3.00(2H,m), 2.82(3H,s), 4.43(2H,d,J=4.9 Hz), 4.81(1H,dd,J=11.1, 4.0 Hz), 7.15-7.30 (1H,m), 7.30-7.50(5H,m), 7.56(2H,d,J=8.6 Hz).

IR (ATR) cm$^{-1}$: 3506, 2931, 1579, 1475, 1394, 1277, 1138, 1084, 1012, 964, 829, 798, 756, 712, 629, 563, 519, 463.

MS m/z: 448 (M$^+$+NH$_4$), 453 (M$^+$+Na).

Example 283 t-Butyl [[6-[2-[(t-butyldiphenylsilyloxy) methyl]phenyl]-6-[(4-chlorophenyl)sulfonyl]hexyl]oxy]dimethylsilane

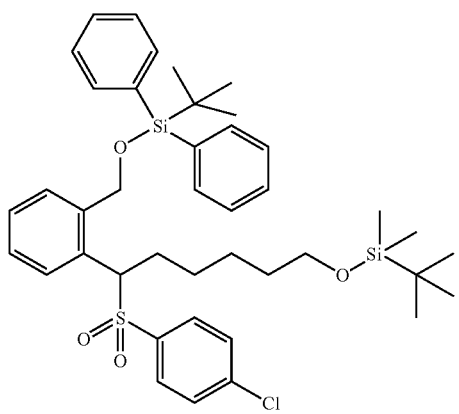

The t-butyl [[2-[[(4-chlorophenyl)sulfonyl]methyl]benzyl]oxy]diphenylsilane (1.00 g, 1.87 mmol) obtained in Example 280 and 5-(t-butyldiphenylsilyloxy)-1-pentanol (0.68 ml, 2.8 mmol) were dissolved in toluene (7 ml), followed by the addition of cyanomethylenetri-n-butylphosphorane (650 mg, 2.69 mmol). Under an argon atmosphere, the resulting mixture was heated under reflux for 14 hours. After the reaction mixture was allowed to cool down, 5-(t-butyldiphenylsilyloxy)-1-pentanol (0.34 ml, 1.4 mmol) and cyanomethylenetri-n-butylphosphorane (300 mg, 1.24 mmol) were added. Under an argon atmosphere, the resulting mixture was heated under reflux for 10 hours. The reaction mixture was then allowed to cool down. The residue obtained by concentrating the mixture under reduced pressure was subjected to flash silica gel chromatography, and the fraction obtained from the hexane:ethyl acetate=15:1 eluate was concentrated under reduced pressure, whereby the title compound (932 mg, 1.27 mmol, 68%) was obtained as a pale yellowish brown oil.

$^1$H-NMR (400 MHz, CDCl$_3$) δ: 0.00(6H,s), 0.80-1.60(6H, m), 0.86(9H,s), 1.04(9H,s), 2.04-2.20(1H,m), 2.28-2.40(1H, m), 3.48(2H,t,J=6.3 Hz), 4.10(1H,d,J=12.9 Hz), 4.35-4.48 (2H,m), 7.16-7.23(2H,m), 7.23-7.55(12H,m), 7.55-7.70(4H, m).

IR (ATR) cm$^{-1}$: 2929, 2856, 1583, 1473, 1321, 1147, 1103, 1088, 1014, 831, 775, 741, 700, 623, 567, 503.

MS m/z: 735 (M$^+$+H), 757 (M$^+$+Na).

Example 284

6-[2-(t-Butyldiphenylsilyloxy)methylphenyl]-6-[(4-chlorophenyl)sulfonyl]-1-hexanol

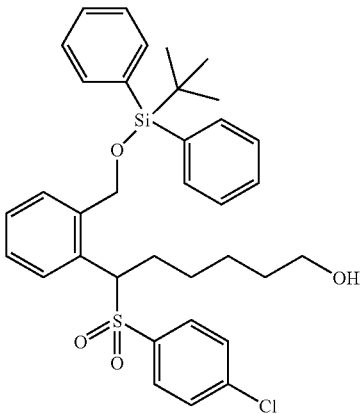

In methanol (30 ml) was dissolved t-butyl [[6-[2-[(t-butyldiphenylsilyloxy)methyl]phenyl]-6-[(4-chlorophenyl)sulfonyl]hexyl]oxy]dimethylsilane (830 mg, 1.13 mmol), followed by the addition of p-toluenesulfonic acid monohydrate (25 mg, 0.13 mmol). The resulting mixture was stirred at room temperature for 2 hours. Triethylamine (0.080 ml, 0.57 mmol) was added and then, the residue obtained by concentrating the resulting mixture under reduced pressure was subjected to flash silica gel chromatography. The fraction obtained from the dichloromethane:methanol=100:1 eluate was concentrated under reduced pressure, whereby the title compound (580 mg, 0.934 mmol, 83%) was obtained as a colorless oil.

$^1$H-NMR (400 MHz, CDCl$_3$) δ: 1.04(9H,s), 1.10-1.50(7H, m), 2.08-2.20(1H,m), 2.30-2.42(1H,m), 3.45-3.56(2H,m), 4.11(1H,d,J=12.7 Hz), 4.40(1H,d,J=12.7 Hz), 4.44(1H,dd, J=11.0, 4.2 Hz), 7.15-7.22(2H,m), 7.22-7.36(5H,m), 7.36-7.51(7H,m), 7.58(2H,dd,J=8.1, 1.5 Hz), 7.63(2H,dd,J=8.1, 1.5 Hz).

MS m/z: 621 (M$^+$+H), 638 (M$^+$+Na).

Example 285

6-[(4-Chlorophenyl)sulfonyl]-6-(2-hydroxy methylphenyl)-1-hexanol

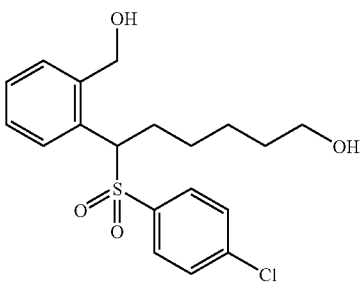

In tetrahydrofuran (5 ml) was dissolved 6-[2-(t-butyl-diphenylsilyloxy)methylphenyl]-6-[(4-chlorophenyl)sulfonyl]-1-hexanol (200 mg, 0.322 mmol), followed by the dropwise addition of a tetrahydrofuran solution (1.0M, 0.7 ml, 0.7 mmol) of tetrabutylammonium fluoride under ice cooling. The resulting mixture was stirred at room temperature for 1 hour. Water (0.2 ml) was then added. The residue obtained by concentrating the resulting mixture under reduced pressure was subjected to flash silica gel chromatography. The fraction obtained from the dichloromethane:methanol=30:1 eluate was concentrated under reduced pressure, whereby the title compound (86 mg, 0.23 mmol, 70%) was obtained as a colorless oil.

$^1$H-NMR (400 MHz, CDCl$_3$) δ: 1.10-1.60(7H,m), 2.08-2.30(2H,m), 2.37(1H,br s), 3.45-3.60(2H,m), 4.44-4.60(2H, m), 4.78(1H,dd,J=11.0, 4.2 Hz), 7.28-7.50(4H,m), 7.43(2H, d,J=8.8 Hz), 7.60(2H,d,J=8.8 Hz).

IR (ATR) cm$^{-1}$: 3367, 2935, 2862, 1579, 1475, 1392, 1308, 1277, 1142, 1082, 1012, 756, 631, 565, 461.

MS m/z: 735 (M$^+$+H), 757 (M$^+$+Na).

FAB-MS: 383.1098 (Calcd for C$_{19}$H$_{24}$ClO$_4$S: 383.1084).

Example 286

[2-[1-[(4-Chlorophenyl)sulfonyl]cyclohexyl]phenyl]methanol

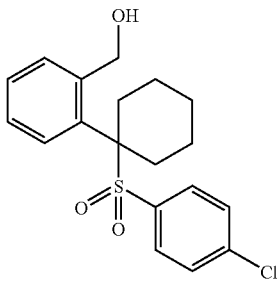

The 6-[2-(t-butyldiphenylsilyloxy)methylphenyl]-6-[(4-chlorophenyl)sulfonyl]-1-hexanol (447 mg, 0.719 mmol) obtained in Example 284 was dissolved in toluene (5 ml), followed by the addition of cyanomethylenetri-n-butylphosphorane (350 mg, 1.45 mmol). Under an argon atmosphere, the resulting mixture was heated under reflux for 14 hours. The reaction mixture was then allowed to cool down. The residue obtained by concentrating the mixture under reduced pressure was subjected to flash silica gel chromatography. The fraction obtained from the hexane:ethyl acetate=15:1 eluate was concentrated under reduced pressure to yield a colorless oil (190 mg).

The resulting colorless oil was dissolved in tetrahydrofuran (5 ml). Under ice cooling, a tetrahydrofuran solution (1.0M, 0.6 ml, 0.6 mmol) of tetrabutylammonium fluoride was added dropwise. At room temperature, the resulting mixture was stirred for 2 hours. Water (1.0 ml) was then added to the reaction mixture. The residue obtained by concentrating the reaction mixture under reduced pressure was subjected to flash silica gel chromatography. The fraction obtained from the hexane:ethyl acetate=4:1 eluate was concentrated under reduced pressure to give a white solid. The white solid was washed with hexane, whereby the title compound (40 mg, 0.11 mmol, 15%) was obtained as a white powder.

$^1$H-NMR (400 MHz, CDCl$_3$) δ: 1.15-1.45(3H,m), 1.45-1.80(2H,m), 1.80-1.98(1H,m), 2.00-2.25(2H,m), 2.40-2.60 (1H,m), 3.05-3.25(2H,m), 4.70-4.90(1H,m), 5.03-5.20(1H, m), 6.85(1H,dm,J=7.6 Hz), 7.09(1H,tm,J=7.7 Hz), 7.24-7.40 (5H,m), 7.62(1H,dd,J=7.7, 1.6 Hz).

IR (ATR) cm$^{-1}$: 3575, 2925, 1574, 1471, 1448, 1389, 1296, 1275, 113.6, 1082, 1011, 989, 835, 785, 706, 615, 577, 467.

mp: 148-150° C. (dec.).

MS m/z: 382 (M$^+$+NH$_4$).

Anal. Calcd for C$_{19}$H$_{21}$ClO$_3$S: C, 62.54; H, 5.80; Cl, 9.72; S, 8.79. Found: C, 62.54; H, 5.73; Cl, 9.70; S, 8.93.

Example 287

4-[[(4-Chlorophenyl)sulfonyl](2,5-difluorophenyl)methyl]tetrahydropyran

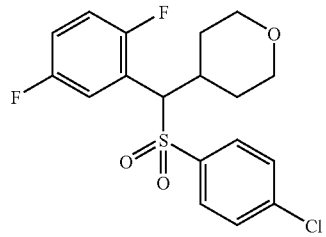

The 2-[(4-chlorophenyl)sulfonylmethyl]-1,4-difluorobenzene (200 mg, 0.661 mmol) obtained in Example 5 and tetrahydro-4H-pyran-4-ol (0.13 ml, 1.36 mmol) were dissolved in toluene (10 ml), followed by the addition of cyanomethylenetri-n-butylphosphorane (330 mg, 1.37 mmol). Under an argon atmosphere, the resulting mixture was heated under reflux for 14 hours. After the reaction mixture was allowed to cool down, cyanomethylenetri-n-butylphosphorane (200 mg, 0.829 mmol) was added thereto. Under an argon atmosphere, the mixture was heated under reflux for 14 hours. The reaction mixture was then allowed to cool down. The residue obtained by concentrating the mixture under reduced pressure was subjected to flash silica gel chromatography. The fraction obtained from the hexane:ethyl acetate=4:1 eluate was concentrated under reduced pressure to give a white solid. The white solid was washed with hexane, whereby the title compound (157 mg, 0.406 mmol, 61%) was obtained as a white powder.

$^1$H-NMR (400 MHz, CDCl$_3$) δ: 1.28-1.48(2H,m), 1.71 (1H,ddd,J=25.3,11.7,4.3 Hz), 2.37(1H,br d,J=12.7 Hz), 2.70-2.88(1H,m), 3.40(1H,td,J=11.7, 2.5 Hz), 3.50(1H,td,J=12.0, 2.2 Hz), 3.91(1H,dm,J=11.2 Hz), 4.02(1H,dm,J=11.7 Hz), 4.46(1H,d,J=8.8 Hz), 6.68-6.80(1H,m), 6.88-6.98(1H,m), 7.31(2H,d,J=8.5 Hz), 7.36-7.45(1H,m), 7.49(2H,d,J=8.5 Hz).

IR (ATR) cm$^{-1}$: 2952, 2833, 1576, 1495, 1308, 1275, 1236, 1144, 1082, 879, 829, 788, 752, 733, 710, 615, 602, 559, 519, 465, 447.

mp: 150-152° C.

MS m/z: 387 (M$^+$+H).

Anal. Calcd for C$_{18}$H$_{17}$ClF$_2$O$_3$S: C, 55.89; H, 4.43; Cl, 9.16; F, 9.82; S, 8.29. Found: C, 55.64; H, 4.27; Cl, 9.41; F, 9.89; S, 8.28.

Referential Example 44

Tetrahydrothiopyran-4-ol

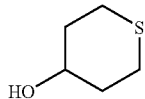

Tetrahydrothiopyran-4-one (5.00 g, 43.0 mmol) was dissolved in methanol (100 ml). Under ice cooling, sodium borohydride (1.6 g, 42.3 mmol) was added and the resulting mixture was stirred at room temperature for 14 hours. The residue obtained by concentrating the reaction mixture under reduced pressure was added with water (50 ml). The resulting mixture was made weakly acidic with 1N hydrochloric acid, and then it was extracted with diethyl ether. The extract was washed successively with 1N hydrochloric acid, a saturated aqueous solution of sodium bicarbonate, and brine. The organic layer was dried over anhydrous magnesium sulfate. After filtration, the filtrate was concentrated under reduced pressure, whereby the title compound (4.40 g, 37.2 mmol, 87%) was obtained as a pale yellowish brown solid.

$^1$H-NMR (400 MHz, CDCl$_3$) δ: 1.47(1H,br s), 1.64-1.80 (2H,m), 2.10-2.24(2H,m), 2.55-2.70(2H,m), 2.73-2.88(2H, m), 3.60-3.75(1H,m).

MS m/z: 119 (M$^+$+H).

Example 288

4-[[(4-Chlorophenyl)sulfonyl](2,5-difluorophenyl) methyl]tetrahydrothiopyran

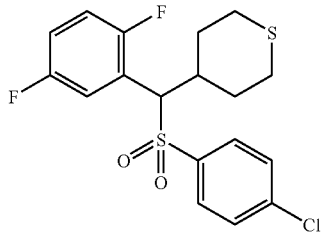

The 2-[(4-chlorophenyl)sulfonylmethyl]-1,4-difluorobenzene (500 mg, 1.65 mmol) obtained in Example 5 and tetrahydrothiopyran-4-ol (400 mg, 3.38 mmol) were dissolved in toluene (20 ml), followed by the addition of cyanomethylenetri-n-butylphosphorane (800 mg, 3.31 mmol). Under an argon atmosphere, the resulting mixture was heated under reflux for 14 hours. After the reaction mixture was allowed to cool down, cyanomethylenetri-n-butylphosphorane (400 mg, 1.66 mmol) was added. Under an argon atmosphere, the resulting mixture was heated under reflux for 14 hours. The reaction mixture was then allowed to cool down. The residue obtained by concentrating the reaction mixture under reduced pressure was subjected to flash silica gel chromatography, and the fraction obtained from the hexane:ethyl acetate=15:1 eluate was concentrated under reduced pressure to give a white solid. The white solid was washed with a hexane/diisopropyl ether mixture, whereby the title compound (404 mg, 1.00 mmol, 61%) was obtained as a white powder.

$^1$H-NMR (400 MHz, CDCl$_3$) δ: 1.47(1H,ddd,J=23.4,10.0, 3.3 Hz), 1.68(1H,ddd,J=25.0,11.4,3.3 Hz), 2.13(1H,dm, J=11.4 Hz), 2.50-2.78(5H,m), 2.82(1H,td,J=12.8,2.6 Hz), 4.47(1H,d,J=7.3 Hz), 6.72-6.82(1H,m), 6.90-7.00(1H,m), 7.31(2H,d,J=8.8 Hz), 7.40-7.60(1H,m), 7.49(2H,d,J=8.8 Hz).

IR (ATR) cm$^{-1}$: 2939, 2887, 1576, 1493, 1425, 1317, 1281, 1240, 1142, 1084, 1012, 866, 831, 781, 750, 731, 710, 631, 615, 548, 467.

mp: 150-152° C.

MS m/z: 403 (M$^+$+H).

Anal. Calcd for C$_{18}$H$_{17}$ClF$_2$O$_2$S$_2$: C, 53.66; H, 4.25; Cl, 8.80; F, 9.43; S, 15.92. Found: C, 53.52; H, 4.21; Cl, 9.00; F, 9.54; S, 15.88.

Example 289

4-[[(4-Chlorophenyl)sulfonyl](2,5-difluorophenyl) methyl]tetrahydrothiopyran-1,1-dioxide (Compound A) and 4-[[(4-chlorophenyl)sulfonyl](2,5-difluorophenyl)methyl]tetrahydrothiopyran-1-oxide (Compound B (Isomer A) and Compound B (Isomer B))

Compound A

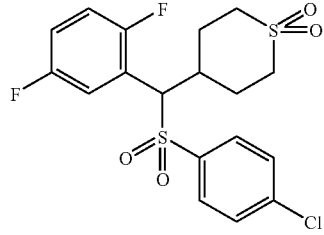

Compound B

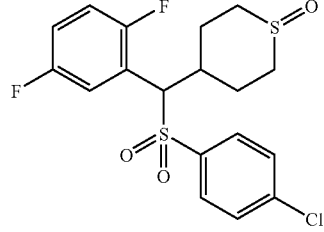

In dichloromethane (15 ml) was dissolved 4-[[(4-chlorophenyl)sulfonyl](2,5-difluorophenyl)methyl]tetrahydrothiopyran (360 mg, 0.893 mmol). Under ice cooling, 3-chloroperbenzoic acid (320 mg, 1.85 mmol) was added to the solution. The resulting mixture was stirred at room temperature for 14 hours. The residue obtained by concentrating the reaction mixture under reduced pressure was subjected to flash silica gel chromatography, and the fraction obtained from the hexane:ethyl acetate=1:1 eluate was concentrated under reduced pressure to give a white solid. The white solid was dissolved in dichloromethane. The resulting solution was washed successively with a 1N aqueous solution of sodium hydroxide and brine. The organic layer was dried over anhydrous magnesium sulfate. After filtration, the filtrate was concentrated under reduced pressure to give a white solid. The white solid was washed with diethyl ether, whereby the title compound A (187 mg, 0.430 mmol, 48%) was obtained as a white powder. The fraction obtained from the dichloromethane:methanol=50:1 eluate was concentrated under reduced pressure, whereby a mixture of the title compound B (Isomer A) and the title compound B (Isomer B) was obtained as a white solid. The resulting mixture was separated and purified by flash silica gel chromatography (dichloromethane:methanol=80:1). The white solids were each washed with diethyl ether, whereby obtained were the title compound B (Isomer A) (low polarity) (78 mg, 0.19 mmol, 21%) and the title compound B (Isomer B) (high polarity) (69 mg, 0.17 mmol, 19%), each as a white powder.

Compound A

¹H-NMR (400 MHz, CDCl₃) δ: 1.85-2.00(1H,m), 2.18-2.35(2H,m), 2.68-2.91(2H,m), 2.98-3.10(2H,m), 3.10-3.28 (2H,m), 4.54(1H,br d,J=7.1 Hz), 6.74-6.90(1H,m), 6.94-7.06 (1H,m), 7.33(2H,d,J=8.7 Hz), 7.35-7.55(1H,m)., 7.49(2H,d, J=8.7 Hz).

IR (ATR) cm⁻¹: 1576, 1493, 1290, 1146, 1120, 1080, 874, 829, 752, 735, 710, 631, 623, 592, 552, 530, 498, 471, 424.

mp: 245-248° C.

MS m/z: 435 (M⁺+H).

Anal. Calcd for $C_{18}H_{17}ClF_2O_4S_2$: C, 49.71; H, 3.94; Cl, 8.15; F, 8.74; S, 14.75. Found: C, 49.38; H, 3.87; Cl, 8.50; F, 8.86; S, 14.62.

Compound B (Isomer A)

¹H-NMR (400 MHz, CDCl₃) δ: 1.76(1H,br d,J=13.4 Hz), 2.18(1H,ddm,J=25.4, 12.5 Hz), 2.32-2.70(4H,m), 2.74-2.90 (1H,m), 2.98(1H,dm,J=14.0 Hz), 3.09(1H,dm,J=14.4 Hz), 4.53(1H,d,J=7.3 Hz), 6.72-6.86(1H,m), 6.90-7.02(1H,m), 7.32(2H,d,J=8.5 Hz), 7.40-7.60(1H,m), 7.49(2H,d,J=8.5 Hz).

IR (ATR) cm⁻¹: 1585, 1495, 1315, 1300, 1242, 1220, 1147, 1086, 1049, 997, 874, 831, 752, 733, 625, 596, 553, 525, 482.

mp: 255-256° C.

MS m/z: 419 (M⁺+H).

Anal. Calcd for $C_{18}H_{17}ClF_2O_3S_2$: C, 51.61; H, 4.09; Cl, 8.46; F, 9.07; S, 15.31. Found: C, 51.51; H, 4.04; Cl, 8.69; F, 9.15; S, 15.20.

Compound B (Isomer B)

¹H-NMR (400 MHz, CDCl₃) δ: 1.42(1H,ddm,J=22.3, 11.7 Hz), 1.92(1H,ddm,J=11.7, 11.0 Hz), 2.14-2.27(1H,m), 2.66 (1H,td,J=12.2, 2.7 Hz), 2.70-2.90(3H,m), 3.10-3.24(1H,m), 3.32-3.44(1H,m), 4.49(1H,d,J=8.1 Hz), 6.72-6.85(1H,m), 6.90-7.02(1H,m), 7.32(2H,d,J=8.5 Hz), 7.34-7.50(1H,m), 7.48(2H,d,J=8.5 Hz).

IR (ATR) cm⁻¹: 2912, 1574, 1496, 1298, 1246, 1144, 1080, 1001, 800, 752, 735, 714, 619, 561, 552, 517, 469.

mp: 184-187° C.

MS m/z: 419 (M⁺+H).

Anal. Calcd for $C_{18}H_{17}ClF_2O_3S_2$: C, 51.61; H, 4.09; Cl, 8.46; F, 9.07; S, 15.31. Found: C, 51.82; H, 4.23; Cl, 8.42; F, 9.12; S, 15.07.

Example 290 t-Butyl 4-[[(4-chlorophenyl)sulfonyl](2,5-difluorophenyl)methyl]-1-piperidinecarboxylate

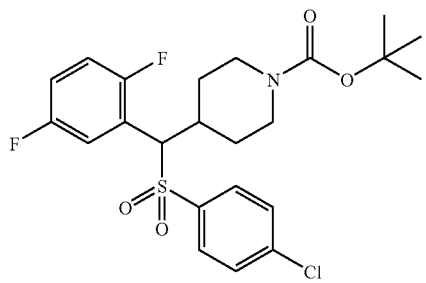

The 2-[(4-chlorophenyl)sulfonylmethyl]-1,4-difluorobenzene (1.25 g, 4.13 mmol) obtained in Example 5 and t-butyl 4-hydroxy-1-piperidinecarboxylate (1.70 g, 8.44 mmol) were dissolved in toluene (50 ml), followed by the addition of cyanomethylenetri-n-butylphosphorane (2.00 g, 8.29 mmol). Under an argon atmosphere, the resulting mixture was heated under reflux for 14 hours. The reaction mixture was allowed to cool down. The residue obtained by concentrating the reaction mixture under reduced pressure was subjected to flash silica gel chromatography. The fraction obtained from the hexane:ethyl acetate=1:1 eluate was concentrated under reduced pressure to give a white solid. The white solid was washed with diethyl ether, whereby the title compound (1.68 g, 3.46 mmol, 84%) was obtained as a white powder.

¹H-NMR (400 MHz, CDCl₃) δ: 1.10-1.25(1H,m), 1.40-1.70(2H,m), 1.44(9H,s), 2.30-2.50(1H,m), 2.60-2.95(3H,m), 4.00-4.25(2H,m), 4.45(1H,d,J=7.8 Hz), 6.69-6.80(1H,m), 6.88-6.98(1H,m), 7.31(2H,d,J=8.6 Hz), 7.35-7.50(1H,m), 7.49 (2H, d,J=8.6 Hz).

IR (ATR) cm⁻¹: 2979, 2935, 1682, 1583, 1493, 1421, 1319, 1281, 1240, 1165, 1122, 1078, 881, 835, 793, 752, 634, 534, 472.

mp: 193-196° C.

MS m/z: 486 (M⁺+H), 508 (M⁺+Na).

Anal. Calcd for $C_{23}H_{26}ClF_2NO_4S$: C, 56.84; H, 5.39; Cl, 7.30; F, 7.82; N, 2.88; S, 6.60. Found: C, 56.41; H, 5.43; Cl, 7.77; F, 7.61; N, 2.99; S, 6.58.

Example 291

4-[[(4-Chlorophenyl)sulfonyl](2,5-difluorophenyl)methyl]piperidine Hydrochloride

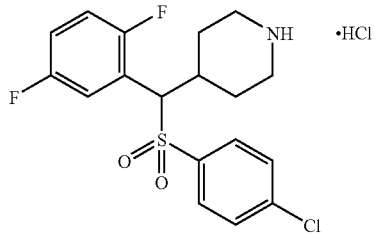

In dichloromethane (50 ml) was dissolved t-butyl 4-[[(4-chlorophenyl)sulfonyl](2,5-difluorophenyl)methyl]-1-piperidinecarboxylate (1.56 g, 3.21 mmol). Under ice cooling, trifluoroacetic acid (5.0 ml) was added dropwise to the resulting solution. After stirring at room temperature for 2 hours, the reaction mixture was concentrated under reduced pressure. Dichloromethane (10 ml) and a 1N ethanol solution (10 ml) of hydrochloric acid were added, followed by concentration under reduced pressure to give a white solid. The resulting solid was washed with diethyl ether, whereby the title compound (1.36 g, 3.12 mmol, 97%) was obtained as a white powder.

¹H-NMR (400 MHz, CD₃OD) δ: 1.38-1.52(1H,m), 1.70-1.92(2H,m), 2.73(1H,br d,J=14.2 Hz), 2.86-3.00(1H,m), 3.05(1H,td,J=12.9, 3.1 Hz), 3.13(1H,td,J=13.1, 3.1 Hz), 3.30-3.40(1H,m), 3.48(1H,dm,J=13.0 Hz), 4.72(1H,d,J=8.6 Hz), 6.82-6.98(1H,m), 7.04-7.12(1H,m), 7.40-7.55(1H,m), 7.44(2H,d,J=8.6 Hz), 7.57(2H,d,J=8.6 Hz).

IR (ATR) cm⁻¹: 2950, 2719, 1583, 1491, 1317, 1146, 1084, 831, 752, 617, 596, 552, 470.

mp: 184-190° C.

MS m/z: 386 (M⁺+H).

Example 292

2-[1-[(4-Chlorophenyl)sulfonyl]-2-methylpentyl]-1,4-difluorobenzene (Isomer 292-A and Isomer 292-B)

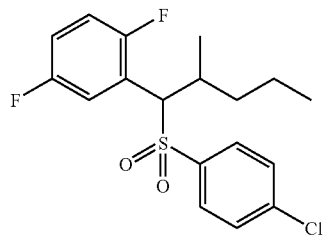

The 2-[(4-chlorophenyl)sulfonylmethyl]-1,4-difluorobenzene (200 mg, 0.661 mmol) obtained in Example 5 and 2-pentanol (0.144 ml, 1.33 mmol) were dissolved in toluene (3 ml), followed by the addition of cyanomethylenetri-n-butylphosphorane (0.320 ml). Under an argon atmosphere, the resulting mixture was heated under reflux for 14 hours. The reaction mixture was then allowed to cool down. The residue obtained by concentrating the reaction mixture under reduced pressure was separated and purified by flash silica gel chromatography (hexane:ethyl acetate=50:1), whereby obtained were the title Isomer 292-A (low polarity) (67 mg, 0.18 mmol, 27%) as a white powder and the title Isomer 292-B (high polarity) (45 mg, 0.12 mmol, 19%) as a white solid.

Isomer 292-A $^1$H-NMR (400 MHz, CDCl$_3$) δ: 0.91(3H,t,J=7.1 Hz), 1.08 (3H,d,J=6.9 Hz), 1.20-1.52(3H,m), 1.52-1.68(1H,m), 2.72-2.90(1H,m), 4.51(1H,d,J=5.9 Hz), 6.73-6.85(1H,m), 6.88-6.99(1H,m), 7.32(2H,d,J=8.6 Hz), 7.46-7.60(1H,m), 7.52 (2H, d,J=8.6 Hz).

IR (ATR) cm$^{-1}$: 2970, 2866, 1583, 1496, 1475, 1394, 1303, 1277, 1234, 1176, 1140, 1078, 1014, 883, 831, 790, 752, 727, 708, 621, 598, 561, 534, 472.

mp: 85-87° C.

MS m/z: 373 (M$^+$+H), 395 (M$^+$+Na).

Anal. Calcd for C$_{18}$H$_{19}$ClF$_2$O$_2$S: C, 57.89; H, 5.14; Cl, 9.51; F, 10.19; S, 8.61. Found: C, 57.96; H, 5.14; Cl, 9.44; F, 10.19; S, 8.75.

Isomer 292-B $^1$H-NMR (400 MHz, CDCl$_3$) δ: 0.81(3H,t,J=7.2 Hz), 1.00-1.12(1H,m), 1.15-1.45(3H,m), 1.34(3H,d,J=6.6 Hz), 2.60-2.72(1H,m), 4.43(1H,d,J=8.8 Hz), 6.67-6.78(1H,m), 6.88-6.95(1H,m), 7.29(2H,d,J=8.6 Hz), 7.36-7.45(1H,m), 7.48 (2H,d,J=8.6 Hz).

IR (ATR) cm$^{-1}$: 2976, 2933, 1585, 1495, 1394, 1323, 1238, 1178, 1149, 1086, 1014, 868, 829, 783, 754, 729, 710, 625, 559, 528, 472.

mp: 47-50° C.

MS m/z: 373 (M$^+$+H), 395 (M$^+$+Na).

Anal. Calcd for C$_{18}$H$_{19}$ClF$_2$O$_2$S: C, 57.89; H, 5.14; Cl, 9.51; F, 10.19; S, 8.61. Found: C, 57.97; H, 5.11; Cl, 9.45; F, 10.21; S, 8.69.

Anal. Calcd for C$_{18}$H$_{18}$ClF$_2$NO$_2$S.HCl.0.75H$_2$O: C, 49.61; H, 4.74; Cl, 16.27; F, 8.72; N, 3.21; S, 7.36. Found: C, 49.57; H, 4.75; Cl, 15.79; F, 9.16; N, 3.34; S, 7.25.

Example 293

2-[1-[(4-Chlorophenyl)sulfonyl]-2-ethylpentyl]-1,4-difluorobenzene (Isomer 293-A and Isomer Mixture)

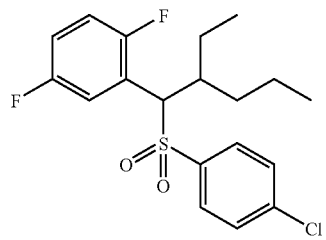

The 2-[(4-chlorophenyl)sulfonylmethyl]-1,4-difluorobenzene (200 mg, 0.661 mmol) obtained in Example 5 and 3-hexanol (0.150 ml, 1.35 mmol) were dissolved in toluene (3 ml), followed by the addition of cyanomethylenetri-n-butylphosphorane (0.320 ml). Under an argon atmosphere, the resulting mixture was heated under reflux for 14 hours. The reaction mixture was then allowed to cool down. The residue obtained by concentrating the reaction mixture under reduced pressure was separated and purified by flash silica gel chromatography (hexane:ethyl acetate=200:1), whereby obtained were the title Isomer 293-A (low polarity) (37 mg, 0.096 mmol, 15%) and the title Isomer mixture (44 mg, 0.11 mmol, 17%), each as a white powder.

Isomer 293-A $^1$H-NMR (400 MHz, CDCl$_3$) δ: 0.84(3H,t,J=7.5 Hz), 0.95 (3H,t,J=7.3 Hz), 1.00-1.16(1H,m), 1.30-1.50(2H,m), 1.55-1.90(3H,m), 2.50-2.63(1H,m), 4.59(1H,d,J=7.6 Hz), 6.69-6.80(1H,m), 6.88-6.95(1H,m), 7.31(2H,d,J=8.4 Hz), 7.40-7.50(1H,m), 7.50(2H,d,J=8.4 Hz).

IR (ATR) cm$^{-1}$: 2966, 1583, 1496, 1475, 1306, 1277, 1242, 1176, 1140, 1086, 881, 831, 802, 752, 725, 710, 621, 561, 538, 478, 462, 451.

mp: 85-89° C.

MS m/z: 387 (M$^+$+H), 409 (M$^+$+Na).

Anal. Calcd for C$_{19}$H$_{21}$ClF$_2$O$_2$S: C, 58.98; H, 5.47; Cl, 9.16; F, 9.82; S, 8.29. Found: C, 59.18; H, 5.65; Cl, 9.16; F, 9.83; S, 8.38.

Isomer Mixture $^1$H-NMR (400 MHz, CDCl$_3$) δ: 0.84(3H,t,J=7.5 Hz), 0.90-1.00(3H,m), 1.00-1.16(1H,m), 1.20-1.50(2H,m), 1.55-1.90 (3H,m), 2.50-2.63(1H,m), 4.55-4.65(1H,m), 6.69-6.80(1H, m), 6.88-6.95(1H,m), 7.31(2H,d,J=8.4 Hz), 7.40-7.50(1H, m), 7.50(2H,d,J=8.4 Hz).

IR (ATR) cm$^{-1}$: 2956, 1583, 1572, 1495, 1479, 1319, 1298, 1279, 1230, 1142, 1090, 1016, 887, 812, 752, 715, 660, 615, 563, 534, 469.

mp: 95-99° C.

MS m/z: 387 (M$^+$+H), 409 (M$^+$+Na).

Anal. Calcd for C$_{19}$H$_{21}$ClF$_2$O$_2$S: C, 58.98; H, 5.47; Cl, 9.16; F, 9.82; S, 8.29. Found: C, 58.99; H, 5.37; Cl, 9.19; F, 9.88; S, 8.43.

Example 294

2-[2-[(4-Chlorophenyl)sulfonyl]-2-(2,5-difluorophenyl)ethyl]tetrahydrofuran (Isomer 294-A and Isomer 294-B)

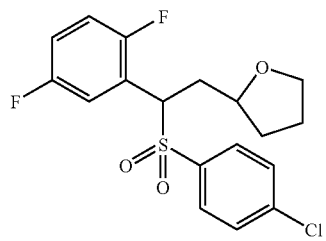

The 2-[(4-chlorophenyl)sulfonylmethyl]-1,4-difluorobenzene (200 mg, 0.661 mmol) obtained in Example 5 and tetrahydrofurfuryl alcohol (0.13 ml, 1.34 mmol) were dissolved in toluene (3 ml), followed by the addition of cyanomethylenetri-n-butylphosphorane (0.320 ml). Under an argon atmosphere, the resulting mixture was heated under reflux for 14 hours. The reaction mixture was then allowed to cool down. The residue obtained by concentrating the reaction mixture under reduced pressure was separated and purified by flash silica gel chromatography (using a hexane/ethyl acetate mixed solvent) to give a white solid. The white solid was washed with hexane, whereby obtained were the title Isomer 294-A (low polarity) (102 mg, 0.264 mmol, 40%) and the title Isomer 294-B (high polarity) (39 mg, 0.10 mmol, 15%), each as a white powder.

Isomer 294-A $^1$H-NMR (400 MHz, CDCl$_3$) δ: 1.50-1.65(1H,m), 1.75-2.05(3H,m), 2.26(1H,tm,J=12.9 Hz), 2.48(1H,tm,J=10.4 Hz), 3.50-3.60(1H,m), 3.60-3.70(1H,m), 3.76-3.88(1H,m), 4.86(1H,dm,J=12.2 Hz), 6.78-6.90(1H,m), 6.92-7.01(1H,m), 7.20-7.30(1H,m), 7.38(2H,d,J=8.6 Hz), 7.54(2H,d,J=8.6 Hz).

IR (ATR) cm$^{-1}$: 2960, 2852, 1576, 1.493, 1309, 1281, 1194, 1132, 1084, 1065, 1012, 903, 831, 810, 775, 746, 727, 708, 596, 575, 536, 471, 436.

mp: 99-105° C.

MS m/z: 387 (M$^+$+H).

Anal. Calcd for C$_{18}$H$_{17}$ClF$_2$O$_3$S: C, 55.89; H, 4.43; Cl, 9.16; F, 9.82; S, 8.29. Found: C, 56.28; H, 4.80; Cl, 8.94; F, 9.63; S, 8.19.

Isomer 294-B $^1$H-NMR (400 MHz, CDCl$_3$) δ: 1.42-1.58(1H,m), 1.76-1.04(3H,m), 2.22-2.33(1H,m), 2.58-2.70(1H,m), 3.60-3.70(1H,m), 3.70-3.80(1H,m), 3.88-3.99(1H,m), 4.64-4.73(1H,m), 6.75-6.88(1H,m), 6.92-7.01(1H,m), 7.20-7.30(1H,m), 7.38(2H,d,J=8.7 Hz), 7.52(2H,d,J=8.7 Hz).

IR (ATR) cm$^{-1}$: 2976, 1585, 1496, 1311, 1277, 1221, 1153, 1088, 1061, 922, 879, 829, 779, 752, 712, 629, 607, 561, 532, 472.

mp: 98-105° C.

MS m/z: 387 (M$^+$+H).

Anal. Calcd for C$_{18}$H$_{17}$ClF$_2$O$_3$S: C, 55.89; H, 4.43; Cl, 9.16; F, 9.82; S, 8.29. Found: C, 55.88; H, 4.54; Cl, 9.22; F, 9.96; S, 8.42.

Example 295

2-[2-[(4-Chlorophenyl)sulfonyl]-2-(2,5-difluorophenyl)ethyl]thiophene

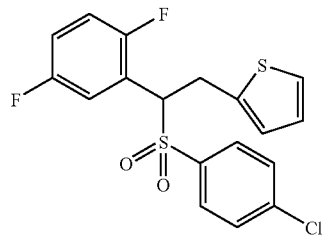

The 2-[(4-chlorophenyl)sulfonylmethyl]-1,4-difluorobenzene(100 mg, 0.330 mmol) obtained in Example 5 and 2-thiophenemethanol (0.065 ml, 0.69 mmol) were dissolved in toluene (3 ml), followed by the addition of cyanomethylenetri-n-butylphosphorane (0.160 ml). Under an argon atmosphere, the resulting mixture was heated under reflux for 14 hours. The reaction mixture was then allowed to cool down. The residue obtained by concentrating the reaction mixture under reduced pressure was purified by flash silica gel chromatography (using a hexane/ethyl acetate solvent mixture) to give a white solid. The resulting white solid was washed with hexane, whereby the title compound (92 mg, 0.23 mmol, 70%) was obtained as a white solid.

$^1$H-NMR (400 MHz, CDCl$_3$) δ: 3.60(1H,dd,J=15.1, 11.9 Hz), 4.02(1H,dm,J=15.1 Hz), 4.80(1H,dd,J=11.9, 2.5 Hz), 6.69(1H,dd,J=3.5, 1.1 Hz), 6.70-6.84(2H,m), 6.92-7.00(1H,m), 7.04(1H,dd,J=5.3, 1.1 Hz), 7.32-7.44(1H,m), 7.39(2H,d,J=8.8 Hz), 7.57(2H,d,J=8.8 Hz).

IR (ATR) cm$^{-1}$: 1496, 1319, 1244, 1219, 1149, 1084, 1014, 881, 825, 775, 758, 694, 629, 532, 467.

mp: 127-130° C.

MS m/z: 399 (M$^+$+H).

Anal. Calcd for C$_{18}$H$_{13}$ClF$_2$O$_2$S$_2$: C, 54.20; H, 3.29; Cl, 8.89; F, 9.53; S, 16.08. Found: C, 54.19; H, 3.31; Cl, 9.20; F, 9.51; S, 16.24.

Example 296

2-[2-[(4-Chlorophenyl)sulfonyl]-2-(2,5-difluorophenyl)ethyl]furan

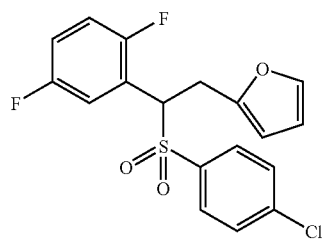

In a similar manner to Example 295 except for the use of the 2-[(4-chlorophenyl)sulfonylmethyl]-1,4-difluorobenzene (100 mg, 0.330 mmol) obtained in Example 5 and furfuryl alcohol (0.060 ml, 0.69 mmol), the title compound (26 mg, 0.068 mmol, 21%) was obtained as a white powder.

¹H-NMR (400 MHz, CDCl₃) δ: 3.43(1H,dd,J=15.4,11.6 Hz), 3.78(1H,dd,J=15.4, 3.7 Hz), 4.93(1H,dd,J=11.6,3.7 Hz), 5.89-5.91(1H,m), 6.14(1H,dd,J=3.2, 1.7 Hz), 6.73-6.82 (1H,m), 6.90-6.99(1H,m), 7.19(1H,dd,J=1.7, 0.7 Hz), 7.25-7.34(1H,m), 7.40(2H,d,J=8.8 Hz), 7.58(2H,d,J=8.8 Hz).

IR (ATR) cm⁻¹: 1585, 1495, 1319, 1151, 1086, 1014, 926, 831, 762, 613, 594, 573, 552, 532, 472.

mp: 90-93° C.

MS m/z: 383 (M⁺+H).

Anal. Calcd for C₁₈H₁₃ClF₂O₃S: C, 56.48; H, 3.42; Cl, 9.26; F, 9.93; S, 8.38. Found: C, 56.53; H, 3.39; Cl, 9.17; F, 9.92; S, 8.55.

Example 297

1-[3-[(4-Chlorophenyl)sulfonyl]-3-(2,5-difluorophenyl)propyl]-1H-pyrrole

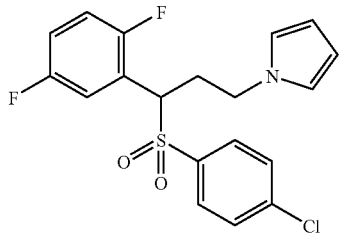

In a similar manner to Example 295 except for the use of the 2-[(4-chlorophenyl)sulfonylmethyl]-1,4-difluorobenzene (100 mg, 0.330 mmol) obtained in Example 5 and 1-(2-hydroxyethyl)pyrrole (0.070 ml, 0.67 mmol), the title compound (46 mg, 0.12 mmol, 35%) was obtained as a white powder.

¹H-NMR (400 MHz, CDCl₃) δ: 2.42-2.57(1H,m), 2.88-3.00(1H,m), 3.79(1H,ddd,J=14.3,8.5,5.9 Hz), 4.06(1H,dtm, J=14.3, 7.1 Hz), 4.34(1H,dd,J=10.0,3.9 Hz), 6.11(2H,t,J=2.2 Hz), 6.49(2H,t,J=2.2 Hz), 6.80-6.88(1H,m), 6.98-7.06(1H, m), 7.18-7.24(1H,m), 7.36(2H,d,J=8.8 Hz), 7.47(2H,d,J=8.8 Hz).

IR (ATR) cm⁻¹: 1576, 1493, 1325, 1306, 1271, 1236, 1176, 1146, 1082, 877, 827, 764, 737, 714, 677, 621, 588, 553, 519, 463, 428.

mp: 108-113° C.

MS m/z: 396 (M⁺+H).

Anal. Calcd for C₁₉H₁₆ClF₂NO₂S: C, 57.65; H, 4.07; Cl, 8.96; F, 9.60; N, 3.54; S, 8.10. Found: C, 57.82; H, 4.05; Cl, 9.05; F, 9.69; N, 3.69; S, 8.23.

Example 298

4-[3-[(4-Chlorophenyl)sulfonyl]-3-(2,5-difluorophenyl)propyl]morpholine

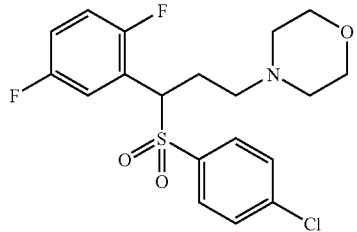

In a similar manner to Example 295 except for the use of the 2-[(4-chlorophenyl)sulfonylmethyl]-1,4-difluorobenzene (100 mg, 0.330 mmol) obtained in Example 5 and 4-(2-hydroxyethyl)morpholine (0.080 ml, 0.66 mmol), the title compound (89 mg, 0.21 mmol, 65%) was obtained as a white powder.

¹H-NMR (400 MHz, CDCl₃) δ: 2.08-2.28(4H,m), 2.30-2.48(3H,m), 2.62-2.77(1H,m), 3.61(4H,t,J=4.6 Hz), 4.80 (1H,dm,J=9.8 Hz), 6.78-6.87(1H,m), 6.94-7.03(1H,m), 7.21-7.30(1H,m), 7.39(2H,d,J=8.7 Hz), 7.54(2H,d,J=8.7 Hz).

IR (ATR) cm⁻¹: 2827, 2792, 1585, 1495, 1477, 1313, 1279, 1238, 1151, 1117, 1084, 1014, 868, 839, 752, 636, 559, 536, 468.

mp: 149-151° C.

MS m/z: 416 (M⁺+H).

FAB-MS: 416.0903 (Calcd for C₁₉H₂₁ClF₂O₃S: 416.0899).

Example 299

2-[1-(4-Chlorophenylsulfonyl)-2-phenylpropyl]-1,4-difluorobenzene (Isomer 299-A and Isomer 299-B)

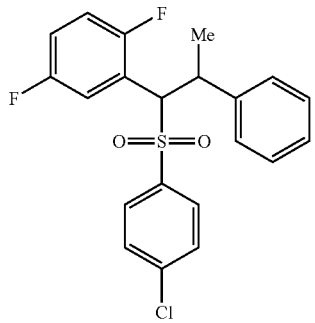

Under an argon atmosphere, the 2-[(4-chlorophenyl)sulfonylmethyl]-1,4-difluorobenzene (100 mg, 0.330 mmol) obtained in Example 5, and DL-1-phenylethyl alcohol (79.9 μl, 0.661 mmol) were dissolved in toluene (3 ml), followed by the addition of cyanomethylenetri-n-butylphosphorane (159 μl, 0.661 mmol). The resulting mixture was heated under reflux for 13 hours under an argon atmosphere. The reaction mixture was then concentrated. The residue thus obtained was separated and purified by flash chromatography on a silica gel column (hexane:ethyl acetate=85:15). The solids thus obtained were each washed with hexane, whereby obtained were the title Isomer 299-A (low-polarity compound) (53 mg, 0.130 mmol, 40%) as a white powder and the title Isomer 299-B (high-polarity compound) (20 mg, 0.0492 mmol, 15%) as colorless columnar crystals.

Isomer 299-A

¹H-NMR (400 MHz, CDCl₃) δ: 1.80(3H,d,J=6.6 Hz), 3.83-3.94(1H,m), 4.81-4.92(1H,m), 6.40-6.51(1H,m), 6.63-6.72(1H,m), 7.02-7.26(6H,m), 7.28(2H,d,J=8.6 Hz), 7.50 (2H,d,J=8.6 Hz).

IR (ATR) cm⁻¹: 3087, 2931, 1575, 1492, 1452, 1427, 1394, 1315, 1282, 1243, 1195, 1174, 1137, 1089, 1012.

mp: 160-161° C.

MS m/z: 407 (M⁺+H).

Anal. calcd for C₂₁H₁₇ClF₂O₂S: C, 61.99; H, 4.21; Cl, 8.71; F, 9.34; S, 7.88. Found: C, 61.77; H, 4.23; Cl, 8.83; F, 9.24; S, 7.98.

Isomer 299-B

¹H-NMR (400 MHz, CDCl₃) δ: 1.25(3H,d,J=7.1 Hz), 3.87 (1H,q, J=7.3 Hz), 4.89(1H,d,J=8.1 Hz), 6.89(1H,td,J=8.9, 4.6 Hz), 6.99-7.05(1H,m), 7.11-7.23(6H,m), 7.20(2H,d,J=8.8 Hz), 7.36(2H,d,J=8.8 Hz).

IR (ATR) cm⁻¹: 3062, 2929, 1583, 1496, 1475, 1454, 1394, 1321, 1276, 1243, 1176, 1143, 1085, 1012.

mp: 145-146° C.

MS m/z: 407 (M⁺+H).

FAB-MS: 407.0690 (Calcd for $C_{21}H_{18}ClF_2O_2S$: 407.0684).

Example 300

2-[1-(4-Chlorophenylsulfonyl)-2-methyl-3-phenyl-propyl]-1,4-difluorobenzene (Isomer 300-A and Isomer 300-B)

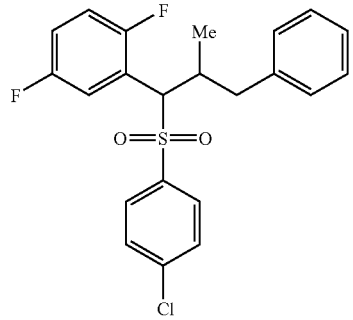

In a similar manner to Example 299 except for the use of 2-[(4-chlorophenyl)sulfonylmethyl]-1,4-difluorobenzene (200 mg, 0.660 mmol) obtained in Example 5, DL-1-phenyl-2-propanol (182 μl, 1.32 mmol), and cyanomethylenetri-n-butylphosphorane (318 μl, 1.32 mmol), the title Isomer 300-A (low-polarity compound) (32 mg, 0.0760 mmol, 12%) and the title Isomer 300-B (high-polarity compound) (25 mg, 0.0594 mmol, 9%) were obtained, each as a white powder.

Isomer 300-A

¹H-NMR (400 MHz, CDCl₃) δ: 1.01(3H,d,J=6.9 Hz), 2.46 (1H,dd,J=13.3, 8.6 Hz), 2.10-3.13(2H,m), 4.56(1H,dd,J=8.9, 4.6 Hz), 6.82(1H,td,J=8.9, 4.6 Hz), 6.94-6.99(1H,m), 7.14-7.28(6H,m), 7.32(2H,d,J=8.6 Hz), 7.50(2H,d,J=8.6 Hz).

IR (ATR) cm⁻¹: 3079, 2977, 1583, 1492, 1452, 1423, 1394, 1321, 1278, 1232, 1172, 1147, 1085, 1012.

mp: 81-83° C.

MS m/z: 421 (M⁺+H).

Anal. calcd for $C_{22}H_{19}ClF_2O_2S$: C, 62.78; H, 4.55; Cl, 8.42; F, 9.03; S, 7.62. Found: C, 62.72; H, 4.59; Cl, 8.53; F, 9.21; S, 7.82.

Isomer 300-B

¹H-NMR (400 MHz, CDCl₃) δ: 1.24(3H,d,J=6.6 Hz), 2.22 (1H,dd,J=13.1, 10.4 Hz), 2.90-2.98(2H,m), 4.51(1H,d,J=7.8 Hz), 6.77(1H,td,J=9.1, 4.4 Hz), 6.92-6.97(1H,m), 7.06-7.28 (6H,m), 7.32(2H,d,J=8.6 Hz), 7.52 (2H,d,J=8.6 Hz).

IR (ATR) cm⁻¹: 2962, 1585, 1492, 1454, 1425, 1384, 1309, 1278, 1240, 1143, 1093.

mp: 116-117° C.

MS m/z: 421 (M⁺+H).

Anal. calcd for $C_{22}H_{19}ClF_2O_2S$: C, 62.78; H, 4.55; Cl, 8.42; F, 9.03; S, 7.62. Found: C, 62.74; H, 4.70; Cl, 8.55; F, 9.23; S, 7.77.

Example 301

2-[1-(4-Chlorophenylsulfonyl)-3-phenylbutyl]-1,4-difluorobenzene (Isomer 301-A and Isomer 301-B)

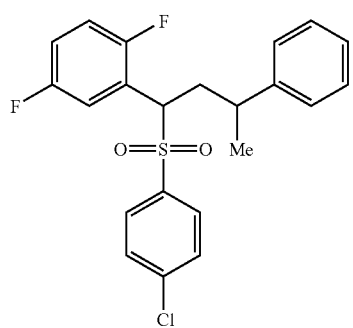

In a similar manner to Example 299 except for the use of 2-[(4-chlorophenyl)sulfonylmethyl]-1,4-difluorobenzene (200 mg, 0.660 mmol) obtained in Example 5, DL-2-phenyl-1-propanol (180 μl, 1.32 mmol), and cyanomethylenetri-n-butylphosphorane (318 μl, 1.32 mmol), the title Isomer 301-A (low-polarity compound) (51 mg, 0.121 mmol, 18%) and the title Isomer 301-B (high-polarity compound) (84 mg, 0.200 mmol, 30%) were obtained, each as a white powder.

Isomer 301-A

¹H-NMR (400 MHz, CDCl₃) δ: 1.24(3H,d,J=6.4 Hz), 2.31-2.40(1H,m), 2.62-2.73(2H,m), 4.59-4.67(1H,m), 6.74 (1H,td,J=9.1, 4.5 Hz), 6.89-6.95(1H,m), 7.06-7.25(6H,m), 7.35(2H,d,J=8.6 Hz), 7.48(2H,d,J=8.6 Hz).

IR (ATR) cm⁻¹: 3085, 2964, 1581, 1490, 1427, 1394, 1309, 1276, 1228, 1174, 1143, 1083, 1010.

mp: 89-90° C.

MS m/z: 421 (M⁺+H).

Anal. calcd for $C_{22}H_{19}ClF_2O_2S$: C, 62.78; H, 4.55; Cl, 8.42; F, 9.03; S, 7.62. Found: C, 62.56; H, 4.59; Cl, 8.53; F, 9.28; S, 7.80.

Isomer 301-B

¹H-NMR (400 MHz, CDCl₃) δ: 1.28(3H,d,J=6.6 Hz), 2.37-2.64(3H,m), 4.13(1H,d,J=12.0 Hz), 6.81(1H,td,J=8.9, 4.4 Hz), 6.91(2H,d,J=6.6 Hz), 6.97-7.03(1H,m), 7.19-7.27 (4H,m), 7.32(2H,d,J=8.6 Hz), 7.41(2H,d,J=8.6 Hz).

IR (ATR) cm⁻¹: 3070, 2960, 1583, 1490, 1455, 1427, 1392, 1319, 1309, 1276, 1224, 1143, 1087, 1012.

mp: 127-129° C.

MS m/z: 421 (M⁺+H).

Anal. calcd for $C_{22}H_{19}ClF_2O_2S$: C, 62.78; H, 4.55; Cl, 8.42; F, 9.03; S, 7.62. Found: C, 62.52; H, 4.53; Cl, 8.51; F, 9.31; S, 7.81.

Example 302

2-[1-(4-Chlorophenylsulfonyl)-2-methyl-4-phenyl-butyl]-1,4-difluorobenzene (Isomer 302-A and Isomer 302-B)

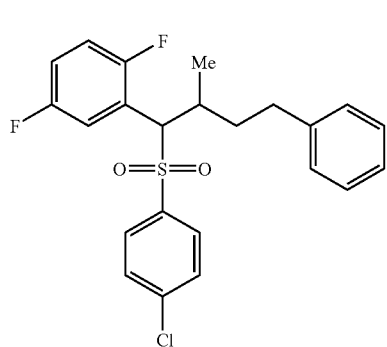

In a similar manner to Example 299 except for the use of DL-4-phenyl-2-butanol (101 μl, 0.661 mmol), the title Isomer 302-A (low-polarity compound) (30 mg, 0.0690 mmol, 21%) and the title Isomer 302-B (high-polarity compound) (33 mg, 0.0759 mmol, 23%) were obtained, each as a white powder.

Isomer 302-A $^1$H-NMR (400 MHz, CDCl$_3$) δ: 1.21(3H,d,J=7.1 Hz), 1.38-1.58(2H,m), 1.99-2.09(1H,m), 2.24-2.33(1H,m), 2.61-2.71(1H,m), 4.41(1H,dd,J=11.5, 3.0 Hz), 6.83(1H,td,J=9.1, 4.5 Hz), 6.94-7.00(1H,m), 7.03-7.28(6H,m), 7.35(2H,d, J=8.8 Hz), 7.47(2H,d,J=8.8 Hz).

IR (ATR) cm$^{-1}$: 2933, 2867, 1583, 1494, 1475, 1461, 1427, 1394, 1344, 1315, 1278, 1228, 1141, 1085, 1012.

mp: 133-135° C.

MS m/z: 435 (M$^+$+H).

FAB-MS: 435.1101 (Calcd for C$_{23}$H$_{22}$ClF$_2$O$_2$S: 435.0997).

Anal. calcd for C$_{23}$H$_{21}$ClF$_2$O$_2$S: C, 63.52; H, 4.87; Cl, 8.15; F, 8.74; S, 7.37. Found: C, 63.98; H, 4.88; Cl, 8.14; F, 8.82; S, 7.58.

Isomer 302-B $^1$H-NMR (400 MHz, CDCl$_3$) δ: 1.19(3H,d,J=6.8 Hz), 1.38-1.59(2H,m), 1.83-1.93(1H,m), 2.26-2.35(1H,m), 2.61-2.68(1H,m), 4.47(1H,dd,J=11.2, 3.2 Hz), 6.84(1H,td,J=8.9, 4.6 Hz), 6.95-7.28(7H,m), 7.35(2H,d,J=8.5 Hz), 7.48(2H,d, J=8.5 Hz).

IR (ATR) cm$^{-1}$: 3082, 2965, 2931, 2869, 1583, 1494, 1475, 1425, 1394, 1315, 1278, 1224, 1182, 1151, 1081, 1012.

mp: 112-114° C.

MS m/z: 435 (M$^+$+H).

Anal. calcd for C$_{23}$H$_{21}$ClF$_2$O$_2$S: C, 63.52; H, 4.87; Cl, 8.15; F, 8.74; S, 7.37. Found: C, 63.34; H, 4.85; Cl, 8.41; F, 8.75; S, 7.53.

Example 303

2-[1-(4-chlorophenylsulfonyl)-4-phenylpentyl]-1,4-difluorobenzene (Isomer 303-A and Isomer 303-B)

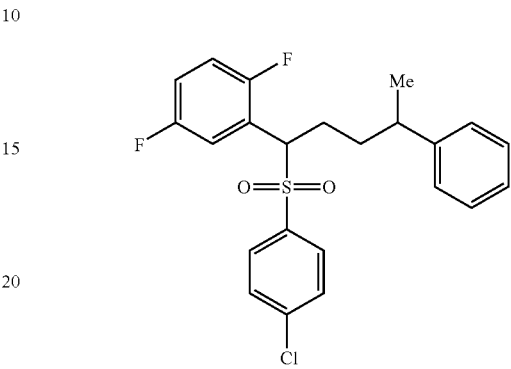

In a similar manner to Example 299 except for the use of the 2-[(4-chlorophenyl)sulfonylmethyl]-1,4-difluorobenzene (150 mg, 0.496 mmol) obtained in Example 5, DL-3-phenyl-1-butanol (153 μl, 0.991 mmol) and cyanomethylen-etri-n-butylphosphorane (239 μl, 0.991 mmol), the title Isomer 303-A (low-polarity compound) (44 mg, 0.101 mmol, 21%) was obtained as colorless plate crystals and the title Isomer 303-B (high-polarity compound) (45 mg, 0.103 mmol, 21%) was obtained as a white powder.

Isomer 303-A $^1$H-NMR (400 MHz, CDCl$_3$) δ: 1.21(3H,d,J=6.7 Hz), 1.38-1.61(2H,m), 2.03-2.09(1H,m), 2.24-2.33(1H,m), 2.64-2.69(1H,m), 4.40(1H,dd,J=11.3, 3.9 Hz), 6.83(1H,td,J=9.1, 4.4 Hz), 6.94-7.28(7H,m), 7.35(2H,d,J=8.6 Hz), 7.47(2H,d, J=8.6 Hz).

IR (ATR) cm$^{-1}$: 2933, 1494, 1475, 1427, 1394, 1315, 1276, 1228, 1141, 1085, 1012.

mp: 135-137° C.

MS m/z: 435 (M$^+$+H).

Anal. calcd for C$_{23}$H$_{21}$ClF$_2$O$_2$S: C, 63.52; H, 4.87; Cl, 8.15; F, 8.74; S, 7.37. Found: C, 63.37; H, 4.79; Cl, 8.18; F, 8.82; S, 7.61.

Isomer 303-B $^1$H-NMR (400 MHz, CDCl$_3$) δ: 1.19(3H,d,J=6.8 Hz), 1.37-1.59(2H,m), 1.83-1.93(1H,m), 2.26-2.34(1H,m), 2.61-2.68(1H,m), 4.47(1H,dd,J=11.8, 2.7 Hz), 6.83(1H,td,J=8.9, 4.3 Hz), 6.93-7.28(7H,m), 7.34(2H,d,J=8.6 Hz), 7.47(2H,d, J=8.6 Hz).

IR (ATR) cm$^{-1}$: 3083, 2933, 1494, 1475, 1425, 1394, 1315, 1278, 1224, 1182, 1151, 1012.

mp: 111-113° C.

MS m/z: 435 (M$^+$+H).

Anal. calcd for C$_{23}$H$_{21}$ClF$_2$O$_2$S: C, 63.52; H, 4.87; Cl, 8.15; F, 8.74; S, 7.37. Found: C, 63.39; H, 4.84; Cl, 8.50; F, 8.82; S, 7.51.

Example 304

2-[1-(4-Chlorophenylsulfonyl)-3-phenylpropyl]-1,4-difluorobenzene

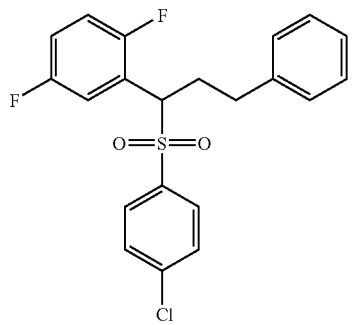

Under an argon atmosphere, the 2-[(4-chlorophenyl)sulfonylmethyl]-1,4-difluorobenzene (100 mg, 0.330 mmol) obtained in Example 5, and 2-phenylethyl alcohol (79.2 µl, 0.661 mmol) were dissolved in toluene (3 ml), followed by the addition of cyanomethylenetri-n-butylphosphorane (159 µl, 0.661 mmol). The resulting mixture was heated under reflux for 13 hours under an argon atmosphere. The reaction mixture was then concentrated. The residue thus obtained was subjected to flash chromatography on a silica gel column and the fraction obtained from the hexane:ethyl acetate=93:7 eluate was concentrated. The solid thus obtained was washed with hexane, whereby the title compound (100 mg, 0.246 mmol, 74%) was obtained as a white powder.

$^1$H-NMR (400 MHz, CDCl$_3$) δ: 2.37-2.52(2H,m), 2.60-2.78(2H,m), 4.44-4.49(1H,m), 6.85(1H,td,J=9.0, 4.5 Hz), 6.77-7.29(7H,m), 7.36(2H,d,J=8.6 Hz), 7.49(2H,d,J=8.6 Hz).

IR (ATR) cm$^{-1}$: 3068, 1583, 1496, 1477, 1457, 1423, 1394, 1315, 1278, 1214, 1176, 1147, 1081, 1012.

mp: 111-113° C.

MS m/z: 407 (M$^+$+H).

Anal. calcd for C$_{21}$H$_{17}$ClF$_2$O$_2$S: C, 61.99; H, 4.21; Cl, 8.71; F, 9.34; S, 7.88. Found: C, 61.76; H, 4.16; Cl, 8.88; F, 9.37; S, 8.02.

Example 305

2-[1-(4-Chlorophenylsulfonyl)-3-(2-methylphenyl)propyl]-1,4-difluorobenzene

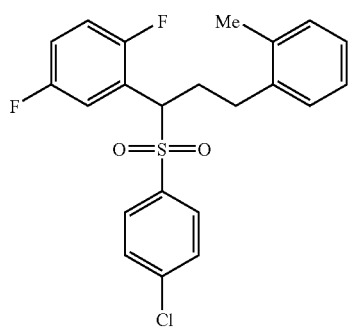

In a similar manner to Example 304 except for the use of 2-(2-methylphenyl)ethanol (89.0 µl, 0.661 mmol), the title compound (108 mg, 0.257 mmol, 78%) was obtained as colorless plate crystals.

$^1$H-NMR (400 MHz, CDCl$_3$) δ: 2.18(3H,s), 2.29-2.39(1H, m), 2.46-2.62(2H,m), 2.67-2.75(1H,m), 4.53(1H,dd,J=11.1, 2.6 Hz), 6.86(1H,td,J=9.0, 4.4 Hz), 6.96-7.12(5H,m), 7.28 (1H,ddd,J=8.7, 5.4,3.2 Hz), 7.37(2H,d,J=8.6 Hz), 7.51(2H,d, J=8.6 Hz).

IR (ATR) cm$^{-1}$: 3091, 2946, 1583, 1573, 1496, 1425, 1392, 1311, 1276, 1213, 1151, 1143, 1083, 1010.

mp: 105-106° C.

MS m/z: 421 (M$^+$+H).

Anal. calcd for C$_{22}$H$_{19}$ClF$_2$O$_2$S: C, 62.78; H, 4.55; Cl, 8.42; F, 9.03; S, 7.62. Found: C, 62.48; H, 4.63; Cl, 8.52; F, 9.16; S, 7.75.

Example 306

2-[1-(4-Chlorophenylsulfonyl)-3-(3-methylphenyl)propyl]-1,4-difluorobenzene

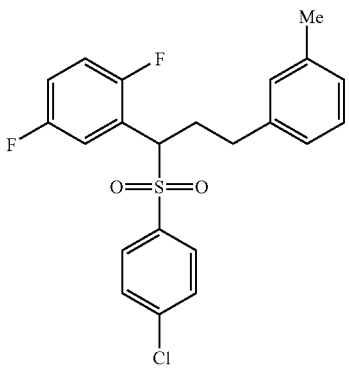

In a similar manner to Example 304 except for the use of 2-(3-methylphenyl)ethanol (90.0 µl, 0.661 mmol), the title compound (115 mg, 0.273 mmol, 83%) was obtained as colorless plate crystals.

$^1$H-NMR (400 MHz, CDCl$_3$) δ: 2.29(3H,s), 2.35-2.48(2H, m), 2.56-2.64(1H,m), 2.68-2.77(1H,m), 4.46-4.49(1H,m), 6.83-6.88(3H,m), 6.97-7.03(2H,m), 7.14(1H,t,J=7.8 Hz), 7.26(1H,ddd,J=8.7,5.4,3.3 Hz), 7.36(2H,d,J=8.6 Hz), 7.49 (2H,d,J=8.6 Hz).

IR (ATR) cm$^{-1}$: 3072, 2969, 1581, 1496, 1475, 1423, 1394, 1319, 1276, 1211, 1147, 1081, 1012.

mp: 87-88° C.

MS m/z: 421 (M$^+$+H).

Anal. calcd for C$_{22}$H$_{19}$ClF$_2$O$_2$S: C, 62.78; H, 4.55; Cl, 8.42; F, 9.03; S, 7.62. Found: C, 62.58; H, 4.60; Cl, 8.49; F, 9.21; S, 7.77.

Example 307

2-[1-(4-Chlorophenylsulfonyl)-3-(4-methylphenyl)propyl]-1,4-difluorobenzene

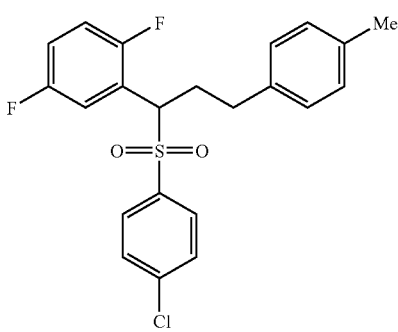

In a similar manner to Example 304 except for the use of 2-(4-methylphenyl)ethanol (91.9 μl, 0.661 mmol), the title compound (106 mg, 0.251 mmol, 76%) was obtained as colorless columnar crystals.

$^1$H-NMR (400 MHz, CDCl$_3$) δ: 2.31(3H,s), 2.34-2.46(2H,m), 2.57-2.65(1H,m), 2.67-2.72(1H,m), 4.46-4.48(1H,m), 6.85(1H,td,J=9.0, 4.5 Hz), 6.92(2H,d,J=8.1 Hz), 6.97-7.03 (1H,m), 7.06(2H,d,J=8.1 Hz), 7.25(1H,ddd,J=8.7,5.3,3.3 Hz), 7.35(2H,d,J=8.6 Hz), 7.45(2H,d,J=8.6 Hz).

IR (ATR) cm$^{-1}$: 3070, 2935, 1585, 1496, 1486, 1423, 1394, 1321, 1292, 1278, 1216, 1182, 1147, 1083, 1014.

mp: 82-84° C.

MS m/z: 421 (M$^+$+H).

Anal. calcd for C$_{22}$H$_{19}$ClF$_2$O$_2$S: C, 62.78; H, 4.55; Cl, 8.42; F, 9.03; S, 7.62. Found: C, 62.67; H, 4.60; Cl, 8.31; F, 8.95; S, 7.79.

Example 308

2-[1-(4-Chlorophenylsulfonyl)-3-(4-methoxyphenyl)propyl]-1,4-difluorobenzene

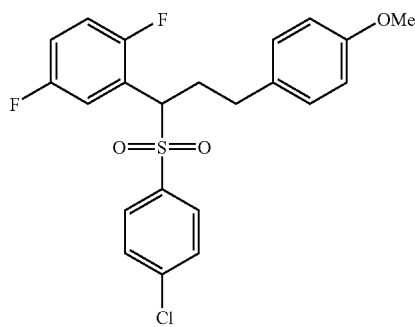

In a similar manner to Example 304 except for the use of 2-(4-methoxyphenyl)ethanol (100 mg, 0.661 mmol), the title compound (86 mg, 0.197 mmol, 60%) was obtained as a white powder.

$^1$H-NMR (400 MHz, CDCl$_3$) δ: 2.36-2.44(2H,m), 2.57-2.75(2H,m), 3.79(3H,s), 4.36-4.47(1H,m), 6.78(2H,d,J=8.3 Hz), 6.84(1H,td,J=8.8, 4.3 Hz), 6.93(2H,d,J=8.3 Hz), 6.97-7.03(1H,m), 7.24-7.28(1H,m), 7.35(2H,d,J=8.1 Hz), 7.47 (2H,d,J=8.1 Hz).

IR (ATR) cm$^{-1}$: 3089, 2954, 2836, 1612, 1583, 1513, 1494, 1459, 1427, 1394, 1322, 1270, 1245, 1222, 1180, 1153, 1083, 1031, 1012.

mp: 118-120° C.

MS m/z: 436 (M$^+$).

FAB-MS: 436.0717 (Calcd for C$_{22}$H$_{19}$ClF$_2$O$_3$S: 436.0712).

Anal. calcd for C$_{22}$H$_{19}$ClF$_2$O$_3$S: C, 60.48; H, 4.38; Cl, 8.11; F, 8.70; S, 7.34. Found: C, 60.00; H, 4.34; Cl, 8.39; F, 8.99; S, 7.60.

Example 309

2-[1-(4-Chlorophenylsulfonyl)-3-(4-fluorophenyl)propyl]-1,4-difluorobenzene

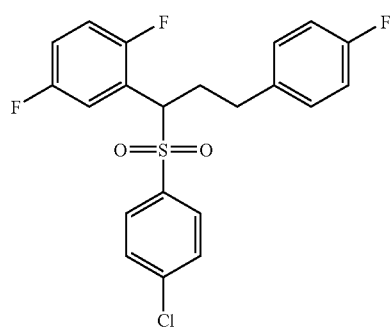

In a similar manner to Example 304 except for the use of 2-(4-fluorophenyl)ethanol (82.5 μl, 0.661 mmol), the title compound (70 mg, 0.165 mmol, 50%) was obtained as a white powder.

$^1$H-NMR (400 MHz, CDCl$_3$) δ: 2.34-2.50(2H,m), 2.61-2.76(2H,m), 4.43(1H,dd,J=11.2, 2.9 Hz), 6.83(1H,td,J=8.9, 4.4 Hz), 6.92-7.03(5H,m), 7.24-7.28(1H,m), 7.35(2H,d, J=8.6 Hz), 7.47(2H,d,J=8.6 Hz).

IR (ATR) cm$^{-1}$: 3079, 1583, 1509, 1492, 1477, 1423, 1394, 1317, 1276, 1251, 1216, 1176, 1145, 1081, 1012.

mp: 131-132° C.

MS m/z: 425 (M$^+$).

Anal. calcd for C$_{21}$H$_{16}$ClF$_3$O$_2$S: C, 59.37; H, 3.80; Cl, 8.34; F, 13.41; S, 7.55. Found: C, 59.41; H, 3.85; Cl, 8.64; F, 13.33; S, 7.67.

Example 310

2-[3-(4-Chlorophenyl)-1-(4-chlorophenylsulfonyl)propyl]-1,4-difluorobenzene

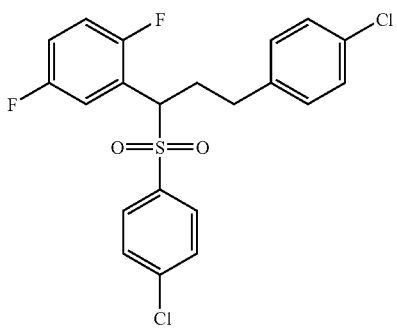

In a similar manner to Example 304 except for the use of 2-(4-chlorophenyl)ethanol (89.3 μl, 0.661 mmol), the title compound (103 mg, 0.233 mmol, 71%) was obtained as a white powder.

$^1$H-NMR (400 MHz, CDCl$_3$) δ: 2.35-2.50(2H,m), 2.62-2.77(2H,m), 4.42-4.43(1H,m), 6.84(1H,td,J=9.0, 4.4 Hz), 6.97(2H,d,J=8.6 Hz), 6.96-7.04(1H,m), 7.22(2H,d,J=8.6 Hz), 7.23-7.28(1H,m), 7.36(2H,d,J=8.6 Hz), 7.48(2H,d,J=8.6 Hz).

IR (ATR) cm$^{-1}$: 3079, 2931, 1581, 1492, 1475, 1461, 1425, 1394, 1317, 1274, 1214, 1178, 1139, 1083, 1012.

mp: 124-126° C.

MS m/z: 441 (M$^+$+H).

Anal. calcd for C$_{21}$H$_{16}$Cl$_2$F$_2$O$_2$S: C, 57.15; H, 3.65; Cl, 16.07; F, 8.61; S, 7.27. Found: C, 56.96; H, 3.68; Cl, 16.28; F, 8.78; S, 7.44.

Example 311

2-[3-(4-Bromophenyl)-1-(4-chlorophenylsulfonyl)propyl]-1,4-difluorobenzene

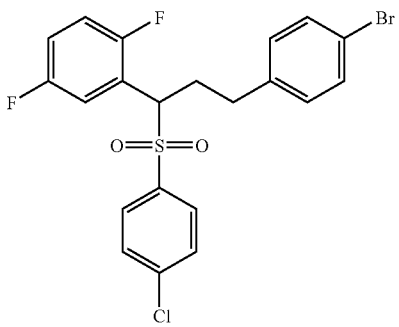

In a similar manner to Example 304 except for the use of 2-(4-bromophenyl)ethanol (89.7 μl, 0.661 mmol), the title compound (97 mg, 0.200 mmol, 61%) was obtained as a white powder.

$^1$H-NMR (400 MHz, CDCl$_3$) δ: 2.34-2.49(2H,m), 2.58-2.76(2H,m), 4.42-4.45(1H,m), 6.84(1H,td,J=9.0, 4.3 Hz), 6.92(2H,d,J=8.1 Hz), 6.98-7.04(1H,m), 7.26(1H,ddd,J=8.3, 5.5,3.4 Hz), 7.36(2H,d,J=8.3 Hz), 7.38(2H,d,J=8.1 Hz), 7.48(2H,d,J=8.3 Hz).

IR (ATR) cm$^{-1}$: 3081, 2927, 1573, 1486, 1459, 1425, 1396, 1317, 1272, 1247, 1216, 1178, 1139, 1083, 1010.

mp: 122-124° C.

MS m/z: 486 (M$^+$+H).

FAB-MS: 485.9728 (Calcd for C$_{21}$H$_{16}$ClBrF$_2$O$_2$S: 485.9690).

Example 312

2-[1-(4-Chlorophenylsulfonyl)-4-phenylbutyl]-1,4-difluorobenzene

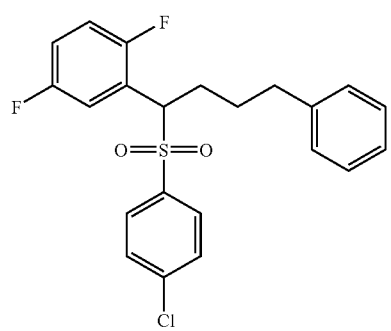

In a similar manner to Example 304 except for the use of 3-phenyl-1-propanol (90.0 μl, 0.661 mmol), the title compound (106 mg, 0.251 mmol, 76%) was obtained as a white powder.

$^1$H-NMR (400 MHz, CDCl$_3$) δ: 1.50-1.65(2H,m), 2.06-2.16(1H,m), 2.40-2.49(1H,m), 2.53-2.69(2H,m), 4.52(1H, dd,J=11.4, 3.1 Hz), 6.83(1H,td,J=9.0, 4.5 Hz), 6.94-7.00(1H, m), 7.05-7.26(6H,m), 7.37(2H,d,J=8.6 Hz), 7.52(2H,d,J=8.6 Hz).

IR (ATR) cm$^{-1}$: 3070, 2956, 2861, 1914, 1583, 1488, 1461, 1423, 1392, 1319, 1278, 1249, 1207, 1174, 1143, 1081, 1012.

mp: 107-108° C.

MS m/z: 421 (M$^+$+H).

FAB-MS: 421.0834 (Calcd for C$_{22}$H$_{20}$ClF$_2$O$_2$S: 421.0841).

Example 313

2-[1-(4-Chlorophenylsulfonyl)-5-phenylpentyl]-1,4-difluorobenzene

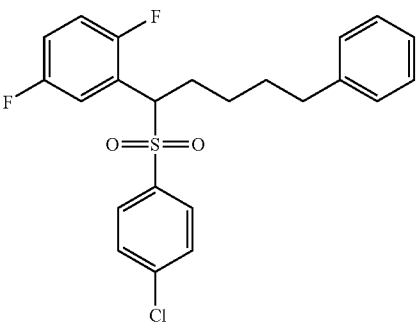

In a similar manner to Example 304 except for the use of 4-phenyl-1-butanol (102 μl, 0.661 mmol), the title compound (107 mg, 0.246 mmol, 75%) was obtained as a white powder.

¹H-NMR (400 MHz, CDCl₃) δ: 1.26(2H,q,J=7.6 Hz), 1.57-1.67(2H,m), 2.06-2.16(1H,m), 2.40-2.62(3H,m), 4.49 (1H,dd,J=12.0, 3.3 Hz), 6.81(1H,td,J=9.0, 4.5 Hz), 6.94-7.00 (1H,m), 7.08-7.26(6H,m), 7.37(2H,d,J=8.3 Hz), 7.52 (2H,d, J=8.3 Hz).

IR (ATR) cm⁻¹: 2942, 2856, 1583, 1494, 1475, 1463, 1427, 1394, 1324, 1276, 1240, 1211, 1182, 1151, 1083, 1049, 1014.

mp: 88-90° C.

MS m/z: 435 (M⁺+H).

Anal. calcd for $C_{23}H_{21}ClF_2O_2S$: C, 63.52; H, 4.87; Cl, 8.15; F, 8.74; S, 7.37. Found: C, 63.32; H, 4.74; Cl, 8.19; F, 8.93; S, 7.65.

Example 314

2-[1-(4-Chlorophenylsulfonyl)-2-(4-fluorophenyl)ethyl]-1,4-difluorobenzene

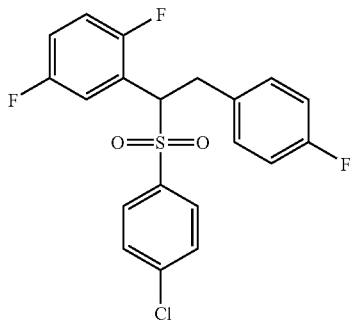

In a similar manner to Example 304 except for the use of 4-fluorobenzyl alcohol (71.2 μl, 0.661 mmol), the title compound (118 mg, 0.287 mmol, 87%) was obtained as a white powder.

¹H-NMR (400 MHz, CDCl₃) δ: 3.29(1H,dd,J=14.0, 12.0 Hz), 3.81(1H,dd,J=14.0, 3.7 Hz), 4.75(1H,dd,J=12.0, 3.7 Hz), 6.70(1H,td,J=9.0, 4.5 Hz), 6.84-7.00(6H,m), 7.38(2H,d, J=8.6 Hz), 7.56(2H,d,J=8.6 Hz).

IR (ATR) cm⁻¹: 3079, 2964, 1600, 1573, 1511, 1492, 1427, 1392, 1307, 1278, 1220, 1172, 1143, 1081, 1010.

mp: 151-153° C.

MS m/z: 411 (M⁺+H).

Anal. calcd for $C_{20}H_{14}ClF_3O_2S$: C, 58.47; H, 3.43; Cl, 8.63; F, 13.87; S, 7.80. Found: C, 58.27; H, 3.39; Cl, 8.80; F, 13.80; S, 8.00.

Example 315

2-[1-(4-Chlorophenylsulfonyl)-3-cyclopentylpropyl]-1,4-difluorobenzene

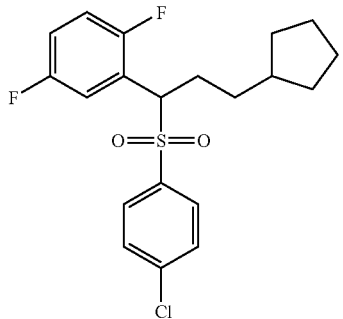

In a similar manner to Example 304 except for the use of 2-cyclopentane-ethanol (81.9 μl, 0.661 mmol), the title compound (79 mg, 0.186 mmol, 60%) was obtained as colorless plate crystals.

¹H-NMR (400 MHz, CDCl₃) δ: 0.94-1.07(4H,m), 1.09-1.18(1H,m), 1.23-1.33(1H,m), 1.45-1.59(3H,m), 1.67-1.79 (2H,m), 2.03-2.14(1H,m), 2.41-2.50(1H,m), 4.49(1H,dd, J=12.2, 2.9 Hz), 6.82(1H,td,J=9.0, 4.4 Hz), 6.94-7.00(1H,m), 7.22-7.26(1H,m), 7.37(2H,d,J=8.8 Hz), 7.52(2H,d,J=8.8 Hz).

IR (ATR) cm⁻¹: 2952, 2852, 1583, 1494, 1475, 1427, 1396, 1313, 1278, 1214, 1176, 1147, 1081, 1014.

mp: 93-94° C.

MS m/z: 399 (M⁺+H).

FAB-MS: 399.1004 (Calcd for $C_{20}H_{22}ClF_2O_2S$: 399.0997).

Example 316

2-[1-(4-Chlorophenylsulfonyl)-3-cyclohexylpropyl]-1,4-difluorobenzene

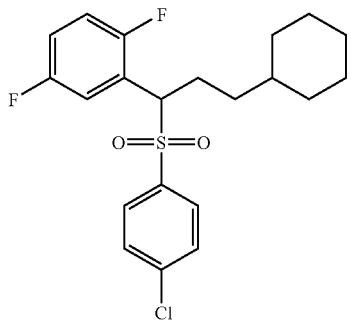

In a similar manner to Example 304 except for the use of 2-cyclohexane-ethanol (92.0 μl, 0.661-mmol), the title compound (86 mg, 0.208 mmol, 63%) was obtained as a white powder.

¹H-NMR (400 MHz, CDCl₃) δ: 0.75-0.89(2H,m), 0.97-1.25(6H,m), 1.61-1.68(5H,m), 2.01-2.12(1H,m), 2.42-2.50 (1H,m), 4.46(1H,dd,J=11.5, 2.9 Hz), 6.82(1H,td,J=9.3, 4.4 Hz), 6.94-7.00(1H,m), 7.20-7.26(1H,m), 7.37(2H,d,J=8.1 Hz), 7.52(2H,d,J=8.1 Hz).

IR (ATR) cm⁻¹: 2925, 2842, 1581, 1496, 1450, 1423, 1392, 1315, 1276, 1238, 1176, 1149, 1085, 1010.

mp: 82-83° C.

MS m/z: 413 (M⁺+H).

Anal. calcd for $C_{21}H_{23}ClF_2O_2S$: C, 61.08; H, 5.61; Cl, 8.59; F, 9.20; S, 7.77. Found: C, 60.80; H, 5.58; Cl, 8.79; F, 9.45; S, 7.92.

Example 317

2-[1-(4-Chlorophenylsulfonyl)-4-cyclohexylbutyl]-1,4-difluorobenzene

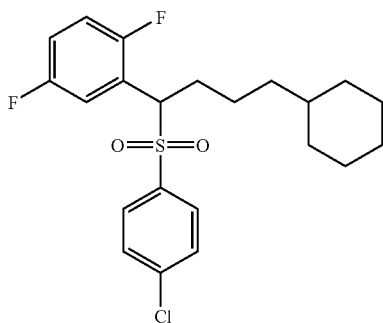

In a similar manner to Example 304 except for the use of 3-cyclohexyl-1-propanol (103 μl, 0.661 mmol), the title compound (96 mg, 0.224 mmol, 68%) was obtained as a white powder.

$^1$H-NMR (400 MHz, CDCl$_3$) δ: 0.72-1.73(15H,m), 2.01-2.12(1H,m), 2.33-2.41(1H,m), 4.51(1H,d,J=9.0 Hz), 6.80-6.86(1H,m), 6.94-7.00(1H,m), 7.22-7.26(1H,m), 7.38(2H,d,J=7.8 Hz), 7.53(2H,d,J=7.8 Hz).

IR (ATR) cm$^{-1}$: 2919, 2852, 1583, 1496, 1488, 1475, 1425, 1394, 1317, 1274, 1236, 1207, 1149, 1081, 1012.

mp: 47-49° C.

MS m/z: 427 (M$^+$+H).

FAB-MS: 427.1342 (Calcd for C$_{22}$H$_{26}$ClF$_2$O$_2$S: 427.1310).

Example 318

2-[3-(4-chlorophenylsulfonyl)-3-(2,5-difluorophenyl)propyl]pyridine

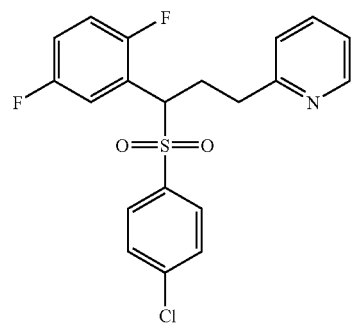

In a similar manner to Example 304 except for the use of 2-(2-hydroxyethyl)pyridine (74.5 μl, 0.661 mmol), the title compound (74 mg, 0.181 mmol, 55%) was obtained as a white powder.

$^1$H-NMR (400 MHz, CDCl$_3$) δ: 2.49-2.58(1H,m), 2.68-2.93(3H,m), 4.60(1H,dd,J=10.9, 3.3 Hz), 6.84(1H,td,J=8.9, 4.5 Hz), 6.95-7.00(1H,m), 7.03(1H,d,J=7.6 Hz), 7.11(1H,dd, J=6.9, 5.1 Hz), 7.29-7.38(1H,m), 7.39(2H,d,J=8.6 Hz), 7.54 (2H,d,J=8.6 Hz) 7.51-7.58(1H,m), 8.48(1H,d,J=3.9 Hz).

IR (ATR) cm$^{-1}$: 3075, 1585, 1569, 1496, 1473, 1425, 1394, 1311, 1278, 1205, 1145, 1081, 1012.

mp: 129-131° C.

MS m/z: 408 (M$^+$+H).

FAB-MS: 408.0649 (Calcd for C$_{20}$H$_{17}$ClF$_2$NO$_2$S: 408.0637).

Anal. calcd for C$_{20}$H$_{16}$ClF$_2$NO$_2$S: C, 58.90; H, 3.95; Cl, 8.69; F, 9.32; N, 3.42; S, 7.86. Found: C, 58.57; H, 3.87; Cl, 8.90; F, 9.34; N, 3.53; S, 7.96.

Example 319

5-[3-(4-Chlorophenylsulfonyl)-3-(2,5-difluorophenyl)propyl]-4-methyl-1,3-thiazole

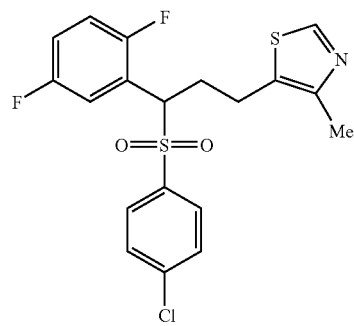

In a similar manner to Example 304 except for the use of 5-(2-hydroxyethyl)-4-methylthiazole (78.9 μl, 0.661 mmol), the title compound (87 mg, 0.203 mmol, 62%) was obtained as a colorless solid.

$^1$H-NMR (400 MHz, CDCl$_3$) δ: 2.21(3H,s), 2.36-2.47(1H, m), 2.70-2.87(3H,m), 4.49(1H,dd,J=10.9, 2.6 Hz), 6.86(1H, td,J=9.1, 4.4 Hz), 6.99-7.05(1H,m), 7.24-7.28(1H,m), 7.39 (2H,d,J=8.8 Hz), 7.51(2H,d,J=8.8 Hz) 8.57(1H,s).

IR (ATR) cm$^{-1}$: 3085, 2933, 1583, 1571, 1494, 1477, 1405, 1315, 1278, 1220, 1147, 1083, 1012.

mp: 183-184° C.

MS m/z: 428 (M$^+$+H).

FAB-MS: 428.0355 (Calcd for C$_{19}$H$_{17}$ClF$_2$NO$_2$S$_2$: 428.0357).

Example 320

1-[3-(4-Chlorophenylsulfonyl)-3-(2,5-difluorophenyl)propyl]piperidine

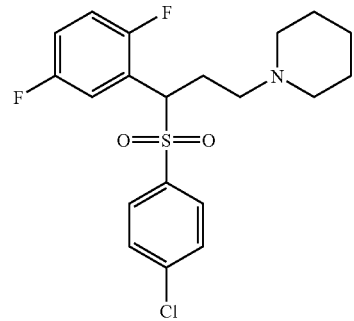

In a similar manner to Example 304 except for the use of 1-piperidine-ethanol (87.3 μl, 0.661 mmol), the title compound (32 mg, 0.0773 mmol, 23%) was obtained as a white powder.

¹H-NMR (400 MHz, CDCl₃) δ: 1.34-1.40(2H,m), 1.44-1.49(4H,m), 2.09-2.34(7H,m), 2.59-2.67(1H,m), 4.76-4.79(1H,m), 6.83(1H,td,J=9.0, 4.3 Hz), 6.94-7.00(1H,m), 7.23(1H,ddd,J=8.9,5.8,3.7 Hz), 7.39(2H,d,J=8.8 Hz), 7.55(2H,d,J=8.8 Hz).

IR (ATR) cm⁻¹: 2942, 2800, 2761, 1579, 1492, 1427, 1396, 1355, 1309, 1284, 1243, 1189, 1118, 1085, 1014.

mp: 106-107° C.

MS m/z: 414 (M⁺+H).

FAB-MS: 414.1118 (Calcd for C₂₀H₂₃ClF₂NO₂S: 414.1106).

Anal. calcd for C₂₀H₂₂ClF₂NO₂S: C, 58.04; H, 5.36; Cl, 8.57; F, 9.18; N, 3.38; S, 7.75. Found: C, 57.76; H, 5.34; Cl, 8.79; F, 9.44; N, 3.39; S, 7.89.

Example 321

2-[3-(4-Chlorophenylsulfonyl)-3-(2,5-difluorophenyl)propyl]-5,5-dimethyl-1,3-dioxane

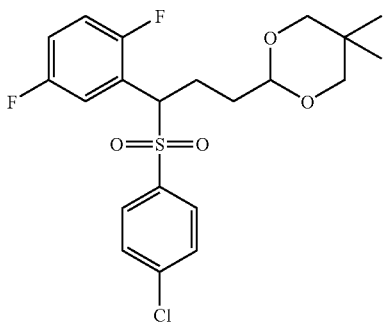

In a similar manner to Example 304 except for the use of 5,5-dimethyl-1,3-dioxane-2-ethanol (103 μl, 0.661 mmol), the title compound (72 mg, 0.162 mmol, 49%) was obtained as a white powder.

¹H-NMR (400 MHz, CDCl₃) δ: 0.70(3H,s), 1.12(3H,s), 1.53-1.58(2H,m), 2.15-2.25(1H,m), 2.55-2.65(1H,m), 3.35(2H,d,J=10.7 Hz), 3.55(2H,d,J=10.7 Hz), 4.39(1H,t,J=4.4 Hz), 4.64(1H,dd,J=11.2, 3.4 Hz), 6.83(1H,td,J=8.9, 4.6 Hz), 6.94-7.00(1H,m), 7.21-7.26(1H,m), 7.38(2H,d,J=8.6 Hz), 7.55(2H,d,J=8.6 Hz).

IR (ATR) cm⁻¹: 2958, 2842, 1583, 1498, 1467, 1396, 1317, 1278, 1214, 1147, 1130, 1081, 1041, 1012.

mp: 69-71° C.

MS m/z: 445 (M⁺+H).

FAB-MS: 445.1031 (Calcd for C₂₁H₂₄ClF₂O₄S: 445.1052).

Anal. calcd for C₂₁H₂₃ClF₂O₄S: C, 56.69; H, 5.21; Cl, 7.97; F, 8.54; S, 7.21. Found: C, 56.29; H, 5.16; Cl, 8.09; F, 8.73; S, 7.43.

Example 322

2-[1-(4-Chlorophenylsulfonyl)hexyl]-1,4-difluorobenzene

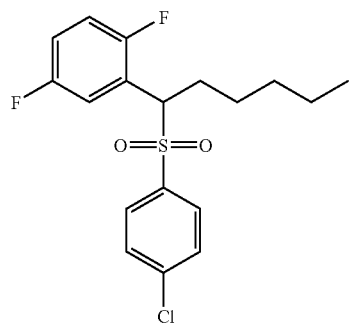

In a similar manner to Example 304 except for the use of 1-pentanol (71.8 μl, 0.661 mmol), the title compound (88 mg, 0.236 mmol, 72%) was obtained as a white powder.

¹H-NMR (400 MHz, CDCl₃) δ: 0.83-0.45(2H,m), 1.18-1.31(7H,m), 2.03-2.12(1H,m), 2.37-2.46(1H,m), 4.50(1H,dd,J=11.4, 3.3 Hz), 6.82(1H,td,J=9.0, 4.5 Hz), 6.95-7.00(1H,m), 7.22-7.26(1H,m), 7.37(2H,d,J=8.6 Hz), 7.52(2H,d,J=8.6 Hz).

IR (ATR) cm⁻¹: 2946, 2923, 2867, 1585, 1494, 1477, 1425, 1396, 1317, 1278, 1247, 1211, 1176, 1149, 1081, 1014.

mp: 68-69° C.

MS m/z: 373 (M⁺+H).

Anal. calcd for C₁₈H₁₉ClF₂O₂S: C, 57.98; H, 5.14; Cl, 9.51; F, 10.19; S, 8.60. Found: C, 57.71; H, 5.14; Cl, 9.65; F, 10.31; S, 8.73.

Example 323

2-[1-(4-Chlorophenylsulfonyl)heptyl]-1,4-difluorobenzene

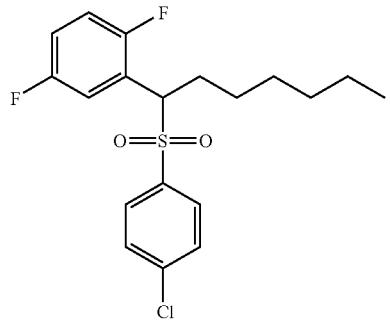

In a similar manner to Example 304 except for the use of 1-hexanol (82.2 μl, 0.661 mmol), the title compound (69 mg, 0.178 mmol, 54%) was obtained as a white powder.

¹H-NMR (400 MHz, CDCl₃) δ: 0.84(3H,t,J=7.0 Hz), 1.17-1.31(8H,m), 2.03-2.13(1H,m), 2.38-2.46(1H,m), 4.50(1H,dd,J=11.1, 3.0 Hz), 6.81(1H,td,J=9.0, 4.5 Hz), 6.94-7.00(1H,m), 7.23(1H,ddd,J=8.6,5.3,3.1 Hz), 7.37(2H,d,J=8.6 Hz), 7.52(2H,d,J=8.6 Hz).

IR (ATR) cm⁻¹: 2962, 2925, 2856, 1583, 1492, 1477, 1425, 1394, 1315, 1276, 1243, 1214, 1174, 1149, 1081, 1012.

mp: 77-78° C.

MS m/z: 387 (M⁺+H).

Anal. calcd for $C_{19}H_{21}ClF_2O_2S$: C, 58.98; H, 5.47; Cl, 9.16; F, 9.82; S, 8.29. Found: C, 58.82; H, 5.54; Cl, 9.31; F, 9.86; S, 8.44.

Example 324

2-[1-(4-chlorophenylsulfonyl)octyl]-1,4-difluorobenzene

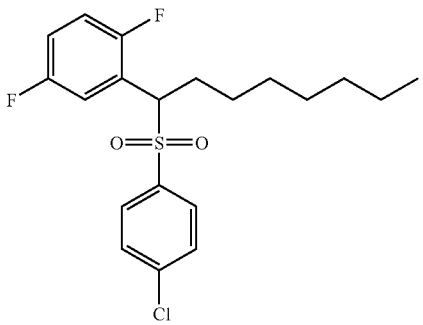

In a similar manner to Example 304 except for the use of 1-heptanol (93.5 μl, 0.661 mmol), the title compound (107 mg, 0.267 mmol, 81%) was obtained as a white powder.

$^1$H-NMR (400 MHz, CDCl$_3$) δ: 0.85(3H,t,J=7.0 Hz), 1.15-1.27(10H,m), 2.03-2.12(1H,m), 2.38-2.46(1H,m), 4.50(1H, dd,J=11.5, 2.7 Hz), 6.82(1H,td,J=9.0, 4.6 Hz), 6.94-7.00(1H, m), 7.24(1H,ddd,J=8.7,5.3,3.1 Hz), 7.38(2H,d,J=8.6 Hz), 7.53(2H,d,J=8.6 Hz).

IR (ATR) cm$^{-1}$: 2925, 2859, 1583, 1496, 1475, 1469, 1425, 1394, 1322, 1274, 1241, 1205, 1147, 1081, 1012.

mp: 47-48° C.

MS m/z: 401 (M⁺+H).

Anal. calcd for $C_{20}H_{23}ClF_2O_2S$: C, 59.92; H, 5.78; Cl, 8.84; F, 9.48; S, 8.00. Found: C, 59.63; H, 5.61; Cl, 8.96; F, 9.59; S, 8.17.

Example 325

2-[1-(4-Chlorophenylsulfonyl)-5-methylhexyl]-1,4-difluorobenzene

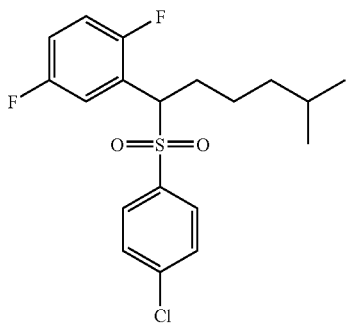

In a similar manner to Example 304 except for the use of 4-methyl-1-pentanol (83.2 μl, 0.661 mmol), the title compound (122 mg, 0.315 mmol, 96%) was obtained as a white powder.

$^1$H-NMR (400 MHz, CDCl$_3$) δ: 0.78(3H,d,J=6.6 Hz), 0.81 (3H,d,J=6.6 Hz), 1.14-1.25(4H,m), 1.41-1.52(1H,m), 2.02-2.12(1H,m), 2.35-2.41(1H,m), 4.51(1H,dd,J=11.6, 2.6 Hz), 6.83(1H,td,J=9.0, 4.4 Hz), 6.95-7.00(1H,m), 7.24(1H,ddd, J=8.9,5.6,3.2 Hz), 7.38(2H,d,J=8.6 Hz), 7.53(2H,d,J=8.6 Hz).

IR (ATR) cm$^{-1}$: 2962, 2925, 2898, 2861, 1583, 1492, 1465, 1427, 1394, 1315, 1278, 1247, 1211, 1176, 1147, 1081, 1014.

mp: 79-80° C.

MS m/z: 387 (M⁺+H).

Anal. calcd for $C_{19}H_{21}ClF_2O_2S$: C, 58.98; H, 5.47; Cl, 9.16; F, 9.82; S, 8.29. Found: C, 58.92; H, 5.42; Cl, 9.28; F, 10.00; S, 8.45.

Example 326

2-[1-(4-Chlorophenylsulfonyl)-4-methylhexyl]-1,4-difluorobenzene

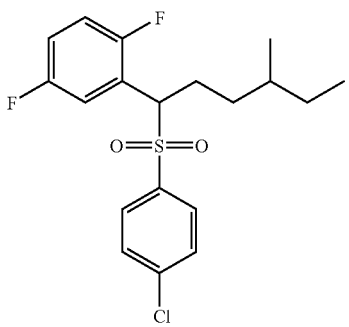

In a similar manner to Example 304 except for the use of the 2-[(4-chlorophenyl)sulfonylmethyl]-1,4-difluorobenzene (200 mg, 0.660 mmol) obtained in Example 5, 3-methyl-1-pentanol (180 μl, 1.32 mmol), and cyanomethylenetri-n-butylphosphorane (163 μl, 1.32 mmol), the title compound (217 mg, 0.561 mmol, 85%) was obtained as a white powder.

$^1$H-NMR (400 MHz, CDCl$_3$) δ: 0.77-0.85(6H,m), 1.07-1.15(2H,m), 1.21-1.33(3H,m), 1.98-2.15(1H,m), 2.39-2.52 (1H,m), 4.44-4.49(1H,m), 6.82(1H,td,J=8.9, 4.1 Hz), 6.94-7.00(1H,m), 7.23-7.26(1H,m), 7.38(2H,d,J=8.3 Hz), 7.53 (2H,d,J=8.3 Hz).

IR (ATR) cm$^{-1}$: 2960, 2919, 2873, 1583, 1496, 1473, 1461, 1425, 1394, 1319, 1278, 1216, 1153, 1083, 1012.

mp: 56-58° C.

MS m/z: 387 (M⁺+H).

Anal. calcd for $C_{19}H_{21}ClF_2O_2S$: C, 58.98; H, 5.47; Cl, 9.16; F, 9.82; S, 8.29. Found: C, 58.87; H, 5.55; Cl, 9.12; F, 9.93; S, 8.42.

Referential Example 45

5-Dibromomethyl-2-(2,5-difluorobenzoyl)pyridine (Compound A) and 5-bromomethyl-2-(2,5-difluorobenzoyl)pyridine (Compound B)

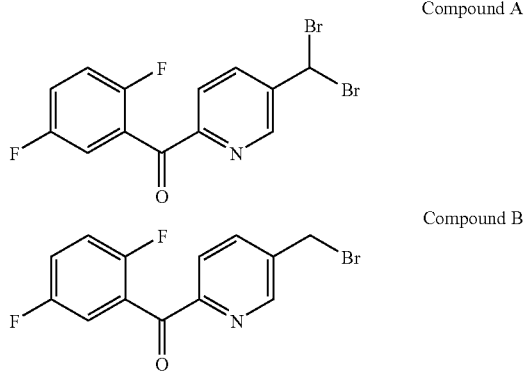

While heating under reflux, N-bromosuccinimide (17.0 g, 95.7 mmol) and a catalytic amount of 2,2'-azobis(2-methylpropionitrile) were added to a solution of the 2-[(2,5-difluorophenyl)-hydroxymethyl]-5-methylpyridine (7.50 g, 31.9 mmol), which had been obtained in Referential Example 15, in carbon tetrachloride (100 ml). The mixture was then stirred. After reflux for 24 hours, the reaction mixture was cooled to room temperature. The precipitate thus obtained was separated by filtration. The precipitate was then added to an aqueous solution of sodium thiosulfate and the resulting mixture was extracted with chloroform. The solution was washed with a saturated aqueous solution of sodium bicarbonate and brine, and then dried over sodium sulfate. The residue obtained by concentrating the solution under reduced pressure was purified by silica gel chromatography (hexane:ethyl acetate=10:1) to yield the title compound A (3.91 g, 31%) and the title compound B (3.34 g, 34%) as oils.

Compound A
$^1$H-NMR (400 MHz, CDCl$_3$) δ: 6.70 (1H, s), 7.12 (1H, m), 7.24 (1H, m), 7.39 (1H, m), 8.12 (1H, d, J=8.4 Hz), 8.19 (1H, dd, J=2.0, 8.4 Hz), 8.77 (1H, d, J=2.0 Hz).
IR (ATR) cm$^{-1}$: 1676, 1487, 1421, 1311, 1193, 827.
MS m/z: 392 (M$^+$+H).

Compound B
$^1$H-NMR (400 MHz, CDCl$_3$) δ: 4.52 (2H, s), 7.12 (1H, m), 7.21 (1H, m), 7.39 (1H, m), 7.94 (1H, dd, J=2.0, 8.0 Hz), 8.08 (1H, d, J=8.0 Hz), 8.67 (1H, d, J=2.0 Hz).
MS m/z: 313 (M$^+$+H).

Referential Example 46

[6-(2,5-Difluorophenylcarbonyl)pyridin-3-yl]methyl Acetate

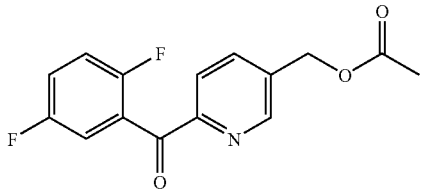

While heating under reflux, N-bromosuccinimide (6.0 g, 33.6 mmol) and a catalytic amount of 2,2'-azobis(2-methylpropionitrile) were added to a solution of the 2-[(2,5-difluorophenyl)-hydroxymethyl]-5-methylpyridine (2.64 g, 11.2 mmol), which had been obtained in Referential Example 15, in carbon tetrachloride (60 ml). The resulting mixture was then, stirred. After reflux for 7 hours, the reaction mixture was cooled to room temperature and added to an aqueous solution of sodium thiosulfate. The mixture was extracted with ether. The solution was washed with water and brine, and then dried over sodium sulfate. The residue obtained by concentrating the solution under reduced pressure was dissolved in toluene and the resulting solution was concentrated again. The residue was dissolved in N,N-dimethylformamide (20 ml). Sodium acetate (4.59 g, 56 mmol) was added to the resulting solution and the mixture was stirred at 70° C. for 17 hours. After cooling, the reaction mixture was dissolved in ethyl acetate (100 ml), followed by washing with water and brine. The solution was dried over anhydrous magnesium sulfate and then concentrated under reduced pressure. The residue was purified by silica gel chromatography (hexane:ethyl acetate=5:1) to yield the title compound (600 mg, 18%) as an oil.

$^1$H-NMR (400 MHz, CDCl$_3$) δ: 2.12 (3H, s), 5.19 (2H, s), 7.10 (1H, m), 7.19 (1H, m), 7.37 (1H, s), 7.88 (1H, dd, J=2.4, 8.0 Hz), 8.07 (1H, d, J=8.0 Hz), 8.62 (1H, d, J=2.4 Hz).
IR (ATR) cm$^{-1}$: 1739, 1678, 1489, 1222, 821.
MS m/z: 292 (M$^+$+H).

Example 327

2-[(4-Chlorophenylthio)-(2,5-difluorophenyl)methyl]-5-[(4-chlorophenylthio)methyl]pyridine

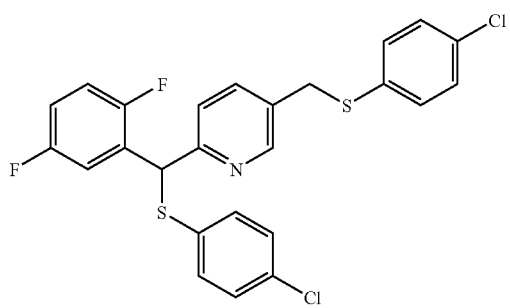

A suspension of sodium borohydride (33 mg, 0.88 mmol) in ethanol (15 ml) was cooled to −78° C. While stirring, an ethanol solution (10 ml) of [6-(2,5-difluorophenylcarbonyl)pyridin-3-yl]methyl acetate (510 mg, 1.75 mmol) was added in portions. After stirring for 30 minutes, an aqueous solution of ammonium chloride was added and the resulting mixture was allowed to stand until the temperature of the mixture increased to room temperature. The resulting mixture was extracted with ethyl acetate (100 ml), followed by washing with water and brine, drying over anhydrous magnesium sulfate and concentration under reduced pressure. The residue was dissolved in methylene chloride (30 ml) and under ice cooling, triethylamine (270 µl) and methanesulfonyl chloride (270 µl) were added thereto. The resulting mixture was stirred at room temperature for 3 days. Water was added and the mixture was extracted with ethyl acetate (60 ml). The solution was washed with water and brine, dried over anhydrous magnesium sulfate and concentrated under reduced pressure.

The residue was dissolved in N,N-dimethylformamide (25 ml). Under nitrogen atmosphere, 4-chlorobenzenethiol (751 mg, 5.3 mmol) and potassium carbonate (718 mg, 5.2 mmol)

were added and the mixture was stirred at 60° C. for 1 hour. After the reaction mixture was cooled to room temperature, diethyl ether (80 ml) was added thereto. The resulting mixture was washed with water and brine, dried over magnesium sulfate and concentrated under reduced pressure. The residue was subjected to silica gel chromatography (hexane:ethyl acetate=10:1) to yield the title compound (237 mg, 27%) as a white solid.

$^1$H-NMR (400 MHz, CDCl$_3$) δ: 3.99 (2H, s), 5.81 (1H, s), 6.90 (2H, m), 7.15 (2H, d, J=8.8 Hz), 7.16 (2H, d, J=8.8 Hz), 7.19 (4H, d, J=8.8 Hz), 7.20 (1H, d, J=7.6 Hz), 7.38(1H, m), 7.49 (1H, dd, J=2.0, 7.6 Hz), 8.38 (1H, br).

IR (ATR) cm$^{-1}$: 1473, 1385, 1092, 1010, 814.

mp: 87-88° C.

Example 328

2-[(4-Chlorophenylsulfonyl)-(2,5-difluorophenyl) methyl]-5-[(4-chlorophenylsulfonyl)methyl]pyridine

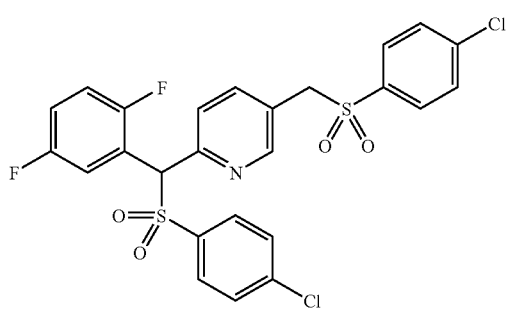

To a solution of 2-[(4-chlorophenylthio)-(2,5-difluorophenyl)methyl]-5-[(4-chlorophenylthio)methyl]pyridine (75 mg, 0.15 mmol) in methanol (6.0 ml) were successively added hexaammonium heptamolybdate tetrahydrate (30 mg) and a 30% aqueous hydrogen peroxide solution (3 ml). The resulting mixture was stirred for 22 hours. Ethyl acetate was added to the reaction mixture. The resulting mixture was washed with water, an aqueous solution of sodium thiosulfate and brine. After drying the solution, it was concentrated under reduced pressure. The residue was purified by silica gel chromatography (2% MeOH/CHCl$_3$) to yield the title compound (70 mg, 62%) as colorless needle crystals.

$^1$H-NMR (400 MHz, CDCl$_3$) δ: 4.29 (2H, s), 5.91 (1H, s), 6.90-7.08 (2H, m), 7.39 (2H, dd, J=1.6, 6.8 Hz), 7.45 (2H, dd, J=1.6, 6.8 Hz), 7.51 (2H, d, J=8.8 Hz), 7.55 (2H, d, J=8.8 Hz), 7.60 (1H, d, J=8.0 Hz), 7.65 (1H, dd, J=2.4, 8.0 Hz), 7.91 (1H, m), 8.23 (1H, s).

IR (ATR) cm$^{-1}$: 1495, 1322, 1149, 1087, 615.

mp: 186-187° C.

MS m/z: 568 (M$^+$+H).

Anal. calcd for C$_{25}$H$_{17}$Cl$_2$F$_2$NO$_4$S$_2$: C, 52.82%; H, 3.01%; N, 2.46%; S, 11.28%; Cl, 12.47%; F, 6.68%. Found: C, 52.88%; H, 3.10%; N, 2.63%; S, 11.38%; Cl, 12.40%; F, 6.83%.

Referential Example 47

2-[(2,5-Difluorophenyl)-hydroxymethyl]-5-(1,3-dioxolan-2-yl)pyridine

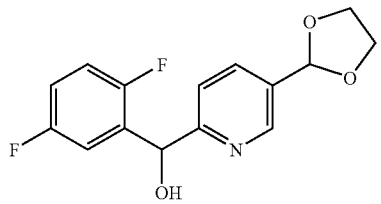

To a pyridine solution (60 ml) of the 5-dibromomethyl-2-(2,5-difluorobenzoyl)pyridine (Compound A) (3.91 g, 10 ml) obtained in Referential Example 45 was added ethylene glycol (6.2 g, 100 mmol). While heating at 90° C., the mixture was stirred for 17 hours. The reaction mixture was concentrated under reduced pressure and the residue was dissolved in ether (200 ml). The resulting solution was washed with water, a saturated aqueous solution of sodium bicarbonate and brine and dried over anhydrous magnesium sulfate. The solution was concentrated under reduced pressure. The residue was dissolved in ethanol (60 ml). Sodium borohydride (190 mg, 5 mmol) was added to the resulting solution under ice cooling, followed by stirring at room temperature for 1 hour. After the addition of water, the mixture was extracted with ethyl acetate. The solution was washed with brine and then dried over anhydrous magnesium sulfate. The residue obtained by concentrating the solution under reduced pressure was purified by silica gel chromatography (hexane:ethyl acetate=5:1-1:1) to yield the title compound (1.52 g, 52%) as an oil.

$^1$H-NMR (400 MHz, CDCl$_3$) δ: 4.0-4.2 (4H, m), 5.84 (1H, s), 6.10 (1H, s), 6.91 (1H, m), 6.99 (1H, m), 7.09 (1H, m), 7.26 (1H, d, J=8.0 Hz), 7.76 (1H, dd, J=2.0, 8.0 Hz), 8.64 (1H, d, J=2.0 Hz).

IR (ATR) cm$^{-1}$: 1489, 1086, 1026, 818, 715.

MS m/z: 294 (M$^+$+H).

Example 329

2-[(4-Chlorophenylthio)-(2,5-difluorophenyl)methyl]-5-(1,3-dioxolan-2-yl)pyridine

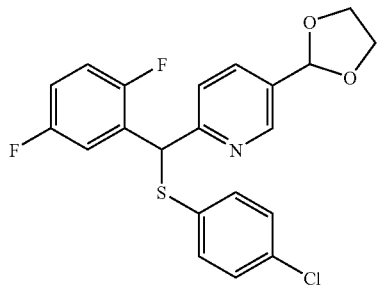

Under nitrogen atmosphere, triethylamine (1.08 ml, 7.8 mmol) and methanesulfonyl chloride (0.52 ml, 6.8 mmol) were added to a methylene chloride solution (30 ml) of 2-[(2,5-difluorophenyl)-hydroxymethyl]-5-(1,3-dioxolan-2-yl)pyridine (1.52 g, 5.2 mmol) under ice cooling and the resulting mixture was stirred at room temperature for 3 hours. After the addition of a saturated aqueous solution of sodium bicarbonate, the resulting mixture was extracted with ether. The solution was washed with brine, dried over anhydrous magnesium sulfate and concentrated under reduced pressure.

The residue was dissolved in dimethylformamide (30 ml). To the resulting solution were added chlorobenzenethiol (901 mg, 6.2 mmol) and potassium carbonate (1.08 g, 7.8 mmol) and the mixture was stirred at 60° C. for 3 hours. After cooling to room temperature, the reaction mixture was diluted with ether. The solution was washed with water and brine, dried over anhydrous magnesium sulfate, and concentrated under reduced pressure. The residue thus obtained was purified by silica gel chromatography (hexane:ethyl acetate=5:1), whereby the title compound (1.56 g, 71%) was obtained as colorless needle crystals.

$^1$H-NMR (400 MHz, CDCl$_3$) δ: 4.0-4.15 (4H, m), 5.84 (1H, s), 5.92 (1H, s), 6.85-6.96 (2H, m), 7.19 (2H, d, J=8.8 Hz), 7.25-(2H, d, J=8.8 Hz), 7.43 (1H, d, J=8.0 Hz), 7.43 (1H, m), 7.77 (1H, dd, J=2.0, 8.0 Hz), 8.70 (1H, d, J=2.0 Hz).

IR (ATR) cm$^{-1}$: 1489, 1475, 1091, 814.

mp: 70-73° C.

MS m/z: 420 (M$^+$+H).

Example 330

2-[(4-Chlorophenylsulfonyl)-(2,5-difluorophenyl) methyl]-5-(1,3-dioxolan-2-yl)pyridine

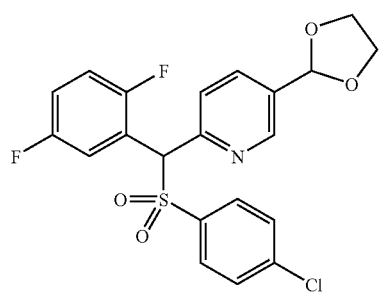

Hexaammonium heptamolybdate tetrahydrate (150 mg) was added to a solution of 2-[(4-chlorophenylthio)-(2,5-difluorophenyl)methyl]-5-(1,3-dioxolan-2-yl)pyridine (1.54 g, 3.67 mmol) in methanol (30 ml). To the resulting mixture was added a 30% aqueous hydrogen peroxide solution (15 ml), followed by stirring for 24 hours. The reaction mixture was diluted with ethyl acetate. The solution was washed with water and brine, and concentrated under reduced pressure. The residue was crystallized from ethanol, whereby the title compound (1.22 g, 74%) was obtained as colorless needle crystals.

$^1$H-NMR (400 MHz, CDCl$_3$) δ: 4.02-4.10 (4H, m), 5.85 (1H, s), 5.97 (1H, s), 6.91 (1H, m), 6.96 (1H, m), 7.38 (2H, d, J=8.4 Hz), 7.53 (2H, d, J=8.4 Hz), 7.63 (1H, d, J=7.6 Hz), 7.82 (1H, d, J=8.0 Hz), 7.94 (1H, m), 8.67 (1H, br-s).

IR (ATR) cm$^{-1}$: 1488, 1319, 1232, 1149, 823.

mp: 167-168° C.

MS m/z: 452 (M$^+$+H).

FAB-MS: 452.0544 (Calcd for C$_{21}$H$_{17}$ClF$_2$NO$_4$S: 452.0535).

Example 331

2-[(4-Chlorophenylsulfonyl)-(2,5-difluorophenyl) methyl]-5-(hydroxymethyl)pyridine

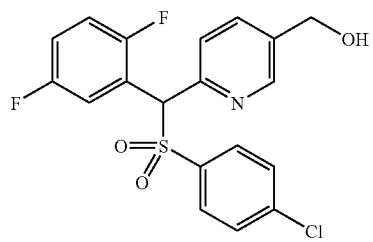

To a 1,4-dioxane solution (30 ml) of 2-[(4-chlorophenylsulfonyl)-(2,5-difluorophenyl)methyl]-5-(1,3-dioxolan-2-yl)pyridine (295 mg, 0.54 mmol) was added 1N hydrochloric acid (30 ml) and the resulting mixture was stirred at room temperature for 18 hours. The reaction mixture was extracted with ethyl acetate. The extract was washed with water, a saturated aqueous solution of sodium bicarbonate and brine, dried over anhydrous magnesium sulfate and concentrated under reduced pressure.

The residue was dissolved in ethanol (10 ml). To the resulting solution was added sodium borohydride (10 mg, 0.27 mmol) under ice cooling, followed by stirring for 1 hour. Water was added and the mixture was extracted with ethyl acetate. The extract was washed with water and brine, dried over anhydrous magnesium sulfate and concentrated under reduced pressure. The residue thus obtained was purified by silica gel chromatography (3% methanol/chloroform), whereby the title compound (205 mg, 93%) was obtained as needle crystals.

$^1$H-NMR (400 MHz, CDCl$_3$) δ: 4.74 (2H, s), 5.94 (1H, s), 6.91 (1H, m), 6.99 (1H, m), 7.38 (2H, d, J=8.4 Hz), 7.53 (2H, d, J=8.4 Hz), 7.62 (1H, d, J=8.0 Hz), 7.76 (1H, dd, J=2.0, 8.0 Hz), 7.98 (1H, m), 8.58 (1H, d, J=2.0 Hz).

IR (ATR) cm$^{-1}$: 3410, 1489, 1321, 1240, 1147, 1012, 818.

mp: 151-152° C.

MS m/z: 410 (M$^+$+H).

FAB-MS: 410.0444 (Calcd for C$_{19}$H$_{15}$ClF$_2$NO$_3$S: 410.0429).

Example 332

Methyl 3-[6-[(4-chlorophenylsulfonyl)-(2,5-difluorophenyl)methyl]pyridin-3-yl]acrylate

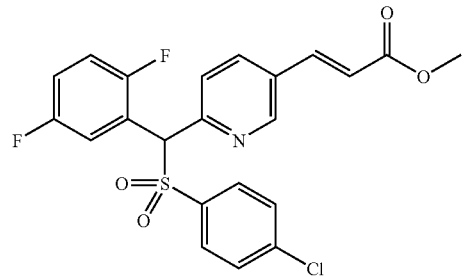

To a 1,4-dioxane solution (10 ml) of the 2-[(4-chlorophenylsulfonyl)-(2,5-difluorophenyl)methyl]-5-(1,3-dioxolan- 2-yl)pyridine (212 mg, 0.47 mmol) obtained in Example 330 was added 1N hydrochloric acid (10 ml) and the mixture was stirred at room temperature for 19 hours. The solution was extracted with ethyl acetate. The extract was washed with water, a saturated aqueous solution of sodium bicarbonate and brine, dried over anhydrous magnesium sulfate and concentrated under reduced pressure.

The residue thus obtained was dissolved in tetrahydrofuran (15 ml) and under nitrogen atmosphere, methyl(triphenylphosphoranylidene)acetate (188 mg, 0.56 mmol) was added to the resulting solution. The mixture was stirred for 17 hours. The reaction mixture was concentrated under reduced pressure. The residue was purified by silica gel chromatography (hexane:ethyl acetate=5:1), whereby the title compound (187 mg, 86%) was obtained as needle crystals.

$^1$H-NMR (400 MHz, CDCl$_3$) δ: 3.80 (3H, s), 5.94 (1H, s), 6.50 (1H, d, J=16.0 Hz), 6.91 (1H, m), 6.99 (1H, m), 7.38 (2H, d, J=8.8 Hz), 7.53 (2H, d, J=8.8 Hz), 7.63 (1H, d, J=8.0 Hz), 7.63 (1H, d, J=16.0 Hz), 7.84 (1H, dd, J=2.0, 8.0 Hz), 7.98 (1H, m), 8.70 (1H, d, J=2.0 Hz).

IR (ATR) cm$^{-1}$: 1710, 1496, 1389, 1327, 1149, 1084, 816, 760.

mp: 145-146° C.

MS m/z: 464 (M$^+$+H).

Example 333

Methyl 3-[6-[(4-chlorophenylsulfonyl)-(2,5-difluorophenyl)methyl]pyridin-3-yl]propionate

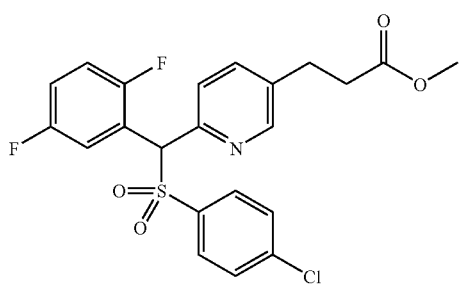

Methyl 3-[6-[(4-chlorophenylsulfonyl)-(2,5-difluorophenyl)methyl]pyridin-3-yl]acrylate (160 mg, 0.34 mmol) was dissolved in ethanol (15 ml). Palladium on carbon (30 mg) was added and the resulting mixture was vigorously stirred under 1 atm hydrogen atmosphere for 24 hours. The reaction mixture was filtered and then, concentrated under reduced pressure. The residue was purified by silica gel chromatography (hexane:ethyl acetate=5:1), whereby the title compound (94 mg, 58%) was obtained as needle crystals.

$^1$H-NMR (400 MHz, CDCl$_3$) δ: 2.63 (2H, t, J=7.6 Hz), 2.95 (2H, t, J=7.6 Hz), 3.65 (3H, s), 5.89 (1H, s), 6.90 (1H, m), 6.97 (1H, m), 7.36 (2H, d, J=8.4 Hz), 7.53 (2H, d, J=8.4 Hz), 7.55 (2H, m), 8.00 (1H, m), 8.45 (1H, d, J=1.6 Hz).

IR (ATR) cm$^{-1}$: 1731, 1489, 1319, 1225, 1147, 821.

mp: 121-123° C.

MS m/z: 466 (M$^+$+H).

Example 334

3-[6-[(4-Chlorophenylsulfonyl)-(2,5-difluorophenyl)methyl]pyridin-3-yl]propionic Acid

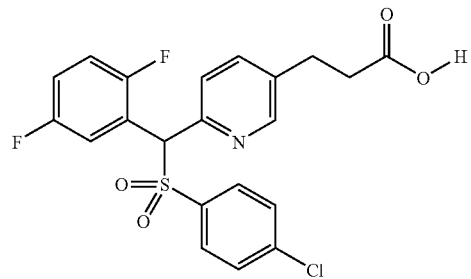

In tetrahydrofuran (5 ml) was dissolved methyl 3-[6-[(4-chlorophenylsulfonyl)-(2,5-difluorophenyl)methyl]pyridin-3-yl]propionate (92 mg, 0.20 mmol). An aqueous solution (3 ml) of lithium hydroxide (23 mg, 0.5 mmol) was added and the mixture was stirred for 2 hours. After the addition of 10% sodium bisulfate, the mixture was extracted with ethyl acetate. The extract was washed with water and brine, dried over anhydrous magnesium sulfate and then concentrated under reduced pressure. The residue thus obtained was crystallized from ethanol to yield the title compound (67 mg, 75%) as needle crystals.

$^1$H-NMR (400 MHz, CDCl$_3$) δ: 2.69 (2H, t, J=7.6 Hz), 2.96 (2H, t, J=7.6 Hz), 5.92 (1H, s), 6.90 (1H, m), 6.98 (1H, m), 7.36 (2H, d, J=8.4 Hz), 7.52 (2H, d, J=8.4 Hz), 7.56 (2H, m), 7.99 (1H, m), 8.47 (1H, d, J=2.4 Hz).

IR (ATR) cm$^{-1}$: 1704, 1489, 1309, 1216, 1149, 1081, 827.

mp: 158-160° C.

MS m/z: 452 (M$^+$+H).

Anal. calcd for C$_{21}$H$_{16}$ClF$_2$NO$_4$S: C, 55.82%; H, 3.57%; N, 3.10%; S, 7.10%; Cl, 7.85%; F, 8.41%. Found: C, 55.70%; H, 3.75%; N, 3.19%; S, 7.12%; Cl, 8.64%; F, 8.11%.

Example 335

[6-[(4-Chlorophenylsulfonyl)-(2,5-difluorophenyl)methyl]pyridin-3-yl]carbaldehyde

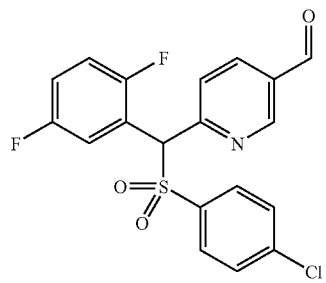

To a 1,4-dioxane solution (30 ml) of the 2-[(4-chlorophenylsulfonyl)-(2,5-difluorophenyl)methyl]-5-(1,3-dioxolan-2-yl)pyridine (602 mg, 1.3 mmol) obtained in Example 330 was added 1N hydrochloric acid (30 ml). The resulting mixture was stirred at room temperature for 18 hours. The solution was extracted with ethyl acetate, followed by successive washing with water, a saturated aqueous solution of sodium

Example 336

2-[(4-Chlorophenylsulfonyl)-(2,5-difluorophenyl)methyl]-5-(piperidin-1-ylmethyl)pyridine

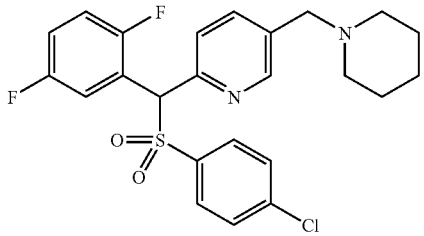

To a methylene chloride solution (5 ml) of [6-[(4-chlorophenylsulfonyl)-(2,5-difluorophenyl)methyl]pyridin-3-yl]carbaldehyde (82 mg, 0.2 mmol) and piperidine (40 μl, 0.4 mmol) were added acetic acid (23 μl, 0.4 mmol) and sodium triacetoxyborohydride (85 mg, 0.4 mmol) at room temperature. The mixture was stirred for 3 hours. After the reaction was quenched by the addition of a saturated aqueous solution of sodium bicarbonate, the mixture was diluted with ethyl acetate (80 ml). The organic layer obtained by separation was washed with water and brine, dried and then concentrated under reduced pressure. The residue thus obtained was purified by silica gel chromatography (hexane:ethyl acetate=1:1), followed by crystallization from ethanol to yield the title compound (89 mg, 93%).

$^1$H-NMR (400 MHz, CDCl$_3$) δ: 1.5-1.6 (6H, m), 2.3-2.4 (4H, m), 3.45 (2H, s), 5.91 (1H, s), 6.90 (1H, m), 6.98 (1H, m), 7.35 (2H, d, J=8.4 Hz), 7.52 (2H, d, J=8.4 Hz), 7.53 (1H, m), 7.7 (1H, br), 8.02 (1H, m), 8.49 (1H, d, J=2.4 Hz).

IR (ATR) cm$^{-1}$: 1583, 1487, 1321, 1149, 827, 725.
mp: 113-114° C.
MS m/z: 477 (M$^+$+H).
Anal. calcd for C$_{24}$H$_{23}$ClF$_2$N$_2$O$_2$S: C, 60.44%; H, 4.86%; N, 5.87%; S, 6.72%; Cl, 7.43%; F, 7.97%. Found: C, 59.87%; H, 4.81%; N, 5.83%; S, 6.87%; Cl, 7.55%; F, 8.02%.

Example 337

4-[[6-[(4-Chlorophenylsulfonyl)-(2,5-difluorophenyl)methyl]pyridin-3-yl]methyl]morpholine

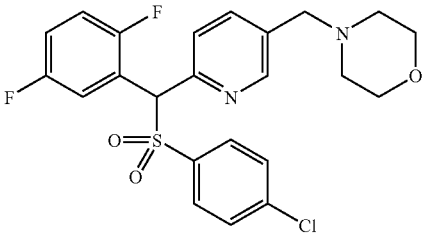

To a methylene chloride solution (5 ml) of the [6-[(4-chlorophenylsulfonyl)-(2,5-difluorophenyl)methyl]pyridin-3-yl]carbaldehyde (82 mg, 0.2 mmol) obtained in Example 335 and morpholine (35 μl, 0.4 mmol) were added acetic acid (23 μl, 0.4 mmol) and sodium triacetoxyborohydride (85 mg, 0.4 mmol) at room temperature. The resulting mixture was stirred for 3 hours. After a saturated aqueous solution of sodium bicarbonate was added to quench the reaction, ethyl acetate (80 ml) was added to dilute the reaction mixture. The organic layer obtained by separation was washed with water and brine, dried and concentrated under reduced pressure. The residue thus obtained was purified by silica gel chromatography (hexane:ethyl acetate=1:1), followed by crystallization from ethanol to yield the title compound (90 mg, 94%).

$^1$H-NMR (400 MHz, CDCl$_3$) δ: 2.4 (4H, m), 3.49 (2H, s), 3.6 (4H, m), 5.92 (1H, s), 6.90 (1H, m), 6.98 (1H, m), 7.36 (2H, d, J=8.4 Hz), 7.53 (2H, d, J=8.4 Hz), 7.57 (1H, d, J=8.0 Hz), 7.71 (1H, br-d, J=8.0 Hz), 8.02 (1H, m), 8.53 (1H, d, J=2.0 Hz).

IR (ATR) cm$^{-1}$: 1583, 1484, 1321, 1149, 1116, 827, 725.
mp: 120-121° C.
MS m/z: 479 (M$^+$+H).
Anal. calcd for C$_{22}$H$_{21}$ClF$_2$N$_2$O$_3$S: C, 57.68%; H, 4.42%; N, 5.85%; S, 6.70%; Cl, 7.40%; F, 7.93%. Found: C, 57.41%; H, 4.43%; N, 5.90%; S, 6.82%; Cl, 7.52%; F, 7.91%.

Example 338

[6-[(4-Chlorophenylsulfonyl)-(2,5-difluorophenyl)methyl]pyridin-3-yl]carboxylic Acid

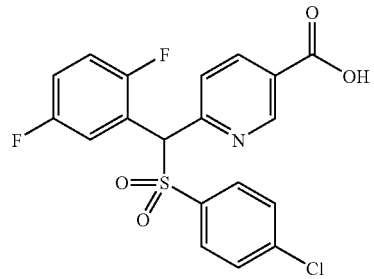

To a t-butanol solution (3.0 ml) of the [6-[(4-chlorophenylsulfonyl)-(2,5-difluorophenyl)methyl]pyridin-3-yl]carbaldehyde (110 mg, 0.27 mmol) obtained in Example 335 was added 2-methyl-2-butene (143 μl, 1.35 mmol). An aqueous solution (0.6 ml) of sodium dihydrogen phosphate (32.4 mg, 0.27 mmol), and sodium chlorite (98 mg, 1.08 mmol) were added successively to the resulting suspension and the mixture was stirred for 2 hours. To the reaction mixture were added water (30 ml) and acetic acid (1 ml). The mixture was extracted with ethyl acetate (100 ml). The extract was washed with brine, dried and distilled under reduced pressure. The residue thus obtained was crystallized from ethanol, whereby the title compound (71 mg, 62%) was obtained as colorless needle crystals.

$^1$H-NMR (400 MHz, CDCl$_3$) δ: 6.03 (1H, s), 6.96 (1H, m), 7.03 (1H, m), 7.42 (2H, d, J-8.4 Hz), 7.56 (2H, d, J=8.4 Hz), 7.73° (1H, d, J=8.4 Hz), 7.97 (1H, m), 8.35 (1H, dd, J=2.0, 8.4 Hz), 9.20 (1H, d, J=2.0 Hz).

IR (ATR) cm$^{-1}$: 1685, 1596, 1498, 1322, 1153, 1085, 754.
mp: >230° C.
MS m/z: 424 (M$^+$+H).
Anal. calcd for C$_{19}$H$_{12}$ClF$_2$NO$_4$S: C, 53.84%; H, 2.85%; N, 3.30%; S, 7.57%; Cl, 8.37%; F, 8.97%. Found: C, 53.47%; H, 2.81%; N, 3.46%; S, 7.65%; Cl, 8.49%; F, 9.00%.

Example 339

3-[(4-Chlorophenylsulfonyl)-(2,5-difluorophenyl)methyl]pyridin-N-oxide

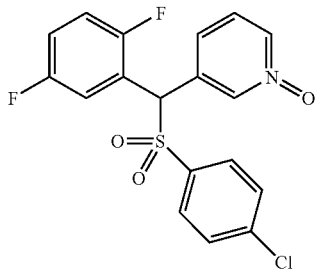

To a methylene chloride solution (15 ml) of the 3-[(4-chlorophenylsulfonyl)-(2,5-difluorophenyl)methyl]pyridine (162 mg, 0.427 mmol) obtained in Example 141 was added 3-chloroperbenzoic acid (81 mg, 0.47 mmol) and the mixture was stirred for 24 hours. The reaction mixture was diluted with ether (60 ml), followed by washing with a saturated aqueous solution of sodium bicarbonate, water and brine. After drying, the solution was filtered and the filtrate was concentrated under reduced pressure. The residue thus obtained was subjected to silica gel chromatography (ethyl acetate), whereby the title compound (68 mg, 40%) was obtained. The compound was crystallized from ethanol and was obtained as colorless needle crystals.

$^1$H-NMR (400 MHz, CDCl$_3$) δ: 5.58 (1H, s), 6.95 (1H, m), 7.03 (1H, m), 7.29 (1H, dd, J=6.6, 8.0 Hz), 7.42 (2H, d, J=8.6 Hz), 7.57 (1H, d, J=8.0 Hz), 7.62 (2H, d, J=8.4 Hz), 7.66 (1H, m), 8.10 (1H, d, J=6.6 Hz), 8.29 (1H, s).

IR (ATR) cm$^{-1}$: 1573, 1492, 1438, 1329, 1248, 1151, 1081, 820.

mp: 183-184° C.

MS m/z: 396(M$^+$+H).

Anal. calcd for C$_{18}$H$_{12}$ClF$_2$NO$_3$S: C, 54.62%; H, 3.06%; N, 3.54%; S, 8.10%; Cl, 8.96%; F, 9.60%. Found: C, 54.19%; H, 2.99%; N, 3.67%; S, 8.27%; Cl, 8.92%; F, 9.53%.

Example 340

4-[(4-Chlorophenylsulfonyl)-(2,5-difluorophenyl)methyl]pyridin-N-oxide

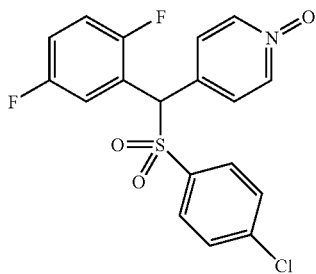

To a methylene chloride solution (20 ml) of the 4-[(4-chlorophenylsulfonyl)-(2,5-difluorophenyl)methyl]pyridine (221 mg, 0.58 mmol) obtained in Example 142 was added 3-chloroperbenzoic acid (100 mg, 0.58 mmol) and the mixture was stirred for 20 hours. The reaction mixture was diluted with ether (60 ml), followed by washing with a saturated aqueous solution of sodium bicarbonate, water and brine. The solution was dried and then filtered. The filtrate was then concentrated under reduced pressure. The residue thus obtained was subjected to silica gel chromatography (ethyl acetate) to yield the title compound (183 mg, 80%). The compound was then crystallized from ethanol and obtained as colorless needle crystals.

$^1$H-NMR (400 MHz, CDCl$_3$) δ: 5.62 (1H, s), 6.97 (1H, m), 7.06 (1H, m), 7.42 (2H, d, J=7.2 Hz), 7.44 (2H, d, J=8.8 Hz), 7.60 (2H, d, J=8.8 Hz), 7.68 (1H, m), 8.17 (2H, d, J=7.2 Hz).

IR (ATR) cm$^{-1}$: 1479, 1322, 1263, 1149, 1081, 813.

mp: 211-212° C.

MS m/z: 396(M$^+$+H).

Anal. calcd for C$_{18}$H$_{12}$ClF$_2$NO$_3$S: C, 54.62%; H, 3.06%; N, 3.54%; S, 8.10%; Cl, 8.96%; F, 9.60%. Found: C, 54.19%; H, 2.92%; N, 3.65%; S, 8.26%; Cl, 8.99%; F, 9.61%.

Referential Example 48

3-Chloro-4-[(2,5-difluorophenyl)-hydroxymethyl]pyridine

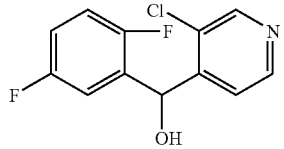

To a tetrahydrofuran solution (14 ml) of diisopropylamine (1.4 ml, 10 mmol) was added n-butyl lithium (6.3 ml, 1.59M hexane solution) at −78° C. and the mixture was stirred for 10 minutes. Then, 3-chloropyridine (1.13 g, 10 mmol) was added to the resulting mixture. Thirty minutes later, 2,5-difluorobenzaldehyde (1.09 ml, 10 mmol) was added to the mixture. The mixture was warmed gradually to 0° C., at which stirring was conducted for further 10 minutes. An aqueous solution of ammonium chloride was added and the mixture was diluted with ethyl acetate (80 ml). The organic layer obtained by separation was washed with brine and then dried. After filtration, the filtrate was concentrated under reduced pressure. The precipitate thus obtained was triturated with ethanol to yield the title compound (1.33 g, 52%).

$^1$H-NMR (400 MHz, CDCl$_3$) δ: 4.87 (1H, br), 6.26 (1H, s), 6.90-7.02 (3H, m), 7.58 (1H, d, J=4.8 Hz), 8.47 (1H, s), 8.48 (1H, d, J=4.8 Hz).

IR (ATR) cm$^{-1}$: 3178, 1592, 1490, 1174, 1039.

mp: 169-170° C.

MS m/z: 255(M$^+$).

Referential Example 49

2,5-Dichloro-4-[(2,5-difluorophenyl)-hydroxymethyl]pyridine

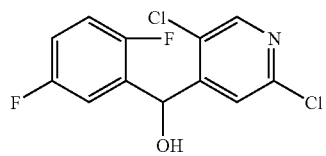

To a tetrahydrofuran solution (14 ml) of diisopropylamine (1.4 ml, 10 mmol) was added n-butyl lithium (6.3 ml, 1.59M hexane solution) at −78° C. After stirring for 10 minutes, 2,5-dichloropyridine (1.48 g, 10 mmol) was added. Thirty minutes later, 2,5-difluorobenzaldehyde (1.09 ml, 10 mmol) was added to the mixture. The resulting mixture was warmed gradually to 0° C. and stirring was conducted for further 10 minutes. An aqueous solution of ammonium chloride was added and the mixture was diluted with ethyl acetate (80 ml). The organic layer was separated, washed with brine and dried. After filtration, the filtrate was concentrated under reduced pressure. The precipitate thus obtained was triturated with ethanol to yield the title compound (1.93 g, 67%).

$^1$H-NMR (400 MHz, CDCl$_3$) δ: 2.64 (1H, d, J=4.0 Hz), 6.28 (1H, d, J=4.0 Hz), 6.89 (1H, m), 7.02 (2H, m), 7.64 (1H, s), 8.30 (1H, s).

IR (ATR) cm$^{-1}$: 3226, 1579, 1492, 1243, 1110, 1062.

Mp: 160-161° C.

MS m/z: 289(M$^+$).

Example 341

3-Chloro-4-[(4-chlorophenylthio)-(2,5-difluorophenyl)methyl]pyridine

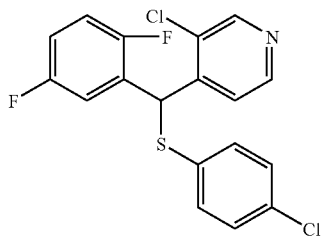

After 3-chloro-4-[(2,5-difluorophenyl)-hydroxymethyl]pyridine (511 mg, 2.0 mmol) which had been obtained in Referential Example 48 was dissolved in thionyl chloride (3.0 ml), a catalytic amount of dimethylformamide was added threto. The resulting mixture was stirred for 17 hours. The reaction mixture was concentrated under reduced pressure. Toluene was added to the residue and the mixture was concentrated further.

The residue was dissolved in dimethylformamide (10 ml), followed by the addition of 4-chlorobenzenethiol (375 mg, 2.6 mmol) and potassium carbonate (414 mg, 3 mmol) under nitrogen atmosphere. The resulting mixture was stirred at 60° C. for 3 hours. After the reaction mixture was cooled to room temperature, diethyl ether (60 ml) was added. The mixture was washed with water and brine. The organic layer was dried over magnesium sulfate, and concentrated under reduced pressure. The residue was subjected to silica gel chromatography (hexane:ethyl acetate=8:1), whereby the title compound (196 mg, 26%) was obtained as a solid.

$^1$H-NMR (400 MHz, CDCl$_3$) δ: 6.07 (1H, s), 6.95-7.08 (2H, m), 7.18 (1H, m), 7.23 (2H, d, J=8.8 Hz), 7.26 (2H, d, J=8.8 Hz), 7.58 (1H, d, J=5.2 Hz), 8.51 (1H, d, J=5.2 Hz), 8.58 (1H, s).

IR (ATR) cm$^{-1}$: 1577, 1473, 1211, 1089, 1012, 817.

mp: 70-72° C.

MS m/z: 382 (M$^+$+1).

Example 342

2,5-Dichloro-4-[(4-chlorophenylthio)-(2,5-difluorophenyl)methyl]pyridine

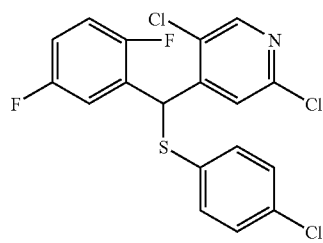

After the 2,5-dichloro-4-[(2,5-difluorophenyl)-hydroxymethyl]pyridine (580 mg, 2.0 mmol) obtained in Referential Example 49 was dissolved in thionyl chloride (3.0 ml), a catalytic amount of dimethylformamide was added and the resulting mixture was stirred for 17 hours. The reaction mixture was concentrated under reduced pressure. Toluene was added to the residue and the mixture was concentrated further.

The residue was dissolved in dimethylformamide (10 ml), followed by the addition of 4-chlorobenzenethiol (375 mg, 2.6 mmol) and potassium carbonate (414 mg, 3 mmol) under nitrogen atmosphere. The mixture was stirred at 50° C. for 17 hours. After cooling to room temperature, diethyl ether (60 ml) was added to the mixture. The mixture was washed with water and brine. The organic layer was dried over magnesium sulfate, and concentrated under reduced pressure. The residue was subjected to silica gel chromatography (hexane:ether=10:1), whereby the title compound (484 mg, 58%) was obtained as a solid.

$^1$H-NMR (400 MHz, CDCl$_3$) δ: 5.96 (1H, s), 6.95-7.04 (2H, m), 7.01 (1H, m), 7.23 (2H, d, J=8.8 Hz), 7.26 (2H, d, J=8.8 Hz), 7.54 (1H, s), 8.33 (1H, s).

IR (ATR) cm$^{-1}$: 1570, 1495, 1473, 1326, 1207, 1090, 1012, 816.

mp: 128-129° C.

MS m/z: 416 (M$^+$+1).

Example 343

3-Chloro-4-[(4-chlorophenylsulfonyl)-(2,5-difluorophenyl)methyl]pyridine

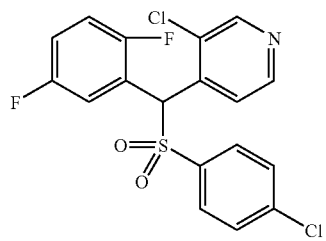

Hexaammonium heptamolybdate tetrahydrate (60 mg) and a 30% aqueous hydrogen peroxide solution (6 ml) were successively added to a solution of the 3-chloro-4-[(4-chlorophenylthio)-(2,5-difluorophenyl)methyl]pyridine (122 mg, 0.32 mmol), which had been obtained in Example 341, in methanol (12 ml). The resulting mixture was stirred for 24 hours. The reaction mixture was diluted with ethyl acetate. The solution was washed with water and brine, and concentrated under reduced pressure. The residue was crystallized from ethanol, whereby the title compound (103 mg, 78%) was obtained as colorless needle crystals.

$^1$H-NMR (400 MHz, CDCl$_3$) δ: 6.23 (1H, s), 6.94 (1H, m), 7.06 (1H, m), 7.41 (2H, d, J=8.0 Hz), 7.53 (1H, m), 7.59 (2H, d, J=8.0 Hz), 8.11 (1H, d, J=5.2 Hz), 8.55 (1H, s), 8.60 (1H, d, J=5.2 Hz).

IR (ATR) cm$^{-1}$: 1577, 1490, 1321, 1311, 1151, 1083, 821.

mp: 160-161° C.

MS m/z: 414(M$^+$+H).

Anal. calcd for C$_{18}$H$_{11}$Cl$_2$F$_2$NO$_2$S: C, 52.19%; H, 2.68%; N, 3.38%; S, 7.74%; Cl, 17.12%; F, 9.17%. Found: C, 52.17%; H, 2.69%; N, 3.44%; S, 7.96%; Cl, 17.12%; F, 9.00%.

Example 344

3-Chloro-4-[(4-chlorophenylsulfinyl)-(2,5-difluorophenyl)methyl]pyridine

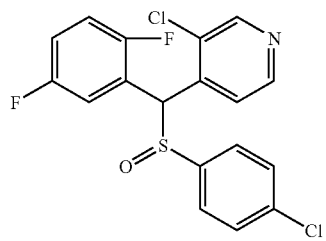

After 3-chloroperbenzoic acid (33 mg, 0.20 mmol) was added to a solution of the 3-chloro-4-[(4-chlorophenylthio)-(2,5-difluorophenyl)methyl]pyridine (75 mg, 0.20 mmol), which had been obtained in Example 341, in methylene chloride (10 ml), the mixture was stirred for 3 hours under ice cooling. The reaction mixture was diluted with ether (80 ml). The solution was washed with water and brine, and then concentrated under reduced pressure. The residue was purified by silica gel chromatography (hexane:ethyl acetate=3:1), whereby the title compound (48 mg, 60%) was obtained as a diastereomeric mixture (1:1).

$^1$H-NMR (400 MHz, CDCl$_3$) δ: 5.53 (½H, s), 5.66 (½H, s), 6.83 (½H, s), 6.95-7.08 (3/2H, m), 7.23 (½H, m), 7.25 (1H, d, J=8.4 Hz), 7.26 (1H, d, J=8.4 Hz), 7.34 (1H, d, J=8.4 Hz), 7.36 (1H, d, J=8.4 Hz), 7.37 (½H, m), 7.76 (½H, d, J=5.2 Hz), 7.98 (½H, d, J=5.2 Hz), 8.47 (½H, s), 8.56 (½H, d, J=5.2 Hz), 8.60 (½H, s), 8.61 (½H, d, J=5.2 Hz).

IR (ATR) cm$^{-1}$: 1577, 1490, 1396, 1168, 1049, 1033, 817.

MS m/z: 398 (M$^+$+H).

FAB-MS: 397.9992 (Calcd for C$_{18}$H$_{12}$Cl$_2$F$_2$NOS: 397.9985).

Example 345

2,5-Dichloro-4-[(4-chlorophenylsulfonyl)-(2,5-difluorophenyl)methyl]pyridine 0.5 hydrate

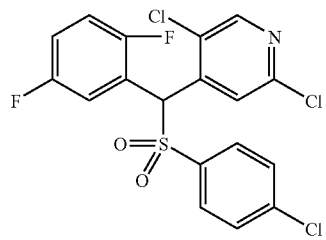

After 3-chloroperbenzoic acid (62 mg, 0.36 mmol) was added to a solution of the 2,5-dichloro-4-[(4-chlorophenylthio)-(2,5-difluorophenyl)methyl]pyridine (60 mg, 0.14 mmol), which had been obtained in Example 342, in methylene chloride (3.0 ml), the mixture was stirred at room temperature for 3 hours. The reaction mixture was diluted with ether (80 ml). The solution was washed with a saturated aqueous solution of sodium bicarbonate and brine, and then, concentrated under reduced pressure. The residue was purified by silica gel chromatography (hexane:ethyl acetate=5:1) and crystallized from hexane to yield the title compound (55 mg, 88%).

$^1$H-NMR (400 MHz, CDCl$_3$) δ: 6.15 (1H, s), 6.93 (1H, m), 7.05 (1H, m), 7.44 (2H, d, J=8.8 Hz), 7.50 (1H, m), 7.59 (2H, d, J=8.8 Hz), 8.13 (1H, s), 8.55 (1H, s), 8.33 (1H, s).

IR (ATR) cm$^{-1}$: 1569, 1492, 1321, 1147, 1118, 1083, 821.

mp: 147-148° C.

MS m/z: 448(M$^+$+H).

Anal. calcd for C$_{18}$H$_{11}$Cl$_3$F$_2$NO$_2$S,0.5H$_2$O: C, 47.23%; H, 2.42%; N, 3.06%; S, 7.01%; Cl, 23.24%; F, 8.30%. Found: C, 47.25%; H, 2.24%; N, 3.21%; S, 7.19%; Cl, 23.25%; F, 8.32%.

FAB-MS: 447.9572 (Calcd for C$_{18}$H$_{11}$Cl$_3$F$_2$NO$_2$S: 447.9544).

Example 346

4-[5-Chloro-4-[(4-chlorophenylthio)-(2,5-difluorophenyl)methyl]pyridin-2-yl]morpholine

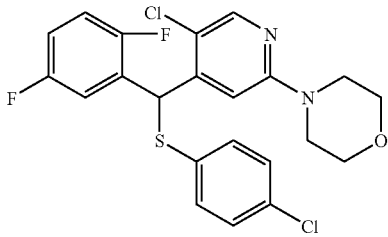

A solution of the 2,5-dichloro-4-[(4-chlorophenylthio)-(2,5-difluorophenyl)methyl]pyridine (100 mg, 0.24 mmol) obtained in Example 342 and morpholine (200 µl) in 1,4-dioxane (1.0 ml) was stirred under nitrogen atmosphere at 100° C. for 2 days. The reaction mixture was cooled to room temperature. After dilution with ethyl acetate (40 ml), the solution was washed with water and brine, dried and concentrated under reduced pressure. The residue thus obtained was purified by silica gel chromatography (hexane:ethyl acetate=5:1) to yield the title compound (100 mg, 89%) as an oil.

$^1$H-NMR (400 MHz, CDCl$_3$) δ: 3.48 (4H, m), 3.82 (4H, m), 6.00 (1H, s), 6.94 (1H, s), 6.94-7.04 (2H, m), 7.09 (1H, m), 7.23 (2H, d, J=8.4 Hz), 7.24 (2H, d, J=8.4 Hz), 8.12 (1H, s).

MS m/z: 467 (M$^+$+H).

Example 347

4-[5-Chloro-4-[(4-chlorophenylsulfonyl)-(2,5-difluorophenyl)methyl]pyridin-2-yl]morpholine

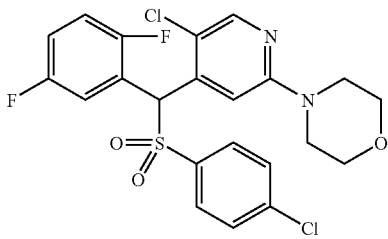

To a solution of 4-[5-chloro-4-[(4-chlorophenylthio)-(2,5-difluorophenyl)methyl]pyridin-2-yl]morpholine (90 mg, 0.19 mmol) in methanol (12 ml) was added hexaammonium heptamolybdate tetrahydrate (60 mg), followed by the addition of a 30% aqueous hydrogen peroxide solution (6 ml). The resulting mixture was stirred for 8 hours. After dilution with ethyl acetate, the solution was washed with water and brine and then, concentrated under reduced pressure. The residue was subjected to silica gel chromatography (hexane:ethyl acetate=3:1) and then, crystallized from, ethanol, whereby the title compound (80 mg, 83%) was obtained as colorless needle crystals.

$^1$H-NMR (400 MHz, CDCl$_3$) δ: 3.54 (4H, m), 3.84 (4H, m), 6.12 (1H, s), 6.90 (1H, m), 7.02 (1H, m), 7.42 (2H, d, J=8.4 Hz), 7.45 (1H, s), 7.46(1H, m), 7.58 (2H, d, J=8.4 Hz), 8.06 (1H, s).

IR (ATR) cm$^{-1}$: 1585, 1494, 1475, 1317, 1240, 1145, 1091, 831.

mp: 180-181° C.

MS m/z: 499 (M$^+$+H).

Anal. calcd for C$_{22}$H$_{18}$Cl$_2$F$_2$N$_2$O$_3$S: C, 52.92%; H, 3.63%; N, 5.61%; S, 6.42%; Cl, 14.20%; F, 7.61%. Found: C, 52.68%; H, 3.56%; N, 5.69%; S, 6.70%; Cl, 14.32%; F, 7.97%

Example 348

4-[2-[5-Chloro-4-[(4-chlorophenylthio)-(2,5-difluorophenyl)methyl]pyridin-2-yl]aminoethyl]morpholine

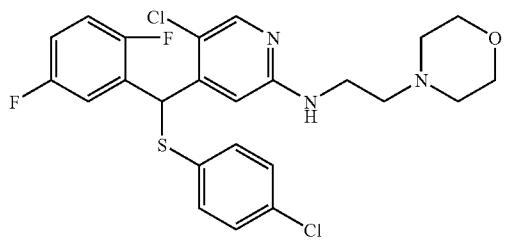

Under nitrogen atmosphere, a solution of the 2,5-dichloro-4-[(4-chlorophenylthio)-(2,5-difluorophenyl)methyl]pyridine (100 mg, 0.24 mmol) obtained in Example 342 and 4-(2-aminoethyl)morpholine (200 µl) in 1,4-dioxane (1.0 ml) was stirred at 100° C. for 2 days. After cooling to room temperature, the reaction mixture was diluted with ethyl acetate (40 ml). The solution was washed with water and brine, dried and then concentrated under reduced pressure. The residue thus obtained was purified by silica gel chromatography (3% methanol/chloroform), whereby the title compound (12 mg, 10%) was obtained as an oil.

$^1$H-NMR (400 MHz, CDCl$_3$) δ: 2.42(4H, m), 2.54(2H, d, J=6.0 Hz), 3.27(2H, q, J=6.0 Hz), 3.67(4H, m), 5.12(br, 1H), 5.90(1H, s), 6.61(1H, s), 6.86-7.0(2H, m), 7.06(1H, m), 7.15 (2H, d, J=8.4 Hz), 7.16 (2H, d, J=8.4 Hz), 7.95 (1H, s).

MS m/z: 510 (M$^+$+H).

Example 349

4-[2-[5-Chloro-4-[(4-chlorophenylsulfonyl)-(2,5-difluorophenyl)methyl]pyridin-2-yl]aminoethyl] morpholine N-Oxide

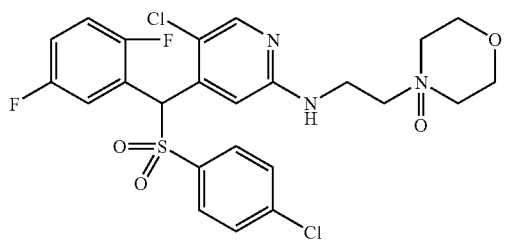

To a solution of 4-[2-[5-chloro-4-[(4-chlorophenylthio)-(2,5-difluorophenyl)methyl]pyridin-2-yl]aminoethyl]morpholine (11 mg, 0.032 mmol) in methanol (12 ml) was added hexaammonium heptamolybdate tetrahydrate (10 mg). A 30% aqueous hydrogen peroxide solution (1 ml) was added to the resulting mixture, followed by stirring for 8 hours. The reaction mixture was diluted with ethyl acetate. The solution was washed with water and brine. After the solution was concentrated under reduced pressure, the residue was purified by silica gel chromatography (3% methanol, 3% t-butylamine/chloroform solution), whereby the title compound (5.0 mg, 42%) was obtained.

$^1$H-NMR (400 MHz, CDCl$_3$) δ: 3.2-3.4 (4H, m), 3.54 (2H, m), 3.81 (2H, m), 3.91 (2H, m), 4.44 (2H, m), 6.09 (1H, s), 6.88 (1H, m), 6.98 (1H, m), 7.22 (1H, s), 7.40 (2H, d, J=8.4 Hz), 7.51 (1H, m), 7.60 (2H, d, J=8.4 Hz), 7.94 (1H, s).

IR (ATR) cm$^{-1}$: 1600, 1494, 1324, 1151, 1085, 754.

MS m/z: 558(M$^+$+H).

FAB-MS: 558.0837 (Calcd for C$_{24}$H$_{24}$Cl$_2$F$_2$N$_3$O$_4$S: 558.0833).

Example 350

5-Azidomethyl-2-[(4-chlorophenylsulfonyl)(2,5-difluorophenyl)methyl]pyridine

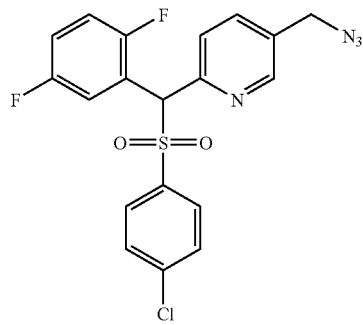

In a mixture of carbon tetrachloride (4 ml) and N,N-dimethylformamide (16 ml) was dissolved the 2-[(4-chlorophenylsulfonyl) (2,5-difluorophenyl)methyl]-5-(hydroxymethyl)pyridine (471 mg, 1.15 mmol) obtained in Example 331. Sodium azide (112 mg, 1.72 mmol) and triphenylphosphine (451 mg, 1.72 mmol) were added and the mixture was stirred at 90° C. for 3 hours. Water was added to the reaction mixture, followed by extraction with ethyl acetate. The organic layer was then washed successively with water and brine, dried over sodium sulfate and concentrated under reduced pressure. The residue thus obtained was subjected to chromatography on a silica gel column. A fraction obtained from the elution portion with hexane:ethyl acetate=3:1 was concentrated under reduced pressure, whereby the title compound (244 mg, 0.561 mmol, 49%) was obtained as a colorless amorphous substance.

$^1$H-NMR (400 MHz, CDCl$_3$) δ: 4.42 (2H, s), 5.96 (1H, s), 6.94 (1H, m), 6.99-7.05 (1H, m), 7.40 (2H, d, J=8.8 Hz), 7.55 (2H, d, J=8.8 Hz), 7.60 (1H, d, J=8.1 Hz), 7.72 (1H, dd, J=8.1, 2.0 Hz), 8.02 (1H, m), 8.57 (1H, d, J=2.0 Hz).

MS m/z: 435 (M$^+$+H).

Example 351

[6-[(4-Chlorophenylsulfonyl)(2,5-difluorophenyl)methyl]pyridin-3-yl]methylamine

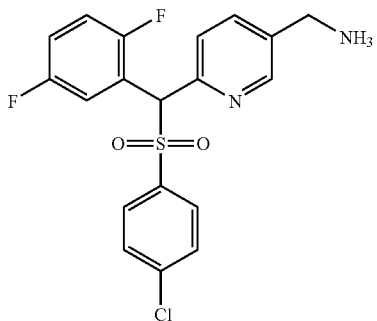

Under argon atmosphere, 5-azidomethyl-2-[(4-chlorophenylsulfonyl)(2,5-difluorophenyl)methyl]pyridine (77 mg, 0.177 mmol), palladium on carbon (14 mg), and ethyl acetate (2 ml) were added to ethanol (10 ml). The resulting mixture was stirred for 50 minutes under 1 atom hydrogen atmosphere. After filtration, the filtrate was concentrated under reduced pressure. The residue thus obtained was subjected to chromatography on a silica gel column. A fraction obtained from the elution portion with dichloromethane:methanol=10:1 was concentrated under reduced pressure, whereby the title compound (28 mg, 0.0685 mmol, 39%) was obtained as a white powder.

$^1$H-NMR (400 MHz, CDCl$_3$) δ: 1.84 (2H, brs), 3.92 (2H, s), 5.94 (1H, s), 6.92 (1H, m), 7.03-6.98 (1H, m), 7.39 (2H, d, J=8.3 Hz), 7.56 (2H, d, J=8.3 Hz), 7.60 (1H, d, J=8.1 Hz), 7.74 (1H, d, J=8.1 Hz), 8.01 (1H, m), 8.57 (1H, s).

MS m/z: 409 (M$^+$+H).

Example 352 tert-Butyl [[6-[(4-chlorophenylsulfonyl)(2,5-difluorophenyl)methyl]pyridin-3-yl]methyl]carbamate

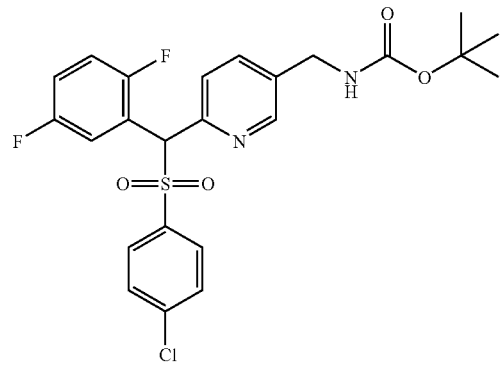

The 5-azidomethyl-2-[(4-chlorophenylsulfonyl)(2,5-difluorophenyl)methyl]pyridine (230 mg, 0.529 mmol) obtained in Example 350 and palladium on carbon (46 mg) were added to a mixture of ethyl acetate (15 ml) and ethanol (15 ml). The resulting mixture was stirred for 45 minutes under 1 atom hydrogen atmosphere. After filtration, the filtrate was concentrated under reduced pressure. The residue thus obtained was dissolved in dichloromethane (5 ml). Triethylamine (70 μl, 0.499 mmol) and di-tert-butyl carbonate (174 mg, 0.996 mmol) were added to the resulting solution. The mixture was stirred at room temperature for 3 days. The reaction mixture was concentrated under reduced pressure. The residue thus obtained was subjected to flash chromatography on a silica gel column. A fraction obtained from the elution portion with hexane:ethyl acetate=4:1 was concentrated under reduced pressure, whereby title compound (78 mg, 0.153 mmol, 37%) was obtained as a colorless amorphous substance.

$^1$H-NMR (400 MHz, CDCl$_3$) δ: 1.45 (9H, s), 4.34 (2H, d, J=5.6 Hz), 4.91 (1H, brs), 5.93 (1H, s), 6.91 (1H, m), 6.98-7.04 (1H, m), 7.39 (2H, d, J=8.8 Hz), 7.54 (2H, d, J=8.8 Hz), 7.59 (1H, d, J=7.8 Hz), 7.67 (1H, dd, J=7.8, 2.2 Hz), 7.99 (1H, m), 8.53 (1H, d, J=2.2 Hz).

IR (ATR) cm$^{-1}$: 1700, 1573, 1492, 1394, 1365, 1322, 1276, 1241, 1149, 1087, 1047, 1014.

MS m/z: 509 (M$^+$+H).

Example 353 tert-Butyl[[6-[(4-chlorophenylsulfonyl)(2,5-difluorophenyl)methyl]pyridin-3-yl]methyl]-N-(tert-butoxycarbonyl)carbamate

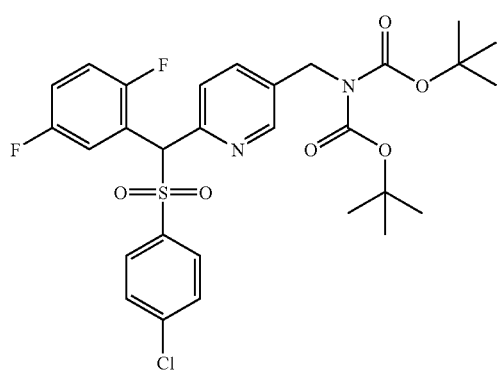

Under nitrogen atmosphere, diisopropyl azodicarboxylate (128 μl, 0.653 mmol) was added to a solution of the 2-[(4-chlorophenylsulfonyl)(2,5-difluorophenyl)methyl]-5-(hydroxymethyl)pyridine (178 mg, 0.435 minol) obtained in Example 331, di-tert-butyl iminodicarboxylate (142 mg, 0.653 mmol) and triphenylphosphine (171 mg, 0.653 mmol) in tetrahydrofuran (5 ml) and the resulting mixture was stirred at room temperature for 5 hours. Water was added to the reaction mixture, followed by extraction with ethyl acetate. The organic layer was then washed successively with water and brine. The organic layer thus obtained was dried over sodium sulfate and concentrated under reduced pressure. The residue thus obtained was subjected to flash chromatography on a silica gel column. A fraction obtained from the elution portion with hexane:ethyl acetate=4:1 was concentrated under reduced pressure, whereby the title compound (78 mg, 0.128 mmol, 32%) was obtained as an oil.

$^1$H-NMR (400 MHz, CDCl$_3$) δ:1.48(18H, s), 4.78(2H, s), 5.94(1H, s), 6.93(1H, td, J=9.0, 4.4 Hz), 6.98-7.04(1H, m), 7.38(2H, d, J=8.6 Hz), 7.56(2H, d, J=8.6 Hz), 7.58(1H, d, J=8.1 Hz), 7.71(1H, dd, J=8.1, 2.4 Hz), 7.96-8.00(1H, m), 8.57 (1H, d, J=2.4 Hz)

IR(ATR) cm$^{-1}$: 2979, 1795, 1727, 1695, 1492, 1392, 1367, 1328, 1255, 1224, 1132, 1087, 1033.

MS m/z: 609(M$^+$+H).

Example 354

6-[(4-Chlorophenylsulfonyl)(2,5-difluorophenyl)methyl]pyridin-3-yl]methylamine Hydrochloride

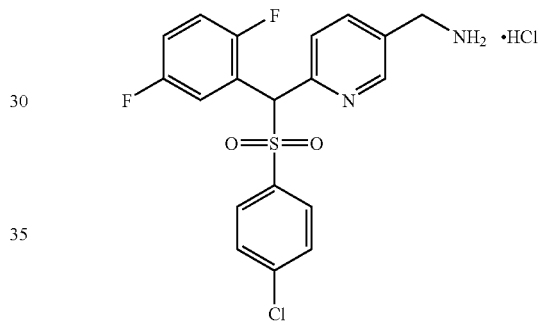

Concentrated hydrochloric acid (2 ml) was added to a solution of tert-butyl [[6-[(4-chlorophenylsulfonyl)(2,5-difluorophenyl)methyl]pyridin-3-yl]methyl]-N-(tert-butoxycarbonyl)carbamate (70 mg, 0.115 mmol) in ethanol (2 ml) and the mixture was stirred at room temperature for 3 hours. The reaction mixture was concentrated under reduced pressure. Ethanol was added to the residue and the mixture was concentrated under reduced pressure, whereby the title compound (51 mg, 0.115 mmol, 100%) was obtained as a white powder.

$^1$H-NMR (400 MHz, CD$_3$OD) δ: 4.18 (2H, s), 6.22 (1H, s), 7.03 (1H, td, J=9.3, 4.4 Hz), 7.11-7.17 (1H, m), 7.52 (2H, d, J=8.8 Hz), 7.64 (2H, d, J=8.8 Hz), 7.79 (1H, d, J=8.3 Hz), 7.92 (1H, dd, J=8.3, 2.2 Hz), 8.05-8.09 (1H, m), 8.71 (1H, d, J=2.2 Hz).

IR (ATR) cm$^{-1}$: 1600, 1571, 1492, 1394, 1349, 1313, 1278, 1232, 1170, 1147, 1079, 1037, 1012.

MS (m/z): 409 (M$^+$+H).

Anal. calcd for C$_{20}$H$_{15}$ClF$_2$N$_2$O$_2$S.HCl: C, 51.25; H, 3.62; Cl, 15.92; F, 8.53; N, 6.29. Found: C, 51.11; H, 3.57; Cl, 15.50; F, 8.39; N, 5.83.

Example 355

N-Acetyl-N-[[6-[(4-chlorophenylsulfonyl)(2,5-difluorophenyl)methyl]pyridin-3-yl]methyl]acetamide (Compound A) and N-[[6-[(4-chlorophenylsulfonyl)(2,5-difluorophenyl)methyl]pyridin-3-yl]methyl]acetamide (Compound B)

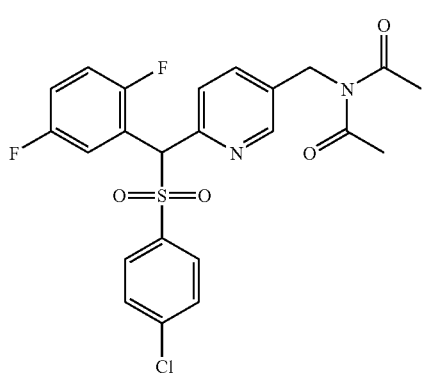

Compound A

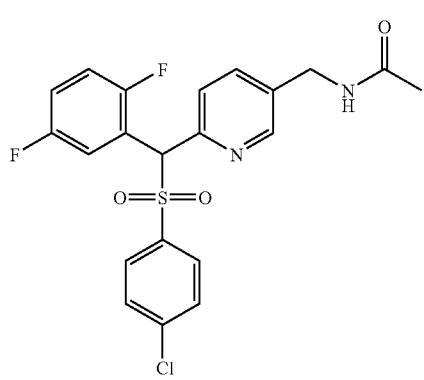

Compound B

Under ice cooling, N-methylmorpholine (26 µl, 0.234 mmol) and acetyl chloride (16 µl, 0.234 mmol) were added to a solution of the [6-[(4-chlorophenylsulfonyl)(2,5-difluorophenyl)methyl]pyridin-3-yl]methylamine (40 ing, 0.0978 mmol), which had been obtained in Example 351, in dichloromethane (3 ml). The resulting mixture was stirred at room temperature for 16 hours. Water was added to the reaction mixture, followed by extraction with ethyl acetate. The organic layer was washed successively with water and brine, dried over sodium sulfate and concentrated under reduced pressure. The residue was subjected to flash chromatography on a silica gel column. A fraction obtained from the elution portion with hexane:ethyl acetate=2:3 was concentrated under reduced pressure, whereby the title compound A (low polarity compound) (15 mg, 0.0304 mmol, 40%) was obtained as a white powder and the title compound B (high polarity compound) (12 mg, 0.0266 mmol, 27%) was obtained as a white powder.

Compound A $^1$H-NMR (400 MHz, CDCl$_{13}$) δ: 2.43(6H, s), 4.96(2H, s), 5.93(1H, s), 6.91(1H, m), 6.98-7.03(1H, m), 7.39(2H, d, J=8.5 Hz), 7.54-7.61(2H, m), 7.55(2H, d, J=8.5 Hz), 8.02(1H, m), 8.51(1H, d, J=1.7 Hz).

IR(ATR)cm$^{-1}$: 1712, 1689, 1573, 1492, 1423, 1369, 1319, 1267, 1201, 1149, 1079, 1029.

mp: 60-64° C.
MS m/z: 493(M$^+$+H).

Compound B $^1$H-NMR (400 MHz, CDCl$_3$) δ: 2.03 and 2.04(3H, rotamers), 4.42-4.50(2H, m), 5.89(1H, brs), 5.93(1H, s), 6.92(1H, td, J=9.1, 4.4 Hz), 6.97-7.02(1H, in), 7.41(2H, d, J=8.1 Hz), 7.57(2H, d, J=8.1 Hz), 7.61(1H, d, J=8.1 Hz), 7.71(1H, d, J=8.1 Hz), 7.98-8.03(1H, m), 8.54(1H, s).

IR(ATR) cm$^{-1}$: 1650, 1673, 1525, 1486, 1430, 1396, 1355, 1319, 1280, 1230, 1147, 1085, 1016.

mp: 177-178° C.
MS m/z: 451(M$^+$+H).

Compound A $^1$H-NMR (400 MHz, CDCl$_3$) δ: 2.43 (6H, s), 4.96 (2H, s), 5.93 (1H, s), 6.91 (1H, m), 6.98-7.03 (1H, m), 7.39 (2H, d, J=8.5 Hz), 7.54-7.61 (2H, m), 7.55 (2H, d, J=8.5 Hz), 8.02 (1H, m), 8.51 (1H, d, J=1.7 Hz).

IR (ATR) cm$^{-1}$: 1712, 1689, 1573, 1492, 1423, 1369, 1319, 1267, 1201, 1149, 1079, 1029.

mp: 60-64° C.
MS m/z: 493 (M$^+$+H).

Compound B $^1$H-NMR (400 MHz, CDCl$_3$) δ: 2.03 and 2.04 (3H, rotamers), 4.42-4.50 (2H, m), 5.89 (1H, brs), 5.93 (1H, s), 6.92 (1H, td, J=9.1, 4.4 Hz), 6.97-7.02 (1H, m), 7.41 (2H, d, J=8.1 Hz), 7.57 (2H, d, J=8.1 Hz), 7.61 (1H, d, J=8.1 Hz), 7.71 (1H, d, J=8.1 Hz), 7.98-8.03 (1H, m), 8.54 (1H, s).

IR (ATR) cm$^{-1}$: 1650, 1673, 1525, 1486, 1430, 1396, 1355, 1319, 1280, 1230, 1147, 1085, 1016.

mp: 177-178° C.
MS m/z: 451 (M$^+$+H).

Example 356

N-[[6-[(4-Chlorophenylsulfonyl)(2,5-difluorophenyl)methyl]pyridin-3-yl]methyl]-N',N'-dimethylsulfamide

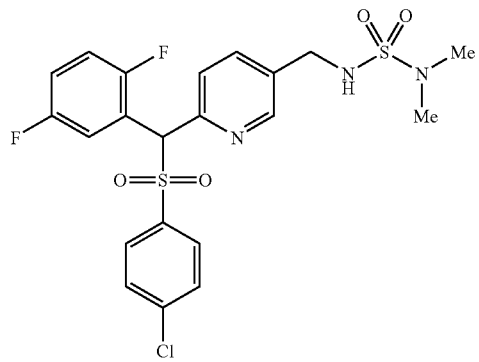

To a solution of the 6-[(4-chlorophenylsulfonyl)(2,5-difluorophenyl)methyl]pyridin-3-yl]methylamine hydrochloride (60 mg, 0.135 mmol) in dichloromethane (5 ml) were added N-methylmorpholine (180 µl, 1.62 mmol), 4-dimethylaminopyridine (10 mg, 0.0819 mmol) and N,N-dimethylsulfamoyl chloride (66 µl, 0.609 minol). The resulting mixture was stirred at room temperature for 24 hours. Water was added to the reaction mixture, followed by extraction with dichloromethane. The organic layer was washed successively with a saturated aqueous solution of sodium bicarbonate and brine. The resulting organic layer was dried over magnesium sulfate and concentrated under reduced pressure. The residue thus obtained was subjected to flash chromatography on a silica gel column. A fraction obtained from the elution portion with hexane:ethyl acetate=3:2 was concentrated under reduced pressure, whereby the title compound (48 mg, 0.0930 mmol, 70%) was obtained as a white powder.

$^1$H-NMR (400 MHz, CDCl$_3$) δ: 2.76(6H, s), 4.29(2H, d, J=6.4 Hz), 4.43(1H, t, J 6.4 Hz), 5.94(1H, s), 6.92(1H, m), 6.98-7.04(1H, m), 7.41(2H, d, J=8.6 Hz), 7.58(2H, d, J=8.6 Hz), 7.66(1H, d, J=8.1 Hz), 7.79(1H, dd, J=8.1, 2.5 Hz), 8.02(1H, m), 8.61(1H, d, J=2.5 Hz).

mp: 177-178° C.

MS m/z: 516(M$^+$+H).

Example 357

Ethyl 2-[[6-[(4-chlorophenylsulfonyl)(2,5-difluorophenyl)methyl]pyridin-3-yl]methylamino]-2-oxoacetate

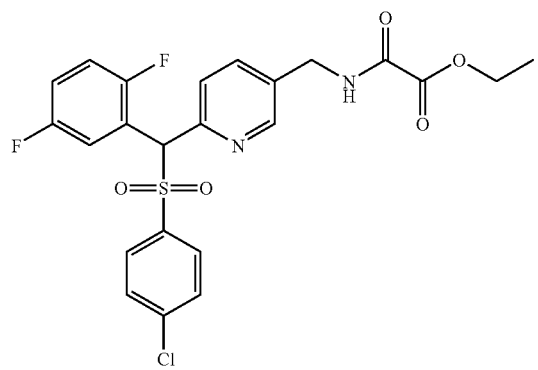

Under ice cooling, N-methylmorpholine (10 μl, 0.0881 mmol) and ethyl chloroglyoxylate (9 μl, 0.0807 mmol) were added to the 6-[(4-chlorophenylsulfonyl)(2,5-difluorophenyl)methyl]pyridin-3-yl]methylamine (30 mg, 0.0734 mmol), which had been obtained in Example 351, in dichloromethane (4 ml). The resulting mixture was stirred at room temperature for 1 hour. Water was added to the reaction mixture, followed by extraction with dichloromethane. The organic layer was then washed successively with a saturated aqueous solution of sodium bicarbonate and brine, dried over magnesium sulfate and concentrated under reduced pressure. The residue thus obtained was subjected to flash chromatography on a silica gel column. A fraction obtained from the elution portion with hexane:ethyl acetate=3:2 was concentrated under reduced pressure, whereby the title compound (28 mg, 0.0550 mmol, 76%) was obtained as a white powder.

$^1$H-NMR (400 MHz, CDCl$_3$) δ: 1.39(3H, t, J=7.1 Hz), 4.37(2H, q, J=7.1 Hz), 4.55(2H, d, J=5.9 Hz), 5.94(1H, s), 6.89-6.94(1H, m), 6.98-7.05(1H, m), 7.40(2H, d, J=8.3 Hz), 7.56(2H, d, J=8.3 Hz), 7.53(1H, brs), 7.62(1H, d, J=8.1 Hz), 7.72(1H, d, J=8.1 Hz,), 7.97-8.03 (1H, m), 8.58(1H, s).

mp: 193-194° C.

MS m/z: 509(M$^+$+H).

Example 358

N-[[6-[(4-Chlorophenylsulfonyl)(2,5-difluorophenyl)methyl]pyridin-3-yl]methyl]-2-(4-methylphenylsulfonylamino)acetamide Triethylamine (45 μl, 0.324 mmol), 4-dimethylaminopyridine (5 mg, 0.0449 mmol), 1-ethyl-3-(3-dimethylaminopropyl)carbodiimide hydrochloride (21 mg, 0.108 mmol) and N-p-tosylglycine (25 mg, 0.108 mmol) were added to a solution of the 6-[(4-chlorophenylsulfonyl) (2,5-difluorophenyl)methyl]pyridin-3-yl]methylamine hydrochloride (40 mg, 0.0898 mmol), which had been obtained in Example 354, in dichloromethane (6 ml). The resulting mixture was stirred at room temperature for 16 hours. The reaction mixture was diluted with dichloromethane, followed by successive washing with water, a saturated aqueous solution of sodium bicarbonate and brine. The organic layer thus obtained was dried over magnesium sulfate and concentrated under reduced pressure. The residue thus obtained was subjected to flash chromatography on a silica gel column. A fraction obtained from the elution portion with hexane:ethyl acetate=2.3 was concentrated under reduced pressure, whereby the title compound (41 mg, 0.0661 mmol, 73%) was obtained as a white powder.

$^1$H-NMR (400 MHz, CDCl$_3$) δ: 2.44(3H, s), 3.59(2H, d, J=6.4 Hz), 4.44(2H, dd, J=6.1, 2.8 Hz), 5.42(1H, t, J=6.1 Hz), 5.95(1H, s), 6.91(1H, m), 6.96-7.03(2H, m), 7.33(2H, d, J=8.3 Hz), 7.41(2H, d, J=8.6 Hz), 7.57(2H, d, J=8.6 Hz), 7.58(1H, d, J=8.1 Hz), 7.66(1H, dd, J=8.1, 2.4 Hz), 7.74(2H, d, J=8.3 Hz), 8.01(1H, m), 8.49(1H, d, J=2.4 Hz).

mp: 217-218° C.

MS m/z: 620(M$^+$+H).

Example 359

N-[[6-[(4-Chlorophenylsulfonyl)(2,5-difluorophenyl)methyl]pyridin-3-yl]methyl]-2-dimethylaminoacetamide

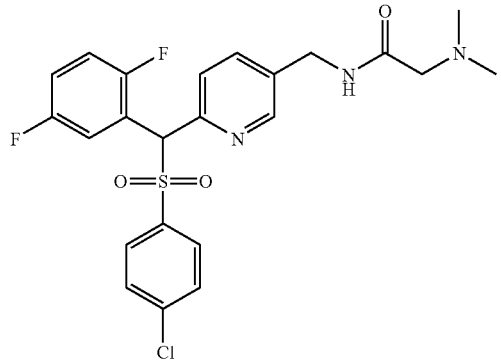

Triethylamine (12 µl, 0.0881 mmol), 4-dimethylaminopyridine (5 mg, 0.0367 mmol), 1-ethyl-3-(3-dimethylaminopropyl)carbodiimide hydrochloride (17 mg, 0.0881 mmol) and N,N-dimethylglycine (9 mg, 0.088 1 mmol) were added to a solution of the 6-[(4-chlorophenylsulfonyl)(2,5-difluorophenyl)methyl]pyridin-3-yl]methylamine (30 mg, 0.0734 mmol), which had been obtained in Example 351, in dichloromethane (5 ml). The resulting mixture was stirred at room temperature for 14 hours. The reaction mixture was diluted with dichloromethane, followed by successive washing with water, a saturated aqueous solution of sodium bicarbonate and brine. The organic layer thus obtained was dried over magnesium sulfate and concentrated under reduced pressure. The residue was subjected to flash chromatography on a silica gel column. A fraction obtained from the elution portion with hexane:ethyl acetate=1:4 was concentrated under reduced pressure, whereby the title compound (21 mg, 0.0425 mmol, 58%) was obtained as a white powder.

$^1$H-NMR (400 MHz, CDCl$_3$) δ: 2.30(6H, s), 3.01(2H, s), 4.50(2H, d, J=6.1 Hz), 5.93(1H, s), 6.91(1H, m), 6.98-7.04 (1H, m), 7.40(2H, d, J =8.6 Hz), 7.55(2H, d, J=8.6 Hz), 7.60 (1H, d, J =8.1 Hz), 7.62(1H, brs), 7.69(1H, dd, J=8.1, 2.4 Hz), 8.02(1H, m), 8.56(1H, d, J=2.4 Hz).

mp: 177-179° C.

MS m/s: 494(M$^+$+H).

Example 360

N-[[6-[(4-Chlorophenylsulfonyl)(2,5-difluorophenyl)methyl]pyridin-3-yl]methyl]-4-(formylmethylamino)benzamide

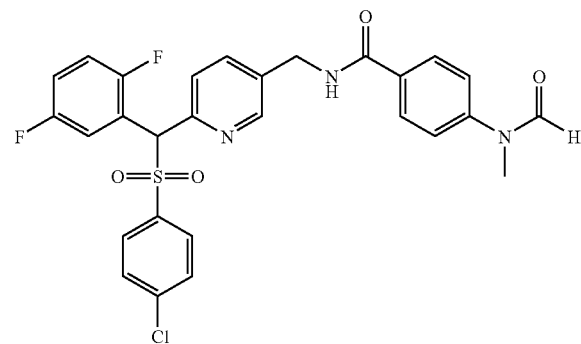

Triethylamine (21 µl, 0.147 mmol), 4-dimethylaminopyridine (7 mg, 0.0610 mmol), 1-ethyl-3-(3-dimethylaminopropyl)carbodiimide hydrochloride (28 mg, 0.147 mmol) and N-formyl-4-(methylamino)benzoic acid (26 mg, 0.147 mmol) were added to a solution of the 6-[(4-chlorophenylsulfonyl)(2,5-difluorophenyl)methyl]pyridin-3-yl]methylamine (50 mg, 0.122 mmol), which had been obtained in Example 351, in dichloromethane (5 ml). The resulting mixture was stirred at room temperature for 2 hours. The reaction mixture was diluted with dichloromethane, followed by successive washing with water, a saturated aqueous solution of sodium bicarbonate and brine. The organic layer was dried over magnesium sulfate and concentrated under reduced pressure. The residue thus obtained was subjected to flash chromatography on a silica gel column. A fraction obtained from the elution portion with hexane:ethyl acetate=3:7 was concentrated under reduced pressure, whereby the title compound (60 mg, 0.105 mmol, 87%) was obtained as a colorless amorphous substance.

$^1$H-NMR (400 MHz, CDCl$_3$) δ: 3.35 (3H, s), 4.67-4.71 (2H, m), 5.94(1H, s), 6.53 (1H, brs), 6.90(1H, m), 6.97-7.03 (1H, m), 7.25(2H, d, J =8.6 Hz), 7.40(2H, d, J=8.6 Hz), 7.56(2H, d, J =8.6 Hz), 7.63(1H, d, J=8.1 Hz), 7.78(1H, dd, J=8.1, 2.2 Hz), 7.86(2H, d, J=8.6 Hz), 8.03(1H, m), 8.61(1H, s), 8.64(1H, d, J =2.2 Hz).

MS m/z: 570(M$^+$+H).

Example 361

N-[[6-[(4-Chlorophenylsulfonyl)(2,5-difluorophenyl)methyl]pyridin-3-yl]methyl]-4-(methylthioformylamino)thiobenzamide

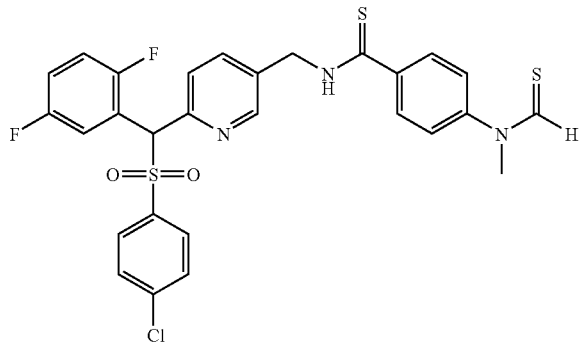

Under argon atmosphere, a lawesson's reagent (69 mg, 0.169 mmol) was added to a solution of N-[[6-[(4-chlorophenylsulfonyl) (2,5-difluorophenyl)methyl]pyridin-3-yl]methyl]-4-(formylmethylamino)benzamide (46 mg, 0.0807 mmol) in toluene (5 ml) and the mixture was heated under reflux for 12 hours. After cooling to room temperature, the reaction mixture was concentrated under reduced pressure. The residue thus obtained was subjected to flash chromatography on a silica gel column. A fraction obtained from the elution portion with hexane:ethyl acetate=4:1 was concentrated under reduced pressure, whereby the title compound (40 mg, 0.0664 mmol, 83%) was obtained as a yellow amorphous substance.

$^1$H-NMR (400 MHz, CDCl$_3$) δ: 3.72 (3H, s), 5.08 (2H, d, J=4.4 Hz), 5.92 (1H, s), 6.89 (1H, td, J=9.0, 4.4 Hz), 6.98-7.05 (1H, m), 7.25 (2H, d, J=8.6 Hz), 7.40 (2H, d, J=8.6 Hz), 7.55 (2H, d, J=8.6 Hz), 7.60 (1H, d, J=8.1 Hz), 7.81 (1H, d, J=8.1 Hz), 7.87 (2H, d, J=8.6 Hz), 8.02-8.06 (1H, m), 8.20 (1H, brs), 8.62 (1H, s), 9.70 (1H, s).

MS m/z: 602 (M$^+$+H).

Example 362

N-[[6-[(4-Chlorophenylsulfonyl) (2,5-difluorophenyl)methyl]pyridin-3-yl]methyl]-2-(pyridin-3-yl) acetamide

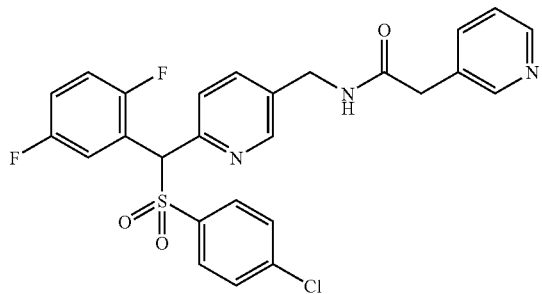

The [6-[(4-chlorophenylsulfonyl) (2,5-difluorophenyl)methyl]pyridin-3-yl]methylamine (30 mg, 0.073 mmol) obtained in Example 351, 3-pyridylacetic acid hydrochloride (16 mg, 0.092 mmol), 4-(dimethylamino)pyridine (5 mg, 0.04 mmol) and triethylamine (0.025 ml, 0.18 mmol) were dissolved in dichloromethane (5 ml). To the resulting solution was added 1-ethyl-3-(3-dimethylaminopropyl)carbodiimide hydrochloride (17 mg, 0.089 mmol). After stirring at room temperature for 14 hours, a saturated aqueous solution (0.1 ml) of sodium bicarbonate was added to the reaction mixture. The residue obtained by concentration of the reaction mixture under reduced pressure was subjected to flash silica gel chromatography. A fraction obtained from the elution portion with dichloromethane:methanol 30:1 was concentrated under reduced pressure, whereby a white solid was obtained. The white solid was washed with ether, whereby the title compound (35 mg, 0.066 mmol, 90%) was obtained as a white powder.

$^1$H-NMR (400 MHz, CDCl$_3$) δ: 3.59 (2H, s), 4.45 (2H, dd, J=5.9, 1.5 Hz), 5.92 (1H, s), 5.96-6.10 (1H, m), 6.86-6.98 (1H, m), 6.99-7.05 (1H, m), 7.24-7.35 (1H, m), 7.39 (2H, d, J=8.8 Hz), 7.55-7.60 (3H, m), 7.60-7.71 (2H, m), 7.96-8.06 (1H, m), 8.50 (2H, d, J=1.6 Hz), 8.55 (1H, d, J=4.8, 1.6 Hz).

MS m/z: 528 (M$^+$+H).

Example 363

[6-(4-Chlorophenylsulfonyl)(2,5-difluorophenyl) methylpyridin-3-yl]methyl Dimethylcarbamate

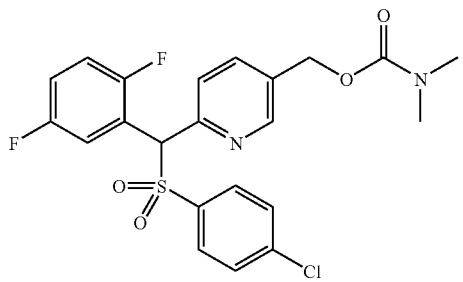

To a solution of the 2-[(4-chlorophenylsulfonyl)(2,5-difluorophenyl)methyl]-5-(hydroxylmethyl)pyridine (20 mg, 0.049 mmol), which had been obtained in Example 331, in dichloromethane (0.3 ml) were added N-methylmorpholine (0.011 ml, 0.10 mmol) and p-nitrophenyl chloroformate (15 mg, 0.074 mmol). The resulting mixture was stirred at room temperature for 30 minutes. At 0° C., N-methylmorpholine (0.033 ml, 0.30 mmol) and then, p-nitrophenyl chloroformate (15 mg, 0.074 mmol) were added further and the mixture was stirred at room temperature for 30 minutes. Dimethylamine hydrochloride (20 mg, 0.25 mmol) was added to the mixture at 0° C. After stirring at room temperature for 13 hours, the reaction mixture was washed with a saturated aqueous solution of ammonium chloride. The organic layer was then dried over anhydrous sodium sulfate. After filtration, the filtrate was concentrated under reduced pressure. The residue was subjected to flash silica gel chromatography. A fraction obtained from the elution portion with hexane:ethyl acetate=7:3 was concentrated under reduced pressure. The resulting solid was washed with hexane and filtered, whereby the title compound (13 mg, 0.027 mmol, 55%) was obtained as a white solid.

$^1$H-NMR (400 MHz, CDCl$_3$) δ: 2.94 (6H, s), 5.14 (2H, s), 5.94 (1H, s), 6.87-7.07 (2H, m), 7.39 (2H, d, J=8.5 Hz), 7.55 (2H, d, J=8.5 Hz), 7.62 (1H, d, J=7.8 Hz), 7.75 (1H, dd, J=7.8, 2.0 Hz), 7.99-8.07 (1H, m), 8.63 (1H, d, J=2.0 Hz).

MS m/z: 481 (M$^+$+H).

Example 364

[6-(4-Chlorophenylsulfonyl)(2,5-difluorophenyl) methylpyridin-3-yl]methyl 4-nitrophenyl=carbonate

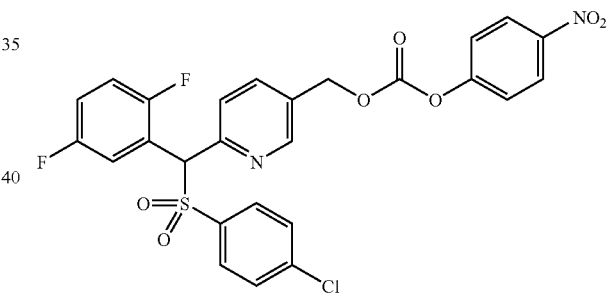

To a solution of the 2-[(4-chlorophenylsulfonyl)(2,5-difluorophenyl)methyl]-5-(hydroxylmethyl)pyridine (41 mg, 0.10 mmol), which had been obtained in Example 331, in dichloromethane (0.5 ml) were added N-methylmorpholine (0.033 ml, 0.30 mmol) and 4-nitrophenyl chloroformate (40 mg, 0.20 mmol) at 0° C. The resulting mixture was stirred at room temperature for 1 hour. The reaction mixture was washed with water. The organic layer was dried over anhydrous sodium sulfate and filtered. The filtrate was concentrated under reduced pressure. The residue thus obtained was subjected to flash silica gel chromatography. A fraction obtained from the elution portion with hexane:ethyl acetate=4:1 was concentrated under reduced pressure. The solid thus obtained was washed with hexane and collected by filtration, whereby the title compound (52 mg, 0.090 mmol, 90%) was obtained as a white solid.

$^1$H-NMR (400 MHz, CDCl$_3$) δ: 5.33 (2H, s), 5.97 (1H, s), 6.87-6.95 (1H, m), 6.98-7.06 (1H, m), 7.39 (2H, d, J=9.0 Hz), 7.40 (2H, d, J=8.5 Hz), 7.57 (2H, d, J=8.5 Hz), 7.71 (1H, d, J=7.6 Hz), 7.85 (1H, dd, J=7.6, 2.0 Hz), 7.97-8.05 (1H, m), 8.29 (2H, d, J=9.0 Hz), 8.72 (1H, d, J=2.0 Hz).

MS m/z: 575 (M$^+$+H).

Example 365

[6-(4-Chlorophenylsulfonyl)(2,5-difluorophenyl)methylpyridin-3-yl]methyl Benzylcarbamate

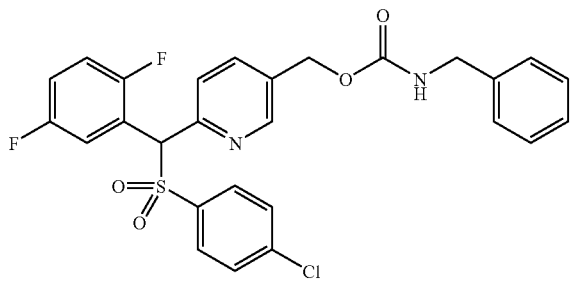

To a solution of the [6-(4-chlorophenylsulfonyl)(2,5-difluorophenyl)methylpyridin-3-yl]methyl 4-nitrophenyl carbonate (51 mg, 0.089 mmol) in dichloromethane (1 ml) were successively added N-methylmorpholine (0.020 ml, 0.18 mmol) and benzylamine (0.012 ml, 0.11 mmol) at 0° C. The resulting mixture was stirred at room temperature for 20 hours. The reaction mixture was washed with a saturated aqueous solution of ammonium chloride. The organic layer was dried over anhydrous sodium sulfate and filtered. The filtrate was concentrated under reduced pressure. The residue thus obtained was subjected to flash silica gel chromatography. A fraction obtained from the elution portion with hexane:ethyl acetate=4:1 was concentrated under reduced pressure. The solid thus obtained was washed with diisopropyl ether and collected by filtration, whereby the title compound (33 mg, 0.060 mmol, 68%) was obtained as a white solid.

$^1$H-NMR (400 MHz, CDCl$_3$) δ: 4.38 (2H, brd, J=5.4 Hz), 5.06 (1H, brs), 5.16 (2H, s), 5.94 (1H, s), 6.87-7.04 (2H, m), 7.22-7.38 (5H, m), 7.39 (2H, d, J=8.3 Hz), 7.54 (2H, d, J=8.3 Hz), 7.62 (1H, d, J=8.3 Hz), 7.74 (1H, d, J=8.3 Hz), 7.96-8.03 (1H, m), 8.61 (1H, s).

MS m/z: 543 (M$^+$+H).

Example 366

N-[[6-(4-Chlorophenylsulfonyl)(2,5-difluorophenyl)methylpyridin-3-yl]methyl]-3-cyanobenzenesulfonamide

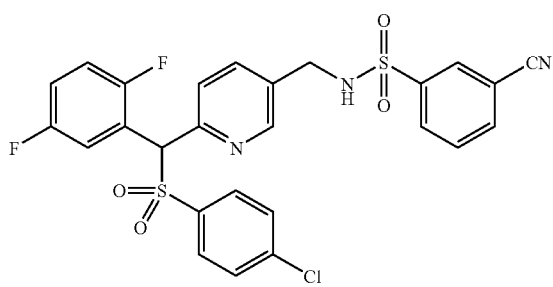

To a solution of the 6-[(4-chlorophenylsulfonyl)(2,5-difluorophenyl)methyl]pyridin-3-yl]methylamine (28 mg, 0.068 mmol), which had been obtained in Example 351, in dichloromethane (0.5 ml) were successively added N-methylmorpholine (0.015 ml, 0.14 mmol) and 3-cyanobenzenesulfonyl chloride (22 mg, 0.10 mmol) at 0° C. The resulting mixture was stirred at room temperature for 6 hours. After washing with 1N hydrochloric acid, the organic layer was dried over anhydrous sodium sulfate and filtered. The filtrate was concentrated under reduced pressure. The residue thus obtained was subjected to flash silica gel chromatography and a fraction obtained from the elution portion with hexane:ethyl acetate=7:3 was concentrated under reduced pressure. The solid thus obtained was washed with hexane and collected by filtration, whereby the title compound (23 mg, 0.040 mmol, 59%) was obtained as a white solid.

$^1$H-NMR (400 MHz, CDCl$_3$) δ: 4.26 (2H, d, J=6.4 Hz), 5.08 (1H, t, J=6.4 Hz), 5.91 (1H, s), 6.86-7.06 (2H, m), 7.40 (2H, d, J=8.1 Hz), 7.55 (2H, d, J=8.1 Hz), 7.57-7.70 (3H, m), 7.81 (1H, d, J=7.4 Hz), 7.94-8.05 (2H, m), 8.11 (1H, s), 8.46 (1H, s).

MS m/z: 574 (M$^+$+H).

Example 367

N-[[6-(4-Chlorophenylsulfonyl)(2,5-difluorophenyl)methylpyridin-3-yl]methyl]-3-cyano-N-methylbenzenesulfonamide

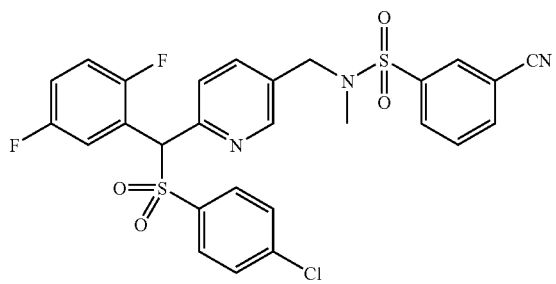

To a solution of N-[[6-(4-chlorophenylsulfonyl)(2,5-difluorophenyl)methylpyridin-3-yl]methyl]-3-cyanobenzenesulfonamide (21 mg, 0.037 mmol) in tetrahydrofuran (0.5 ml) were successively added methanol (0.003 ml, 0.073 mmol), triphenylphosphine (19 mg, 0.073 mmol) and diisopropyl azodicarboxylate (0.014 ml, 0.073 mmol) at 0° C. The resulting mixture was stirred at room temperature for 2 hours. The reaction mixture was concentrated under reduced pressure. The residue thus obtained was subjected to flash silica gel chromatography. A fraction obtained from the elution portion with hexane:ethyl acetate=2:1 was concentrated under reduced pressure, whereby the title compound (13 mg, 0.021 mmol, 58%) was obtained as a white solid.

$^1$H-NMR (400 MHz, CDCl$_3$) δ: 2.70 (3H, s), 4.25 (2H, d, J=6.4 Hz), 5.95 (1H, s), 6.87-7.05 (2H, m), 7.40 (2H, d, J=8.5 Hz), 7.56 (2H, d, J=8.5 Hz), 7.66 (1H, d, J=8.1 Hz), 7.73 (1H, t, J=7.8 Hz), 7.81 (1H, dd, J=8.1, 2.2 Hz), 7.91 (1H, d, J=7.8 Hz), 7.99-8.09 (2H, m), 8.12 (1H, s), 8.53 (1H, t, J=2.2 Hz).

MS m/z: 588 (M$^+$+H).

Example 368

3-[[6-(4-Chlorophenylsulfonyl)(2,5-difluorophenyl)methylpyridin-3-yl]methyl]-1,1-dimethylurea

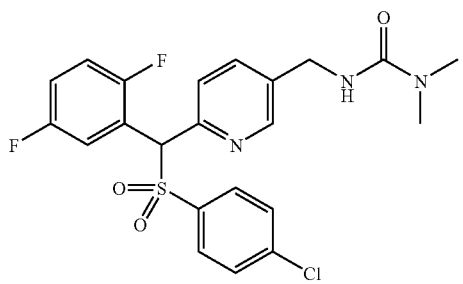

To a solution of the [6-[(4-chlorophenylsulfonyl) (2,5-difluorophenyl)methyl]pyridin-3-yl]methylamine (31 mg, 0.076 mmol), which had been obtained in Example 351, in dichloromethane (1 ml) were successively added triethylamine (0.032 ml, 0.23 mmol), and N,N-dimethylcarbamoyl chloride (0.014 ml, 0.15 mmol) at 0° C. The resulting mixture was stirred at room temperature for 17 hours. Triethylamine (0.032 ml, 0.23 mmol) and N,N-dimethylcarbamoyl chloride (0.014 ml, 0.15 mmol) were added further to the reaction mixture at 0° C. The resulting mixture was stirred at room temperature for 29 hours. After the reaction mixture was washed with a saturated aqueous solution of sodium bicarbonate, the organic layer was dried over anhydrous sodium sulfate and filtered. The filtrate was concentrated under reduced pressure. The residue thus obtained was subjected to flash silica gel chromatography. A fraction obtained from the elution portion with ethyl acetate was concentrated under reduced pressure. The resulting solid was washed with hexane and collected by filtration, whereby the title compound (18 mg, 0.036 mmol, 48%) was obtained as a white solid.

$^1$H-NMR (400 MHz, CDCl$_3$) δ: 2.93 (6H, s), 4.44 (2H, d, J=4.2 Hz), 4.76 (1H, t, J=4.2 Hz), 5.93 (1H, s), 6.85-7.04 (2H, m), 7.39 (2H, d, J=8.3 Hz), 7.56 (2H, d, J=8.3 Hz), 7.58 (1H, d, J=8.5 Hz), 7.74 (1H, dd, J=8.5, 2.0 Hz), 7.98-8.06 (1H, m), 8.57 (1H, d, J=2.0 Hz).

MS m/z: 480 (M$^+$+H).

Example 369

Methyl [6-(4-chlorophenylsulfonyl)(2,5-difluorophenyl)methylpyridin-3-yl]methylcarbamate

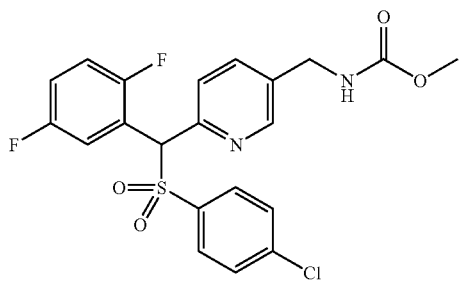

In a similar manner to Example 368 except for the use of [6-[(4-chlorophenylsulfonyl)(2,5-difluorophenyl)methyl] pyridin-3-yl]methylamine (34 mg, 0.082 mmol) obtained in Example 351 and methyl chlorocarbonate (0.019 ml, 0.25 mmol), the title compound (16 mg, 0.034 mmol, 42%) was obtained as a yellow solid.

$^1$H-NMR (400 MHz, CDCl$_3$) δ: 3.71 (3H, s), 4.40 (2H, d, J=6.1 Hz), 5.07 (1H, brs), 5.93 (1H, s), 6.87-7.04 (2H, m), 7.39 (2H, d, J=8.5 Hz), 7.55 (2H, d, J=8.5 Hz), 7.60 (1H, d, J=7.8 Hz), 7.70 (1H, d, J=7.8 Hz), 7.97-8.04 (1H, m), 8.55 (1H, s).

MS m/z: 467 (M$^+$+H).

Example 370

N-[[6-(4-Chlorophenylsulfonyl)(2,5-difluorophenyl)methylpyridin-3-yl]methyl]methanesulfonamide

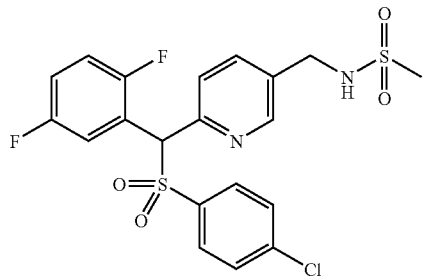

In a similar manner to Example 368 except for the use of the [6-[(4-chlorophenylsulfonyl)(2,5-difluorophenyl)methyl]pyridin-3-yl]methylamine (34 mg, 0.082 mmol) obtained in Example 351 and methanesulfonyl chloride (0.019 ml, 0.25 mmol), the title compound was obtained (20 mg, 0.040 mmol, 49%) as a white solid.

$^1$H-NMR (400 MHz, CDCl$_3$) δ: 2.97 (3H, s), 4.37 (2H, d, J=6.1 Hz), 4.70 (1H, brs), 5.95 (1H, s), 6.88-7.07 (2H, m), 7.40 (2H, d, J=8.3 Hz), 7.56 (2H, d, J=8.3 Hz), 7.65 (1H, d, J=8.1 Hz), 7.80 (1H, d, J=8.1 Hz), 7.97-8.07 (1H, m), 8.61 (1H, s).

MS m/z: 487 (M$^+$+H).

Example 371

N-[[6-(4-Chlorophenylsulfonyl)(2,5-difluorophenyl)methylpyridin-3-yl]methyl]-1-acetyl-4-piperidinecarboxamide

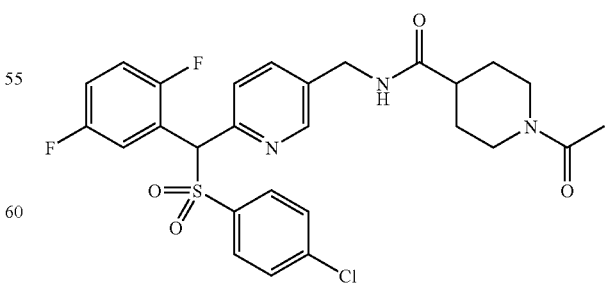

In a similar manner to Example 368 except for the use of the [6-[(4-chlorophenylsulfonyl)(2,5-difluorophenyl)methyl]pyridin-3-yl]methylamine (34 mg, 0.082 mmol) and 1-acetyl-4-piperidinecarbonyl chloride (56 mg, 0.25 mmol), The title compound (24 mg, 0.043 mmol, 52%) was obtained as a colorless foam.

$^1$H-NMR (400 MHz, CDCl$_3$) δ: 1.58-1.79 (2H, m), 1.82-1.95 (2H, m), 2.09 (3H, s), 2.30-2.41 (1H, m), 2.59-2.70 (1H, m), 3.03-3.13 (1H, m), 3.82-3.92 (1H, m), 4.41-4.53 (2H, m), 4.55-4.63 (1H, m), 5.90-5.98 (2H, m), 6.85-6.94 (1H, m), 6.97-7.04 (1H, m), 7.40 (2H, d, J=8.5 Hz), 7.55 (2H, d, J=8.5 Hz), 7.60 (1H, d, J=8.1 Hz), 7.66 (1H, d, J=8.1 Hz), 7.98-8.05 (1H, m), 8.53 (1H, s).

MS m/z: 562 (M$^+$+H).

Example 372

[6-(4-Chlorophenylsulfonyl)(2,5-difluorophenyl)methylpyridin-3-yl]methyl Methyl Carbonate

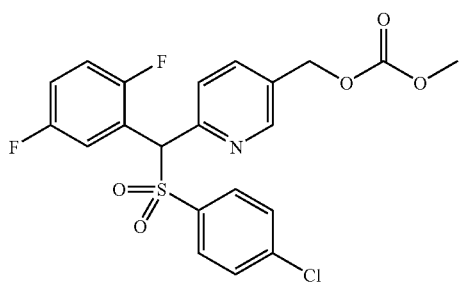

Pyridine (0.040 ml, 0.49 minol) and methylchioroformate (0.019, 0.24 mmol) were successively added to a solution of the 2-[(4-chlorophenylsulfonyl)(2,5-difluorophenyl)methyl]-5-(hydroxymethyl)pyridine (50 mg, 0.12 mmol), which had been obtained in Example 331, in dichloromethane (2 ml) at 0° C. and the resulting mixture was stirred at room temperature for 1 hour. Methyl chloroformate (0.019 ml, 0.24 mmol) was then added to the reaction mixture at 0° C., followed by stirring at room temperature for 5 hours. The reaction mixture was washed with 1N hydrochloric acid. The organic layer was dried over anhydrous sodium sulfate and then filtered. The filtrate was concentrated under reduced pressure. The residue was subjected to flash silica gel chromatography. A fraction obtained from the elution portion with hexane:ethyl acetate =4:1 was concentrated under reduced pressure. The solid thus obtained was washed with hexane and collected by filtration, whereby the title compound (50 mg, 0.11 mmol, 88%) was obtained as a white solid.

$^1$H-NMR (400 MHz, CDCl$_3$) δ: 3.81(3H, s), 5.18(2H, s), 5.95(1H, s), 6.89-7.04 (2H, m), 7.40 (2H, d, J=8.5 Hz), 7.55 (2H, d, J=8.5 Hz), 7.65(1H, d, J=8.1 Hz), 7.78(1H, dd, J=8.1, 2.2 Hz), 7.97-8.03(1H, m), 8.64(1H, d, J =2.2 Hz).

MS m/z: 468(M$^+$+H).

Example 373

[6-[(4-Chlorophenylsulfonyl)(2,5-difluorophenyl)methyl]pyridin-3-yl]carbaldehyde Oxime (Isomer 373-A and Isomer 373-B)

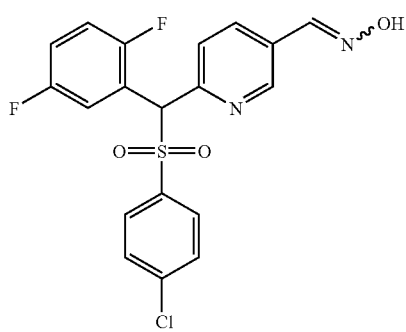

To a solution of the[6-[(4-chlorophenylsulfonyl)(2,5-difluorophenyl)methyl]pyridin-3-yl]carbaldehyde (100 mg, 0.25 mmol), which had been obtained in Example 335, in dichloromethane (3 ml) were added N-methylmorpholine (32 μl, 0.29 mmol) and hydroxylamine hydrochloride (26 mg, 0.36 mmol). The resulting mixture was stirred at room temperature for 3 days. The reaction mixture was diluted with dichloromethane, followed by successive washing with water, a saturated aqueous solution of sodium bicarbonate and brine. The organic layer thus obtained was dried over magnesium sulfate and concentrated under reduced pressure. The residue was subjected to flash chromatography on a silica gel column. A fraction obtained from the elution portion with hexane:ethyl acetate=3:2 was concentrated under reduced pressure, whereby the title isomer 373-A (low polarity compound) (79 mg, 0.19 mmol, 72%) was obtained as a white powder and the title isomer 373-B (high polarity compound) (17 mg, 0.040 mmol, 17%) was obtained as a white powder.

Isomer 373-A $^1$H-NMR (400 MHz, CDCl$_3$) δ: 5.97(1H, s), 6.91-6.96(1H, m), 6.99-7.05(1H, m), 7.40(2H, d, J=8.6 Hz), 7.56(2H, d, J=8.6 Hz), 7.66 (1H, d, J=8.1 Hz), 7.78(1H, s), 7.96-8.02(2H, m), 8.14(1H, s), 8.75(1H, d, J=1.7Hz).

IR(ATR) cm$^{-1}$: 3237, 1589, 1594, 1475, 1428, 1394, 1322, 1280, 1236, 1151, 1083, 1014.

mp: 187-188° C.

MS m/z: 423(M$^+$+H).

Isomer 373-B $^1$H-NMR (400 MHz, CDCl$_3$) δ: 5.98(1H, s), 6.91-6.97 (1H, m), 7.00-7.06(1H, m), 7.40(1H, s), 7.41(2H, d, J=8.6 Hz), 7.57(2H, d, J=8.6 Hz), 7.71(1H, d, J=8.3 Hz), 7.90-8.02 (2H, m), 8.41(1H, dd, J=8.3, 2.1 Hz), 9.00(1H, s).

IR(ATR) cm$^{-1}$: 3037,1569, 1492, 1430, 1394, 1324, 1276, 1236, 1153, 1081, 1012.

mp: 194-196° C.

MS m/z: 423(M$^+$+H).

Isomer 373-A $^1$H-NMR (400 MHz, CDCl$_3$) δ: 5.97 (1H, s), 6.91-6.96 (1H, m), 6.99-7.05 (1H, m), 7.40 (2H, d, J=8.6 Hz), 7.56 (2H, d, J=8.6 Hz), 7.66 (1H, d, J=8.1 Hz), 7.78 (1H, s), 7.96-8.02 (2H, m), 8.14 (1H, s), 8.75 (1H, d, J=1.7 Hz).

IR (ATR) cm$^{-1}$: 3237, 1589, 1594, 1475, 1428, 1394, 1322, 1280, 1236, 1151, 1083, 1014.

mp: 187-188° C.

MS m/z: 423 (M$^+$+H).

Isomer 373-B $^1$H-NMR (400 MHz, CDCl$_3$) δ: 5.98 (1H, s), 6.91-6.97 (1H, m), 7.00-7.06 (1H, m), 7.40 (1H, s), 7.41 (2H, d, J=8.6 Hz), 7.57 (2H, d, J=8.6 Hz), 7.71 (1H, d, J=8.3 Hz), 7.90-8.02 (2H, m), 8.41 (1H, dd, J=8.3, 2.1 Hz), 9.00 (1H, s).

IR (ATR) cm$^{-1}$: 3037, 1569, 1492, 1430, 1394, 1324, 1276, 1236, 1153, 1081, 1012.

mp: 194-196° C.

MS m/z: 423 (M$^+$+H).

Example 374

6-[(4-Chlorophenylsulfonyl)(2,5-difluorophenyl)methyl]-N-cyclohexylmethylnicotinamide

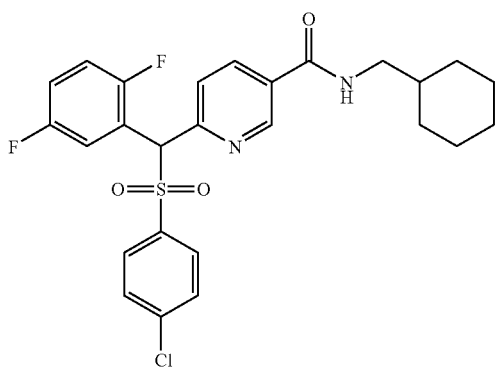

Triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and aminomethylcyclohexane (30 μl, 0.23 mmol) were added to a solution of the [6-[(4-chlorophenylsulfonyl) (2,5-difluorophenyl)methyl]pyridin-3-yl]carboxylic acid (80 mg, 0.19 mmol), which had been obtained in Example 338, in dichloromethane (5 ml). The resulting mixture was stirred at room temperature for 4.5 hours. The reaction mixture was diluted with dichloromethane, followed by successive washing with water, a saturated aqueous solution of sodium bicarbonate and brine. The organic layer thus obtained was dried over magnesium sulfate and then concentrated under reduced pressure. The residue was subjected to flash chromatography on a silica gel column and a fraction obtained from the elution portion with hexane:ethyl acetate=3:1 was concentrated under reduced pressure, whereby the title compound (58 mg, 0.11 mmol, 59%) was obtained as a white powder.

$^1$H-NMR (400 MHz, CDCl$_3$) δ: 0.95-1.80(11H, m), 3.32 (2H, d, J=6.4 Hz), 5.98(1H, s), 6.13-6.16(1H, m), 6.90-6.96 (1H, m), 7.00-7.06(1H, m), 7.40(2H, d, J=8.6 Hz), 7.55(2H, d, J=8.6 Hz), 7.69(1H, d, J=8.3 Hz), 7.97-8.02 (1H, in), 8.13 (1H, dd, J=8.3, 2.2 Hz), 8.94(1H, d, J=2.2 Hz).

MS m/z: 519(M$^+$+H).

Example 375

6-[(4-Chlorophenylsulfonyl)(2,5-difluorophenyl)methyl]-N-(5-chloropyridin-2-yl)nicotinamide

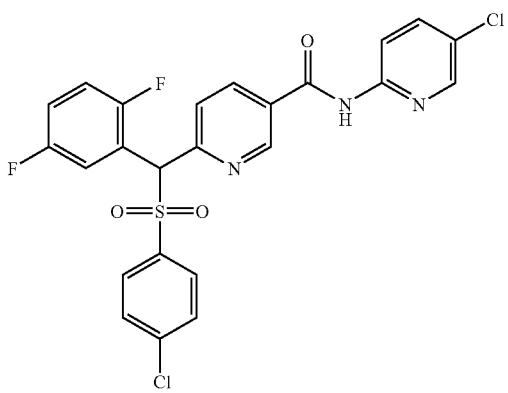

Triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and 2-amino-5-chloropyridine (29 mg, 0.23 mmol) were added to the [6-[(4-chlorophenylsulfonyl) (2,5-difluorophenyl)inethyl]pyridin-3-yl]carboxylic acid (80 mg, 0.19 mmol), which had been obtained in Example 338, in dichloromethane (5 ml). The resulting mixture was stirred at room temperature for 5 hours. The reaction mixture was diluted with dichloromethane, followed by successive washing with water, a saturated aqueous solution of sodium bicarbonate and brine. The organic layer thus obtained was dried over magnesium sulfate and then concentrated under reduced pressure. The residue was subjected to flash chromatography on a silica gel column and a fraction obtained from the elution portion with hexane:ethyl acetate=3:1 was concentrated under reduced pressure, whereby the title compound (27 mg, 0.051 mmol, 27%) was obtained as a white powder.

$^1$H-NMR (400 MHz, CDCl$_3$) δ: 6.04(1H, s), 6.92-6.97(1H, m), 7.01-7.07(1H, m), 7.42(2H, d, J=8.6 Hz), 7.57(2H, d, J=8.6 Hz), 7.75(1H, dd, J=9.1, 2.4 Hz), 7.80(1H, d, J=8.1 Hz), 7.97-8.01(1H, m), 8.26(1H, dd, J=8.1, 2.2 Hz), 8.28(1H, d, J=2.4 Hz), 7.80(1H, d, (1H, d, J=9.1 Hz), 8.51(1H, s), 9.12 (1H, d, J =2.2 Hz).

MS m/z: 534(M$^+$+H).

Example 376

6-[(4-chlorophenylsulfonyl)(2,5-difluorophenyl)methyl]nicotinic acid N',N'-dimethyl hydrazide

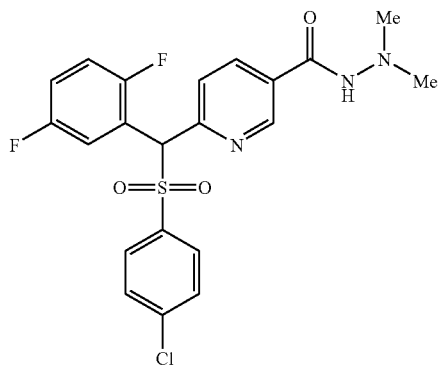

Triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and 1,1-dimethylhydrazine (21 μl, 0.23 minol) were added to the [6-[(4-chlorophenylsulfonyl) (2,5-difluorophenyl)methyl] pyridin-3-yl]carboxylic acid (80 mg, 0.19 mmol), which had been obtained in Example 338, in dichloromethane (5 ml). The resulting mixture was stirred at room temperature for 7 hours. The reaction mixture was diluted with dichloromethane, followed by successive washing with water, a saturated aqueous solution of sodium bicarbonate and brine. The organic layer thus obtained was dried over magnesium sulfate and then concentrated under reduced pressure. The residue was subjected to flash chromatography on a silica gel column and a fraction obtained from the elution portion with dichloromethane:methanol =50:1 was concentrated under reduced pressure, whereby the title compound (60 mg, 0.13 mmol, 68%) was obtained as a colorless amorphous substance.

hu 1H-NMR (400 MHz, CDCl$_3$) δ: 2.57(0.9H, s), 2.72 (5.1H, s), 5.98(1H, s), 6.48 (0.15H, s, 6.90-7.06(2.85H, m), 7.41(2H, d, J=8.6 Hz), 7.56 (2H, d, J=8.6 Hz), 7.68 (1H, d, J=8.1 Hz), 7.97-8.04(1H, m), 8.13-8.17(1H, m), 8.94 (0.85H, s), 9.07(0.15H, s).

MS m/z: 466(M$^+$+H).

Example 377

6-[(4-Chlorophenylsulfonyl)(2.5-difluorophenyl) methyl]nicotinic acid N'-(furan-2-carbonyl) hydrazide

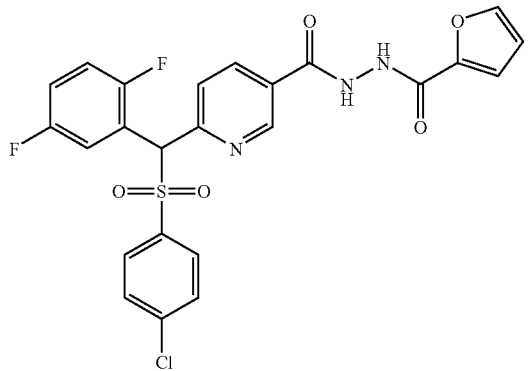

Triethylamine (32 μl, 0.23 mmol), 4-dimethylaminopyridine (12 mg, 0.095 mmol), 1-ethyl-3-(3-dimethylaminopropyl)carbodiimide hydrochloride (44 mg, 0.23 mmol) and 2-furancarboxylic acid hydrazide (29 mg, 0.23 mmol) were added to a solution of the [6-[(4-chlorophenylsulfonyl)(2,5-difluorophenyl)methyl]pyridin-3-yl]carboxylic acid (80 mg, 0.19 mmol), which had been obtained in Example 338, in dichloromethane (5 ml). The resulting mixture was stirred at room temperature for 7.5 hours. The reaction mixture was diluted with dichloromethane, followed by successive washing with water, a saturated aqueous solution of sodium bicarbonate and brine. The organic layer thus obtained was dried over magnesium sulfate and then concentrated under reduced pressure. The residue was subjected to flash chromatography on a silica gel colunm and a fraction obtained from the elution portion with dichloromethane:methanol=50:1 was concentrated under reduced pressure. The solid thus obtained was recrystallized from dichloromethane-hexane, whereby the title compound (58 mg, 0.11 mmol, 58%) was obtained as a white powder.

$^1$H-NMR (400 MHz, CDCl$_3$) δ: 6.01(0.7H, s), 6.02(0.3H, s), 6.55(0.7H, dd, J=3.4, 1.7 Hz), 6.91-6.96(1H, m), 6.99-7.04(1H, m), 7.21(0.7H, d, J=3.4 Hz), 7.41(2H, d, J=8.6 Hz), 7.53(0.3H, dd, J=1.7, 0.7 Hz), 7.56-7.60(3H, m), 7.74(1H, d, J=8.3 Hz), 7.77(0.3H, d, J=8.8 Hz), 7.95-7.99(1H, m), 8.15-8.19 (1H, m), 8.99(0.3H, s), 9.03(1H, d, J=2.2 Hz), 9.14 (0.7H, brs), 9.67(0.7H, brs), 9.98(0.3H, brs).

MS m/z: 532(M$^{30}$ +H).

Example 378

N-[[6-[(4-Chlorophenylsulfonyl)(2,5-difluorophenyl) methyl]pyridin-3-yl]methyl]-(E)-3-(pyridin-4-yl) acrylamide

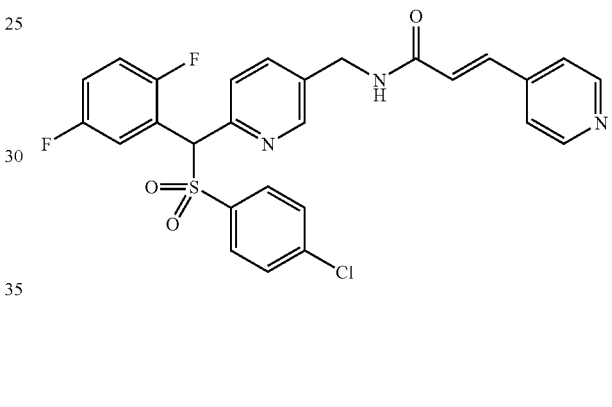

To a solution of the [6-[(4-chlorophenylsulfonyl) (2,5-difluorophenyl)methyl]pyridin-3-yl]methylamine (41 mg, 0.10 mmol) obtained in Example 351, (E)-3-(pyridin-4-yl)acrylic acid (15 mg, 0.10 mmol), benzotriazol-1-ol (14 mg, 0.10 mmol), and N-methylmorpholine (0.011 ml, 0.10 mmol) in dichloromethane (1 ml) was added 1-ethyl-3-(3-dimethylaminopropyl)carbodiimide hydrochloride (19 mg, 0.10 mmol) at 0° C. The resulting mixture was stirred at room temperature for 19 hours. The reaction mixture was washed with a saturated aqueous solution of sodium bicarbonate. The organic layer thus obtained was dried over anhydrous sodium sulfate and then filtered. The filtrate was concentrated under reduced pressure. The residue was subjected to flash silica gel chromatography and a fraction obtained from the elution portion with ethyl acetate was concentrated under reduced pressure. The solid thus obtained was washed with diethyl ether and then collected by filtration, whereby the title compound (35 mg, 0.065 mmol, 65%) was obtained as a white solid.

$^1$H-NMR (400 MHz, CDCl$_3$) δ: 4.53-4.66 (2H, m), 5.93 (1H, s), 6.09-6.17 (1H, m), 6.57 (1H, d, J=15.6 Hz), 6.86-6.93 (1H, m), 6.96-7.04 (1H, m), 7.34 (2H, d, J=5.9 Hz), 7.40 (2H, d, J=8.5 Hz), 7.56 (2H, d, J=8.5 Hz), 7.60 (1H, d, J=15.6 Hz), 7.61 (1H, d, J=8.1 Hz), 7.74 (1H, dd, J=8.1, 2.2 Hz), 7.99-8.06 (1H, m), 8.59 (1H, d, J=2.2 Hz), 8.64 (2H, d, J=5.9 Hz).

MS m/z: 540 (M$^+$+H).

Example 379

[6-[(4-Chlorophenylsulfonyl)(2,5-difluorophenyl)methyl]pyridin-3-yl](thiomorpholin-4-yl)methanone

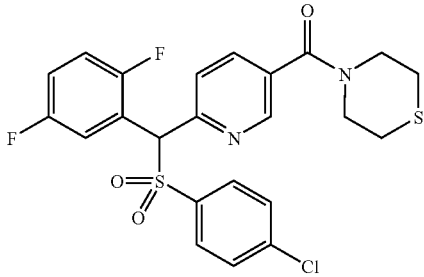

In a similar manner to Example 378 except for the use of the [6-[(4-chlorophenylsulfonyl)(2,5-difluorophenyl)methyl]pyridin-3-yl]carboxylic acid (212 mg, 0.50 mmol) obtained in Example 338 and thiomorpholine (0.047 ml, 0.50 mmol), the title compound (240 mg, 0.47 mmol, 94%) was obtained as a white solid.

$^1$H-NMR (400 MHz, CDCl$_3$) δ: 2.61 (2H, br s), 2.74 (2H, br s), 3.69 (2H, br s), 4.04 (2H, br s), 5.97 (1H, s), 6.88-6.95 (1H, m), 6.98-7.06 (1H, m), 7.41 (2H, d, J=8.5 Hz), 7.57 (2H, d, J=8.5 Hz), 7.73 (1H, d, J=8.1 Hz), 7.79 (1H, dd, J=8.1, 2.2 Hz), 7.95-8.02 (1H, m), 8.64 (1H, d, J=2.2 Hz).

MS m/z: 509 (M$^+$+H).

Example 380

[6-[(4-Chlorophenylsulfonyl)(2,5-difluorophenyl)methyl]pyridin-3-yl](1,1-dioxo-1λ$^6$-thiomorpholin-4-yl)methanone (Compound A) and [6-[(4-chlorophenylsulfonyl) (2,5-difluorophenyl)methyl] pyridin-3-yl](1-oxo-1λ$^4$-thiomorpholin-4-yl) methanone (Compound B)

Compound A

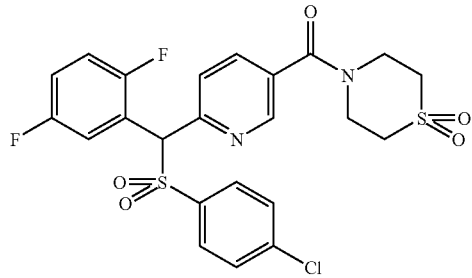

Compound B

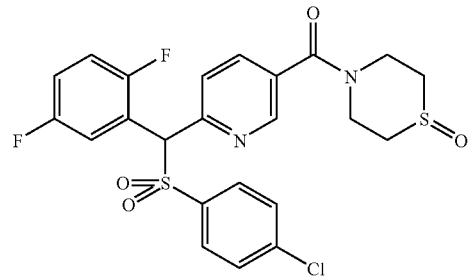

Under ice cooling, 3-chloroperbenzoic acid (96 mg, 0.36 mmol) was added to a solution of [6-[(4-chlorophenylsulfonyl) (2,5-difluorophenyl)methyl]pyridin-3-yl](thiomorpholin-4-yl)methanone (153 mg, 0.30 mmol) in dichloromethane (3 ml) and the mixture was stirred at room temperature for 2 hours. The reaction mixture was diluted with dichloromethane, followed by successive washing with a 1N aqueous solution of sodium hydroxide and brine. The organic layer thus obtained was dried over magnesium sulfate and concentrated under reduced pressure. The residue was subjected to flash chromatography on a silica gel column. A fraction obtained from the elution portion with hexane:ethyl acetate=1:2 was concentrated under reduced pressure, whereby the title compound A (low polarity compound) (81 mg, 0.15 mmol, 50%) was obtained as a white powder. A fraction obtained from the elution portion with dichloromethane:methanol=10:1 was concentrated under reduced pressure, whereby the title compound B (high polarity compound) (73 mg, 0.14 mmol, 46%) was obtained as a white powder.

Compound A $^1$H-NMR (400 MHz, CDCl$_3$) δ: 3.10 (4H, brs), 4.13 (4H, brs), 5.99 (1H, s), 6.88-6.93 (1H, m), 7.00-7.06 (1H, m), 7.42 (2H, d, J=8.5 Hz), 7.58 (2H, d, J=8.5 Hz), 7.79 (1H, d, J=8.1 Hz), 7.86 (1H, dd, J=8.1, 1.7 Hz), 7.97-8.02 (1H, m), 8.71 (1H, d, J=1.7 Hz).

MS m/z: 541 (M$^+$+H).

Compound B $^1$H-NMR (400 MHz, CDCl$_3$) δ: 2.70-3.00 (4H, m), 3.74 (1H, brs), 4.10 (2H, brs), 4.63 (1H, brs), 5.98 (1H, s), 6.88-6.94 (1H, m), 7.00-7.06 (1H, m), 7.42 (2H, d, J=8.6 Hz), 7.58 (2H, d, J=8.6 Hz), 7.77 (1H, d, J=8.1 Hz), 7.84 (1H, dd, J=8.1, 2.2 Hz), 7.98-8.02 (1H, m), 8.70 (1H, d, J=2.2 Hz).

MS m/z: 525 (M$^+$+H).

Example 381

N-(3-Methylthiopropyl)-6-[(4-chlorophenylsulfonyl)(2,5-difluorophenyl)methyl]nicotinamide

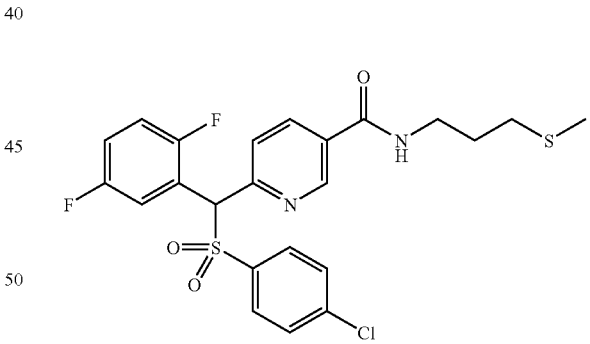

In a similar manner to Example 378 except for the use of the [6-[(4-chlorophenylsulfonyl)(2,5-difluorophenyl)methyl]pyridin-3-yl]carboxylic acid (212 mg, 0.50 mmol) obtained in Example 338 and 3-methylthiopropylamine (0.055 ml, 0.50 mmol), the title compound (238 mg, 0.47 mmol, 93%) was obtained as a white solid.

$^1$H-NMR (400 MHz, CDCl$_3$) δ: 1.92-2.01 (2H, m), 2.14 (3H, s), 2.63 (2H, t, J=6.8 Hz), 3.58-3.64 (2H, m), 5.99 (1H, s), 6.57-6.64 (1H, m), 6.90-6.97 (1H, m), 6.99-7.06 (1H, m), 7.41 (2H, d, J=8.5 Hz), 7.56 (2H, d, J=8.5 Hz), 7.71 (1H, d, J=8.1 Hz), 7.96-8.03 (1H, m), 8.16 (1H, dd, J=8.1, 2.2 Hz), 8.96 (1H, d, J=2.2 Hz).

MS m/z: 511 (M$^+$+H).

Example 382

N-(3-Methylsulfonylpropyl)-6-[(4-chlorophenylsulfonyl) (2,5-difluorophenyl)methyl]nicotinamide (Compound A) and N-(3-methylsulfinylpropyl)-6-[(4-chlorophenylsulfonyl)(2,5-difluorophenyl)methyl]nicotinamide (Compound B)

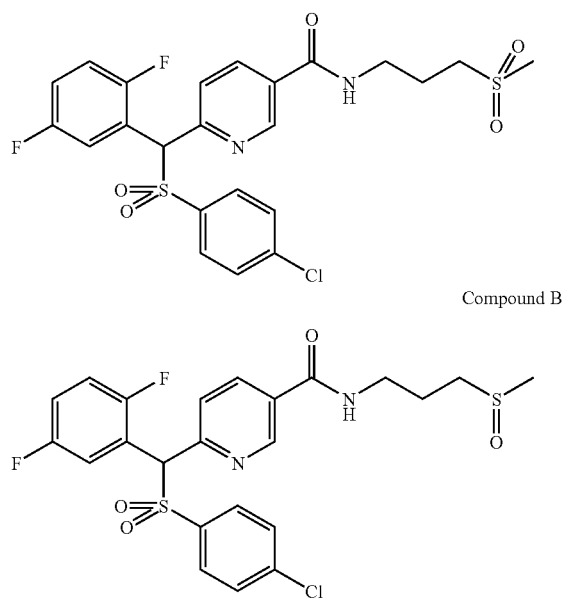

To a solution of N-(3-methylthiopropyl)-6-[(4-chlorophenylsulfonyl) (2,5-difluorophenyl)methyl]nicotinamide (153 mg, 0.30 mmol) in dichloromethane (3 ml) was added 3-chloroperbenzoic acid (purity: 65% or greater) (96 mg, 0.36 mmol) at 0° C. The resulting mixture was stirred at room temperature for 3 hours. The reaction mixture was washed with a 1N aqueous solution of sodium hydroxide. The organic layer was dried over anhydrous sodium sulfate and filtered. The filtrate was concentrated under reduced pressure. The residue was subjected to flash silica gel chromatography. A fraction obtained from the elution portion with ethyl acetate was concentrated under reduced pressure. The solid thus obtained was washed with diethyl ether and then collected by filtration, whereby the title compound A (53 mg, 0.098 mmol, 32%) was obtained as a white solid. Then, a fraction obtained from the elution portion with dichloromethane:methanol=15:1 was concentrated under reduced pressure. The solid thus obtained was washed with diethyl ether and collected by filtration, whereby the title compound B (68 mg, 0.13 mmol, 43%) was obtained as a white solid.

Compound A
$^1$H-NMR (400 MHz, CDCl$_3$) δ: 2.20-2.30 (2H, m), 2.98 (3H, s), 3.17 (2H, t, J=6.8 Hz), 3.65-3.72 (2H, m), 5.99 (1H, s), 6.82-6.88 (1H, m), 6.90-6.97 (1H, m), 6.99-7.06 (1H, m), 7.41 (2H, d, J=8.5 Hz), 7.56 (2H, d, J=8.5 Hz), 7.72 (1H, d, J=8.1 Hz), 7.96-8.02 (1H, m), 8.16 (1H, dd, J=8.1, 2.2 Hz), 9.00 (1H, d, J=2.2 Hz).
MS m/z: 543 (M$^+$+H).

Compound B
$^1$H-NMR (400 MHz, CDCl$_3$) δ: 2.11-2.23 (1H, m), 2.26-2.37 (1H, m), 2.63 (3H, s), 2.78-2.86 (1H, m), 2.92-3.00 (1H, m), 3.51-3.61 (1H, m), 3.66-3.75 (1H, m), 5.99 (1H, s), 6.90-6.98 (1H, m), 6.99-7.06 (1H, m), 7.40 (2H, d, J=8.5 Hz), 7.55 (2H, d, J=8.5 Hz), 7.69 (1H, d, J=8.1 Hz), 7.88-8.01 (2H, m), 8.22 (1H, dd, J=8.1, 2.2 Hz), 9.08 (1H, d, J=2.2 Hz).
MS m/z: 527 (M$^+$+H).

Example 383

2-Chloro-5-[(3-chloropyridin-4-yl) (2,5-difluorophenyl)methylthio]pyridine

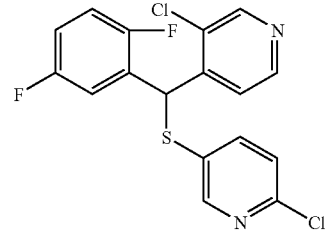

A 1N aqueous solution of sodium hydroxide (7 ml) was added to a solution of the S-(6-chloro-3-pyridyl) O-ethyl dithiocarbonate (164 mg, 0.70 mmol) obtained in Referential Example 33 and the mixture was stirred at 80° C. for 3 hours. After cooling the reaction mixture to room temperature, 1N hydrochloric acid was added, followed by extraction with dichloromethane. The organic layer was dried over anhydrous sodium sulfate and then filtered. The filtrate was concentrated under reduced pressure to yield 6-chloro-3-pyridinethiol as a yellow solid.

To a solution of the 3-chloro-4-[(2,5-difluorophenyl)-hydroxymethyl]pyridine (153 mg, 0.60 mmol), which had been obtained in Referential Example 48, in dichloromethane (3 ml) were added triethylamine (0.167 ml, 1.20 mmol) and methanesulfonyl chloride (0.070 ml, 0.90 mmol) at 0° C. and the mixture was stirred at room temperature for 2 hours. The reaction mixture was washed with a saturated aqueous solution of sodium bicarbonate. The organic layer was dried over anhydrous sodium sulfate and filtered. The filtrate was concentrated under reduced pressure.

A solution of 6-chloro-3-pyridinethiol in N,N-dimethylformamide (2 ml) and potassium carbonate (100 mg, 0.72 mmol) were added successively to a solution of the resulting residue in N,N-dimethylformamide (3 ml). The resulting mixture was stirred at room temperature for 18 hours. Ethyl acetate was added to the reaction mixture. The resulting mixture was washed with a saturated aqueous solution of sodium bicarbonate. The organic layer was dried over anhydrous sodium sulfate and filtered. The filtrate was concentrated under reduced pressure. The residue was subjected to flash silica gel chromatography. A fraction obtained from the elution portion with hexane:ethyl acetate=17:3 was concentrated under reduced pressure, whereby the title compound (111 mg, 0.29 mmol, 48%) was obtained as a white solid.

$^1$H-NMR (400 MHz, CDCl$_3$) δ: 6.04 (1H, s), 6.95-7.05 (2H, m), 7.10-7.20 (1H, m), 7.25 (1H, d, J=8.1 Hz), 7.57 (1H, d, J=5.1 Hz), 7.60 (1H, dd, J=8.1, 2.5 Hz), 8.31 (1H, d, J=2.5 Hz), 8.54 (1H, d, J=5.1 Hz), 8.59 (1H, s).
MS m/z: 383 (M$^+$+H).

Example 384

2-Chloro-5-[(3-chloropyridin-4-yl)(2,5-difluorophenyl)methylsulfonyl]pyridine

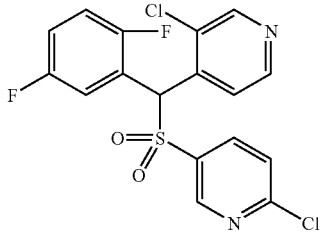

A 31% aqueous hydrogen peroxide solution (2 ml) and hexaammonium heptamolybdate tetrahydrate (30 mg) were added to a solution of 2-chloro-5-[(3-chloropyridin-4-yl)(2,5-difluorophenyl)methylthio]pyridine (109 mg, 0.28 mmol) in methanol (4 ml) were added and the mixture was stirred at room temperature for 17 hours. Ethyl acetate was added to the reaction mixture, followed by washing with a saturated aqueous solution of sodium bicarbonate. The organic layer was dried over anhydrous sodium sulfate and filtered. The filtrate was concentrated under reduced pressure. The residue was subjected to flash silica gel chromatography and a fraction obtained from the elution portion with hexane:ethyl acetate=17:3 was concentrated under reduced pressure, whereby the title compound (108 mg, 0.26 mmol, 92%) was obtained as a white solid.

$^1$H-NMR (400 MHz, CDCl$_3$) δ: 6.26 (1H, s), 6.94-7.03 (1H, m), 7.06-7.15 (1H, m), 7.44 (1H, d, J=8.3 Hz), 7.50-7.56 (1H, m), 7.89 (1H, dd, J=8.3, 2.7 Hz), 8.12 (1H, d, J=5.1 Hz), 8.59 (1H, d, J=2.7 Hz), 8.61 (1H, s), 8.66 (1H, d, J=5.1 Hz).

MS m/z: 415 (M$^+$+H).

Example 385

5-[(3-Chloropyridin-4-yl)(2,5-difluorophenyl)methylsulfonyl]-2-fluoropyridine

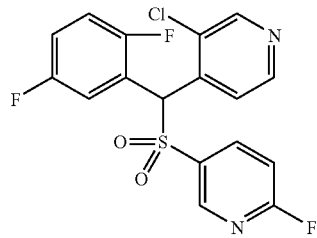

Potassium fluoride (94 mg, 1.60 mmol) and tetraphenylphosphonium bromide (134 mg, 0.32 mmol) were added to a solution of 2-chloro-5-[(3-chloropyridin-4-yl) (2,5-difluorophenyl)methylsulfonyl]pyridine (66 mg, 0.16 mmol) in acetonitrile (2 ml). The resulting mixture was heated under reflux for 16 hours. The reaction mixture was cooled to room temperature. Dichloromethane was added and the mixture was washed with water. The organic layer was dried over anhydrous sodium sulfate and filtered. The filtrate was concentrated under reduced pressure. The residue was subjected to flash chromatography on a silica gel column and a fraction obtained from the elution portion with hexane:ethyl acetate=17:3 was concentrated under reduced pressure, whereby the title compound (4.5 mg, 0.011 mmol, 7%) was obtained as a white solid.

$^1$H-NMR (400 MHz, CDCl$_3$) δ: 6.26 (1H, s), 6.93-7.13 (3H, m), 7.50-7.56 (1H, m), 8.01-8.08 (1H, m), 8.13 (1H, d, J=5.1 Hz), 8.48 (1H, d, J=2.2 Hz), 8.60 (1H, s), 8.66 (1H, d, J=5.1 Hz).

MS m/z: 440 (M$^+$+H+MeCN).

Example 386

N'-[6-[(4-Chlorophenylsulfonyl)(2,5-difluorophenyl)methyl]pyridin-3-ylmethylidene]-2-thiophenecarbohydrazide

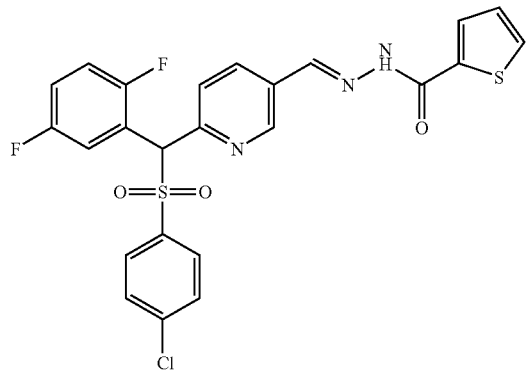

The [6-[(4-chlorophenylsulfonyl)-(2,5-difluorophenyl)methyl]pyridin-3-yl]carbaldehyde (100 mg, 0.245 mmol) obtained in Example 335 and 2-thiophenecarbohydrazide (41.7 mg, 0.294 mmol) were dissolved in ethanol (3 ml). The resulting solution was stirred at room temperature for 3 days. The solid thus precipitated was collected by filtration and washed with ethanol. The resulting solid was recrystallized from ethanol, whereby the title compound (91.0 mg, 0.171 mol, 70%) was obtained as a white solid.

$^1$H-NMR (400 MHz, CDCl$_3$/DMSO-d$_6$) δ: 5.98 (1H, s), 6.93-7.01 (1H, m), 7.02-7.09 (1H, m), 7.14-7.20 (1H, br m), 7.42 (2H, d, J=8.5 Hz), 7.57 (2H, d, J=8.5 Hz), 7.62-7.73 (2H, br m), 8.02-8.20 (3H, m), 8.95 (1H, s), 11.5 (1H, s).

IR (ATR) cm$^{-1}$: 3302, 1655, 1597, 1541, 1489, 1419, 1394, 1321, 1279, 1149, 1078, 1016, 966, 889, 831, 822, 762, 725, 710, 611, 552, 509, 465.

MS m/z: 532 (M$^+$+H).

Example 387

6-[(4-Chlorophenylsulfonyl)(2,5-difluorophenyl)methyl]nicotinamide

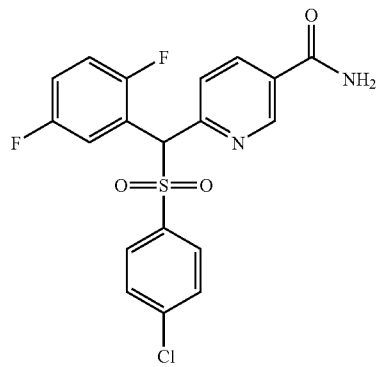

Thionyl chloride (1.00 ml) and N,N-dimethylformamide (one drop) were added to a suspension of the [6-[(4-chlorophenylsulfonyl)(2,5-difluorophenyl)methyl]pyridin-3-yl]carboxylic acid (100 mg, 0.236 mmol), which had been obtained in Example 338, in dichloromethane (4 ml). The resulting mixture was stirred at room temperature for 18 hours. The reaction mixture was concentrated to dryness. The residue was then dissolved in dichloromethane (6 ml), followed by the addition of 28% aqueous ammonia (2 ml). After the reaction mixture was stirred at room temperature for 3 hours, it was acidified with 1N hydrochloric acid. The resulting mixture was concentrated and the solid thus formed was collected by filtration. The solid was washed with water and ethanol and then recrystallized from ethanol, whereby the title compound (47.9 mg, 0.113 mmol, 46%) was obtained as a white solid.

$^1$H-NMR (400 MHz, CDCl$_3$/DMSO-d$_6$) δ: 6.00 (1H, s), 6.38 (1H, br s), 6.94-6.99 (1H, m), 7.02-7.08 (1H, m), 7.43 (2H, d, J=8.5 Hz), 7.56 (2H, d, J=8.5 Hz), 7.67 (1H, d, J=7.6 Hz), 7.65-7.75 (1H, br m), 7.99-8.04 (1H, m), 8.26 (1H, dd, J=8.1, 2.4 Hz), 9.12 (1H, d, J=1.7 Hz).

IR (ATR) cm$^{-1}$: 3442, 3165, 2954, 1670, 1624, 1595, 1496, 1410, 1373, 1313, 1279, 1232, 1176, 1147, 1086, 1012, 831, 816, 754, 710, 667, 606, 552, 499, 465.

MS m/z: 423 (M$^+$+H).

Example 388

6-[(4-Chlorophenylsulfonyl)(2,5-difluorophenyl)methyl]-N-(4-methylcyclohexyl)nicotinamide

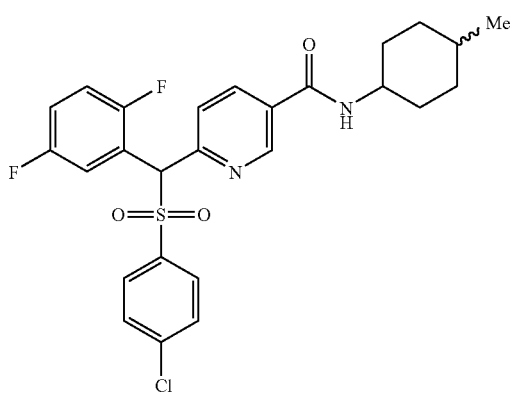

Thionyl chloride (1.00 ml) and N,N-dimethylformamide (one drop) were added to a suspension of the [6-[(4-chlorophenylsulfonyl)(2, 5-difluorophenyl)methyl]pyridin-3-yl]carboxylic acid (100 ing, 0.236 minol), which had been obtained in Example 338, in dichloromethane (4 ml). The resulting mixture was stirred at room temperature for 6 hours. The reaction mixture was concentrated to dryness. The residue was then dissolved in dichioromethane (6 ml), followed by the addition of N-methylmorpholine (51.8 μl, 0.472 mmol) and 4-methylcyclohexylamine (37.4 μl, 0.283 mmol). After the reaction mixture was stirred at room temperature for 18 hours, the mixture was diluted with dichloromethane. The solution was washed successively with 1N hydrochloric acid, water and brine, dried over magnesium sulfate and concentrated. The residue was subjected to flash chromatography on a silica gel column. A fraction obtained from the elution portion with hexane:ethyl acetate=3:1 was concentrated, whereby a white solid was obtained. The resulting solid was recrystallized from ethyl acetate-hexane, whereby the title compound (70.3 mg, 0.135 mmol, 57%) was obtained as a white powder.

$^1$H-NMR (400 MHz, CDCl$_3$) δ:0.92(1.8H, d, J=6.6 Hz), 0.96(1.2H, d, J=6.4 Hz), 1,05-1.30(3H, m), 1.32-1.43(0.6H, m), 1.55-1.83(4.4H, m), 2.03-2.12 (1H, m), 3.86-3.97(0.6H, m), 4.20-4.28(0.4H, m), 5.88(0.6H, d, J=7.1Hz), 5.98(1H, s), 6.18(0.4H, d, J=7.3 Hz), 6.90-6.96(1H, m), 6.98-7.06(1H, m), 7.41 (1.2H, d, J=8.1 Hz), 7.41(0.8H, d, J=8.1 Hz), 7.56 (1.2H, d, J=8.1 Hz), 7.57(0.8H, d, J=8.1 Hz), 7.67-7.72(1H, m), 7.97-8.05(1H, m), 8.10-8.18(1H, m), 8.93(0.6H, d, J=2.2 Hz), 8.96(0.4H, d, J=2.2 Hz).

IR(ATR)cm$^{-1}$: 3381, 2935, 1643, 1595, 1525, 1489, 1394, 1317, 1281, 1234, 1171, 1147, 1078, 1016, 966, 897, 831, 823, 764, 729, 609, 548, 469, 413.

MS m/z: 519(M$^+$+H).

Example 389

6-[(4-Chlorophenylsulfonyl)(2,5-difluorophenyl)methyl]-N-methoxynicotinamide

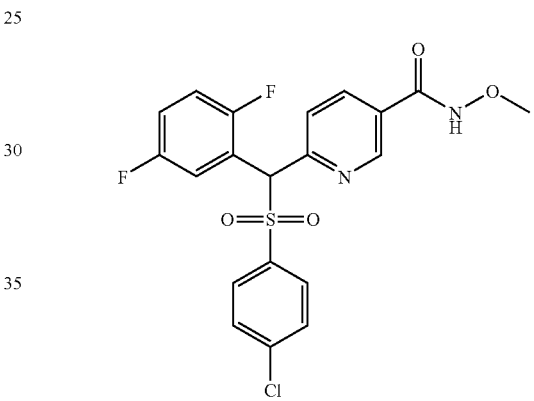

To a suspension of the [6-[(4-chlorophenylsulfonyl)(2,5-difluorophenyl)methyl]pyridin-3-yl]carboxylic acid (100 mg, 0.236 mmol), which had been obtained in Example 338, in dichloromethane (6 ml) were added N-methylmorpholine (77.7 μl, 0.708 mmol), o-methylhydroxylamine hydrochloride (23.6 mg, 0.283 mzmol), and 1-ethyl-3-(3-dimethylaminopropyl)carbodiimide hydrochloride (54.3 mg, 0.283 mmol). After stirring at room temperature for 1 hour, tetrahydrofuran (1 ml) was added to the mixture. The reaction mixture was stirred at room temperature for 18 hours. The mixture was then diluted with dichloromethane, and washed with water and brine. The organic layer thus obtained was dried over magnesium sulfate and concentrated under reduced pressure. The residue was subjected to flash chromatography on a silica gel column and a fraction obtained from the elution portion with hexane:ethyl acetate=1:1 was concentrated, whereby a white solid was obtained. The solid was washed with ethyl acetate, whereby the title compound (55.1 mg, 0.122 mmol, 52%) was obtained as a white powder.

$^1$H-NMR (400 MHz, CDCl$_3$) δ: 3.90(2.4H, s), 3.97(0.6H, s), 5.97(0.2H, s), 5.98(0.8H, s), 6.90-7.07(2H, m), 7.39-7.46 (2H, m), 7.54-7.59(2H, m), 7.63(0.2H, d, J=8.3 Hz), 7.73 (0.8H, d, J =8.1Hz), 7.94-8.00(1H, m), 8.10-8.15(1H, m), 8.76(1H, br s), 8.92(0.8H d, J=1.7 Hz), 9.01(0.2H, d, J=1.5 Hz).

MS m/z: 453(M$^+$+H).

Example 390

N,N-Dimethyl-6-[(4-chlorophenylsulfonyl)(2,5-difluorophenyl)methyl]pyridin-3-yl]methylamine

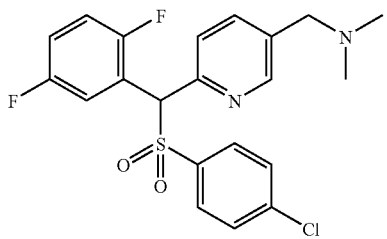

After the [6-[(4-chlorophenylsulfonyl)(2,5-difluorophenyl)methyl]pyridin-3-yl]carbaldehyde (100 mg, 0.245 mmol) obtained in Example 335, a tetrahydrofuran solution (2.0M, 0.25 ml, 0.50 mmol) of dimethylamine and acetic acid (0.029 ml, 0.51 mmol) were dissolved in 1,2-dichloroethane (5 ml), sodium triacetoxyborohydride (115 mg, 0.515 mmol) was added to the resulting solution at room temperature. The resulting mixture was stirred at room temperature for 3 days. A saturated aqueous solution of sodium bicarbonate and ethyl acetate were added to the reaction mixture. The mixture was separated and the organic layer thus obtained was washed successively with a saturated aqueous solution of sodium bicarbonate and brine and dried over anhydrous magnesium sulfate. After filtration, the filtrate was concentrated under reduced pressure. The residue was subjected to flash silica gel chromatography and a fraction obtained from the elution portion with dichloromethane:methanol=40:1 was concentrated under reduced pressure to yield a white solid. The solid was washed with hexane, whereby the title compound (88 mg, 0.20 mmol, 82%) was obtained as a white powder.

$^1$H-NMR (400 MHz, CDCl$_3$) δ: 2.23 (6H, s), 3.43 (2H, s), 5.94 (1H, s), 6.88-6.98 (1H, m), 6.98-7.06 (1H, m), 7.38 (2H, d, J=8.6 Hz), 7.52-7.62 (3H, m), 7.71 (1H, dd, J=8.1, 2.1 Hz), 7.98-8.08 (1H, m), 8.51 (1H, d, J=2.1 Hz).

MS m/z: 437 (M$^+$+H).

Example 391

N-[[6-[(4-Chlorophenylsulfonyl)(2,5-difluorophenyl)methyl]pyridin-3-yl]methyl]bis(2-methoxyethyl)amine

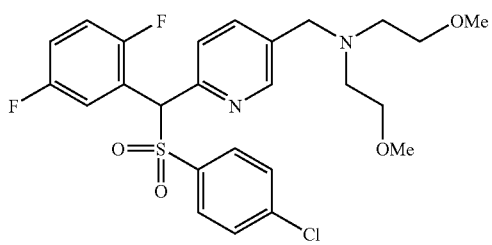

After the [6-[(4-chlorophenylsulfonyl)(2,5-difluorophenyl)methyl]pyridin-3-yl]carbaldehyde (100 mg, 0.245 mmol) obtained in Example 335, bis(2-methoxyethyl)amine (70 mg, 0.53 mmol) and acetic acid (0.029 ml, 0.51 mmol) were dissolved in 1,2-dichloroethane (5 ml), sodium triacetoxyborohydride (115 mg, 0.515 mmol) was added to the resulting solution at room temperature. The resulting mixture was stirred at room temperature for 3 days. A saturated aqueous solution of sodium bicarbonate and ethyl acetate were added to the reaction mixture. The mixture was separated and the organic layer thus obtained was washed successively with a saturated aqueous solution of sodium bicarbonate and brine and dried over anhydrous magnesium sulfate. After filtration, the filtrate was concentrated under reduced pressure. The residue was subjected to flash silica gel chromatography and a fraction obtained from the elution portion with hexane:ethyl acetate=3:2 was concentrated under reduced pressure to yield a white solid. The solid was washed with hexane, whereby the title compound (101 mg, 0.192 mmol, 78%) was obtained as a white powder.

$^1$H-NMR (400 MHz, CDCl$_3$) δ: 2.73 (4H, t, J=5.8 Hz), 3.31 (6H, s), 3.47 (4H, d, J=5.8 Hz), 3.75 (2H, s), 5.93 (1H, s), 6.88-6.97 (1H, m), 6.97-7.07 (1H, m), 7.38 (2H, d, J=8.8 Hz), 7.50-7.60 (3H, m), 7.76 (1H, dd, J=8.1, 2.0 Hz), 7.98-8.08 (1H, m), 8.54 (1H, d, J=2.0 Hz).

MS m/z: 525 (M$^+$+H).

Example 392

6-[(4-Chlorophenylsulfonyl)(2,5-difluorophenyl)methyl]-N,N-dimethylnicotinamide

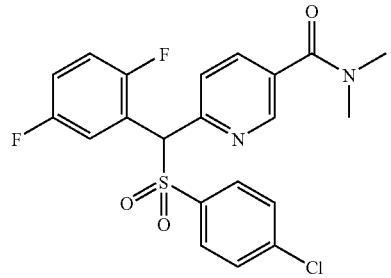

After the [6-[(4-chlorophenylsulfonyl)(2,5-difluorophenyl)methyl]pyridin-3-yl]carboxylic acid (90 mg, 0.21 mmol) obtained in Example 338, a tetrahydrofuran solution (2.0M, 0.21 ml, 0.42 mmol) of dimethylamine, 4-(dimethylamino)pyridine (15 mg, 0.12 mmol) and triethylamine (0.045 ml, 0.32 mmol) were dissolved in dichloromethane (5 ml), 1-ethyl-3-(3-dimethylaminopropyl)carbodiimide hydrochloride (61 mg, 0.32 mmol) was added to the resulting solution at room temperature. The resulting mixture was stirred at room temperature for 14 hours. The reaction mixture was concentrated under reduced pressure. The residue thus obtained was subjected to flash silica gel chromatography and a fraction obtained from the elution portion with hexane:ethyl acetate=2:1 was concentrated under reduced pressure, whereby the title compound (35 mg, 0.066 mmol, 90%) was obtained as a white powder.

$^1$H-NMR (400 MHz, CDCl$_3$) δ: 3.01 (3H, s), 3.14 (3H, s), 5.97 (1H, s), 6.88-6.99 (1H, m), 6.99-7.08 (1H, m), 7.40 (2H, d, J=8.7 Hz), 7.57 (2H, d, J=8.7 Hz), 7.70 (1H, dd, J=8.0, 0.7 Hz), 7.82 (1H, dd, J=8.0, 2.2 Hz), 7.93-8.04 (1H, m), 8.68 (1H, dd, J=2.2, 0.7 Hz).

MS m/z: 451 (M$^+$+H).

Example 393

[6-[(4-Chlorophenylsulfonyl)(2,5-difluorophenyl)methyl]pyridin-3-yl](4-methylpiperazin-1-yl)methanone

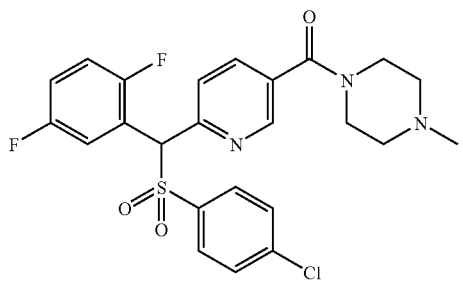

After the [6-[(4-chlorophenylsulfonyl)(2,5-difluorophenyl)methyl]pyridin-3-yl]carboxylic acid (90 mg, 0.21 mmol) obtained in Example 338, N-methylpiperazine (0.036 ml, 0.33 mmol), 4-(dimethylamino)pyridine (15 mg, 0.12 mmol) and triethylamine (0.045 ml, 0.32 mmol) were dissolved in dichloromethane (5 ml), 1-ethyl-3-(3-dimethylaminopropyl)carbodiimide hydrochloride (61 mg, 0.32 mmol) was added to the resulting solution at room temperature. The resulting mixture was stirred at room temperature for 14 hours. To the reaction mixture, N-methylpiperazine (0.036 ml, 0.33 mmol), triethylamine (0.045 ml, 0.32 mmol) and 1-ethyl-3-(3-dimethylaminopropyl)carbodiimide hydrochloride (61 mg, 0.32 mmol) were added further. The resulting mixture was stirred at room temperature for 14 hours, followed by concentration under reduced pressure. The residue thus obtained was subjected to flash silica gel chromatography and a fraction obtained from the elution portion with dichloromethane:methanol=25:1 was concentrated under reduced pressure, whereby the title compound (86 mg, 0.17 mmol, 80%) was obtained as a white powder.

$^1$H-NMR (400 MHz, CDCl$_3$) δ: 2.33 (3H, s), 2.38 (2H, br s), 2.50 (2H, br s), 3.44 (2H, br s), 3.81 (2H, br s), 5.97 (1H, s), 6.87-6.98 (1H, m), 6.98-7.08 (1H, m), 7.40 (2H, d, J=8.8 Hz), 7.57 (2H, d, J=8.8 Hz), 7.71 (1H, dd, J=8.1, 0.7 Hz), 7.81 (1H, dd, J=8.1, 2.2 Hz), 7.94-8.04 (1H, m), 8.66 (1H, dd, J=2.2, 0.7 Hz).

MS m/z: 506 (M$^+$+H).

Example 394

4-[2-[5-Chloro-4-[(4-chlorophenylsulfonyl)-(2,5-difluorophenyl)methyl]pyridin-2-yl]aminoethyl]morpholine

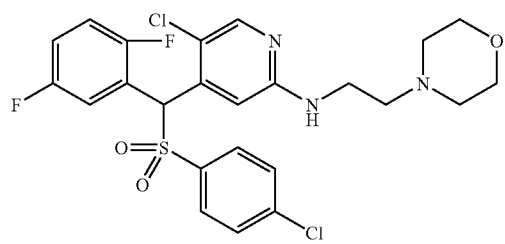

The 4-[2-[5-chloro-4-[(4-chlorophenylsulfonyl)-(2,5-difluorophenyl)methyl]pyridin-2-yl]aminoethyl]morpholine-N-oxide (78 mg, 0.14 mmol) obtained in Example 349 was dissolved in a mixed solvent of acetic acid (2.0 ml) and water (2.0 ml). The resulting mixture was heated to 60° C. Iron powder (40 mg, 0.72 mmol) was added and the mixture was stirred for 30 minutes. After cooling, the reaction mixture was poured into a saturated aqueous solution of potassium carbonate, followed by extraction with ethyl acetate (60 ml). The solution was washed with brine, dried and then concentrated under reduced pressure. The residue was purified by silica gel chromatography (3% methanol/chloroform solution), whereby the title compound (30 mg, 40%) was obtained.

$^1$H-NMR (400 MHz, CDCl$_3$) δ: 2.5-2.8 (6H, m), 3.59 (2H, br), 3.81 (4H, br), 5.45 (1H, br), 6.10 (1H, s), 6.88 (1H, m), 7.01 (1H, m), 7.25 (1H, s), 7.42 (2H, d, J=8.8 Hz), 7.49 (1H, m), 7.60 (2H, d, J=8.4 Hz), 7.97 (1H, s).

MS m/z: 542(M$^+$+H).

Example 395

Tert-Butyl 2-[N-[5-chloro-4-[(4-chlorophenylthio)-(2,5-difluorophenyl)methyl]pyridin-2-yl]-N-methylamino]ethyl-methylcarbamate

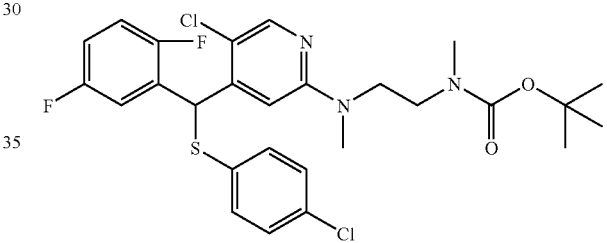

A solution of the 2,5-dichloro-4-[(4-chlorophenylthio)-(2,5-difluorophenyl)methyl]pyridine (78 mg, 0.19 mmol) obtained in Example 342 and N,N'-dimethylethylenediamine (400 μl) in 1,4-dioxane (2.0 ml) was stirred at 100° C. for 2 days under nitrogen atmosphere.

After cooling to room temperature, the reaction mixture was diluted with ethyl acetate (40 ml). The solution was washed with water and brine, dried and then, concentrated under reduced pressure.

The residue thus obtained was dissolved in tetrahydrofuran (10 ml), followed by the addition of triethylamine (31 μl, 0.22 mmol) and di-tert-butyl dicarbonate (49 mg, 0.22 mmol) at room temperature. The resulting mixture was stirred for 15 hours. After the solution was concentrated under reduced pressure, the residue was purified by silica gel chromatography (hexane:ethyl acetate=4:1), whereby the title compound (68 mg, 64%) was obtained as an oil.

$^1$H-NMR (400 MHz, CDCl$_3$) δ: 1.26 and 1.32 (9H, br-s, rotamer), 2.75 and 2.78 (3H, br-s, rotamer), 2.95 (3H, br-s), 3.30 (2H, m), 3.65 (2H, m), 5.92 (1H, s), 6.6-6.8 (1H, m), 6.84-6.97 (2H, m), 7.05 (1H, m), 7.14 (2H, d, J=8.8 Hz), 7.17 (2H, d, J=8.4 Hz), 7.98 (1H, s).

MS m/z: 568(M$^+$+H).

Example 396

Tert-Butyl 2-[N-[5-chloro-4-[(4-chlorophenylsulfonyl)-(2,5-difluorophenyl)methyl]pyridin-2-yl]-N-methylamino]ethyl-methylcarbamate

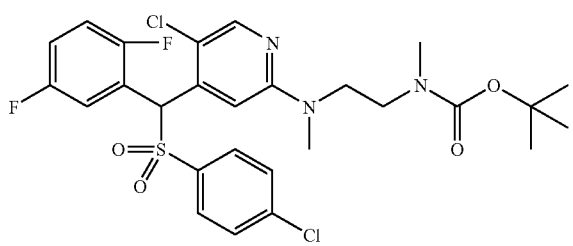

To a solution of tert-butyl 2-[N-[5-chloro-4-[(4-chlorophenylthio)-(2,5-difluorophenyl)methyl]pyridin-2-yl]-N-methylamino]ethyl-methylcarbamate (67 mg, 0.12 mmol) in methanol (6 ml) was added hexaammonium heptamolybdate tetrahydrate (30 mg). A 30% aqueous hydrogen peroxide solution (3 ml) was then added and the mixture was stirred for 17 hours. After dilution with ethyl acetate, the solution was washed with water and brine, and concentrated under reduced pressure. The residue thus obtained was purified by silica gel chromatography (hexane:ethyl acetate=3:1), whereby the title compound (64 mg, 91%) was obtained as an oil.

$^1$H-NMR (400 MHz, CDCl$_3$) δ: 1.33 and 1.38 (9H, br-s, rotamer), 2.87 and 2.89 (3H, br-s, rotamer), 3.11 (3H, br-s), 3.3-3.4 (2H, m), 3.6-3.9 (2H, m), 6.12 (1H, s), 6.89 (1H, m), 7.00 (1H, m), 7.26 (1H, m), 7.41 (2H, d, J=8.4 Hz), 7.53 (1H, m), 7.59 (2H, d, J=8.4 Hz), 8.00 (1H, s).

MS m/z: 600 (M$^+$+H).

EI-MS: 599.1204 (Calcd for C$_{27}$H$_{29}$Cl$_2$F$_2$N$_3$O$_4$S: 599.1224).

Example 397

5-Chloro-4-[(4-chlorophenylsulfonyl)-(2,5-difluorophenyl)methyl]-2-[N-methyl-N-[2-(methylamino)ethyl]amino]pyridine

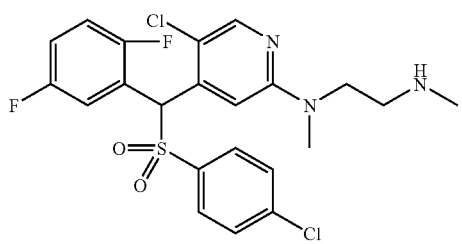

In methylene chloride (2.0 ml) was dissolved tert-butyl 2-[N-[5-chloro-4-[(4-chlorophenylsulfonyl)-(2,5-difluorophenyl)methyl]pyridine-2-yl]-N-methylamino]ethyl-methylcarbamate (61 mg, 0.10 mmol), followed by the addition of anisole (40 µl) and trifluoroacetic acid (200 µl) at room temperature. The resulting mixture was stirred for 1 hour. The residue obtained by concentrating the reaction mixture under reduced pressure was purified by silica gel chromatography (3% methanol/chloroform→3% methanol, 3% tertbutylamine/chloroform), whereby the title compound (21 mg, 41%) was obtained as an oil.

$^1$H-NMR (400 MHz, CDCl$_3$) δ: 2.51 (3H, s), 2.90 (2H, d, J=6.0 Hz), 3.14 (3H, s), 3.72 (2H, m), 6.13 (1H, s), 6.89 (1H, m), 7.00 (1H, m), 7.36 (1H, m), 7.41 (2H, d, J=8.4 Hz), 7.52 (1H, m), 7.60 (2H, d, J=8.4 Hz), 8.00 (1H, s).

MS m/z: 500 (M$^+$+H).

FAB-MS: 500.0770 (Calcd for C$_{22}$H$_{22}$Cl$_2$F$_2$N$_3$O$_2$S: 500.0778).

Example 398

(2'S)-5-Chloro-4-[(4-chlorophenylthio)-(2,5-difluorophenyl)methyl]-2-[2'-(hydroxymethyl)pyrrolidin-1'-yl]pyridine

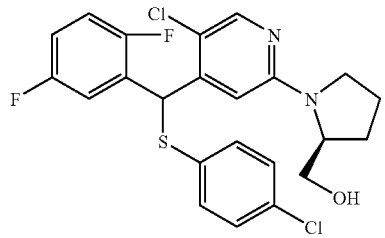

A solution of the 2,5-dichloro-4-[(4-chlorophenylthio)-(2,5-difluorophenyl)methyl]pyridine (60 mg, 0.14 mmol), which had been obtained in Example 342, and (S)-2-pyrrolidinemethanol (200 µl) in 1,4-dioxane (1.0 ml) was stirred at 100° C. for 3 days under nitrogen atmosphere. After cooling to room temperature, the reaction mixture was diluted with ethyl acetate (50 ml). The solution was washed with water and brine, dried and concentrated under reduced pressure. The residue was purified by silica gel chromatography (hexane:ethyl acetate=5:1), whereby the title compound (40 mg, 58%) was obtained as an oil.

$^1$H-NMR (400 MHz, CDCl$_3$) δ: 1.78 (1H, m), 2.06 (3H, m), 3.29 (1H, m), 3.50 (1H, m), 3.66 (1H, m), 3.72 (1H, m), 4.33 (1H, m), 5.97 and 5.98 (1H, s, rotamer), 6.73 and 6.77 (1H, s, rotamer), 6.92-7.15 (3H, m), 7.25 (4H, m), 7.98 (1H, s).

MS m/z: 481 (M$^+$+H).

Example 399

(2'S)-5-Chloro-4-[(4-chlorophenylsulfonyl)-(2,5-difluorophenyl)methyl-2-[2'-(hydroxymethyl)pyrrolidin-1'-yl]pyridine

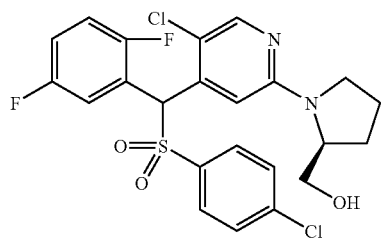

Hexaammonium heptamolybdate tetrahydrate (30 mg) was added to a solution of (2'S)-5-chloro-4-[(4-chlorophenylthio)-(2,5-difluorophenyl)methyl]-2-[2'-(hydroxymethyl)pyrrolidin-1'-yl]pyridine (39 mg, 0.08 mmol) in methanol (6 ml). A 30% aqueous hydrogen peroxide solution (3 ml) was added to the resulting mixture, followed by stirring for 17 hours. The reaction mixture was diluted with ethyl acetate (60 ml). The solution was washed with water and brine, and concentrated under reduced pressure. The residue was purified by silica gel chromatography (hexane:ethyl acetate=1:1), whereby the title compound (33 mg, 79%) was obtained as an oil.

$^1$H-NMR (400 MHz, CDCl$_3$) δ: 1.75 (1H, m), 2.02 (3H, m), 3.3-3.5 (1H, m), 3.52-3.75 (3H, m), 4.2-4.35 (1H, m), 6.05 (1H, br-s), 6.84 (1H, m), 6.96 (1H, m), 7.36 (1H, s), 7.36 and 7.37 (2H, d, J=8.8 Hz, rotamer), 7.43 (1H, m), 7.53 and 7.54 (2H, d, J=8.8 Hz, rotamer), 7.89 and 7.90 (1H, s, rotamer).

MS m/z: 513 (M$^+$+H).

FAB-MS: 513.0627 (Calcd for C$_{23}$H$_{21}$Cl$_2$F$_2$N$_2$O$_3$S: 513.0618).

Example 400

T-Butyl [4-[5-chloro-4-[(4-chlorophenylthio)-(2,5-difluorophenyl)methyl]pyridine-2-yl]morpholine-2-yl]methylcarbamate

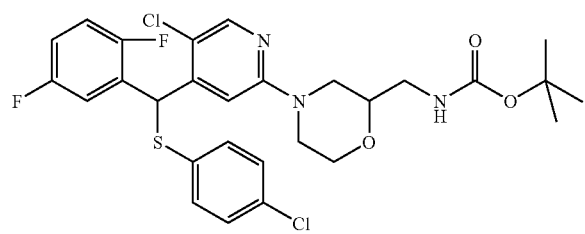

A solution of the 2,5-dichloro-4-[(4-chlorophenylthio)-(2,5-difluorophenyl)methyl]pyridine (60 mg, 0.14 mmol) obtained in Example 342 and (morpholin-2-yl)methylcarbamate tert-butyl (200 mg) in 1,4-dioxane (1.0 ml) was stirred at 100° C. for 2 days under nitrogen atmosphere. After cooling to room temperature, the reaction mixture was diluted with ethyl acetate (50 ml). The solution was washed with water and brine, dried and concentrated under reduced pressure. The residue thus obtained was purified by silica gel chromatography (hexane:ether=5:1), whereby the title compound (45 mg, 52%) was obtained as an oil.

$^1$H-NMR (400 MHz, CDCl$_3$) δ: 1.46(9H, s), 2.72(1H, m), 3.00(1H, m), 3.22(1H, m), 3.44 (1H, m), 3.6-3.75(2H, m), 3.9-4.1(3H, in), 4.95 (1H, br), 5.99 and 6.00(1H, s, rotamer), 6.96 and 6.97(1H, s, rotamer), 6.9-7.1(3H, m), 7.24 (4H, s), 8.11(1H, s).

MS m/z: 596(M$^+$+H).

$^1$H-NMR (400 MHz, CDCl$_3$) δ: 1.46 (9H, s), 2.72 (1H, m), 3.00 (1H, m), 3.22 (1H, m), 3.44 (1H, m), 3.6-3.75 (2H, m), 3.9-4.1 (3H, m), 4.95 (1H, br), 5.99 and 6.00 (1H, s, rotamer), 6.96 and 6.97 (1H, s, rotamer), 6.9-7.1 (3H, m), 7.24 (4H, s), 8.11 (1H, s).

MS m/z: 596(M$^+$+H).

Example 401

Tert-Butyl [4-[5-chloro-4-[(4-chlorophenylsulfonyl)-(2,5-difluorophenyl)methyl]pyridin-2-yl]morpholine-2-yl]methylcarbamate

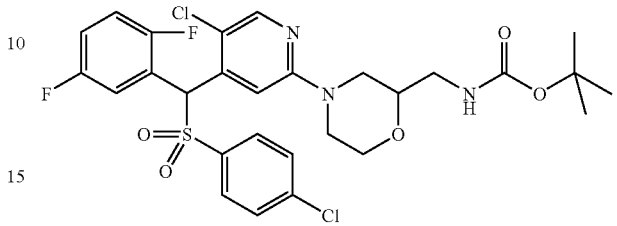

Hexaammonium heptamolybdate tetrahydrate (30 mg) was added to a solution of tert-butyl [4-[5-chloro-4-[(4-chlorophenylthio)-(2,5-difluorophenyl)methyl]pyridine-2-yl]morpholine-2-yl]methylcarbamate (44 mg, 0.074 mmol) in methanol (6 ml). A 30% aqueous hydrogen peroxide solution (3 ml) was added to the resulting mixture, followed by stirring for 17 hours. The reaction mixture was diluted with ethyl acetate (60 ml). The solution was washed with water and brine, and concentrated under reduced pressure. The residue thus obtained was purified by silica gel chromatography (hexane:ethyl acetate=3:1), whereby the title compound (31 mg, 67%) was obtained as an oil.

$^1$H-NMR (400 MHz, CDCl$_3$) δ: 1.40 (9H, s), 2.69 (1H, m), 3.02 (1H, m), 3.18 (1H, m), 3.41 (1H, br), 3.6-3.75 (2H, In), 3.92 (1H, m), 4.02 (1H, m), 4.13 (1H, m), 4.91 (1H, br), 6.07 (1H, s), 6.85 (1H, m), 6.99 (1H, m), 7.37 (2H, d, J=8.4 Hz), 7.35-7.45 (2H, m), 7.53 (2H, d, J=8.4 Hz), 8.17 (1H, s).

MS m/z: 628(M$^+$+H).

FAB-MS: 628.1255 (Calcd for C$_{28}$H$_{30}$Cl$_2$F$_2$N$_3$O$_5$S: 628.1251).

Example 402

2-Aminomethyl-4-[5-chloro-4-[(4-chlorophenylsulfonyl)-(2,5-difluorophenyl)methyl]pyridin-2-yl]morpholine

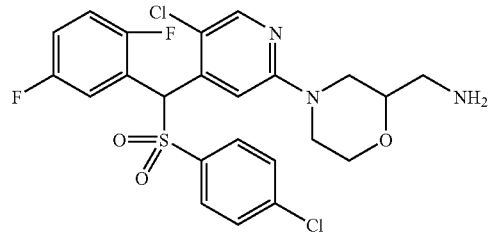

In methylene chloride (1.5 ml) was dissolved tert-butyl [4-[5-chloro-4-[(4-chlorophenylsulfonyl)-(2,5-difluorophenyl)methyl]pyridine-2-yl]morpholine-2-yl]methylcarbamate (30 mg, 0.05 mmol). After addition of anisole (30 μl) and trifluoroacetic acid (150 μl) at room temperature, the mixture was stirred for 1 hour. The residue obtained by concentrating the reaction mixture under reduced pressure was purified by silica gel chromatography (3% methanol/chloroform→3% methanol, 3% tert-butylamine/chloroform), whereby the title compound (17 mg, 67%) was obtained as an oil.

$^1$H-NMR (400 MHz, CDCl$_3$) δ: 2.77 (1H, m), 2.9-3.3 (2H, m), 3.5-3.85 (3H, m), 3.97 (1H, m), 4.04-4.25 (2H, m), 6.12 (1H, s), 6.90 (1H, m), 7.02 (1H, m), 7.42 (2H, d, J=8.4 Hz), 7.4-7.55 (2H, m), 7.58 (2H, d, J=8.4 Hz), 8.05 (1H, s).

MS m/z: 528(M$^+$+H).

FAB-MS: 528.0695 (Calcd for C$_{23}$H$_{22}$Cl$_2$F$_2$N$_3$O$_3$S: 528.0727).

Example 403

5-Chloro-4-[(4-chlorophenylthio)-(2,5-difluorophenyl)methyl]-2-(4'-hydroxypiperidine-1'-yl)pyridine

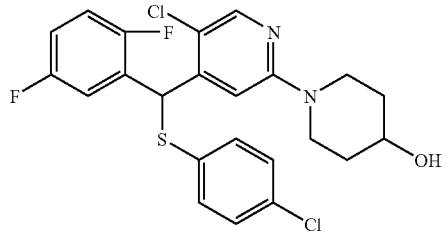

A solution of the 2,5-dichloro-4-[(4-chlorophenylthio)-(2,5-difluorophenyl)methyl]pyridine (60 mg, 0.14 mmol) obtained in Example 342 and 4-hydroxypiperidine (200 mg) was stirred at 100° C. for 1 day under nitrogen atmosphere. After cooling to room temperature, the reaction mixture was diluted with diethyl ether (50 ml). The solution was washed with water and brine, dried and then concentrated under reduced pressure. The residue thus obtained was purified by silica gel chromatography (hexane:ethyl acetate=3:1), whereby the title compound (30 mg, 43%) was obtained as an oil.

$^1$H-NMR (400 MHz, CDCl$_3$) δ: 1.62 (2H, m), 2.05 (2H, m), 3.30 (2H, m), 3.98 (3H, m), 5.97 (1H, s), 6.96-7.12 (3H, m), 7.23 (4H, m), 7.26 (1H, s), 8.10 (1H, s).

MS m/z: 481(M$^+$+H).

Example 404

5-Chloro-4-[(4-chlorophenylsulfonyl)-(2,5-difluorophenyl)methyl]-2-(4'-hydroxypiperidin-1'-yl)pyridine

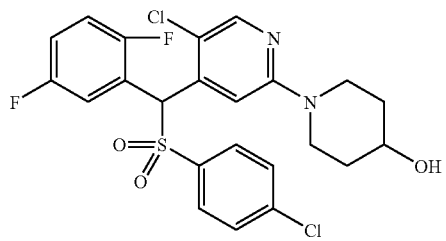

Hexaammonium heptamolybdate tetrahydrate (30 mg) was added to a solution of 5-chloro-4-[(4-chlorophenylthio)-(2,5-difluorophenyl)methyl]-2-(4'-hydroxypiperidin-1'-yl)pyridine (29 mg, 0.06 mmol) in methanol (6 ml). A 30% aqueous hydrogen peroxide solution (3 ml) was added to the resulting mixture, followed by stirring for 17 hours. After dilution with ethyl acetate (60 ml), the solution was washed with water and brine and concentrated under reduced pressure. The residue thus obtained was purified by silica gel chromatography (hexane:ethyl acetate=2:1) and crystallized from ether, whereby the title compound (17 mg, 55%) was obtained as a solid.

$^1$H-NMR (400 MHz, CDCl$_3$) δ: 1.64 (2H, m), 2.02 (2H, m), 3.33 (2H, m), 3.98 (1H, m), 4.08 (2H, m), 6.11 (1H, s), 6.92 (1H, m), 7.02 (1H, m), 7.42 (2H, d, J=8.8 Hz), 7.45 (1H, m), 7.53 (1H, s), 7.58 (2H, d, J=8.8 Hz), 8.05 (1H, s).

MS m/z: 513 (M$^+$+H).

IR (ATR) cm$^{-1}$: 3359, 1589, 1495, 1317, 1234, 1081, 829.

mp: 146-148° C.

FAB-MS: 513.0588 (Calcd for C$_{23}$H$_{21}$Cl$_2$F$_2$N$_2$O$_3$S: 513.0618).

Referential Example 50

(3,6-Dichloropyridin-2-yl) (pyridine-4-yl)methanol

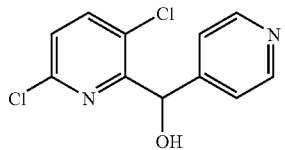

Under stirring at −78° C., tert-butyl lithium (1.51M pentane solution: 4.6 ml) was added dropwise to a solution of 2,5-dichloropyridine (1.02 g, 6.89 mmol) in ether (20 ml). After stirring at −78° C. for 2 hours, pyridin-4-carbaldehyde (0.65 ml, 6.89 mmol) was added to the reaction mixture. The resulting mixture was stirred at −78° C. for 1 hour. Water was added to the reaction mixture and the temperature was raised to room temperature. The mixture was extracted with methylene chloride. The extract was dried over anhydrous sodium sulfate and filtered. The filtrate was then concentrated under reduced pressure. The residue thus obtained was subjected to chromatography on a silica gel column. A fraction obtained from the eluate with methanol:methylene chloride (1:50) was concentrated under reduced pressure. The solid thus obtained was washed with ether and collected by filtration, whereby the title compound (819 mg, 3.21 mmol, 47%) was obtained as a white powder.

$^1$H-NMR (400 MHz, CDCl$_3$) δ: 4.64 (1H, br d, J=6.3 Hz), 6.00. (1H, br d, J=6.3 Hz), 7.27 (1H, d, J=8.6 Hz), 7.31 (2H, d, J=5.8 Hz), 7.67 (1H, d, J=8.6 Hz), 8.57 (2H, d, J=5.8 Hz).

MS (m/z): 254 (M$^+$).

Example 405

3,6-Dichloro-2-[(4-chlorophenylsulfonyl) (pyridine-4-yl)methyl]pyridine

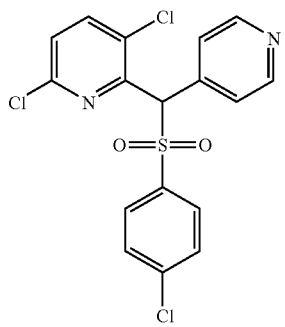

Triethylamine (208 μl, 1.89 mmol) and thionyl chloride (138 μl, 1.89 mmol) were added to a solution of (3,6-dichloropyridin-2-yl) (pyridin-4-yl)methanol (161 mg, 0.631 mmol) in methylene chloride (10 ml). After stirring at room temperature for 4 hours, the reaction mixture was concentrated under reduced pressure. Ethyl acetate was added to the residue thus obtained. The resulting mixture was washed successively with a saturated aqueous solution of sodium bicarbonate and brine, and dried over anhydrous sodium sulfate. After filtration, the filtrate was concentrated under reduced pressure. The residue thus obtained was dissolved in acetonitrile (10 ml), followed by the addition of 4-chlorobenzenethiol (137 mg, 0.947 mmol) and potassium carbonate (131 mg, 0.947 mmol). Under nitrogen atmosphere, the reaction mixture was stirred at room temperature for 2 days and then at 60° C. for 4 days. The reaction mixture was cooled to room temperature and then, concentrated under reduced pressure. Ethyl acetate was added to the residue thus obtained. The mixture was washed successively with water and brine, dried over anhydrous sodium sulfate and filtered. The filtrate was concentrated under reduced pressure. The residue thus obtained was subjected to flash chromatography. A fraction obtained from the eluate with 40% ethyl acetate/hexane was concentrated under reduced pressure. The residue thus obtained was dissolved in methanol (10 ml) and to the resulting solution, were added a 30% aqueous hydrogen peroxide solution and hexaammonium heptamolybdate tetrahydrate (73 mg). The reaction mixture was stirred at room temperature for 5 hours. Methanol was distilled off under reduced pressure. A saturated aqueous solution of sodium bicarbonate was added to the concentrated solution thus obtained, followed by extraction with methylene chloride. The organic layer was dried over anhydrous sodium sulfate and filtered. The filtrate was concentrated under reduced pressure. The residue thus obtained was subjected to flash chromatography. A fraction obtained from the eluate with methanol:methylene chloride (=1:80) was concentrated under reduced pressure, whereby the title compound (49 mg, 0.118 mmol, 19%) was obtained as a white solid.

$^1$H-NMR (400 MHz, CDCl$_3$) δ: 6.08 (1H, s), 7.31 (1H, d, J=8.3 Hz), 7.41 (2H, d, J=8.8 Hz), 7.45 (2H, d, J=6.0 Hz), 7.51 (2H, d, J=8.8 Hz), 7.69 (1H, d, J=8.3 Hz), 8.58 (2H, d, J=6.0 Hz).

IR (ATR) ν cm$^{-1}$: 3068, 2923, 1594, 1562, 1475, 1415, 1394, 1313, 1280, 1213, 1184, 1132, 1089, 1035, 1012, 993, 838, 813, 784, 744, 703, 595, 572, 536, 485, 458.

MS (m/z): 413, 415 (M$^+$+H).

Example 406

2-[1-(4-Chlorophenylsulfonyl)-1-(2,5-difluorophenyl)ethyl]-5-methylpyridine

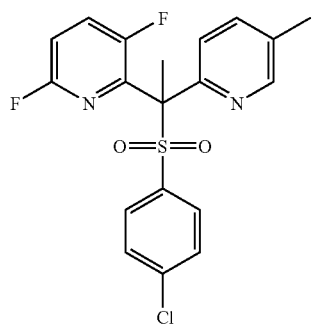

Under ice cooling, a solution of the 2-[[(4-chlorophenyl)sulfonyl](2,5-difluorophenyl)methyl]-5-methylpyridine (52 mg, 0.132 mmol), which had been obtained in Example 137, in N,N-dimethylformamide (5 ml) was added dropwise to a suspension of sodium hydride (a 60% oil dispersion, 30 mg, 0.75 mmol) in N,N-dimethylformamide (5 ml). The reaction mixture was stirred for 15 minutes under ice cooling, and then, methyl iodide (12 μl, 0.198 mmol) was added. After stirring at room temperature for 1 hour, water was added to the reaction mixture under ice cooling, followed by concentration under reduced pressure. Water was added to the residue, followed by extraction with ethyl acetate. The organic layer was washed with brine, dried over anhydrous sodium sulfate and filtered. The filtrate was concentrated under reduced pressure. The residue thus obtained was subjected to chromatography on a silica gel column. A fraction obtained from the eluate with hexane:ethyl acetate (=8:1) was concentrated under reduced pressure. The residue thus obtained was solidified with hexane and collected by filtration, whereby the title compound (50 mg, 0.122 mmol, 93%) was obtained as a white powder.

$^1$H-NMR (400 MHz, CDCl$_3$) δ: 2.14 (3H, s), 2.33 (3H, s), 6.80-7.10 (2H, m), 7.23-7.34 (4H, m), 7.39-7.51 (2H, m), 7.88-8.00 (1H, m), 8.15 (1H, s).

MS (m/z): 408 (M$^+$+H).

Example 407

3,6-Dichloro-2-[(6-chloropyridin-3-ylthio)(pyridine-4-yl)methyl]pyridine

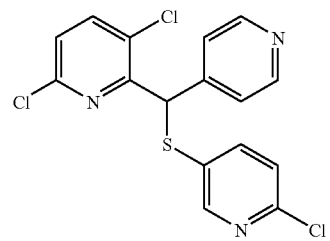

A 1N aqueous solution of sodium hydroxide (7 ml) was added to a solution of the S-(6-chloro-3-pyridyl) O-ethyl dithiocarbonate (164 mg, 0.70 mmol) obtained in Referential Example 33 in ethanol (7 ml) and the mixture was stirred at 80° C. for 3 hours. After cooling to room temperature, 1N hydrochloric acid was added to the reaction mixture. The mixture was extracted with dichloromethane. The organic layer was dried over anhydrous sodium sulfate and filtered. The filtrate was concentrated under reduced pressure, whereby 6-chloro-3-pyridinethiol was obtained as a yellow solid.

Triethylamine (0.167 ml, 1.20 mmol) and then, methanesulfonyl chloride (0.07 ml, 0.90 mmol) were added to a solution of the (3,6-dichloropyridin-2-yl)(pyridin-4-yl)methanol (153 mg, 0.60 mmol), which had been obtained in Referential Example 50, in dichloromethane (3 ml). The resulting mixture was stirred at room temperature for 2 hours. The reaction mixture was washed with a saturated aqueous solution of sodium bicarbonate. The organic layer was then dried over anhydrous sodium sulfate and filtered. The filtrate was concentrated under reduced pressure.

A solution of 6-chloro-3-pyridinethiol in N,N-dimethylformamide (2 ml) and potassium carbonate (100 mg, 0.72 mmol) were successively added to a solution of the resulting residue in N,N-dimethylformamide (3 ml). The resulting mixture was stirred at room temperature for 18 hours. Ethyl acetate was added to the reaction mixture. After washing with a saturated aqueous solution of sodium bicarbonate, the organic layer was dried over anhydrous sodium sulfate and filtered. The filtrate was concentrated under reduced pressure. The residue thus obtained was subjected to flash silica gel chromatography. A fraction obtained from the elution portion with hexane:ethyl acetate=7:3 was concentrated under reduced pressure, whereby the title compound (83 mg, 0.22 mmol, 36%) was obtained as a yellow oil.

$^1$H-NMR (400 MHz, CDCl$_3$) δ: 5.69 (1H, s), 7.20 (1H, d, J=8.3 Hz), 7.24 (1H, d, J=8.3 Hz), 7.35 (2H, d, J=6.1 Hz), 7.52 (1H, dd, J=8.3, 2.4 Hz), 7.62 (1H, d, J=8.3 Hz), 8.32 (1H, d, J=2.4 Hz), 8.55 (2H, d, J=6.1 Hz).

MS m/z: 382 (M$^+$+H).

Example 408

3,6-Dichloro-2-[(6-chloropyridin-3-ylsulfonyl) (pyridin-4-yl)methyl]pyridine (Compound A) and 3,6-dichloro-2-[(6-chloropyridin-3-ylsulfinyl)(pyridine-4-yl)methyl]pyridine (Compound B (Isomer A) and Compound B (Isomer B))

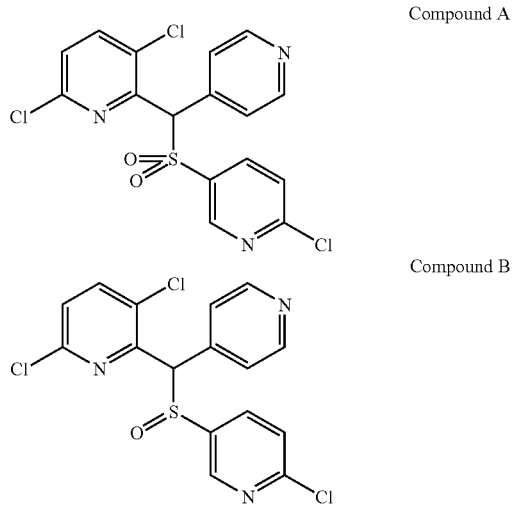

A 31% aqueous hydrogen peroxide solution (2 ml) and hexaammonium heptamolybdate tetrahydrate (30 mg) were added to a solution of 3,6-dichloro-2-[(6-chloropyridin-3-ylthio) (pyridin-4-yl)methyl]pyridine (82 mg, 0.24 mmol) in methanol (4 ml). The resulting mixture was stirred at room temperature for 2 hours. Ethyl acetate was added to the reaction mixture. After washing with a saturated aqueous solution of sodium bicarbonate, the organic layer was dried over anhydrous sodium sulfate and filtered. The filtrate was concentrated under reduced pressure. The residue was subjected to flash chromatography on a silica gel column. A fraction obtained from the elution portion with hexane:ethyl acetate=3:2 was concentrated under reduced pressure, whereby the title compound A (41 mg, 0.098 mmol, 46%) was obtained. A fraction obtained from the elution portion with hexane:ethyl acetate=1:1 was concentrated under reduced pressure, whereby the title compound B (isomer A) (low polarity) (8 mg, 0.020 mmol, 9%) and the title compound B (isomer B) (high polarity) (8 mg, 0.020 mmol, 9%) were obtained, respectively each as a white solid.

Compound A $^1$H-NMR (400 MHz, CDCl$_3$) δ: 6.11 (1H, s), 7.35 (1H, d, J=8.3 Hz), 7.36 (2H, d, J=6.1 Hz), 7.40 (1H, d, J=8.3 Hz), 7.73 (1H, d, J=8.3 Hz), 7.78 (1H, dd, J=8.3, 2.4 Hz), 8.48 (1H, d, J=2.4 Hz), 8.61 (2H, d, J=6.1 Hz).

MS m/z: 414 (M$^+$+H).

Compound B (Isomer A)

$^1$H-NMR (400 MHz, CDCl$_3$) δ: 5.54 (1H, s), 6.99 (2H, d, J=6.1 Hz), 7.27 (1H, d, J=8.3 Hz), 7.37 (1H, d, J=8.3 Hz), 7.55 (1H, dd, J=8.3, 2.2 Hz), 7.73 (1H, d, J=8.3 Hz), 8.47 (1H, d, J=2.2 Hz), 8.51 (2H, d, J=6.1 Hz).

MS m/z: 398 (M$^+$+H).

Compound B (Isomer B)

$^1$H-NMR (400 MHz, CDCl$_3$) δ: 5.40 (1H, s), 7.26 (1H, d, J=8.5 Hz), 7.42 (1H, d, J=8.3 Hz), 7.53 (2H, d, J=6.1 Hz), 7.57 (1H, d, J=8.5 Hz), 7.96 (1H, dd, J=8.3, 2.4 Hz), 8.34(1H, d, J=2.4 Hz), 8.68 (2H, d, J=6.1 Hz).

MS m/z: 398 (M$^+$+H).

Example 409

2-[[(3-Chloropyridin-4-yl)(2,5-difluorophenyl)methyl]sulfonyl]pyrimidine

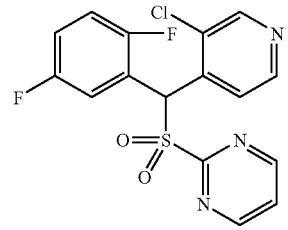

Triethylamine (0.112 ml, 0.80 mmol) and methanesulfonyl chloride (0.046 ml, 0.60 mmol) were added successively to a solution of the 3-chloro-4-[(2,5-difluorophenyl)-hydroxymethyl]pyridine (102 mg, 0.40 mmol), which had been obtained in Referential Example 48, in dichloromethane (4 ml) at 0° C. The resulting mixture was stirred at room temperature for 17 hours. After washing with a saturated aqueous solution of sodium bicarbonate, the organic layer was dried over anhydrous sodium sulfate and filtered. The filtrate was concentrated under reduced pressure.

To a solution of the resulting residue in N,N-dimethylformamide (4 ml) were added 2-pyrimidinethiol (45 mg, 0.40 mmol) and then, potassium carbonate (83 mg, 0.60 mmol) and the mixture was stirred at room temperature for 23 hours. Ethyl acetate was added to the reaction mixture. After washing with water, the organic layer was dried over anhydrous sodium sulfate and filtered. The filtrate was concentrated under reduced pressure.

To a solution of the resulting residue in dichloromethane (4 ml) was added 3-chloroperbenzoic acid (purity: 65% or greater) (212 mg, 0.80 mmol) at 0° C. and the resulting mixture was stirred at room temperature for 3 hours. After washing with a 1N aqueous solution of sodium hydroxide, the organic layer was dried over anhydrous sodium sulfate and filtered. The filtrate was concentrated under reduced pressure. The residue thus obtained was subjected to flash silica gel chromatography. A fraction obtained from the elution portion with hexane:ethyl acetate=2:3 was concentrated under reduced pressure, whereby the title compound (19 mg, 0.049 mmol, 12%) was obtained as a colorless foam.

¹H-NMR (400 MHz, CDCl₃) δ: 6.26 (1H, s), 6.93-7.13 (3H, m), 7.50-7.56 (1H, m), 8.01-8.08 (1H, m), 8.13 (1H, d, J=5.1 Hz), 8.48 (1H, d, J=2.2 Hz), 8.60 (1H, s), 8.66 (1H, d, J=5.1 Hz).

MS m/z: 382 (M⁺+H).

Test Example

Cell-Based Assay for Screening of a Compound Which Inhibits Production or Secretion of β-Amyloid Protein E35 cells which were established by transfecting APP751 gene which is a wild type human β-amyloid protein precursor into human glioma cells (H4 cells), were used to analyze inhibitory activity of a compound against β-amyloid production. The amount of β protein (Aβ) secreted in a culture medium was measured by the sandwich enzyme-linked imunosorbent assay.

E35 cells were seeded in Dulbecco's Modified Eagle's Medium containing 10% inactivated fetal bovine serum on 96-well plates and cultured in humidified air and 5% $CO_2$ at 37° C. in a $CO_2$ incubator. Twenty-four hours after seeding of the cells, a test compound dissolved in DMSO was added to the medium. The DMSO solution of the compound was prepared so as to give the final concentration of DMSO in the medium 0.05%. The cells were cultured for additional twenty-four hours, and then the cultured medium was collected. The medium collected was applied to a 96-well ELISA plate on which a monoclonal antibody 25-1, which recognized Aβ25-35, was immobilized, followed by the incubation at 4° C. for 16 to 20 hours. After washing with a phosphate buffer (pH 7.4), a biotinylated monoclonal antibody MA32-40, which recognizes Aβ1-8, was added to the plate, and the plate was incubated at 4° C. for 2 hours. Then alkaline phosphatase-conjugated streptavidin was added to the plate. Alkaline phosphatase activity was measured by a calorimetric assay using BlouPhos (manufactured by KPL) as a substrate. An amount of Aβ in the medium was calculated using a calibration curve separately created. $EC_{50}$ of the test compound was presented as the concentration that gives 50% inhibitory activity compared to the control cells which were not treated with the compound.

On the other hand, cytotoxicity of the compound was assayed according the following. The compound was added to the cultured H4 cells and after incubation for 72 hours, a calorimetric assay was performed using AlamarBlue (manufactured by BIOSOURCE) and the absorbance of the wells was measured. Concentration of the test compounds which gives 80% or less of the absorbance compared to that of the control cells was defined as the concentration at which cytotoxicity was appeared. When a significant difference between the $EC_{50}$ and the concentration at which cytotoxicity was appeared was observed, then the compound is judged as an active compound.

The results of evaluation of the compound (1) using an above-mentioned assay are shown in Table 1. Compounds exhibiting EC50 not greater than 50 nM are evaluated as +++, those exhibiting EC50 ranging from 50 nM to 500 nM are evaluated as ++ and those exhibiting EC50 ranging from 500 nM to 5 μM are evaluated as +.

| Compound | Activity |
| --- | --- |
| Example 2 (Isomer 2-B) | + |
| Example 3 | ++ |
| Example 10 | ++ |

-continued

| Compound | Activity |
| --- | --- |
| Example 12 | + |
| Example 14 | + |
| Example 17 | + |
| Example 27 (Compound A) | ++ |
| Example 29 | ++ |
| Example 32 | ++ |
| Example 33 | +++ |
| Example 35 | + |
| Example 36 | ++ |
| Example 43 (Isomer 43-A) | ++ |
| Example 43 (Isomer 43-B) | ++ |
| Example 45 | +++ |
| Example 46 | ++ |
| Example 47 | +++ |
| Example 48 | +++ |
| Example 136 | +++ |
| Example 141 | ++ |
| Example 142 | ++ |
| Example 145 | +++ |
| Example 287 | ++ |
| Example 288 | ++ |
| Example 330 | ++ |
| Example 331 | ++ |
| Example 334 | ++ |
| Example 343 | +++ |
| Example 344 | +++ |
| Example 345 | +++ |
| Example 347 | +++ |
| Example 349 | +++ |
| Example 370 | ++ |
| Example 372 | ++ |
| Example 397 | +++ |
| Example 399 | +++ |
| Example 402 | +++ |
| Example 404 | +++ |

INDUSTRIAL APPLICABILITY

Compounds represented by the formula (1), salts, N-oxides and S oxides thereof, and solvate of any one of them have an inhibitory action against production or secretion of β-amyloid protein. They are therefore pharmaceutically effective for the prevention and treatment of various diseases such as Alzheimer disease, Down syndrome and the other diseases associated with amyloid deposition.

The invention claimed is:

1. A compound represented by the formula (3):

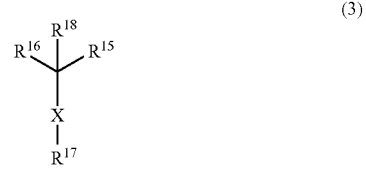

wherein $R^{15}$ represents a pyridyl group substituted with at least one group represented by the formula $-Q^{201}-Q^{202}-Q^{203}-Q^{204}-Q^{205}-Q^{206}-Q^{207}$, wherein $Q^{201}$ represents a single bond, an alkyl group having from 1 to 6 carbon atoms, an alkenyl group having from 2 to 6 carbon atoms or a heterocyclic group;

$Q^{202}$ represents a single bond, —O—, —NH—, —CH=N—, —C(alkyl)=N—, —N(alkyl)— or —S—;

$Q^{203}$ represents a single bond, —CO—, —CS—, —SO—, —SO$_2$— or —CONH—;

$Q^{204}$ represents a single bond, an alkyl group from 1 to 6 carbon atoms, an alkenyl group having from 2 to 6 carbon atoms, a cycloalkyl group, a cycloalkenyl group, an aromatic hydrocarbon group or a heterocyclic group;

$Q^{205}$ represents a single bond, —NH— or —N(alkyl)—;

$Q^{206}$ represents a single bond, —O—, —CO—, —CS—, —SO$_2$—, —SO— or —S—; and $Q^{207}$ represents a hydrogen atom, a halogen atom, a hydroxy group, an oxo group, a $C_{1-6}$ alkyl group, a $C_{2-6}$ alkenyl group, a $C_{3-8}$ cycloalkyl group, a $C_{1-6}$ alkoxy group, a $C_{2-6}$ alkenyloxy group, an azide group, a cyano group, an amino group, a $C_{1-6}$ alkylamino group, a di($C_{1-6}$ alkyl)amino group, a $C_{2-6}$ alkanoylamino group, a di($C_{2-6}$ alkanoy)amino group, a carboxyamino group, a $C_{1-6}$ alkoxycarbonylamino group, a di($C_{1-6}$ alkoxy)carbonylamino group, a heterocyclic group, an aromatic hydrocarbon group, a cycloalkenyl group, a heterocyclic oxy group, an aromatic hydrocarbon-oxy group, wherein, the alkyl group having from 1 to 6 carbon atoms, alkenyl group having from 2 to 6 carbon atoms, cycloalkyl group, cycloalkenyl group, heterocyclic group, heterocyclic-oxy group, aromatic hydrocarbon group or aromatic hydrocarbon-oxy group may be substituted with 1 to 3 substituents selected from halogen atoms, $C_{1-6}$ alkyl groups, $C_{1-6}$ alkoxy groups, $C_{2-6}$ alkenyl groups, carboxyamino $C_{1-6}$ alkyl groups, $C_{1-6}$ alkoxycarbonylamino $C_{1-6}$ alkyl groups, formyl group, $C_{2-6}$ alkanoyl groups, oxo group, nitro group, cyano group, azide group, amidino group, $C_{2-6}$ alkenyloxy groups, hydroxy group, carboxyl group, $C_{7-16}$ aralkyl groups, thioxo group, $C_{2-7}$ alkanoyl groups, $C_{2-7}$ thioalkanoyl groups, thioformyl group, amino group, $C_{1-6}$ alkylamino groups, di($C_{1-6}$ alkyl)amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, $C_{1-6}$ alkoxycarbamoylamino groups, $C_{1-6}$ alkoxycarbamoyl($C_{1-6}$ alkyl)amino groups, $C_{2-7}$ alkanoylamino groups, $C_{2-7}$ alkanoyl ($C_{1-6}$ alkyl)amino groups, thio $C_{2-7}$ alkanoylamino groups, thio $C_{2-7}$ alkanoyl ($C_{1-6}$ alkyl)amino groups, formylamino group, formyl($C_{1-6}$ alkyl)amino groups, thioformylamino group, thioformyl($C_{1-6}$ alkyl)amino groups, $C_{2-7}$ alkanoyloxy groups, formyloxy group, $C_{1-6}$ alkoxycarbonyloxy groups, carbamoyloxy group, $C_{1-6}$ alkylcarbamoyloxy groups, di($C_{1-6}$ alkyl)carbamoyloxy groups, aminocarbonylamino group, ($C_{1-6}$ alkyl)aminocarbonylamino groups, di($C_{1-6}$ alkyl)aminocarbonylamino groups, aminocarbonyl($C_{1-6}$ alkyl)amino groups, $C_{1-6}$ alkyl)aminocarbonyl($C_{1-6}$ alkyl)amino groups, di($C_{1-6}$ alkyl)aminocarbonyl($C_{1-6}$ alkyl)amino groups, mercapto group, $C_{1-6}$ alkylthio groups, $C_{1-6}$ alkylsulfinyl groups, $C_{1-6}$ alkylsulfonyl groups, aminosulfonyl group, $C_{1-6}$ alkylaminosulfonyl groups, di($C_{1-6}$ alkyl)aminosulfonyl groups, $C_{1-6}$ alkylsulfonylamino groups, $C_{1-6}$ alkylsulfonyl($C_{1-6}$ alkyl)amino groups, aminosulfonylamino group, $C_{1-6}$ alkylaminosulfonylamino groups, di($C_{1-6}$ alkyl)aminosulfonylamino groups, aminosulfonyl($C_{1-6}$ alkyl)amino groups, $C_{1-6}$ alkylaminosulfonyl($C_{1-6}$ alkyl)amino groups, and di($C_{1-6}$ alkyl)aminosulfonyl($C_{1-6}$ alkyl)amino groups, wherein said heterocyclic group is selected from the group consisting of piperazine, morpholine, piperidine, thiophene and 1,3-dioxilane;

$R^{16}$ represents an unsubstituted phenyl group or a phenyl group substituted with at least one substituent represented by the formula -$Q^{201}$-$Q^{202}$-$Q^{203}$-$Q^{204}$-$Q^{205}$-$Q^{206}$-$Q^{207}$, wherein $Q^{201}$ represents a single bond, an alkyl group having from 1 to 6 carbon atoms or an alkenyl group having from 2 to 6 carbon atoms, $Q^{202}$ represents a single bond, —O—, —NH—, —CH═N—, —C(alkyl)═N—, —N(alkyl)— or —S—;

$Q^{203}$ represents a single bond, —CO—, —CS—, —SO—, —SO$_2$— or —CONH—;

$Q^{204}$ represents a single bond, an alkyl group from 1 to 6 carbon atoms, an alkenyl group having from 2 to 6 carbon atoms, a cycloalkyl group, a cycloalkenyl group or an aromatic hydrocarbon group;

$Q^{205}$ represents a single bond, —NH— or —N(alkyl)—;

$Q^{206}$ represents a single bond, —O—, —CO—, —CS—, —SO$_2$—, —SO— or —S—; and $Q^{207}$ represents a hydrogen atom, a halogen atom, a hydroxy group, an oxo group, a $C_{1-6}$ alkyl group, a $C_{2-6}$ alkenyl group, a $C_{3-8}$ cycloalkyl group, a $C_{1-6}$ alkoxy group, a $C_{2-6}$ alkenyloxy group, an azide group, a cyano group, an amino group, a $C_{1-6}$ alkylamino group, a di($C_{1-6}$ alkyl)amino group, a $C_{2-6}$ alkanoylamino group, a di($C_{2-6}$ alkanoy)amino group, a carboxyamino group, a $C_{1-6}$ alkoxycarbonylamino group, a di($C_{1-6}$ alkoxy)carbonylamino group, an aromatic hydrocarbon group, a cycloalkenyl group, an aromatic hydrocarbon-oxy group, wherein, the alkyl group having from 1 to 6 carbon atoms, alkenyl group having from 2 to 6 carbon atoms, cycloalkyl group, cycloalkenyl group, aromatic hydrocarbon group or aromatic hydrocarbon-oxy group may be substituted with 1 to 3 substituents selected from the group consisting of halogen atoms, $C_{1-6}$ alkyl groups, $C_{1-6}$ alkoxy groups, $C_{2-6}$ alkenyl groups, carboxyamino $C_{1-6}$ alkyl groups, $C_{1-6}$ alkoxycarbonylamino $C_{1-6}$ alkyl groups, formyl group, $C_{2-6}$ alkanoyl groups, oxo group, nitro group, cyano group, azide group, amidino group, $C_{2-6}$ alkenyloxy groups, hydroxy group, carboxyl group, $C_{7-16}$ aralkyl groups, thioxo group, $C_{2-7}$ alkanoyl groups, $C_{2-7}$ thioalkanoyl groups, thioformyl group, amino group, $C_{1-6}$ alkylamino groups, di($C_{1-6}$ alkyl)amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, $C_{1-6}$ alkoxycarbamoylamino groups, $C_{1-6}$ alkoxycarbamoyl($C_{1-6}$ alkyl)amino groups, $C_{2-7}$ alkanoylamino groups, $C_{2-7}$ alkanoyl ($C_{1-6}$ alkyl)amino groups, thio $C_{2-7}$ alkanoylamino groups, thio $C_{2-7}$ alkanoyl($C_{1-6}$ alkyl)amino groups, formylamino group, formyl($C_{1-6}$ alkyl)amino groups, thioformylamino group, thioformyl($C_{1-6}$ alkyl)amino groups, $C_{2-7}$ alkanoyloxy groups, formyloxy group, $C_{1-6}$ alkoxycarbonyloxy groups, carbamoyloxy group, $C_{1-6}$ alkylcarbamoyloxy groups, di($C_{1-6}$ alkyl)carbamoyloxy groups, aminocarbonylamino group, ($C_{1-6}$ alkyl)aminocarbonylamino groups, di($C_{1-6}$ alkyl)aminocarbonylamino groups, aminocarbonyl($C_{1-6}$ alkyl)amino groups, $C_{1-6}$ alkyl)aminocarbonyl($C_{1-6}$ alkyl)amino groups, di($C_{1-6}$ alkyl)aminocarbonyl($C_{1-6}$ alkyl)amino groups, mercapto group, $C_{1-6}$ alkylthio groups, $C_{1-6}$ alkylsulfinyl groups, $C_{1-6}$ alkylsulfonyl groups, aminosulfonyl group, $C_{1-6}$ alkylaminosulfonyl groups, di($C_{1-6}$ alkyl)aminosulfonyl groups, $C_{1-6}$ alkylsulfonylamino groups, $C_{1-6}$ alkylsulfonyl($C_{1-6}$ alkyl)amino groups, aminosulfonylamino group, $C_{1-6}$ alkylaminosulfonylamino groups, di($C_{1-6}$ alkyl)aminosulfonylamino groups, aminosulfonyl($C_{1-6}$ alkyl)amino groups, $C_{1-6}$ alkylaminosulfonyl($C_{1-6}$ alkyl)amino groups, and di($C_{1-6}$ alkyl)aminosulfonyl($C_{1-6}$ alkyl)amino groups;

$R^{17}$ represents an unsubstituted phenyl group or a phenyl group substituted with at least one substituent represented by the formula -$Q^{201}$-$Q^{202}$-$Q^{203}$-$Q^{204}$-$Q^{205}$-$Q^{206}$-$Q^{207}$, wherein $Q^{201}$ represents a single bond, an alkyl group having from 1 to 6 carbon atoms or an alkenyl group having from 2 to 6 carbon atoms, $Q^{202}$ represents a single bond, —O—, —NH—, —CH=N—, —C(alkyl)=N—, —N(alkyl)— or —S—;

$Q^{203}$ represents a single bond, —CO—, —CS—, —SO—, —SO$_2$— or —CONH—;

$Q^{204}$ represents a single bond, an alkyl group from 1 to 6 carbon atoms, an alkenyl group having from 2 to 6 carbon atoms, a cycloalkyl group, a cycloalkenyl group or an aromatic hydrocarbon group;

$Q^{205}$ represents a single bond, —NH— or —N(alkyl)—;

$Q^{206}$ represents a single bond, —O—, —CO—, —CS—, —SO$_2$—, —SO— or —S—; and $Q^{207}$ represents a hydrogen atom, a halogen atom, a hydroxy group, an oxo group, a $C_{1-6}$ alkyl group, a $C_{2-6}$ alkenyl group, a $C_{3-8}$ cycloalkyl group, a $C_{1-6}$ alkoxy group, a $C_{2-6}$ alkenyloxy group, an azide group, a cyano group, an amino group, a $C_{1-6}$ alkylamino group, a di($C_{1-6}$ alkyl)amino group, a $C_{2-6}$ alkanoylamino group, a di($C_{2-6}$ alkanoy)amino group, a carboxyamino group, a $C_{1-6}$ alkoxycarbonylamino group, a di($C_{1-6}$ alkoxy)carbonylamino group, an aromatic hydrocarbon group, a cycloalkenyl group, an aromatic hydrocarbon-oxy group, wherein, the alkyl group having from 1 to 6 carbon atoms, alkenyl group having from 2 to 6 carbon atoms, cycloalkyl group, cycloalkenyl group, aromatic hydrocarbon group or aromatic hydrocarbon-oxy group may be substituted with 1 to 3 substituents selected from the group consisting of halogen atoms, $C_{1-6}$ alkyl groups, $C_{1-6}$ alkoxy groups, $C_{2-6}$ alkenyl groups, carboxyamino $C_{1-6}$ alkyl groups, $C_{1-6}$ alkoxycarbonylamino $C_{1-6}$ alkyl groups, formyl group, $C_{2-6}$ alkanoyl groups, oxo group, nitro group, cyano group, azide group, amidino group, $C_{2-6}$ alkenyloxy groups, hydroxy group, carboxyl group, $C_{7-16}$ aralkyl groups, thioxo group, $C_{2-7}$ alkanoyl groups, $C_{2-7}$ thioalkanoyl groups, thioformyl group, amino group, $C_{1-6}$ alkylamino groups, di($C_{1-6}$ alkyl) amino groups, $C_{1-6}$ alkoxycarbonyl groups, carbamoyl group, $C_{1-6}$ alkylcarbamoyl groups, di($C_{1-6}$ alkyl)carbamoyl groups, thiocarbamoyl group, $C_{1-6}$ alkylthiocarbamoyl groups, di($C_{1-6}$ alkyl)thiocarbamoyl groups, $C_{1-6}$ alkoxycarbamoylamino groups, $C_{1-6}$ alkoxycarbamoyl($C_{1-6}$ alkyl)amino groups, $C_{2-7}$ alkanoylamino groups, $C_{2-7}$ alkanoyl ($C_{1-6}$ alkyl)amino groups, thio $C_{2-7}$ alkanoylamino groups, thio $C_{2-7}$ alkanoyl($C_{1-6}$ alkyl)amino groups, formylamino group, formyl($C_{1-6}$ alkyl) amino groups, thioformylamino group, thioformyl($C_{1-6}$ alkyl)amino groups, $C_{2-7}$ alkanoyloxy groups, formyloxy group, $C_{1-6}$ alkoxycarbonyloxy groups, carbamoyloxy group, $C_{1-6}$ alkylcarbamoyloxy groups, di($C_{1-6}$ alkyl)carbamoyloxy groups, aminocarbonylamino group, ($C_{1-6}$ alkyl)aminocarbonylamino groups, di($C_{1-6}$ alkyl)aminocarbonylamino groups, aminocarbonyl($C_{1-6}$ alkyl)amino groups, ($C_{1-6}$ alkyl)aminocarbonyl($C_{1-6}$ alkyl)amino groups, di($C_{1-6}$ alkyl)aminocarbonyl($C_{1-6}$ alkyl)amino groups, mercapto group, $C_{1-6}$ alkylthio groups, $C_{1-6}$ alkylsulfinyl groups, $C_{1-6}$ alkylsulfonyl groups, aminosulfonyl group, $C_{1-6}$ alkylaminosulfonyl groups, di($C_{1-6}$ alkyl)aminosulfonyl groups, $C_{1-6}$ alkylsulfonylamino groups, $C_{1-6}$ alkylsulfonyl($C_{1-6}$ alkyl)amino groups, aminosulfonylamino group, $C_{1-6}$ alkylaminosulfonylamino groups, di($C_{1-6}$ alkyl)aminosulfonylamino groups, aminosulfonyl($C_{1-6}$ alkyl)amino groups, $C_{1-6}$ alkylaminosulfonyl($C_{1-6}$ alkyl)amino groups, and di($C_{1-6}$ alkyl)aminosulfonyl($C_{1-6}$ alkyl) amino groups;

$R^{18}$ represents a hydrogen atom or a $C_{1-6}$ alkyl group; and

X represents —S—, —SO— or —SO$_2$—;

or an N-oxide or S-oxide of thereof; a salt thereof; or a solvate thereof.

2. The compound according to claim 1, wherein $R^{18}$ represents a hydrogen atom.

3. The compound according to claim 1, wherein X represents —SO$_2$—.

4. The compound according to claim 1, wherein $Q^{201}$, $Q^{202}$, $Q^{203}$, $Q^{204}$, $Q^{205}$ and $Q^{206}$ in the definition of $R^{15}$ each represent a single bond.

5. The compound according to claim 1, wherein $Q^{201}$, $Q^{202}$, $Q^{205}$ and $Q^{206}$ in the definition of $R^{15}$ each represent a single bond.

6. The compound according to claim 1, wherein $Q^{203}$ in definition of $R^{15}$ represents —CONH—.

7. The compound according to claim 1, wherein $Q^{201}$, $Q^{202}$, $Q_{203}$, $Q_{204}$, $Q^{205}$ and $Q^{206}$ in the definition of $R^{16}$ each represent a single bond.

8. The compound according to claim 1, wherein $Q^{201}$, $Q^{202}$, $Q_{203}$, $Q^{204}$, $Q^{205}$ and $Q^{206}$ in the definition of $R^{17}$ each represent a single bond.

9. The compound of claim 1, wherein $R^{16}$ represents an unsubstituted phenyl group;

or an N-oxide or S-oxide of thereof; a salt thereof; or a solvate thereof.

10. The compound of claim 1, wherein $R^{16}$ represents said substituted phenyl group;

or an N-oxide or S-oxide of thereof; a salt thereof; or a solvate thereof.

11. The compound of claim 1, wherein $R^{17}$ represents an unsubstituted phenyl group;

or an N-oxide or S-oxide of thereof; a salt thereof; or a solvate thereof.

12. The compound of claim 1, wherein $R^{17}$ represents said substituted phenyl group;

or an N-oxide or S-oxide of thereof; a salt thereof; or a solvate thereof.

13. The compound of claim 1, wherein $R^{18}$ represents a $C_{1-6}$ alkyl group;

or an N-oxide or S-oxide of thereof; a salt thereof; or a solvate thereof.

14. The compound of claim 1, wherein X represents —S—; or an N-oxide or S-oxide of thereof; a salt thereof; or a solvate thereof.

15. The compound of claim 1, wherein X represents —SO—; or an N-oxide or S-oxide of thereof; a salt thereof; or a solvate thereof.

16. A method for treating Alzheimer's disease, comprising administering an effective amount of the compound of claim 1 to a subject in need thereof.

17. A pharmaceutical composition, comprising the compound of claim 1, or N-oxide or S-oxide of the compound, salt thereof, or solvate thereof and a pharmaceutically acceptable carrier.

18. A method of preparing a medicament, comprising adding the compound of claim 1, or an N-oxide or S-oxide of thereof; a salt thereof; or a solvate thereof, to a pharmaceutically acceptable carrier.

* * * * *